US010501798B2

(12) United States Patent
Davezac et al.

(10) Patent No.: US 10,501,798 B2
(45) Date of Patent: Dec. 10, 2019

(54) METHOD AND KIT FOR PROGNOSIS OF OPA1 GENE INDUCED DISEASES, E.G. KJERS OPTIC ATROPHY

(71) Applicants: UNIVERSITE TOULOUSE III-PAUL SABATIER, Toulouse (FR); CENTRE NATIONAL DE LA RECHERCHE SCIENTIFIQUE, Paris (FR)

(72) Inventors: Noelie Davezac, Toulouse (FR); Pascale Belenguer, Pompertuzat (FR); Aurelie Millet, Toulouse (FR)

(73) Assignees: UNIVERSITE TOULOUSE III-PAUL SABATIER, Toulouse (FR); CENTRE NATIONAL DE LA RECHERCHE SCIENTIFIQUE, Paris (FR)

( * ) Notice: Subject to any disclaimer, the term of this patent is extended or adjusted under 35 U.S.C. 154(b) by 287 days.

(21) Appl. No.: 15/129,020

(22) PCT Filed: Mar. 27, 2015

(86) PCT No.: PCT/EP2015/056814
§ 371 (c)(1),
(2) Date: Sep. 26, 2016

(87) PCT Pub. No.: WO2015/144924
PCT Pub. Date: Oct. 1, 2015

(65) Prior Publication Data
US 2017/0101679 A1 Apr. 13, 2017

(30) Foreign Application Priority Data
Mar. 27, 2014 (EP) ..................................... 14305448

(51) Int. Cl.
*C12Q 1/68* (2018.01)
*C12Q 1/6883* (2018.01)
*G01N 33/573* (2006.01)
*G01N 33/68* (2006.01)

(52) U.S. Cl.
CPC ......... *C12Q 1/6883* (2013.01); *G01N 33/573* (2013.01); *C12Q 2600/118* (2013.01); *C12Q 2600/156* (2013.01); *C12Q 2600/158* (2013.01); *G01N 33/6893* (2013.01); *G01N 2800/16* (2013.01)

(58) Field of Classification Search
None
See application file for complete search history.

(56) References Cited

U.S. PATENT DOCUMENTS

| 2004/0023207 | A1* | 2/2004 | Polansky | A61K 31/00 435/5 |
| 2005/0256207 | A1* | 11/2005 | McGrath | A61K 31/13 514/673 |
| 2008/0085878 | A1* | 4/2008 | Wang | A61K 31/21 514/182 |
| 2010/0305187 | A1* | 12/2010 | Guelow | A61K 31/155 514/44 A |

FOREIGN PATENT DOCUMENTS

| WO | 02/27022 A2 | 4/2002 |
| WO | 2008/097596 A2 | 8/2008 |

OTHER PUBLICATIONS

D. Nguyen, et al., A new vicious cycle involving glutamate excitotoxicity, oxidative stress and mitochondrial dynamics, Cell Death and Disease, 2011, pp. 1-10, vol. 2, Macmillan Publishers Limited.
Antonio Federico, et al., Mitochondria, oxidative stress and neurodegeneration, Journal of the Neurological Sciences, 2012, pp. 254-262, vol. 322, Elsevier B.V.
A. D. Kraft: "Nuclear Factor E2-Related Factor 2-Dependent Antioxidant Response Element Activation by tert-Butylhydroquinone and Sulforaphane Occurring Preferentially in Astrocytes Conditions Neurons against Oxidative Insult", Journal of Neuroscience, vol. 24, No. 5, Feb. 4, 2004 (Feb. 4, 2004), pp. 1101-1112.
Malone et al: "4-Hydroxynonenal, a product of oxidative stress, leads to an antioxidant response in optic nerve head astrocytes", Experimental Eye Research, Academic Press Ltd, London, vol. 84, No. 3, Feb. 7, 2007 (Feb. 7, 2007), pp. 444-454, XP005938156, ISSN: 0014-4835, DOI: 10.1016/J.EXER.2006.10.020.
A. Kanamori et al: "Superoxide is an associated signal for apoptosis in axonal injury", Brain, vol. 133, No. 9, Sep. 1, 2010 (Sep. 1, 2010), pp. 2612-2625, XP055127741, ISSN: 0006-8950, DOI: 10.1093/brain/awq105.
A. M. Bertholet et al: "OPA1 loss of function affects in vitro neuronal maturation", Brain, vol. 136, No. 5, May 1, 2013 (May 1, 2013), pp. 1518-1533, XP055127098, ISSN: 0006-8950, DOI: 10.1093/brain/awt060.
Neville N Osborne et al: "Maintenance of retinal ganglion cell mitochondrial functions as a neuroprotective strategy in glaucoma", Current Opinion in Pharmacology, vol. 13, No. 1, Feb. 1, 2013 (Feb. 1, 2013), pp. 16-22, XP055127112, ISSN: 1471-4892, DOI: 10.1016/j.coph.2012.09.002.
Osburn W O et al: "Nrf2 regulates an adaptive response protecting against oxidative damage following diquat-mediated formation of superoxide anion", Archives of Biochemistry and Biophysics, Academic Press, US, vol. 454, No. 1, Oct. 1, 2006 (Oct. 1, 2006), pp. 7-15, XP024943041, ISSN: 0003-9861, [retrieved on Oct. 1, 2006], DOI: 10.1016/J.ABB.2006.08.005.

(Continued)

*Primary Examiner* — Samuel C Woolwine
(74) *Attorney, Agent, or Firm* — Young & Thompson

(57) ABSTRACT

Providing Nuclear factor (erythroid-derived 2)-like 2 (NRF2)-activated genes products, e.g. SOD1 and CAT, in their use in the prognosis of an OPA1 gene- or OPA1 gene product-deficit-induced disease, or related complications, e.g. optic atrophy and optic neuropathy, in a biological sample selected from fibroblasts, epithelial cells, blood samples or a mixture thereof, of a patient affected or suspected to be affected by the disease.

Figure 1A:
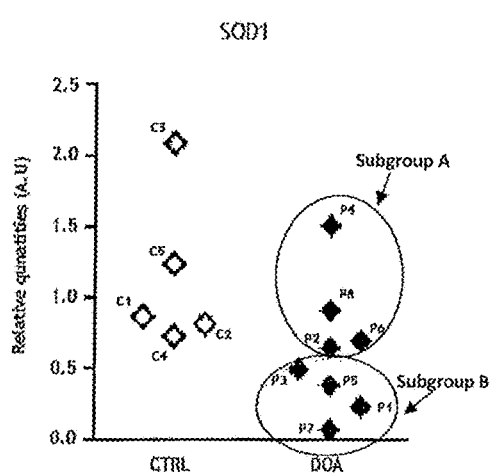
Figure 1A:
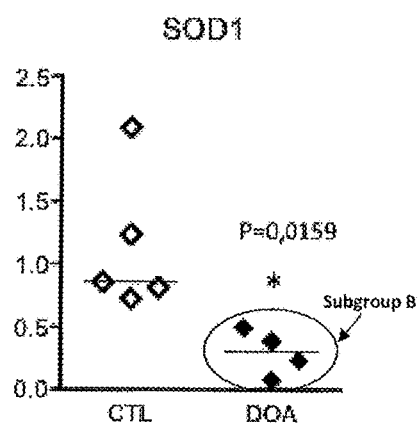

5 Claims, 11 Drawing Sheets
Specification includes a Sequence Listing.

(56) References Cited

OTHER PUBLICATIONS

E Croze et al: "Interferon-beta-1b-induced short- and long-term signatures of treatment activity in multiple sclerosis", The Pharmacogenomics Journal, vol. 13, No. 5, Jun. 19, 2012 (Jun. 19, 2012), pp. 443-451, XP055127108, ISSN: 1470-269X, DOI: 10.1038/tpj.2012.27.
J.-M. Lee: "Nrf2, a multi-organ protector?", The FASEB Journal, vol. 19, No. 9, Jul. 1, 2005 (Jul. 1, 2005), pp. 1061-1066, XP055127103, ISSN: 0892-6638, DOI: 10.1096/fj.04-2591hyp.
Amati-Bonneau P; Milea D; Bonneau D; Chevrollier A; Ferre M; Guillet V et al.: "OPA1-associated disorders: phenotypes and pathophysiology", The International Journal of Biochemistry & Cell Biology, vol. 41, No. 10, 2009, pp. 1855-1865.
International Search Report, dated Jun. 3, 2015, from corresponding PCT application.
EP Search Report, dated Jul. 9, 2014, from corresponding EP application.

\* cited by examiner

With only healthy volunteers C1 to C5 and patients P1, P3, P5 and P7

With the fours patients <0.5

With only healthy volunteers C1 to C5 and patients P1, P3, P5 and P7

With the fours patients <0.5

A  HeLa cells

B  Neurons

A HeLa cells

B Neurons

Aconitase activity

Catalase activity

SOD1

SOD2

Catalase

A. 10 months

B. 15 months

OPA1

A. 10 months

B. 15 months

SEQUENCE LISTING

```
<160> NUMBER OF SEQ ID NOS: 46

<210> SEQ ID NO 1
<211> LENGTH: 9310
<212> TYPE: DNA
<213> ORGANISM: human

<400> SEQUENCE: 1
gtttggggcc agagtgggcg aggcgcggag gtctggccta taaagtagtc gcggagacgg      60
ggtgctggtt tgcgtcgtag tctcctgcag cgtctggggt ttccgttgca gtcctcggaa     120
ccaggacctc ggcgtggcct agcgagttat ggcgacgaag gccgtgtgcg tgctgaaggg     180
cgacggccca gtgcagggca tcatcaattt cgagcagaag gcaagggctg ggacggaggc     240
ttgtttgcga ggccgctccc acccgctcgt cccccgcgc acctttgcta ggagcgggtc      300
gcccgccagg cctcggggcc gccctggtcc agcgcccggt cccggcccgt gccgcccggt     360
cggtgccttc gcccccagcg gtgcggtgcc caagtgctga gtcaccgggc gggcccgggc     420
gcggggcgtg ggaccgaggc cgccgcgggg ctgggcctgc gcgtggcggg agcgcgggga     480
gggattgccg cgggccgggg aggggcgggg gcgggcgtgc tgccctctgt ggtccttggg     540
ccgccgccgc gggtctgtcg tggtgcctgg agcggctgtg ctcgtcccct gcttggccgt     600
gttctcgttc ctgagggtcc cgcggacacc gagtggcgca gtgccaggcc cagcccgggg     660
atggcgactg cgcctgggcc cgcctggtgt cttcgcatcc ctctccgctt tccggcttca     720
gcgctctagg tcagggagtc ttcgcttttg tacagctcta aggctaggaa tggtttttat     780
atttttaaaa ggctttggaa aacaaaaata cgcaacagag accgtttgtg tgacactttg     840
cagggaagtt tgctggcctc tgttctaggt catgattggg ctgcaagggc agagaaggta     900
gccttgaaca gaggtccttt tcctcctcct aagctccggg agccagaggt ttaactgacc     960
cttttgggga tttttgaggg cagtgatctt aactttgggt gcacagttag cttatttgaa    1020
gatcttacta aaaatacacc agagcccaac ctccgaccaa ttacatcaaa acctgtccta    1080
```

```
gtgcagggtg agtattgctg ttttttgaaa gtttccaaaa gtgattttga tgtgcaccta    1140
cgattgagaa ctgtcgtttg aggacagtgg gtggagtttc gtatttggaa attagaagac    1200
ctggagtttc cattacaccg aattggcact taataactgt tgtcggagca tttcttaagc    1260
cacattttcg taaagtggct ttaaaattgc tctgccagta ggcaggttgc taagatggtc    1320
agagacaaac ttctgaacga ctcttgtaaa atatacagaa atattttcag aacttttatc    1380
agtaaaatta caaacgtgt tgcaaggaag gtgcttgtga taacactgtc cccagaacct    1440
tagtgaagtt accaactggt ggaaaatttt ctcttgcact cggcttaaaa atcatgaggg    1500
aatatttact atacgaatga gattcagtct ttaaaggggt ttacagaaac gtgagaggac    1560
aggaacagtt agtctgtgta aatgtctgaa atatatgtga gggagataat gagtttagcc    1620
tttttcttta ataggtctcc agattttctg gaaaaggttc tttggcattt gactccattt    1680
tgctgtttca tttgtcagac ttcttttgt ccctctttac ttctccccac ataattcacc    1740
agtactagtg ttttgttttt cagaccaagt ctcgctctgt cgcccaggct ggagtgcagt    1800
ggcgcgatct cagctcactg caacctccgc ctcccaggtt caagcaattc tcctgcctca    1860
gcctcccggg tagctgggac tacaggcgcg cgccgccacg cctggctaat ttttatatt    1920 ttagtagaga cggcgtttca ccatgttggc caggatggtc tcgatctgtt gacgtcgtga    1980
tccacccgcc tcggcctccc aaagtgctgg gattacaggc gtgagccacc ccgcccggcc    2040
accagtgcta ttcttaagac gcctctgagg aatcccttct ccctggccat tgagaatcca    2100
tgcatgaacc caggttttcc accttccctg agcagcttgc atagttcctt cttttaagcg    2160
cctgacttcg ttttgtttgg tgcccgttgt acctgagaat gagccttgga tagtggagca    2220
ttccagcttt ccagatatgc agagataata cattggctat cagctacttg gcttggccta    2280
ttccgtgttt aaaatcttgg actctttgct agttttaca gatcagaatt ttcacgtat    2340 taatccagtt ttcctagctt ctcttgaaga atttttggag atctcttcat actgagcctt    2400
cattagccca ggacagtact gctgtagcag ttcatatatt ttttcgcttc ccaggcctgt    2460
gttattcact taagttcata gcctggtccc tgcaggggttg tacccgagca cagctactta    2520
gatgtcctga atgtattacc ggttaaatgg aggtttcaaa gaacctgctg ttttttggccc    2580 tgtgctcttg ataacagagt gtttgaggga caactttcac atttgagttt ttccaaaatt    2640
aaaggttgta gaagagtcac agtatctatt gtcaaaaga aaagaattta aaaaggcagc    2700
aattgccagg atacttcatt tgagcaatga tattttccag tggaaagtca catcttaagg    2760
gttaatgccc cttaactgtt ggccgtattt gaaaacaaac caagctaaaa acaagagaca    2820
ctgacatgtt gtatgacggt gtggtgtgga tgttgtgttt attttagtcc tgagatctag    2880
ttgtaacttc cttgatttct gtatgtagcc acggagcacc attacctgtc accattacct    2940
gaatggctat actgcttgct ttcatttttgg tagagtggaa aggttaccta ggtttcagtg    3000
cttgaaaaga tttcagaaag cagtagtacg tctggttaga ctagaatcag tcctctcctg    3060
ggggcagtgg aatataatat tttctgactg ctaattaaaa atacctgtga tagccgggcg    3120
tggtggctta cgcctgtaat cccagcactt tgggaggccg agacgggtgg atcacgaggt    3180
cagcagatgg agaccatcct ggctaacacg gtgaaacccc gtctctacta aaaatgcaaa    3240
aaaattagcc gggtgtggtg gtgggcgcct gtagtcccag ctactcagga ggctgaggca    3300
ggagaatggc atgaacctgg gaggcggagc ttgcagtgag ccgagatcat gtcactgcac    3360
tccagcctgg gcgacagagc gagactcgtc tcaaaaaaaa aaagaaaaaa acttatgatg    3420
gacacttaaa aacactcact gagtggggag tggagagcag gggtcccagg gtagcctgtt    3480
```

```
ggacatttcc agggcgactt tttcttttt  ttttttaaa gtcaagtgag tatgccatat      3540 gaaaagggt  gtgcgtggag aaaaagcaag gggctccaga gtgtaggatg agacatacac     3600
cttttgggtt aaaaggctg  aggcaggaga atggcgtgaa cccgggaggc ggagcttgca     3660
gtgagctgag atcatgccac tgcactccag cctgggcgac agagcgagac tcttgtctca     3720
aaataaaaaa cgtttacatg tacatgtata ttcaacatgt acaaatataa cctattcaaa     3780
agtatttact acataaatag gtacttacat tacctattta ctgtaatagt caaagcctat     3840
gaagtatcta acactgatgt gtaggtactc actttgcttg ccactctatt aggtgctttt     3900
tatgttattt aatcatgaag cctggccaca gggtgcttgt gcattgagtg tgggaacaag     3960
attaccatct cccttttgag gacacaggcc tagagcagtt aagcagcttg ctggaggttc     4020
actggctaga aagtggtcag cctgggattt ggacacagat ttttccactc caagtctgg     4080 ctgcttttta cttcactgtg aggggtaaag gtaaatcagc tgttttctt  gttcagaaac     4140 tctctccaac tttgcacttt tcttaaagga aagtaatgga ccagtgaagg tgtggggaag     4200
cattaaagga ctgactgaag gcctgcatgg attccatgtt catgagtttg gagataatac     4260
agcaggtggg tgttgtgctg tgctggtgac ccatacttgt tcaccctagt tagataaaca     4320
gtagagtagc ccctaaacgt taaaaccccct caacttgttt ttgtttttga gaaagggtct     4380
tgctctgtcg ctcaggctgg agtgcagtgg cgctgtgcga tcatggctga ccttagcctt     4440
gacctcccag gctccattga tcctcatgcc ttggcccgta gctgggacta caggtacaca     4500
ccaccacgcc tggctaattt ttgtattttt tctagaggt  ggggtttcat catgttgccc     4560
aggctggtct tgaactgctg gctcaagtg  gtctatcctc ctcgacctcc caaagtgctg     4620
ggattacatg tgtgagccac tgtgcctggg aaaaccctca actttctctt taaaaaagag     4680
gtcaacttta ttgtatataa gcactgtgct aaaattgcag gaactgggac catatcctga     4740
tttttgtaat aatgccagca gagtacacac aagaaaagta actgcactag attgtgaaga     4800
ctggggtgga cctgcttctg aaggtccagt gcccttttgtc ttaagatttg gtgtagtgtg     4860
tctttagaaa ccaaaaaaag agaagaagat caaccttaag attagccaca aaactgggct     4920
ttgataccta ggtgtggaaa agaaagggaa agagttgatg ttttgtctta cagcatcatt     4980
gtagaagagg gtgttttttt gtttgtttgt ttttgagac  ggagtcttac tctgtggccc     5040
aggctggagt gcagtggcgc gatctcggct cactgcaagc tccgcctccc gggttcatgc     5100
cattctcctg cctcagcccc ctgagtagct gggactacag gtgcccgcca ccccgcctgg     5160 ctaattttt  gtatttttag tagagacggg gtttcactgt gttagccaag atggtctctc     5220
tcctgacctc gtgatccgcc tgtctcagcc tcccaaagtg ctgggattac aggcatgagc     5280
caccgcaccc agccagaaga gggtgttttt taaagaaggc aaataggaaa taaaaacttg     5340
ggctcttaac ttttgtaatg atcccaggtg tttgagctgg gggttgaggg tgggtgcctc     5400
gagcaaaggg gctgcattta tttgcataat gccatgtaag agtagctcta caccccaaac     5460
acaggcttct tagtgggacc aaagtatgat acaaactgaa gatggaatgc agaggattat     5520
tggtactttg gaatatgctt aaaaaaaatt tttttaaagt atttttaaaa aatcaggcaa     5580 ccctgaacc  agagtaggtt cagagaaact gccaattttt attttcttaa tttgggattg     5640
gaagcaagtt aacagaagtt tatgagttaa gttgcattta tgtgatctttt gccatatttg    5700 agtaataatc tgattttttt gtttatagat ttccttcttaa attaacttta ttcatcttgc    5760
taatttagtt tcaaatagtg atttgtaatg atcagatttg atccatttct gtaattgctg    5820
```

```
aaattccccc gagttgcttt ttggcttta c gcctctggt ctgggaggtg attgctctgc    5880
tgcttcctgt aacttgcctg cctttctccc tgtgtgggac tcctgcgggt gagagcgtgg    5940
ctgaagacag ccgtgttatg aaagggcctc ctgtgctgtc gaggttgtgc tctgtgaatg    6000
tcatcccctg gtgcacagca gcaccttcta cacaggatac agttggaatg ccgccccctc    6060
gagttgtgta aggcagcagc cttggccctt gcacataaga tgctgttgaa tattctgcct    6120
gcaccaagta aagggcacag atagaactgc ttggcatatg ttgctgggga gatgagtttt    6180
ttgtaaagta tactacgttc ttaagaattt ggatcataac catgggattt taataataga    6240
aaaactgttg aagatcagtc tggtcccta ttttacagt gaagaagcca aagcccagag    6300
aagggtgtta actttacaag tgtcagacag tagttagaac ttggtggggt tttttttttt    6360
ttttttttga gatggagtct tgctctgttg cccaggctgg agtgcagtgg tgcgatctca    6420
gctcactgca acctctgcct cccaggttca agcgattctc ctgcctcagc ctactaagta    6480
gctgggacta taggtgcgca ccaccacgcc tagctaattt ttgtatttt tcagtagaga    6540 cagggttttg ctatgctggc caggctggtc tcaaactcct gacctcagat gatccagcca    6600
cctcagcttc ccaaagtgct ggggttccag gtgttagcca ccatgcctgg ccatagactt    6660
gtttctgttc ccttctcact gtggctgtac caaggtgttg cttatcccag aagtcgtgat    6720
gcaggtcagc actttctcca tgggaagttt tagcagtgtt tctttttaga atgtatttgg    6780
gaactttaat tcataattta gcttttttt cttcttctta taaataggct gtaccagtgc    6840
aggtcctcac tttaatcctc tatccagaaa acacggtggg ccaaaggatg aagagaggta    6900
acaagatgct taactcttgt aataatggcg atagctttct ggagttcata tggtatacta    6960
cttgtaaata tgtgctaaga taattccgtg tttcccccac ctttgctttt gaacttgctg    7020
actcatctaa acccctgctc ccaaatgctg gaatgctttt acttcctggg cttaaaggaa    7080
ttgacaaatg gggacactta aaacgatttg gttttgtagc atttattgaa tatagaacta    7140
atacaagtgc caaggggaa ctaatacagg aaatgtcatg aacagtactg tcaaccacta    7200
gcaaaatcaa tcatcattgt gaaacatagg aagcttctgt agataaaaaa aaaaattgat    7260
actgaaaact agtcgagact ccatttatat gtgtatgttt tctgaaagcc tttcagaaaa    7320
atattaaatt taaggacaag atttttatat cagaggcctt gggacatagc tttgttagct    7380
atgccagtaa ttaacaggca taactcagta actgagagtt tacccttt gg tacttctgaa    7440 atcaggtgca gccccatctt tcttcccaga gcattagtgt gtagacgtga agccttgttt    7500
gaagagctgt atttagaatg cctagctact tgtttgcaaa tttgtgtcta ctcagtcaag    7560
ttttaattta gctcatgaac taccttgatg tttagtggca tcagccctaa tccatctgat    7620 gcttttcat tattaggcat gttggagact tgggcaatgt gactgctgac aaagatggtg    7680
tggccgatgt gtctattgaa gattctgtga tctcactctc aggagaccat tgcatcattg    7740
gccgcacact ggtggtaagt tttcataaaa ggatatgcat aaaacttctt ctaacataca    7800
gtcatgtatc ttttcacttt gattgttagt cgcggtttct aaagatccag ataaactgta    7860
cttgcagttc aaattaggaa aagcaatttt attggacaat tacggtgaaa atgaattatt    7920
ttatctaggt cagttaagaa cactgttctg ctaagatgca gtaaaaagca ggttacattt    7980
gaccatatta gatctgagtt tggaaaacag aagtagtctt tagttttaaa atggccagat    8040
tttcttgcca ggattgggtt tctcacttgt taaacagaac attttgttaa gtttaaaacc    8100
tgggatggac ttaagtattc atgttcattc atgttcattc aggactgcag ttatcatga    8160 cttgtttaac ttgtgggaag ctgttgtccc aagttatcct ggggaactgc atctggttct    8220
```

-continued

```
tgcaaaacac caagtagaca ggctctcttt tacctcccct tgagggcatt aacattcagt    8280
agtcacttcc attcagttaa ccctttattt ttatggtttt tcttgagcca tagttgtaaa    8340
gcagaaaaat catttataaa ggtttgttga acaaaattca aaatactgtt gcttaaagta    8400
ttaagatttt ttaggattat accttactta taggcccgtc attcatttgg catgaaattt    8460
tgagttttat tcactttcac tttccttttt ttccaaagca attaaaaaaa ctgccaaagt    8520
aagagtgact gcggaactaa ggttactgta acttaccatg gaggattaag ggtagcgtgt    8580
ggtggtctac aacatagtta tttgggtttt agtatttcat ttagacagca acacttacct    8640
aatgtttaaa ggtaatgtct ttgcaacacc aagaaaaagc tttgagtagt agtttctact    8700
tttaaactac taaatattag tatatctctc tactaggatt aatgttattt ttctaatatt    8760
atgaggttct taaacatctt tgggtattg ttgggaggag gtagtgatta cttgacagcc    8820
caaagttatc ttcttaaaat ttttacagg tccatgaaaa agcagatgac ttgggcaaag    8880
gtggaaatga agaaagtaca aagacaggaa acgctgaag tcgtttggct tgtggtgtaa    8940
ttgggatcgc ccaataaaca ttcccttgga tgtagtctga ggcccttaa ctcatctgtt    9000 atcctgctag ctgtagaaat gtatcctgat aaacattaaa cactgtaatc ttaaaagtgt    9060
aattgtgtga cttttcaga gttgctttaa agtacctgta gtgagaaact gatttatgat    9120
cacttggaag atttgtatag ttttataaaa ctcagttaaa atgtctgttt caatgacctg    9180
tattttgcca gacttaaatc acagatgggt attaaacttg tcagaatttc tttgtcattc    9240
aagcctgtga ataaaaaccc tgtatggcac ttattatgag gctattaaaa gaatccaaat    9300
tcaaactaaa                                                           9310
```

<210> SEQ ID NO 2
<211> LENGTH: 14206
<212> TYPE: DNA
<213> ORGANISM: human

<400> SEQUENCE: 2

```
gcggtgccct tgcggcgcag ctggggtcgc ggccctgctc cccgcgcttt cttaaggccc      60
gcgggcggcg caggagcggc actcgtggct gtggtggctt cggcagcggc ttcagcagat     120
cggcggcatc agcggtagca ccagcactag cagcatgttg agccgggcag tgtgcgggtg     180
agaagaaagg ggacccggtc acggcccaa gggcgaaggg gctcgcggcg ggcagggcct     240
ccgcggcaat ggcgacagtg gccgcaccgg gcctggcggg accggggcac ctgcaggcgg     300
ttctcccggg agtgccggc gcggcggctg gagcggggat ccgcagggag gggacgcggg     360
gactcggggg acgccgcgcg ctgccgttcc tcggcagccc agcctgcgta gacggtcccg     420
cggcgctgac tgaccgggct gtgctttctc gtcttcagca ccagcaggca gctggctccg     480
gttttggggt atctgggctc caggcagaag cacagcctcc ccgacctgcc ctacgactac     540
ggcgccctgg aacctcacat caacgcgcag atcatgcagc tgcaccacag caagcaccac     600
gcggcctacg tgaacaacct gaacgtcacc gaggagaagt accaggaggc gttggccaag     660
ggtaggttcc aggctgagcg gcgggaggca gtccccggca gaggcgaccc cagggagcca     720
ggccccatac ggacgggcct ctccgtggag gagaactcgc ttcgtatttg taccggttcc     780
gagttttcca ggcacgatag tctctctttt aaacacatgg tctacctcat tgtagaagga     840
gtgcctcgat gggtttgaac acacttctgt catctcaggg aacttggggt cctgcgaagg     900
agcttgcctt actgttgtga gccacattcc gttacacata ttgccagcac tggtgaattg     960
```

```
tagggcctga aaagaaagct ctactgtgtc actcgttttt tttgcaaatt gaaattgttc    1020
ttgttgtata atgtgctttg gggaaatgtt tggtctctca ggtaggtgtg ccagccgttt    1080
gcaggagggc tgagagcgcc tgtccactgg tggccagaca tcatcgggtc cgcaggtgtc    1140
tctgagtgtc agggtcacct cctgatagaa gtgggagtgg tgtcttactg ccaggtcaca    1200
ctgaaggtgg gagacaggag gacactactc cgtgctagga accatggtcc ttgtcatctt    1260
cctgagagca acggggtcg ggactccagc ctaggacttg gagactccct gcatccccag     1320
ctaccctgca ggtgaaactt cactgagccc acttgacttc aggtgggaga ggaggaggca    1380
caccgttgtg gtgtgcgtta ccaaaaaagc agtaacctaa ctgtggaaca gttcaggatc    1440
tttagacttg atacttttct tgatttccct taggggtcaa agttcacaag gaaaatagcc    1500
ctttagtggg aaactgaaac aggcttgttt ttatttacta tttactcata tttgtaatgc    1560
aattaaaata tatgttgtta acttttttttt tttttctcaa gagctcggtt gataaaacca    1620
ggggtatgtg gactttttga gtctgtgcct tttgggggtg tgtatgggaa tgttatgttt    1680
taacgttttt tacaaaatag tattgtcttt ttaatttatt cgttagtggt ttgcacaagg    1740
aagataatcg atagtcatgt ttttagact ctctgtattg cttggtaagc tacgtagtaa     1800
aaaatgttta cttttcctta aatgttttga atttcggggt tatgaaattt gttgagtaat    1860
ttttagacag tcacatcttg ttgactggag gcatctagtg gaaaaatgca gtatttcagc    1920
ctgattgtgt ttgaagtaaa tgattaaaag aggaggaagt taccacattc tggaagattt    1980
acttgagaca gacgaacctt gaattacggg aaaaggcccc gtgatttagg aaataacaaa    2040
tttgggaaac atgtaatggg gagagactgg ggaatacccc agttgtgaaa gtacttcctg    2100
taaggcaaca tctgacacca ggaacctttc tcttcagtat tttaaaaaca acttaatttc    2160
agtcctttac ttgtggaatc agagccttac ttatgtaata caacccactg gaaaaaagct    2220
ttttattgta ttgtactata ttgtttataa gtgattgagt acctgcagag ctttcttta    2280 cttaaacata ttttaaaaat tattaaaaag attttcatgt ttgaaaactt ggggaaaaaa    2340
gataaaacaa tgtcataatc tcatcacatt taactgacta atatgaatat ttttcaacaa    2400
aaagcatttg acttttatta ttatttgagg caaaaactaa actgaaacca ataaaaatgt    2460
tgaatttcag aaaagtgttc ttaaaagcag atattaagcc ctcaattttt attaatttta    2520
aaatgagtaa gcaaactgta agatgttaag attattaaat tatctctcat taagcatgta    2580
tctttcccat tttaaaaatt cagttactat tgatttatta aaaacaata gaaaagttac     2640 atctatttt agtgactc tcaagaaaat ttaataaggg aaacacagat ctataaaaaa       2700
ctgtttgtaa acctaacaaa ggaaaaaaaa agttggtgtc tttaaaaaac cctttgagat    2760
tagctgtgta ttcagatatc agttggttct ctcctttctg aatcgctaaa caactggagc    2820
ttgtttcaga aagcagcatt gtctacgtat gttccttta aaaatttttt ttttaattct     2880
gtctaaaaaa aacagacggg gtcacactat gttgcccagg ctgctcttga attcctgggc    2940 tccctatcc acgcacctcg gccttccaga gtgctgggat tacaggtgtg agccaccgtg     3000
cctagtcaga catacttttt ttttttttttt ttttttgac ggaatctcag tctgtcccgc    3060
aggttggagt gcagtgatgt gatctcggct cactacaacc tccgtctcct gggttcaagc    3120
aattctcctg cctcagcctc ctgagtagct gggattacag gcgtacgcca ccacgcctgg    3180
ctactttttg tgggtttttt agtagagaca gggttttcc atgtcgtcca ggctggtctg     3240
gaactcctga cctcaagtga tccgcccatc tcagcctccc aaagtgctgg gattacaggc    3300
gtgagccacc tcacctggcc ttgtatgtat gttttttttct ttctctttct tttttttttt    3360
```

```
ctgtgacgga gtattgccct gtcgcccagg ctggagtgca gtggcgtgtt cttggttcac    3420
tgcaacctct gcctcctggg ttcaagccat tctcctgcct catgctcctg agtagctggg    3480
attataggca cgcgccacca tacctggcta atttctgtat ttttagtgaa gacagggttt    3540
caccatgttg gccaggccgg tcttgaaatc ctgacctgaa gagagctgcc cgcctcggct    3600
tcccaaagtg ctgagattac aggcgtgagc caccgcaccc ggcccagaca tatgttctta    3660
acgtacactt tcagaacagc agttgagaac ttttccaaa atgtaagctc cttgagagca    3720
aagctctcag tgggtctctg tgtcctttac tttgcttctc ttggtatctt gtggataata    3780
tgcacaaaat atttattaaa caagaggatt tccattttt tctaatatta atagttcatt    3840
tagtctgtag cttcttgaag gcatagaaaa gactatttta ttttgcctac ttatttggca    3900
aggtacccat gcagtatgcc aggagttaca gggcctattg agaaggagta aagggtctgg    3960
gaggggtggc agggagttgc taattcatgt atggtggcta gagaaggctt cactgatggg    4020
gttgatgttt cagtggagac ttgaaggagg aacaggaacg cagcatgaga ctgtcttggg    4080
gaagagtgtt cagcagaggc agcagtgctc agctagcctt gaggggaaca tccaagttgg    4140
tcatgtgagt gcaaaaaggc cagtgaggct gcagctgcgt gagcacgtgc tcaatgacgg    4200
ggtcaagtgc agcgcctctt ggtagtaaga gtagctgagt gtaaacacct agggttcgct    4260
ccagtgagaa ggggagcctt tggaggggc aaggcccacc cccacccccc aaaactgagg    4320
ggatagtggc accagtgcag tgagaaatac tggtcctctg tcccaatgag gtggcagtag    4380
agttagggag aagggattag gttctgcttg tgttttattt ttttcttta tttttctctg    4440 tgtgcttta tatagattgg atgtatttta aaggtagagc tggctttgct aatggatatg    4500
ctggtggatt ggatgtgggg tgaagggaga ggagtcaaaa atgacatcag gttcccaagg    4560
atgtcctgag ggacagagct ggcatttact gagacgtgga ggacaatagg aggagtaagt    4620
ttggggtaga acatcaggag ttcaatttg agtatgttga gtttcttgtt aatgtgactt    4680
ggagatattt cccaatgaat cgtcgtctgt cttgaaagtg agagttgaag gttttctgta    4740
cagtctgtat gttgagccat acattttagc attctattat tttgattgtc ctctttggtg    4800
tttcatttcc taaaatctct tctatctaag agatccctga gcctagcagc caggagtgaa    4860
ttttctagct tttccacctc tgctaggtcc ttcatcagtt gttcagcatg tctgggacaa    4920
ataattttgg ggcgggggg tgctgaattt taggacaaac ggatgttata gataagctgg    4980
tcccattatc taatagctta caaagaaaaa aatataatgt atacagtggt tgaaaaagta    5040
ggagttacaa aaaaatgtgt ttgcatttta acttttcagg agatgttaca gcccagatag    5100
ctcttcagcc tgcactgaag ttcaatggtg gtggtcatat caatcatagc attttctgga    5160
caaacctcag ccctaacggt ggtggagaac ccaaaggttg gtatatattg gtgcaccctt    5220
atctacattt tgtgcacagt aggaatcgat tgttgattta ctgaagttac cttatacttg    5280 tttttgttt tttttgttgt tgttttttg agacaagagt tttgctcttg ttgcccaggc    5340
tggagtacag tggcgcagtc ttggctcact gcaacctccg cttcctgggt tcaagtgatt    5400
ctcctgcctc agcctcccaa gtagctggga ttacaggcgc ccgccaccac gcctggctaa    5460
tttttgcatt tttagtagag atgaggtttc attccaccat gttggccagc tggtcttgaa    5520
ctcctgacct catgatctgc ccaccttggc ctcccaaagt gctgggatta caggcatgag    5580
ccaccgtgcc tggcctaagt taccttattc ttaccgagg tatcatagtg gcatattttt    5640
cataacaacg agtatgataa aagttgtaac tttcaaaagg acacaagtag gaatggagaa    5700
```

```
tgctttcatg gggttatgtc ataagatttt atgttcacgc aacatagaa tatcacatca   5760
actccacctt ctggtttctg gatggtactt catattaggg aaagactgag agacttcatt   5820
ttatgaactt ttttttttg agacggagtc ttacagtcgc ccaggctgga gcgcagtggt   5880
gcaatgtcgg ctcattgcaa cctccgcctt tcaggttcat gcaattcttg tgtctcagcc   5940
acccaagtag ctgggattac aggcatgtgg catcactccc ggctaatttt tatattttg   6000
gtagagacag ggtttcacca tgttggcggg gctggtctcg aactcctggc ctcaagtgat   6060
ccacccacct tggcctccca agtgctgtg gtatggatgt gagccaccgc gccagtctag   6120
aaaagatgaa ctttctgtct actagtttct agggcctgga ttagatagtt aaccgtctgt   6180
acctttttc atctatgtga tacagggata acaatggtgt tgttttgaga attaaattat   6240
agtgtcattt gctatttttc actctttcct aactgataaa aagtcagttg ttccaggaaa   6300
ttaggtttc tgggtatttt taaaaagtgt tcagggaatg aggagagtac agggctagat   6360
ggtcttgttc gctatcactg tttccttgac ttcctgtgta gcttgtggag gcccagatga   6420
ctttaattat cttcttcacc cagggagggc atgaggcgta aatgtagttc ttgtctcttg   6480
tttctgggct ccggatatgc accctaagtt tctgtggttt tattgttcat ttttaatcag   6540
tgttatggaa ggcagcctat cttatgcact tgaaataagc aatttcattt taaggtaatg   6600
atgaatgagg agagtaagct tgggaaactg ggcaactttt tctttatttt tgttttatt   6660
tattattatt ttggagatgg agtttagctc tttcgcccag gctacagtga agtggcttga   6720
tcttggctca ctgcagcctc tgcccatccc gggttcaagt gattctctgc ctcagcctcc   6780
cgagtagctg ggattatagg tgcctgccac catgcccggc taattttttt gtatttttag   6840
tagagaggag tttctccatg ttggtcaggc tggttttgaa ctcctgacct caggtgatcc   6900
acctgtctcg gcctcccaaa gtactaagat tacaggtgtg agccaccgtg cctggccaac   6960
ttattttttt tctgagttca gtcttctaga ctatcggtta atacttttga agttttgtca   7020
gttaccagaa tatcagatat attcatatgc aaccagtggt tttggtatgc tgccattttt   7080
gtttaatctg taccacattc catcatttgt gcttataaag atgattactt ttaaacccgt   7140
agaataagag aagtgagatt ttgacccagt tgatttagtt gatgtgacta atctagaatt   7200
atattctgta ttactacaga ataaaaggat tacagctctt aaagtatacc cttagttcag   7260
tcgtagagaa aactgcccat caagacagga agagctgggc tgccttggag aagaacaatg   7320
actttattcc caaatggagg cgtagaagaa ggagggtaga agtcaaagga aaattttcta   7380
ttcagggaaa agaaaaagct aacagaaagt agtatttctt tcctaacaaa gatagtacag   7440
tgagtgggga aatccctcta acacgattca ttaaaaaatg tgaactacgc agctggaggc   7500
cattatccta agcgaattaa cccaggaaca gaaaaccaaa taccacatgt ctcacttgca   7560
agtggaagct aaacatggag tacttatgga tataaaaatg gcagcaacag acactgagga   7620
cagagcaggg agggagaaag aaggggacgg ggggtgaaaa ctgttgtata ctaagctcgc   7680
tacctgggtg atggcatcaa ttgcacccca gacctcagca tcatatgata cccgtgtaac   7740
aaacctgtgc gtgtacccct gaatttaaa ataaaatttg aaccgggcac ggtggctcac   7800
gcctgtattc ccagcacttt gggaggccaa ggcgggtgga tcacctgagg ttgggagttt   7860
gagaccagcc tgaccaacat ggagaaaccc tgtctctact aaaaacacaa aattagccgg   7920
gcgtgatggc acgtgcctgt aatcgcagct gctcggagg ctaaggcagg agaattgctt   7980
gaacctggga ggcagaggtt gcagtgaccc agatcatgg cattgcactc cagcctgggc   8040
aacaagagtg aaactccgtc tcaaaaggta aaaatgaaa aaaaaaaaa aaaaaaaaa   8100
```

```
aagttgaagt tataaaaaac aaaaacgtga attaaaattg tgaaacttag atccaggtgt     8160
cgcattctga tgttgtctaa tttcttgggc cctatgacaa aaatattta  atacatgtaa     8220 tataacattt tactgtaatt attgaaatct gttcattgt  gggtggtttt ggatttttt      8280 tttaataggg gagttgctgg aagccatcaa acgtgacttt ggttcctttg acaagtttaa     8340
ggagaagctg acggctgcat ctgttggtgt ccaaggctca ggttggggtt ggcttggttt     8400
caataaggaa cggggacact tacaaattgc tgcttgtcca aatcaggatc cactgcaagg     8460
aacaacaggt tagatttaaa aattgtgatt tcatttggga gagatgctct actgtaaagc     8520
attcaactag aaataaggaa aactaacagt gttttaagaa catgtaataa tttgcaaatc     8580
ttaacagata acacccagag tcttgtgtaa gtaaaaatgt tttagaagtc ctgatatttc     8640
ataaaattaa gtacacgtaa ttttataggt acattaacaa acatgtttta tttttattta     8700
ttttttttga gacagatctc actgttgccc aggctggagt gcagtggtgc gatctcggtt     8760
cactgcaacc tccgcctcct gggttcaagt gattctcctg cctcagcctc ccaaatagct     8820
gggattacag gcacatacca ccatgcccag ctaatttttg tgtttttagt acagacaggg     8880
tttcaccatg ttggccaggc tggtcttgaa ctcctgacct caggtatctg cctgcctcgg     8940
cctcctgaag tgctgggatt acaggcatga gccaccatgc ccagccaaat gttttactta     9000
ttaaccctgc ttcattctac agagaattaa tatcagctta gataattata tgtactaaaa     9060
taaaaaaaaa attagctata gaacaagagt gaggaaaaga aatacaagca gagactgatt     9120
tcagagcttg tactgttacc tcctctgctg agcatttgag gttaaactgg gactagatct     9180
caggtttcca gaccttctgc ctttctgggg ctctttggta gagtatatga aaatattcgg     9240
cttggaagtg ccaggctggg ctcaccaaat actttgctgt tgagcctaat tggatttaaa     9300
aaatgtcact gaagagtatg ggaaatagag ccatgagttg tctggcagag ggttgggact     9360
ttgaacttaa agtgatacct tcacatcaac aacagtcatt ctctgcccct tcttctaccc     9420
ctgacattgg aatactcttg atctgtggct cacttcacag gatagaccca gattttggca     9480
gaatctgaac agctctttg  ggacagtgac atggcataac aatttgtaaa agccacaaaa     9540
aatttgtaag caccgatctg tagagtcagg ttatttgtag agctgcatga ccagaaaggc     9600
tgatatttgt aagtgagtcc cagctacact ccttcctctc cctgtggaaa gcacattaga     9660
aggaaaatga gggaatgtca tggccttttg tttataaaaa tcattaataa attttgctac     9720
ttgaaattat taataataaa ttactagtga cctccctcac aactgatcaa gacatactgg     9780
ttaagaattg tttttgtaga gagagctata atttattttg agtgttttg  tgtgtgcgtg     9840 atggagtctc actctgttgc ccaggctgga gtgcagtggc gcaatcttgg ctcactacaa     9900
cttccgcctc ccaggttcaa gcaattctcc tgcgtcagct tcctgagtag ctgggattac     9960
aggcgcctgc cacctcgcca ggctaatttt ttgtatttt  agtagaggcg gggtttcacc    10020
atgttggcca ggctggtctc gaacgcctga cctcaagaga tctgcctgcc tcggcctccc    10080
aaagtgctgg gattacaggc ctgagccact gcgcccagac caaaagtttt tttaaatgga    10140
tgttttacag atagaactaa attcttcatt tacctcactt aatttctgaa aacactgtgt    10200
cctccaactg ctctgtattc ccaaagatta aaattagcct tggggagcag agctggttcc    10260
tcgtaaaccc ctgtgagtgc ccagacccct tggaggaggt tctcagtggg cttttgcctg    10320
ctcccacaga tgtaacccac ccttcctgct gctcctaaga ccaccatgag gaaggctggg    10380
aattggctct tgaattaatt tgttggtatt tttaagaata gctattaaag tactgttgtt    10440
```

```
aattttcccca agtctatttt attgttagta tttgtcacat tttctttgta aacagtgaat   10500
taaaaatatt ttataggaat attcattctt atctagattt cctacttata taaaaaaaca   10560
agtgaatgag attgttacaa agggtaattt tgtgtgagta gaataataaa agttgaaatt   10620
gagaagatgc aatgttttag actgaaactg atggttggtt tgttttcccc ttctttctaa   10680
caggccttat tccactgctg gggattgatg tgtgggagca cgcttactac cttcagtata   10740
aaaatgtcag gcctgattat ctaaaagcta tttggaatgt aatcaactgg gagaatgtaa   10800
ctgaaagata catggcttgc aaaaagtaaa ccacgatcgt tatgctgagt atgttaagct   10860
ctttatgact gtttttgtag tggtatagag tactgcagaa tacagtaagc tgctctattg   10920
tagcatttct tgatgttgct tagtcactta tttcataaac aacttaatgt tctgaataat   10980
ttcttactaa acattttgtt attgggcaag tgattgaaaa tagtaaatgc tttgtgtgat   11040
tgaatctgat tggacatttt cttcagagag ctaaattaca attgtcattt ataaaaccat   11100 caaaatatt ccatccatat actttgggga cttgtaggga tgcctttcta gtcctattct   11160
attgcagtta tagaaaatct agtcttttgc cccagttact taaaaataaa atattaacac   11220
tttcccaagg gaaacactcg gctttctata gaaaattgca cttttttgtcg agtaatcctc   11280 tgcagtgata cttctggtag atgtcaccca gtggttttg ttaggtcaaa tgttcctgta   11340 tagttttgc aaatagagct gtatactgtt taaatgtagc aggtgaactg aactggggtt   11400
tgctcacctg cacagtaaag gcaaacttca acagcaaaac tgcaaaaagg tggttttgc   11460 agtaggagaa aggaggatgt ttatttgcag ggcgccaagc aaggagaatt gggcagctca   11520
tgcttgagac ccaatctcca tgatgaccta caagctagat tatttaaagg cagtggtaaa   11580
tttcaggaaa gcagaagtta aaggcaaaat tgtaaatcag tcgagatcgg gtgccttcag   11640
ggtggtatgg ctgtatacca aaattgtaaa tcactacatg aagcttatat attggtttgg   11700
cctgaaaggt gaagtggggt aggcaggggg cgggcttaca ggttatggtg gattcaaaga   11760
ctccctgatt tgtgattggt taaggaagca aagctttgtc taaaaacttg gggtccgcag   11820
aaaggaacat taaggtctgg ccaggcccct caggaagaaa ctgagagcaa agaatggagg   11880
tcagagttta gtccctggtg ttccccctta tctgacgtct gtgtgaatcc atttggtggg   11940
ggtctgggtt tctgaaaagt agctcagggg cacgtgttaa ggatgtctct aggtgactct   12000
aacttccctg gctattgttt gaaactgtta tgaccttctt gcttatcagc ttgctggttt   12060
ccttctcggg gcgagctggg tgcctggagt tttcggtgaa ggaaactcaa gattctcctt   12120
tatttctgtg cttgtgggaa tcccctggc acacccaaa gaggggtccc tgctccgtct   12180
cacagggatc ttttttgtata tttggcttag catcatacat ttgccatgtt gtttcatcat   12240
ctgcctaatt tactgttttt gaatatttca tttgtttcta attgttacta cagataatgc   12300
tggggtgagc aactctgtgt acataggttt atctcctatt ggaatatttt ctttatatag   12360 gcgtttttt tttttctttt tttttggaga cagagtcttg ctctgttgcc caggctggag   12420
tgcagtggcg cgaccggagc tcactgcaac ctccacttcc cgggttcaag tgattgtccc   12480
acctcagcct cctgaatagc tgggattaca ggtgcatgct accatgcctg gctactttt   12540 gtattttag cagagacagg gtttcaccat gttggccagg gtggtctcga actcctgacc   12600
tcaagtgatc cgtctggctc agcctcccaa agtgctggga ttacaggtgt gagccactgc   12660
acctggccta tataggcttt ttcttaaac ctatttagta atgttttccc aagtttattt   12720
tttattttta attttttccc caagtttatt tttctatttt tttttcatgg aaaatgggg   12780 taacttagca gtttcaatat tgaagactga agtttaaaaa aaatttaaat tcaaggtact   12840
```

| | | | | |
|---|---|---|---|---|
| tttaaaattc | agttagaaaa | gtaggcttta | aaaattatta | gagacaagag taccaaagcg 12900 |
| gtgtgtgtat | gtgtgtgtgt | gtatgcatgc | ttgtggattg | gaaaaacttt ggagactgat 12960 |
| tactttcat | tatatatgtg | tcacagtgaa | acagcttta | tgtgtcatgt aagattactg 13020 |
| cttgcctctc | taaggaaggt | cgtgactgtt | taaatagacg | ggcaaggtgg aaccttttga 13080 |
| aagatgagct | tttgaatata | agttgtctgc | tagatcatgg | tttgtattga actaacaagg 13140 |
| tttgcagatc | tgctgactta | tataaagctt | tttgattcct | actaagcttt aagatttaaa 13200 |
| aaatgttcaa | tgttgaaatt | tctgtggggc | tctatttttg | cttttggcttt ctggtgagag 13260 |
| agtgaggaag | cattctttcc | ttcactaagt | ttgtctttct | tgtcttctgg atagattgat 13320 |
| tttaagagac | taagggaatt | tacaaactaa | agattttagt | catctggtgg aaaaggagac 13380 |
| tttaagattg | tttagggctg | gcgggggtga | ctcacatctg | taatcccagc actttgggag 13440 |
| gccaaggcag | gcagaacact | tgaaggagtt | caagaccagc | gtggccaacg tggtgaaacc 13500 |
| ctgtctctac | taaaaataca | aaaattgttt | agctctgttt | ttcataatag aaatagaaaa 13560 |
| ggtaaaattg | cttttcttct | gaaaagaaca | agtattgttc | atccaagaag ggttttttgtg 13620 |
| actgaatcag | cagtgcctgc | cctagtcata | gctgtgcttc | aaaaacctca gcatgattag 13680 |
| tgttggagca | aaacaaggaa | gcaaagcaaa | tactgttttt | gaaattctat ctgttgcttg 13740 |
| aactattttg | taataattaa | actttgatgt | tgagaaatca | caactttatt gtacacttca 13800 |
| ttgcaacttg | aaattcatgg | tcttaaagtg | agatttgaat | ttctattgag cgcctttaaa 13860 |
| aaagtaatac | caaaccataa | agttaaaatc | tatgtatatt | gagtcatatc taaaaccacg 13920 |
| tataaacata | aattgtattt | cctgttttaa | ttccagggga | agtactgttt gggaaagcta 13980 |
| ttattaggta | aatgttttac | aaattactgt | ttctcactttt | cagtcatacc ctaatgatcc 14040 |
| cagcaagata | atgtcctgtc | ttctaagatg | tgcatcaagc | ctggtacata ctgaaaaccc 14100 |
| tataaggtcc | tggataattt | ttgtttgatt | attcattgaa | gaaacattta ttttccaatt 14160 |
| gtgtgaagtt | tttgactgtt | aataaaagaa | tctgtcaacc | atcaaa 14206 |

<210> SEQ ID NO 3
<211> LENGTH: 33136
<212> TYPE: DNA
<213> ORGANISM: human

<400> SEQUENCE: 3

| | | | | |
|---|---|---|---|---|
| actcggggca | acaggcagat | ttgcctgctg | agggtggaga | cccacgagcc gaggcctcct 60 |
| gcagtgttct | gcacagcaaa | ccgcacgcta | tggctgacag | ccgggatccc gccagcgacc 120 |
| agatgcagca | ctggaaggag | cagcgggccg | cgcaggtaca | ctctgtgctc cccgagcggg 180 |
| cccgaaggtc | cgtttagaaa | gcgggggcgt | cggcaagtaa | aggcccggct tccccgggg 240 |
| cggcgcttgg | agggactgta | ccgcggctca | ctgggcaggg | gggatcccct tcggtgcaga 300 |
| cggactttta | cattcgccga | agcaggggag | ggggtccgg | gtagtggggc gcggactgc 360 |
| aggctttgtt | gtccgcgaca | ggctcgggtg | gttgcttcag | aattttgcac ttttgccaac 420 |
| tgggacagag | gtcgcagctt | gaggacagat | tgagggctca | tggggaaaga ggcagagagc 480 |
| tgcagctgca | aggaagtcag | tgagggggaga | agtggaacca | ggctctaatg gtgcccttct 540 |
| tgaaatactg | tttacacgct | ttcatagttg | tggggtccca | gcagggcagg gattgtgttt 600 |
| tacaatcttg | aggtctccag | caccagtcac | agtgactggt | acgtactatg cacattatta 660 |
| aacgactaaa | taaaagaact | tttacattca | ttgtctcatt | tgcacttcaa aatgtcaagc 720 |

```
ctagcatttt agagctgggg ggtgacatta gggattgatt aatgcgttta ttctattctt     780
tgagcacctg taggtgctag gcactgttcg gggcaaggtg tacaaattcc agtgcggcaa     840
gaacaacacc cttgagaagc tgagagtcta gtctgggaga cgagacacat aaacagatga     900
ttacactcca gcgtggtgag ggctctaata gaggttatct gtagaatgta gagggagtga     960
ccaggtgggc cggacaaagc aggtgacatt tgaacaggaa ttttttttaaa tgagtaggat    1020
tttaacttgg tggtggggga ggcattcctg gcctgtgccc acggctgcag agtctcagag    1080
ggcatctatg aggaggttgg attagatgag accacatctg gtctgagtct actgttggca    1140
gattggccca gggagtctaa aggtcttgcc ctgttccctg gctgctggtt aatggtagac    1200
agaggactgc agccctgttt tccctattct gcctagtgct cttgctcaaa actcaggttc    1260
gtgaactggg gtattaatgc taagtgctca tggattgctt taatggttcc ctgtttggga    1320
aaaggctgcc attctcctcc aagggcctgg aaaatctccc ctcttggccc tgttctttgt    1380
tatataccat taggttggtt catgagctct taaagtaaac cagagagagg tagagtctta    1440
gtaaaggatg tgccactact tactggcaga gacaaggtta gaattcagct tcttggaccc    1500
aagactcttt ccttacccag tgggtgcaaa tcctggttca cactgaagtt ttcatgaata    1560
ctcggtgaat tgagaaaagt gtggacaaag tagtgagatt tttacaaaac aaaatatttt    1620
cttttctttt ttcttttctt ttcttttttt tttttgaga cggagtcttg ctctgttgcc    1680
caggctggag tgcagtggta tgatctccac tcactgcaaa ctccgcctcc cggattcaag    1740
caattctcct gcctcagcct cccgagtagc tgggattaca ggtgtccacc accacaccca    1800
gctaattttt gtattttag tagagatggg gtttcaccat gttggccagg ctggactgga    1860
actcctgacc tcaggagatc tgcccgcctt ggcctcccaa agtaccgaga ttacaggtgt    1920
aatatttca tttttaaagg actcccttt attctgagac tagctgcctt cttccttgtt    1980
tgggagaatc atgaactgtt gaagtccctg ctgttgattt accttacata gttgcccatg    2040
tgagaaatgg ctgactccaa aacacatcta tagttgggag gctcttaatt gaaatacagc    2100
catcccttt gtccatgaca tctcagggca ctgtgtacat cgtcctgatt ggcagtcaca    2160
ttgatgtctt actgttcctc agttttagct gctcttagta aaaaccgctt acttctttta    2220
ggcacttctc cctccaccca gggccctcca aaaggaatta tgcatatgcc ttatagccta    2280
tataattttc aaacactttt tttaaatgaa aaatttcaaa tattcagaaa agttgaaaaa    2340
attttgcagt gtatatctat atatctgcca tctagattct acaaggaaca ttttgccctg    2400
tgtcttttat tacgttactc catctgtctg tccatccttt aattcattca agttgtttca    2460
tgtattagca gtttgttctt ttcattgctg agtaagattc cattatttga atataccacc    2520
atttggatat cctgttgctg gacacctggg ctatttaatt ttttttctat tgtaagtaaa    2580
gctgctgtgg ctgggcatga aggcttatgc ctataaccct accactttg gaggctgagg    2640
tgggaggata gtttgagctc aggagttgag accagcctaa gcaacatggt gaaaacccat    2700
ctctacaaca aataaaagaa gtagccagac atggtgacac atgcctgtag tcccagctac    2760
tcgggaagtt gagttgggag gattgcttga gcttggggtg tggaggctgc agtgagccat    2820
gattacatga ctgcactcta gcctgggtga cagaggagga ccctgtctta aaaattaaaa    2880
ataaataaag ctgctataaa aattcttaca taagtctttt tgtgcacagg tggttttatt    2940
tctcttagga aatacctagg agtagattta ttgggtcata aggtaagtga atgtgttatg    3000
agaaactgct gagcctttt ccaaagtggt tgtaccattt tatacttcat cagcagtgta    3060
tgggagttcc agttgctcca catcctacca acttttggtg ttgtcagtct tttacattta    3120
```

```
gttgttgggt gtgcagtggt atctcattat ggttttaatt tgctttgctc tgatgactaa    3180
tgatgcaaag catctttta  catgcttatt gaccattggt atatattcct ttgaagtata    3240
tgttcaaatt ttctgtcttt ttaaaaattg aattgctttt aaattattaa ttcatagccc    3300
atattttaag ttcaatcatg tggaatcatg tgtaggctaa gtgttataat aataaatctc    3360
aacatgtatc atggtataaa catattagaa atttatggcc gggtgcagtg actcacacct    3420
ataatccagc actttgggag gctgaggtgg gcggatcacc tgaggtcagg agttcaaaac    3480
tagcctgacc aatatggaga accctgtct  ctactaaaaa tacaaaatta gctgggcgtg    3540
gtggcacatg cctgtaatcc cagctgcttg ggaggctgag gcaggataat cacttgaacc    3600
ctggaggcgg aggttgcagt aagccgagat cctgccattg cactccagcc tgggcaacaa    3660
gagtgaaact ccatctcaaa aagaaaaaaa aagaaatgta ttcctttcct acatgaatgg    3720
cccaaagtgg tttgaggttg aaggaggtgg gtgggtgctc tgcttcccac agttattgag    3780
ggcaccaggc tgaaggaagc tcccccttgg tcaaacatgg cttttatggg cgtcactgtc    3840
cagcacagaa ggctcaagag cgtggagaag ggtatatgag tgtgggaagg tttagggtcc    3900
agggtcactg ccacttacat tctgttggct agaactctgt tacaggccac acctggggta    3960 gtctacccc  tgtccaggaa gctgactcta ctatattatc caaagcgtac atttcatatt    4020
tggtgaaaat ctgtccagcc atttctttgt gatgcggcaa tggacatgca acataatttc    4080
tttttaaaga atatgtcatt tttactttct gacattaaga tattctgtta gaaaattatg    4140
acagtaacag atggtattaa aaaaaaatct ccccttgctt ggtaaatgct tttatctaag    4200
tgggcagctt tgtgctaata tgatgtcttc cacttcccaa ttagttgtga tgctttactg    4260
atctaggaga gctttatggt ttgggactac tataggcgaa cactctgttg cctcctctct    4320
caagaatcag agtgtcctat tttggaaaca cagtcaacca tgtgaaagca atttattggg    4380
cgtatcttct gtggtcagat ttggtttgct gacaggtgaa ttgggagttt tgtaaacttt    4440
aataagtgag cattgagtca gatgtgttca tgagtatgac ctcgatccac ttaaaaattc    4500
ttatttcttt ttctctcttg gcaggaggga ggtggttgtg caggtattcc cagccacttt    4560
gaagggaact taaatgggaa ctttattgct cactgcttag aatgccatgg gctcttcttt    4620
tgagatactt accttaacc  catttccttt ttttttttt  aagtgcagct tgctgccagt    4680 gctctttct  tggggtaaa  tgggaaatgt taataagtag cctctgatcc ctttaaaatg    4740
ggagaatttg aacatttcaa accttacctt tttatacagt tctcttatta cctgggagag    4800
aggttaagtc ttagactatc catttctgtc agtgagttgc ctatgcatta tagcctgtga    4860
gggtctatat ttttttaggg taatcctggt aataactgca ttgatgttac actgctaaca    4920
tttgggatgg agaaggggtg actgagtgac ttaacccttg gtccacatgt gctttcattt    4980
ctcctgaaat atacctaggt atggaatcgc taagtcatta tgtgcagtgg gagagactat    5040
gggagatggg acagaaattt ttaaggtttc atttctttt  tttagctttt gcatggtggg    5100
taggtctatg caaacctacc cccaaagtct gaggaagctg agaggccaaa gaaagaggct    5160
gacaaatcaa gtttctcaga aagaaatgtt tagtagggac ttaggaccag aaaccatgtc    5220
tgtgtcttgc gtgttggcga gacaagatgg tggatcccat accattaccc ctcagaccca    5280
gggcttaata ccatagggaa gggcgattca gaagggaggt atggcatgac tgaagtatga    5340
taatgtcaag gttgttgac  ctcagggcag gatttatagt aaatagggc  tctttcacaa    5400 ggaataatag ataaactgga aatcttaaaa ctggagttaa tcagaagtca gcatggtgga    5460
```

```
tcagtatcta agacggaatt gctttagctt ccacagcagt caatatctag accacccttta    5520 ttatttttccc acagaccaag aaatttgaag gtcaggacag tctttggttt cctgtacgtg    5580
ggtgtatacg ttgtaggcac ttgaatcttt gttgaataaa tggagaatgt taggcagtta    5640
tttgctagaa aacgctaggc acattcttta tcacagaatg aaaagacgtc attatgactc    5700
ctctgggact gatgggcaat tgcattaac caatctttta attaaaagtg gaagaatatg    5760
tttaggttct tgaaacttct gtgagtgaag ggaactacta agtggaaagt gtaatatgtt    5820
gataaaatat ttcaccagat gaagccaacc ttactcctcc caggaaaact tcttcattta    5880
tgtattagct ctggccaaaa gaagcctata aaggcagcaa agtcaaaata gaattttact    5940
ttaagtccct acttctaata attgtgctag ttttttagcca agctaatttc tgtggcagtt    6000
ttcataacaa gtgtgtctaa aggtgtttga tcagaattta taaattaaaa tatttctctc    6060 atttttttgga ggggcgatgc agggagaggg atagactgtt gctgcttcct cctgcttgtt    6120
agaaaggctc ttggccatat catattggtc cgtggtttag tttatttgca tgctgaatcc    6180
acacacattt gttttatgtt tgttagtata ttgagcagtg tattagggat caggtatata    6240
gatgtaaaag gagtacacag tctagagagg aaaaatagtg acaggctggg cgcggtggct    6300
cacgcctata atcccagcac tttggggaggc caagatgggc ggatttcttg aggtcaggag    6360
tttgagatca tcagcctggc caacatgatg gaaccctgtc tttactaaaa atacaaaaat    6420
tagctgggtg tggtggtggt cgcctgtaat cccaactact tgggaggctg agacgggaga    6480
attgcttgaa cccgggagga ggtggaggtt acagtgagct gagaccatgc cactgcactc    6540
cagcctgggc aatagagcga gactccatct caaaaaaaaa aaaaaaaaaa aaaaaaaga    6600 aaaacagtga cataaacagg caattacaat attttgttat atgggcaca agaagatgcc    6660 cttggccctg cttcatgagt ggtgtggggc agggtagaga gagcagttca ggagaggtac    6720
gtatggatgt catgggagct agcagccagg aagatgtaaa catgttaaca aggacctctc    6780
cagagagagg tcttaaaatt atccagccat agagaagctt ttctctcttt aaaaatattc    6840
tggctctaaa gttattcatt gagttaaaaa caataattgc aagttggagg aaatctcttt    6900
gcctgtcctt acgtgttaca tgtaacaagt aaacctgtgc cacaacactg acatctctgc    6960
aaagttactt aagttttctg agtttgtagt atcgcccatt aaatgggatt aataatattg    7020
atctctggat tattgacagg cttaagtgag ataacttgcg tggtccgttt tctagcccca    7080
ccctctcatt tcatctagta aatcttcatt gcattaatta ttttcatctt aaatacaccg    7140
catcctgctc ctcaccttct aatattaata ctctatcttt cagtttagat cagttcctct    7200
tatccaatgt tgcgctaaac atcccctgaa gttggggat cttttccttt ctagttttttg    7260 ctccctggct tccctttttct gttgctgact gttgaagctt tcctgcccca ctggctttga    7320
aggtaaattg tatatacatg agcttgtggg gaaagctgtt atataaatga ggacaattga    7380
tctaactgtt agagtgggga aatggaagag attctgaagc ctccatttgt aacttaaaaa    7440
ctcaggtttc atttcttaac aggattgatg ttaaggaggg gattccttca ttgggcagga    7500
gggaggactg ccataattcc agcattccca ctcttaatag tcagtgtcat caggaaagac    7560
cacctcaagc tttagtactt tattcattta tccaactctg cacctgctgc ctttgggtgt    7620
ggtatttatt cttgaccata tcaccctgac ccggtaacca gaagggaaca tgtgatgtgc    7680
tctcatctct gccttagggg cagctccctc cccacgttaa gaatgctggc atgtaaataa    7740
cactctcatc tgtttagcgt tccttttact gagcttcttg gtatcttttc tcatacttgt    7800 acctttatg ggatgtcccc ccctttttttt ttttgagacg gagtttcgct gctgttgccc    7860
```

```
aggctggagt gcaatggcac gatctcagct caccgcaacc tccgcctgct gggttcaagc    7920
gattctcctg cctcagcctc ccgagtagct gggactacag tcacccctcc actgcacctg    7980
gtactaattt tgtattttta gtagagacag ggtttctcca tgttggtcag gctggtctcg    8040
aactcctgat ctcaggtgat ccacctgctg cagcctcccg aagtgttggg attacaggtg    8100
tgagccaccg cgcccagcct ggatgtccct ttattttta aaggcttcct taaatacctt     8160
gtttgtaagt tgaaaagagc atttaaagag tgaacagatt tggtttgctc tggctctcta    8220
attattttaa ctttgttatc acccaatagt tctaggttag tggttttcaa tcctagcttg    8280
aacaggagtc atttaaaaat agcccaggcc tcacccaggg cacttctatc agacatctct    8340
aggggggatg gcccaggcat caggaggctt taaaaagctc ctcaggtgat tttagtgcat    8400
tgccaaggtt gaaaaccaag gctttaggtt taaactaaag gtgaaattgc tcttttctg     8460 gttcattttc tactttagaa agtagaaatt ttttttctgg ttcattttct actttaaatt    8520
aaaaataaac ctacagaggg taacacgtat tagcacgtca cagagggtca cacgtattag    8580
caacatatgt atcttcaaaa gagtgatgtg actgggtggt aagtgttgat tggaccctta    8640
aactgtgaca gttagaagg  ggctttgcta gatgggttta gggacagaga tggtagagtg    8700
agagagtgtg gatggaggag tatgcatctg tcatgattac tagaaaaata aaacttcaaa    8760
tgctttgctc cttctgctgc gaggtcatgt tctcacagcc agtgaagtga cagcatatat    8820
gtgttgaatg tgtggcttgc attttacatt taactctttt aattcatgtg ttaaccttag    8880
gaggtactta ttattctatt ttgcagatga aaatggagac tcataaataa gtaacttacc    8940
agcagctaca tagctggtaa ttggtagaac tggaagttgg acccaggctc tagtgctggc    9000
actcatagtt tctccctgct gccatgttgg cctcttccta cttggatgaa gatataactc    9060
tagtggcaag ggcatttact agtgtgtgag agggtcttgt ttattagttt tgcaaattgc    9120
acggtctcct ttattcaata tcttttttca aacagctcac agatcttttg tggttttgta    9180
agtgcctact ccccaccgta ttgccttcta gagaagaggc aggaatttat tttaatgtac    9240
aggacagaca tgcatgggga gtaaaactac agactccact ctaggtgtgt ggaaatacta    9300
aaaatagtgc ttttctctgt gtgtgaagtt ggtctgttga gttttgtcat agacagcgtt    9360
gagttcctct cccaggtgga ggtggcgtag ctttgcgtca cttacgtgtc tctcctgatt    9420
tccagtgacc cggggaagac actgcagagg cagttgtctg tggtcaaaag tattctctga    9480
ccatggaact agatgaagct atgagcttcc aggatcatgt ggggctagaa gaatgccgct    9540
ctaaccctag aggagggaca gctgagtgtc ttctgatgta actgaaattg gagaatcagg    9600
tggattaaaa ttaattattt attacagtaa aataacctat cccatttcag agacatttgc    9660
tatctttaaa acattaatac tataatccac cttaccagta acagtttact tttagtgaca    9720
gtgaaagcca ttgactttt tttttaatt gaaagagat gttgcaaata gctggtgtac        9780
atttcttgag atgcactaaa caaggtagcg cacttgaaga tcgtggcagt aataaagcgt    9840
ttgtaagttc tgagtaaagt attgaccagc acagcttccc tggagaccgt cttctcattg    9900
ctggattgga catttcactg ttaagcttgt aggacgcttt tgggcacctc tctgactggg    9960
agctttgcag aacccagtgg cttttctctgg agcaggtgct gagcacattt tcaggctcca    10020
aaatcatctt tctgctcttc agagcaagtt tcttagcaga ttagtgttga gatttgtcaa    10080
gggtttctgg ggcatcacta aaagtttcag gcaatggccc atcctgtcag attttagtac    10140
tttggacaca ggaaattaaa aaagagggca gatggtataa acattgcaaa gctatgtacc    10200
```

```
cgtgacagtg taaatgaaag gtttgattgt gctaactctc ctgcactttc tttctgtgtt    10260
cctgtagaaa gctgatgtcc tgaccactgg agctggtaac ccagtaggag acaaacttaa    10320
tgttattaca gtagggcccc gtgggcccct tcttgttcag gatgtggttt tcactgatga    10380
aatggctcat tttgaccgag agagaattcc tgagagagtt gtgcatgcta aaggagcagg    10440
taagtgctgt gtttatttgc tgtaaaaaga ttgtttcaca gcacctgggt caagtgttat    10500
ttcccaaagg attggaagac ctttaacaca agtgtcaaat ctccatttgt gggagaaagg    10560
aaaaacatcc agcagtaggg aaattagtaa ataaatgatg gttatttcct caggttaaac    10620
attatatata aaatagtttc ttttaaaaat agcagtcttc catttctccc atcattgaag    10680
gaataaaaat acaataagtc ctcacttaac atcaataggt tcttggaaac tttgacttta    10740
aacgacatgt aatgaaacca attttatgat aggctaattg acgtaagcaa gagttaagtt    10800
cctatggcat atttctgatt gataaaacat catcaaactt ctaaatagag actcaaaata    10860
cctcttatat taaacattga aataaatgtg agccatacat acctttaaga aagattagta    10920
aaataagata gttatttact agcttattcc agttcaaggt ggtgggaggc cagagcctgt    10980
cctggcaggt tggggtacaa ggcaagagcc agccctggac aggatgctgt ccattgcagg    11040
gtggactcac actgggacca ttcagacatg ccagttcacc taacacgcac atctttggga    11100
tgtgggggga agctggagta ccaggagaaa acctatctag acatggggag aacatgcaga    11160
ctccacacag atggtggcct cagctaggaa tagattttt tctcatcaac gttataatga    11220
aacaacgttg aacaaaacaa tgttgtttga ggacctgctg tacagaaata cagacataga    11280
cacatgcact gcaattgcaa ctaagtttaa atgatgtact tactgggtaa ttactggaat    11340
gagctgcaaa atttggggta gttatgttag ggtggtgggt ttgtgatgat ttttcctttc    11400
cttttttcca acaatttctg taaaactttc tttatcgctg ttatatcaga cacaaaagat    11460
gggggtggta tttgaaagaa agtgaaaaac tcagttggaa aaagagctcc acagaaagga    11520 agttttctc ttagcttgct gacttggact tccagttagg acttctgcat tcttcatct     11580 cttcttcctg gataaggttt ctccccatct tctccagtgg tttgtgtgta ttttttccatc    11640 ttgacttgtt tagtttattg cttgctttgt atcatcgttg ctaagtgttg aaaagattct    11700
ttctcttatg ttttcatctc ctcttctctc tgttcttcac tttctctcat aggtcctacc    11760
tgtacttcag gcccctctga gaccctgtgt ccttgggcca accttgacga cttctagcct    11820
cactcacctc cttctcttgg ctccagctat gtggcattcg acttagcact gaatgataga    11880
atagggcttt gcatttcacc ctctttattt tgtgtttggg catttcccct tcctccaaca    11940
tactggaagc tcccagaagg ctggtgctaa ccatcatttt ctcttgtcac ccaggtgcct    12000
gttgaggacc tgaatgtctg agtaatggtc tcatggtaag gatttctgtg tctttctcgt    12060 tagggggcctt tggctacttt gaggtcacac atgacattac caaatactcc aaggcaaagg    12120
tatttgagca tattggaaag aagactccca tcgcagttcg gttctccact gttggtaagt    12180
tggtttattg gcgtgattgg tatggcttaa ctcaacttca ccttttgggg atgtttataa    12240
cttaaagaaa aagttattag aaaataggaa gcaagcactt ctccaaatta tgtcaaggtt    12300
ttacagtaga agacatattt ggagacacat aggaagttac ttgtatttct gtttgttgag    12360
gtcttaggaa atcacactta cacagaggct acctctgcaa ttctgtgaca tttggaaaga    12420
gctttcctaa aagtggttgc ctctaacaga agaatagagt ggaaatctta tttaataact    12480
atgcctacag ctgaccttta ttgagaatta attctgtgcc aactgtggtt aggtgcttta    12540
cagatataat ctctgatttg tagatctact ttgcagagtg ggattctttt tatttttgag    12600
```

```
aggctaagtg atgtttctca cgttacagag atagtattag atctatcata ctatatttca   12660
acatacctag tgcttcacta gttccgtttc tgtgtcagtc tctgcatttt aaaaatactg   12720
tggaatgtaa aaataaatga aattaagaac taagaaccaa tattttaact cattttctta   12780
atgttaacct catcattttg acaactcact tattctgttt gtcactactt taagcctcat   12840
aattattttc ttcccttatt ttaattaaaa gttcaattac ctgtttgaac aaagttatct   12900
tattatggta aatgaatgac attgtcagct gttattacat gtgttctctt attgctctca   12960
attaattatt ttgtttgatt tgtggactga attagctggt gggtagaaat aataacccgg   13020
gcacttaaat acctaattta gttcttggaa gtggattaga aaggatggat ccaggtgctt   13080
ctttatgtct ccaggcttct tggatgcaaa gtgctgtggc ttatgcttcc tgtttccatt   13140
tgaatattgt agctggagaa tcgggttcag ctgacacagt tcgggaccct cgtgggtttg   13200
cagtgaaatt ttacacagaa gatggtaact gggatctcgt tggaaataac accccatttt   13260
tcttcatcag ggatcccata ttggtaggta atagagtatt ttgcactcaa caaatgtttg   13320
ttgacttaaa ttgatttcaa ataggttggc atttgaggag aagccgtggg aaaggcagaa   13380
agaaaagaat gcgagttgtc tggactactt ttttcaacac attttctgt atttaataag    13440 ataaagtaag aacagttacc attggtctta gatttgtcat tttaagacag attgacttaa   13500
tgggaagtga gtttagtttt ccttgcagag catcgaagat tagtaaaaag agggacttta   13560
ctttggaaac aagcagaggg tgtctctaca tgctctgagt cagcaggagg gggtgtgtgt   13620
gcgtgcgcgc atgcgggagg gtgggtatat ttttccgtg aagaaatact ataaatccca     13680
gcactttggg aggccaaggc aggcagatca ctggagtcca tgagttcgag accagcctgg   13740
gcaacatggc aaaccatat ctctgcaaaa aaatacaaaa attagccaag tgtggtggct     13800
catgcctata gtcccagcta cttgggaggc tgaggtggga gatttgcttg agcccaggag   13860
gtcaaagctg cagtgagctg tgatcatgcc attgcaatca gcctgggtga cagagtgaga   13920
ccctgtctta aaaaaaaaaa aaaagaaaag actatagttt tgagtatatt tgaaatactt   13980
tagggtatct tagatgctag ttgtctatgc tgagtaaatt tcatattatg gtttggcagt   14040
ttaaaattct aggattgtat ttagaattat aatccataaa cctagtaata ggcatatata   14100
atgaaagaca ccataattcc tgtaaactta gttttggat ttttttctct ctttttctta     14160 tttagttttcc atctttatc cacagccaaa agagaaatcc tcagacacat ctgaaggatc   14220
cggacatggt ctgggacttc tggagcctac gtcctgagtc tctgcatcag gtatgaaccc   14280
ttttttgcca ttgtattata tcacctggga tgcagtgttt aattatgcct cttcataaag   14340
tgtctctcca gttttggcta ttttattgga atcagcttcc tcagatttct tgatcgtgaa   14400
gagttttgta gtaactggct ttactaatca tcccccattc atcggcctta aatgatgatg   14460
atgatgatga tagatagcta gcaacattgt cagttgatat ttagcagtag taaggatgaa   14520
agtctgtagt gtaaggtaaa gctctgtatt aaggaagtgg ggggaaagta gtaccaaaca   14580
aatttgctat gcaaataaat tttgaataac aaattaggcc agttttcagg ttgtttggc    14640 tttccttcat agaattttga gtcatagtat tagtgatttg catatcattt tgatttaaaa   14700 ttttttctgtt tgttattttc tacaagtgaa ataataatgg taaccccttcc catgggaaat  14760 tggctagtat gttttatgtc attaagggac tttctggaaa ctaaggaata tcttaaaaat   14820
caaggatgtt ttgatttaaa tgaaacatt ttaggcttta tatttctgtt ctttaggttt     14880 cttctcttgtt cagtgatcgg gggattccag atggacatcg ccacatgaat ggatatggat   14940
```

```
cacatactttt caagctggtt aatgcaaatg gggaggcagt ttattgcaaa ttccattata   15000
aggtatgtgt taccctttggg gcagagggta caaggctcct accgcatacc tccttatttt   15060
tcctgaagga ttgagcaaag attaaggctt ctcccacttt tccctcacct ccatccccaa   15120
agttgggaag tattgatctc attgatcagt actgattttg ttggctacca tctgaggacc   15180
ttggagcgta tcccaatctc attatcactt ccaacatcca atagtgtctt tccaatatca   15240
tttcttttaa cttttaagt catccatcta tttacttagc atttattgag gttttattat     15300
gaacaaggca tataagtaaa atcaattaca aatgtcagaa aacaaaatta tactgttttt   15360
aaaaatttgc attcatatag ccagatcaaa tcagttacat ctggggaggg ttttgagaat   15420
gttttaatca actgaaatat tataaagggc cctcttttgg tataagcatg gcatttgtta   15480
caatgagcaa tattgccagt gaaccctggc atgttagtga tattcccaga gaactcccaa   15540
gggctagtca gaaacaagcc tgagaacctc tgtttccaaa tactgctgct aagataagca   15600
gaaagaagtg ggctcgtgac cagtactgga taatctctct cttagtgaca tccaaaagcc   15660
ctattttctt ctatcctgct ttcttcttta tctgaacaat ttaatgtagg tatatcaaac   15720
aggaaaacta tcacctcttt ttatattcat aacttggatc tataatattt gacaaggaaa   15780
aattttatga aacagttgac ccattggctt gtaattgcca aaagggtcaa tgtagtatta   15840
cttagaataa gactaagtgg ttgtatctag gacagccagt ctagttggta gccttggagt   15900
tatgccagcc tgaactcaaa tttctactct cctagataat tgtggccttg gcatagtat    15960 taaaagttct ttgagctcca gttcttttca ctgtgaagtt ggcataatat taccagctat   16020
acaagtcctg gaaagattgg attgcttgtg ggtcttttat cctagggccc taaggtagcc   16080
tgagatctac atggattcat cagtctggat tattctgacc taagattatt cttttctaaa   16140
cctaaaggat tcagttaaaa tcagaaaggt attgcagtgt tattgtacta cttaatatat   16200
tagctctttg ggcgatctgt acatggtgac cttcattgtt ttaatcctga aggtggcttt   16260
acttcttgtt cagtagtaag agttcaaacc ttttcactga tgagacagtt gggatttctg   16320
tggtagaaat agaccagcgt tcagagttga ttttttgctaa ggaaatcttt ctgcggcact   16380
tggcttgttg ggaggtcttt gagaataaga tcacatggtc agtccatcaa agaacagtat   16440
gatatgataa caggagcact tatgaagtga cacagcttct ctgggttta atgtcttgct    16500 tggaaagtca gaatattaat tttgcctgct catagtcaga gaactagttc caggtggctg   16560
tactgaagtt cttttcaact ctatgagcta tgattctatg atttattaaa aaaaaaaaaa   16620
aaaggaatag gacaggggtg aagggatact ggccgagcac agtctcagta attgatttga   16680
gctgtcatga aatggaatta aaacattact tcatgataaa aggcaagtag tcctttaatt   16740
ttattaatct tttgcctact tttaagtata ttttgatttt tctgatttgg aaagtaacat   16800
gagtgtaaaa attcaaataa tagaatacat aaagggaaag ataggactga ttttaaatat   16860
gaaatgtgta gatgggattc ccttgacatt taaaagtatt gggataatca agtgaatttt   16920
cttgttgata aattcattag tatcagattt gaacaataga agtattgttg taaagaaagt   16980
tcattctttg ggcagtgtta ctcataatcc ttcaatgaat tactgatgaa attttgataa   17040
ctttgacaat aagtttccat tggagcttct ttctttcatt ttgtagactg accagggcat   17100
caaaaacctt tctgttgaag atgcggcgag actttcccag gaagatcctg actatggcat   17160
ccgggatctt tttaacgcca ttgccacagg aaagtacccc tcctggactt tttacatcca   17220
ggtcatgaca tttaatcagg cagaaacttt tccatttaat ccattcgatc tcaccaaggt   17280
gagtcagtaa acaactatat tgttttcttt tttaagtctc ttcttaccta attagaaaaa   17340
```

```
aaatctagtc aaacaattat aataatgggg aagtcatata caaaatacag agggtaccac    17400
ttcagagtgt cctaagctgt gaatgagtgc ttaccagcat cttacttcca cgttcctgtt    17460
tgtcatttca ttgagtatgt gtatgtggct tcatatattg ttattaacag gaacagatt     17520 atgaaaagct gatgtacttt ttcctgggga aactgtcagt atttaccact tactattgtg    17580
aaagatttaa ctaaggcact catcttaaat tcttatgttt tattggattt aaaaattatt    17640
ttcattggct tgattgtatt tgaaatctgg tattttgtg ggtagctttg atttccttca     17700
gttgattgcc tggtaattgt gaatatgaca tcattttcag gtttggcctc acaaggacta    17760
ccctctcatc ccagttggta aactggtctt aaaccggaat ccagttaatt actttgctga    17820
ggttgaacag atagccttcg acccaagcaa catgccacct ggcattgagg ccagtcctga    17880
caaaatgctt caggtgagcc tggtggattg agatgttctg aggcaggtgt ccatgtgagc    17940
atgcacacac aaaatatgca gcttggcatg atctttatgt gaggaattaa caagaacatt    18000
acttaaactt taatctgggt gcttggttac cttgtgggat tcactgaggt gaactattct    18060
tcaatgagca ttccttgagt aaaccaagta taaacaaaag tccatggtaa gatccctaca    18120
tatgtgaaga caagaatact tactctctta attaaaaaaa aaagacataa tagaaatacc    18180
ttaagtattg atagagtgaa gcatggtttg ttctgtctgt agctgaagta tggttaatta    18240
attataatac cttggtaagc ctaactttat tttcttgttc ttttttttt ttttttttt     18300 tttttgtga cagagtcttg ctctgtcgcc caggctggag tgcagtggca tgatctcggc    18360
tcactgcaac ctccgcctcc caggttcaag cgatcctcct gcctcagcct cttgattagc    18420
tacaggcgcc cgccaccatg cccagctaat ttttgtattt ttagtagaga cggggtttca    18480
ccctgttggc caggctggtc tcaaactcct gacctcaagt gatctgcctg cctccgcctc    18540
ccaaagtgct ggattatagg cgtgagccac cgtggctggc ctcatttct gtttcatggt     18600 gatgcttgaa ttttccatt tgtaaaaaga gatctaggga tgatcttat gaactacatg      18660 tatgctgcca gtgataaaag cagtggatta accattcacc ttgctaatgt taagccatca    18720
gtatgtttta catcacttt taatatctct ttcaagagta ccaagagtga aaaattgtac     18780
tttggatcag aatcagtaag aaaataattg gcttaataat tactgtataa atcaatcttt    18840
tgtggtttta gactgtgacc ttgaaacaaa ggttaaagat tgtaccctaa atcagaccac    18900
agcgactgaa ggttacttct tatgtaagta tctgattcca gttcaggttt cagtctgcat    18960
ggaggacaag ctaagattcc gttttttaaaa aataactttt ttgcttatga cattggggaa    19020
catctgaggc ttttatagaa agtaagtttt tcattagttt ttagtccaat tcaactgtta    19080
caaattgagt acctgtctgt tgtgtatggt ggactgtctt gggtgccata atgtaaggca    19140
gaatgccatg gtgatccaga aagcaaaatt ttgtctgata ggaggtcagc cacgaagttt    19200
catgaacgag gtagcatttg agattgtttt gaagaataga taggattttg attttagta    19260 ggtaaaatgc ggcaggagaa ggacatgagt ataggcacaa aggtgggaca tgttaggtgt    19320
gttgaaacta taaacagtca ctctctcctg aatgagaaga atagagtttg ggtaggttca    19380
ttgagtatat gtcagagggg accttaaatg cttgagtagg agtgaaaagc tttcttcagt    19440
tttgagaagt gtggtctggg atatattgag tagaatcact cctcttggtg ataaataaaa   19500
aaagcgacaa ctagggattg ggaatagcaa aaggaaagtc aggcagttct cagaggaaaa    19560
gcagaagttt gcattgaaac cagggagtag aggaagccaa aacaaggtaa tcctgggccc    19620
taaaactccc tacctggtgg ctgaactgtg agaggatgag gctaatggga tttgccaagg    19680
```

```
catgaaattg tcatgggcag agcagaggct gcataaccct ggttacccag ggagggaacg   19740
gattgaggaa tacaaggtta cctaaactct tttcacaaga atccaagtca ccatgggtct   19800
ctggaaccac agtgggaccg tgaggcagtc agcagcactg agtcatataa tttgaagaac   19860
aatgaagatt tgaatggaga actaggcccc cgggaaaagg actgcaaagc aaatacgtat   19920
tctctacatt cctaagaaag caaatgtcta aggcagctat tcaaacagtg gggaagagag   19980
ttctgaaaaa ggatgacaag tagaaagtaa tataatttct gttagtatta attttagttc   20040
tggcaaatat atctatttta aattcagtgt actctttata ggttgttttt tttttaaatg   20100
agttttagaa actgttcgaa agagctttca taagtttgtc gagttattgt ttctagccta   20160
gctttccccc atccttctta ggtcatttag ctatcagttc caataccatg gagcctgtga   20220
ggagccatac agtggggaa ggactgttgt actcatttag ccatttggtg accattaagg   20280
aatgatttga gattttttga gtaggtgagt agggaatatg tagattgtct tgttggacag   20340
gaagtggaaa gccagttagg ggggcttttgg ggttattcct gctgagagct catgagtatt   20400
gtagcctagg cagtggcggt tgatatatta atgggcagtg tttacaggtg ccttttaaca   20460
aggtcatgtt attaagttttt ataactttat ccaaagtggt gagccacacc atggtgaaat   20520
ggacaaataa tataatacaa gtcatagaga gactgtcctg tcccctgagt acctgaggac   20580
acaggtgcag cctttcttgc tctcattctc tgcattttgc caagagttgg agaagttggg   20640
ccggttgctt gggtgggaaa ggcttttccca ctcacgcagg tccagcaagg gagttcaggc   20700
acagggcctt ggggaaggcc tagattcaag ctggtgtcag ggtatggcct cactgtgccc   20760
atttcccaac ctttgttggt ctccacccat aggtgggggta aggttgcctg ataaacacag   20820
ggtgacacaa aatcagaatt aggtgataga ggctacatcc aggagctgcc catggcagga   20880
ttgtatctcc tatcctgttg atggagtcaa gagcacaact ttttgagcca aggagacaa   20940 ccagcttcca acctatagct gagttttggt catggccgca tggctagtca tctaaatatg   21000
accttaggct atttgaaatg atgataagag ggagtcattc agccaaaagc aaaatattga   21060
cagaacactg ggactggatt aagtctgttg gtatcagtga tttggaacaa agttattgct   21120
taagttgccc tattcaattt ggttttttatt ttgcctcata gaattaggga tataaaata   21180 cttttaaggt tcaaggccaa tgataaattc aatggaagaa aaattgctca tagaaaagga   21240
gtatgaataa tgagaatagt tcaataatta gatattaaga ttaatgcaga atttatcata   21300
aagcttttgt ttgagcatta actgaaagaa atttcaagat gcttgccatc tttgccttga   21360
ttaacatgga acataattta atcttagatt gattacctttt ggcattgtag ggcttttcatt   21420 ttgaaccaca gatttttgt tattgttgtt tatatctaga aagtctcaga gctcaaagtg   21480
tttctgagat aattcagaag gcagcatggg agtgggcggt acttttttt tttttttttt   21540 ttttttctg atcttgctttt gttgcccagg ctggattgca gtgacacgat tgcagctcac   21600
tgctgcctca atccctgggg ccaagcagtc ctcccacttc agcctgttgg agtagctggg   21660
actacaggca catgccacca tgctcggcta atgtttaat tttttttttt gtagagacag   21720
gtctcgctgt gttgcccagg ctggtctcaa actcctgggc ccaagcgatc ctctcacctt   21780
ggccttccag agtgctggga ttataatagg catgggccac tgtgcccagt tggaagtgct   21840
tatttgaaga atttcccatg ctgttggttt tgtagaaatg tgttgctttt tgtaaagagc   21900
aaatgattgg ttccttccct ggagtggggg aatgaggagg aatagaatta attcaatatt   21960
tcagttagtt aacgttctag cacatttatt ttataatgca atacttcctt gggaatagga   22020
agtaatactg tataagacaa gacactaact tgttatgcag aaggaaaaaa aaagatatt   22080
```

```
attaccaaaa acagatgtga agatttatgg ttggccagag ggcctgggaa attcagaact    22140
gttcagttag ggagaactcg tttcataaga gtagaggctt cactcttaag tagcgggaaa    22200
ggcagaattt tgtggtaacc atgtacagag tgctttgtac ttcaaatttc agaatgaagt    22260
ttacagccca ttcctatgtt atatgttact gcccctagtc agtgtctatt gtatttatta    22320
ctgcagggcc gccttttgc ctatcctgac actcaccgcc atcgctggg acccaattat    22380 cttcatatac ctgtgaactg tccctaccgt gctcgagtgg ccaactacca gcgtgacggc    22440
ccgatgtgca tgcaggacaa tcagggtagg cctaaagacg ttgggctccc cctgcgtggg    22500
cagagggcac gtggagcaga tgggcgggag gccaggccag tggctctcaa gctggccccg    22560
caggacctcc tgcttggtaa aggtgctccc caggtgctgc taactgggcg cttttttgcc    22620
cagcagtgaa gatttaggct gcctgaggac tctccatgct ttttatctat tttatatatt    22680
ttattgagca tttccacctc agatgttact tgtatccagt agttaaaagc agggagaaag    22740
atctttcaca ctggctagag tacagtaaca tccagcttgg gagttaggtt ttgaagacac    22800
ttcaccaaaa tggacaattc cttaactcac tgtgaaatca ccaagactta gacccttgga    22860
agtgcgaaag ccaagagttg gagtcttctg tttctctttg cagttctgct gtggccctgg    22920
aggagcaggt ctagctagaa tttggagggg agctagaatt agcagggaag gctggggaga    22980
agagagtagg ggaggcagag caagtcaaag gattcccctc ccttcatttt ttcctaagtg    23040
aataaagtta ggtgaatcaa cttaccactt tttgtttttt ggaactcatt tatcaaactt    23100
aggatctttt tcttttaact acttttttttt tggtgtcgta tacaaacagc ctctggttct    23160 aattacttt tctaataagt caagcagaat gcttgattaa agttttttcc ttttactatt    23220
ccacagttta atatagatct tagttatttt cttttcccat ttaggacacg tgttttagta    23280
atatagactg catgcattga tccctttaga aattttactg atgatttata tttatagcca    23340
cagatgtcta tattcaaaca aagtttattt ttctatgata aaaataatac aagtgtccta    23400
aagaaaattt ggaatatata ggaaaaagaa gaaaaaagaa aaattcccat atagtcccaa    23460
cacccaaagg tcatagctat tacattttgc tatatttatt tatctatta tttattttt    23520 agacagagtc tcactctgtt gcccaggctg gagtgcagtg catgatcttg gctcactgca    23580
gcctctgcct ctgggttcaa gagattctca tgcctcagcc tcccgagtag ctggaagtat    23640
aggagtgtgc caccacgcca gctaattttt gtattttag tagagacagg gtttcattgg    23700
ccaggctggt cctgaactct tgacctcagg tgacccaccc actttggccc cccaaagtgc    23760
tgagattaca ggcatgagcc accgcgcctg gcttgattgt aaaagtagag catttgggct    23820
gtgaccctga agctcagtga aagagcttaa ttgttcctgt ggtcagtgct ttaaagacaa    23880
ctaccacttt gagtaaaggt cagggctcat ttggaagtag gattttaaaa attaactagg    23940
cacatttcaa agagctagtt cttaatgaag aaaacactgt gatggctggt ttttggagca    24000
ttttgctttt catgtagatg tgactgatct gttgaatttg ttgagtgaat aattgggctc    24060
tataatagta tggtgttctt ccttccccta cacacacact tggtgtcttg atgaatgtca    24120
tacataggca cctcttgatt atccactgtg gataatctat tacggcagtg agctggctaa    24180
aattccaacc ccagattggt ttgctcaaac cacttaatat gtttctgggc cactcctgtt    24240
taggcagtgt gtgctcgggt aatgaaagct tctgctaatg tcagccaaag catagttgag    24300
aaaataaata tgctaaaacg aaaaaaaagc cttataattt atttcaaaag tcatagaaaa    24360
tattttgatt gtatttgtca ctgtttctta taagtccaga taagtaagtg ctgatataca    24420
```

```
attaccacat tttaaaaaat tctttgttta ttggtctgtg gagggtatga aagtgaagct    24480
acaatggaac aaagtcatca ttgtcagtaa aggagagata ccctgagaat cctaaaaaca    24540 cttttacggaa tagcaaagta gagttctgta atggaaatac tgtatatgct gggctggagg   24600
agacaaaaaa cccagagttc caaccccata tctaccactg ctaccgtgt gaccttgcag     24660 cagtcaggtc ccatcacaga gctccatgct tgtgtctgta gattcaagga gcagaaccag    24720
aactttcaga tttccctcaa gaattttgtg atgcagtgtt tgaattgagc ccaagtccaa    24780
atgacacaat ttttcaagtc aattttgaaa tgtgtctttg agcctcatcc ctatatggtg    24840
gccaaatcaa gcctgtataa acttctacat gtgctgtacc cctcagaaga cttgatagat    24900
gagacccttt gaagtgtcaa aagggacttt gagattcatt cataaagtgc ggcagcctgt    24960
gcaagcattt agcagatggc agcgttccct aagaatcttc atactacctg tagctaaatg    25020
cgggaaatta aaaataatat gtgtgcgttg tgtttatatc tgtgtatgtg tacgtgtgta    25080
tttgattacc acttgaattt atttctcatc acagtgatta tttgcagact tacttgactt    25140
ttcttattcc taagtgcatc tgggtggttt tgttttgaag gtggtgctcc aaattactac    25200
cccaacagct ttggtgctcc ggaacaacag ccttctgccc tggagcacag catccaatat    25260
tctggagaag tgcggagatt caacactgcc aatgatgata acgttactca ggtaatgact    25320
tctctttatc tgctatggaa gtcacctgct aattctcctt gtcaatgcct gcataatccc    25380
cctccctgca aatgccccaa ctgtctgatg tatcttaaat tgaattcaag gaagactcat    25440
ctgtaatagt aaattgggcc ccttactggg tggagttgaa gggttatatt actctggtct    25500
tttgcctcaa agcatgcaga ctccgtctca gtttcttcaa actttattga agggatatgg    25560 ggaggggca ttggggaaac agttatctca tgggaattta agaaatgagc atgtacagct     25620
tacgtggaga caaatctaag aatctgggca ggacagtcca ggttcaagga ctagaactag    25680
agatccaaaa tagctccagg agcctcggcc acaagagtgt gggcgtttcc actgcagggc    25740
tcgtccttca cgtggcttat tctccatctg tctgcttctg cttgccaatg ctaattgatt    25800
atttttacca cagcttcctg ttttctccta tctgcgtcag agcttctgtt ttatcatggt    25860
tgtggctctt ccacaacaat ggaaaactct cctttatggc gtctttctcc attattactt    25920
tttttttttg gaccaccttt tactccttct ctcaacatgt ctatctctag attctagaga    25980 gatgaatcc tattgacttg gctaatcttt tcacccagg ttgcaccatt ggccttggtc      26040
aggctctagt taaccgcccc agggcaaatg ctcatcctct ttccagttgc ctatggctgc    26100
cctaagagct gtttcagcac atgctatgaa ggaggcccct tggacttggaa gggctgtagg   26160 tgggcagctg cctccttaat gtgtccagtg caacttatac cacacacaat aaaataataa    26220
agttaaaggt atagttgttc tagagctctg tttgagcagt tagtgttaaa cttagtattt    26280
aaattagatt agaacctatt tctagtttct cagtttgtga atgtgggttc caagtaaaaa    26340
atacttatac atgaattaat tcgctgtgag gatatctttg cttgaaaagc atttacgtat    26400
atacatatat acgtatatat aaaaaagaaa ttacattatt gtgggatata aaccattttt    26460
agatgagctt aaaacatttc ctgcatacct tttatgtaac tgcattattt ttggtgatgc    26520
agatgacacc aagtatatta cagtacattc cctgcctctc aaagaatttt gcctatgtga    26580
ggtcaataca ggtattaaac cagctcatac aacccctgca aaaattaatg aggctattgc    26640
ttacacatga aaatttatta tgtgctcatt cttattgaga gaatttctta tcactatata    26700
ggatatagtg tggtttttaa gtaatcacaa tactattgtt atagattcat agcataattc     26760
tgtgatgatg tatcacatgg gaaatacata agaaggtcca gatttattct cttaaaaatg    26820
```

```
attcacttgg gcttgcatct gtctatggca gactagcttg tatcttactt accgtttcat   26880
ggagaacatt gaaaaggtag gtaaaataca taaagcactt gtttgaaggc tttggagagc   26940
taacaaagca acaaggattt aagggaccaa gatcaaagat ggaaagaag tgcaggaaaa   27000 aaaagtgcag tgaagtaagc ttgacatttg gtttcctttc ctcttaaggt atttgttaat   27060
ttgtaagcac tggtccagaa gctgagtggt gtttacagca gtctcatgag tctgaaggga   27120
caaaaattgg aattcaaggt ctgctaagaa gcagagcctc tagttatact caaggctttc   27180
agttgaaatc cttaaagggc catgcctagg aataagggca acatgaaat aaacttgctt   27240 tcacaataca ggaaacataa ctttgcctct gctcagtctc agattggatt aaggtgatct   27300 cttttctacgc catctgtcag aagcaaacaa aattttcttt ggtggaaaat agaaactcaa   27360
atgattctag acctttttat atggaaatgt tcagcattca acaataaatg accaggcacc   27420
taacacatta agaccttatg actgaaaatc aagagggaga aaaaccccc tacaaactga   27480 cagtagaaac aaacctaatg gaggcttaaa taatggaact gtcagataca ggttttaaaa   27540
tgactgatta ataggtttga gaaaatagat gggctgggcg cggtggctca cgcctgtaat   27600
cccagcactt tgggaggctg aggtgggcgg atcacgaggt caggagatca agaccatcct   27660
ggctaacacg gtgaaacccc gtctctacta aaaatacaaa aaaaaatta gccgggcgtg   27720 gtggcgggcg cctgtagtcc cagctactca ggaggctgag gcaggagaat ggcgtgaacc   27780
cgggaggcgg agcttgcagt gagccgagat cgcgccactg cactccagcc tgggcgacag   27840
agcgagactc cgtctcaaaa aaaaaaaaa aaaaaaaaa gaaaatagat gactgcttga   27900
agaatttagt aagagaactt taagctatag aaaagagtt gaatggacat aactagaaaa   27960
tgtaacaact gaaattagaa tttaatagat ggcttttaaa ggaggttaac atggctgaag   28020
agaagattag tgaattggaa gatagaacaa tagatgttat caagactact tcatctgatg   28080
agtcatagtg aaaaattaga atacatacaa ggaaatccaa tgagaaatta cacatgcaat   28140
aatagatgga agaatcatag acatgataat tggaagagg ctttaaaata aacatacata   28200
tttaaagaga tgcaaaaaag gaatattatt aagacaatag gatatgagga gaaaacagg   28260 tagatttgaa aaataaccaa ataatatttt ctagaaacaa aaattacaat ctgtgaaata   28320
aaaagtcaac agatatagtg acccagtcga tgttttcacg caatatgtca aatacagctg   28380
aagagagaat tagtgaattg gagataggtc tgaggaaatc cccaggatat agtactttga   28440
ttagattgtg ttaatcgaaa atgtctgatt aactttggta tcaggtttaa actttactca   28500
aaaatttaaa aacataatta tagcctgata tttgatgact tatggaaatg atgcatctct   28560
taatatttta tgaagttgat actttggata attggatatt attggacttc ataacatta   28620 atagaacagc acgtagaaca gagtctcgca cattatagat actcaatatt tgttgaatga   28680
gtggaatgaa tgaatgaaat gtaagaataa aatcatagct acaaccttt gatttcagaa   28740 tggggcagag gctgctcgga ttcacatatc tgatactaag ctcctatttt tcattttaat   28800
ttatggatat ttattttaga ggtcaaccca ataatctagc aaaatatcac tattaatatg   28860
tcttgcttaa gaaatattgg cttctgaata actacagata cacatgtata aatgaggtag   28920
ttttttagat gtctatatat agatataatt atctatatat caaattatat ctctagctaa   28980
attagttaat tttcctccat ggttctggga gaattgaaca aaggtattgt gctaagttta   29040
cattcaaagg cagcttgcac attttagact tgtcagtatt aagaatgtgg tgaggtttta   29100
aattgtagat ctatttataa gagatttata gcagttacta taaggatat tattagaaag   29160
```

```
caggtatgag ctattaacaa atgaattta cttatttgc ttaaaacaaa aagtgaagga   29220
cacaacccaa atttaaaatt taaaattatt cttaacttct aaagttttt ttatcattga    29280 tttcctaagt gttgtagtag gtgaattttg ttggtgataa actggtgatt caattctctg   29340
cacttgctct tttctctgag caggtgcggg cattctatgt gaacgtgctg aatgaggaac   29400
agaggaaacg tctgtgtgag aacattgccg gccacctgaa ggatgcacaa atttcatcc    29460 agaagaaagc ggtgagtctt tgtaagctga agggtgtcct ctgctggcta aggaagacag   29520
tgcagctgtg tgggagaacc ctaaaaagaa agtgccattt ctgttttact tgacttaaga   29580
gaacttaaaa aaaaaaaaat aaactagtaa tccccaacca acttctgatt attttctttc   29640
catgttttat ctggtctggc atatccatcg tccttagctg tttgtccagt gtgtactaat   29700
ttagttgtgt tcagactgaa ttttgtccta ttctgtttaa ttcagctgca gccaagttct   29760
gtgcaagata gtaaatgtgc aatatcaaaa tgtgagtcct gctgcaattc tacttaaact   29820
ttggatgata ataaatatat cagccggtgt gatggcatgc acctgtagtc ctagctactt   29880
aggaggttga gatgggagga tcgcttgagc ccaggaatac agggccagcc tggacaacat   29940
agggagaccc tgtctctaaa atcagtcaat cagtcaatca gtctgtcttt ctttttgca    30000 tttttatggt ttaaaacctg cctaaaggct taatgtcata atacctcgat cctccttcag   30060
atgcagacta gaaatttgca tgatttctgg aataagaact gcaatgcttc caaaaggcag   30120
gctagacttt catgctaagg tgctggggta tttctgatgg ccgctcatcg agctgagtga   30180
agccctctca cttctggttt cctggcctgt cccagagcta agcttttgc aaatctagaa    30240 atccccttt ttccttggcc cctagttgct gcttctcagt tcctagggc agctgggcta     30300 gcagctgtct gggctgtgtc ccagagcctg ggttccagta tcagcagaga gcttgacagg   30360
cgctctgtgt ggtaggcagg gcaggattta tctcctttta ctggagagaa tggatacgac   30420
agcttgtaaa tagcagaact gggctggaac ccttggcatt ctcctttcac atatgctgaa   30480
actgtaaggc ttttatgggt tcccaatgcc ctgcctcctc ttgctgtcca ctggggaatt   30540
cctgcctgaa gtgtgtggag ttgtgctgca tgtaccagtg ttcttgtatc cttcacatta   30600
actttaggct gtgtctgggc ccgtttctca atgtaaatca ctgtaatttg ttaagcgctt   30660
actctgaggt cagctctttt catgcagtaa atgcacctca cttctcagca ttttctcac    30720 agcatcctgt gaggtaggtt gtgtgggttt ttttttttta agatggagtc ttgttctgtc   30780
acccaggctg gactgcagtg gcatgatctc ggctcactgc aacctctgcc tcctgggttc   30840
aagagatttt cctgcctcag cctccccagt agcttggact acaggcatgc ccaccatgc    30900 ccgactaatt tttgtgtttt tagtagagat ggggttttgc catgttaacc aggctggtct   30960
tgaactactg acctcaggtg atccacccat cttggcctcc caaagtgctg ggatttcggg   31020
cgtgagccac tgcgcctggc ctaggttgta tgggtttttt tccccgacaa taagcaattc   31080
tgtaattctt tgacagtaac tgtgtgtcct ataactcaat tcaattctaa cagtagctcc   31140
tggagctaga gtcagaaccc aaagatttag gggtcatttc ccactttaga taacaaatga   31200
ggtaccctgg ctatgcacac ttctgcagat tctgactgca aatcaaaccc tttcctcagg   31260
tttgataatt tgctggaaag actcatgaaa ctcaggaaaa tgatttactt atgattacca   31320
atttattata aagaatacaa ctcaggaata gacaaatgga agaggggcat gggggaaggc   31380
ctcggagctt ctgtgcctcc ctgagtggac caccttcta gctcctggat gtgtgcacta    31440
atccagacac tccctgacct tgccagttgt gggtttttct ggaggtttta tgacataggc   31500
atgattgatg aaattattgg ctatgggtga ttgaatacaa tctccagccc ctctcccatc   31560
```

```
cctggaggtt tgggggtggg gctagaagtt ctaaccttct gatcgcgtgc ttgttcttcc    31620
tggtgtgagc ctccatcagg aatctatgta ggcccccatg aatcatctta gtagtatata    31680
aaagacagta cattcgaagg gttttagatc tgtgtcagga atgggggaca aagaccaaat    31740
agtattttta aaattatact gattaggtgt cattttcttg cgcatttcgg cagagggaca    31800
taagctcagt aagttaagtg acctatccga ggttgctcag ccagtatatg tcagagtgtt    31860
cactggacct gcatcttaac tctgaggctg gcattgttaa acacctgtag tactgcctcc    31920
tgctgaaacg tctttcctcc cctatggaat aaacactggg aaaccacagt ccctggggag    31980
tgatatagta gggagttaga gtaatgcttg catttatttt cctttggcct taggtcaaga    32040
acttcactga ggtccaccct gactacggga gccacatcca ggctcttctg gacaagtaca    32100
atgctgagaa gcctaaggta agctgggagc agcctggcca tgcagaggct gtgtgtgctg    32160
ggttggagta ggcatgactt agttaccact tagcattaca gtctgcaggg gccattacct    32220
gccactgtta gatttcttag gcagctgtgc agaaattcat ttgagagata agaattcac    32280 tggcaaaaca catactcttc attttagcgc tgggcaattt aagacagtta aagtgaatga    32340
attctgaatt attattttca tttgcataca tattaaaact gagtaaatat cacgttgctg    32400
cccatgaggt gattaacctg ctcatcttgt tcttttaaaa cagaatgcga ttcacacctt    32460
tgtgcagtcc ggatctcact tggcggcaag ggagaaggca aatctgtgag gccgggccc    32520 tgcacctgtg cagcgaagct tagcgttcat ccgtgtaacc cgctcatcac tggatgaaga    32580
ttctcctgtg ctagatgtgc aaatgcaagc tagtggcttc aaaatagaga atcccacttt    32640
ctatagcaga ttgtgtaaca atttttaatgc tatttcccca ggggaaaatg aaggttagga    32700
tttaacagtc atttaaaaaa aaaatttgtt ttgacggatg attggattat tcatttaaaa    32760
tgattagaag gcaagtttct agctagaaat atgattttat ttgacaaaat ttgttgaaat    32820
tatgtatgtt tacatatcac ctcatggcct attatattaa aatatggcta taaatatata    32880
aaaagaaaag ataaagatga tctactcaga aatttttatt tttctaaggt tctcatagga    32940
aaagtacatt taatacagca gtgtcatcag aagataactt gagcaccgtc atggcttaat    33000
gtttattcct gataataatt gatcaaattc atttttttca ctggagttac attaatgtta    33060
attcagcact gatttcacaa cagatcaatt tgtaattgct tacattttta caataaataa    33120
tctgtacgta agaaca                                                    33136

<210> SEQ ID NO 4
<211> LENGTH: 3059
<212> TYPE: DNA
<213> ORGANISM: human

<400> SEQUENCE: 4
tgggaaagag ggaaaggctt ccccggccag ctgcgcggcg actccgggga ctccagggcg      60
cccctctgcg gccgacgccc ggggtgcagc ggccgccggg gctggggccg gcggagtcc     120 gcgggaccct ccagaagagc ggccggcgcc gtgactcagc actgggcgg agcggggcgg     180 gaccacccctt ataaggctcg gaggccgcga ggccttcgct ggagtttcgc cgccgcagtc    240
ttcgccacca gtgagtacgc gcggcccgcg tccccgggga tggggctcag agctcccagc    300
atggggccaa cccgcagcat caggcccggg ctcccggcag ggctcctcgc ccacctcgag    360
acccgggacg ggggcctagg ggacccagga cgtcccagt gccgttagcg gctttcaggg    420
ggcccggagc gcctcgggga gggatgggac cccggggggcg gggagggggg gcagactgcg    480
```

```
ctcaccgcgc cttggcatcc tccccgggc tccagcaaac ttttctttgt tcgctgcagt        540
gccgccctac accgtggtct atttcccagt tcgaggtagg agcatgtgtc tggcagggaa       600
gggaggcagg ggctggggct gcagcccaca gcccctcgcc cacccggaga gatccgaacc       660
cccttatccc tccgtcgtgt ggcttttacc ccgggcctcc ttcctgttcc ccgcctctcc       720
cgccatgcct gctccccgcc ccagtgttgt gtgaaatctt cggaggaacc tgtttccctg       780
ttccctccct gcactcctga cccctccccg ggttgctgcg aggcggagtc ggcccggtcc       840
ccacatctcg tacttctccc tccccgcagg ccgctgcgcg ccctgcgca tgctgctggc        900
agatcagggc cagagctgga aggaggaggt ggtgaccgtg agacgtggc aggagggctc        960
actcaaagcc tcctgcgtaa gtgaccatgc ccgggcaagg ggaggggtg ctgggcctta       1020
gggggctgtg actaggatcg ggggacgccc aagctcagtg ccctccctg agccatgcct       1080
cccccaacag ctatacgggc agctccccaa gttccaggac ggagacctca ccctgtacca      1140
gtccaatacc atcctgcgtc acctgggccg caccttgt gagtcttgaa cctccaagtc        1200
cagggcaggc atgggcaagc ctctgccccc ggagcccttt tgtttaaatc agctgccccg      1260
cagccctctg gagtggagga aactgagacc cactgaggtt acgtagtttg cccaaggtca      1320
agcctgggtg cctgcaatcc ttgccctgtg ccaggctgcc tcccaggtgt caggtgagct      1380
ctgagcacct gctgtgtggc agtctctcat ccttccacgc acatcctctt cccctcctcc      1440
caggctgggg ctcacagaca gcccctggt tgcccatcc ccagtgactg tgtgttgatc        1500
aggcgcccag tcacgcggcc tgctccccct cacccaaccc cagggctcta tgggaaggac     1560
cagcaggagg cagccctggt ggacatggtg aatgacggcg tggaggacct ccgctgcaaa      1620
tacatctccc tcatctacac caactatgtg agcatctgca ccagggttgg gcactggggg     1680
ctgaacaaag aaagggggctt cttgtgccct cacccccctt accctcagg tggcttgggc     1740
tgaccccttc ttgggtcagg gtgcaggggc tgggtcagct ctgggccagg ggcccagggg     1800
cctgggacaa gacacaacct gcacccttat tgcctgggac atcaaccagc caagtaacgg     1860
gtcatggggg cgagtgcaag gacagagacc tccagcaact ggtggtttct gatctcctgg     1920
ggtggcgagg gcttcctgga gtagccgag gtggaggagg atttgtcgcc agtttctgga      1980
tggaggtgct ggcacttta gctgaggaaa atatgcagac acagagcaca tttggggacc      2040
tgggaccagt tcagcagagg cagcgtgtgt gcgcgtgcgt gtgcatgtgt gtgcgtgtgt     2100
gtgtgtacgc ttgcatttgt gtcgggtggg taaggagata gagatgggcg ggcagtaggc     2160
ccaggtcccg aaggccttga acccactggt ttggagtctc ctaagggcaa tgggggccat     2220
tgagaagtct gaacagggct gtgtctgaat gtgaggtcta aaggatcct ccagagaagc      2280
cagctctaaa gcttttgcaa tcatctggta agagaaccca gcaaggatgg acaggcagaa     2340
tggaatagag atgagttggc agctgaagtg gacaggattt ggtactagcc tggttgtggg    2400
gagcaagcag aggagaatct gggactctgg tgtctggcct ggggcagacg ggggtgtctc    2460
aggggctggg agggatgaga gtaggatgat acatggtggt gtctggcagg aggcgggcaa    2520
ggatgactat gtgaaggcac tgccggggca actgaagcct tttgagaccc tgctgtccca    2580
gaaccaggga ggcaagacct tcattgtggg agaccaggtg agcatctggc ccatgctgt     2640
tccttcctcg ccaccctctg cttccagatg gacacaggtg tgagccattt gtttagcaaa    2700
gcagagcaga cctaggggat gggcttaggc cctctgcccc caattcctcc agcctgctcc    2760
cgctggctga gtccctggcc cccctgccct gcagatctcc ttcgctgact acaacctgct    2820
ggacttgctg ctgatccatg aggtcctagc ccctggctgc ctggatgcgt tcccctgct    2880
```

| | | |
|---|---|---|
| ctcagcatat gtggggcgcc tcagtgcccg gcccaagctc aaggccttcc tggcctcccc | 2940 |
| tgagtacgtg aacctcccca tcaatggcaa cgggaaacag tgagggttgg ggggactctg | 3000 |
| agcgggaggc agagtttgcc ttcctttctc caggaccaat aaaatttcta agagagcta | 3059 |

<210> SEQ ID NO 5
<211> LENGTH: 17268
<212> TYPE: DNA
<213> ORGANISM: human

<400> SEQUENCE: 5

| | | |
|---|---|---|
| atcctccgcc cagcacccca ggattcaggc gttgggtccc gcccttgtag gctgtccacc | 60 |
| tcaaacgggc cggacaggat atataagaga gaatgcaccg tgcactacac acgcgactcc | 120 |
| cacaaggttg cagccggagc cgcccagctc accgagagcc tagttccggc cagggtcgcc | 180 |
| ccggcaacca cgagcccagc caatcagcgc cccggactgc accagagcca tggtcggtga | 240 |
| gtgctgcaaa gggcggggtg cttggcggtc gtctctcgag cactggtgcc tgtgaggag | 300 |
| gttgtagggg cttggccctg aattttgttc cttgactcaa acccacaaa gggaagagat | 360 |
| tagggacctg ggatgagcct tgatcggact ccggagaag gagagcttct gtttgtatcc | 420 |
| ggtgtcgcgg atccttcctc actccacccc acgaactcta gtgggcattt aggagaaact | 480 |
| tgaccttgga agcagaaatt ccctccaaaa ctgtggtcag aaactggccg tcagaggcca | 540 |
| aatcaggctt acggtcacag cccataccctc ttttggtcta tagtatctaa aacactttga | 600 |
| aataagttgc taacattaaa atgggtgatt tcacttaaaa atgtggattc cgagcttctg | 660 |
| aagaaaatga gaatatctgg cgattggtgg acaggagtgg aggaaactga tgcctttggt | 720 |
| ttgacggaga ccagaaccgg ctccaggctg ccaggcacag gttttgtttt gttttgtttt | 780 |
| gttttgtttt gtttgagacg gagttttgct cttgtcgccc aggctgtagt gcaatggcgc | 840 |
| tatctcagct cagcgaaact tccgcctccc gggttcaagc gattctccca tctcagcctc | 900 |
| ccgagtagct gggattacag gagtgcgcca tcatgcgcgg ctaattttta tattttagt | 960 |
| acagacgggt ttcgccaagt tggccagcgc ggtcttgaac tcctgacctc aggtgatcca | 1020 |
| cccacctcag cctccccaag tgctgagatt actgacgtga gccaccgtgc ctggccttgg | 1080 |
| gaggcatttt ccattgaggc ccttggatta ggcaaacctg atcagatcgt actggatccg | 1140 |
| tttctagtat tgggtccact tcagtgatag agccttccca ctcggccatc gaccctaggg | 1200 |
| gaactcagag gtcaccccag ctccacccaa ggcataaata accagctgag acaactgcag | 1260 |
| ggattgagag ctgtttccca ataatctca ctctgagatt ggacagtact aagatttaga | 1320 |
| aagctgttgc ctcatctggg gcagaatcct gtgttttgta atttccttcc ctgtggacct | 1380 |
| ggtcctgcct ctaaaaatgc gcctgtacac aaagaagccc atcttggtca aagtgagtgg | 1440 |
| aggaacagac tgcccttgca gttgacaaac tgaaattatc aggatctctg agaaagggac | 1500 |
| taagctgggg attggtagcc cagcatgagt tactggcaga gacagcaggg aatagattct | 1560 |
| gacagctgag aggcttgccg catacacggt ggttgctgtt tcccttgtat ttcattcttc | 1620 |
| agcgtcgagg cactggcacc ctctcctcca atactgggc aggaactatt tcctgacttt | 1680 |
| tcaatcttac agaatgttct gtatttacgt gtagcttaaa cacaaaaaag gcggtggta | 1740 |
| atgaggtgaa aagggaagac ttggatcttg tataattagt tttagctgta cccagctaac | 1800 |
| caaatcttga ggttaactaa agcatccagg ttttttgttt gcaactaata gatgcatctg | 1860 |
| atttgcactc atgttccctg gagcactcaa gtgagaagag aaggcagaag gagaatgcat | 1920 |

```
gaaactgata caaaggctta tctttatcat acttctttt  ttcttttga  gacagggtct  1980
tgctttgttg  cccaggctgg  agtgcagtgg  catgatcagg  gctcacttca  gccttgacct  2040
cctgggctca  agtgattgtc  ccatctttgc  ccccgagtag  ctgggactac  aggtgtgtgc  2100
caccacaccc  agctaatttt  ttttggtcag  agcagaagaa  cttgaaaccc  agctaattaa  2160
aaaaaaaaaa  aattttggct  gggagtggtg  gctcattcct  gtaatcccag  cacttttggg  2220
aggctgaggc  gggaggactg  cttgaggcca  ggagttcaag  accaagattc  agctcaaatg  2280
gcaagctcct  ctgagggcct  ttccgaatgg  gccagccctg  aggtcctgaa  gttttcctct  2340
gttgaacttt  ttgagatgga  gtctcactca  ctctgttgcc  caggctgtag  tgcagtggcg  2400
tgatcttggc  tcattgcaat  ctccacttcc  caggttcaaa  cgattcttgt  gctgcagcct  2460
cccaagtagc  tgggattaca  ggcgcccacc  accacgccca  gctaattgtg  tattttagt   2520
agagacgggg  tttcaccatg  ttggccaggc  tggtctctag  ctcctgacct  caagtaatcc  2580
acccgcctcg  gtctcccaaa  gtgctacgat  tacaggcatg  agccaccaca  cccagccttc  2640
tgttgaactt  tgtcccttac  ctctcctaac  acactaatgc  cattgtaccc  tgaagaggtt  2700
atccgtgtgt  gcatcttgtg  gcctctctca  gggtaaactc  taatagtcta  actcctccca  2760
ggtcatgttg  ctcagctagt  taagtggcag  gaagggaaaa  tgaaccctcc  agggcccaga  2820
aaacttttaa  attgcctatt  cacaagcatc  ttttgtttg   tttgtttgag  acagaggctt  2880
gctctgttgc  gcaggctgga  gtgcaatggt  gcgatctcgg  ctcattgcaa  cctccgcctc  2940
ctggattcaa  gcaattctcc  tgcctcagcc  tcccgattag  ctgggattac  aggcacctgc  3000
cactacacct  ggttaatttt  tttttgtatt  tttagtagag  acggggtttc  accatgttaa  3060
ccaggctggt  ctctaactcc  tgacatgagg  tgatctgccc  gcctcagcct  cccaaagtgc  3120
tgagattaca  ggtgtgagcc  accgcgaccc  acccacaacc  ttcttttgat  cattttctt   3180
ttgagttgtt  ttggggatct  acctattcca  ggtactgcac  tttgatggtt  atatttgttg  3240
caaatatatt  attcctgctt  gtgtgttgcc  ttacatgaaa  aattgtaaag  tcacaggcct  3300
gcttatagct  attagagtct  gagctccttg  aaagagcaag  agatggatat  cctgatttgc  3360
tcattttctg  agaagtgcct  tgactgtctt  actacttaga  aaatgcttgt  taacattgat  3420
gagaagtcaa  taaaataaaa  actgttggct  gggcgctgtg  gctcacgcct  gtaatcccag  3480
cagtttggga  ggccgagaca  ggcggatcac  gaggtcagga  aatcgagacc  atcctggcta  3540
acacggtgaa  accccgtctc  tactaaaaat  acaattagcc  gggcgtggcg  gcgagcgcct  3600
gtaatcccag  ctactctgga  ggctgaggca  ggagaatggc  gtgaacctgg  gaggcggagc  3660
ttgcagtgag  ccgagatcgc  gccactgcac  tccagcctgg  gcgacagagc  gaaactctgt  3720
ctcaaaaaaa  caaacaaaca  aaaactgtca  gagcggcgat  cagtaaacat  tgataagact  3780
aatggcaagg  taagttacaa  agaaaatgcc  tgttagagct  gaatatgctc  acttccctcc  3840
caatcatgtt  aaatccatgg  gttaaagagg  taggaatttg  ttgaggcagc  ctcagagctt  3900
cctttttcctt tttccaagct  atcccaagca  agtcaatcac  ttccagcgca  ttgaaatcat  3960
caccagacac  ctattccact  gagtcttagt  tttaagagtc  caaaaccctca ggaccaagtt  4020
tggaaatccc  ctggtttggc  atattgggcc  ctgaaagtta  cacttcgctg  aatttagccc  4080
aagaggcact  tgccttgcta  gatgtggtca  ataataaaag  caggaagaga  gcttaaggtt  4140
taaatgtgcc  tttctagtta  ttttagttat  ttctagttat  tcagatggtg  caaaaaagtt  4200
gcagatgccg  gctgggcgcg  gtggctcacg  cctgtaatcc  cagcactttg  ggaggccaag  4260
gcaggtgggt  catgaggtta  ggacatcgag  accatcctgg  ctaacatggt  gtctctacta  4320
```

| | |
|---|---|
| aaacaaaaaa tacaaaaaat tagccgggcg tggtggcacg cgcctgtaat cccagctatt | 4380 |
| cggaggctga ggaaggagaa tcgcttgaac ccggggaggca gaagttgctg taagccgaga | 4440 |
| tggcgccact gcactccagc ctgggtgaca gagcaagact ccatctcccc cgcccccacc | 4500 |
| cccaccctgc caaaaaagtt gcagatgcct tctctcccag ctccacccac tgttcatggt | 4560 |
| agggtatgaa gtagcagcgc acattatcag gagcaactgt gggggtaagc gtcctttctc | 4620 |
| tggcaattcg ctctatgccc ttgtacgctg ttgtttgtat ttctcactgt ttgtaagtct | 4680 |
| cactgtcgcc caggctggag tacagtggtg tgatcacggc tcactgcaac ctccacctcc | 4740 |
| ctggctcaaa tgatcttccc acctcagctt cctaagtagc tgggactaca ggcacacacc | 4800 |
| actacgctca gctaattttt ttttttttt ttttttggt agaaacgggg tttctccatg | 4860 |
| ttagccaggc tggtctcaaa ctcctgggct caagcaagct gcctgcctcg gcttcccaaa | 4920 |
| gtgctgggat tacaggtgtg agccaccacg cccagccact ctctgtgttt ttaaattatt | 4980 |
| ccagcttcac cacttaatga ctacacactt gggtaacttg cttctctcct gtgcctcagt | 5040 |
| tttctcatct gtaacatggg gctactcatg gtattgacct cataggtgt gtctcagtct | 5100 |
| attttgtgct gccatacata atacttggga ctaggtagtt aataaaaaag agaaattgat | 5160 |
| ttctcacagt tctggaagct gggaagtcga agatcaaggt gctggcaggt ttggctgtct | 5220 |
| ggtgagagct gcatttggag gaatgctgcg tccttacata gacggtggga ggtagaaggt | 5280 |
| ggaagggcag gtgagccccg tgctgggcga agcctcttt atgagggcct taatcccact | 5340 |
| catgaggaag gagaccccct cgcctaatca cctatcacag gccccatctg ttaatcctct | 5400 |
| cacattggca gcacctgaat tttggagggg gacacgttta aacatagca ggttgtcctg | 5460 |
| acaaaggaag aaagtgcagg ccgggcgtgg ttgctcacac ctataatccc aacattgtag | 5520 |
| gaggctgagg caggcaaaat gccccagcc tgggcaacac ggctccaaat ttgaccagcc | 5580 |
| tgggcaacat ggcaaatccc tgtctctaca aaaaaaaaa aaaaattagg tgtggtggtg | 5640 |
| cacacctgta gtatcagcta ctcaggaggc tgaggtggga ggatagcttg agcctgagag | 5700 |
| gtcaaggctg cagtgacctg agatcatgcc actgcattcc agcctgggca acagatcgag | 5760 |
| accctgtctc agaaagagaa aaagaaaaaa aaggaatgca aagcacttag ggcagtgcct | 5820 |
| agcactaagg atccactaaa tactgttctt gcaaattgaa gcatgctgcc tctgacaacc | 5880 |
| ttgttaatat aaaagaggcc catttccctt ctacctgtac ctctttgcca tttcttataa | 5940 |
| aggaagctga gctgttaata gttcaatgtg attggcctgg cacggtggct cacacctgta | 6000 |
| atcctagcta ctggggatgc tgaggcagga gaatcgcttg aacctgagag gcggaggttg | 6060 |
| cagtgagcca agttcatgcc actgcactcc agcctgggca acagagtgag actgtcaaaa | 6120 |
| aaaaaaaaaa gtttaatgtg atcactgcac attttcccc ctcataccaa ggtgctgcaa | 6180 |
| gtctacatac aaatatatgt catttctttt tttcttttt ttttgtattt tcttttttct | 6240 |
| tccttccctt ccctctctcc cttcctctca cttctttcat tttaaataaa aatgggttca | 6300 |
| tattcacttg ctttttatc agttaataat atagcatgga tatcttttg agtcactaca | 6360 |
| tatagttaat tcattttaat ttttttaatt tttaaattt gtttatttga cagggtct | 6420 |
| ccctctgtca cccaggctgg agtgcagtgc ggcgatcacg gatcactgca gcctcaacct | 6480 |
| cctgggttca agtgatcctt ccatctctca gcctcctgag tagttgggac tacaggcata | 6540 |
| caccaccatg cccagctaat ttttgtacgt tttgtagaga agggatttcg cttttgtcat | 6600 |
| gttgcccagg ctggtcttga actcctgggc tcaagcaatg ttcccgcctt ggcctcccaa | 6660 |

```
agtgctggaa ttagaagcgt gagcaaccgt acctggtcaa cagtctctaa aaattttttt   6720
ttatgacaag gtgtcactat gctgcccatg ctggtctcca tctcctggcc tcaagggatc   6780
ttgccgcctc agccttccaa gtagctggat tacaggctcc agccactgtg cccagccagt   6840
ttaactcatt ctttttttata tattttttac ttttatctta atttatttat ttttctgaga   6900
cagggtctta ctctgtcacc caggctggag tgcagtggca agatctcagc tcactgcaac   6960
ctctgcttcc tgggttcaag cgattctcct gcctcaggct cccgaatagc tgggattaca   7020
ggtgcccgct accacaccca gctaattttt gtattttttgt agagacaggg tttcaccatg   7080
ttggccagga tggtcttgat ctcttgacct cgtgacctgc cgcctcagc ctcccaaagt    7140
gctgggatta caggctcgaa ccaccgtgcc tggccaactc attcttgtta acagcaaaat   7200
atcctgtagt gtggatgtac ccataatttc ttaaaatgtt ccccatagac aatcaggtta   7260
tatctaattt ttgccagtga aaagcatggt gtaatacaca tctttgctct tatagcctga   7320
agcttttagt ctgtagaaca gattccccca aattggagag cgagataaaa gatttatgtg   7380
tctttaaagt ttcaagagat tctgcctcat tactttccct aaaggttgag gcagttctta   7440
tccccaccag taaggtgcca atttttctgt tggtacaatc ttaataaccc tgggtgttat   7500
ttgttttaca ttttgtgggt aaatgtaaac tcacggtaaa tgtaaacaca gtacccatgt   7560
aaacgaatgg gtaaatgtct cattttaatt ttgcttttcc tgacaggtca cgcagagcat   7620
cttttttttt ttttgagacg gagtctccca ttgtcaccca ggctgagtg caatggtgca    7680
atcttggctc actgcaacct cccccctcccg agttcaagtg attctcctgc ctcagcctcc   7740
caagtagctg ggattacagg tgcctgccac cacacccagc taattttgt attttagta     7800
gagacagggt ttcaccatgt tggccaggct ggtctcaaac tcctgacctc aggtgatctg   7860
cccaccttgg cctcccaaag tgctgggatt acagttatga ccacagagc ccagttgtca    7920
acattattta ttaaatcagc cactgattta aatgcttcct ttaatcttca gtgcttttaa   7980
ggggaaaata catttctggc tacaggagat ggaatgcaat aacctaatgt caaacaaagc   8040
cgccccctcc tttacagact gcaactcccc tgtagctgaa ggtttgctgg ttggtaatgg   8100
gttttccgtg tgtgctttgt gtgtgtctct gtaggcagaa gagcactgat cgtactggct   8160
cactcagaga ggacgtcctt caactatgcc atgaaggagg ctgctgcagc ggctttgaag   8220
aagaaaggat gggaggtggt ggagtcggac ctctatgcca tgaacttcaa tcccatcatt   8280
tccagaaagg acatcacagg taggaggagt tcctcctccc ctctttaatt agttctttgc   8340
ggatctcctt gcctgtgggt cctctggccc agctttggcc cctctggccc cagcctctct   8400
ttttcttctc tgcaggtaaa ctgaaggacc ctgcgaactt tcagtatcct gccgagtctg   8460
ttctggctta taagaaggc catctgagcc cagatattgt ggctgaacaa agaagctgg     8520
aagccgcaga ccttgtgata ttccaggtat gggggacat cggaaggggt gtcagggaca    8580
tttgcgtgct tattgtccta gacatgtacc taattagcta tgagatctta aacagttacc   8640
cactttactg cattctctgc aaataagggt gattacttta aaggtgcagt attacatgga   8700
tttcacagat attgggaatc tggctgtatt actgttgcat gtgtaaatgc aactgcaagg   8760
ccaggcacgg tggctcacgc ctgtaatccc agcactttgg gaggcaagg caggtgaatc    8820
acaaggtcaa gagaccaaga ccatcctgac caacatggtg aaaccctgtc tttactaaaa   8880
gtacaaaaat tagctgggcg tggtggcatg tgcctgtagt cccagctact ctggaggctg   8940
aggcaggaga atcacttgaa cccgggaggt ggaggttgaa gtgaaccaag attgcgccac   9000
tgcaccccat cctggtgaca tggcgacaga gcgagattct gtctcaaaaa aaaaaaaaaa   9060
```

```
agaaagaaag aaatgcagct gcagagatga tgtacagtcc ttgagcttgc tttcttccag    9120
gtacttagtc tccccttcag ttagcgattc cttcagttag cgattccttc agttagcgaa    9180
tcctgcggtt agcgattcct gttggactct ctcaaaattt gcagttctcc tcctttctcc    9240
ataagaatcc caaatacttt gtagaataat ccatgagaca ttgacttctc tgccattgta    9300
gcctgccagc tgaaggggc tttgaaaccc tgctgaatgt gttcctgcag caaaccacgg     9360
cctttcttct tcgggaagct gccttaccgt ttagcagaca atgctgggat tgtgcgtgca    9420
tctcgtcagt gatctttcct ataaatgtga ctgtactcaa tgactttgct tttacaattc    9480
cagccagtct tttgatattg aacatagaat gtatatgatc ctggaaacca cgaggagggt    9540
ggtacaggct gtgtttttt tttctctctc tctctctttt ttttttttag ttattcaatc     9600
agctacaaaa catccaatcc ttgaagtcct ttattttacc cacaggcctg ttgctaagaa    9660
tcaaagccac atgccactag ccagtacccc aaaggacggc tttaaaaaaa aattaaattg    9720
gagacaaggt ctcacggtca cccaggatgg agtgcagtgg catgatctct gctcactgct    9780
gcctcaacct cctgggctca aatgatcctc ccacctcagt ctcccgaata gctgggacta    9840
tcagtgcaca ccaccatgcc ctgctaattt ttttaatttt ttgtacaaat agggtctcac    9900
catgttgccc aggctggtct caaactcttg ggctcaagtg atctgcctgc ctggacctcc    9960
caaaaggctg ggattatagg catgtgcctt tcatatcttt aaatcatgaa tcaaggataa   10020
gaaaacctcc tggtatagtc cttactctgc ttttattagg ataagaggtc agacaagact   10080
ttctcatggg aagtccctga tgaaccttag tcacccctaat tattatttat tataattttt  10140
attttttaac attttattta tttatttatt tgttttttgag atggagtctc gctctgttgc  10200
ccaggctgga gtgcaatggt gcaatctcgg ctcactgcaa cctccgcctc ccgggttcaa   10260
gccatttttcc tgcctcagcc tcccaagtag ctgggactac aggcatgcac caccacgctt  10320
gactttttgt attttttagta gaaacagggg ttccccatgt tggccaggct ggtctcaaat  10380
tcctgacctc aagtgatcca cccaccttgg cctccaaaag tgctagaatt aaaggcatga   10440
gcaactgcac ctagccacgt tgatgatgat gatgattatt attattatta ttattattat   10500
ttagagatgg agtcttgctc tgtcacccag gctggaatac agtggtgatc acagctccct   10560
gcagcctcca actcctgggc tcaagcaatc ctcctgcctc agcctctcat atagctggga   10620
ctagagatgt gcaccatcac atcaggctaa tttttaaatt ttttttgtaga dacaaagtct  10680
cactttgttg cccaggctgg tctcaaactc ctgggctcaa gtggtcctcc caccttggcc   10740
tcccaaaata ctgggattat aggcatgagc aaccacactc agccatcaca ctgattatta   10800
gtttgcattt ttgagtgatt ttgtttattc taagtgatat gatttttcat ccacgataac   10860
aagggacagt cataaaatga agaaggccta cattttttttc cacgatgggg tctcactctg   10920
tcacccaggc tggagtgcag tggcacgatc tcggctcact gtaacctcca cctcccgggt   10980
tcaagtgatt ctcctgcctc aacagcccga gtagctagga ctacaggcgt gcgccaccac   11040
gcccggttga ttttggtatt tttagtagag atgaggtttc accatgttgg ccaggctggt   11100
ctcaaactca tgcccctcaag tgatccaccc gccttggcct cccaagggc tgggattaca   11160
ggcttgagcc actgcgcctg gccaacagtc atattgttga taccacacct actaaagcaa   11220
actcttggga aaatactgat tgaagcaaca gcatgaagca aaccttgttt gcaatccttg   11280
ctatttagac tttgctgcca aatgtgattt catacaaaca agtttcatat caacaagtct   11340
tctgtgtatc tagctttact cggacccact caatatttgc attttcaggg aaaaagaaga   11400
```

```
ctgtcaagtt ggctgaccaa ggacaataat gatctctttc cttaaagtgc taactcccca   11460
ggaggaatgg gaaaggtgtg aagaggggct tcccacacag tgccatcatg gggagcggct   11520
cagcactccg agccaccttc tgggcttggg gagccctgg tcttacctca atgatgtctt    11580
ctgtcccaca gttccccctg cagtggtttg gagtccctgc cattctgaaa ggctggtttg   11640
agcgagtgtt cataggagag tttgcttaca cttacgctgc catgtatgac aaaggaccct   11700
tccgggtagg tggatggttc tgaatgctct gacagccagc ttctgggtgg tctgtcctga   11760
tgcagggtg tttgtttgtt tgtttgtttg agatggagct ccctcttgt tgcccaggct     11820
ggagtgcagt ggcgggatct cggctcactg caacctccac ctcctgagtt caagcgattc   11880
tcctgcctca gcctcccgag tagctgggat tacaggcata tgccaccatg cccggctaat   11940
tttgtatttc tagtagagac ggggtttctc catgttggtc aggctggtct tgaactcctg   12000
acctcaggtg atctacccgc ctcagcctcc caaagtgctg tgattaccgg tgtgagccac   12060
tgtgcccggc tctgatgcag ggttttgagc acaattagat cctaagccta ggctccaggt   12120
ccttcgggag agacgcatga tcaagttttt acagatggaa tgacatgatg tttgggattt   12180
gttttaaaat gctccagagg ccgggcgcag tggctcacgc ctgtaatttc agcactttgg   12240
gaggccgagg caggcagatc acctgaggtc aggagtttga ccagtctg gccaacatgg     12300
cgaaaccccg tctctaccaa aaatacaaaa attagctggg tgtggtggcg gcatctaca    12360
atcccagcta ctcaggaggc tgagccagga gaattgcttg aaacccagga ggtggaggtt   12420
acagtgagcc aagatcgcgc cactgcactc cagcctgggc aacaaagcaa gactccatct   12480
taaaaataa aaggccaagc acggtggctc atacctgtaa tcccagcact ttgggaggcc    12540
gaggcaggcg gatcacaagg tcaggagatc aagactatcc tgcctaacac ggcgaaaccc   12600
cgtctctact aaaaatacaa aaaacttag ccgggtgcgg tggcacgtgc ctgtagtccc    12660
aggtactcgg gaggctgagg caagatagtt gcttgaaccc gggaggcaga ggttgcagtg   12720
agccgagatc gcaccactgc actccaggct gggtgacaga gcgagcctcc atatcaaaaa   12780
caaaaacaaa aaaaaaatta gccggatgtg gtggtgggca cctgtaatcc caactatttg   12840
ggaggctgag gcaggagaat cacttgaacc cgggagacag tttgcagttg gttgagatgg   12900
tgctactgca ccccagcctg gcaacagag ccagactctg tctcacagga aaaaaaaat    12960
gaaataataa aataaaataa aacgctccag agaaaagg ggtcatgggt cgagctaaaa    13020
ctagaatagc agaatactga gaggtgaagg tgagtgatag atgcagcact attttctcat   13080
ttacatgtgt taaaaatttc cataataaaa acaaaagaag gcctgtcttc atttttttgga  13140
ggcccaaatc ctgcacaggg aacccttcga gaccttccag atgaaagagc ttgtcctacg   13200
ccatgcctag cccgtgggag gatggataag aacaaccaat aactccacct aggcagccag   13260
cagccagcac tgattttgga tatggtgaca gcctcgtcct aagccacatg tggggtttg    13320
gaatccttca tttgcccag gccaccggtc tgtagaccat ctaggctggc actcctgcag    13380
agtcatatta tgtagctcag gggagccaaa gtatgaagta atataaacag caaataggac   13440
agacttgtgt gttctttcc ctggagctgt tcattaact tcttgtcacc aagggggatgt    13500
ggagggaagt gaagtttgtt attgcttttt cttttgcaga gtaagaaggc agtgctttcc   13560
atcaccactg gtggcagtgg ctccatgtac tctctgcaag ggatccacgg ggacatgaat   13620
gtcattctct ggccaattca ggtacctcat tttctttct tttctttttt ttctttgaga   13680
cggagtctca ctctgtcatc taggctggag tgcagtgaca ccatcttagt tcactacaag   13740
ctccgcccgc tgggttcgag caattctcct gcctcagcct actgacaggc acccgccacc   13800
```

```
acactcggct aattttttgta ttttttagta gagacggggt cttgccatgt tagccaggct    13860
ggtttcaaac acttgacctc aaatgattct cctgcctcag cctcccaaag tgctgtgatt    13920
acaggcgtga gccactgcac ctggccaggt acctcatttt caacgaacct tcagggggaat   13980 tcattcattg agccttcgtg gggttcaaaa cctcaagata gcatctgaaa atagatcttg    14040
agttgtgaag atgaaagcat ggtcataatt cagaatgatg ggagcctcct ttaagaacct    14100
gcctgccttc ccaggtgcct gtgtgtgaac acacctgcgt gtgcatgtgt tcaaacagca    14160
ttctgtccca gccaaggact agtgtgaatc actactcttg atttgtatag ccgtgggccc    14220
tggtctcacc agatgactga catctctctc cagccttcct gtccttctcc aggttgctga    14280
tacagtccca tagactatta gagcccaaga caatttaaga aatgatttac tgggaggctg    14340
aggcagaagg atcgcttgag cccaggactt tgagaccagc ctgggcaaca tataagacct    14400
catctctaca aaaaaaaaaa acaaaattag ctgggtgtag tcatacacct gtggtcccag    14460
ctacttggga gtctaaagtg agagaccag gagttcgagg ctgcaatgag ctatgatcac     14520
accactgcat gccagcctgg gatacagggc gagaccctgt ttcgaagaaa aaggaaataa    14580
tttagtccag ccagtttata catggataaa actgaagcct ggggtgggct tattggtgtt    14640
accaaaccct caagataatt tctataaaga gggaggttgg agagaagagc cagtgagtgg    14700
ccacttatga aaatcattta tcaagactca tctgggcctg taatcccagc actttgggag    14760
actgaggcag gcggatcact tgaggtcagg agttcgagac cagcctggtc aacacagtga    14820
aaccctgtct ctactaaaga tacaaaaatt atctgggcat ggtggcgcat gcctgtaatc    14880
ccagctactc gggaggctga ggcaggagaa ccgcttgaac ccaggaagtg gaagccgcaa    14940
tgagccgaga tcgtgccatg gcactccagc ctggacgacc gagcgagact ctgcctcaaa    15000
aaaaaaaaaa aaaagaaaaa gaaaaaaagg actcatctag ttatatggag aggcagaaa    15060 atgcacccac gcaggtcttg gtgagtcacc tgccaagaaa ctgagactcc ctaaagtaac    15120
agaacttcca gccttcttgg caaaggatcc aggttggcac agtttcaagg tttatgcatt    15180
taaagaagaa cacacctgag aaggctaaaa ttggtaacgg ctaggtagag ggtaagagag    15240
agacgctagc tctgaactga ttctctagtg tgcctgaggc ctccttatca gagtgtctta    15300
ctgagaagcc cagaccaact tctgttgttt atagtacaac tgcatggaat tggttgactt    15360
acctctctgt gctttctgta tcctcagagt ggcattctgc atttctgtgg cttccaagtc    15420
ttagaacctc aactgacata tagcattggg cacactccag cagacgcccg aattcaaatc    15480
ctggaaggat ggaagaaacg cctggagaat atttgggatg agacaccact gtattttgct    15540
ccaagcagcc tctttgacct aaacttccag gcaggattct taatgaaaaa agaggtacag    15600
gatgaggaga aaaacaagaa atttggcctt tctgtgggcc atcacttggg caagtccatc    15660
ccaactgaca accagatcaa agctagaaaa tgagattcct tagcctggat tccttctaa     15720 catgttatca aatctgggta tctttccagg cttccctgac ttgctttagt ttttaagatt    15780
tgtgtttttc ttttttccaca aggaataaat gagagggaat cgactgtatt cgtgcatttt    15840
tggatcattt ttaactgatt cttatgatta ctatcatggc atataaccaa aatccgactg    15900
ggctcaagag gccacttagg gaaagatgta gaaagatgct agaaaaatgt tctttaaagg    15960
catctacaca attttaattcc tcttttttagg gctaaagttt tagggtacag tttggctagg    16020
tatcattcaa ctctccaatg ttctattaat cacctctctg tagtttatgg cagaagggaa    16080
ttgctcagag aaggaaaaga ctgaatctac ctgccctaag ggacttaact tgtttggtag    16140
```

| | | | | | |
|---|---|---|---|---|---|
| ttagccatct | aatgcttgtt | tatgatattt | cttgctttca | attacaaagc | agttactaat | 16200 |
| atgcctagca | caagtaccac | tcttggtcag | cttttgttgt | ttatatacag | tacacagata | 16260 |
| ccttgaaagg | aagagctaat | aaatctcttc | tttgctgcag | tcatctactt | tttttttaat | 16320 |
| taaaaaaaat | ttttttttga | agcagtcttg | ctctgttacc | caggctggag | tgcagtggtg | 16380 |
| tgatctcggc | tcactgcaac | ctctgcctcc | caggttccag | caattctcct | gcctcagcct | 16440 |
| ccctagtagc | tgggatgaca | ggcgcctgcc | atcatgcctg | actaattttt | gtattttttag | 16500 |
| tagagacggc | gtttcaccat | gttggccagg | ctggtctcaa | actcctgacc | tcaggtgatc | 16560 |
| cgcctacctc | agcctcccaa | agtgctggga | ttacaggcgt | gatccaccac | acctggccct | 16620 |
| tgcaatcttc | tactttaagg | tttgcagaga | taaaccaata | aatccacacc | gtacatctgc | 16680 |
| aatatgaatt | caagaaagga | aatagtacct | tcaatactta | aaaatagtct | tccacaaaaa | 16740 |
| atactttatt | tctgatctat | acaaattttc | agaaggttat | tttctttatc | attgctaaac | 16800 |
| tgatgactta | ctatgggatg | gggtccagtc | ccatgacctt | ggggtacaat | tgtaaaccta | 16860 |
| gagttttatc | aactttggtg | aacagttttg | gcataatagt | caatttctac | ttctggaagt | 16920 |
| catctcattc | cactgttggt | attatataat | tcaaggagaa | tatgataaaa | cactgccctc | 16980 |
| ttgtggtgca | ttgaaagaag | agatgagaaa | tgatgaaaag | gttgcctgaa | aaatgggaga | 17040 |
| cagcctctta | cttgccaaga | aaatgaaggg | attggaccga | gctggaaaac | ctcctttacc | 17100 |
| agatgctgac | tggcactggt | ggttttttgct | ctcgacagta | tccacaatag | ctgacggctg | 17160 |
| ggtgtttcag | tttgaaaata | ttttgttgcc | ttcatcttca | ctgcaatttt | gtgtaaattt | 17220 |
| ctcaaagatc | tgaattaaat | aaataaaatt | catttctaca | gacccaca | | 17268 |

<210> SEQ ID NO 6
<211> LENGTH: 49909
<212> TYPE: DNA
<213> ORGANISM: human

<400> SEQUENCE: 6

| | | | | | |
|---|---|---|---|---|---|
| tcctcctggg | tcttgcctag | cggcgggcgc | atgcttagtc | accgtgaggc | tgcgcttgcc | 60 |
| cggggcccgc | gccccctac | cccgggggacc | gccccgggc | cgcccgcccc | acttggcgcg | 120 |
| ccacttccgc | gtgcatggcc | ctgctgcccc | gagccctgag | cgccggcgcg | ggaccgagct | 180 |
| ggcggcgggg | ggcgcgcgcc | ttccgaggct | tcctgctgct | tctgcccgag | cccgcggccc | 240 |
| tcacgcgcgc | cctctcccgt | gccatggcct | gcaggcagga | gccgcagccg | cagggcccgc | 300 |
| cgcccgctgc | tggcgccgtg | gcctcctatg | actacctggt | gatcggggc | ggctcgggcg | 360 |
| ggctggccag | cgcgcgcagg | gcggccgagc | tgggtgccag | ggccgccgtg | gtggagagcc | 420 |
| acaagctggg | tggcacttgc | gtgagtaccg | ccgttttgtt | cggcgggggg | gcgcctcttt | 480 |
| gtctcggtct | ttcgggggac | agcctgtgct | cgttcctatg | gcgatcctgt | ccccggcgc | 540 |
| tgggcttttcc | tcttttccac | ccccgcaact | ccccattccg | aagccaggaa | cccagcaggt | 600 |
| ggaggagaga | gaggcgtccg | ggggcttctc | tgcggcccgc | aaagccgagc | cagcgtctgc | 660 |
| ttccgcacgg | atgcgatatt | gaccagggcc | ggggcgggtt | agattaaccct | tcctccatcc | 720 |
| tcacttgtcc | aagtgggaga | ggattggatt | ctgttcttga | ccgcgtgaaa | cacaaaactg | 780 |
| catctgggaa | cattgctggt | ggcctgtgtg | tagggacgag | ggtgacggtg | ccatagatcc | 840 |
| tggttcttga | aaaatgtaga | tcctggttct | cccgtttcaa | gggcagaatg | atttatagcg | 900 |
| gttgttgtca | accttggcta | cacattcgaa | tcacctgagg | gtgcctggat | tcccgactta | 960 |
| attggtctga | ggtgcacttg | ggctttggga | tgtttcccga | cttaattggt | ctgaagtgca | 1020 |

```
gcctgggctt tgggattttc gggtgatctg aattgcagcc aaggcgacct tgagtaggtg      1080
agttctcaga gcttttgttt tgtcttggtt ttatgtggat tgcaaaacta aaaacagagg      1140
gatgtaaatc ctgagattta caaaattcat aattttttgaa ataagggtt tttgtttgtg      1200 tttgtttttt gagacagggt cttgccctgt cacctaggct agagtgcagt ggccatcata      1260
gctcactgca gcctcgaact cccgggctca agggatcctc tcaccttggc ctcctgagta      1320
gctggaacta caggggggcta atcaccacgc ctagttaatt attattattt tttgtagaga      1380
tgggggtctc gctatgttgc ccttgctgat ttcaacctct tggactcaac cgatcttccc      1440
gcctcagcct cccaaagtgc tgggattaca agcctgagcc actgcactca ttctaaaaat      1500
aaatgttgtt tccaagttat tggtgtgccc gcccttttct atcacaagat ttgggtgttg      1560
acgattaaaa tgctgtatcc aagaggaacc tgggatttgg gataggttct ctaaattcct      1620
ttggagatga atatttaaat tatgtcaaat tgggagctct ttaaggacag ggatgggctt      1680
ctgtgtttgt gtgtctctta tcaccttaaa atcccttgct caataagcac ttgtgcaatg      1740
aatgaaacta aaaatggaca gttatgaaaa ggttgacttc attgttcagt gccttggaga      1800
tgaacatgga gatgaagaga aaggaaaaat ctctgttaat tatcaacttg cactttgaca      1860
ccatagtcca gacagaaggt tagaaatctg tctctccaga aggcagattg tggggtgcca      1920
ctaagtgccc ccctcccaca cctcatgaga gtacttgatc acttctcact tctgttctgc      1980
tctccacatt ttctctgtct tcctctttct ctacttatgt tataatgtgc ttcagaggtt      2040
cacccacttt accttcctgt tatgaattct tttttttttt tttttttga gagggagtct      2100 cactctgtca cccaggctgg agtacagtgg tgcaatctgg gctcactgca acctctgcct      2160
cccaggttca agcagttctc cgtctcagc ctcgagta gctgggaatg caggtgcatg      2220
ccaccatgcc cggctagttt ttgtactttt aatagagatg gggttttgcc atgttggcca      2280
ggctggtctc aaactcctga cctctggtaa tccacccacc ttggcctccc aaagtgcttg      2340
gattacaagc atgagccacc acacccagct aatttttttat ttttaaaatg tatttatcta      2400 ttttttttc gatatggagt cttgctctgt cacccaggct ggagtgcagt ggtgcaatct      2460
cggctcactg caacctccgc ctcctgggtt caagcaactc tcctgcctcg gcctcccaaa      2520
ttgctgagat tacaggtgcc actacaccca gctaactttt gtattttag tagagccagg      2580 ctggtcttga actcctgacc ttgtgatccg ctcacctcag cctcccaaag tgctgggatt      2640
acaggcgtga gccaccacgc ctggcctgtt tttattttat ttattgtttt ttagaaacag      2700
ggttttgcca tgttgcccaa actggtctct tatgcctgtg cttaagcagt cggcctgcct      2760
tggcctccca aaatgctggg attacaggca tcagccacca ctcctgtccc atttttttgta      2820 ttttaagtgc tgggattggg ggtgggtagg gagaaaacga tagatataaa catttgtgag      2880
acatgtccct tcccttaagg aattttgtgg ttgtgaaaga aaaaaatatt ggaaccccaa      2940
agtatgccag aaggaaagtt cagcttggga actgaatcac acaaatactg cttttccttt      3000
tgttcccaaa cagacagctg taatttcaca atcccatgtc atagccttat ctcctctact      3060
cctgcttttc acttttactt tatcttatgt aaaatgtaga tttactgagg ctcataagaa      3120
cctcacaaga atgtaaccat ctaggctggg cgtgatggct cacgccagca ctttgggagg      3180
ccaaggtggg cagatcacct gaggtcagga gttcgagacc agcctggcca acacggtgaa      3240
actccgtctc tactaaaaat acaaaaatta gccgggtgtg gtggcacatg ctacttggga      3300
ggctgaggca tgagaatcac ttgagcccag gaggcagagg ttgcagtgag ccaagatcat      3360
```

```
gcctctgcac tccagtgtgg gcaacagagt gagactctgt ctcaaaaaaa aaaaaaaaaa    3420
aaaaaggtgg ggggttgggt agtattcttt gacattcgga acctcaaaag atgggtccca    3480
ggcctaggca tcaaaacggg atatgttgtg taatcaaatt tggagcacag agtgtctctt    3540
taatagaaat aagagatgag aagctgatgg gtaggttgtg gtttgaaaaa tgtggagttt    3600
ctggacacac agtgaactat gggggcaggg gtgggtttga gcaaaccagt gactcagtga    3660
aagtagtttt gtggtaagcc ataggattga gatctcaccc ttggcgatgc ccaatagaag    3720
tttgtctttc tgtcttttc tttttctttt cctttcagtt tatagagata gggtctcact    3780
acattgccta ggctggtatt gaactcctgg actcaagcaa tcctcctgct ttggtctccg    3840
aaagtgttag gattacaggc gtgagccact gtgcacggca gaagtttaag attggttctc    3900
ccatgagttc tttcctaaat aaaatccatt aatttctaac gcttgggaa gttttaaagt    3960 tgtggtgaat gaactcacac ggaaggttca aattagaatg tgtgtctagc agtggtcatt    4020
tacaggtagt gagattggtt ggttttcat tgtttatca gtgttccttc atttaattgt    4080
tcaaccgtta agtttatgg gaggccattg ttttggacca gtctcctgta ctaggtccca    4140
gcagacctgg gtgtgtgtgt gtgtgtgtgt gtgtgtgtgt gtgtgtttgt tgctctgtca    4200
cccaggctgg agtgcagtgg ggtgatctcg gctcactgca acctccgtct cctgggttca    4260
aggaattcat gtgcctcagc ctcgtaagta gctgggacta caggcgcagg ccaccacgcc    4320
tggcaaattt tttgtatttt tagtagagat gaggtttcac catgttggcc aggctgatcc    4380
cgaactcctg acctaaagtg atccacccgc ctcagcctcc caaagtgctg ggattacaag    4440
tatgagccac cgcgtctggc atgttgtttc atttttaaga dacagggtct ccctctgttt    4500
cccaggctgg agggcagtgg tgtgatctca gctcactgta gcctcaaact cctgggctca    4560
agcgatcctc ccacctcaac ctcccgacta gctggttctg caggtagata ccactgagcc    4620
ttgcttgaat tcagcatttc aagtctccaa aaggttaagt atattgctta tctcatgatc    4680
tcgtgtagac tggagagaaa tgcaaagatc gcccaaagtc aaggtgaatt agagccttct    4740
gggagctttg cctctgtggt tcgcttctct gcctacacac gtgatgggag agtcagctta    4800
aggaaaagtt gttttctaaat tgctgctccc tttgccccag ggcctgggga acttgcggtc    4860
ctgggttcct gctgagtgta ctgattctgt gataagaata accaggttcc tgtggttttg    4920
gcgagtagta cttaccaatg agagttgggt agtaagggtt gatcatgtga caaaagttca    4980
tgattgccaa gtcacagtga actatgctgc acagcagcag ttggagaggc ctaggggaga    5040
gagaggtagg ggcttttgaaa gatcagtgaa cagcaggctg ctcagtgaat cattgttcat    5100
ctaggctgaa aacaattacc cagcaacatg taaatcataa cctcatttgg aagtgatact    5160
gtgtactttg atattatgat gtctataccc tggtaaagct gaacactgga catgcttttt    5220 ttttttttt tttttttga gacagggtct cattgtgtca cccaggctgg agtgcagggg    5280
catgatcata gctcactgca accttgaact cccaagctca agtgaccctc ccacctcagc    5340
ctccccagta gtcaggacca caggcacatg gccaccacca tgccctggct gatttttaa    5400 attttttagta gagacaaggt cttgctttgt tgcccaggct ggtctcgaac tcctgagctc    5460
aagcagtcct cccaccttag cctctcaaag tgctgggatt acaggcatga gccaccgtgc    5520
ccagcctgaa catgcattat taaatgcaat ttactaaaag gaggtcagtt taaaggaact    5580
ctgtcatcag ttcctgcaat attgacagat agccctccga aatagaaggt taccctaatg    5640
tgtctcctgg gtttagaatt tcatagaatg gggcccaccc atattcataa gtgacaaata    5700 aggagtggc cataaagggt ggggctagtt aaagcaagca aatgctattg ttgaaatttg    5760
```

```
gcttttaact taccttgttg actgcttcct tttttttgtac tagtcttcat atactgttgc    5820
tttgccatct gcctcaaaac ccactaaatc tgcagggcta ggaaaagata gactgcctct    5880
gaatccttca gggtgtctat ttctttgtaa aacatacttt gaaaagtaac cacagagaat    5940
gctttttttt tttttttgaga cagagtctgg ctgtcaccca ggctggaatg tagtggtacc    6000
atcttggctc actgtaacct ctgcctcccg ggttcaagcg attctcctgc ccagcctcct    6060
gagtagctgg gactacaggc gtgtgccact acacccagct aattttttt ttgtagagac    6120
gaggtttcac cacgttggcc aggctggtct cgaactcctg acctcaaccg atccacccac    6180
ctcggccttc caaagtgctg ggattataga aatgagccac cgtgtctgtc caagaatcca    6240
agaacttttt ttatagaggg aaactaaagg aatgatatgg aaatactgat acccttggc     6300
tttttttttt tcttcttgac acgaagtctc actctgtcac cctggctgga gtgcagtggc    6360
acgatcttgg ctcacggcaa cctccacctc ccaagttcaa gtgattctcc tacctcagcc    6420
tcctgagtag ctgggattac aggtgcccgc caccacacct ggctaatttt tttatatttt    6480
tagtagagac tgagttttgc catgttggcc aagctggtct caaactcctg acttcaagtg    6540
atccgcccac cttggcctcc caaagtgctg ggattacagg cctgaaccac catgcccgga    6600
ccactttggc atttgtaagt ggcttccagt cagtgagaat tcattacctt ctattcacta    6660
ggtgttgcaa cattaaatat tactgcagtt acttttgcac cagcctaata ggatgtggag    6720
gtcctaggtc cttttctttt tggggacgg gagatggtgg gtatcaggta atagtgggga     6780
ctgacatcca gaagagttgt ctcacaaaac tctttcttct tctccccgga tgcccgtaac    6840
aattattttt attttttaaa ttttttttgtt ttttgaggca gggtctcact ctgtcgccca    6900
ggctggagtg cagtggcacg atcatggctc actgcagcct caatatcctg ggttcagatg    6960
atcctcctgc ctcagcttcc caactggctg agactacagg ctgttatttg tggtgatggg    7020
gtctcgctgt gttgtccagg ctcctctcaa actcctgggc tcaaaggatc ctccagtctt    7080
gacccgtcaa aagtgctagg attacacacc tgtgtgtgag ccacggcacc cagtcacact    7140
ttttaaaaat ctggtgattt cctgagactg gaaggttcag gttaatgttc tgcttagcta    7200
agaattgaac aaaaacagcc tttgttaata tctcttgcaa atgtatccat tgattttctt    7260
gctttagatt ctgctttaca cagactgctt ttttttttct ctttttctca agtttgatgc    7320
ctccctgaac taaccttcat ctgaaatgaa aaaaagact ttgaaggtgg agacatggat     7380
attgaatagt gaatatgtgc cagggacagg gccatgtcca gacagcatta tatttagtca    7440
tggttggtgt aaagctgatg aaatgcaaca gagacaggga tctttatctg tttaagtcat    7500
cagtatagtc caagccccta gaacagtgtt ttgcacatag caagtactca gtatatagtt    7560
gctgaaataa ttgagttgat aaatcgatag tgttttgcct tggaaattat gactcgtcta    7620
ttttctgagt agttctcatt ctggtcttga attagatttt aggcagcaaa gaaggacgac    7680
agagggagga aactgtaggc aattctgtgg tgggaggttg tggggaacca gaggaaggaa    7740
gttaacaatt tttttttgag acagggtctt gctctgtcac ccaggctgga gtgcagtggt    7800
gcaatatagc tcatggcagc ctcaaactcc tgggctcaaa cgatcctccc acctcagcct    7860
cccatgtagc tgggactaca ggcgtgcaac accacacccg gctaattttt aaattttta     7920
tttgtggaga cgaggcctta ctatgtttct caggccggtc tctaactcgt gggctcaagc    7980
agtcctccca cctcacctcc caagttttg ggattacagc gtgagccacc acacccagcc     8040
gcaagttcac tattgaacac agttgatgtt cttggcaggc gcaattgcag attaaccaag    8100
```

```
ttcttgtttt actgccaaca tgggcaatgt gaagtttcta cctggctagg caggattgaa    8160
ggtaacgagg caggccctag gaaaaatggt gaagcttctg aattttgcca cctgttatca    8220
ccagataaca ggcggcccac tgatcgggat tctgaacact agattgatgc cagcaggccc    8280
actgatcggg gttctgaaca ctagattggt tggaaaagga agctctcagg aatggatcat    8340
cggtttggaa agggaggctg agttacagga gtctccttga tgatgtattt actgaacagc    8400
ctgtgaaatt tgttttctta gctggtgtgt gtggctcacg cctgttatcc cagcactttg    8460
ggaggctgaa gtgggtggat cacttgaggc caggagtttg agaccagcct ggtcaacatg    8520
gtgaaacccc atctctccta aaaattcaaa aattggccag gcgcgtggc tcaggccagt     8580
aatcccagca ctttgggagg ccgaggtggg cggatcatga ggtcagtaga tcgacaccat    8640
cctggctaac acggtgaaac tccgtctcta ctaaaaatac ataaaaaaaa aaaaatttat    8700
ccaggtgtgg tagtacacac ctgttgtccc agctactcgg gaggctgagg caggagaatt    8760
gcttgaaccc aggaggcaga ggttgcagtg agccgagatc gcaccactgc acttcagcct    8820
gatgacagag tgagacctcg tctcaaaaaa aaaaaaaaaa aaaatttaa aaattagctg     8880
ggcgtggtgg cgggcacctg taatcccagg tactcgggag gctgaagctg gagaattgct    8940
tgaactcagg aggcagaggt tgtgatgaac cgagatggca ccactggact ccagctgggc    9000
aacaagagtg agactccatc tcaaaacaaa acaaagcaaa aaaaaaaaac aaaacacctt    9060
agcagggcat agtggtgcgt gcctataatc tcagctactc gggaagctaa gaatcactgg    9120
aacctgggag gcagaagttg cagtgagctg agattgtgtc actgcacact ccagtctggg    9180
cgacagagtg agactctgtc tcaaaagaa aaaagaaac ttgtttctta tccctcatta      9240
atgcccacct ggagaaccgg ggaatctgcc agtgttgtat gctgagggtc ttagcaatgt    9300
gcaactctgg gcaaccagag ccctgagaac tcatctgata tgctccagt ctgggaggca     9360
aacttccttt gtgatcagct gatgtgtttt aggtaggaag gccctggggg aatttatctc    9420
cgcctttccg tatgccttgt gtgcgtgtgg ggagccagca gacgcagaaa taattcagag    9480
gtatcagagt caccatcaca tctatcatag attagaaata gatgctttat ataccttatc    9540
tctgacctgc tcaaaatctc cataatggaa gcattcttcc cttaactgag ctaggagaaa    9600
tttggaaact caccccacctc tagccactaa atgggagagc tgagagtcaa actcctatct   9660
gtctgacttg aggcctgtgc tccctctaac aacctgatgc acaggtcagc tagagcagca    9720
gtccccagcc ttttttggcac caggaaccag ttttgtggaa gacaattttt ccacggacca    9780
gcagtggggt atggtttcag gatgattcag gattcaagtg aatcacattt atttatttat    9840
ttatttattt atttattttt attttttga cacagaattt cactcttgtt gcccaggctg     9900
gagtgcaatg gcatgatctc ggctcactgc agcctctgcc tcctgggttc aagcgattct    9960
cctgcctcag ccttccaagt agctgggatt acaggcaccc accaccacac ctggctaatt   10020
tttgtatttt tattagagac ggaggtttca ccatgttggc caggctggtc ttgaactcct   10080
gacctcaggt aattgcccgc ctcggcctcc caaagtgctg caattacagg cttgcggcac   10140
cacgcccagc ctgcatcaca tttattgtgc actttatttc tattattatt atgttgtaat   10200
atataatgaa ataattatgc aactcaccat aaactagact ccgacggagc cctgagcttg   10260
ttttcctgca actagttggt cccatctggg gctgatggga gacagtgaca gatcatcagc   10320
aattagattc tcataaggag tgtgcaacct acatcccttg catgcacagt tcacaatagg   10380
gttcacgctc ctatgagaat ctaatgccgc cactgatctg aaaggaagtg ggtggagctc   10440
aggcagtaat gctagcgacg gggagcagct ataaatacat atgaagcttc gctcacttgc   10500
```

```
ccgccactca cctcctgctg cagcctggtt cctaataggc acctggcggt cagggagccc   10560
tgagctagag aaaggggaaa gaaggctgag tgcggtggct catgcttgta attccaactt   10620
ttgggaggct aacgtgagag gactgcttca gcccagcatt ttgagaccag cctgcgcaac   10680
atagtaagac cctgtctcta atgtgttgt ttgtttgttt ccttttctt ttgagataga   10740
gtttcgctct tgttgcccag gctggagtgc aatggcacga tctccgctca cggcaacctc   10800
cacctcctgg gttcaagcga ttctcctgcc tcagcctccc aagtagctgg gattacaggc   10860
atgtgctacc acgcccagct aattttgcat ttttagtaga acagggtttt ctccatgttg   10920
gtcaggctgt cttgaacta ccgacctcag gtgatctgcc cgcctcggcc tcccgaagtg   10980
ctgggattac aggcataagc caccatgccc agcctccgtc tctaatttgt aagaaattga   11040
aaaaaaaaaa atttgggggg aaagagaagg gagcagcaga ggggatgggt gagcgagagc   11100
atgccagctt ttcaccctg gcctccccag ctctcactgg aactaagtgt atgtgtattt   11160
tttgagatag ggtctcattc tgttgcccaa gctggagtgc agtggtgcta tctcggctca   11220
ctgtagcctt gacctcccaa gctcaagtga ttctcctgcc tcagcctccc cagtagctgg   11280
gactacaggc ttcactatca cacctggcta atttttgtat tttttctaga gacagtgttt   11340
caccttgttg cccaggctca tcttgaactc ctggcctcaa gcgatccacc tgccttggcc   11400
tcccaaagtg ctgggattat aggcatgagc cgccactccc agcctaaatg tgcttttcgt   11460
tccttccaag tcagaggcgc tgaagtcatg tcatgttgct ggcatgtaaa taggcctcta   11520
aaagcagtgg aaatccctgg aggcctgttc acaggagctg gcaaaatagg acagtggtat   11580
ttcagggtca taggcttcct ttcaaccagt gccccaggcc ccaaagtgtg ttgtgctggg   11640
gcgcagcttc tctggcccaa caaggccaca attttccacc atcctcttcc tctggtttct   11700
ggcccagtgc tcttcaattt tagggaatgt ggagattctg ctgctgcccc ttgagtcagt   11760
atcttggaca ggctcagagc ctctctctgg ctggcactgt aggccaagat actgatacag   11820
tccccaagag cagggactgt atctgtttag tgccttacct tgcataatgc ctggcacaag   11880
tgagtgctta ctcagtacct ctgaatgaat gcctgcaagc taagacgacg tagaagcaaa   11940
aaaggcagaa acttctaaaa aaacaaacca gagttataga caccaggcac cagtgaaagc   12000
ccaccttggc gcttagaaga aacatattcc aaaaaaagaa tatgttttaa aattaaacat   12060
atttttttaaa aacttttta aaaacatat ttttaaaatt agaaaaagaa gccttaaata   12120
actttaaagt agcttcaaat atacatgagg aacaaactga tggtatgtga gagtagttta   12180
gaacattgag tgctttatga cacccttgga ttgcttttga tgattcttgg gaagccagaa   12240
atggtgactg gaagaccagc agtatttatg tagcagacaa atcatctcta cctttgggaa   12300
aattgctttt ggagtctgtc ctagttgaag ccacttagtg aacttaaatg gtgaactgca   12360
gggtataaag gtgtgggtgg aaggcacggg gaagcacgtt gcctgccaaa taactggaaa   12420
aggcaggttg gatgagaaaa tcattcccat tatgggcta gcattgttct cccacagag   12480
tttcgacctc ctttctctgc tcttaccatt aggaaacccc tgctgtgcgt cctcctttct   12540
tagaaatggc ttattctatt tatcccagta atgttgtcag gtactgggg gttgagaagt   12600
agcatatcct cagcttggcc agatgaaagg gcactctaga tagaaagcca tacgtttatt   12660
attattattt atttttagag gtagggtctg gctctgttac ctaggctgga gtgcagtggt   12720
atgatcagag cttattgtag ccttcaactc ctgggctcaa gagatccttc cgcctcagcc   12780
tcctgaatag ctggaactac gggcatgcac caccaaaccc aactaatttt ttatttttta   12840
```

```
tttttttaca gagatggggt ctcagggtct cactgtgttg cccaggctgg tccctaactc    12900
ctgggctcaa gcaatcatct ttcttttcgg cctcccaaag cgtggggatt acaggcgtga    12960
gccaccacac ccagcccata aattattcta attttagta tgaagtactt gtgatactct     13020
gccatgaagg atgcagtgct ggcaggaata gtggaataat tgctgcttgt aaacatttaa    13080
gattctcctg tggattttgg tgagtgatca ttaaactgtt ttccaaaagc atatacaggc    13140
caagcgtggt ggctcatgcc tataatctca gcactttggg aggctgaggc aggagaatca    13200
cttgatctca ggagttcaag accagcctgg gcaatatact gagaccttgt ctctattttt    13260
ataaagtatt tttaattttt atttaaaaaa taaaataaaa agcatataca ggccacgtat    13320
ggtagctcac acctgtaatc tcaacacttt gggaggccga gttaggagga ttgcttgagc    13380
ccaggagttt gagaccagcc tgggcaacat agtgagaccc tgtctctata ttttagaaa     13440 aatatttttt attttttttt aaaagtata tccaggcgtg atggctcacg cctgtaatcc     13500
cagcactttg gatgccaag gcgggtggat cacttgagct caggagttta agaccagcct     13560
gggcaacatg gtgcgactct gtctctacta aaaataccag gcatggcggt gaacgcctgt    13620
ggtcccagct actcgggggc tgaggaggga gaattgtttg atcccgggga gcggaggttg    13680
cagtgagctg agattgcacc atggcactcc agcctgagtg acagagcaag actctgtctc    13740
aaaaaaaaaa aaaaaaaaaa aaaaaagca tatagaacaa aatgtgaaag ttttctccct    13800
ctccagagaa acactgttga ctgcttggag tatagccaaa ctgtgtttac acccatatat    13860
acatacacac atactgcata tgaatacgaa ttgggttgtg gcataactac tattctgcaa    13920 ctttctttt gatgcataac agtgtatgtt agaactcttt ccatatagtg catagaaatc     13980
taccttgccc ttttaaatgg ctgcagaata ttccacagac tcaatgtata actatttact    14040
acttccctgc cgatggatat ttaacctgtc tgtagttacc cgttatcacc aagcttcaag    14100
gaatagcccc ataaatgcat cttttggacac gggagcataa tatgtgacta cttttctagg    14160
ttactgtaaa agtagaattg ctgggccaat caggatatgt ttgctaacac tagttatagt    14220
caacctttaa aattttgcc aatctgacag atgaaaaata tttcattatt taaattatct     14280
tttatcttta cttttaaaaa atgtagattt cgtctgggcg tggtggctca tgcctgtaat    14340
tccagcactt tgggaggcca aggtgtgtgg atcacttgag gtcatgagtt cgagaccagc    14400
ctggccaaca aggcgaatcc ccatctctac taaaaataca aaaattagcc aggcaggatg    14460
gcaggcgcct gtaatctcag ctactcggga ggctgaggca tgagaattgc ttgagcctgg    14520
gaggcagagg ttgcagtgag ctgagatctt gccactatac tccagcctgc gcgatatagt    14580
gagactcagt ctcaaaaaaa aaacaaccaa acaaaaaaat aatgtagttt tctggctggg    14640
cacagtggct catgactgta atcccagcac tttgggaggc tgaggcaggt ggatcacctg    14700
aggtcagtag ttcgagacca gcatggccaa catggcaaaa ccccatctct actgaaaata    14760
caaaaattag ctgggcatgg tggtgcacac ctacagtccc aactattcaa gaggctgagg    14820
caggagaatc gcttgaatct gggaggtgga gtttgcagta agctgtgatc gcaccattgc    14880
actccagcct gggcaacaaa gcgagactcc gtctcaaaaa aaaaaaaag tagttttctg     14940 agtcttgctt tttctacttt tattccataa gtgtatttct atatattaac taagagtgaa    15000
atggaaatga ttgtaaccaa atatgtattt gtacataaca tgataatctg tgcatttgtg    15060
catttcgctt ttctacatct ttggttactt ctttaggcca aatgcctagt agttataaat    15120
caaagtcatt ttatgagatc taatatttat ttaggttttc tcaagttct gtactaatgg     15180 ttaatcaata tcctaagttc catgccatgt actttaaatt tttgtgcttt tggtgagtat    15240
```

```
tcaccagtat ctcaatgttc agcctttctt tgtgtgtgtg tttctttttt gaggcagagt   15300
ctttcagtgt cacccaggct ggagtgcagt ggcatgatca tgatcatggc ttactgcagc   15360
cttgtctttc caggctcaaa gggtcccccc acctcagcct cctgagtagc tgggaccaca   15420
ggcatgcacc accacaccca gctactttt tttgtagaga cgtggtctcg cttgttgccc   15480
aggctggtct cgaattcatg gcttaagca atccaactgc ctcagctccc aaagtgctgg   15540
aattacaggt gtgaactacc aagccctggc ccatcttggg tgtttatcca tgtattctgc   15600
agtactttcc cgagaagtcc tcttagacag cagctcaaat gggctgattg ttctttctcc   15660
gtccaagaaa aatgctgatg aatgaacttc tctccctcat tacagaagga aaataatgtt   15720
cttatctttt tgtaacaaag aaagtaacta gaatttagta cactgtgact tagaacccaa   15780
ggaagactcc tcgcttgatg cttagcgtgc atttcttgca gatttcgttt gatggtttga   15840
attcaatatt cttaaagtgt gtctctttt tttttttcca ggtgaatgtt ggatgtgtac   15900
ccaaaaaggt agaatttta tttctctttc cctttacaat cctttttcta tttggtaaat   15960
cataatcaaa atcagaatgt ttccaaatag atcagttaaa attctttctg caaaaaaac   16020 ccctagaccc tactaaaagt agcttaagca ataggattgt ttttgtttga tttgtgttt   16080 ttaaattttt ttattatt ttaattactt tttattttta ttattattgt ttttttgaga   16140
cggagtttcg ttcttgtcac ccaggctaga gtacagtggc gcgatcttgg ctcaccgcaa   16200
cctctgcctc ctgggttcaa gtgattctct tgcctcagcc tcccaagtag ctgggatgac   16260
aggcgtgcgc cactgcactt gactgatttt tgtatttta gtagagatgg gggtttcacc   16320
gtgttggcca ggctggtctc gaactcctga cctcaggtga tctgcccacc tcagcctccc   16380
aaaatgctgg gattataggc atgagccaca gaccccagcc aaggcctggt catctacacc   16440
acaggatagt tttttctcag caaaaagacc cagccagcaa accaaactgt tgaatggaat   16500
cttctcaagt tctgtgggtt catggatttt ctgtatcaca ttagtgattt tttcgttgtt   16560
aatatctgtg gtgcaggtca cattgaatga attcattttt tttacccttg acaaagagga   16620
aaaaacagca gctcttattt gtaaagctgc ctcttgctta tacttgcaaa gaattttacc   16680
actcatttga atgtactttc aacatatgtt gtaatctcaa gcttaccacc tttattaatg   16740
acattccatt ttaacttgtc atctttttgg tattatataa gcaaatctcc taatctcatc   16800
agtgatgcat acctgagttt aattccaaaa agtcttttg aagtctttc cgtggtatag   16860 gtaaggtgtt tttctttctg tcttaggaag actttcttc tctgggacat tttccctcaa   16920
ctatttcctt tcctattagt catacttttt gtaatctgtt ctacttggag ccatgcaatt   16980
atgactgtat gaattatata aattaattat aaggtggttt tatgtagttt aaaccagtta   17040
tggtggtaaa tttcgtgttg attggtacaa gtttattttt ttttaaatat accactgggc   17100
taatactgca cagtaaactg attttgtaat gttttagtct catatttact tattccttct   17160
gatcacatgc ggtagacatt tatgtatgtt catttatata ttttttttc tttttttct   17220 tttcttttt ttttttttt ttttttttt ttttgagac agagtctcac tcttgcccag   17280
gccggaatgc agtggtgtga tttcagctca ctgcaatctc cacctcccag gttcaagtga   17340
ttctcctgcc tcagcacaag tagctgggac tacaggcgtg catcaccatg cctggctaat   17400
tttttttgta tttttattag aaatgagatt tcaccatgtt ggccaagatg gtctcgaact   17460
cctgacctca gtgatctac ctccctctgc cttccaaagt gctgggatta tagtcatgag   17520
ccactgtgcc cggccttgtg tttgtttctt tttagtctgt ttttaatagc tttcccctta   17580
```

```
tctctttaaa aaaaaatgtt ttaagttagc aaggtatagt agattttatt tattattatt    17640
attattattt tatcttttga gacagagact ctgtcactca ggctggagtg cagcagtgtg    17700
atcttggctc actacaacct ctgccctcag ggttcaagca attctcctgc ctcagcttcc    17760
caagtagctg ggactacagg tgtgtgccac catacccagc taattttgt attttaata     17820 gagatgggt tttgccatgt tggccaggct ggtcccgaac tcttgacctc aagtgatcca     17880
cctgcctcgg gctcccaaag tgctgggatt acagacgtga gctgccgtgc ccagctaggt    17940 ttgttttaa tttaaagggc agtatttta tctgctgtta cctagttacc attcattcat      18000 gattccttt ttccctcagg actgatttac tgctgttttg gatccttttt ttttttttt     18060 tttacaggta atgtggaaca cagctgtcca ctctgaattc atgcatgatc atgctgatta    18120 tggcttttcca agttgtgagg gtaaattcaa ttggcggtaa gtgtcaacac tcagagggtt   18180
cagtttccaa gtgtagatat ttttctttta taactgagcc ataaactttt ttagggatgg   18240
aggaggaatt gcggtaaata ttcacaatac gagatttaca gtttagccat ttttaagtat   18300
acaattgagt gccattaagc gcattcacat tgttatacag tcgtcaccac tattaccact   18360
tccagaactt ttctgctatc ccaaacagaa actattctat taaacaataa ccctcattc    18420 tcttctcccc ctggccctg gaacctcta ttctgctttc tgtctctatg aatttgccaa     18480
ttctagggaa ctcatataag tggaatcata caatatttgt tcctttatgt ctagtgtatt   18540
ttgttttcac ggtttgtcca tgttgtagta tgtatcagaa cctcattcct tttttgttgt   18600
ttgttaagac agggtcttgc tctgttgtcc acgctggagt gcagtggtgc aatcatagct   18660
cactgctatc ttgagctcct gggctcaagc tatcctccca cttcagcctc ctgagtagct   18720
gggactacag gcacgtgcca ccatgcctgc ctattttttt taattttgt ttttagtaga    18780 gatgaggtct cactgtggtg cccaggctag tcttgaactc ctgagctgaa gtgatcctcc   18840
cgcctcagcc tcccaatgtg ctgggattac aagtgtgagc cactgtgccc agccttcatt   18900
ccttttaaag gcagaataag atttcttcat atggataaaa ccacattttg tttatccatt   18960
catttgttag tgaattttg ggttgttttt acctttttt tttttttttt tgagacggag     19020
tctcactctg tcacccaggc tggagtgcag tggtgcgatc tcggctcact gcacgctccg   19080
cctaccgggt tcacgccatt ctcctgcctc agcctcctga gtagctggga ctacaggcac   19140
ccaccagcat gcctgggtaa ttttttgtat ttttttagt agagacggga tttcactgtg    19200
ttagccagaa tgatctcgat cttctgacct cgtgatccgc ccacctcagc ctcccaaagt   19260
gctgggatta caggcgtgag ccaccgcgcc cggcctgttt ttaccttttg gttattgtga   19320
acaatgctgc tatgaacatt cgtatatggg tatctgttca ggtctctgct tccagtttct   19380
tttgggtctg tacttagaag tgaaattgcc gaatcgtatg gtagttttgt gtttaactat    19440
ttaaggaact gctgtaaatc ctttgaagcc attaacagtt ttgaagaaat ttagcaaatt   19500 tatttatta gcaagtgttt attaagtgcc caccacgtcc tgtgcacatc atgttctagg    19560
cactttgcca aaacatttct ccttgtcttc tgcgcagaaa gatgatgcca actgagtgtg   19620
ttctccactg agtggcacag aggcttttaa cacatggggc agcagaatga cacagggaag   19680
ggatgactgt cttcggagac attcactcac tgcggttgct gttgacagtc agtgattctc   19740
tgctcggggt gttcagggac agatgcctta gttactaact agaaggggaa gatcctgttt   19800
ctgaatactg acttgggttt cattgcagtg ttattaagga aaagcgggat gcctatgtga   19860
gccgcctgaa tgccatctat caaaacaatc tcaccaaggt gtgtatgctg ggttttaac    19920 tttgagaaag agctgttccc ttcttgagta ctcagctaag tcttgccaga ctgtagccct   19980
```

```
atttatttat ttattttat  tattattttt  ttggagacag  ggtctcgctc  tgtcgcccag  20040
gctggagtgc  aggggcgcaa  tctcggctca  ctgcaacctc  cgcctcctga  gttcaagcaa  20100
ttctcctgcc  tcagcctcct  gagtagctgg  gactacaggc  gtgtgccacc  acacccatcg  20160
aattttttgta ttttttagt   agaaacaggg  tttcaccatg  ttggccaggc  tggtctcgaa  20220
ctcctgacct  caggtgatct  gcccaccttg  tcctctcaaa  gtgctgagat  tacaggcatg  20280
agccactgca  cccggccta   tttattttt   aacgaccagg  tctctatctg  tcgccaggct  20340
ggagtacggt  ggtgcaatga  tagctcactg  tagcctccaa  gtcctgggct  caagcagtcc  20400
tcccacctca  gtctccttag  taactaggac  tgtaggcatg  caccaccaca  cctggctaat  20460
ttttaaaata  ttttgtagag  atttctcact  gtgttgccta  ggctggtctt  taaactcctg  20520
ccttagcctc  ccaaagtgtt  gggattatag  agatgagcca  ctgtgcctgg  cctcttactt  20580
tttctattat  tgaaattgac  ctgtcagagc  agaagcctct  gacctagatg  gccagtctct  20640
tctgcagaga  gagggtggca  tgtgccagag  ctggcagacc  aggcctcacc  taatggctgc  20700
accttgagta  ggtctggcct  ggcaattaga  ttcagaagtc  acatacgaga  gactttgtgc  20760
accagtatac  cagtttatta  attaaaatga  ggagtgctat  ctagctgaaa  acctgccatt  20820
gtgtgtttgt  ttgttttttg  agacagagtt  tctctattca  cccaggctgg  aatgcacaat  20880
ctcagctcag  tgcaacctct  gcctcccgcc  aggttcaagc  aattctcctg  cctcagcctc  20940
ccaagcagct  gggattagag  gtgtgcacca  ccacgcctgg  gtaattttg   tatttttact  21000
agaaacggga  tttcaccatg  ttggccaggg  gtctcgaact  cctgacctca  agtgatttgc  21060
ccacctcggc  ctcccaaagt  gctgagatta  taggcgtgag  ctaccgcacc  tggccaaacc  21120
taccattgtt  tatttgccta  gagtaagacc  tccttaagag  accaaattag  gattcagaag  21180
gttgttttta  tgaatgacat  ctgatcaaga  aaactgggca  gaggtgtgtt  tgcctccagc  21240
aactgtatgt  catccttcac  tatcctgatg  cttttccccc  atagtgctgg  gatgtcacac  21300
ctttcccacc  aggaccatgt  aggtgacatt  gacaacctgt  gcatcactta  actctccttt  21360
tccttgacaa  tatcttcccg  ccaccccttca ttttgtctttg tggtctcact  ttgctgtttc  21420
taagatttct  tacggttgtt  tgtttgtttg  tttgtttgtt  tatttgtgaa  acagaatctt  21480
gctctgtcgc  ccaggctgga  atgcagtgat  gtgatctcgg  ctcactgcga  cctctgcctc  21540
ccaggttcaa  gcaattcttg  tgcctcagcc  tcccgagtag  ctgggactac  aggcacgtgc  21600
ccccacacct  gcctaatttt  ttttgtattt  ttagtagaga  tagggtttca  ccatgttggc  21660
caggctggtc  ttgaactcct  agcctgaagt  gatctgcctg  cctcagcctc  ccaaagtgct  21720
gggattacag  gggtgaacaa  ccactcctgg  ccctcttagg  ttatatttag  atcagtaact  21780
tttttttttt  tttttgaaaa  gggtcttact  ctgtcaccca  ggctgaagtg  cagtggcatg  21840
atctcagctc  actacagcct  cgacctccca  ggctcaagtg  atcctcctgc  tttggccttc  21900
caacatgctg  ggattacagg  catcagccac  tacacctggc  ttagatcagt  agattcttga  21960
tgataattag  gccactgtga  tctcagtagc  agcatattta  taaaccaatt  tttaggacga  22020
gttacttcat  acatagctaa  ctgtgtacag  ttttatattc  ttattcattg  ggtttatttt  22080
ttggagggtg  aattttccaa  ccttaatcct  caatccaggg  ggaaaatat   ttaaaggcct  22140
gcagtcctta  agcacaggag  attttaaggc  tgagtataga  gtaacactgg  cagtactaaa  22200
acacaccaag  ttttttattt  ttatttttta  ttttttgaa   gtcaggatct  cactctcttg  22260
agcagactgg  agggcactgt  cgtgatcaca  gctcactgca  gccttaacct  cccaggctca  22320
```

```
agcaatcctc ccacctcagc ccctgagta gcttgggcta aagcactgt cccaccacac   22380 cctactactt ttaaaaaacg tttgtagagg ccgggcgcgg tggctcacac ctgtaatccc   22440
agtactttgg gaggccgaag cgagtggatc atgaggtcag gagattgaga ccatcctggc   22500
taacacggtg aaaccccagc cctactaaaa atacaaaaa ttgaccaggt gtggtggcgg   22560
gcgcctgtat tcccagctat ttggaaggct gaggcaggag aatggcgtga accctggagg   22620
cggagcttgc agtgagctga gatcacacca ctgcactcca gcctgggcaa aaatgcaaga   22680
ctctgtctca aaaaaaaaa ttttttttgta gagatgaggt cttgctatgt tgcccacgct   22740
gatcttgaac tcctggactc aagcaaccct tctgccttgt cctcccaaaa tatgggaatt   22800
ataggcataa accactgcat ctggcctttt ttttttttaa tggagctgac tgaaatactt   22860
ttgcaaaaga ggtaggaaaa ttattcagga accagcattt tgtaatactt agaaatcttg   22920
gtgtgtacta tagcttatgg tgatcttatg gggaaggaat tacctatagt tgacccagaa   22980
attctatatt gcaaaggaaa ctttctatct aatatcctgg aaactgaaag taaaaatctc   23040
actgcttcct cctctgaact agtgtctgtc ctatcgccac gcgagccata ctccttttg   23100 tctagcattg cagatgaagt cattaagacc tgagggaatg gtgttctgga ggcctgtgga   23160
ttttgtcttt gaccttgatt cagcttgatt aagcctggca cctgcaggaa caggcctgga   23220
gggtgcaggg aaagaagaag ataactcaat tcagaatcaa gcacgttcca atatgttaaa   23280
gcattccact ttgtaatcat gcttacatgg ttccattatt cttgtaagtt gaccacattt   23340
gcatgcccct gcatgtatca tggctggcga aagcgtgcca gcagcccta agtgaaggcc   23400 tgggtacaga ggattccagt aagagcaaat ccaaaagtaa gagtctgagt tctcaccgtc   23460
tccagcgtag aacttcagtg tcatgtactt ttgtggtatt cttcccattt tacgaaagca   23520
caagcattgc gtttccctcc cttggccaga gtattcctct cttgctcttg cctctgttca   23580
tttcaccatt atcctgttgt ctttcttagc cttctgcctc tcctccagac acaccagtct   23640
ttttgagaga gggtcttgtc tctgtcgccc aggatggagt gcagtggcgt aatctcggct   23700
cactgcaacc tctgcctccc aggttcaagg aattctcgtg cctcagcctc ctgagcagct   23760
gggattacag gtgcccgcca ccacttctgg ctaattttta tattttagt agagatgggg   23820 tttctccatg ttggtcaggc tggtctcgaa ctcccgacct caggtgatct gcctgcctcg   23880
gccttccaaa gtgctggaat tacagatgtg agccaccatg cccaggccag acacaccatt   23940
ctgtaatgtg attacattgc acataaggaa ctttcgccct caattcttgg gggcaaagat   24000
gtcatctttc ttacggggt gccttgcata tacttttttg tctctgggtt ttggcccaag   24060
ttagcacttt tatttcttct tcttttttcct ccttcttcct tctttcttct ttccttcctt   24120
cttctaactt ctttctttct tcctcctcct cctcccctctt ctcctcctcc tcttcttcc   24180 ttccctgct cccttccct ccttccttct tcttcttct cctcctcctc cccctcactt   24240
tgtcatccag gctggagtgc agtggtgcca ctcagctca ctgcagcctc aacctcccag   24300
attcaagcaa tcctcctgcc tcagcccctc aaagagctgg gactacaggt gtgcagcacc   24360
atgcatggct aatttttgta tttttagtag agactgggtt ttgacatgtt tcccaggctg   24420
gtctcgaact cctgagctca agctatccac ccacctctgc ctcccaaagt gctaggatta   24480
caggtgtaag ccacctgtgc ccagcctatt tcatcttact gtatacttcc ggcaactaat   24540 ggcaaccct ttcctaagta taggttgcca gttagaagtt ctacagaaac ttgaaaacg   24600 gagaattgtg ttggcatcag caaaccaaga atcaaaatgt tcagtagaga aatgaaagtt   24660
ctgataagtt gcagtaggtg tctttgtttt tattctaaga acaggctaat gtcatggttc   24720
```

```
cttctttagt cccatataga aatcatccgt ggccatgcag ccttcacgag tgatcccaag    24780
cccacaatag aggtcagtgg gaaaaagtac accgccccac acatcctgat cgccacaggt    24840
ggtatgccct ccaccoctca tgagagccag atccccggtg agtcatacaa caggtactca    24900
ttaacagcag tcaggagttt actgttgctt tcaacctgaa aagccatgcc aggggatctg    24960
cctaaaccag ttctctcttt ggagccaggc catgggagaa ggtctctgca gaacctaact    25020
ccagttggct tagtggtagc tagtgatgca gtcgcccagg ctggagtgca gtggcacgat    25080
cttggctcac tgctacctcc gcctcctggg ttcaagtgat tctcctgcct cagcctccca    25140
agtagctggg actacaggca tgccaccacc acacttggct agttttggta ttttagtag     25200 agatggggtt tcatcatatt ggccaggctg gtcttgaact cttgacctca ggtgatccac    25260
ccaccttggc ctcccaaagt gctgggatta caggccaccg tgcccagcca agagatttca    25320
tttggcccca ggctcagaca tattgcaggt aacagaggga gagaaatcaa tgaaagcctc    25380
attctttcct tcttagctta gcatacattg tttccagcct cagtttgtca gacgggttgt    25440
tatttacaag acacgtgata atttattgtt ttgttcaaga gagagaaatc ttgtaaggat    25500
gtagcttgag tagctaagtg agcttttata tgcatatttt tctcttttaa gtagagactt    25560
atagaagatt aaagctgtaa ggaatctcag agatggtcat aacttctttt gcattttatt    25620
ttattattta tttatttatt tatttattta gagacagagt ctggctctgt cacccaggct    25680
ggagtgcagt ggcacaacct cagctcactg caacctccac ctcctgggtt caagcgattt    25740
tcctgcctca gactcccgag tagctgggat tacaggtgtc cgccaccacg cccagctaat    25800
tatgtacttt agtagagaca gagtttcacc atgttggtca catgggccca cctcggcctc    25860
ccaaagtgct gggattacag gcgtgagcca ctgtgcccgg cctattattt tattttatat    25920
tattttattt ttttgagaca gggtcttgct ctgttgtcca ggctggagtg cagtggtgtg    25980
atcacagctc actaaggcct tgaccaggac gtttagatgg gagatggctc aagcgatatc    26040
tttctttttt cccagctaga ttataaggac tttgtggatg gtgaacatag tttatacatc    26100
ttttgaattt tccatggatt agcttcataa gatccattat caaggtgaat ttttttttt    26160 tttttttttt tttttgtgag acagattctt gctctgccac ccaggctgga gtgcagtggc    26220
gcaatctcca ctcactggaa cctctgcctc ccgggtttaa gcaattctcc tgcctcagcc    26280
tccttagtag ctggtactac aggcacatac caccatgtcc agctaatttt ttttgtattt    26340
ttagtggagg tggggttttg ccacgttgtc caggccagtc tcaaactcct gacctcagtt    26400
gatctgccca ccttggcctc ccaaagtgct gggattacag gtgtgagcca ctgcacccgg    26460
ccaaaatgca acatatatat ttttttgttt gtttgtttgt tcagagacag agttttgctt    26520
ttgtcaccca ggctggagtg caatgggagg atcttggctc actgcaacct ctgcctcctg    26580
tgttcaagca attctcctgc cccagcctcc tgagtagcag ggattacagg catgcgccac    26640
cacactcagc taattttgt  attttagta  gagacgggt   ttcaccatgt tggccaggct    26700
agtctcgaac atttgacctc aggcgatctg cctgtcttag tctcccaaag tgctgggatt    26760
ataggtgtga gccactgcac ctggcctaat atatttaata actgatgaga aatgagggta    26820 gggggggctac agagagaagg aatcagcagt tgacaactga aggctttgtc tgcattattg    26880
ggagcaggtg gtaactgaag tggtaaactt gagagagata tgggttggaa gataaaatta    26940
aggttcagtt ctaaatagac taagtttgaa gccaatgtaa aattgtgtgg cgagatagtt    27000
agaaacatgg aactgcaacc tggggagaag gtcaaacctg gaagatgca  tctggaagtc     27060
```

```
ctgcaagata ggacctgcta tcctatatcc aaaggtttca atctccttt cactacatgt    27120
atatttcact atataggttg tacctcttgt aattcaatgt gtacaccata taggttgaaa    27180
cctttgaaag aataagcaga gaggaaaggg ccacgtcgat tttttttttt tttttttttt    27240
tttttggag acaaaatctt gctctgttcc caggctggag tgcagtggca cgatctcggc    27300
tcactgcaac ctccacctcc caggttcaag tgattctcct gcctcagcct cccaagtagc    27360
tgggactata ggtgcgtgcc accatgccca gctaatttt gtattttag tagagacagg    27420
gtttcaccac gttggccagg ccacatagat tttgaactac atagaaattt gtcttttcag    27480
gcaggaacgg tgtctcacac ctgtaatgag ctgagcccca gggttcctac ctgcccttgg    27540
ggtgggaggg tgaacagatc caacagagtc tgttcatgac cactgagatc ttcattcttc    27600
agagaaatgt aaaagttatt tagccatcat ggcttctgtt tctagagaga aaataaaaat    27660
gttaactcag ggaggatttg gttggcagct ttccaagcag agactttaac aaaacttgtc    27720
aaaacggaga ctatgttggc tgtgaaagtg tttggttttt ggcataaaat gttgtgatta    27780
ctttgcaaga gaaagagcag tcttgtgtga tctatgttgc cttttctac ataggtgcca    27840
gcttaggaat aaccagcgat ggatttttc agctggaaga attgcccggg taagccaacc    27900
tgacctgacc tcagtgactc attcttcctt actgtctcct ggtaactttt cttcgtcttc    27960
tcctcccaag catttaatgt aggccttcc tgaattccct cctcttacag cttctctttt    28020
catgaccttg tatatctcat tcctagaact cctcagtaga tccctcaaat cttcatgct    28080
ttcaatcaga ggccaaagtc aaatgcaggg taatttgaag actgcatagc aaagtcctaa    28140
aactgtcttc tttcttcaac ttaatacagc atcaattaag aatgtgtcta aagtagcttg    28200
tatttagaa tagaatagct ggttttggcc agatgtggtg gctcatggct gtaatcctag    28260
cactttggga ggctgaagcg gcagatcac ctgaggtcag gagctcgaga ccagcctggc    28320
caacatggtg aaaccctgtc tctactaaaa ctatggaaat tagctgggtg tggtggtgtg    28380
ggcctgtagt ctcagctact cgggaagctg aggcaggaga atcacttgaa ttctcaaggc    28440
ggagttgcag tgagacaaga tcacaccaag aaagaaagaa agagagagag agtgccacca    28500
cgccccgcta attttgtatt tttagtagag gtgggttttc tccatgttgg tcaggctggt    28560
ctcaaactcc tgacctcagg tgatccgccc gcctcagcct cccaaagtgc tggaattaca    28620
gatgtgagcc accacctg gccagatttt ctttaatga acaaacattt ttttttttag    28680
agacagggtc ttcttccatc gcccaggcag gagtgcagtg gtgccatcat ggcttgtggt    28740
agccttgagc tcttgggctc aagcaatcct ttcacctcag cctcccgagt agctgggact    28800
acaaacgtgc accaccatac ctggttaact ttttaattta aatttttgta gagatggggt    28860
ctcgttctgt tgtccaggct ggtctagaat tcctggcctc aagcaatcct cccaccttgg    28920
cctctcaaag cagtaggaat acaagcatgg gccaccgtgc tgaatggatt tagattcata    28980
gaggggcaaa aagatcatga ggaagtttgt ttctctgatt tgaagttgct gtacattgca    29040
ggctttctag tttagaggga tgctcctgtc acttgtgaga agaggtgatg cctggaaaca    29100
ggtggaggga cccaatgtgt tggcgcaggg actggccttc attcatcttc tgagtggcac    29160
tcactgtgga gtttgcattg ctcaactctt ctgctccctc aggggctgtg ctaatccagt    29220
ttgaggtcct aatcctatgc ttttagaagg cttttaggg agagtgactc atagtccatg    29280
agcctatctt cactttgatt cacccagagt catggacagt tcagacagca cgaggcagtt    29340
cagaaaggac cagggagctg ctttgcagtt ccataggatg gtgaaaatgt cccttgaaga    29400
tacctcagac caggcaggct tctgacttgg aggagttcta agaaaaccat acaatctttt    29460
```

```
ttggtttgct atcaggtcgc agaaatgtgt tagagaacag ccttccttcc ctgtgatcca   29520
ccctgcattg tttgatttta gggttgagtg acatgacata tgtgaggatg tagtgagaca   29580
tacagtcatg actcattatg tttggataat gtaatttcat tccggactca ccctcaaaga   29640
agtttcatta taaatagctg ttcattagca attttaaata tttacattta tgcatgtcat   29700
caacaaaagg ctctgaaaca caagaaaatg aatttacgat tgatacgtga ttcttcaagt   29760
ctactttatc tttgttacgg tgttggtgaa taagtaataa ctgggcaagt acataaataa   29820
tgtagggaag atagcatgat ttagtttttg cactgagggg gcttctgttt ggatggagca   29880
tgaaccttgt ggaatactgt gcatgagtag tcctggggct gcaacgaggt aaagagaaat   29940
cttttaggga ttcagccgcc tgaaagatca gttccagaag ccaggcacag tggcttatgc   30000
ctgtaatctc agcactttgg gaggcctgag gcgagcgaat tcttgagcc caggagtttg    30060 aaaccagcct aggcaacaca gcacaaccg atctctgcaa aaaaaataca aaaattagct     30120
gggtgtgttg gcacatgctg gtagtcttgg ctacttggga ggctcaggcc ggaggatcac   30180
ttgagcctag gagttcgaga ccagcctggg caacataggg agatattgtc tctgcacaga   30240
gttttttcct ctctgaagaa atgaggctaa agagctttaa aaacaatgaa aaatacattt   30300
cccttctgtg acgggatatt agggattttt cttttctttt gagatagggt cttttgctct   30360
gtcacccagg ctggactgca gtggtatagt catagctcac tgcagcctcc acctcccaga   30420
cacaagttat cctcctgcct cagcctctca gtaactggg accacagaca tggaccatca    30480
tacttggata atttttattt ttacttttag gggttttttg tttgtttgtt tgtttgtttg   30540
tttgttttgt tttttgaga cagagtctcg ctctgtttcc caggctggag tgcattggtg    30600
caatcttggc ttactgcatc ctctgcctcc taagggcaag cgattctcct gcctcagcct   30660
cccgagtagc tgggattaca ggcacacacc actgcacctg gctaactttt tgtattttta   30720
gtagagacgg ggttcaccat gttggccaga ttggtctcga actcctgacc aggtgatcca   30780
cccacctcag cctcccaaag tgctaggatt atgggcatga gccaccgtgc ctggccttac   30840
ttttatgttt ttgtagagat ggggtctcac tttattgccc aggctcaaag gaatattttc   30900
tacttaaagt tgcagtggta tccaggattg gatcttggaa cagaaaaaaa aaagattaa    30960 tagaaaaact gggctaggca aggtagctta cacctgtaat gccggcactt gggaggcca    31020 aggtaagagc attgcttgag cccaggagct aagactagcc tgggctaaca tggtgagact   31080
ctgtctctac aaaagaaaat ataaaactta gctgggtgtg gcgatgaatg tctgtagtcc   31140
cagctactca ggaggctgag gctggaggat ggcttgagtc ctggaggttg aggctgcagt   31200
gagccgtgtt cacaccacta cactccagcc tgggtgacag agaccctgtc tcaaaaaaaa   31260
gggaaaaagt gaaaatctgc agtctagggt ttagtcatta gtaatgtacc aatgtcaatt   31320
tcttattttg acaaaggtat cctaattaag taaaatatta actttaggga aaactgatca   31380
aggggtataa taagggaaat ctctgtacta tctctgcaac ttttctgtaa acgtgaaatt   31440
attccaaaat tagtttattt aagaatacta accctctgct cgcgtctcag ccgcagcgtc   31500
attgttggtg caggttacat tgctgtggag atggcaggga tcctgtcagc cctgggttct   31560
aagacatcac tgatgatacg gcatgataag gtaaatgcca cctttttctt ttcgcttttc   31620
ttgatgttaa tttaaaaaat gaagaatttt tccttatgtt gtcgttaaat actagggtgc   31680
aaagcaggtg tggggtcat ttggttggtt tcatatggtg ctgtatccaa gttacctgaa     31740
tttggcctat atccctccca gttgctggtt gatgatgata attttgagtt ggtcaaattg   31800
```

```
gctggtaatt tcatcactaa gtggtagata gtcatgagat gccctcatag ggagacgtgg   31860
ggcctaaaca taactattag ctaaattaaa cagactgtta ggttaattta tttttttatt   31920
tttatttttt gagacagagt ctcactcttt tgtccaggct ggagtgcagt ggcaccatct   31980
cggctcactg caacctctgc ctcctgggct caagcgagtc tcatgcctca gcctcccaag   32040
tagctgggat tacaggtatc caccaccatg cccaactaat ttttgtattt ttagtagaga   32100
tggggtttca ccatgttggc caggctggtc tcgaactccc tacctcaggt gatccaccca   32160
cctcgacctc ccaaagtgct gggattacag gtgtgagcca ccagcccccg ccaggttaat   32220
ttattaattt ctggaaatca attttatatg atcaagtaat gttagattgt taccactcat   32280
tctaaacaat ttactaaatt ctttgcatta aagcaggggt gtccaatctt ttggcttccc   32340
tgagccacac tggaaggagt agaattgtct tggactacac ataaaataca ctaacacaaa   32400
caatagctga tgagctaata aaaaaataaa ttgcagactg ggcacagtgg ctcacgcctc   32460
taattcccag cactttggga ggctgaggcg ggcggatcac ttgaggtcag gagttggaga   32520
ccagcctggc caacatggtg aaaccccatc tctactaaaa atccaaaaat tatccaggca   32580
tggtggcagg caactaatca cagctacacg ggaggctgag gcataagaat cgcctgaacc   32640
caagaggcag aggttgcaga gagccaagat tgcaccactg cactccagcc tgggcaacag   32700
agcaagactc tgtctcaaaa caaaaaacaa aacaaaacaa aaaaactgca aaaaaatctc   32760 atagcattt aagaaagtgt acaaatttgt gttgggccac attcaaagtc atcctggtcc    32820
gcacacggcc tgcaggctgc aggtcgaacg agcttacatt aaagggaatc ttgtagatca   32880
tacacttgaa attttttttt tttttaagag acagagtctt gctatgttac ccagtctgca   32940
gtacagtggc atgatcatag ctcactgcag ccttctgagc tcataggatt ttcctgcctc   33000
agccttccaa gtagctgagg ctacaggtgt gggccaccat gccctgacta atttttttttt  33060 tttttttttt ttgagacaga gtctcactgt gttgcccagg ctagagtgcg gtggcacatc   33120
atggctcatt gcagcctcaa ccttctgggc tcaagcgatc ttcccacccc agcctcccaa   33180
atagccagga ctacaggaac atgccaccac acccagtgag gtttcaccat gttgcccagg   33240
ctggtctcaa actcctgagc tcaagtgatc cgcccacctc ggcctcccaa agtgcttggg   33300
attacaggca tgcgccacct gactactttt tatatatttt tagagatgag gtcttactat   33360
gttgcccagg ctggtctcga actcctggcc tcaagctatc ctcctgcctc agcctcccaa   33420
gtagcaggtg gagttcaaga ccaacctggg caacatagtg agaccccat ctctactaca    33480 aaaaattaaa aaattagcaa ggtgtagtgg tatacgcctg tagttgcagc tacttgggag   33540
gctgaggtag gagaatcact tgaatccagg aggtcaaggc tgcagtgagc aaagattgtg   33600
ccactgcact ctagcctggg cagctgactg tccctaacaa acttgtgact taggcaagcc   33660
acataatgcc tttggggcct agttctgcag ggacagaatt tatcagatcc ctgactacca   33720
agatgctatg attctaattc ttatgtgagc agatggaggg agacagggat tctgagaatc   33780
ctaggcagta tgtactttaa ggaactttct ctgtggcttt gaaactggtt atataattag   33840
ctccaggaga ttgaggtcct gaataatatt ttttcatagg taagtattat tttgctagaa   33900
tatatccagc aaattagaag gatggggaaa ggtagaggag ttcctagctt gaatttatat   33960
atagataagt aaataaactg cagcagtctg tcaataaagg gggtaattct tgcatctgta   34020
aaattggcta ctttgcagag agccacatct acttgggctt cctgccctct cccatcccaa   34080
atgcaccaag ttcattctcc cttttttttcc cagtgttaac tccattttag agctactctg   34140
tgggtgggca tggtggctca cacctataat cccagcactt tgggaggcct aggtgggcgg   34200
```

```
atcacctgag gtcaggagtt cgaggccagc ctggccgaca tggcgaaacc ccgtctctac    34260
taaaaataga aaagttagcc aggcatggtg gtgggcgcct gtaatcccag ctcctcggga    34320
ggatgaggcg ggagaattgc ttgaatccag gaggcggagg ttgcagtggg ctgagatggt    34380
accactgcac tccagcctgg gtggtagagc aagactccct ctcaaaaaaa taaaaataaa    34440
agaactactc tgtgaataac tcatgacctc ccacctgaac tccacatgtg gatggtcaca    34500
gatatatctc caaggccata ctgttgagat ttatggctag acaagatttt gctagtaaat    34560
cttcccttca atcatatcag agggaaagca gaccttgaga tacgaaaagt ggaaagagaa    34620
tttctgttcc ctggacttaa ggaaaagaga agcaagcttt gtgaggagaa gacagtggac    34680
aatggctgtc catttaactg taggacagga gttggtgaag tcatatgtat tgcagatggt    34740
ggtggtgatg taggaaaata gggaatttat taatactcca ctcccaatat ggccataagt    34800
aaggaggaaa taattagggg agagataatg ctgaagtttc cctcccaagt ttgtggtgtg    34860
tctttgctca gttttcttc ctctcgcatt acccatccct atgttgatat gcaggtactt     34920
agaagttttg attcaatgat cagcaccaac tgcacggagg agctggagaa cgctggcgtg    34980
gaggtgctga agttctccca ggtacagtgc aagcccagg catgcacgcg ccccccagtc     35040
aatcacactt tctgcttgtg gcttcgccca gttagtttaa aaacacaaac actatgtcta    35100
ccccggtcca tatattccac ctctagggta ctccctatta tttccttcct cctaagaagc    35160
tgtattttag ccaggtgcgg tggctcacac ttgtaatccc agcactttgg gaggctgagg    35220
tgggcggaac acttgaagtc aggacttcga gaacagcctg gccaacatgg tgaaaccctc    35280
tctctattaa aaatacaaaa atcagctggg cgtggtggtg tgcacctgta atcccagcta    35340
ctctggaggt tgaggcagga gaattgcttg aacccagaag gtggaggttg cagtgagccg    35400
agattgtgcc actgcactcc agcctgggcg acaagagcga gactccgtct caaaaaaaaa    35460 aaaaaaaaa aaagtctgg gtgtggtggc tcacacctgt tatcccagca ctttgggagg      35520
tcgaggcagg cggatcacct gaggttggga gtttgagacc agcctgacca acatggagaa    35580
actccatctc taccaaaaat acaaaattag ctgggcgtgg tggcgcatgc ctgtaattcc    35640
agctactcgg ggcaggagca tcacttgaac tcaggaggtg gaggttgtgg tgagctgaga    35700
ttgtgccatt gcattccagc ctgggcaaca agagcgagag tccatctcaa aaaaaaaaa     35760 aaaaaaaaa aaagctgtat tttacattca gccttgaagt caagggtaaa atattagaaa     35820
tctggcagtt gaatttagat gaactttgat tttttttttt tcttttttgag acagtgtctc    35880 actttgtcac ccaggctgga gtgcattggt gcaatctcag ctcactgcag cctcaacctc    35940
ctgggctcaa gcaatccttc cacctctgcc cccaccaagt agctgggact acaggcacat    36000
gccaccacgc ctggctaatt tttttgtatt ttttgtaaag atagggttga gccatgttgg    36060
ccaggctggt cttgaactcc tgagctgaga ctatctgccc accttggcct cccaaagtgt    36120
aaggattaca ggtgtgaccc accacacccg gcccctgatt ttttaaattt ggattttaaa    36180
actttgattt ttgtgctcag gtgtcttatt acacatcctt aatattttta gatttatatt    36240 tatttttag gaaatattat ggaatctaat tttatctttt ttttttttg agatagaatt      36300 tctctctgtt gctcaggctg gagtgcagtg gtgccatctc ggctcactgc aacctctgcc    36360
tcctagattc aagggattct cctgcctcag cctcctgagt agctgggatt acagtcacgc    36420
accaccatgc ctggctaatt tttgtatttt cagtagagac ggggtttcac cattttggcc    36480
aggctggtct ccaactcctg acctcaagtg atccgctcac ctcagcctcc cagggtgctg    36540
```

```
ggattacagg agtgagctac tgtgcccagc ctatctttct tgggtttttt ggtttgtttg    36600
ttttgttttg ttttgagac agggtcttgc tctgtcaccc aggctggagt gcagtggcac    36660
agtcacagct cactgcaacc tccacctccc aggttcaagt gattctcctg cctcagctgg    36720
gaatataggc acctgccaac aagcccaact aattttgta ttttgttta gtacagatgg     36780 gtttcaccat gttggcaggc tggtcttgaa ctcctggtct caagcgatct gcccacctca    36840
ccctcccaaa gtgctgggat tacaggcatg agccaccatg cctggcctct atctttcatt    36900
tttaaaatta ttttttcttga cacaaggtct tgctgtgttg cccaggctgt agtgcagttc   36960
catgatcatt gctcactgca gtctccaact cctgggctca gcaatcctc ccacctagct     37020 tctacaggtg catgccacca tgcctggcta attaaaaaaa aaattttgt agacatggag     37080 tctcactatg ttgcccaggc tgttctcaaa ctcatgagct caagtgatcc tctagcctcg    37140
gcctcccaaa gtgttgagat tacaggtgtg agccaccatg tccagcctag aatctaattt    37200
taaatcatac cctttgaatt ttgtagttag aaagaattac aaagtgcttt attcctcaag    37260
caatcacttg aatttcaggc agtattttcc tagagaatta gccttttaaa aatgatcttc    37320 ccttcccca cacagcctca ccttttcagt atagaccaca tcaaataaaa ttgtgaatgt     37380
aaaaatgctc ggctggtgga ggaggctacc atcataacca ccttaggacc ttcagtaaac    37440
tatttatttt ctccactctc caaacccaag tcttactttc cttcattcca attaagaata    37500
tacagagatc ccaggcacag tggctcacac ctgtaatccc agcacttgca aggccaaggc    37560
aggaggagaa tcagttgagg ccatgagtta gagaccagcc tgggcaacat aacaagatgc    37620
catctctatg aaaatttaa aaattagcca gatgaggtag cacgtgcctg ttgtcctagc     37680
tacccaggag gctgaagtgg gaggagagct tgagtccagg aggctgatct tgccactgca    37740
ctccagcctg ggcaacagag caagaccctg tctcttaaag aaaaataaat aaataaataa    37800
ataaataaat atattatttt atttatatgt aaatgtatat ttatataaat agatttatat    37860
atgtatattt tatttatata tttatatttt atatatgtat attttattta tatgtatatt    37920
tatatataat atacatatat aaatatacgt attatataat atatgtatat aaatatacat    37980
atatatacat ttatatatat aataaataaa aatatacata tatttaatac atatatttaa    38040
taaaaacatt aaatacatat atttaataaa aatataattt atatataata tacatatatt    38100
tatatataaa tatatttata tataatatgc atatgtttat tttacatata taaatatatt    38160
tatatataaa tatacgtata tttatttttat atatatatgt gtgtgtgtat atatatatat   38220
atacacacac acacgtatat acccagggag aggcactaat tgtgcagttt tgaaaagttt    38280
cctagtgatg ctgccgtggc ctactttcaa agcactatgc ttaggtttac cacttaaaat    38340 gttattcat ttttccagaa gtacacttta aaatactttg tttttaaagt gaggcattac     38400
aatggtgtca tgagctgaca ttcccagcca ctgactggaa gatttgggtc aacccaggga    38460
acaggcttgg tttaagggag ttcaagtgtt ggtggccttt gggtaaaagt ttatgtctat    38520
ctttgtatgt gggattcagt agggattttc tttaatgtta aaaattctag tttcctctgt    38580
atttgctttc cttcttcccc tgtcctccct gagcctccac acatgtgtaa cacattttat    38640
ttgccaatag gtcaaggagg ttaaaaagac tttgtcgggc ttggaagtca gcatggttac    38700
tgcagttccc ggtaggctac cagtcatgac catgattcca gatgttgact gcctgctctg    38760
ggccattggg cgggtcccga ataccaagga cctgagttta aacaaactgg taagctggct    38820
tggtctgccc gaaacatttg tgaatctact aggagtctta tggttttatt ttcccccag    38880 acacccaaaa cttgggtgga ttccattgga ttcttttctc ttttttcccat gtattcagtt   38940
```

```
tgtgatcaaa tttcattgct tcttcctttg aaattaaaaa aaaaagtttt ctcttctctt   39000
ctttcctttt cctttctttt ctgttttgt tttttctttt tgttttga gaaaggtctt   39060
gctctgtcac ccaggctgga gttcagtggt gtgatcatag ctcaccgcag tcttaacctc   39120
ctaggctcaa gtgatccacc cacctcagct tctggagtag atggaactat gtgtgtgcca   39180
caatgcccag ctaattttt tatttttatt tttttagag atgaggtttc accatgttgc   39240
ccaggctggt ctcctcggct caagcgattc gcccatctca gcctcccaga gtgctgggac   39300
tataggcatg tcccagcatg tcccagaaaa aggccgccac gtctggcctt tttctttttt   39360
gttttctttc cttttttttt tttttttttt tgagacaggg tcttgctttg tcacccaggc   39420
tagtgtacag tggcatgatc atagctcact gcagtcttga attcctgggg tcaactgatc   39480
cttctgcctc agcttcccaa gtagctggag ctacaggaat gtgccaccac acctggctaa   39540
tttttaagtt ttctgtagag atggagtctt actatgttgc ccaggctgct cttgaactcc   39600
tggcctcaag tgatccttcc acctcggcct cccaaagtgc tcggattata acatgagcc   39660
tccatgccca gccggcctgc cacctctaac ctagtttcct attggcctcc ctcttacaga   39720
cttcgttttt gctatgtgaa tgtctctttc aagtcctatg ctgatctttt agcatctgta   39780
gtaggtaatc cagattgctg ggtgggtaac tgtcttgtac attgtacaca gggatgggaa   39840
cagatgtgaa gctgtctctc ttggctctac ccgtgctgtc tgtatttgtg acagttggc   39900
attcttactt gttcttttaa atgttgaagt aaaatctaga atgggagctt ggggtttggt   39960
tcccagagtt tgacccaaat ttgaaccta gttcttacaa cataacagtt gcatggcttt   40020
gagcaagcag cttaatttct ctgcttcaag tggttcatat tcacaatggg aatgaaaaaa   40080
gttcttgcct cattgggtta tacagaagag taaatgaaaa agtgcatgca aagtaattta   40140
taactgagac cctagcttac attatgaaca caatgaatgt tcacctgcta ttgataatga   40200
tgatgatttt tctgatatgc tatactactc tattagtaat aataggatat tttatgtttg   40260
aggtgcatat atttatttg ttctgggttt ttttgtttgt ttgtttgttt gtttgtttgt   40320
tttgagacag agtcttgccg tgttgcccag gctggagtac agtgttgtga tctagctcac   40380
tgcaacctct gcctcctggg ttctagcgat tcgcctacct cagcctcccg agtagctggg   40440
attccaggcg tgtaccacca cgcccgtcga attttttgtat ttttttaata gagacaggat   40500
ttcaccatgt tggccaggct ggtctcgaac tcctgacctc aggtgatcca cccaccgtgg   40560
cctctcaaag tgctgggatt acaggcgtaa gccactgcgc ccagcctgag gcgtatatat   40620
ttgatagagc tgcttgagca gtgtataccct tttgacttat gttctaatac taagttcctg   40680
ttgtaatgtg gattcctttt ctgtttctgt aaaaggtcat ttttctgcat gttaacttat   40740
aaaatattca gggagatgtt ttgattgttt gtaatcttat tcaatgacat ttagtaaaat   40800
taattgccta ttttcatatt aacaaaacta gtcagccagg cgccgtggct cacacctgta   40860
atcccagctc tttgggaggc tgaggcgggt ggatcacctg aggtcaggag ttcgagacca   40920
gcctgggcaa cgtggtgaaa tgccgtctct actaataata caaaaattag ccaggcatgg   40980
tgacgcatgc ctgtaatccc agctacttgg gaggctgagg caggagaatc gcttgaaccc   41040
aggaggctga ggttgcagtg agccgagatc acgccattgc actccagccc tggcaacaaa   41100
agcaaaactc cgtctcaaaa aaaaaaaacc aaaaaaaaac accaaaagaa aacaacaaca   41160
acaaaaaact ggtcattcag cttttcacct ttcaagagat attttgccat tgtacagatg   41220
taagcactga taggtccagt tttcaactaa atttgctaac ttttttgggg ggggttggat   41280
```

```
agggtcttgc tctgtcacct aggctggagt acagtggtgc catcatggct cactgcatcc    41340
ttgcagcatc aaactcctgg gctcaagcca tccttctacc ttagtctccc aagtagtagg    41400
aactacaggc gtggtccacc acacctggct aattttttaaa aaaattttt gtagacacaa    41460 ggtctcgctg tattacccag gctaattttg aactgggctc aagcgatcct tccacctcag    41520
cttcccaaag tgctgggatt acaggcatga gccattgcac ccagcctata tttgctaaat    41580
ttttgaagaa tgaggcaaaa aaaaaaggtt cagtctcatt tgacattaag atatatttat    41640
ataatgcaaa ttgagtgatt actatgtgct aggtcttgtc aacatgttac taatctaatt    41700
taatcttgcc aacaaccggc aaggtataag gaagccagga gcacagagat actagataat    41760
ttactgggct gtaaactcta tggtgtaggg agaatgtctg tcttaccatg gtattctcag    41820
tgatgaagtc aaagtctcat ttgtaataga agcttaaata tttgttgata aacaggtggt    41880
tatacaaggt ctcataaccg gtaagttgca gagctaggat ttgaattttg gtctgtctgt    41940
accaaaggtt gtactctttt tttttttttt ttttttttt ttttgaggca gagtctcttt    42000
ctgttgccca ggctggagtc agtggtgcca tctcagctta ctgcaatctc cgcccctgg    42060 gttcaagtga ttctcctgcc tcagcttccc aagtagctgg gacttgccaa gtaggtgggc    42120
atgcaccacc atgcctggcg aattttttagt attttttagta gagacagggt ttcaccatgt    42180
tggccaggct ggtctcaaac tcctgacctc aggtgatccg cccgccttgg cctcccgaag    42240
tgctaggatt tacaggcctg aaccactgcg cctggccagt tgtactctta agctctgtgg    42300
ctacttactt cctacttctg ccatatctct acttctcata tatacttagg atttgcaaag    42360
ccacatgata agcataacat gtcttcttaa agcaaaaatt tgactacata taggaaaata    42420
tttttggtta agggaaacat caatatgtgt ttttgttttg ttttgctttt acttttcttc    42480
tgggagtctg aaaaaaacat cagtatgttt tagagtagag tgcaaaagtt gcttggattt    42540
ttaaagacaa aatggtaagc ttcatagaaa tgtgcttttg gccaggcatg gtggctcaca    42600
cctgtaaccc cagtgctttg ggagacctag gcgtgaggat cacttgaggc cagaagtttg    42660
aggtcagcct gggaaacagc aagacctatt ctataaaaaa atgttaaaaa ggctaggcgt    42720
ggtggttcac gcctgtaatc ccaacactct gggaggccga ggcaggtgga tcacgaggtc    42780
aggagatcaa gaccatcctg gctaacatgg tgaaaccccg tctctactaa aaatacaaaa    42840
aaattagctg ggtgtggcgg cgggcacctg tagtcccagc tactcgggag gctgaggcag    42900
gagaatggcg tgaacctggg aggcagagct tgcagagagc ctagatcgcg ccagcctggg    42960
cgacagagcg agactccatc tcaataaata aataaataaa taaataaata aataaataaa    43020
taaataaata aataaataaa tgtatgttaa aaaattatcc aggtgtgatg gcacatgcct    43080
ctagttctag ctactcggga ggctaagcag gaggattgct taagcccagg aggtcaagat    43140
tgcagtgagc catgatcaca ccactgcact ccagcctggg taacagagcg agaccctgtc    43200
tctaaaaaaa aactaaataa acatagatat gcttttggtg actgcttgag tcagtgttcc    43260
tcaggagcag tgcttccatg ggacaagttg aaaagctgga ctccagaggg attccaagtg    43320
gcacacctga tagttgagtg atcctcttca tgtctgcctg gccagttgaa ttgtacattg    43380
caatgtcaaa tcctgttaaa acatctcaaa agtggataaa atactacctt ttatgttaag    43440
caagatatga aacttgccaa cttttttttt tctaatttct aacagaggca gggtctcact    43500
gtgttgccca agctgatctc aaactcctgg gcttaaggga tcctccctct tcggcttctc    43560
aaagttctgg ggttacaggt gtgggcccac tgtacccagc ttgaaacttg ccagctgtaa    43620
atgcctttcg tgttgcagct gagtctcatg gtttcttgga gattctggct gcagttccca    43680
```

```
tgtgaaatga ggaagggaga tccagaggtt tgatctacct tttttagtag gtgggccaag    43740
tggttacatg atatctcttt gtaattttag gggattcaaa ccgatgacaa gggtcatatc    43800
atcgtagacg aattccagaa taccaacgtc aaaggcatct atgcagttgg ggatgtatgt    43860
ggaaaagctc ttcttactcc aggtaaggtc tcttcccttc ttggtgaggg agggtctgcg    43920
tgttacatga tccatctggc tcttcactgt caaatctgca gtctgcttaa gcaaagttaa    43980
aaggatgagt gtctttatat tgtcaaaatg gtacaatgtg ttgaaataga tattggttgg    44040
atacctgaca ttatctgaat aaaagactta aaatgcttag cacagactga agttttcatg    44100
tagacaatat gatcacccgt tgcggaactc tcttaggagc agacttgtgc ttggtggcag    44160
tggaaggaag tggcatttgg aagaagtaat ttagattggc attttttttt tttttggaga    44220
cactctgtta cccaggctgg agtgcagtgg catgatcacg gctcactgc agtttcaacc     44280 ttcctgggct caggtgatcc tcccacctca gactcccaag tagctaggat cacaggtgca    44340 tttttttgtag agacagggtt ttaccatgtt gtcttgaacc cctgtgctta agcagactgc   44400
ctgcctcagc ctcccagaat gttaggatta caggcatgag ccaccacaca tggcctagat    44460
tgtcattctt gtatgactgg tcttgataca accaagactg atttccttct ctccggcatc    44520
ccacacctca gcccgcttcc taagcaccat tgcaagctct gtcccatctc tatccattaa    44580
tgatcacttg atctactttc agtctgtacc tagaacctca tcagcgattc cagcgtgtcc    44640
cagggcctta tatcaggatg aaaacctaca ccagtcacac acccaaaccc ttttagctcc    44700
tttagaaagt tcttgctctt ggctaggtgt ggtggctccc atcactttca gaggctgaag    44760
ttgggggatc gcttgagtct agtagtttga gaccaggctg ggcaacatag tgagatgttg    44820
tctgtattaa aaaaataaag attcagctgg gcacggtggc tcacgcctgt aatctcagca    44880
ctttgtgagg ccgaggtggg cagatcacga ggtccagaga tcgagacctt cctgaccaac    44940
atggtgaaac cccatctctg ctaaaaatac aaaaattagc tgggcgtggt ggcacacgcc    45000
tgtagtccca gctacttggg aggctgaggc aggagaattg cttcaacccg ggaggcagag    45060
gttgcagcga gctgagatgg cgccactgct ctccagcctg gcaacaagag cgagactctg    45120
tctaaaaaaa aaaaataata atataataat aatgataata ataataaaga ttctaggcgc    45180
agtggctcat gcctgtaatt ccagcacttt agggttataa aatagaacta aagatgctga    45240
aaactaatat agcttgttcc ataaatattg tattaaaaag ctaatatctt cattaagtag    45300
attaactgcc aggtaagtga gaacttgtga atgtgtcttt tgggagtggg gccagacagg    45360
ttgagcatcc cttatctgaa atgcttggga ccagaagtgt tttcagtttc agattttgga    45420
atatttgcat atatataatg agatattttg cagatgcgac ccaagtcgaa acacggaatt    45480
catttgtttt acatacacct tatacacata gttggtaggt aactttatac gatattttaa    45540
atgtgtgcat gaggcatact tttgtctgcg ttttgactg caaccccttca catgaggtca    45600 ggtgtggaat tttctgcttg tggcatcatg gtgctccaac attttggatt ttggattttg    45660
aatttctgga ttagggatgc tcaacctgta atagaatgta taggattctc ataagccaat    45720
cattttgagt tgttcgctga ggcatgacat atcttcgctg tattaaacta tctagatagt    45780
gtaatgaaca atggtgtgaa actgtcagaa ctagggcatt aaggtagatg gataaatggc    45840
tagtggaaca atttagctat gttaaaacag acagtaagat aaacactgat tttaaaatat    45900
ctccatagtt gcaatagctg ctggccgaaa acttgcccat cgactttttg aatataagga    45960
agattccaaa ttagattata acaacatccc aactgtggtc ttcagccacc cccctattgg    46020
```

```
gacagtggga ctcacggaag gtaggtattt aaaaactgaa ggtcatttgt ggtttccttc   46080
ctctttcccc tgcccccaac tttaaattag gtctctgtca gctgatgaaa cctatctcag   46140
ccccagatta cattgctttt tggttactct cttgtcacag ttccagtttt ctcccctgct   46200
actactttga gtgtacagta tctttccttc acaccaccct atctctttga tcttttttt    46260 ttagcttttt tatttgaact aattttaaat ttaaagaaaa gctctaaaaa taatacaaag   46320
gactcctctc taaccttaat attttgctt tttattttt tcactctaca cacacacatg     46380
tctatctttc ctaagaactg gcccttacat aaaccgagta tcattttctt ttttttttc    46440 tttttgagac aagctctccc actgtcaccc aggctggagt gcagtggcac gatctctgct   46500
cactgcaacc tccgcctctg ggttcaagca attcttctgc ctcagcctcc cgaatagctg   46560
ggactaccag gcctgcacca ccaccatgcc tggctaattt tttgtagaga tggggtttca   46620
ctgtgttgcc caggctggtc tcaatctcct gggctcaagc gatccacctg cctctgcctc   46680
tcaaagtgca gggattacag gcatgagcca ctgtgcctgg cctttctttt catctagagg   46740
cagaattcct cagcccttct tttgtcttat atgacactga catttatttt gtagaatact   46800
tctcattttg gcgtggtttg atatttcctc gtggtttgat tgaggttatg tatttctggt   46860 catctcccctc tttgatagtt cagtgtaatt gtttagtttt ctgatagatg cttttttaa   46920 tgtgcattgt agatgaagcc attcataaat atggaataga aaatgtgaag acctattcaa   46980
cgagctttac cccgatgtat cacgcagtta ccaaaaggaa aacaaaatgt gtgatgaaaa   47040
tggtctgtgc taacaaggaa gaaaaggtaa ggaaaaatcc agcaaactaa atagtgcctt   47100
gcaaaatgga cagggatggc agtattttgc aggggtggaa aggagggaga ccaagcagtt   47160
gagccttctg attcaactgg acaggcccac tttgatctgt cttacctgca ttttggggtt   47220
cttcataata tttcatctag aaggaggttc cactcctttt aaaaaataaa gacgatgcca   47280
ggcgtggtgg ctcacacctg taatcccagc acgctgggag gccgaggcag gcatatcacc   47340
tgaggtcagg agtttgagac tagcctgacc aacgtggtga aaccctgtct ctactaaaaa   47400
cacaaaaatt agccaggcat gatggtgcgt gcttgtaatc ccagctactc gggaggctga   47460
ggcaggagaa tcacttgaac ctgggaggcg gaggttgcag tgagccaaga tcatgctact   47520
gccctccagc ctgggagaca aagcgagact ccatctcaaa gcaaaaaaaa aaaaaaaaa   47580 aaaaaaaca ggagaggcca gggccaggcg ctgtggctca cgcctataat cctaacactt    47640
tgggaggcca aggtaggcgg attgcctgag ctcaggagtt tgagagtagc ttgggcagca   47700
tggtgaaacc ccatctctac taaaaataca aaaattggcc gggcatggtg gtgccatgaa   47760
cattcctcag tagcctatga tttctggata ttgaatcatg aaggctccta cttagttatt   47820
tcttcatgcc agttatcatt cattcagttg ataaacatta tttgtcattc ttctcaagac   47880
taagaactgc tatatagaga ggaataatat gaagagctgg ccatcaccag aggctcttta   47940
taagttcaat taagatcaca atatcagtca gacaccgtgg ctcaccctg taatcccagc    48000 actttgggag gctgaggtgg gtggatcact tgagcccagg agttcaagac cagcctggcc   48060
aacatggtga aaccctctct ctgctaaaaa tacaaaatta gccaggcgtg gtggtgcgcg   48120
cctgtaatcc cagctactcg ggaggctgag gcaggagaat cacttgaacc cgggaggtgg   48180
aggttgcagc gagccgagat catgccattg cactccagcc tgggcaacaa gagtgaaact   48240
ccgtctcaaa aaaaaaaaa aagaagaaa gaaagaaaa tgtttctctt cttttcccag      48300
gtggtttgga tccatatgca gggacttggg tgtgatgaaa tgctgcaggg ttttgctgtt   48360
gcagtgaaga tgggagcaac gaaggcagac tttgacaaca cagtcgccat tcaccctacc   48420
```

```
tcttcagaag agctggtcac acttcgttga gaaccaggag acacgtgtgg cgggcagtgg    48480
gacccataga tcttctgaaa tgaaacaaat aatcacattg acttactgtt tgagttttat    48540
gtatttcttt attttaatca ggatcttctg atagtggaaa ttttagtac ataatagaac     48600
ttatttatgg agttagaaat ttgtagtgtt atccaggatt gattttcatt tgatcacatc    48660
tcacagtaat taatattttc aagtttttt tttattaaca gctctgtgct agttttttt     48720
ttctgtttta gcctcatccc aaatataaag ctttgtgaag tacaattaac ttaatgtact    48780
tgaatgaata gaacttgcta ctttttttt tttttttt gagacagagt tttgctctca       48840
ttgcccaggc tggagtgcgg tggtgctatt tcagctcacc acaacctctg cctcctgggt    48900
tcaagtgatt ctcctgcctt agcctcccga atagctggaa ttacaggcac gcaccaccat    48960
gcctgactaa ttttgtattt ttagtagaca tggggtttct ccatgttggt caggctggtc    49020
tcaaactccc accttcaggt gatccgccca cctcggcctc ctgaggtgct gagattacag    49080
gcgtgagcca ctgtgccagc ttgctaattt tcacagaagt tgatggcaat tcttcacatg    49140
taaacagtgc cagtgcacag aacctttata tatttttga agccagtact gtgctctgca    49200
tataacaaag ctgcttcaag gatgagacct ttttctaaaa gcatgtaatg tgagaagccg    49260
gcctgcctta ttttcttttt tctttttaa tgattaaaaa tagtttgtgg caaggcacgg    49320
tggctcaggc ctgtaattct agcactttgg gaggccgagg caggaggatt acttgagcct    49380
acaagtttga ggccagcatg cacagcatag caagactgca tctctacaga gagtaaaaaa    49440
aattacccga gtgtggtgat gtgcatctgt aatctcagct acttgggagg ctgaggtgag    49500
aggatcactt gagcttgggt gaggtgaggc tgcagtgagt cctgatcatg ctgctgcact    49560
caatcttgga caacagagca agaccctgtc tcaaaaaaaa aaaaaaaaaa tatatatata    49620
tatatatatt attttttatga ggtgaagtgc atcaaacttg ggaaagattt gaggaggctg    49680
ggaacctcct ggaaaaccac tccttgaaga aagatatgag agacatttag aagtgattcc    49740
tgctttcaga aggaggtgga ttcaaataca tcaaaagtcc cttcctctgc taagtgttta    49800
tagttcaatg aataatttca atatttgtat gtgttcttgt cattttattt ttttctgaaa    49860
aacttccaaa aatttgaaaa taaaattaca gccttttctt cttataaaa              49909
```

<210> SEQ ID NO 7
<211> LENGTH: 134529
<212> TYPE: DNA
<213> ORGANISM: human

<400> SEQUENCE: 7

```
agttcccaca gggccttgtg cgacatgggc tgcgccgagg gcaaggcagt ggcggcggcc      60
gccccaacgg agctgcagac gaaaggcaag aacggcgatg gccgccgtag gtcaggtacg     120
accgagggcg aaggcctggt ccccaggtcg acgggccgaa gcgggccttc cggccggggt     180
tgggataaa gtgccccgga gcctggcct tgaagcccct cactggagtc agtgactgac       240
cgcgcgccac gctggagacc ccagaaacgc tcccccaggt caccccggga gacggaggcc    300
ggcggccggc cgagggctgc cccgcccgct ggctgtgaga gaggtgggag gtggaaggag    360
gagcgggccc gccgcgagga cctgcccgga aacctgtcgg aaaccgaacc gagatctcgg    420
cagcgacccg cctgatttcg ctcagggccc gttagggcgt cctcttccta caagcaccgt   480
gtttccaatg aaaggttacg ggggaagcga ccaaaccgac agccgagtcc gggggtgccc    540
cttcacctct ccagaagccc ccggcccact cccagcatcc tcctccatcg agaatcttgt   600
```

```
ccgacacgcc ttcccggccc cctttctcca tccccttgaa ttttgggcac atttctccca    660
ccatcatccc gctttatcct ttcacttgtt cttccagaag agaaagctcc cagtctcttc    720
tccattgtcc ggataatgcc aataatggct agtggttact aagcactgac atgagagggg    780
cctttggaag cactagacat gggtaataat cttggttcat gtttccagcc atactgagag    840
atttatcata aaccccatta tacagatgaa gaaactgaga agcaaagagg ttataaaact    900
tacccaaagc acacaactag taagtggaag agctgggata ccagttgagg ccatctgact    960
caaaagccct ggtcatagtc atatggccgc ctccaccttt tttataggct tgagaaagtg   1020
aggctccaaa aagtgccttg cccaatggct agaattatta aatgctgtag gatctgcctc   1080
tttcaaaggc ttacagttta gttacaaggc agcatatggt gaagggctaa aaggagtggt   1140
aaaaacagcc aagtggggat ggcagctccc atagatgagg taggatttgg tagaggtgtc   1200
tgaagggaga acattcttgt tagggaagc agccggtgag accatgctag agatagggag    1260
gcctgtatat cctgctggag ttaaggactt ggattagggg aagggaagaa taaaggaaca   1320
gggtaggagc aaggtcaggc aaggtccagg tcaggcagct aatttgtggc cattagtaca   1380
atgaaggagt ttgagcaggt gcatcccaaa ttgacgtttc atgtgccatc ctcaggatct   1440
tcttgatatc tatgtccttc catttattta ctgtttttct ttagctacat tctttttgtg   1500
tgtggttaaa aaaaaaaaat ttaccatctt aacaattttg tttttttttt tttttagtt    1560 tcgctctcgt tgcccaggct ggggtgcaat ggcgccatct tggctcacct cagcctccac   1620
ctcccaggtt gaagcgattc tcctgcctca gcctcccaag tagctgggat tacaggcatg   1680
caccaccacg cctggctaat tttgtatttt taatagagac aggttttcac catgttggtc   1740
aggctggtct tgaactcctg acctcaggtg atctgcccac ctcagctccc aaagtgctg    1800 ggattacagg catgagccac tgcacccagc tgaccctaac cgttttttaag tatacagttt   1860 tcagcagtat taagtatatt cacattgttg tgaagcagat cccctgaact ttttcatctt   1920
gcaaatctga aactccatgc caactcgtta acttttcatt tgccgtttcc cccagcccct   1980
ggtatccatc attctacttt ctgtttctgt gaaatttggc tactttagat tgcttatata   2040
agttggtatc atacagtgtc tgtcttttg tgactggctt gtttcactta gcatacttgt    2100
cttcgagttt catctgtatt gtagcatgcg acaggatttc cttactttt aaggctgaat    2160 aatattccat tgtgtgtgtg tatatgtaca tacacacaca catatataca cacacacaca   2220
cacaaaatgg aatatatata cacacacaca ccacattttt tttttcccga gatggagtct   2280
tgctctatcg ccaggctgga gtgccgtggc atgatcttgg ctcaccacaa tctccgcctc   2340
ctgggttcaa gcaattctcc tccctcagtc tcccaaatag ctgggattac aggcccgcca   2400
ccatgcccag ctaatctttg tattttagt agtgacgggg tttcaccatg ttggccaggc    2460
tggtcttgaa ctcttgacct cgtgatcttc ccgcctcagc ctcccaaagt gctgggatta   2520
caggcttgag ccaccacgcc cggcctgaac tattttataa tacagaaaag ctcactcgtt   2580
ataatacaac ttgctaaatt tttacaaacg aagtatatgc atgcagccca cactcagctg   2640
aggaaataaa cgtttccagt accccaggag cccctctaat gtctcttacc cccataccaa   2700 gggcaaaacac tactctgatt tctaacagca tagaagaatt tcacctatt acatttactt    2760 tttgaaactt aaatttaggc atattttaag cattaatcta ttaaagcacg ctttatact    2820 aggtattttt cttttctttt tcttttcttt tttttttgaa atagggtctt gctctgttgc   2880
ccaggctgga gtgcagtggc ccaatcatag ctcattgcag cctcaaccgc ctggtcttaa   2940
acaatcctcc cacctcagcc tcctgtgtgg taaagtgtgc caccaagccc agctaatttt   3000
```

```
tttacatttt gtagagatga ggtcttgcca tgttgcccag gctggtctca aacttctggg   3060
ctcaagtgat cttcccacct tggcctccca gagtgctggg attacaggtg tgagccactg   3120
tacccagcct agatatttt ctatacacat acatatatac ataatgatga ttattatttt    3180
tctagagatg ggtctcactc tgttgcctag attagagtgc agtggcatga atcatagctc   3240
actgaaactg aactgctggg ctcaagtaat cctcctgcct cagcttcctg agtagctagg   3300
attacaggga cacaccacca tgcctagcct caatttttaaa ttttttgtag agataggtct  3360
cactaagcaa cagccccatc tgatctcgaa cacctggcct caagtgatcc tcctgcctca   3420
gcctcccaaa gtatactgca ccaggcccat attatacata actattgaca ttaaaaatgt   3480
tcttttgtgt gtcacctaca aacactctag aagccacctt ccttaagtac catatgatct   3540
ctaagttcct tctcaaatta aaattatgtg gttaagtttc aagaaactaa tttcttaatg   3600
atgcagaagg ttttgcttga atgactcttc aaccgagcat ctattattta tcaggcactg   3660
ggaactcagg gataaacaag gcatgatctc agtccttgaa catagagtct cgtggagaag   3720
aatggcgtag aaaatgcagt gtcatgatgt gtaatcataa aagtagatgg gtacacacca   3780
cttcaggaga atggcagagg gagttaacat cttggcactt agcatttagt atttcttctg   3840
taacacacat tccattctat tttaatgagc ttgcaaacat ttttcctgct ggattttga    3900 ggatcaggaa tgtgttttgt tcactatctt atctcctaca gtccttggca tactgcccta   3960
caaatcagta aatgtgttta tatgactcat atggcaaaag gcaattttt tttttttaat    4020 aagtgaggaa tgttccaaaa gccaatgcta ttaacattga ccagcttctt ctagtaagga   4080
gaggagacag tattttttca aagtgcggtc ctaagaccac ctgcaagaga attaattaca   4140
tgctgggaat gtgtagatta aaaactcatt ttcctgttct ccatttcaga cctactaaat   4200
cagcctcaga gtgaaggaag cttcatttt ggtgtctcaa gtgattctat ttgaaccaag    4260
gcctgagaac actgcagtga ggtgtttagg ccagcgtcaa atcacctatt tctgggcaga   4320
ggtgcctatc cttagcaatg gggctgaggc tggggtggag gttgctactg cagatcactg   4380
aggctgataa gggtgagtca gatgccccaa gaggaaattg aaagctttgg aatggaacca   4440
aagatcgtga ctgacatgca gtcatgcaat ctgcaatcag aagttagtat tacacgatgc   4500
gctagataat tgtagagtaa tcttgctttt tgttgatttt aaccaggtaa tttaaagtca   4560
ttactcatta tttggatttt cacatttgaa tgtttactct ttgtattaat gtgtactgag   4620
tatttaaagc ttttaaatta gcttttttaa aaagtgtatt ttaggccagg tgcggtagat   4680
catgcctgta atcccagcac tttgggaggc caaggcgggt ggatcatctg aggtcaggag   4740
ttcgagacca gtctggccaa catggtgaaa ccccatctct actaaaaaaa tacaaaatta   4800
gctgggcgtg gtagcacaca cctgtaatcc cagctactca ggaggctgag gcaggagaat   4860
tgctttaatc caggaggcag aggttgcagt gagctgaggt cgtgccattg cactccagcc   4920
tgggtgatga gaacgaaact ccgtctccaa aaaaaaaaa acggtggggg ggaggcggta    4980
ttttagattt acagttggat taaatccttg aaagaactca aagaaggaa ttaatctgtt    5040 aatgcctttt ctttaccttc ataaaacatc agggaatatt tcatgaatat tccttatatc   5100
ctactttcta gctctgagca ttactttgct ggtagaaact agtctacatg tatataacta   5160
taaatgacta tcacaaatca ctctttgatg ttaaaaacaa actatctggc tggttgtggt   5220
ggctcatgcc tgtattcctg gcactttggg aggcccagct gggaggattg cttgacacca   5280
ggagttcaag accagcctgg gcaacaaagt gagcctcagt ctctgcaaaa acaaatagct   5340
```

```
gggcatggtg gcgtgcgcct gttagtcaca cctgctcagg aggttaaggt gggaggatcg    5400
catgagcgtg ggaggtcgag gctgcagtga gccatgatca ggctactgca ctccagcctg    5460
ggtaacagag ggagaccctg tctcagaaaa acagcaacaa atctacctgt tgggttttc     5520
gtttgtttgg attttatttt tatttattt tattttgaga cggagtttca ctcttgttgc    5580
ccaggctgga gtgcattggc atgatcttgg ctcactgcaa actccatctc ctgggttcaa    5640
gcgattctcc tgcctcagcc tcccaagtag ctgggattac aggcatgcac cacaacgccc    5700
gactaatttt gtattttttg taaagacaag ggtttctcca tgttggtcag gttggtctcc    5760
aactcctgac ctcaggtgat ctgcccacct cagcctccca aagtgctgag attataggca    5820
tgagccaccg ctcccggcca cctgttggtt ttagtggtag tgcagtggtt ttcagctttc    5880
aacattcaag tacgctccca actttgacaa atatagaaaa gttattttg ccacaattta     5940
gtgtgtttat ggaaggtgta tacagaaact tcagatgaca gtgtctgtta gatgaaaaac    6000
tgagctgggc aggtggtggg aagttgtata gacccagaaa taacttgtta tgggaagaat    6060
taagaggcca caattaatgg gttgaaaatt aaaaatctgc agggacaggc aggtcatata    6120
aatgagtgac ccaggcaggt agtaaacagc agggagtggt ggagactggg gtggactgag    6180
gagagaatgc tgtacagaca gggcaatttc tactgagctt ccctttcttt gggtgggaaa    6240
atgagtgtag tgtggccaga cctgcttttt ttcaagagaa actagaaatc tctatttatc    6300
attttgtga cttccccagc ttgtgaatgt cagcagtaat gcaattaagc aaaatactga     6360
gggtcaaaca agatgtgatt gcaggtaaat atggtctgtg aatgtgtaga ataatgtcaa    6420
gctggcacac atttaaaaaa tgagaaaaag atggtgtctt ttgaatgtat agaagtggct    6480
gggacagaaa acagtttttc ttagatagta acacagtgca gagaagtgtc tgagtgaaca    6540
gtgtaaatga ccgctgtcaa agtatggttt tcgaaacgtt aaaaatatga tcttgtacag    6600
aaaaaaaaac aggtatcaaa acttagtcat taattaaacc aataaatgaa agaaccaata    6660
aaatggtaaa gctaatttaa aggcaaattc aaggactagg gacatataat caagaaaatg    6720
atgaattgaa tttgctagta cagtagttac aaagctggtt aatgtctcac agagcaataa    6780
aactaacttt tgggccagat gcagtggctc atgcctgtaa tcccagcact ttgggagact    6840
gaggcaggca gatcacttga ggtcaggagt tcgagaccag tctggcgaac atggtgaaac    6900
ctcatctgta ctaaaagtac aaaaattagc caggtggtgg catgcgcatg taatcccagc    6960
tactcaggaa gctgaggcag gagaatcact tgaacctgag aggcggaggt tgcagtgagc    7020
cgagattgca ctgctgcact ccagcctggg tgaaatagtg agactctgtc tcaaaaaaca    7080
aacaaacaaa caaaactaac ttttgggatt attgagcaga aatgtacgag ttaacatgaa    7140
acttcagtgt ctaggctgta ataaaatagt aaacagcaaa gtcaagtaca gatcactct     7200
cttaagaaaa ttaaatgatc cttgggtggg cttgttaaac atggtccagt atgacattga    7260
aaggacattt agtcaacttc tttctttact tccaagtttg acattttc ttaagattgt      7320
ggatattaca gtgtagctat ggctgccttg agattattgc tcacttatat agtggcattt    7380
taagctgctt aatcccctca aatgtgctgc caaaattcta ctttttcaag tatgtgcagc    7440
agcttttctc aagtatgtgc atttaaactt ttaaaaatgt ttaaacaac tgtgagcaaa     7500
tcgaaggctt gctgcactct atatagggtc aatgtttcat taagtgcttt atcacaaaga    7560
tttgtttaga agtgggcaca aggctcttgg tcatcaaatt cgttttaggt ttagagaagt    7620
aatcttacct cttggagcaa gagctagatt tcactctttt atgtatagag tgagatcaag    7680
gaagaagggg aatagaagga atagaactta gcaaacagct ccccactccc aagtcaagtt    7740
```

```
tgttagaaat gtaacactgg actaccattg ttgggagacc aaggagcatg gtttcgctgt    7800
accattcctt tcacgggatt ccatgggatc tttctagatg tgctggactg gtaaaaatcc    7860
ttacctgtgg gaagggaggg tgtgtccagt tgaagcagaa taaaaggaaa gctaaaccgg    7920
gaggtgaccc ttgatcaagc actgggaaaa agtggtaaaa gctcttgaat cactcactga    7980
gaggcagctg aaggtgggga ctggtgagga gggagcatga actgctgcat ctggcagcca    8040
gctttgggga ccagtggctg gtgcagactt gctaaggagt gctaatggtg tttattaaaa    8100
caacaacaaa agcaatttag ttactctggc cctgggtgtg ggcagagtag tgtgggaagg    8160
ggagagggca gattgcaaag gaaatatatg tgagattgtt tcttttttgca taggcactga    8220 tgcataacca ttcgcactgg attagtcaaa gctgtaactc ctgatgaaat ttctttaagg    8280
atgaaggacg tgtgacaagt ttaggtctcc ttttaagctt gtggcacaag ttttttttcc    8340
cctgttccct gaccttgcca gactccctca ctcatctgtt catgaatggt tgttctcttt    8400
tacctaaaat atccttcctt ctctttgctg ggcaaactct cctcacacat caagacccag    8460
tccaaatgac agttttgtaa ttccccaagt agagatagtt ttgcccttttc tggacatctg    8520 tggctcttct cattttttttt gtaggacata tagtgtattg tgtagcattc tattagactg    8580
ggctcctggg ggtaaggatg tcttgtttat tttttattta tgttttttttg aaacagagtc    8640 ttgctctgtc cccaggctag agtgcagtgg cgcaatctcg gctcactgca acctctgcct    8700
cccaggttga ggcaattctt ctgcctcagc ctcccgagta gctgggatta caggtggcca    8760
ccacacccag ctaattttttg ttttttttagt aaagacgggg tttcaccatg ttggccaggt    8820
tggtctcaaa ctcctgacct tgtgatctgc ctgccttgga ctcccaaagt gctgggatta    8880
taggcatgag ccaccgcacc tatagctgtc ttgtttagag ttgaatttcc tgtttgggat    8940
agttcatggc acatagtaga tgctcggtaa atgttcaaat atagttgtgt caagttattc    9000
cctcctgatt ttctccccca ctgtttgatc aacccaggaa tctctttccc ccttggaaac    9060
ttcttttatc tacctctctg cccctgactc actggaatcc tacaaatggg acatctcagg    9120
caggtaaaat tgccattgtt atgagggtga gagaatgcag atttttttaca gtgtatttcc    9180 aatgtcccat atggaacatt gtatttccca gtaatacagt tttttttgaaa gaggggataa    9240 caccaaagta gtcttgttaa ttagataata tttattcatt taatacttac taaccatctt    9300
ccatatgtta ggcattgttg taggtgctgg ggatctgtga gtaaatatgc ccatatggag    9360
ttgttttcta gagtaatgta gaacttctga gagctttaat aaaaaggagt aacatttatt    9420
gaatgcttat tatgatccag gtactgtgct gagtgcttta tatgtattaa cacatttaat    9480
cactgcaaga ggcaaatgag gaaagtgagg cccagagagg taacaagcat acaactatta    9540
agtagtggag cgaggattct catgctggaa gctagtgtac ttaaccactg tgctctactg    9600
ccttgcttaa tagagtgatt gggcacgtct aatgaaacct tggtgatatg gtttagctct    9660
gtgtccccac ccaaatctca ccttgaattg taatgatccg catgtgtcaa gggcagtacc    9720
agatggagat aactgaatca tgggggtggt ttctgccatg cctgttctca tgatagtgag    9780
tgagttctca tgagatatga tggttttata aagggcttcc cccttcactt ggcactcatt    9840
ctctctcctg ccaccatgtg aagaggtgcc ttctgccatg actaaaagtt tcctgaggcc    9900
tccccagcca tgcagaacta tgaatcaatt aaacctcttt tttttttttt ttttataaat    9960
tacctagtct cagatatgtc cttatagcag cgtgagaatg gactaataca cctggattcc   10020 tccatcccctt cataagacct gaacaggaag cactgtttcc cattaaaata agcagttgaa   10080
```

```
ataaaatcaa acttttagt ggattaccag tatctggaaa caatagaaaa aggagcttat    10140
gccgggcaca gtgtctcacg cctgtaatcc cagcacttcg ggaggccaag gtgggcggat    10200
cacctgaggt caggagttca agaccagcct gaccaacatg gagaaacccc atctctacta    10260
aaaatgcaaa aaattagctg ggcgtgtggt gggcacctgt aatcccagct acttgggagg    10320
ctgaggcagg ggaatcattt gaaccctgga ggtggaagtt gcagtgaacc aagatggcac    10380
cattgcactc aagcctgggc aacaagagtg aaactctgtc tcaaaaaaaa caaaaaaaga    10440 aaagaaaaa ggagcttatt cataacagtt taaccttata tttagggaca ggtagacagt    10500
tatacggatg ctgaagacag ccaaaaatgt ctagcttagg ttgtagatgc tgaacgctgt    10560
gggctcactg acccttgcct atgaagcact gtagaatacc tttatcactt catttccata    10620
agttcagtta tgtccctgga atataatctt gaagcagaag agcctgatat aataacagtg    10680
tagcctctaa ggttgatccc caatataaga tgatctttac agagatctcc tgttatattt    10740
caggctactt atttagatta tggctccaca agtcatttga ggcaaagtgg aaagagaatt    10800
agagtgaaga gaacggaatt ctagtttctg ttatatcctt aaatagctgt gtgattttag    10860
acaagttcca aagcacctat gcgccttagt tccctcattt gcaaaatgaa gtgaatggat    10920
gaatattaag tcctctcaag ctgtaaaatt ctgtaggtct gtctcccata aaattaaaat    10980
taggcccgta aatgcgtaga aaatgtaata attccaaata aaaataccta gcattttgg     11040 attccacaat agcaaggtaa tttcccatgt attatctaag atgtgtcttt ttttccggtc    11100
ttggctcctg gaatgcatgc ctgaatgact actaaggttt taactcattc actttatttt    11160
atatggtaag tcagtagctc aagatagtaa ggaataactt gctttaaagt aataaatatg    11220
ttaagaccca aaagactgtc aattatattt ggaaagatt tgggtagagg aatttgctac     11280
attcaagtac atttctggaa ccagttatct gaaagtagtg atccttaaat tcatgtcctc    11340
ctcctaagat ctctagtgca gtgttttata caactgctg agtaacaaat atatctagta     11400
ggatatcttt ttaattttat ttttaaaatt ggtatacaaa taaaatagat ttttggtgtc    11460
cttttaattt tttattattt attttaattt atttctttt ggagaaaggg tcttgctctg     11520
tcacccaggc tcaagtgcaa tggtgtaatt atagctcaca gcagcttcaa actcctgggc    11580
tcaggtaatc ctcctgcttg agcctcctga gtagctatga ccacaggtga gtggtaccat    11640
gcctggctaa ctttttatt ttattttta tagaaatgaa gtcttcttat gatgccagg       11700 ctggtctcaa actcctggca tcaagccatc ctccctcctg ggcctcccaa agtgctgtga    11760
ttacaggtgg gagccaccgt gtctggcctt tggtgttcat tttatgaatt ttaacatatg    11820
tatacatgat cgggttacat aacagttccg ttaccccaca aaatttcacc catgctatcc    11880
ctttgtggtt acagcctccc cagttgatta ggatacaact gtattccaat ctctggagcc    11940
actgacctgt tctccatcaa tatagttttg tcttttcagg aatgcgatat aaatggaatc    12000
acaaaataac attttgagat tgatttttc acacagcata atactttga gattcatcta     12060 atttgtcatg tgtatctata gtttacttca ttttattact gagtggtatt acattataca    12120
agtgtaccat aatttttttg tcctttcatt cattgaagga tatttagatt ttttccattt    12180
tttagtgatt atagagttgc tataagcatt ggtatataag ttttttaaaa attgatatat    12240
aaggctgggt gcagtggctc acacccgtaa tcccggcact tgggaagcc gagcggggca      12300 gatcacctga ggtcaggagt tagagaccag tctgaccaac atggagaaac cccatctcta    12360
ctaaaaatat aaaattagct gggtgtggtg ttgcatgcct gtaatcccag ctactcggga    12420
ggctgaggca ggagaatcac ctgaacccag aaggcggagg ttgcagtgag ccgagattgt    12480
```

```
gccactgcac ttcagcctgg caacaagagc aaaactccat ctcaaaaaaa aaaaaaaaaa   12540
aatctgtatt tgattaacat accataaata taggccggtt gtggtggctt actcctgtaa   12600
tcccagcact ttggaggctg aggcaggtgg atcacctgag gttgggagtt tgagaccagc   12660
ctgaccaaca tggagaaacc ccgtctctac taaaaataca aaattagtcg ggcgtggtgg   12720
cacatgcctg taatcccagc tacttgggag gctgaggcag gagaatcgct tgaacccagg   12780
aggcagagat tgtggtgagc caagattgca ccattgcatt ccagcctggg caacaagagt   12840
gaaactctct ctcaaaataa agtgggggcg gcagggaat aaccatttaa aagtgcacag    12900
tttagagtgc aaccttcacc actattgaat ttgagaacat tttcttttct ttttttttg    12960 agacggagtc tcgctctgtt gcccaggctg gagtgtaatg atttgatctc ggctcactgc   13020
aacctccgcc tcccgggttc acgccattct cctgccttag cctcctgagt agctgggact   13080
acaggcgccc gccaccacac ctggctaatt tttggtattt ttagtagaga tggggtttca   13140
ctgtgttagc caggctggtc tcgatctcct gacctggtga tccccccgcc tcggcctccc   13200
aaagtagtgg gattacaggc gtgagccacc gtgcccagcc tagaacattt tcattactcc   13260
aaaaagaaac cccatacccca ttagcagtaa attttcactc tttccctagc aattgctagc   13320
ctactttctg tctctataga tttgcctatt ccgagcatta cttttctttt tttttttttt   13380
tttttttgag acagggtctc actttgtcac ccaggctgga gtgtagtggt gtcatcttgg   13440
ctcattgcaa cttctacctc ctgggctcaa gcaatcctcc cacctcagcc tcctcagtag   13500
ctgggactac gggcacacac caccatgtct ggctaatttt tgtacgtttt gtagagtcag   13560
ggtttcaccg tgttgcccag gctggtcttg aactcctgag ctcaagtgat ttgcctgcct   13620
tggcctattc tgggcatttc ttataagtgg aatcatacaa tctatggtct tttatgagtg   13680
gcttctttca cttagcataa tattttcaag gtttattcac attgcagcat gtattagtac   13740
ttctttttat tgttaataa cagtgcattg tatgaatata caacatttta ttttatttta    13800
ttttatttta ttttatttta tttattttt ttgagatgga gtctcaccct gtcgcccagg     13860
ctggagtgca atggcgagat ctcagctcac tgcatcctct gcctcccggg ttcaaccgat   13920
tcttctgcct cagcctcctg agtagctggg attataggcg cacgctacca cgcctggcta   13980 attttttgtat ttttagtaga gatggggttg caccatgttg gtcaggctgg tcttgaactc   14040
ctgacctcgt gatccacctg cctcggcctc tcaaagtgct gggattacag gtgtgagcca   14100
ctgtgcccgg gcaattttta tttctatttt aaccacttct tggacatttg ggttgtttcc   14160 acttttggc tgttatgaat aatgctgaga accatcatgt acaagtttca tgtacacatg    14220 tatttttat ttatcttagg catatacttt gaaatagaat tgttggacca tatggtaact    14280
atatgtttaa catttttttc attttttttg acagagattc ttgctctgtc acccaggctg   14340
gagtgcagtg gtgtgatctt ggctcactgc aacctccacc tcccggttca agcaattctt   14400
ctgcttgagc ctcctgagta gctgggacta caggtgcatg ccaccacgcc cggctaattt   14460
ttgtattttc agtagagatg gggtttcacc atgttggcca ggatggtctc gaactcccaa   14520
cctcaggtga tccacccacc gcagcctccc aaagtgttga gattacaggc atgagccact   14580
gtgcccagcc atgtttaact ttttgaggaa tttctaaact gtttcccaaa gtgtctatac   14640
tattttacat ttctgccagc aatgtattag agttccaaat tttccacatc cttgttaaca   14700
ctagttattg tctatctttt ttattctagc catcctagtg gtgtgaagtg gtatctcact   14760
gtggtttgat ttgcatttcc gtaatgaata atgatgttga gcatattttc atgtgcttac   14820
```

```
tgtttatctt ctttggataa atgtctgttc aaagtcttt tccattttt aattgggttt     14880
tgttttgttt tgttttaagg agcagaaagt ttaataggca agaaagaagg aagaagctcc   14940
cccatacaga gacagaggga aagtcaagag gaaaccctgt gtggggcaga aaagtggcta   15000
cttatatgag gaggctggag gaggtggtgt ctgatttgca tagtgctcag tggattggtt   15060
tgatcagcat gtcattcacg aagcccctga aaaatctggc cctcacaccc tagccttta   15120
atatgcaaat gcagggcgcc atgatgtttt acacacgtga ggatgtgtgg gggtgaccat   15180
gttgccaggc acatgtcggg gcaagggcaa gaaaagagg gtgggaatca ccatgtttgg    15240
gtggactcag tttctaatgg cttgcatttt catatcaaag gttgcctgcc cggctctaag   15300
agcccggtct tccctgctag acaagaaaca tttctggagc tgctttaaaa gaaacgaaaa   15360
cttcccaagg accccttttc ctgtctctct gcctaaaata atttattaat aactcctata   15420
acattctccc ctgtggagag gtcaccctaa ctgctgttag ggggttttgg gcaacaacta   15480
tttctggcta cttcctgctg aaaagggtg tcgaatgggg aacagcagct agggcccctc    15540
ctggggtcga taagggtcct cagaagaatg gcatgtccat gcatggttca gtttgcagca   15600
gcatttggag ttggattgct tctaggcgag aggaaacaat ttgatttata gtattgagaa   15660
tacagggttc aaatattaat acaagacata taagcaagag agggcttaat aaaggggtta   15720
accaattcca taagaagac tggaatgcat taagagggga ttgtagccac ccggggctga    15780
agcctccatt tttccgtcag cctgtcaata gttttgattt gatctttaag tacctggtgt   15840
agtaaataat tttcatctaa aattttactt gccaagatat agaatttccc tctgggggt    15900
gtctatgaag ttccttgatt ttatttccc aaacaaagaa acctctgggt tatgggcacc    15960
ctactcactt tcattacctg gcagaatttg caggataatt gctcagaact accatattga   16020
tctggatttt tacgttaccc atcccttttt gtttcttcca agctgcaggt gatcaccact   16080
tggtccacag gaataagcag ggttagttta aatgtaggc aaaaagctta aaacaatta     16140
atgagactag gatttaatga caaatgtatg ataagctttg gagaacaatt tctctctcca   16200
gtccttattt ttggtaaaaa caaattatta taggactgtg tgtgttgttc atagaataaa   16260
ctttagtctt atacttggcc tgattatttg cataaagtgc agcaagaatg gttatttctg   16320
cataggactt ttggattggc tttgatgaaa cactattcca caaggaattt cagataagac   16380
cttttaaagcc aagcccagcc atgggattgt atcctcaaat atctgtaagt tgggtgatcc  16440
tcttctcctt gaggtcccaa gataaacttg gagctcctgg cctattagaa agtgacattc   16500
ttaggctggc acggtggctc atgcctataa tcccaacact tgggaggcc gaggtgggca    16560
gatcatgagg tgaagagatc aagactatcc tggccaacat ggtgaaaccc ctcatctcta   16620
ctaaaaatac aaaaattagc tgggtgtggt ggtacacaac tgtaatccca gctacttggg   16680
aggctaaggc aggagaattc cttgaacctg ggaggtggag attgcagtga gccgatggag   16740
ccactgcact ccagcgtagg tgacagagcg agacaccacc tgaaaaaaaa aagtgacgtt   16800
ctttactgac cacaggttag gaaccctgtg cggggactgg gtagacaaga catgaggcca   16860
gtgctcccca agggctttta ttggctctgc atgtcaagtt tgattcctta agagaaaca    16920
caccctttta gtcaaagcct tgatcttgtt agacataaat tttcggtgct gcaaaggaaa   16980
tagcgctcga atatgaattt tctcagcaag gcaactttac ttttctgcag aaaagatgct   17040
tctaagaagc ctgattgtca tgagagcata ccaaacaaag aaaagcagag gttttttatcc  17100
ctgacacatt gggtccttac tgcagtgtcc tatctccatt ggctggagct ggaccgcaca   17160
atctagactg atcctgattg gctaaaaact taaaactttc ctaaataggt aaatgcacaa   17220
```

```
tggagaacaa aggaaggaag ggggttgttt acaaactagg agaataataa catttccaaa    17280
taaggaagag atgtatgctg taagctggga atgcctgggc attttcagac atgtctgagc    17340
aggttataag ccagaacaaa taacttggtt aaagtacaag dacatagaat gtacttattc    17400
ccttactata tttaacagct acataggget taacaaagag ttactagcaa aaagcaagga    17460
agcttgacgg aagttagttt ttaaaagaaa ctattatttc taacatttat tatttattct    17520
ttaacaaaaa gggaaacttt tgaagaggaa cttttttactt ttcacggtaa aataaccagt   17580
ttttccaatt gtgtcctgtt gacaagaaa aatggatttt tattgcactg atgcaaacaa     17640
ttatattgcc ataagttaag agtactcaca gagagtttcc aaattctaga ggaaccagac    17700
agagaaaaat aaaaatgctc caaattttgt tcacaggagt ataccttact cattttttc     17760 tggatggagt ttcgctcttg ttgcccaggc tggagtgcaa tggcacaatc tcggctcact    17820
gcaacctctg cctcccagga tcaagtgatt ctcctgcctc agcctcccga gtagctggga   17880
ttacaggtgc cagccactac gcctggctaa ttttcgtatt tttagtagag atgggggtttc  17940 accatttttgg ccaggctggt cttgaactcc tgacctcagg tgatctgcct gcctcggcct  18000
cccaaagtgc tgggattaca ggtgtgagcc accgcacctg gcccccttac tgaattattt   18060
agggccgtaa atatatcaaa ataagttttcc ttaactctga aaatcaaaac aaggatcagc  18120
aatatttcaa gcaaaagtca aagggttgc tttaactttc tgagtgcagt ccatttagtt    18180
aactcttatt ttgcttgata tttgtgaata tgtcagttct gtatgagtcc catacattct   18240
tcttctattt caatattaca atcttcaaag ctattaaaaa cctgtgtttg agaatacctg   18300
ttaaagtcct taatatagct tgattataaa ctgtcttcga gaaggaacaa agcaagacaa   18360 tttgttttgca aatgacaaaa tatgtaggag ttacagttaa aaacatgget gtagactacc 18420 tatttgcatt ttgatgatac ttgcattttg ccaataatct ttgagactgt ttttatttct   18480
taaagtcaca tgaactaaaa agtatttgat ttaagcacat ctttttctttt ttttgagacg 18540 aagtctcact ctgtcaccca ggctggagtg cagtggcatg atctcagctc actgcaacct  18600
ctgcctcctg ggttcaagtg attcttctgc ctcagcctcc caagtagctg agactacaag   18660
cacgcaccac catgcctggc aaattttttgt attattggtg gagaagggggt ttcaccatat 18720 tggccaggct ggtcttgaac tcctgacctc atgatccacc cacctcagcc tcccaaaagt   18780
tctgggatta caggtgtgag ccaccgtgcc tggccaaaaa gcaactaatt ttttaaaaaa   18840
taaacatttt aaagtcaggg aaaaaaaaa aaaaaaaga agccttccaa aatttaactc     18900
aggtatttga cctctcatga aggaatgtta tgctgcttct gagccaaact ctaactgcag   18960
ctagaacagg cagctctgca agcagaagaa aattttggag atgagcaata tatctcctat   19020
agtaggccag aagggaaaag aaaaaatagg gaaggcaaag aaatagggggg aacaccattc  19080 ccaataggaa aagaggcaat acctcttgat gaccctcaat tggaactcct ttctatggtg   19140 ttttttccttc atttgcagtt taaaatggct tctatctctt atgtaatgtt cttctaacct  19200
gggaaaagtt aattttccaa atcttaaaat gcttggctta gagttgagct ggggggaaggt 19260 gttggatata agagctcgga gtcgcaaaga aaatgagcac tcaaagaatt tctcagcaag   19320
gcaaatttac ttctgcagaa aggtgctgct cattcttctg gtcactgtga gagcacactg   19380
aacaaaggag ggaagggttt ttatcccctaa tgcagtcagt ccttgctact gtgtccgatc   19440
cccattggtt ggggttggac cgcacaatct aagctgatcc tgatttgcta cttgaaatgg   19500
agcaggggtg gggggctacaa aagtaagggt gccaaataag gaacagatgt gggttgttac   19560
```

```
agattgggaa cggatgtgcg ttacagattg ggaatggctg gaaggttgtt taccgtacct    19620
aggggcaagg aggcaaggaa gttaggcttt gaaaatagag gacaagcaga acctttaaag    19680
aagaactcac tgtttccagc aaagggaacc cagaagcctg atatgacatc aagagggtaa    19740
aaaggtttac cagtcgggct tttggcttct ctctccttgt gcaaaccagt aaaagggata    19800
ataaggatca ttgtttatat tctctgtaaa tttatagtta atgaaaaagg atttgtgagg    19860
ttagtcttaa gctgtagaca atctggtgtg ctttgcatgt ctttctgtgt ggttctgttg    19920
aggaaagggt atcttaggtt agaatgcagg cccagaaacc cataagcctg ctgtttgagc    19980
caccccaaca aaatggtcag taacaaactt agctacaagc ttccatgttg tttcatgtcc    20040
ttgggaacat aacctgtagc cacgtggcaa tactttattt tagtccctgc aattttacaa    20100
tggtggctgt cttcttgtgc taagtcagtt cctgggtgag ggccacaaaa tcaagtaaac    20160
cagtttgtta atctgggtgg tgccagctga tccatcaagg gcagggttta caaatatct    20220 taagtgctaa ccttaagagc ggtttaggga gggtgaaaat cttgtagcct ccagctgcag    20280
gctcctgggc catggtttct aatcttgtgg ctagttcttt ggtctgttcc caggcaagag    20340
ggaagtatat cttgggaaat actgttatca tctttgtttt agactataga ctgtaaatcc    20400
gactcctccc aaagttggtt cggcctaaac caggatggg caaggacagc ttggggctg    20460 aaaacaaaat ggaattgttt gggtcagatc tctttcactg tctcagtcac aattttgcaa    20520
tgacagtttc aaaagcttcc tatcactcct ttgaaaatac cttgtacact tgcattaagt    20580
cataacctaa ttaaggctca ttggtttcac ctgtgaggtt actgtttgta aagttcaaaa    20640
gccaaaaatc ttaactgctt ggcatggcta aagtcgagta acaagggatt ttaaaggatt    20700
ttcttaaaga gcactgagct taattaaaag ttcaggcatg gtggctcaca cctgtaatcc    20760
cagcactttg ggaggctgag atgggaggat cacctgaggt cgggagtttg agaccaacct    20820
gaccaacatg gagaaaccct gtctctacta aaaatacaaa attagccggg tgtggtggtg    20880
catgcctgta atcccagcta cttgggaggc tgaggctgga gaatcgcttg aacccaggag    20940
gcagagctgt ggtaagctga gattgcacca ctgcatgcca gcctgggcaa caagagtgaa    21000
aactgtctca aaaaaaaaa aaaaaaaaa gtggatattc aagttacagg gttataggta    21060
tatttaaggc ctttatgttt ttctcttctt ggatcttgtt tttctggaaa aaggctcttt    21120
tcttctcagt tgactgaatt atttttctcc atttttttgtc ttaccactct taatgcatgc    21180
atgagaggcc ctaagataac ttctggtaac atgggactgc tggagaaaaa cagaggaggc    21240
atcacagact ccgttctggg ggggttggga gggaacaaga aacaaatcaa aaaaacctct    21300
gttttcctca tgaaactctc caaattaaaa gcagatagtt ccctcaaaat caaaggctct    21360
gtactgttat gtattgtgtt atctaccgct tttgagtttt ggggtatcaa attacttcac    21420
attgtgggag agctttggtg tgtaataact tacagtgtag aaaatacact gtaaggggtg    21480
gctaatagta gttataaatc agagaagcat gctctgcgcc atctgaaaga tatgagaca    21540 tccccatacc ccaataagag atgagactcc cttgagggat gggctaatta caaattaagc    21600
caattagctt ggagttgcct tgcaatgaaa tgcatggtag aagcactaca ctgtcttctc    21660
ccatagtatc ttcctccttt tggggaccca aatccagta taaatggca ccgttaattt    21720 tagggatctc tctttgcctt cagttgtgcc tgcttattag gccctaaaaa acgcatacta    21780
cccggccctg ttcctccaag ggtttcaccc taaagccagt aatacaatta agaaactggc    21840
aaatgaaaaa tcttaacaag tgctgaatat tctgtctgtg ttgttataga tgtgttgtgt    21900
gtaatgtcta taaaaacagc tctaattgat tggcttaaag aaaaataagc actaggccag    21960
```

-continued

```
acgtggtggc tcatgcctgt aatcccagca ctttgggagg ctgaggcagg cggatcatga    22020
gatcagaagt tcgagaccag cctggccaat atggtaaaac cgtctctact aataatacaa    22080
aaattagctg ggtgtggtgg cgcatacctg tagtcccggc tactcgggag gctgaggcag    22140
aagaatcgct tgaacccacg aggctgaggt tgcagtgagc tgagatcacg ccactgcgct    22200
ccagcctggg tgacagagca agacttcatc tcaaaaaaaa aagaaaaaaa gaaaaaagaa    22260
aaataaacgc ttaaataaaa aattttctag ttcacatgac tttaagaaat aaaaatagtc    22320
tcaaggatta ttggtaaaat gcaagcgtca tcaaaatgca aataggtggt ctacagtcat    22380 gttttttaact aacctgcaaa ttttgtcatt cgcagacaat tgttgtcttg ctttgttctt    22440
tctcaaaaga cggtttataa tcaagctata ttaaggacgt taacaggtgt tctcaaatgc    22500
aggtttttaa tagcttttaa tattgtaaca ttgacataga gaaagaatgt atgggactca    22560
taaagaactg acatgttcac aaatatcaag caaaacacaa gttaactaaa tggattgcac    22620
tcagaaagtt aaagcaccct ttttgacttt tgcttgaaat gttgctgatc cttgttttgt    22680
ttttcagagt caaggaaact tatttttgaac tatttacagc cttaaaaaaa aagatgttgt    22740 gggttttca tagatgacct ttatcaggta gaaaagtttc cttttattcc tagtttgttg    22800 agtgttttt atcatgaaag ggtgttagac tctgtcaaat gtttgtatct gttgaaataa    22860
ctgtgtggtt ttcattcttt attctattaa tatgatgtat tgcattgatt gattctcata    22920
tgtttaatca acctgtgcaa ggtttatcct gggataaatt tcactcagtt gtggtgtata    22980
aaatttttat atattgctgg atttggtttg ttaatgtttt gtggataatt tttttttgtct    23040 atatttacaa agggcattgg tctgtggttt tcttttcttt ttttttgcga cagagtcttg    23100
cactgttgcc caggctagag tgcaatggtg tgatctcagc tcactgcaac ctttgcctcc    23160
cgggttcaag tgattctcct gtctcagcct cccaagtagc tgggattaca gatgcccgcc    23220 accacccct tttcatgtga tgcccttgtc tggttttgga atcagggtaa taccaatctc    23280
atagaatgaa ttggaaagta tcccctcctc ttctgttttt ggaaagagtg tgaaaaattg    23340
ctgataattc tgtgttagac gtttgggaga atttatcagc aacaatcatc tgagcctggg    23400
cttttctttg tgggaatttt tttttttttt ttgagacgga gtttcgctct tgctccacag    23460
gctggagtac aatggcgcga tctcggctca ctgcaacctc tgcctcctgg gttcaagcga    23520
ttcttctgtc tcagcctcct gggtagctgg gattacaggc gtgtgccact acaaccggct    23580 aatttttttgt ctttttagta gagacagggt ttcaccatat tggtcaggct ggtctcaaac    23640
tcctgaccct cagatgatcct cctgcctcgg cctcacgaag tactgggatt acacgtgtga    23700
gccactgcac ctggccaaga gttttttattg ctaattcaat ctcttgtcta ttcaagatta    23760
taagtctatt tagcttctca ttccttttt ttccctagac tcaagtgatt ctcatgcctc    23820
agcctcccaa gtaactggga ttacaggtat gtgccaccat gcctggctaa attttgtatt    23880
tttagtagag tcagggtttt caccttgttg gccatgctgg tctccaactc ctagcctcag    23940
gtgatccacc caccttggcc tcccaaagtg ctaggattac aggcatgagc caccacaccc    24000
agcctcattt cttcttgact cagtttgggt aatcatgtct ttctaggaat ttgttcattt    24060
catgtagatt atctaattcg ttggcatata attgaattt ttatactgtt aatatgagca    24120
gtctaaacca gccttgcatt cccaggacaa acccccactag ctcgtggaat attattattc    24180
cttttatata ttgctggatt caatttgcca ttattttgtt gaagaatttt gcatctttgt    24240
ttatgaggga tattgattta cagtttcctt ttcttgtact gtctctgtct agtttgagta    24300
```

| | |
|---|---|
| tcaggatgct actgacctca taaaataagt ttgaaaatgg cccctcccct tgtatttct | 24360 |
| ggacaagatt gtatagattg gtagggtatc ttttattaag ttttattttc ctccagatat | 24420 |
| cctgtttgta ggtgtgtgtg agaaacagaa aatgttactg aatcagagag agtctaagta | 24480 |
| ccattgtttt ctgcagtttt ctcttaaacc ttggggttaa aagaaatctg ttgaaataca | 24540 |
| gtgtaaccac atgtcttatt tctcagcttt tgtgagaga tctcaactgg gaagattgag | 24600 |
| gtagtttctt ttaagccctg ttgttggtca cattgactga acattttagt gaactaggat | 24660 |
| tactccactt actggatatt cttaatacta aggtaacaat atgaaaaaag aacatatttt | 24720 |
| ctgtatatat gtataaagca tatttagtga aattgtgaga gttattggtc tagtataggc | 24780 |
| aagagaactt tttagcttaa ttgagttctc aactggtata tagtatgtgt ttatatgaag | 24840 |
| gatcagttta gtaattgtcc acagattcct tttatatttt aatgactgta attcaggttt | 24900 |
| tacaatcaga aaaagcacct acattgtctt ctgtgtatat gttttttgtc cagaaaaggt | 24960 |
| atctttgtgg aattttttt tttttttgga gtgttgctct gtcacccagg ctggagtgca | 25020 |
| atggcactat ctcgactcac tgcaacttct gcctcctggg ttcaagcgat tctcttgcct | 25080 |
| cagcctcctg agtagctggg actacaggcg cccgccacca tgcctggcta attttttgcat | 25140 |
| ttttagtaga gatggggttt caccgtgtta gccaggatgg tctcgatctc ctgacttcgt | 25200 |
| gatccgcccg cctcggcctc tcaaagtgtt gggattacag gcatgagtca ctgcgcccag | 25260 |
| ttttttttt tcttttttg agacagagtc tcactctgtc gcccaggctg gagtgcagtg | 25320 |
| gcatggtctc ggctcactgc aacctctgcc tcacaggttc aagtgattct cctgcctcag | 25380 |
| cctcccaagt agctgggact acgggctcac gccaacatgc ctggctaatt tttgtatttt | 25440 |
| tcagtagaga tgggtttca ccatgttggc caggctggtg tcaaactcct gacctggtga | 25500 |
| tccgcccgcc tcagcatccc aaagtgctga gattacagac gtgagccact gtgcccggct | 25560 |
| gccaatggta tttctctcac agatgagaaa agtctgattt cttttttttt gagatggagt | 25620 |
| tttgctgttg ttgcccaggc tggagagcaa tggcaaatct cggctcaccg caaacttcgc | 25680 |
| ctcccacgtt gaagcgattc tcctgactca gcctcccaag tagctgggat tataggcatg | 25740 |
| tgccaccacg accggctaat tttgtatttt tagtagagac ggactctcca ctttggtcag | 25800 |
| gctggtctcg aactcctgac ctcaggtgat tgcccgcct cagcctccca aagtgctggg | 25860 |
| tttacaggcg tgaaccacca cacccagcca gtctgatttc tttttaaatt ttacttttat | 25920 |
| ttatttattt atttatttat tttgtagaga tgggttctca ctgtgttgcc caggctagtc | 25980 |
| ttgaactcct aggctcaagt gatgctcctt cctcagcctc cctgttggga ttacaggcgt | 26040 |
| gagccaccat gctcagtgaa aagtctgatt tcttaagtca gttttaaaag gtgatatgct | 26100 |
| aagaaaaact ttaacatttt atttttttcat ttaacatctt ttattttta tactaatgat | 26160 |
| tttttttttt tttttttt gagatggagt ctcactgtcg cccagactag agtgcagggc | 26220 |
| acgatctcag ctcactgcaa cctccacctc cctggttcaa gcaatttccc tgcctcagcc | 26280 |
| tcctgagtag ctgggattac aggcgcacgc caccacacct ggctattttt ttgtattttt | 26340 |
| agtagagatg gggtttcacc aagttggcca gagtggtctt gaacacctga cctcaggtga | 26400 |
| tccacccacc ttggcctccc aaagtcctgg gattacaggc atgagccact gtgtccggcc | 26460 |
| tactaatgat ttttaaaag ctctgtagtg tctgggtgcg gcggctcacg cctgtaatcc | 26520 |
| cagcactttg ggaggccaag gcgggtggat catgaggtca ggagttcgag accagcctgg | 26580 |
| ccaagatggt gaaaccccgt ctgtactaaa aacacaacaa ttagccaggc atggtggcgc | 26640 |
| acgcctgtag tcccagctac ttgggaggct gaggcaggag aatcgcttga acctgggagg | 26700 |

```
tggaggttgc agtgagctga ggttgtgcca ttgcaatcca gcatgggcga caagagtgaa   26760
actccgtcta aaaaaaaaaa agctctgtag tattgctttt aaaatgattt tcttatctta   26820
ttaacagcat caatattaaa tttacagcta ggtgaaagaa aggatatgtt tttcttcttc   26880
catttggtcc ttcagtacct cttccacgtt ccctgtggta gagcccaacc ctgacaggag   26940
actcttggtg ctgagtgatc cagtaaacca agactaaccc ccaccctctc ctacctcaaa   27000
cacacagtgt ctagttacag tggtagccta catggatttc tggcgtaatt tctcttatca   27060
tgaaccattc cataaaccag tcctctgcag aaaagagagt tcctttcaaa tgtgtattct   27120
caggctcacg cagccactga atcctggacc tggcatataa tcatattaga atacaactgt   27180
ggagtgaggc aagtgggaat tcttggctag gaccccaaca taactaaggt ttaatcttaa   27240
ccttaaataa gactcctttg aaggaggtac aagcacaaga gctataaaca ggatattgta   27300
gtccttttta tagcacttaa gttcttctta tgacatttat ttgtaaaaac taaaaatcct   27360
tttaaggcta aaaaacctac ctagggtttt atttcaattt ggtaaataaa taatactaat   27420
aactacaatg tacttattat taatttcaac actagaaatt cattatcatg tccttttagg   27480
gagtctttag tcttccttcc gtgtgtttcc ataaagactt ctgttttatt tttccagctt   27540
gtctcatatc ctacagactt tcagaaacac atataactac tttcttgtct tcacttgatt   27600
tatagacact gtaatgggta tagcttaccc atttaagctt ccccactctt gggtctctta   27660
tggagtaact tctttacttg atggggtctt gtcagaccca agagtaatat ttgtgtgtct   27720
tgtgggttga atataatatt gtaataattc ttactttgtt aaaaggaatc ttctgagagt   27780
ggtggtgtgt ttgccatact ccttgagctt gaactgaatg agttttgtta agaggtctgg   27840
ggttctgtgg aaatccttga tttcttctga cttgcagtcc agatgctttt aaccacaggc   27900
aacgagtaaa aatatgtgca tgacaaacct gtaaaccaga aagtgaagac agcaggcaga   27960
gtggcgtgct ataaaatttt tatcatcaca cttgaagtga tcgtgttgct cattaatggc   28020
gaaaactcaa gttctaacac atggcagttt tagtctgtgt ttagccttgc catgtgcttt   28080
catctgccag gctcctcttt gctttcccct ttgtttccct gctttgaagt tcattcattg   28140
tcctggttta ctgtgaaatg ccacttgggg ataactcaaa ataggacagt ggctttatta   28200
cctgtgcttt tcatatttca tgctaccttt ctgttttcca gtttccccca gttaagttgc   28260
attccttatg taccgtgatg ttcctctgtt gtcaaactag agcttcttcc cacagctaag   28320
tggctgatca aggtttctcc aaagagataa gtatcagtta tatagctctc taagcaatgt   28380
gtagactgag agccactcaa aacctggctc tctgcaggct ttcaggtggc agtagtcatg   28440
ggtgagagtc agtggttttg gcaggtacaa acacatatga attgtatgaa gatgtttctt   28500
gaggaggagt gtcctggagt ggaagtgttt tcctttagta atcccttta c taatcccaca   28560 gttcaaatat cttgctttat atccctaaga gtacaaagat ttcaatgaat ttctctgttt   28620
agtgaagtca gagacaggaa caaatgcaat aggctggtat gcaactttaa ttttttttt   28680 aagtttggga aatacaggaa agaaaagtca tggataattc tgtcacgcca atataactaa   28740
tatgaccatt ttgcacattc tttttcagga ttcctatatg tcgagtttca cagaattgta   28800
aaactatggt acataggact tggtattcta ggttttttaaa aaactaacaa ttgtgtcaaa   28860
ctatttctac attatttga atcttgaata gtatgcagcc actaaataag gttagaacaa   28920
gagagctact gtaatttagc cattcctcta atgtcagaca tttgttgttt ctaattttt   28980 gcaatagcta atgatgttac aatgaaatca ttggtaataa ttggataaaa agaagggatt   29040
```

```
gaagacaggg aaaagaaagg ggtgtaggct gtagagcagg gagagaacct ctttgcagct    29100
taggcttggg agagagaaaa gctgtggcaa ggtataactt tgtccctgta tctagaaagg    29160
ttatggacat gttcaggagg tccggaatgg tgagtattga taggcctgtg gcctgttttg    29220
ttccactggg ttttacagga agttaacatg attgatccta aagctatagc acttttattg    29280
aaagggaatt tgggactatc cccatttaac taggtgataa tagctatgtt aataaaaact    29340
actgaaagct tttcctaaga gaaggctagg aggtaggggt cttcaatgt tttcattatt     29400 ttagatttt ttttttaaag ctagtcgtca caaataagaa tactgagtta aggctcggcg      29460
cggtggctca cgcctgtaat cccagcactt tgggaggctg cggcaggcgg gtcacctgag    29520
gttgggagtt ccagaccagc ctgaccaaca tagtgaaacc ccgtctctac taaaaataca    29580
aaattagctg gcatggtgg cacaggcaca tgtcggtaat cccagctact caggaggctg      29640
aggcaggaga atcacttgaa cctgggaggc agaggttgcg gtgagccgag atcacaccat    29700
tgcactccag cctgggcaac aagagcgaaa ctccatctca aaaaaaaaa aaaaaaaaa       29760 aaagaatac tgagttaaaa ggtatggcca tctcaggagg ttgcagtgag ccgagatccg      29820
agatggagcc actgcactgc agcctgggtg ttggagcaag accctgtctc aaaaaaaaaa    29880
aaaaaaaaaa aagtatggcc atttgagtag tttttgaccc acactgtcaa attgtttttc    29940 aaagaatag tattagcttg tgttacacag ccctgtggac tcacttcagt gtacatttat      30000
cagcactggg agttttcatt ttttttgtat gtaagaaatg acatttcggg gccgggcgcg    30060
gtggctcacg cctgtaatcc cagcactttg ggaggccgag gcgggcgtat cacgaggtca    30120
ggagttcgag accagcctgg ctaacatggt gaaaccccgt ctctactaaa caaaatacaa    30180 aaaattagc caggcgtggt ggcgggctcc tgtagtccca gctactcggg aggtcaaggc      30240
aggagaatgg cgtgaactcg ggaggcggag cttgcagtga gctgagatcg cgccgctgca    30300
ctccagcctg gagcctgggc gatacagcga gactctgtct caaaaaaaaa aaaaaaaaac    30360
ttttcccagc tgggcacagt ggctcacacc tgtaatccca gcgctttggg aggccgaggc    30420
gggtggatca tgaggtcagg agatcgagac catcttggct aacacggtga aaccccgtct    30480
ctactaaaaa tacaaaaaaa ttagccaggc atggtggcgg gcgcctgtag tcccagctac    30540
tcgggaggct gaggcaggag aatggcatga acctgggagg cggaacttgc agtgagccaa    30600
gatcgcgcca ctgcactcca gcctgggcga cagtgcgaga ctccatctca aaaaacaaa     30660 aaacaaaaa aacaaaaaac ttttcccaa attatcaagt catcattgcc atactatttt       30720
gaaagtacat tttattgctt tgtgatggtt tttttttttt tttgagatgc agtctcgctc    30780
tgtcaccagg ctggagtgca gtggtgcgat ctcggttcac tgcaacctct gcctcccagg    30840
ttcaagccat tctcctgcct cagcctcctg agtagctggg attacaggcg tgcaccacca    30900
tacccagcta attttgtat ttttagtaga gactgggttt caccatgttg accaggatgg      30960
tctcgatctc ctgactttgt gatccgcccg cctcggtctc ccaaagtgct gggattacag    31020
gtgtgagcca ctgtacccgg ccacatgatg cttttttaaa aatcataaat gattctgtat    31080
ttgtctcttt ctggtctatc taatctcttt tactgatctc tgtttacttt tataaataca    31140
agtagggaga ctattttatt attactcttt agtttcagtt gttacaagtg gatagtaagt    31200
acttcatgga tccaaatatt aggaattgat cttaggcaaa aaagttgggg caaaatgaaa    31260
gcaacttatc attacagttt tttgtttgtt tgtttgtttg tttgttttg agacagagtc      31320 tcacggtcgc ccaggctgca gtgcaatggc gcaacctcag ctcactgcaa actatgcctc    31380
ccgggttcaa gtgattctcc ctcctcagcc tcccaagtag ctgggaatac aggcacccgc    31440
```

```
cattatgcct ggctaattttt tgtattttc attgtgacag ggtttcacca tgttggccag    31500
ggtggtctca aactcgtgac ctcaggcaat ctgcctgcct tagcctccca aagtgctggg    31560
attacaggtg tgagccacca cgcctggccc attacagttt tatctgcatt tttctgactg    31620
cctggttctg tgctgttcct gcaacattta cttaacatat ttctttgaat gctgcttcaa    31680
attttatttc aaaattgagg gggaaaaata agcaaatgat aaacataaac aaaattttat    31740 tttcctttt tgttagaggc agaatttaag gaaaaattct gatgattttg attacagtta    31800
gtggctaacc tcttatgatt tatttaccta tctatttatc tttccatcta tttgtacatt    31860
tttttgtttg tttgtttttt tggtaaacag tctctcccca gtaagaatgc agttcttctt    31920
aatcacagaa gttattcctt tccttgtaat ggccttctct gttctgtgtc ttggcaaata    31980
tctgagccta atagttgggt ggtgcccttg gcatagatgt tatgtaagga attgtcacct    32040
gcttttagag tcagtcatcc catgaaatcg aaggagtcag taaggcgtta tggaatcagg    32100
aggcttgtgt gacagctctg acgctgatac caattaatga cctgactgga cctcagtttc    32160
ctcatcagtg gaatgaacac agttggccta gtgacccag atgtctctcc caagctaaca    32220
ttctgtgatt ctcattctct gaaatgttac cacgaggaat gtttacttat acgttacttt    32280
ttaaaataag aaaaatggag aacagaaaat gagaactaga gtttaatttt aaaattttga    32340
agtgtcatgg atgaggctat cgtcatgtgt catgttgctt tagtccaata gttcttaatt    32400
aacagtatgc attagaacta ccagtgaaca tttaaagtat atgcatatat gtgtgtgaac    32460
atatatgaat atatacacac ataaaatatgt ttgtttattt atttatttac ttatttattt    32520
attggagaca gagtctcact ctgttgccca ggctggagtg cagtggtgcg atcttggctc    32580
actgcaacct ccacctcctg ggttcaagca gttctcctgc ctcaacctcc caagtagctg    32640
ggattacagg cgcgtgccac aacacccagc taattttcgt attttaagta gagatggggt    32700
ttcaccatgt tggtcgggct ggtctcaaac tcctaacctc aggtgatcca actgcatcgc    32760
ctcccaaagt gcaggaatta cgggcgggtg tgagccacgc gcctggccac acacacaaat    32820
atgcatgctt aggcccatgc cttgcaagtc tgattcagta ggttagggac aaggatgaga    32880
cctaggaagt cttggttatt cagatgcaaa taagggttga aaggcctccc ttccacttac    32940
ggcagatact gcaggtatag attggtctgg tatactctgc aacaaataag tcccattgct    33000
cttctgggat cctataatta attggcacag atgttagttt ttcttttctt tttttttctt    33060
tttttgagat agtctctcgc actctcacct gggctggagt gcacgatctc ggctcactgc    33120
aacctccccc gcccaggttc aagtgattct cctgcctagc ctcccagtgc tgggattaca    33180
ggcatgagcc accgccccgg gcccagagaa attacaagcg agaaattaca acaagctagt    33240
ttttctttaa gaagaaccca cttctcattt tcttatctgt tcaggctggt aaaacaaaat    33300
aacataaact aggaggctta tcaacaacag aaaacaattt cttacagttc tgtggcctag    33360
gaagtccaag atcaaggtgc cagtagattc cacgtctggt gagggcccac ttcctgattc    33420
tcagtaggta ccttcttgct gtgtcctcac atggtggaag gggagatggg ctctctggag    33480
tttctttcat aactgcgcta atcccattct tgagggctcc taatcacctc ccaaaggccc    33540
ctccttctaa tgctgtcact ttgagaatta agattttgac agagaaattt tagaggtata    33600
gaagcattca gatcatagcg cttatatctc aaagataagg agatttctat gttcctcttc    33660
acttttctat ccatatgtta agtattagta acatttgatt gtctggtata taatgaaaca    33720
gtctcttggt tgttgaccct gtcttgacat tgtatgatag gggttattta aaatttcctt    33780
```

```
aaattaacta tctttctaaa aactatttt  ataaaataat acatgttcat ggtttaaaaa  33840
cacatagtac caaaagtacg atgaaagtga aagcttgcca ggcgcggtgg ttcacgcctg  33900
taatcttagc actttgggag gccaaggtgg gcagatcacg aggtcaggag atcaagacca  33960
tcctggctaa catggtgaaa ccccgtctct actaaaaata caaaaaatta gccgggcgtg  34020
gtggcaggcg cctgtagtcc cagctactcg cgaggctgag gcaagagaat ggcgtgaacc  34080
cgggaggcgg agcttgcagt gaggccgaga tcgtgccact gtactccagc cttggcaaca  34140
gagcgagacg ccgtctcaaa aaaaaaaaa  aaaaaagtg aaagcttact agacataatg  34200
attaataata ataatgatta ataataaca  ttttggggat ttagctgatt ttattaacac  34260
catttaaata tcagtctagg tgtagtgaca gtataacata ctggttaaaa gcatgggcgc  34320
tacctttaca tttatggtca attgattttt gacaaggttg gcaagataca tcaatagga   34380 aagattagtc ttttcaacaa atggtgctga cacagcaggt tatccacatg caaaagaaga  34440
aagtggatgc ctgcctcata gaacacatgc aaattaactt aaaatggatc atagtcctaa  34500
agtaagaact aaaactataa gactcttaca aaaaaaataa aatccttgtg actttggaat  34560
aggcaatagt ttcttagata tgacaccaaa agtataagca aaaagaaaa  agataaattt  34620 gacttgatca aaatttaaaa ctatatttca aaaagacttc tatattttaa agctgttttt  34680
tttaaagtgt aggttctaga gaatgataac ctaagtttga atttagctc  cattacttat  34740 tgtaagctgt gcaaccctga ggaagttgca taacctctct gagtctgtgt ccttgtttgt  34800
aaaatgggga tgatggtagc agtgcccacc taacgatatt gctggaagga ttaaatgaaa  34860
ggaggcatat aaacattaac cctctgtcta gttctggata aatacaaata tcaactatga  34920
agatgataag gagattgaag aaggatgaat ggcttacttg gatcagcaga aatgagaaga  34980
aatcacctaa ggaacaagta gtaagggtgg gcttgaactt ggtttattca tgggccctga  35040
agaagatgga tagtttaaac atttttacaa gttggaggta gcaatctctt ggtggttttg  35100
actggtgatg atgcccagga tgacagtgct gtcatgtggg aataacatac cactaagctg  35160
gatcatgttt gttttgatgc ctgattgggc cagcacaaaa tcctgaggag aaaataattc  35220
gcagtaagta tttttattgc agtccttgctg catcttgcct gaagatcctg tgtctgctta  35280
tccaggagtt aacctgggag aaaacatgta agccttggtt tgagtggtct gccctatgt   35340 ctgtaagcag ggttgtgttg gaagggggaca tctgtctgac atttggcctc tctgcattta  35400
aaccatggtt gggaatagag atggcataaa atgtggcctc agtatttcca acctgttact  35460
tattttcctg tgtccaggga aggttctgat tatggcttgt tggcaggatc ccctgagaac  35520
atatcttgac tgtgatctga gttaggaata ttgaataata tgtcagaggt tccagtcaga  35580
tgaaagaagt aaatctataa tcttcattag agtccttcct tcctcagatt ccttattttg  35640
gcctgtggga cttaaatggt aatgctttta gagtgaacct aatattagaa aatgcatcat  35700 catgtttcc  tttgtgataa ttaccatcct tacttccatt acttctagct aaagatcatc  35760
accctggtaa aactttgcca gagaacccag caggattcac cagcacggcc actgcagact  35820
ccagagccct gcttcaggcc tatatagatg gtcactctgt ggtcatcttc agtaggtcca  35880
catgcacacg ctgtactgag gtaaggcttt aaactcaagg ggtttaaatg gaattgaagg  35940
aatttgacag acttttgagc tcaaatgtaa acaactggat tttacctta  ggaagagtgt  36000 atgtaggctg ggcgcggtgg ctcacacctg taatcccagc actttgggag gccaaggtga  36060
gtggatcaca aggtcaagag atcaagacca tcctggccaa catgatgaaa ccccatctct  36120
actaaaaata caaaaattag cccaacgtgg tgtcatgtgc ctgtagtcgc agctactcgg  36180
```

```
gaggctgaga caggagaatc acttgaaccc aggaggcaga ggttgcagtg agccgagata    36240
gtgccactgc actccagctt gggggacaga gtcagactcc atctcaaaaa aaaaaaaaaa    36300
aaaaggaaaa gtatatgtag gtgtaacttg cttcagagta attgtaaaat gtggatttga    36360
taacaaaata ttgtttgaat aatctttctg agcttttggg aagtatgaga catattcagg    36420
tagtcgaggt cagggaaggt tagggtgggg gagttaccaa accggttgat ttgcggccct    36480
ttcagatatg tctgtaggga atatttcata aggaatggtt acttagggta ctaccaaatt    36540
ttgataaata tctcttcatg ctttggttta ttatggggaa ataacttca caagaataa     36600 actgtttcct acttggttct taatcttaga ttatcagaga gaaaaggtca gtggttacag    36660
ccaaggggag gattagttta gtccaccctg aataaaccag ggtggactta accattaacg    36720
aaggtgagaa ttgaaaggca aacctgatct gtctggtgct tcataggaag ctgagggca    36780 tttaaatgtc actgaagttt agctctaggc ctacacaatg gagtcttagg taaatataac    36840
tggccatctg tccaggttca ctgagaggtt aatttattat ttttatata tatatatata    36900 tatatatata tattttttt ttttttttt tttttttttt ttgagacgga gtctcgctct    36960
gttgccaagg ctggagtgca gtggcgcgat ctcagctcac tgcaagctcc gtctcccggg    37020
ttcatgccat tttcctgcct cagcctcctg agtagctggg actacaggtg cccgccacca    37080 cacccgcta atttttgta tttttagtac agacgggttt tcactgtgtt agccaagatg    37140
gcctcgatct cctgaccttg tgatccacct gcctcggcct cccaaagtgc tgggattaca    37200
ggcgtgagcc accgcgcccg gccgatttta ttattaagtt taattttctc tcaacttgtc    37260
tgccccatga cttactttcc agatctcaag gagtttgaat tcagaagtct ttttattctg    37320
gaagccttac atagaaataa atgggcttat gggcttttg gactctctct ctctgtttct    37380
ctctctcgtt ctgcatgtgt gtgtgtctgt gcacacgtgc acttttttcc caagtaaaga    37440
aaaaggaagg tgggcggcaa aaacactgag gtacggagac cctttcatcc ttgtgtctct    37500
cctgaacaca ttctgcatcg atgccacctt aggcttcatc cctatcaata tgatagtgat    37560
gcctttcatg taggacatca tattgggagt aggattgcaa agaggcagaa gacacagtcc    37620
catccctggg ggtttagctc aactgagggc agaacatagg cttaagaaga aaatgatct    37680 cagataaccc atgctaaatt ctacatgatt ggacaggcag caagtgctag agaatttaga    37740
agagggctgg gcattagaaa tctgctatgt aattcttggc ctctaggggc ttaattatgt    37800
agctctgcaa ttcttatctg cttttgggac ctactgcccc tccccgcac cgcctgccac    37860 ttcctttttt ttaatcttta aaatgaaggg cttgaactag ttgcttattg agggtttttt    37920 tgttttttgtt tttgagacag agtctcgctc tgttgcccag gctggagtgc agtggtgtga    37980
tctcggctcg ctgcaacctc cgcctcctgg ttcaagtgat tctcctgcct cagcctccca    38040
agtagctggg actacaggtg cacaccacca tgcctggcta atttttgtat ttttagtaga    38100 gatgggttt cactatgtgg ccaggctggt ctcgaactcc tgagcttgtc gtgatcctcc    38160
caccccagcc tccaaaagtg ctgggattat aggcgtgagc cactgcgccc agcctgaggg    38220
ttttcttagt tctgaaatta cgtgcttgtc tagtctttt cgttaccaaa caggttaaga    38280
gcctggactc taaagtcaga gtgtggatct tggctctgtg atttatcagc catgtgactt    38340 tagttatta cctgtggtgc cacagtttcc ccatctgtaa aatgtggatg ataatagtat    38400
ctatatcgta agtttgttat gaggattaaa ttaattaata tttataaaag ccatagaaca    38460
tacctgagac atagtaaaca ctatatcagt gtttgttaaa taaagaact acttgcattt    38520
```

| | |
|---|---|
| ttcctttttcc tatcaggact taaaaccttg ggtggttaat cttccttctg tcagtactga | 38580 |
| ggctagatta atggtaatc aacaaatacc tgacataatg ctaagtacaa ttaatcctat | 38640 |
| cagtgggtaa atagctacca tttgagtgcc aactatgtgc caggcattcg gtcactctac | 38700 |
| tcatattttc aaacattatt aaagaatcgg gagctgggca cagtggctta tgcctgtaat | 38760 |
| ctcaatgctt tgggaggcca aggcaagagg ttcacctgaa gccaggagtt cgagaccagt | 38820 |
| ctgggcagca taacaagact ctatgtctat ggaaaaaaaa aaaaaatat atatatatat | 38880 |
| atatatatca gcatggtttg catgtgcctg tagtcctagc ttctcaggag gctgaggtga | 38940 |
| gaggatcact tgagcccagg agttaaaggt tacagtgagc tatgattata ccactgcacg | 39000 |
| ccagccttgg tgacagagtg agaccctgtc tctaaaataa atacatatgg gcgcagtggc | 39060 |
| tcacacctgt aatcccagca ctttgggagg ctgagacagg cagatcactt gaggccagga | 39120 |
| gttcaagacc agcctaggca acatggtgaa accctgtctc ttctaaaact acaaaaatta | 39180 |
| gccaggcatg gtggtgaatg cctgtaatcc cagctactca ggaggcacag gcatgagaat | 39240 |
| cacttaaaac tcaggaagct gaggggggcag tgagccaaga tcgtgcctct aagctacagc | 39300 |
| ctgggtgaca gagcaagact ctatctaaat aaataaataa aaaaaataaa aattaagaaa | 39360 |
| taaataaata aacagaaaat tccaatttta accctgctgt agttctggaa tgaaaagttg | 39420 |
| ggctagcggt caggattgct actagtggta gatagtcagt atgctccttg caatcccaga | 39480 |
| tctctttgac ctatcattgt tctttttttc ttttcttttt tttagtccct attatgcccc | 39540 |
| agaatgttct tattcttact gttatctctg aaatctacta actccctcat ttcccagctc | 39600 |
| tcctgcctat ccctgaaaat gtaaagcctt gcctatattt cccccagttt tacttaatta | 39660 |
| aaactagcct gggaatgaag aacttttcct ataacatttg ttggttagtt atttgcatgc | 39720 |
| ttatttaaac atacagttgc ccgagcgcag tgactcacac ctgtactccc agcactttgg | 39780 |
| gaggccgagg cgggcggatc acctgaggtc aggagaccag cctgaccaac atggagaaac | 39840 |
| cccgtctcta ctaaaaatac aaaaattagc cgggcttggt gatgcatgcc tgtaatccca | 39900 |
| gctactaggg aggctgaggc aggagaattg cttgaacccg ggaggcagag gttgcagtga | 39960 |
| gccaagatcg caccattgca ctccagcctg ggcaacaaaa gtgaaactgt ctcaacaaca | 40020 |
| acaacaacat atagtcatcc tggcaaattt atttaatatc attatccaaa caatccctgg | 40080 |
| gtatgtcaag tcttctagat aaacatcccc tggttttacc ttgttgattt cagattgttt | 40140 |
| tcagattggt gccagttaat ttggaaatta attttcgatg tctttggcca tgaaagatga | 40200 |
| ttaggtgctt ttcctggtaa agtggtgaat ttcttctgag ggtgtacaac tcatatactt | 40260 |
| agctgttcac atttatttat ttatttaaat taccttgaag tagaattttc ccaggttatt | 40320 |
| ttctttagtt tttatttaat catctcattt aacaactggg atatgagtaa atcagaatag | 40380 |
| agaaactttg tttttatatt tgtacttggt ctgatgaatg tgtatttctc tatgggatga | 40440 |
| gtaatgtcat ttgcattaat tcaaggtggg aagtgcccat aaggaaacta acgtctacgt | 40500 |
| aaaggtagct ttccgctctt gcataacaca ttagttacca tatgtgtttt gcgtgcatct | 40560 |
| tgctgtgaag aggttttaaa gtgcaaagat aatccctctc caccttttca gaattgcaat | 40620 |
| atttatttct tatagctatt tcagagtggt gggggaact gaattcagat tcagactggg | 40680 |
| gcttaggtga catctaaaag agtttaagaa aaaggctact ggctgcgtat ggtggctcat | 40740 |
| gcctgtaatc ccagcacttt gggaggccga ggtgggcaga tcacgaggtc aggagataga | 40800 |
| gaccatcctg gccaacatgg tgaaaccgcg tctctactaa aaatacaaaa attggctggg | 40860 |
| tgtggtggcg catgcctgta accccaccta attgggtggc tgaggcagga gactcgcctg | 40920 |

```
aacccgggga ggcagagatt gcagtgagcc gagatagtgc cactgcactc cactggtgac    40980
aaagtgagac tctgtctcaa aaaaaaaaaa aaagaaaaag aaaaagaaag aaaaagaaga    41040
ctaatgaggt tgtatgaatg aacatatttt cccattttat caaaatgttg aatttggtcc    41100
tatagaaatg atagaaatct ccgagtgtac ttccatacaa taggaagtac tgttttagta    41160
gttaagttta gaatgagatg agaatatatt ttcttttctt tttttttttt tttcaagaat    41220
cattttcctc attgatcatc tctgtgaact tcaggctact ctggccttt aaattttatt     41280 gtataactgg aggaatatgg ttctaaactt tcctaaatta ttgacaggct gtttgtgtct    41340
tgtacataaa agtctcttgt gtcagtagtt taaatgttat ctagtagtat aagtaacttt    41400
taaataaaat tttgttttt accagtataa tttgtataac catgagcata agattttttg     41460
tttgtttgtt ttatttaata gtctcagagc ataataggtt ttttgtaact gatttattgg    41520
ttgagggtta ctcagccaaa aaagaaataa tactttaact attgtagaat atattttccc    41580
caggtttgcc acataatgct ttggaaacat taagtgttcc aatgcttttt tttttttttt    41640 tttttgaaa cagagtctta ctctgtcgcc caggctggag tgcagtggta caatcctggc     41700
tcactgcaac ctccgcctcc tgagttcaag tgattctcct gcctcagcct cccgagtagc    41760
tgagattaca ggtgcccacc accacgcccg gctaattttt ttgtatattt aatagagacg    41820
gggtttcccc atgttggcca ggctggtctt gaactcctga cctcaggtga tccaccgtc    41880 tcagcctccc aaagtgctgg gattacagac gtgagccacc gcaccggcc tgctttttta    41940 aacatagtat taaacccatt ttataatgag gtagactgag tcactaaaca tataaatgt    42000 atcttatgaa gcgatacaga tgaatcattg acaattgaat agaatcaaca gacttcagat    42060
actcttgtaa atatcatttc tgtcaacagg gagaatctta tgggttacat aaaagtgaat    42120
tggaaagttt tcaaaggtga aggctggttg aggaaggaag taacaaagct ggataagaga    42180
ttctcttgtt ggttataacc tcattttca ttttcctcct tgttttcaa cttcttccag      42240 gtaaagaagt tatttaaatc tctgtgtgtt ccttattttg tgcttgaact tgatcaaaca    42300
ggtaagtttc tgtttaatat gtaaatcata gctgctgact gtacatttta tctcatttat    42360
tctatctggc tttaatttgt cttccttgag gtttttattg tttagtgagc acttgctagc    42420
tgattcttct ttttggtctt ttagacaggg tactctcctg gagctaatca tattcacctt    42480
tagcctttac ctagtgtata gccttggtat tacccagagt ttcctcttat tgaaattatt    42540
cttcttatta ctcatgaatc tagttacaga tacagtattt gctggtttta tggtaacttt    42600
acttttgcaa atttgtctcc tttctgataa gtaatacaaa tagtatttga attaaatata    42660
aactgagatg cattcagaaa ttttggcagg gacatacaaa gatcagtaaa ggtgaaagat    42720
ccatgaaaag tgctactggg aaatcccagg gagagaaaga ttggtggagt aaaatggaaa    42780
gcttctttct aggaccatgg tgctccttt ttgtgggtca gaaaatccca agggctcaca     42840
gacaaacatt attaagaatc taatctaggc ctgttggtga ctcatgcctc taatcccaac    42900
acactgggag gccagggtag taggatcgct tgaggccagg agtttgagtc cagcctgggc    42960
aagagtgaga gcttgtctct acaaaaataa agaattaaaa agttaaccag gcacagtggc    43020
atgagcccat agttctagct actcaggagg ctgaggcagg aggtttgctt gagccaagga    43080
gttcaaggtt acagtgagct atgattgcac cattgcactc tagcctggat tactgagtga    43140
gaccttgtat cgaaaacaa aaaggatctg ctagtggcca gcaccatcat ttctattagg     43200
aaaagtgggc tcttccagat taggaagagg aggtaaactt catgcctagt agctttaagg    43260
```

```
aagcagagtc ctgggcattg acagcttctg ctcagtctcc aaaggaatac aaagaaaggg    43320
cctggcatgg tggctcgctt ctgtagtccc agcacttggg gaggctgtgg tggctggatt    43380
ccctgaggta aagagtttga ccagcctg gccaatatgg tgaaccctg tctctactaa       43440 ataataaaaa aaattagctg ggtgtggtgg tgtgcacctg tagtcccagc tacctgggag    43500
gctgaggcag gagaattgct ggaacccagg aggcagaggt tacactgagc caagatcgca    43560
ccacagcatt ccagcctggg tgacagagtg agactctgtc tcagaaccac aacaacaaca    43620
acaacagcaa caacaaagaa aggattcaac tagacagaga aagatatatg caattggga    43680 gatatgaaca attggcatat aagtttcatt tctttttttt tttttttttt gagatggagt    43740
ttcgctcttg ttgcccaggc tggagtgcaa tggtgcgatc tcagctcacc gcaacctccg    43800
cctcccaggt tcaagcaatt ctcctgcctc agcctcctga gtagctgaga ttacaggcat    43860
gcaccactac gcctggctaa ttttgtattt ttagtagaga tggggtttct ccatgttgag    43920
gctggtctcg aactcctgac ctcaggtgag ccgcccgcct cagcctccca aagtgctgag    43980
attacaggtg tgagccacca cgcccggcca taagtttcat ttctagggtc aggaggaagg    44040
aggtagttgt gtggcaagac atattacttg atgtttctaa agacaggttc tctaacacag    44100
agagcatcac ataataacta ccatatatag agtgttagtc cctgttttac atggactatg    44160
ctgggttaag tatagtcacc tatcctcaca tgaactcagc aagggagata ttctctatat    44220
tttataaatg aggaaattga atcccagaga agtcaattaa cttccttaac attgacccgg    44280
tgcagtggct cacgcctgta atcccagcac tttgggaggt ggaggtggga ggattgcctg    44340
aggtcaggag ttcaagacca gcctgaccag tatggagaaa ccccgtctgt actaaaaata    44400
caaaattagc cgggcatggt ggctcatgcc tctaatccca gcactttggg aggcagaggc    44460
gggaggatta cctgaggtcg ggagttcaag accagcctga ccagtatgga gaaacccgt    44520 ctgtactaaa aatacaaaat tagccgggca tggtggctca tgcctgtaat cccagctatt    44580
cgggaggttg aggcaggaga attgcttgga cccgggaggc agaggttgcg gtgagccaag    44640
atcacaccat tgcactccag cctgggcaac aagagcacaa ctccatctca caaaacaaac    44700
aaaaaaaaaa cacaaaaaac aacaacaaca gaaaacttcc ctaacttcat ataaatactg    44760
gatctataat ttgaacacag gcccatgtaa ttctgaagcc tgtgttattt ccataatacc    44820
atgttgtctg gctcctctac ggtgacccctt ctattccttc atcaaggaag gctcttgccc    44880
ctaaatactc catagtatga aaggtaatct caataaataa aatttcttct gggtccaaaa    44940 gtagccttt ataaaaatat aaattttcct gggaaactta agtcacttgc aacttgctgt    45000
gaattaggga aaaataacca aacggaacaa taaccaaaca agcaaattaa actaatataa    45060
gataaagcaa atgaacatgt ccttcaagga tgggaaggt aaaggaggta acatcggaag    45120
agatgggcag gatgaatgca ctaagtgctt ggggagcatg atttgtaagg atttactctc    45180
tgaatgtgga aaacttgtgt ttttggtaa caaatggcag atgttttatt tctaaatctg    45240
ttagtaagtg gctaaggaag ttttaagagt ctgtgattta atacatgtat gaactttatt    45300
ttcagtccca gaaaataagc attggattat gaattgactt ttgtcccggt ggttccccag    45360
ttatacttcc cttgctcttt cttttctttt ttttttttaa ttgagatgga gtttgctct    45420 tgttgcccag gttggagtgc gatggcacga tctgggcttg ccacaacctc cacctctagg    45480
gttcgagcga ttctcctgcc tcagccccca gagtagctgg gatcacaggc atgcgccacc    45540
acggccaatt tattttgtat ttttggtaga gacagagttt ctccatgttg gtcaggctgg    45600
tcttgaactc ctgacctcag gtgatccatc cacctcggcc tcccaaagtt ctgggattac    45660
```

```
aggcgtgagc caccatgccc gtcccccttg ttctttctta aatgtcctct ttactttctc   45720
tatcattttt cagactattc ttatctittt taaatgtgtg ttgccagtgg ggaggtgcgg   45780
tgactgaaaa atctattaaa tttctccttt tccaactact tttctgtgtg agactggatt   45840
tttcatttac ttctgccaaa acaacgtata ttgcaacaaa ttaatccaga agcaaatatg   45900
ggaatctagt tgttttttat taggaccaat gctaaaaaaa ttcaaaaaaa tgtgaaacaa   45960
tgccagtctt ctcactatgt ttatttattt tgagacgaaa taagtgcatt ctcagctcag   46020
tgagcaaagg tgcaatctca gctcactgca acctctgcct cctggattca agcaattctc   46080
ctgcctcagc ctcccaagta gatgggatta caggcatgtg ccaccatgcc tggctaattt   46140 tgtgtttta gtagagacag gttttcaccg tgttggtcag gctggtctca aactcctgat   46200
gtcaggtgat ccacctgcct cggcctcaca aactttggg attacaggcg cgagaccagc   46260
ttggccaaca tggcaaaatc ctgtctctac taaaaataca aaaattagcc aggcatggtg   46320
gtgggcgcct attatcccag cgactcagga ggctgaggca ggagaattgc ttgaacgcag   46380
gaggcggagg ttgcagtgcg ctgagattgt gccattgcac ttcagcctgg caacaagag   46440 caagactctg tattaaaaaa aaaaaaaaaa aaaaaaaga ccaagtttga caccccgttc   46500
taaggcaagt aggaagcatg aatattaaca cagttttgat tttgtgagat ttatttgtcc   46560
caagcatagg aggaacaccg ttctacatgt gcagttggcc ttagccacac aggagaggtg   46620
tgatctggtt catgtcttcg aggagcttgt aatcatggag ctggaactgc tgatgcagtc   46680
ttctaagtgc tggtttcatg aataaacacc tcctttatct gtttcttctg ggttccaaaa   46740
gaaccctcca taggcatgat tttcacacca gtgttggcta cgtaatcttc ccagggcctg   46800
gatcatagtg ggtatttaaa aagtcagaag atcaattggt agacaggagt atttggcata   46860
gaatcacatg ggtgcattta ttcattcagc atatttattg agtgcctgct gtgcactagg   46920
ctctgtatac taagcactgg gaatacagta gtatactagg caggtgtgct tcctgtctaa   46980
aggaattaga cttgtttgtg ttttttttt ctttttttc ccagcaaatt ccttttattt   47040
tcctttagag ttgagggcct gtgtactgcc taactggatt ggtaatggag tgagtgcccc   47100
atgaattcct gtgtttgcaa tagtatcacc tctcacagaa aatcaagaag agaagttgtg   47160
ctaccagggg atcctctctc ttcaccctaa cattttcttc ttccttcttt tggctgtatt   47220
ttggccagtc tacataaatt aaggttatta tttgaaaaca accatcaggg tccactgagt   47280
tctactgaga ttggtattgg agagagaaac tcagaaccgg gaggcctggc attcatgtcc   47340
tgtgtgtagg tagtggtagt agtcatacat gctatcctcc ttgtgccaga ggctcatgca   47400
tgttctccta tttaatcttc agaataccac caatcaggta ggtggtgata tcaccttctt   47460
atgatgagga aataaaaaca tagtaaagta ttagtataca gggtggctgg ctttctagtg   47520
aacctactgg caattcgtgg cccctcccac tacttcctga gactatctcg tagaaccttc   47580
catgacttgc ccccagtgtc ttatgtataa tgttcatggt gtcgatatca tgataggtgt   47640
tcctagatgt gatggtgtct gttgcacaca catgtggtgg tgtgtttggt ggcagaggtt   47700
gtacaatctg ccaccatgcc agctacacac atcttggcta tccctgtgga tgagctgcca   47760
ctcacagggc ctgttgattt acaaagactt gtatctatac ttcaggtgtc ttcctaggag   47820
ctttgatcta aggaacagac aacatcagtg taatcatctt aatttggtct ggcagctgct   47880
gacattctat agctataaat gtggaaaaca gacataagat ttcaggagtt tgccaaaagt   47940
gtgcatctgg atgccacatg tcactagctt aggggttctg atgtgtatta ttcatgtctc   48000
```

```
ctggctgctt atggaggaca tggctttaat gccttcagca agagggagag gaactaatat    48060
ttgagtttct ttttatggca gtgtctcata tctctcttac ttaatcctca caacagcttt    48120
gtgtggttgt tggaattaat tctgttgttg tgaggaagca gatgctcagc atttgaataa    48180
cttgctcaat gttgctgtgt caagcccagg cctgtctgct tccctagttg cctctttggc    48240
attgttttcc ttgaacaaat aaaaacccct cacaagcaga ggtaccctag ctagctcagt    48300
tctcaccact ttggtattga tacttactca ttcaacagat ttgctttggg cacctattta    48360
tatgccaagc actggcagga gagaaaagat gagtaaggca caacctcatt ctttaagatc    48420
attttacttg tttgcctctg cctcacttcc aatttcagtg taatctggta tctctaaagg    48480
ctgtaggatc acgggtggac aaaggtagtg ggtaagacat ttaaagctgt aaacaaaagc    48540
aacttagaaa acatcatggc atgttcattt agagcaaaac tggcaaggcc tgggcagag    48600
aacgatgaga ggttaagagt tgaaaagtaa agaggctttc tcccatagcg aatgaggaga    48660
catgggaggt tgttctattt attttatgaa tgaggctcaa aatattcttt aagcattttg    48720
gttttgtcta taaaaatgtt aatttttta aatttggaga ccacagtata ataaaataca    48780
aaaaatcaca tataattgca tccagagata gccactatta atattttatg tcttttttgt    48840
aaactctgtt ctgttttatt atttaatatt ttacatgtta tataagttct taattttctc    48900
aatgactaca aaatagtcca tgtatttact tagccattct actatatttg gacagtctat    48960
tgccaattt ttgctattgt ggaataatag gttagaaatg ttttctttg tacgtgaagt    49020
ttttgctgta tttagaatta ttttcttagg atagattact ggaatggatt tatgggtcag    49080
agtatgaaca attctaaggt tctagagccc tttaaatggt gtgtactaat taataacttc    49140
ataagctcaa agagttccct gtacttagta gtaagaaata ataataggtt ttgggccagg    49200
tgcagtggct cctgcctgta attccagtgt tttgggaggc tgaggcaggc agatcatgag    49260
gtcaagagat caatactagc ctggccaaca tggtgaaacc ccgtctctac taaaaataca    49320
aaaattagct gggcgtggtg gcatgcgcct gtagtcccaa ctacttggga ggctgaggca    49380
ggagaatcgc ttgaacccgg gaggtggagg ttgcagtgag ctgagatcac accactgcac    49440
tccagcctgg tgacagagtg agactccgtc ttaaaaaaaa aaaaaaaaaa acttcctttt    49500
gcgggtggcg gcgaacgcgg agagcacgcc atgaaggcct cgggcacgct acgagagtac    49560
aaggtagtgg gtcgctgcct gcccacccc aaatgccaca cgccgccct ctaccgcatg    49620
cgaatctttg cgcctaatca tgtcgtcgcc aagtcccgct tctggtactt tgtatctcag    49680
ttaaagaaga tgaagaagtc ttcaggggag attgtctact gtgggcaggt gtttgagaag    49740
tcccccctgc gggtgaagaa cttcaggatc tggctgcgct atgactcccg gagcggcacc    49800
cacaacatgt accgggaata ccgggacctg accaccgcag gcgctgtcac ccagtgctac    49860
cgagacatgg gtgcccggca ccgcgcccga gcccactcca ttcagatcat gaaggtggag    49920
gagatcgcgg ccagcaagtg ccgccggccg gctgtcaagc agttccacga ctccaagatc    49980
aagttcccgc tgcccaccg ggtcctgcgc cgtcagcaca agccacgctt caccaccaag    50040
aggcccaaca ccttcttcta ggtgcagggc cctcgtccgg gtgtgcccca aataaactca    50100
ggaacgcccc ggtggaaaaa aaaaaaaaaa aaagtgatc tggctggaca aactgagcca    50160
gtcccacaca aaatcttaaa aaaaaaaaaa gaaagaaat aataataggt ttttaaaaat    50220
cattatttgc ctattggaga ggtaaaaaca gatttcttta tcttaatttg tatcactttg    50280
attattaatg aggcacaata ttttttcctg tatgttgtat ttcctatgtg taccttgctg    50340
ggctcaggtg gtcctcccac cttagccttc caagtagctg ggactatcta aattgtagtc    50400
```

```
actgtgttgt atttcattat ctgaattgcc tgttcatttt cctcatggga taataatact   50460
aggaagagcc ccggtgcggt ggcttacgcc tgtaatccca gtactttggg aggctaaggt   50520
gagtggatca cgaggtgggg agatcgagac catcctggcc aacatggtaa aaccctgtct   50580
ctactaagaa tacaaaaatt agctgggcat ggtgacgcat gcttgtagtc ctacctacta   50640
gggaggctga ggtaggagaa tcgcttgaac ccgggaggtg gaggttgcag tgagttgaga   50700
tcacgccact gcactccagt ctggtgacag agcgagaatt catctcaaaa aaaaaaaaa   50760 aaaaaattag ttggctgggc gtggcggctc acgactgtaa tcccagcact tgtgaggcc   50820 gaggcaagcg gatcacaagg tcaggagatc aagaccatcc tggctaacac ggtgaaaccc   50880
tgtctctact aaaaatacaa cagggccggg cgcggtggct cacgcctgta ctcctagcac   50940
tttggggagc cgaggcgagc ggatcacgag gtcaggagat caagaccatc tggctaacag   51000
ggtgaaaccc cgtctctact aaaaacacaa aaaattagcc gggcgtgttg gcgggcacct   51060
gtagtcccag caactcggga ggttgaggca ggagaatggt gtgaacccgg gaggcggagc   51120
ttgcaataag ccaagatcga gccactgcac tccagcccag gcgacagagc gagactccgt   51180
ctcaaaaata aataaataaa ataaaataaa ataaaaataa aaaataaaaa tacaacaaat   51240
tagccaggcc tggtggcggg cacctgtagt ccagctactt gggaggctga ggcaggagaa   51300
tggcctgaac ccgggaggca gaacttgcag tgagccgaga tcgcgccact gcactctagc   51360
ctgggcaaca gagtgagact ccctctcaaa aaaaaaaaa aataatataa taattaataa   51420
taataggaag aaaccttat atatagctct ttattttctt ttctctttct ttctttcttt   51480 cttctttct ttctttcttt cttcctctt tctgtctgtc tgtctgtctt gctctattgc   51540
ccaggctata gtgcagtggt atgatcttgg ctcactgcag ccttgaactc ctggcttcat   51600
gcaatcctcc cacctcagcc tcccgagtag atgggagtac aggtatgtgc caccataccc   51660
agctaatttt tgtattttct gtagagctgg agtctcatga gccaccatgc ccagcctgcc   51720
ttacttcttc ctttccttct ttccttttcc ttccttttctt tcttttttct gagactatcc   51780
cgtagaacct tccatgacct gccccacctg tcttatgtat aatgttcatg gtgttgatat   51840
catgataggt gttcctagat gtgatggtat ctttctttct ttctttcttt cttcttttc   51900 ttctttcttt cttctttcct ttctctcttt ctttctttct ttctctttct tctttccttt   51960
tcttccttcc ttccttcctc cctccctcc ctttccttcc cttccctcct tcttccttc   52020 tttccttcct tccttccttc cctccctccc tccttccctc cttccttcct ctctctcttt   52080 tttttttga gactgagttt tgctcttgtt gccctggctg gagtgcaatg gcgtaatctg   52140
ggctcactgc aacctccatc tcccgggttc aaacaattct cctgcctcag cctcctgagt   52200
agctgggatt acaggcacct gccaccacgc caggctaatt ttttatattt ttagtagaga   52260
cagggtttca tcatgttgtc caggctggtc tcaaactcct gacctcaggt aatccaccta   52320
cctaccttgg cctcccaaag tgctgggatt acaggtgtga ccacttgga cccggcccct   52380 tcctctttct ctctgtctct ctctttcttt ctttatttt ttatttttat tttttgaaat   52440
ggagtatcac tggctgggtg cggtggctca cgcctgtaat cccagcactt gggaggctg   52500 aggtgggctg atcacgaggt caggagatgg agaccatcct ggctaacatg gtaaaacccc   52560
gtctctacta aaaatacaaa aaaaaaccc acccatatta gccgggcatg gtggcaggcg   52620
cctgtagtcc cagctactcc ggagggtgag gcaggagagt ggcgtgaacc cgagaggctg   52680
agcttgcaga gagctgagat cgcgccactg cactctagcc tgggtgacag agcgagactc   52740
```

| | |
|---|---|
| cgtctcaaaa aaaagaaag aaagagagta tcactctgtc cccaggctgg agtacagtgg | 52800 |
| cacgatctcg gctcactgca aactctgcct cccaggttca agcaattatc ctgcctcagc | 52860 |
| ctcctgagta gctgagacta caggctgcac taccacgcct ggctaatttt gtattttag | 52920 |
| tagagacgga gttccaccac attggccagg ctggtctcga actcctgacc tcatgtaatc | 52980 |
| cacccgcctt ggcctctcaa agtgatggga ttacagtcgt gagccaccgc acctggcgta | 53040 |
| cagtagagct tctttcaaaa ctggaaccaa tcctctcaaa ccctgccact gcttatcaat | 53100 |
| taaatttatg tcatattata aatccgttgt tgtcatttct ttttttttt tttttttgag | 53160 |
| atagagtctc actcttttg cccaggcact atctcaactc actgcaacct ctgcctctcg | 53220 |
| ggttcaagtg attctcctgc ctcagcctac tgggtagctg ggattacagg cgcctgccac | 53280 |
| catgcctggc taattttgt attttagta gagatggggt ttctccatgt tggccaggct | 53340 |
| ggtctcaaac tcctgacctg aggtaatctg gcccgcctgg cctcccaaag tgctgggatt | 53400 |
| ataggcgtga accactgtgc ccagcccttg ttgtcatttc aacaatgttc acagcatctt | 53460 |
| catcaggagt agattctatt tctagaaaaa cattatttgc tcatccataa aaagcagctc | 53520 |
| ctcatccatt caaattttac atgagattac attaattcag tcatgtcatc agactctatt | 53580 |
| ttttgtgggt tctttttttc ttcttttct gtgtttcttt cttttttttt ttttttttg | 53640 |
| agacagggtt tcactctgcc acccaggctg tgctgcagtg atgtagtcat ggctcactgt | 53700 |
| ggcctcaacc tcccgggctc aagtgatcct cctgcctcag cctctcaagt acttgggact | 53760 |
| acaggcacat gctaccacac ctagctaatt tttgttgttg ttgttgttga gatggagtct | 53820 |
| tgctctgtcc ccaggctgga gtgcagtggc gcgatctcgg ctcacagtaa cctctgcctc | 53880 |
| ccaggttcaa gcaattctcc tgcctcaacc tcccaagtag ctgggactac aggcacgcga | 53940 |
| caccatgccc agctaatttt ttttgtattt ttagtagaga cagggttta tcatgttggc | 54000 |
| caggatggtc tcgatctcct gacctcgtga tccgcctgcc ttgtcctccc aaagtgctgg | 54060 |
| gatgacaggt gtgagccccc gcgcccagcc cacccagcta attttaatt ttttttgtag | 54120 |
| agacagggtc ccactatgtt gcccaggcta gtcttgaatt cctgagctca agcaatccta | 54180 |
| cgttggcctc ccaaagtgct aggattatag atgtgcacca ccatgcctgg ccttctcttc | 54240 |
| taattctatt tctcttgtta tttccaccat atcttcagtt acttcctcca ctgaagtctt | 54300 |
| gaattcatca aagttactca taagggttgg aatcaccttc ttccaaactc ctgttaatgt | 54360 |
| tgatatatta ttgacttctt cccatgaatc atgaatgttc tgaatggcat ctagaatagt | 54420 |
| gaatctttc cagaaggttt tcagcttact ttgcccagat ctgtcagagg aatcactgtc | 54480 |
| tatggcagct atagccttat aaaatatatt tcttaaataa taagacttga aagtcaaaat | 54540 |
| taatccttta tccctgggct gcagaatgga ttttgttagt agtcatgaaa acaacattca | 54600 |
| tctccttgta catctccatc agatctcttg agtgaccaca tgcactgtca atgagcagta | 54660 |
| atattttcaa aagtcttctt ttctgagcaa taggtctcaa cagtgggctt aaaataaacc | 54720 |
| aagttgtaaa cagatgtgct gtcattcagg ctttgttgtt ccatttctaa agcaaaggca | 54780 |
| gagtagattt atcataattc ttaagggccc taggattttc attgtaagtc catttgtctc | 54840 |
| ctgtttaaat cataagtata gaaacaccct aaatatggcca ttatttgata gtagtgacat | 54900 |
| ggaaaatact ttgccatctt agaaagggca atgactaaat actggcctaa tgtatgtttt | 54960 |
| tcctccgaga aggaggaaag ccacttaatg gtcaacattg aatcctgtca agcagagtag | 55020 |
| gaggcaatat agcctccttt atagcaatac agcctcagga tattcctgag attattgaaa | 55080 |
| gattaactag ccgggtgtgg tggctcacgc ctataatccc agtactttgg gaggccgagg | 55140 |

```
ggggtggatc acctgaggtc aggagtttga gaccagcctg gccaacatgg tgaaaccctg   55200
tctctgctaa aaatacaaaa aaattagccg ggtgtggtgg tgcaagcctg taatctcagc   55260
tactcagttt cacgtgcatc cgtgtgaaaa gaccaccaaa caggctttgt gtgagcaaca   55320
agcctgttta tttcacctgg gtgcaggcag gctgagtcag aaaagagagt cagcaaaggg   55380
tggtgggatt atcattagtt ctttcttttt tttttttttt tttgtgagac ggagtctcgc   55440
tctgtcgccc aggctagagt gcagtggtgc gatctgggct cactgcaagc tccgcctccc   55500
aggttcatgc cattctcctg cctcagcctc ctgagtttct gggactacag gtgcccgcca   55560
ctaattttt gtgtttttt agtagagacg gggtttcacc gtgttagcca ggatggtctc   55620
gatctcctga cctcgtgatc tgcccgcctt agcctcccaa agtgctggga ttacaggcat   55680
gagccaccac acctggccat atcattaaat gttcttatag gttttgggat aggcggtgga   55740
gttaggagca atgttttgtg ggcaggggat ggatctcaca aagtacattc tcaagggtgg   55800
ggagaattac aaagaacctt cttaagggtc agggagatta caaagtacat tgatcagtca   55860
gggtggggca gaaacaaatc acaatggtgg aatgtcatca gttaaggcta ttttcacttc   55920
ttttgtggat cttcagttgc ttcaggccat ctggatgtat acgtgcaggt cacagggat   55980
atgatggttt agcttgggct cagaggcctg acactcatga ggcagaggtt gcagtaagcc   56040
aagatcacat caatgcactc cagcctgagc aacagagcga gactccatct caaaaaaaaa   56100
aaaagtagaa gaaagaaaga tgtatttgga ttcactttaa gaaagagcaa ataagcattt   56160
agggccaggc gcggtgactc accctgtaa tcccagtggc caacatggtg aatccctgtc   56220
tctactaaaa atacaaaaat tagccaggca tggtggcgag tgcctgtaat cccagctact   56280
ctggaggctg atgttataag taaagttttcg gtgccgcaaa agaaatagca ctggaatata   56340
aagttttctt ttgaattctc agcaaggcaa gttacttcta tagaagggtg cgcccttaca   56400
gacggagcaa tggtgagcac acacttcgat aagggagagg aagggttct tatccctgac   56460
acacgtggcc cctgctgctg tgtctttccc ctattggcta aggttagatc gcaaaggcta   56520
aacattccaa ttcactaatt taaagagagg gacagggtga gtggtttggt gggaaaaatc   56580
attatgacag agcaggtaat cggaatgagt cagggtgggg taggtaatcg gaatgactta   56640
agggtggagc agataatcgg aatgagtcag agtggagtag gtactcgaaa aggttgcttt   56700
acgaggaagt taagttttaaa agtagaaggc aaaagtcccg gcgctgtggc tcacgcctgc   56760
aatcccagta ctttgggagg ccaaggcgag cagatcacga ggtcaggaga tcaagaccat   56820
cctggctatg gtgaaaccca gtctctacta aaaatacaaa aaattagct gggcgtggtg   56880
gcgggcgcct gtagtcccag ctactcggga ggctgaggca ggagaatggc atgaacctgg   56940
gaggcggagc ttgcagtgag cccagatcgc accactgcac tctagcctgg gcaacagagt   57000
gagactccac ctaaaaaaaa aaaagaaaa gaaaaaaaag tagaaggcaa agaattgaac   57060
atactgacat attgattctt tgaaagaaa tttagaactc atatctaaca ctgaggcagg   57120
agaattgctt gaacctggga ggcagaggtt gcagtgagcc aagatcacat cattgcactc   57180
cagcctgggt gacaagagtg agactccatc tcaaaaaaaa aagcatttaa aatctataga   57240
taattttcag tctccggctg cggctgcgaa agaagccgcc atgtctgcat atctgcaacg   57300
ggtggttggc actgctccag tttcctgatc aagaggaata agcagaccta cagcaccatg   57360
cccaataact tgaaggcctg caactgcttc cactacaatg ggcttattca acgcaagact   57420
gtgggcgtgg agccggcagc ccacggcaaa ggtttcatag ttgtgaagca gagatccagc   57480
```

```
cagtggaagc ctgccacctt ctacatgcag accaccatta acaagaatgc tcgggcaggg    57540
cggggtggct caggcctgta atcccagcac taatgggagg cggaggtggg tggatcacaa    57600
ggtcaggagt tcgagaccag cctggccaac gtagtgaaac cccgtctgta ataaaaatac    57660
aaaaattagc caggcatggt ggtgcgcgcc tatagtccca gctactcagg aggctgaggc    57720
aggagaatcg cttgaaccca ggaggcagag gttgtggtga gccgagattg cgtcactgca    57780
ctccagtctg ggcaacagag tgagaatcca tctcaaaaga acaaacatac aaacaacaga    57840
aaaaaacaag aatgctcgcg ccaccctcag cagcatcaga cacaggatcc tcaagagcaa    57900
gtaccgcccc gacctgcgcg tggcagcctt ctgcaggcca gcgccatcct gcacatccag    57960
aagcctgtga tggtgaagaa agaggaagag gattagaaaa cctgccccca aagcaatagt    58020
cagctggctt tctcaaaaac aaaaacatga atcaagaggt caggagatcc agaccatcct    58080
ggctaacacg gtgcaaccct gtctctacta aaaatacaaa atgtagccag gcgtggtggc    58140
gggcacctgt agtcccagct acttgggagg ctaagacagg agaatggtgt gagttctccg    58200
ggaggtggag ttgcagtgag ccgagatagt gacactgcac tccagcctgg gcgacagagc    58260
gagactccat ctcaaaaaca aaacaaaaca aacaaacaa aaaacaaaaa atctatagat    58320
aaaggaattc agatatatac tggtggagaa ctataaggtt ctcatctgtc tttggggtgg    58380
agaaattggt ctgaatgcct cttaatgaga cataggtcac tctcaattca aaccagggcc    58440
tagagcatta gaaagatcca aggctccttc aggcccagct ccatgaagtg accatagctt    58500
tccattaacg actggtagcc atcaactgtc tcgggcttct gggattttgg ctctcagaga    58560
aattagaggg ggatgttctt ctcaagatca actatctaat agtgtttaag aatttagagg    58620
ttaataataa taagctgccg ggcacggtgg ctcacgcctg taatcctagc actttgggag    58680
gccgaggcgg gtggatcgcc tgagttcagg agttcgagaa cagcctgggc aacacggtga    58740
aaccctgtct ctaataaaat acaaaaaaaa attagctggg cgtggcagcg tgcacctgta    58800
gtcccagcta ctcggtaggc tgaggcagga gaattgcttg aacccgggag gcagaggttg    58860
cagtgagcca agatcatgcc actgcactcc agcctgggta acagagtgag actccatctc    58920
aaaaaaaaaa aattaataat aaaaaaaata ataataataa gctatatggc acttcttca    58980 tcttaggttc taatagctgt ttaccactac taattagtat gtaactcctt ggctggtggt    59040
gagggtggtt gatctgcact tttatgagat gaaacatctg agagttgact ggaatggagc    59100
ctgtacctct tgaggtactt ctggtcagtg gttttctacc tgaaaacttt ttcttttcctc    59160 taagattgaa atgggacact gagcgaccaa aagcaaatgg attgcagaag ggaaatattc    59220
tgcatgtact agcatgtgca tattacgcat gtgtgtacat gtaatgcaga atgcaggcac    59280 taattttta agaggttttt catgttcctt tcactccttt tagcaagttg tttaagaaaa    59340
ttatgttttt ctagccaggt gtggtggcgc atgcctgtaa tcccagctac tcgggtggct    59400
gaggcaggag aaccacttga acccaggagg cagaggttgc agtgagctga gatcgcacca    59460
ttgcactcca gcctgggcaa caagagccaa actccatctc aaaaaaaaaa gaaaattatg    59520
tttttcttct tctggcaaga aaagacaagc tctgggtaat gagaatatat gcactgcgga    59580
aaatggcatg cttagccaca gactgcttgc taattaaaag taaatgaaa aaatgaatgt    59640 gctactccag gctggagtgc aatggtgcaa tctcggctca ctgcaacctc tgcctcccag    59700
gttcaagcga ttctcctgcc tcagcctcct gagtagctgg gattacaggc atgcaccacc    59760
atgcctggct aattttgtat ttttagtaga gaaggggttt ctccgtgttg gtcaggctgg    59820
tctcgaactc ctgacctcag gtaatccacc ggccttagcc tcccaaaatg ctgggattac    59880
```

```
aggcatgagc cactgcaccc agccttgagt taagttttga tcggtgtcca ctgtaatgct   59940
ttgttgacag ttactgtgaa tgaccaacct gtaaaagggg aaaatccaaa cttctaacca   60000
cactgaggtc atcatggatt tataccatgc atgaggacat aatgattata ataactaagc   60060
tattgagtct tttacatcta tttacatcct ttacatctat ttactcatct cgttttccac   60120
aatcaccaca tgaagtgtag atactgtatt tatcaccatt ttatagatga gtaaacaaag   60180
gcacagagag gtaacagaag ttgcctaagg cacacagtt tgccagcaga aaagccaggt    60240
tacgtgattt cattgcgggc tcttataact attgagctat actgcttgtt agtagaacgc   60300
cagatgatgc tatgggatta gcccagagat ttacaaaaga ggagacctgg gcacatttga   60360
aggcggaatg gcttaaacgg ccctgaatac aagataggaa gaggatgttg aagaaaggtg   60420
gggtcccca agaccacttg gaattgggat aggttatagg ttgtagtgct ctggtaaagg    60480
cgagctttag cagaggtaga acaatcctta ttcttctgag gttgcagtga catgtaagta   60540
tagagagctg ctgggaagag aagacagaga agtgaaagta acttgtacct gacgacttga   60600
gcctttgggc agtgtgctgg agctggctcg taccagctca agagacccct tgttaaacat   60660
caaggaattt tgcaagtagg ttggtagctt gaaattagcc aaagtgggag tattcaactc   60720
cagaaattag caaatactac aaatcagggc ctccccacca ccactcagaa ctggtttacc   60780
agaacacctt acactccctt tcttctcttt tccacttcac taacagtcaa aagcctgctg   60840
aagtgccagt tgaatttgaa gcttgagtga gtgcccatta tgggaaaggc actgtgccag   60900
atgccagggt aagaaagacc aaccctcaa gtaaataata ctgtggtgga gagtgaagag    60960
catgcaggcg taaatcctgg actagctgtc ggctcttggg acagtcactt aaacttgggt   61020
tactcatctg taaatggaga taataatata tatcccaaag ggttattgag atgactgaga   61080
acatgtaaag ttcctggcac agaggtgttc attaagtgat ggttctaaga gtggggacat   61140
gtaaacagat gtcttttcata tagcttgata taagaaataa agatgggagc cgggcacagt   61200
ggctcatgcc tataatccca gcactttggg aggctgaggt gagaggactg cttgagccca   61260
ggagtttgat accagcctgg gcaacaaagc gagaccctgt ctctacaaaa cattttttta   61320
aatgaagcat aggccgggtg cggtggctca tgactgtaat cccagcactt ggggaggccg   61380
aggcgggtgg atcacaagat cgggagatca agaccatcct ggctaatgcg gtgaaacccc   61440
gtctctacta aaaatacaaa aaaaaaaaaa aattagctgg gtgtggtggc gggcgcctat   61500
agtaccagct actagggagg ctgaggcagg agaatgacat gaacccggga ggcggagctt   61560
gcagtgagct gagatcgcgc cactgcactc cagcctgggc aacaaagtaa gactctgtct   61620
caaaaaaaaa aaaaaaatta gtcaggcacg gtagtgtgtg cctctggcca gctacttggg   61680
aagctgaggc atgaggatca tttaaaccca ggagtttgag gctgtggtga gctatgattg   61740
tgccactgca ctccagcctg gatgacagag caagattctg tctccaaaaa acaaacaaat   61800
aaacaaaaga aataaagaca gaatgactac aggtcatagt cccctcagta gattccagag   61860
ttttcagggt ggatgattca tggatgattt tccttgtttg ttatcagaag gttaccgggg   61920
tttttttttt gtccctacaa atcaagttta ccggatttac ttgttgtttt taccggtttt   61980
tagcctgttc ctcactctat attatttaat tgtaagacaa acaatggatt tggaggtagg   62040
cacagttgga tttatatacc agctccaaca cttacctggt ttgtgacctt tggcaagatt   62100
cttttttttt tttttttgaga cgaagtctca ctctgtcacc caggctggag tgcagtggcg   62160
tgatcttggt tcactgcaac ctccgcctcc cgggttcact ccattctcct gcctcaccct   62220
```

```
cccgagtagc tgagactaca ggcgcctaca accacgcccg gctaattttt ttgtattttt   62280
agtagagagg gggtttcatc gtgttagctg ggatggtctt gatctcctga ccttctgatc   62340
caccccgcctc agcctcccaa agtgctggga ttacaggtgt gagccaccat gcctggcctc   62400
tgatcaaatt cttttttttt tttttttttt tttttttttt gagacggagt cttgctctgt   62460
cgcccaggct ggagtgcagt ggcgtgatct cggctcactg caagctccac ctccccggtc   62520
cacgccttt tcctgcctca gcctcccgag tagctgggac tacaggcgcc cacccccaag    62580
cctggctaat ttttgcgtt tttagtagag acgggtttca ccatttagc caggacggtc     62640
tcgatctcct gacctcgtga tccgcccgcc ttggcctccc aaagtgctgg gattacaggc   62700
ttgagccatt gcgcccagcc taattttttt tttttttttt tgagatggag tctcactctg   62760
tcacccaggc tggagtgcag tggtgccgtc ttggctcact gcaacctcca cctcccgggt   62820
tcaagcagtt ctcctgcctc agcctcctga gtagctggga ctataggtgc acgccaccac   62880
acctggctac ttttttgtat tttagtagag acagggtttc caccacgttg gccaggctgg   62940
tcttgatctc ctgacctcgt gatccgcccg cctcggcctc ccaaagtgtt gggattacag   63000
gcgtgagcca ccgcacccag cctctgatca aattcttaaa ggccaaatta cctttataaa   63060
actgaggacc cctaacatt taccttgtaa agcttttttt ttctccttt ctctgtgaaa     63120
aagatggaat atacaaatta actaagtaat atctgcattt ttacagattt aatctctcaa   63180
caattattta ttgatcaatt actatgtgtg catactatat taagtgctgg gaacatgatg   63240
gtgagcataa ctaatcctgg tccctgctca catgtggcta tgtacatcta tattaattaa   63300
acttaaataa cattagaact tcacatccac acctgtacta gccatctttt atgtacttaa   63360
tagtcacatg tggtgagtgg ctattgggtt ggacagtgta gatttagaat attttcatca   63420
ccacagaaag tcctcttgga ctgtgctatt ctagagtgag ggaggtggac attgatcaaa   63480
tactcataaa agtatgattg caattgtagt aagtactagg cagaaagaat agatggtaac   63540
atgagaacat ttcatagggg gatttgactt ctctgttggt tttcccaagg aaaacctgtt   63600
caaactagat ttgctcaatg cttggaagtt agcaaagccc tgtggtggga gggaggacag   63660
taattacagg gactgaaagc aagctaatga ctgaatcatg gggattgagg agaagtttgg   63720
gtgagatgaa ggggtggaag gaccacaaag ggccttgtag aaagaagatg aagaagcaga   63780
gaggcttagt aacttggctt tgcagttagt aatagaacct ggatttgact tcaaagtcta   63840
cactgcataa taagggtata ttcaacagac tttggttctg caattatctc ttttttgctcc  63900
ttctttggaa attgccaaag ttccctctac tggattattc ctttagcata aaaacatgct   63960
gtaataattt ccttcttaga caaaccaaaa aaaccaaaaa gtctggccag gcacggtggc   64020
tcaccctgt aatcccagca ctttgggagg ccgaggaggg tggatcacga agtcaggagt   64080
tgaagaccag cctggccaac atggtgaaac cctctctcta ctgaaaatac aaaaattagc   64140
tgggtgtggt ggcatgcacc tgtagtccca gctactcgag aggctgaggc aggagaattg   64200
cttgaaccca ggaggcagag gttgcaatga gctgagatcg tgcctctgca ctccagcctg   64260
ggtgacagag tgagactctg tctcaaaaaa aaaaaaaaaa aaaaattcct ctatcctaca   64320
tccctcttta gctcctttcc tattgttgtt ttgttttgtt ttgttttat agcaaaaccc    64380
ctttaagagt tgcctatact tactccctcc atttccttat tttctgtttc ttgctgaact   64440
tcttctaatt aggatttctt acctaccacc attttcataa gtgacctcca tgactcagcc   64500
cttaccttat aggatttctt ggcagtgctt gaaatagttg atcttccttt ttggagcact   64560
tcttcattgg cttctgagac accacacagt cttggttttc ctcctacctc ctgccagctc   64620
```

```
cttcttaggc tccattgctg ggttctttc ccctttgca gtttgagcgt gccagggctc    64680
tgtcctgggc catctttatt tctctaaata cattaactcc tgggtaattt catctagtcc    64740
catggagtga cagttaattt tatgtgtcaa cttggctagc atacggtgcc cagttgtttg    64800
gcagataaaa gcatagatgt tgctgtgaag gtatttttta gatgtgactt acaatgaaat    64860
cagtaggctt tgagtaaagc tagtgaccct ccataatgtg gatgggcttc atccaattag    64920
ttgaagacct tagagaaaag atggaggttt cccaaagagg aagcaattct gcacccagac    64980
caccgttagt ctcaagattg ccacatcaat gcctgcttga atttccagcc tatcagccag    65040
ccttggagtt ttcagactta tcagccctca caactgtgtg agtcaattct ttaaaaaaaa    65100
gaaaagaaaa aaatctctct atatatacat gtatcctatt ggttctgttt ctctgaagag    65160
ctgtgactaa tacacatggt attaaatatc ttttatgttt gacaccaaat gtttatttct    65220
agccttgact tctcccttga actccatact tacatatcca actgcttagt caacctctcc    65280
atttggataa taatagatct gttaacccat actatggatt tgtcccaaac tattgttttc    65340
ccccacctcc catctttctt cctcctctct gggtgttcct gcttttcatt gaagagtgct    65400
attatttacc ccattgctaa agccagaaat ctagcgttat cattgattct ctttctctta    65460
catctcttat tccatccatc tgtacaactg tacaacatat atctgtgcaa ttagctttac    65520
cttcaaatgt atttttaac ctcactaatc agcctttatc atctctagct tggaccagga    65580
cagtaacttc ctagcaggtc tgtatatctc catatctcca cttttttttt tttttttttt    65640
cttttttgaga tggagtctca ctgtgtcgcc cgggctggag tgcagtggtg ggatctcggc    65700
tcactgcaaa ctccgcctcc cgggttcacg ccattctcct gcctcagcct ccccagtagc    65760
tgggactaca ggcgcctgct accacgcccg gttaatttt tgtatttta gtagagatgg    65820
ggtttcactg tgttagccag gctcatctca atctcctgac ctcgtgatcc gcccgcctca    65880
gcctcctgaa gtgctgggat tacagacatg agccaccgag cccggccata tctccacttt    65940
taagtccctg ccctccttag cctatttcc acacaactga gcaattattt tatcatacaa    66000
caatcatttc cttctcttct cttcacactc tggcatctta ccacatttaa aatgaaatcc    66060
aaaatcctga ctatggcctg atgatggatg tgaccccctgg ctattcctct gacctcactt    66120
cctaccactt tttttctcac tcattaggct ttagacatac tggttacttt gtggattctt    66180
ggataagtca agcagactcc tagcttaggg ctttagtatg ttgaagccag aataaaaatg    66240
tgagacaagt ctctaaatta aaatttttta tttggaaaga aagaatagca atttggggca    66300
tatatgcaga cagggtggtc ttcagtatgt ctgaagaaca aagagaaggt tagaggtttt    66360
agaaacagga gagctgttac atattgctct tcaagaaagt tctttgggac tagttagggt    66420
ttggggagct agcaagctct ggtgagtgat ggcagtgggc aaaattagtc ctagagtttc    66480
agcaagttct cttagcattt atagataaag ctggtctcag gttacaacag gcagtttcag    66540
cagtcaggct tgcagagaat tacattcttg gagcaatgtt ttgtaccctg agtgcttttc    66600
ccctagccc cttggctctg atttaattgg gaatgacaag aatgacccaa ttttatgatc    66660
agctttcaca agtacctcct cttcctctg cttagaaaga tttcttccct aggtactctc    66720
atggcctgtt ccctcatagc actgtgggct ctgctcaagc atcacattct gagatctttc    66780
ctgacttccc taccctactt tattcttctt caaggtacaa agaactcttt cagaaaagct    66840
ttgtgtgtgt gtgtgaagga gagcaatgaa atggggtggg ggtaactgca agggttgggg    66900
cacatgggat catgagagcc ttttcttct ttttgggaac agttttgctc tgtcatccag    66960
```

```
gctgaagagc agtggcatga tcatggctta ctgcagcctc aaactcctgg gctcaagtga    67020
tcctcccacc tcagctttcc aagtagctag gactacaggc aggtaccacc acacctggct    67080
gactttata atttttttg tagagacaag gtcttgctat gttgtacaca ctagtcttga      67140
actgctggcc tgaagcaatc ctcctgcctc agcctcccaa catgctggga ttacaagtgt    67200
aagttactgc accaggtcgg gaggctttt taaaatggta aaacaacaat gcatttgtat     67260
gatgatgtaa atgatcaggt agagaacaag caattgatga tgccagagag ggaggctaac    67320
ttcaagagtg atgttcatta atattaagaa ggaaataaaa gatgagaatc catacacaag    67380
tgaagttgga cttcactatt ctccacataa cagcaattct ttgaatgtac aacaatcatt    67440
tccttctctt ctcttcacac tgtcttttt gttttgttt ttgttttttt gagacggagt      67500
cttgctcttg ttgtccaggc tggagtacaa tggcatgatc tcggctcacc gcaacttccg    67560
tctcctgggt tcaagcgatt ctcctgcctc aacctcctga gtagctgaga ttacaggcgc    67620
ccaccaccat gcccagctaa ttttgtatt tttagtagag acggggtttc accatgttgg     67680
ccaggctggc ctcgcactcc tgacctcgta atccacctgc ctcgcctcc caaagtgttg     67740
ggatttcagc cgtgagccat tgcacccggc ctcacactct ggcttcttaa cactttaaa    67800
atgaaatcca ggctgggtgc agtggctcac acctgtaatc ccagcacttt gggaggccga    67860
ggcaggcgga tcacctgtag ttgggagttg gaggccagcc tgaccaacat ggagaaaccc    67920
cgtctatact aaaaatacaa aattagccag gcgtggtggc acatgcctat aatcccatct    67980
actcaggagg ctgaggcagg agaatcactg gaacctgaga ggcggaggct gcggtgagcc    68040
gagatagtgc cattgccctc cagccagggc aacaagaaca aaactctctc tctcaaaata    68100
aataaataaa taaaaataaa atgaaatcca aaatcctgac tgtggcctga taatgggtct    68160
gacctctggc tactcctgac ttcactacct accacttttt ttctcatcag gaaataataa    68220
gagtgaaggc agagaatatg gcagcttgct ggttaaggga gttctgtctg attgatgcta    68280
tttctctaaa gtagaaagta ggtcatgagc taatgcaagg tgtaggggca ttagaagttt    68340
gaggaaagag ggatacgtgt gaaatggtca ttttggatcc tgagaaaaca aatattccag    68400
ggatgcaaag gattgctggg caaccttgag gatacatttg aagtttgtgg tcttaacttt    68460
aaagtgaaat cacttttaat ttctgtgttt ccttcagcaa tgtttcctgc tttaagtgga    68520
gtacagaata tgtggacagc taggttcagc aagggtgggc cttgccatgt caacgcgact    68580
gagaagcttg gacttcatat tgagggccct agagagctac tgaaggtttg agtaaagaag    68640
atttaggtgt tagaaagatc attctagctc agtatggtgt gtgtgtgtgt atgagagaaa    68700
ggcttattat aggtagaaca gtagtttaat acaataggag cctttatcaa acacctgcat    68760
aaatttgtta tagcttagat gacagttcag gaacatagag aggtctattt ccagcatttt    68820
ctgagtacct actatatacc agattctgta aagacaaaat aaacaagggt ttgcctatcc    68880
aaagctcttg tagaagattt gtaattatta ttaggtattt gggggacaaa gaagagggaa    68940
ggagcaatta acactgggtg aaaatccagg aagactccca gaggaggtga catttcagat    69000
gagctttgaa ggactaggcc cttagggagg aagataatt ctgaaaagga agaatgagcc     69060
cagtcaagag atgcgaaatg tatgattaaa acatttatg tttatgattt gctacggcca     69120
ggcacagtgg ctcacacctg taatcccagc actttgggag gctgaagcag acggatccct    69180
tgaggctagg agtttgacca tcctggccaa cgtgttgaaa ccccattcct actaaaaata    69240
caaaaaatta gccaggtgtg gtggtgcatg cctgtagtcc cagctacttg ggaggctgag    69300
gcatgagaat cgctggaagc agggaggtgg aggttgcagt gagctgagat cgccactgc     69360
```

```
actccagcca gagcaacaga gcaagagact gtcaaacaaa caaacaaaca aacaaataaa   69420
taaataaatt gctgcatgat gagaaatggt ggaagaagat gaggttcttc ttccattaac   69480
cagcaactaa atagaactaa ggagttttc ctctagaatt cacgacaagg gtaaggcatc    69540
tgggctctta acagcagcaa gaaggatttg aaagaaaaga agatggtttt aaaatggtga   69600
ttttaattta aagaaaaata actacatggt gctactctgg gcatctttgc tataatttgc   69660
tcacttagga acaatgtgaa gttaaaatgc cttatctagc ctgttttgga atgccgttag   69720
aaaatattaa ttataatcac tctgagctgt ctatacaaga tgcttttaat ggcaagcctc   69780
ttcaaatcaa tccttattac ttgcttttag tacattattt caagttaaat gatccttctg   69840
tgtcctaagt catgcttttg aaataaggtg tattttcaat atatttctaa gaatgaggag   69900
tttatgaccc tggttcatgg gtcattcggt agactaaatg agataaaggc atataaaatt   69960
attaatacag aacttggctt gggagccagg agtaaatgtt ttttgttctc ccttagaccc   70020 agtctttca tgttttcct tctttcctcc ttaaatcaca ttgtttcctc aacacccacg     70080
tactagatcc attctctgtt ctagggactc cagaatcagg tgaaacactc atgtcaataa   70140
tcaaacactc atgtcaataa tcaccttaca ggggaagtgt caagttagtg tgtgtagtgt   70200
gtgtgtgtgc ccatttagag ggtgaagaag ctaaatcaag cctctgagtt tcaccttgga   70260
agggcctggc aggacctggc agtggttgcc tgtttgttta gagggagtgt ggcttctgct   70320
ggctgttagg agcccgcaac gctctcagct gagagtgctt caatctggca ttatccaaag   70380
aagtgggaaa gacattcctt ccttccttcc ttcattcagt tattatgtat ttattcagca   70440
aatattcata gcctgctagt gcacagtgct gaataagaac atgagtaaga gcagggaagc   70500
atgagagagc atggctcacc ttagtagctg caggtggctg ggtgcagctg gagttaaaag   70560
acactctgag tttttcttaa aaaaaacaat aaataccaaa cttagaatct aataaggaag   70620
aggtgctctc aggggaagtt aggtgtgttc ctaagaattt gtcatttctt ttcaggatta   70680
gtcaggatga actagacatt tctttcaaa agcctaataa cttcctttag ggaactgcca     70740
aactgactaa tccatgacct taaggcagtg ggtcccaaac tttgctgcca actcaatcac   70800 cttttggagtt ttttttttt ttttaaacgc agaggcccag gtcacactcc acaccaatga   70860
catcagaatg tctaggggtg ggagccaggc accaggattc taaagaccct cacgtgatga   70920
caacagctag caaagttctg tagctactgc cttagggcat agtctaattt cttcagtaaa   70980
aacacactta ttccaaattt ggttccagaa ttgccttaaa ttgttttgc tctgttctta    71040 ggttggggc ggctatgagc aggcagagga tgtggtgtca cccaattagg agctctcagc    71100
ttacgaggca attagcatag gttgccaggg ctgcacgagg agtggatttc tgctttgtca   71160
ttctgactct ggcagttagc ccgcccgctc ggcgcagggc gtggcttctc gtagccatta   71220
ggaaacagca acccttcac ctcagttttc ttcactccgg catttgcagc agagcgaaag    71280
gtggtcgagt cctgaaggag ggcctgatgt cttcatcatt ctcaaattct tgtaagctct   71340
gcgtcgggtg aaaccagaca agccgcgag cccaggatg ggagcacgcg ggacggcc       71400 tgccggcggg gacgacagca ttgcgcctgg gtgcagcagt gtgcgtctcg ggaagggaa    71460 gatattttaa ggcgtgtctg agcagacggg gaggcttttc caaacccagg cagcttcgtg   71520
gcgtgtgcgg tttcgacccg gtcacacaaa gcttcagcat gtcatgtggt aggtgaggcc   71580
ggcgcctgta ggctggcggt ttccttcctc ttggtctttg tagagacagt ttgcagaaca   71640
gcggagaaaa tgggtattgt atcgtttctt acagagtccg agtcttgaaa tgtagatgac   71700
```

```
aatgtgttga gtggactgac agatccttga gaatattaag aaagtataac tatgtaagaa    71760
tgcttctcta ggaattttca caccatttaa tcctcagaaa tcctgagacg ttggcaaaac    71820
acatggggtc tccatgtttt tacaagtagg gaaagcaagg ctcagaaaga tcaagtggcg    71880
tgcccagctg gacacagact attaaatggg gcggcgacga cgaccccagg cttcctcac    71940 tctctcaggc agtacaggac agtgattaaa cgcgtcgacc acattgcctg ggtttgaatc    72000
ctgccgctgc ttttgagtag ctccttgagc ttggacaagt ttcttagctt ttctgtacct    72060
gtttccctgt ctgtaagttg ggcctggtaa tacttacttg tagagtggtt gtgaagttga    72120
aatgtaaata tatgtgaagc agtatagaca tgttagctac tattattaca attaagcagc    72180
tatactttgt ttttttgtttt ttgttggttt tttttgtttg tttgttttttt gagacggagt    72240 ctcattctgt cgcccaggct ggagtgcagt ggcacgatct gggctcactg caaccttcgc    72300
cccctgggtt caagcgattc tcctgcctca gcctcctgag tagctgggat tacaggcacc    72360
tgccaccgcg cccgactaat ttttgtattt ttagtagaga cagggtttca ccatcttggc    72420
caggctggtc ttgaactcct gacctcatga tccacccgcc tcggcctccc aaataagcag    72480
ctatactttt gaatgttggc gtgatttatg tctaatgaat aggcctcatg tcagtgtaac    72540
tgtggaatct gtatgttcca ctgagttcac ccctttgtga aattttacca ttagtgccta    72600
gtttcatctg tagcgttgtg tattgcttca ggattctttt taagaatgca ccaggtaggc    72660
agagtgttct taattttgct ccacggtttc aaatgtcaag gaaacgttgg aagttggatt    72720
ttggcattca gtatagatgc agagttgaaa gcaagatcaa actgggaggt gttttgtgaa    72780
agttgagata aacgtgtatt aagcttcttt tttgaagctt ttctgaattc gggatttacc    72840
gggaaagtag gacgtttaat tttagcggag tagtgcaatg atttaaccct gactagaact    72900
ctgacgttta cagctagcct tgaggccatg ttttcagcca gtgtgcggat ttgccggggt    72960
cagactccaa gcttgattgt gagttctagc ctttgtcaga aatgcagcaa gtcatgctaa    73020
cttgcaaggg agtcaacaga gggcacgcgg tgcctgcggg gccggacgg aagccccgcc    73080 cccggcgcag ttcccgcctg ttagcggggg agaagcacct tacacgctcc gctctgcttt    73140
tgtgccacac agaggacggt cgggccctgg aaggaacgct ctcggaattg gccgcgaaa    73200 ccgatctgcc cgttgtgttt gtgaaacaga gaaagatagg cggccatggt ccaaccttga    73260
aggtaggaga gagtaacgta tcttttttaaa cggggggatga gctcgttgag ctcagcgtgg    73320
tcacagcctg ccttttaaag ccagcgtgga tgtgacccctc caaacgggac gcagcgctgg    73380
gaaatgacga aaaacgctcg tgggctagcg catgtgttaa tcgaagttga tgagacgttg    73440
gacaaatttc acatctcggg aaacttgaaa tttctaacgc ttttttatctt ttaaaatagc    73500 ttttttaaaaa tgtcctttttt ctcctatttc cccttcctct ttccctccca gttgtaaata    73560
acatttttta gcagcaatgt aatctgctaa atgttagttg tttagggaag tcctgagaaa    73620
aggggatcag gaaatgctta tctttgtcat caaggtggcc ctgtaatctt cctcttaatt    73680
ctctcagggg tagggacccc ggaaacccca gggtctggag gagagcaacc aggaagctct    73740
tggggtgact tcgttttcct tcaggtgtgt cttttagcc cagagttaat agttgggtga    73800
agggaaagga agaagtcttc cctttggctg gtagcaaacg cagtagaaat ccttccttag    73860
acctatgcta ctgaggagtt atagccactg agggatttat agcctacagt gttagaaaaa    73920
tgcttggagg ctgggtgtat gtatgttttta tttatgtatt taaaaaaaaa aaacagtctt    73980
gctctgtcac ccagagtgca ctggagtgca gtggcgtgat cttgtatcac tgcaacctcc    74040
acctcctggg ttcaagcaat tctcctgcct cagcctcccg agtagctgag attacaggtg    74100
```

```
cccgccacta cacccagctt caccatgctg gccaggctgg tctcaaactc ctgacctcag    74160
atgatccacg gctgggtgca tgtttaaggg aacaggacac ctgggtgatg ttctatctca    74220
cctgtggtag attaccaggt tagaaaactt cccgtagtcc catcaccacg atccatgtga    74280
tttttgtcct tatccattta tatctctgta attttttaaga aatgaaaaca ttgccttctt    74340
agaagtaaac ctaacgcctg cgttaaatgt aaaaatatat ttagatgtgt tgcagcctta    74400
ggaaaaatac taataatttg aattttttatt tattacccttt tcttttaaaa gtattttatt    74460
tattttttgac aaatggttat agggaatgga tctagacttc aaacagcaaa ttaatggaaa    74520
attaatggaa atacagaggc ttttagcttt agttaaaata tattgtgtta ctcagacctt    74580
tagtttgcag gtaaaaagag ataacggtct attatattaa tattccttcc tggccgggtg    74640
cggtggctca cacttgtaat cccagcacct gggaggccg aggcaggcgg attgctttga    74700
gctcaggagt tccagatcag cctgggcaac acggtgaaac cccgtctcta ctagaaataa    74760
aaaaattagc cagggcttgg tggcacatgc ctctggtccc agctactctg ggactgaggc    74820
tgaggctggg gaatcaactt gaacctggag gtggaggttg caatgagctg agattgcgcc    74880
actgcaccct ggcctaggtg acagtgagac cctgtctcaa aaaaaaaaaa aaagaaatat    74940
acatatatat atatatatat atatatatat atatatatat gtatatttct tcctgtctga    75000
ttattctatt attttcacct gtgccataag tttacattta caaagttata tagtaatttg    75060
atctttatgt aattctactg atactcctgg ttttaatggc aatgggagta aaaagagtca    75120
ctctttttat aagctttgga actcacttaa ttgatttggt ctgatgttct gatgtttttt    75180
cttttttttt aattgaaaac tttttttttct ttagagatgg aggtctcatt atgttgtcca    75240
ggctggtctt gaactcctgg gctcaagcga tcatccggcc tcggcctcct aaagtgctgg    75300
gactgcaggt cacgacattt agtgaggtat agtgccatga atgaaaagca taccatcaag    75360
aacacttaaa agaaatcatt tagcatattt cttaagtaaa cttattctac tttgtgtctt    75420
tttttttttt ttttttttttt gagacaaagt ctcgctctgt tgctcaggct ggagtgcagt    75480
ggcatgatct tggcttaccg caacctctac ctcccaggtt caagcgattt tcctgcctca    75540
gcctcccgag tagctgggat tacaggcaca cgccaccaca ccctgctaat ttttgtattt    75600
ttagtagaga tggggtttca ccatgttggt caggctggtc tcgaactcct gaccttgtag    75660
tccaaagcgc tgggattaca gtgtgaccc accgcaccca gcttttttttt tttttttttt    75720
tttgagaagg agtctcactc tgttgcccag gctggagttc agtggcgcga tcttggctca    75780
ctgcaacctc tgcccctcgg gttcaagtga ttctcctgcc tcagcctccc gagtagctgg    75840
gattacaggc gcctgccacc gtgcctagct aattttttgta ttttttagtag acaaggtt    75900
tcaccatctt ggccaggctg gtcttgaact tttgacgccg tgatccaccc acttcggcct    75960
tccaaagtgc tgggattatg gcgtgagcc accgggccca gccctatttt tgtttttttaa    76020
tgagtgctaa aaaatgaaag gagaaacagc aaggtaagga ctattggttt gaaagatctg    76080
tgaacttttc agccaattat tgcccacatt tgggggctaaa tggtaggttt tgaaacccctt    76140
aagggagctt tgggtttcag tggagaaagg catttatttta gtggagaatt gagtgcttat    76200
agtcctaaag gccacacctt taaaagaag gttaagattt catactttaa ttgcaacata    76260
aataatggag ggagctcttc aaaatgtcca cttttccttt ctccttttaa tattgtttct    76320
tcctcatccc ctttttccctg aataaacaac agcagcaaaa cctaccctgc tttcacagtg    76380
agtgtactat agaagacaag ggagaaagaa tcctgctgga agaagttggt gagcctaggt    76440
```

```
gactcccttg ataaaggatg aaagctttgc agaagagtgt tccaaaaaag tgtagtctcc   76500
agaccacctg ctcagaatcc cctggagtac tcgttaatta tgcatgccca ggctttaccc   76560
gagttctttt gaagtagact cgggaaagag ctaggaatct accccgccc cccgccttt    76620
ttttttgag atggagttct gctcttgttg cctgggctgg agtgcagtgg catgaactca   76680
gctcactgca acctccacct cctgggttca agtggtgtgg ttctcctgcc tcagcctctc   76740
aagtagctgg gattataggc atgcaccacc atgcctggct aattttgtat ttttttagta   76800
gagatgtggt tttgccatgt tggtcgggct ggtctcgatc tcctgaccac aggtgatcca   76860
cccacctcgg cctcccaaag tgctgggatt acagtgtgag ccaccacgcc cggcttgcct   76920
tattgttttt gttttgtttt aaataagctc cctccaataa ttttaggat aaatgtcaag    76980
tttgagacgc tttaatatta ttgtacatag ggtagtttga tcaagatcat ttgatgagat   77040
aattagaatt gcggaaaaca aaggactagt ctttaatacc caaaacatat ttgttagaaa   77100
acagcaaata ggaacccaat gggggaggaa cacttttttgt tgaacacttt aacaatgaat   77160
agaaaaatag ggaaccaagc tgtttgcagc cagggcttt gtatgtccat gtataaagtt    77220
ggaactaggg acctccaaga tggttaagaa ctatgaatag agttcctact gctcaaagat   77280
gtggctttca taaacatctt ggttttttaaa gcaaagttcc agtattctta tagggaacct   77340
cttttgtatg taaatcagca tctccctcag gattccaggg ttttgaaatc acttgtagag    77400
aggcctattg tggtactga gaggagaagc agagtgagtg aaaaagtatt tactggaata    77460
ataccaagtg tcagacatag ttaagacttt agtagtttga ggtaatcctg ggagataaga   77520
ctaaaactga caactcaggg cttaaataat ttcttcaggg caatattagg agagatgaca   77580
ggcaccaagc aatgcgggat taatatccag gtgaattttg cagacagttg cggtggcccc   77640
atgttccagt cttgggggt agatgctgag acaaaggcag gtctccttttt atgttttgag   77700
acaaggtctg gctctattgc ccagtgcagt ggcttgatat tggctcattg caaccttcgc   77760
ctcctgggct taacccatcc tcccacctca gcctccgaa tagctggaac tacaagcgca    77820
caccacctca cccagcttat ttttgtattt tttgtatatt gggggtttca ccatgttgtc   77880
cagtgtaggg accagcccca cagggtcggt gggtctctcc ctgtgtgcgg cgacgagaga   77940
gtgtagaaat aaagacacaa gacaaagaga taagagaaaa ggcagctggg cccgggggac   78000
cgctaccacc aatgcgcgga gaccggtagt ggccccgaat gtcgggctgc actattattt   78060
attggataca aggcagaagg ggcagggtaa agaatgtgag tcacctccaa tgataggtaa   78120
ggtcacgtgg gtcatgtgtc cactggacag ggggccccttc cctgcctggc agccgaggca   78180
gagagggaga ggagacaaag agaaagacag cttacgccat tatttctaca catcagggac   78240
tattagtatt ttcactaatt tactactgct gtctggaagg cagagccagg tgtacaggat   78300
ggaacatgaa ggcggactag gagtgtgacc actgaagcac agcatcacag ggagacggtt   78360
aggcctccgg ataactgcgg gcgagcctga ctgatgtcag gccctccaca agaggtggag   78420
gagcagagtc ttctctaaac tccccggg aaaggcccc cccccgccg ccggctttcc        78480
cggtctgcta agtagcgggt gttgtttctt gacacctttt gctactgctg gaccacgatc   78540
ctcttggtga cgggcgtctt cccagatgct ggcatcaccg ctagaccaag gagccctccg   78600
gtggccctgt tcgggcataa cagaaggctc gcactcttgt cttctggtca cttctcacta   78660
tgtcccctca gctcctatct ctgtatggcc tggttttcc taggctatga ttattgagtg    78720
aggattatca taatattgga ataagaagta attgctacca actaatgatt aatgatactc   78780
atatataatc acatctaaga tctatatctg gtataacaat tcttgtttta tattatactg   78840
```

```
gaacagctcg tgtcctctgt ctcttgcctc ggtgcctggg tggcttgcca cccacagtcc   78900
aggctggtct caaaactcgt gagtttaagc catctgccta ccttggcctc ccaaagtgct   78960
gagattacag gtgtgagcca ctgcacccag ccaggtctcc tttcaagtct aacttctaaa   79020
gttaccagaa accagaatct taagtgaata gacatcagga catgagtggt aattgaataa   79080
ctctccaacc atccccttc ttaactattc ttaactgcag aggctaccag aacttgacag   79140
aaaacacaat ttattttgtt tctatcctct taaataatcc cttcttttg gaggcattag    79200 taatgtatct gcttttggct tgattaaagt tgaggcctga ggaggactgg aggattgctt   79260
tgaagatgag ggaagtgaca gattctctgg cgtacattaa aaggaagtaa gggttgagga   79320
ctaccaagat ttattagagt cttagactgt tagaactgca ataaacgta gaaatttact    79380 ggttgtagag tcgtgttgag ctcctcctac ttctaccagg tgtaaacaca aatctctttt   79440
tttgctgtgt atctgttctt taatagtagc gtcaaaattc tggtggtata gacttcagat   79500
ttccggtcac ttctcctgtt tactcaccag cgcctgacta ttctaggcat caccttcttg   79560
cccctattta cttttgcctg gaccatttca tcagtcttta actggcctcc cacttctgat   79620
ctcccttctc ttccagctca tattgccagt catcttcctg attgctactc gctggcccca   79680
gatctgcatc cagaacgaaa tgggagctcc ttagcttggt attcaatgcc ctccagggtc   79740
tagccccaac ctgcttttct ggttatctcc tgctctgctc cctcacttac tggaggctcc   79800
cgggactatc attgcagcta aaatatttct ccctacagtt ttcctcctca cttctattct   79860
ttatttcaac acctgtcttc tcttcctacc acaacccact tttccaactg cctacccgtt   79920
cagaatacaa gaccaaagtt ttccattcct ttcctcctct gttcccacga caatcccata   79980
agtctttatt tttggaaaag gaggaatcct gccaatgata acttttttggc ttacatatcg   80040 aggtcagaga gctagtctta ttctttatgc ctgtggtccc aggcatatgt tagagcccag   80100
cagataccta agcaaatatg cctgttaatg attataacat ttatttgttg aatacctatt   80160
atgtgttaga ctctaaatgt tgttaatact tagtgattaa atccccacaa cagtcctgtg   80220
aaggaggtga tattatccag gtttacagaa gagaaaataa aagccttgag aatttaagga   80280
gcatgcccag attacaagct agttaagtgg cagagtcagg actagaaccc aggcctgttt   80340
gcctgcaaag ctcactctca tgtactcata cttctggcac ttggccttat gttattgcta   80400
ttgagataca tgcttgtgtc cttgatgaga tgctgtggtg tgctcatgat tcgaggtcag   80460
gcccatgcaa atcttggtat tcctagcata gtgctggcat atggtaggtg ttcattcatt   80520
acatgcttgc tgaatggaac ttcattcttc tgtgcctact tgtactttct ttaagagaac   80580
aatgaggctg ggcttctaaa aaaaaatata catttaata tcttccatat attgaaaaaa    80640
atttctttag aggcaaggtc ttgctctaac ccaggctgga gtgcggtggc actatcatgg   80700
ctcgctgcag cctcaacccc cctgggctca gcaatcctc ttgcctcagc cgcctgagta    80760
tctgggaata caggcatgta ccaccacacc tggccaattt ttaaattttt tgtaagataa   80820
ggtctttaca aaaggctttt tgttggctta ggcttatttt ttaataccta gtgtgcattc   80880
agtaaatatg tattgagtga atagatcgtg gtagggccag aagagactca cttaaaggat   80940
ttagctctaa ggtatctggt tttattgaag atgggctatc aggaaccaag ctctaggttg   81000
ttcagaagag attctaggca gcatattgga aagcagttca gaattaaaag ctgtatgaca   81060
gcaacattgt ctgccttcag cattctatgc aggtgtgtcc aggtcagttg ggaacaaagt   81120
cacttcacat ctatttagct agtatttact gagcacctgt gttgacatcg ggctaggcac   81180
```

```
tatctttgta atctctaacg caagtctgta gagcaatgta cttatttaaa aattcatttg    81240
tcaggctggg tgtggtggct catgcctgta atcccagcac tttgagaggc cgaggcgggt    81300
ggatcacttg aggtcaggag tttgagactg acctggccaa catggtgaaa ccccttccct    81360
actaaaaata caaaaaatta gccgggtgtg ttggcgggcg cctgtaatcc cagctactca    81420
ggaggctgag gcaggagaat cgcttgaacc tgggaggtgg aggttgcggt gagcggagat    81480
cctgccattg cactccagcc tgggcaacaa gagtgaaact ccatctcaaa aaaaaaaaa     81540
aaaagtaata tacaaacact tgttgacaaa taaatttata tttatttatt tatttattta    81600
gtttttgaaa tggagtcttg ctctgttgcc caggctggag tgcactgtgt gatctcagtt    81660
cactgcaatc tccgcctcct gagttcaagc aattctcctg cctcagtctc ccgagtagct    81720
gggattgcag gcatgcgcca ccacgtctgg ctaattttgt attttttagta gagacaagat   81780
ttctctatgt tggtcaggct ggtctcgaac tcctgacctc aggtgatccg cctgcgtcag    81840
cctccaaaag tgctgagatt acaggtgtaa gctaccatgc ccggcctgat tttgttttta    81900
atgatgacaa ccactctgta tggcagagtg agacatctga tagacttctg ttacaatttt    81960
cgaagaaagt aagtggaaac taataatgca gatatttttc atttgatccc tgagtggagt    82020
tcctagaatg ctgcatcctt tagtagccac atacccagtc cttcttaccc tccctgtcta    82080
tcaaaataac actcctagtc attgctgcct tttgaggtgt tgtggaggct ctcgtaacct    82140
gaaaggttgt tcttttcatc tcacgccctt atttatattc ttgaggcttg gcaagtcagc    82200
cagcactggg ttttttaaagt gtcattaagt atatgatttg accacagagc aagggtggag    82260
attttatcta ctccaaagta tttcaaatga gtgagtccag attatttagt gagactcttc    82320
tacttctcca ataataatgc catcttattt gaataaagca gttattcaaa gcctctttta    82380
gatactagac ttaagaatct gctgaaatct aaggagctat tcctgagaaa aatgcacata    82440
aataattttg catataaact cagactattt gtggatctgc ttcagaatat ctggtacaga    82500
gaattacccct tcaaagtgtt actgtacaca ctttgaatag ttgaagcctt cgtaggtttt    82560
taaaattttg ttatatggca aatttctttt cactggtatt tgttatagtg aatatattc     82620
ctgtgttcct ccttactgat ttaaccttta aaaatatttt tctggggccg ggcgcagtgg    82680
ctcacacctg taatcccagc actttgggag gctgaggcag gtggatcacg agatgaggag    82740
tttgagacta gcctggccaa catggagaaa ccccatctct actaaaaata caaaacttag    82800
ctgggcgcgg tggcacacac gtgtaatccc agctactcgg gaggctgagt caggagaatc    82860
acttgaaccc gggaggcgga ggttgtagtg agctgagatc acaccattgc actctagctt    82920
gggcaaccaa gcgagactct atctaaaata aaaataaaaa ataaaaaaaa ttaaattttt    82980
ttctgttcct aaagcaacat tcagaagtga aactactggt ttgtatacag ttttttttt     83040
tacatttgct atctttggga ttgtttgatt tattaagtac ctactcagta gttgaaaaca    83100
ctgtcagata tattacataa ttttcattca ctgtagtaat tatatggtat aaatacagtt    83160
gtccctcggt atcttcaggg gattggttcc aggacccttg tgtatacccca aattcataca   83220
tactcaagtc ccaaagtcca ccctgtggaa ccagcatata tggaaagtca gctctctgta    83280
ttcaccggat gtgaaacatc acatctcaca aatacagtat ttatttcttt atttctcaca    83340
agcttttttcc tctttaagga gcaggcagac ctgtattttt tattgctttt ggtataagtg    83400
gatctgtgca attcaaagct gtttccttca agggtcaact gcagtagtat tcccgtctta    83460
taaataaaga cactgaggc tgagaggtta agcaagctgg ctaagataat actaataggt     83520
aataggtcaa gattggaacc cagatcgtcc cctcccacag tctgtggtct tttcagaaac    83580
```

```
taattttcat taaaaaaaaa aatacagata tctgtcttat catagcaaag ttcaccttta   83640
ataataacaa aacacaaaat atatacacac aaacataact ttaaagaaaa ttacgatgaa   83700
agagaaactg ccaggcacag tggctcacgc atgtaatccc agcattttgg gaggctgagg   83760
cgggcggatc acgaggtcag gagttcgaga ccagcctggt caacatgctg aaaccctgtc   83820
tctactaaga atacaaaaat tagccaggcg tggtgactcg tgcctgtaat cccagctact   83880
cgggaggctg aggcaggaga atcacttgag tccgggggt gtaggttgca gtgagccgag    83940
atcgtgccat tgcactccag cctgggtgac aagaacaaga ctccgtctca aaaaaaaaaa   84000
aaaaaaagtt aagatgaaag agaaactata cctaatgtcc tgctaattct ggcaaatcaa   84060
actaggaatt ttaccacatt tcttcacaac tcaatattaa acagaagcca tggtggtatg    84120
aagggagaaa agctgctatg aaagaaggaa cagaaaagtt tagggaggta gctattagga    84180
taagtgtata tgttagagtg tgggactcaa acctgactga ttcctggctt tggctccaaa    84240
aagtctctta aaaatccatt tgttataggt aagtgttaac agcaaaacct cactggagaa    84300
aaatagtgga ctcgtgactt cttcctttat ttggttacag ggagacatgt gacctttgtc    84360
atccacccta tcacgtttgt gttgagcagt atgggttgtg ggaaagagct caagaatgct    84420
tggaattaac ctaaactcct agaaaaggaa ctgaaaatat aggagaaaag ggtgaagaaa    84480
agaggaaagg aaatggaggt ctgtattgaa ccctgggtag caactcttga gcgaagaaag    84540
aggaaaaagg ggaaagaggg gagctaaatt atctctgagg caactcagtc tcatggttgc    84600
ctgaactagt ctatactgcg ggaataaggt agacgccact ggtttctttg aagtaccagt    84660
gcgcttcttg ctttctattc ctggtcacag acaaatttat cagtagtgca gtttcttctt    84720
tttaagcttc atttaaataa ttattagtag cacttggacc ttaggttagg aaatcactgt    84780
ttaatgactt aaagattaac cggcatggaa atcccattct ttatatgatt ggggagagtt    84840
attgaacttg agattgtttt actttgtagc aatgtctaaa ggcagatttg ttttgttttg    84900
ttttgttttt gaggcggggt ttcgctcttg ttgcccaggc tggagtgcaa tggtgcaatc    84960
ttgtctcacc cgcaacctct gcctcccagg ttgaagtagc agggattaca ggcatgtgcc    85020
accacgccca gctaattttc tatttttagt agagacgtgg tttctccata ttgatcaggc    85080
tggtctcaaa ctcctgacct caggtgagcc acccacctcg gcctcccaaa gtgctgggat    85140
tacaggtgtc agccaccgca cctggcctaa aggcagattt ttaaaggtgg aacataatgc    85200
aagtctgcct ttcttaggat gatctaagtt acatgttaat aaagttcttg gagatctagc    85260
atagaatgca ttcagcactg taaatcacaa cttaatgttt gcctcgatat gctctgttgc    85320
tctgagcaag ttgtgtgggc tgttatctcc tgagaaatcc ctgtaaatgg tattagtaat    85380
actttataag caggttggga gaatatagtt ttctaaggca ttttgaaatt cttagatgaa    85440
agggtcttta tgtagcaaat tggtgtcagc ctattttcct tcctctgagc cagaagaaaa    85500
taggcaccat agggtgggaa gggttggctt atctgttaga gttcttttgt aagtagcttt    85560
tgttgaattt ttttttgag atggagtctc gctctgtcgc ccaggctgga gtgcagtggc    85620
gcgatcttgg ctcactgcaa gctccgtctc ctgggttcag gctagtctcc tgcctcagcc    85680
tccagagtag ctgggactac aggcgcctgc aaccacgccc ggctaatttt ttgtattttt    85740
agtagagacg gggtttcacc gtgttagcca ggacggtctt gatctcctga cctcgtgatc    85800
cgcccgcctc agcctcccaa agtgctggga ttacaggcgt gagccaccgt gcccggctgc    85860
ttttgttgaa tttaaagtgg atgtgagaag ctcctaagaa tatcgttcac tgtaaaagca    85920
```

```
gactttttg   gatttgggtc   ttggaattct   taactgtatt   ttcacctaag   atttaaaaca    85980
agttcaaata  ctagtttgta   attggccaga   ctagggacag   atacgatcct   tgaatgatcc    86040
tgggtctcaa  cttacctttc   tttcattttt   cctttatttt   agaagaggga   taagaacttt    86100
ttctgaagag  cagtcaactt   ttcctttcag   tgtgtaggat   taattccacg   aatctgtgaa    86160
cttaaatctt  tgctgccaaa   taacttgcag   tagatgctgg   gatagtttta   aatctatttt    86220
aagttataca  ttcagtacat   aagtgcatct   ccgtgtaaaa   acagctatgt   ttggaagatc    86280
taaaacgcag  cttttgtttt   tgagaagcca   acaatctaat   agggtaggat   catatatatg    86340
tacaactaac  cgtaatgcat   ggtgttttga   aaaatgcacg   tatctccctg   aattacccct    86400
agttaataaa  ataattggga   gcaaatggta   atataaggat   tttggagtaa   cttaatacta    86460
ctagattttg  ctgtttatac   atttacaaaa   aactttctgc   taatgctaaa   gaaatagaac    86520
aagtctatat  gcataaagga   aggtagggct   aatttacttc   ctggtgctat   gaaactggca    86580
attggacagg  tgcaattgtg   ggtgtctttt   tttttttaag   gtgtacctgt   tgcaggtttg    86640
aaaagctgtt  gatgctcatg   ggttgtttgt   gtgcatgttc   tctttaaaaa   ccagatgtat    86700
tcattccctt  tttttttttt   tttttttttg   agacggagtc   tcgctctata   gcccaggctg    86760
gagtgcagtg  gcccgatctc   ggctcactgc   aaactccgcc   tcctgggttc   acgccattct    86820
tctgcctcag  cctaccgagt   agctgggact   ataggcgcct   gccaccgcgc   ccggctaatt    86880
ttttgtagtt  ttagtagaga   cggggtttca   ccgggttagc   caagatggtc   tcgatctcct    86940
gacctcgtga  tccgcccgcc   tcggcctccc   aaagtgctgg   gattgcaggc   gtgagccacc    87000
gcgcccggcc  attcccattg   ttatgtatac   tttgctattt   gctgctggtg   agacagataa    87060
ggagtcacgt  ctttaactgc   acttgagttt   ccagtgaccc   cattaaatcc   aatgggtaaa    87120
ttttcccacg  cagattactc   acccagttta   cagattaagc   tttcatatcc   ttagactgta    87180
tctgaaattt  tcatagcttt   gcccaccttt   tagggttcag   agttactacc   cattcagtgt    87240
cggtggcctt  tagctgttgg   caagcttcca   agtaaatagc   tcttttgcag   agatctctac    87300
ccattctatt  cttccactcc   tgggtagtgg   agaaccaaag   ttcacctgag   taatgcccgt    87360
gcccagcacc  cagtttcctg   caggggttag   cacggatatt   ggaggctccc   ccgatcccac    87420
agatactcag  gatgggtatt   ggaggggggct  tggttttttaa  gaggacatgt   gaaagtaatt    87480
aacccgattt  acatttgtat   aatgagtcca   acaccacct    tgcaaaagaa   ctgagagttt    87540
agcctgctta  atggagtttc   tgcttttcac   ggtccttggc   cttaccgacg   gtttacagtc    87600
cagccagatt  tagttcacaa   aaaaccaaaa   ccaggtcgac   ctcactgcag   tatatgatgg    87660
cagcgagcgt  tttaaagcgc   aggacctta    gtctcctcaa   tagttttgtg   taaagttgtc    87720
caaaagtgtt  tttttttaaa   gtgaggtgat   ccagtcggta   aacgctttga   aaagaatag    87780
ctgtcccctg  agcgggcatt   agtcgcgtgt   gaggtcaggg   cccatcattg   cgcgtgttgg    87840
gagcgccgcg  ctggtctatg   agcgagcgcc   tcggcttgtg   gctgggccgg   gccggggcgg    87900
ggctgtcttc  ccgcggagcg   tgctgggggc   gggtcgcgcc   gggccgggcc   gctagtgcgc    87960
atgggcgggc  gtcctcggct   ctaactgccg   ccactttcca   cacgctggga   gggccgttac    88020
ctcagagata  cccgtggccg   gcatgttggt   tgaaaaagct   tcccggaagg   gagacgaaga    88080
gaaaggagag  gagcagctcg   tgatcatccc   cggtagcgag   tacgcggcga   agtaggcggc    88140
ggcggaggga  gcgctgatga   agatggatgt   gtcagtgagg   gccgcgggct   gctccgacga    88200
cctcagctct  ggggaggccg   acgtagaccc   aaagctcctg   gagctcaccg   ctgacgagga    88260
gaagtgccgc  agcatccgca   ggcagtaccg   gcagctcatg   tactgcgtgc   ggcagaaccg    88320
```

```
ggaggacatc gtgagctcgg cgaacaactc cttaaccgag gctctggagg aagccaacgt   88380
cctctttgat ggcgtgagcc gaaccagaga agcagccctc gacgcccggt ttcttgttat   88440
ggcttctgat ttgggtaaag aaaaggcaaa gcagttaaac tcagatatga acttctttaa   88500
tcagttagca ttttgtgact ttctgtttct gttcgtgggt ctgaattgga tggaaggcga   88560
tcctgacaag ttgagtgatt gtgatgatag catagctctt tccttctgga aggcaataga   88620
aaaggaagca acatcctgga tggtaaaagc tgagacattc cattttgttt ttggttcatt   88680
caagctagaa cgttctgcac caaagccccg acttgaacac cagaaaaaag ttcgcaagat   88740
ggaagaaaat ggcaacatgc ctacaaagtt gcagaagttg gacctgagta gttatccaga   88800
agcgacagaa aaaacgtag aaaggatttt gggattgttg caaacctact ttcgaaagta   88860
tcctgatact cctgtgtcct attttgagtt tgtgattgat ccaaactctt tttctcgtac   88920
tgtggagaat atattttatg tttctttat tgtaagagat ggttttgcaa gaataaggct   88980
tgatgaagac aggctgccaa tattagagcc gatgaatgtt aaccaaatgg gtgagggaaa   89040
tgattccagt tgccatggca ggaaacaggg agttatatct ttgactttac aggagtggaa   89100
aaacattgtg gcagcttttg aaatttctga ggctatgatt acatactcct catactaaag   89160
atttcttagt atagcatcct ttttgtgttt tttttctgaa gttagatgga gagtaaaatg   89220
taaactgaag cacatattgt atctcttgta aagtgaaaaa gtattttcaa gaacatcaga   89280
cattgtttta ctgtgcagca tattttcctt agtaatttat aaggtcatga tcttctgtta   89340
ttaaaacaaa ttcactggca tatttatggg aacgttttat tgaatgccct ttaagactat   89400
taataaaaac aagttttgga taccaaatta agggatattt gataatttgc aaaacataat   89460
aatttacgaa aatcagtgat gatgctctgt gatgcgttgc tttctctgtc atagggaacc   89520
aagagaatcc cagaaagggt tcctaaccag gttgggcaaa gagtgggtaa aaaacaaaag   89580
ttaaaaaaaa aaacctgtct gtaaggcagt gaatatgcaa cattaagact aaaaaagtca   89640
ttgcaaggaa gacttaggat ttatgagtga gtatccatat tctaaacaat ttctgttatt   89700
gtactcagca aaagtagtgt ctctgctgta gtagttgagg tatcagctaa gggtgaaagg   89760
tgagtagaaa cacgaagaag gaaaaggcat tctaggcaag agaatagcaa ggtcaaatgc   89820
atggaattgt tagaagttag gcacgagagg accattagat ttatggaaaa actattatat   89880
ttgataagct gggcaacaat tgaataactt catctattaa tatcctgaga agatgttttt   89940
gtcaaactat tatacattga acacaagatc ttgctatcca gttgtagttt ttatctactg   90000
aatttcttct ctggccccta gtgtcccttt gtggtctttg ctagtacata gaatgtcctt   90060
cacaatctac gcttttcat catgtaacaa ctttgaatat ttgtcccact ttaattttgc   90120
atttctatct ttttttttcc ccctcgagac agagtatcac tcttgcccag gctgggtgc   90180 agtggtgcaa tctcggccca ctgcaacctc tgcctgcggg gttcaggcga ttcttgtgcc   90240
tcagcctccc aagtagccgg gattacaggt gtgtgccatc acaccagca aatacttgta   90300 tttttagtag gaacagagtt tcgccatggt agccaggctg gtctcgaaca cctggcccca   90360
agtgatccac ccgcctcggc ctccggaaat gctgggatta caagtgtgag ccaaattttg   90420
catttcttaa tagggctttta aatgccagga aactgacctt gctgaaacta aaacatgtta   90480
gtttatctgg atgttcttca cttagtgtaa agccataaag gcttttttct ttccgttgca   90540
taaattacaa ccttatttgg agattattgc caaaagtttg ggtcattaag aaagtaactt   90600
gagaaggtgc agtaagcata cccataagct ttcttcccct tgatccctat aggagcttaa   90660
```

```
tttttggtag tcgtggaatt ttgccattaa acaatacttt ggcaaatgtt taggtatctg    90720
ttatgcatag cagtggcaaa ctttcctagt aagtctagtg gtacaggaaa gggaaatcca    90780
aagactcaac aaatgacacc aagactgaga ggaaggattt ttcatgtatg gagatgaggt    90840
tcttcaccaa taatagagta gaggttttag caaaaataga actttctcat gaaacttggc    90900
aaattatttt ctaaattagt tactcctttc acatatgaaa gagcgctgac ccttgctagt    90960
gtctagtatc ctttgattta tagtagcagt catggaagca ccatttgatc tcactcatcc    91020
tcatttccag catgtctcta ccaaccaagt tccttgggtt ttgcagagat ctgctgttgg    91080 aagaaaagt actcttaatg acagcaaaaa gatcccgccc cagtacttta ctgacattca    91140
gttgctctgt tgaatgtctc atgtctttac taggagtatt tgacagtgat gatttaaaag    91200
cattaataga gaatctggag gcttaggaga ggtaatttt ttggtcttct ctaaagttaa    91260
tagctgttaa aatataaagt tgaccacttc tgtttctatt tttactggtt ggcatgacac    91320
caaccagtaa aatgatgagg atgatggatt gcctcatcat ttttgaaatt ttgaaattaa    91380
actgactgct taccttgaag aaaaaaggag attaaaaatt tatagaggtt aagaatcaaa    91440
ctgcaaatct gcttgtttct tgctaatacg tttgtatact gaatagaaat aacattatgc    91500
tagtctgtct atatactgga tcaagatttg ttaggaagag ggcatttcaa aatagtggag    91560
attgacgcag ggaagctcag cggaggacac cagtgtaaat acattccagc acttcttgac    91620
ttagttccag gcaatttccc ttcttcagga gatggagaat tagtaactta aagggattaa    91680
ttcctaccag ccactatgct aacatgcatt atctttctta aactcagcca tttgatgagg    91740
tcaggaacct gttagcttcg ttaaggatta ggtgattggt cgaagtcacc tggccttgtg    91800
agtggtagag caagtatttt aacgcaggtt atttctgcat cagagccatc tataatggta    91860
ggggaaataa aagtacaaat ctggcaaagg atagaaacta tgtttagggg aaaagtcagg    91920
attgcttatt ccaattttaa aagactgcca cagttgaatt gctttctgtt ttgtgcccctt    91980 tttggggag cctggagcag tgttttacta ggagtgggtc tggggaaagg gattactatg    92040
acaggcaggt ggatgaaaag gaaggctatc taatgtgtaa gccttgccaa caagtgacag    92100
ttgcctgcag gtcatctcat attctatagc attggttctc aaagtgtatg aggccctttt    92160
ggcatacttt aaggtcagaa ttatttttcat aatagtaaga tgctgtttgc ccttttcttt    92220
cttttttttt tttttgagat ggagtctcac tctgtagccc aggctggagt gcagtggcat    92280
gatcttggct cactgtgagc tccgcctccc gggttcacgc cattctcctg cctcagcctc    92340
tcgagtagct gggactacag gcgcctgcca ccacgcccag ctaatttttt tatatttgtag    92400 tagagacggg gtttcaccgt gttagccagg atggtctcga tctccagacc tcatgatcca    92460
cccgccttgg cctctcaaag tgctgggatt acaggcgtga gccaccacgc ctcgctgccc    92520
ttttcactct taattctctt gcatgtaaac tgtgaagttt tccagaggtt atatgacagg    92580
tgatgtggca acagattgaa tggagaaaca gatatgagct gtcttttgtt gtcagacatt    92640
aaagagaatc gcaaagatac aaaacagtgc cattcttcta attaaaaaat ttttttaaaat    92700 aaaaatacgt taacatttaa taaatatatt attttttaatt tgttaatgaa tattttaagt    92760
ttcttcttag ttttaatttc taatatagta aatagataaa acccacatta acaagctctt    92820
tggagtctca attttaaagc tctgtttaag attgtaaagg agtcctgaga tgaaagagtt    92880
tgagaacctc tgtagcagcc accacagtca gcggacataa tttcaagcag ttgtagttgg    92940
aggaggatgg gggaattttt ctccttttcct tatcccatct ctgtgctacc ttctactgtt    93000
tggggcagct gttttctact gtctgtctta tttatatttc aggtgaagta ccacttaaat    93060
```

-continued

```
ggaactgaat gatagcactt tcaattttaa gtttggttaa aattttaaaa acaatgtttc    93120
tttttttttt ttttttttgag acggagtctt gctctgtcac ccaggctgga gtgcagtgcc    93180
atgatcttgg ctcactgcaa tctccgcctc ctgggttcaa gcagttctcc tgcctcagcc    93240
tcccgaatag ctgggactac aggtgcacgc ctccacgccc ggctaatttt ttttgtattt    93300
tggtagagac ggggtttcac cgtgttgccc aggctgattg tgaactcctg agctcaggca    93360
gccctcccgc ttcggcctcc caaagtgctg gattacagg catgagccac ctcactcagt    93420
ctcataatgt ttcattctaa ggtcaactga atgcttcaat tgcctgtgtc ttgccaattg    93480
gtaaatttta cctacagtgc ttaaaaatgg tgaggttcat tcagagcttt tttggtaaaa    93540
tctgtgcact ggttgataca atttgacttg aagcttgaac caggagaagc caggttacat    93600
acagaatttc agtaaggaac ggattgtaaa cattggtgaa gggaatatgt gacttttcag    93660
catgaggata cattttctgg tatttgttct agtaggtatg ttggaggagg gggattccta    93720
gaaccatggt tttcatttag acagccagtt attgtgttct gtcaccatct ttgctaatttt    93780 catgcagata aaatgaggtt gagataaaaa atgattgtat gttattttc cagcagaaca    93840 tctaactgga tttattagtt aactcttaaa ccaggaagtc atgctctttg agacccagta    93900
gggagtcaca ctagttactt gaagcataat tgatcctttg atcgaatggc tattattacc    93960
aaattgtttt tcccccacag tgctttgtat tgaaggagga accttggcca taatgccagt    94020
tgatgactac tggctgtgtt taccagcctc ttgtgctaga ccttttgtgc agactgtcag    94080
agtggtgcag tcttgccccc actgttgctg gtttccaggt gttctcccctt cagtccctga    94140 gccactacgt atgcccgcca tgctgccaac aggtagccac agtgctgtgc ttcctccttc    94200
acattgctcc accgcacccc cttccacatc ccaagaacct tcttcttccg ctgaccccaa    94260
gctctgcctt tcaccccctca catctgatag taggcaagag agaaatgtgc agtttgggct    94320
ggtaagtttg ggggctttt tttgttatta aagttaaggc ttttgtttg tttgttttt    94380 aaaatgagat ggagtctcac tctgtgagac tcccaggctg gagtgcagtg gcgcaatctt    94440
ggctcactgc aacgtctgcc tcccgggttc aagcgcttct cctgcctcag cctccggagt    94500
agctgagatt acaggcaccc gccactacac ctggctaatt tttgtatttt tagtagagac    94560
agggttcacc ccgttggcca ggctgatctc aaactcctga cttcaagtga tcctcccgcc    94620
ttggcctccc gaagtgctgg gattacaggc gtgagccact gtgcctggcc tacttgattt    94680
tttgaaaaca ttttattgtg cttgttaaca actttctcag tcattatctc ttgttaacat    94740 agattttat tttagtaagc gataatatta aatatatcac caaaatattg tatgaaacga    94800
atatgaaata taattaatgt gtatcagaat tatattagtg gaatgaaatg attttttaaa    94860
aattaagtct aacacctaaa ttataaaagt ctgttacttg ctaagtatat ggaaagtaaa    94920
tattaaatat gggagacttc atgcatatgc aaattaaagg aatgagcttt gcagagttgt    94980
gcctatttaa aatatcctac aaaagcagca acttcacgt ttaacttttc atgcaggtca    95040
gtatcaattg acagttttgt tctgaatttt tagatgttat gccccagcca aacagtatag    95100
aaatgtctta aataaatatt tggctggtct tttaaaattg ttatattgag attaagctat    95160
gcccatattt accaagcccc tatctttaaa acctagttta aaaattctag gaaaaaaagg    95220
ctaatgatta aacctgattt agacctaagt tggtttactt atgtagaggt actatacgaa    95280
cacttcaaag tagttagcag tgaccgtctt tggggttaat aaactaagat aaagcaagca    95340
gttcacaact ttaaggaagg ttgaatattt ccatctgtat gctgtaatta aacagcatct    95400
```

```
tcccttttgaa aattccttttt gttttctttt aagaaaagat tttcttacaa agcttttttgg    95460 acattgctga ttttaagtta aattatttc tcttctgtta ttttcttta ggcttatcag         95520 gagggcagac ttcaaaagct actaaaaatg aacggccctg aagatcttcc caagtcctat       95580
gactatgacc ttatcatcat tggaggtggc tcaggaggtc tggcagctgc taaggcaagg       95640
ctccttgtgt tgtctgttgt ctgttgtctg ggtggtgatt agaatattaa catccctgac       95700
agggttctct cctctctctg tggaatttat ttgatccact cctgtgacat tttgcacatt       95760
aacttgggca ggacatggac atcgtaaggg accactttat aaatcatttt tccagattaa      95820
aatatacatt ccttatatta aagtataggg cccagtattt tggaacacgt ttccgttcac      95880
tttaagttta attgattttt cagagataat aagggtgttg tgcctggtgt ggtgactcac      95940
gcctgtaatc ccagcacttt gggagtccga ggtgggcgga tcacctgagg tcaggagttc      96000
aagaccagcc tggccaatgt ggtgaaactc catctctact aaaaatacaa aaattagcca      96060
ggcgtggtgg tgggcacctg taatcccagt tacttgggag gctgaggcag gagaatggct      96120
tgaaccttgg aggccgagtt tgcagtgagc tgagatcgca ccattgcact ccagcctggt      96180
caacaggagc aaaactctgt ctttaaaaaa tatatatata tatgtgtata tatatgtata      96240
tatacacaca tatatatggg tattgtgtgg aaatggtctg aaattaagca aatatatttc      96300
ttagttaata tttcttagtt aatatttgtc tttttcactt gaatgatttc cctgttcata      96360 acccttctc tccaatataa aaaagatgg ggagcaattg ggtttcttaa acccatttat        96420
taaaaatgat ttgcttttg tatatgtgag gttatctaat aaccactaac tctgtggtct       96480
gagggtgatt gggaagagga tgtataaata aagaaggtta ggagtgaggc tcctggttct     96540
gaatcaagat aaatttccca tgtgaggacc ccttgggcct gtcatcctta cccaacaggt     96600 tccttttaaaa gatgaagtgg ttataattcc ctaaggtata gcttgtgctg aatcagtaat     96660
gggtagaagc tgcccaaata ctgcagacca gtatgtagca tgaagcaatg ctttactgaa     96720
agtaattgag gaataatacc tgatgtattt tactccagtg gtggtgtgtt tgaaagacgt     96780
gtagactcag tcctttcaaa taacctttgg aggtctagtt gccaatattc aaagcttatt     96840
ctctgagaat gataaaagat attctgcaaa acaaacttct aactcttgtt tccctcccta     96900
aaaatatatt tggaaatatc atagatgttg tcaactttt catgagcgcc tcatgtgaaa     96960
attttaggaa atcttgtaat acagaagaaa aacttcttca gtattctgcc ttagaaacca     97020
aattagatta aactttaaaa tgatttttaa aatatcacct tataggatac aggttgcatt     97080
aagggctgta gactatcagt aaacctgctt tttcagctac ttggcaactt gcttggaaat     97140
ggccactttc tttttcagg ttattgctga atctgttatt gtttgagtgg aattatgtga      97200
gagaagtcta aggttccag ctgattctaa caatttact actctattct gcataatttt        97260
aaaatctact ctcagaacta tctgaatatc tgttaatttt tatcctggag tttaactaat     97320
catcatggtg tgtgaagtac ccaggtatta attattcgtt atgctttaag ctctatagct     97380
taaaaaaaaa tcatggattt ttaacagccc atttccaatc tgtcatgtta acctttccaa     97440
ctcactttaa taattttatt ttccaggagg cagcccaata tggcaagaag gtgatggtcc     97500
tggactttgt cactcccacc cctcttggaa ctagatgggg taagcttta agatactcta      97560 gaagtgatgt tgccgaagta gttttcccct ggcaataatc taactggttc ctaaagccta     97620
attaaaaaaa tcaaaaacta agttaaagaa aaaacagccc caaaacatat atatctttta     97680
tttgagccaa gttaaaatgg atcaggttaa atgctaaaaa tttaggttct ttggcacaga     97740
gtcaagaagt aagaaccctg tctacaagct atgatttaaa ggtaaatatt tgagtaatct     97800
```

```
agcatatata gggggcttaat aactgaaaat ttaaactttt catatgtgga tttgttttaa   97860
atctacctcc tacattcaac aagagttgga atcagatacc ctactgtata gcccttgctg   97920
cttctgagtc ttgatgaatt atatgttcat aatatttact gaacatttat tatgaaccaa   97980
ggcaatgacg atatagcagt gaactcggca tattcaaagt tcatgccctt gtgaagctta   98040
tattctaagt ggggagacaa aagataccta agaactttag gagttgtggt aagcggtatt   98100
gaaaaaatta atatagtggc atagagagga agtggataaa ggagaattta acttcgagaa   98160
gattatcaag gaagacatct gaagaggtga catttagaag aggccaaaga atgagaatga   98220
gccagctgtc aaaaggtgag gcagaacctt ccaggcagct tctctttctt tgaggatagc   98280
acatacaaag gccctgaggt aggtaaaagt ccttcatggt tgtggcatgg ataatgggag   98340
ctggaggtgg tagtgtgaga tgagaccaga gaggaaggca ggtgtcacta ttgagggctt   98400
tgtaggccaa gatgaggaat ttggactaat caaagcatat aatttggact aaattggact   98460
aatcagagca tataaatgag cctttgaaga ctcaaggca ggggagccat gtgataatat   98520
aagatttttt aaagattact tggctgcttg cattagaagg aaccaagaag caggaagtcc   98580
agataaggcg atgtcacaat ttctgattca tccattcagc agatatttaa tgtgtcaatc   98640
tgtgtcagac actgctcttg gtactaggta tatcccttct gacctgtgga gcatatactc   98700
cagagtgaca actggtagta ttctactcag aggacttact ttgagctgtg aagtctgttg   98760
ccatctttca ctcttatgtc attttggtca cctgcctgtg ttttgttcta atggaaacaa   98820
gctgtcacca tattctttaa gcttagggat actaaaccta tttttaggga gcaagggaag   98880
tcatgcatcc tttaaaaaac caagtgaatg ctgtaggcca cctccttaaa aaaatgcaca   98940
tatacaccaa aattttttc ttttttttt tttttttttt tgagatggag tctcgctctg   99000
tcgcccggc tggagtgcag tggcgctatc tcggctcact gcaacctcca cctcctgggt   99060
acaagcagtt ctcctgcctc agcctcctta gtagctggga ttacagacac gtaccaccat   99120
gcccagctaa ttttctgtgc ttttagtaga cagggtttt caccgttttg gccaggctgg   99180
tctcgaactc ctgacctcaa atgatccacc cgcctcggcc tcccaaagtg ctgggattac   99240
aggcgtgagc caccacgccc agccaatata caccaaattt tatatgcagt ttaagaccca   99300
ctgcactcta atcatcccca gcatagcaac ccctttatca gttacctctg catagattca   99360
atggcaagtg cagatgctgc ttgaattaca atggggact acatcctgat aaaatccttt   99420
gtaagttgaa acaagtcaa aaatgcattt aatacaccta acctcccgaa catcatagct   99480
tagcctggtc taccttaaac atgctccgaa aacttacatt aacctacagt tgggcaaaat   99540
catctaacac aaagcctatt ttataataaa gtgttgaata tctcatataa tttactgaat   99600
actgaactga aagtgaaaca cagtatgggt gtatgggtat caacataaag agaaaaatcg   99660
taagtcgggt cgtctgtata gggttgtgta catagtaaga tttcaatttc tggcatctt   99720
atcagcagtc agttaattt gtatctttga agtatacgga aattgtggaa atctgcccct   99780
cttttttgttt tgttttagga tgatgttacc gtgtttggta tgtaagggtc tctgaactta   99840
tggatgttgt aagagttagg aataaactt attactgacc acattaagca aatataatac   99900
aatatttctt agagttgtaa taattgttga ctttgttctt tgaatgtttg taaggcttgg   99960
aaagcaggtt ataaactgat ttctcaatgt tgttgtaggt ctcggaggaa catgtgtgaa  100020
tgtgggttgc atacctaaaa aactgatgca tcaagcagct ttgttaggac aagccctgca  100080
agactctcga aattatggat ggaaagtcga ggagacaggt atgagaggga aaagctactc  100140
```

```
ttctgtttgt gcttttgggg gtttgagctg caattttgt gatgcgtcgt ccattttcat    100200
gaagatagca aatagcctag ttgtttttat tgtttacatt tttgatggat ataatcactg    100260
gagttatcct ttgtcaagta tttacatagt tgttatggta acaacagata ctgcatttgg    100320
actatggtat ttctgtaata taaaattaga gttcttttga atatattgtc atgtagtatt    100380
tgtgagaaat catacaatgt ttataatttg taaggaagta ctaattgcat ttgctttctt    100440
tcatgttgca tttttctccc tccaaagaag tctgtttcat gagctgatgt ttgtgggggg    100500
tgggggttgt ttgttcagga gggggtggtt aggctttgtt ggattaaaac tatttagagt    100560
accctagaaa ccctagatga gtttaagaga ttggaattgt taattttatt tttatttatt    100620
tatttatttg agacggagtc tcactctgtc gcccaggctg gagtgcagtg gcacgatctc    100680
agctcactgc aagctccgcc tcccgggttc acaccattct cctgcctcag cctcccgagt    100740
agctgggatt acgggcgcct gccaccacgc ctggctaatt ttttgcattt ttagtagagg    100800
tggggtttta ccatgttagc caggatggtc tcgatctcct gacctcatga tccacctgcc    100860
tcagcctccc aaagtgctgg gattacaggt gtgagccacc gtgcctggtg gaattgttaa    100920
ttttagaaag tagattgcat tatttagtag aagaataaaa tgagatctgg catagcttcc    100980
tggctaattt atgacatatg tcactctgtt gtgaagagtg aaactccaac ccctatgtga    101040
tttgaggttt gagacctatg cattatggag catttgaggg aaaatattcc agccagtagc    101100
caggataaac attttgtggc ttttttgggg ttttaattgt ttattaaatg taaagataag    101160
gcataaatgt atacttggaa aaattttgct ctcactcaaa ctagttatgc ttctcttgtt    101220
gatgctttta cttcctactt aaaataatag tacctttcc aagtctggaa tcttagaaaa    101280
tcactaactt ttaaagtttt ataatgttgg ggtcacattg tttgctcaga cccttaagag    101340
agagagggat ataggaggaa attttgtaaa acattgataa ttactgcagc ttagatgatt    101400
agcacatgtg ggtgagctat atactattct attccactcc tagcagagaa acagcaagtc    101460
ctgagccttt tgtagtggtg gtagacagag gccaggcagg gaggttagtc caagcttcct    101520
gcagccttcc ctacccacaa gctacctggt cctctagaac cataaccgca gtggcatctg    101580
cagttacttt tttttttttt tttttttca gttgaaccaa tttcttaagg tttgctctaa    101640
ttctaacatt atgatcatat gaattcaata tccatgatct atctgttctc ttagaggcta    101700
taaatcaatt ttttgtgctg tcattcccac ttccagaggc tggccagtaa gtgttataag    101760 cctatttca aaacttactg tatagccagc caggatcatg cctgtaatcc caacagttta    101820
ggaggccaag gggaaaggat cagtttgaga ccagaagttc gagactacct tggacaacaa    101880
agcaagagcc tgtctctaca aagaataatt agtcgggcct ggaagccctc tcctatagtc    101940
ccagcttctc aggaggctga agcagggga taatttgagc ccaggagttc aaggctgcag    102000
tgagctgtga ttgattgcac cactgcactc cagcctgggc aacagagtga ccctgtct     102060 ctaaagaaga gattattgag gctgggtgca atgactcatg cctgtaatcc cagcactttg    102120
ggaggctgaa gtcggcagag cacttgaggt cgggagtttg agaccagcct ggccaacatg    102180
gcaaaactgc gtctctacta aaaatataaa caattagctg gcatgatgg cccacacttg    102240 tagtcccagc tactcttgag gctgaggcac gagaatagct tgaaccctgg ttgagggt     102300 acggaggttg cagtgagccc agattgagcc actgcattcc agtctgggca gtctgggcaa    102360
ccaaggggtt gattttatc ctttgaaatt taatattact ttagtgtcct gacttaaagg    102420 attaattaa ttatgacaga atcaaaaaga ataaaaagt tttctctttg ataagatatg    102480
ggagtttgga ggaaatgtga taagactctt aaaatcctgt ctaaatgaat agtcagtgaa    102540
```

```
tttttttccgt aaaaggccat atggtaaata ttttaggatt cttggggcat agggtctcta 102600
gtagctactt aactctgctt atgtagtgtg aaagtagcac tagaaaatat cgaaataaat 102660
aagcatggct gtattttaat aaagctttat ttacaaaaag ctgatgggct ggattggccc 102720
atggtgcagt ttgccagccc ctgacataaa cactgttact agtgtagtaa ctccatactc 102780
ggctacatca gaatctcttg gattttctta caaacacaga atcctaagcc ttaatatatc 102840
ccagaaatca gtaaaattca agttcgtttc tagataaaga aggaaaaagt ttgtgtattg 102900
ttattttagt ttaaaattgt cagggatct gtcttgtatt atttaattgt attagtctta 102960
taagagaata cttgaagatg aaaaagtggc atatgtgctc aaaatggagg atttgccctt 103020
tcagattgcc ttttagagct ctgctccctg tatttcactt gagtggttat tgagaaatga 103080
tctttgccag cagttgaaaa gccaaacaag attttgtttt attttcttat acagttaagc 103140
atgattggga cagaatgata gaagctgtac agaatcacat tggctctttg aattggggct 103200
accgagtagc tctgcgggag aaaaaagtcg tctatgagaa tgcttatggg caatttattg 103260
gtcctcacag gattaaggta attgtgtgac atcctgacta gctttttttt tttctttttt 103320 ctcttttaa aagctttggt tagaaaatgt taaagtatta taataaaagt aatagccact 103380
gtgacccaga ctatccagtt tggtgatttt gctatcatat catcctatgg ggccttgtgt 103440
ggaggtatgg taaagtgtaa gtatgctgga ccagaccgcc tggttttgag gcttggctcc 103500
agcacttact aacattgtga ctttgagtaa gtctgttaac tactcagtct taatttatcc 103560
tttttactat attattgtcc tcattatgag gatgaaatga gacaatgtag tgaatggcct 103620
ttgttaacta tgaagtttac aattctgagg aatgattact taataaggtt ttcatattgg 103680
ttcctttgta ggcaacaaat aataaaggca aagaaaaaat ttattcagca gagagatttc 103740
tcattgccac tggtgaaaga ccacgttact tgggcatccc tggtgacaaa gaatactgca 103800
tcagcaggta aaggaaaaaa gcagggtgga aaagaaaaac ccattgtgga tattgctttc 103860 gcattttttct tcaaacccac tgcgtcaatt tcttgggctt cagacagatt tctttgccac 103920
attgtgccct ctctggggc aggggtttgg gagaaagaga aaaaggaaaa atgattttaa 103980
aggagaacat tttaaatatt gaaaacttca aacattggtc atcttgctac acagagtatc 104040
actaacatac tagtatagat ttacatttgt attcgaaatt tatttatgca tgtatgagta 104100
tgaaagtatg taataaaacc aaatggatat tcacaaacat tttgtaaaat aggtatgata 104160
catatataca tttagatttt gtaaaatgag gatcatgtat tacccttttaa cacttgcaga 104220 gtggctgcta aaagaattag aggctgtcag gccatttaga tttatcagaa tctagaccct 104280
actcaatgct gtttgaatgg ttgcagtgtc agtgtagaag gacctcctga aacaagtcaa 104340
gcaaggagat gttttgctgt gtggtttatt tttgcccgtc aaatggtaac actgctgaca 104400
ttgttcagga gctttcaatt atgaagtcat taagacagag tgttggtaaa tgtgtcttct 104460
tggatgcttt ttgctcagga gtttctgatt gtgttataaa ttactctact ccttcaggct 104520
ctttttggta tatgctttta tcctttctca catggtggga gagggagagg caggtctctg 104580 gggcctttt tatgaggaca gtagccccat tcatgagtgc tctgccctca tggcctaatc 104640
acctcccaaa agcccaaccc ctaatatcat tgccttgggg tttaggatgt taatgtgtgc 104700
attttgggga tacataaaca ttcagacaat agcaggctcc cttccaatat tttttaaaaa 104760
ctcattctct aacatgcttt tatgatctct gtgtccctag ctcaactaga agactttgt 104820 caggttctac tccttatagt tggctttat attataagat attgaaagtt tttttttttt 104880
```

```
tctgcatcct agtccacatt cttgataata attggtgttt cagctgagga caagcaacac   104940 aggttttcc  acctcagagc tgagtggtgg catgaggatg gaggttaggg tttgcaaatc   105000
tataatttgt tccaaacagt tcaaaatcat ttagtgtgaa gatgaattgg actaactgac   105060
taatatcaga agttacacag tttgctgtgt ttagctatgg gtagcttgag ctactcccaa   105120
agcaactgag tggcaagaaa gggtatctaa gaattataaa aacttctcat gtattatgtg   105180
tgtagctagt agaatgttta tcatcttgaa agtatgttct tgtcaaagta aaaatgtgta   105240
cttggattta gtaattattt atataggaac tttcttttc  ttctttcttc ctttttttt   105300 tttttccccc agtgatgatc ttttctcctt gccttactgc ccgggtaaga ccctggttgt   105360
tggagcatcc tatgtcgctt tggagtgcgc tggatttctt gctggtattg gtttagacgt   105420
cactgttatg gttaggtcca ttcttcttag aggatttgac caggacatgg ccaacaaaat   105480
tggtgaacac atggaagaac atggcatcaa gtttataaga cagttcgtac caattaaagt   105540
aagtgggttt gcctgtaggt ttcttgattc tacattcaca gtaaaaggca aaaagagagt   105600
tgagttggtg gtagaagcat cctttcagca ttataaacca tcaggaatgc tgattcccct   105660
actgttgtat actggtatat aaacttgtac ctccctacca tctaaacacc tatatagctt   105720
tgttcttatt tgtagattaa taatctcttc ctttgtcaac tttctaaatt ttggttttct   105780
tctcttctgt ttaatgcttt cctttatgca ttcctttgtc atctttggtc tcttaatact   105840
ttgtttcttc atatgtacca gagatttaaa taagagttca acactaggcc ccacctgcac   105900
tccctggctc cccacaggac atttccccct ggtatatgat aacataaaca ctacataaac   105960
actacatact tctggcatcc ctgaaagtga ttatctcatt tatttatgtg tgctaacctt   106020
tttcgctctt ttaatctttt gaaaggagct aatactatgc caagtcacac ctgggatttg   106080
ttaccattat cacaaatgtt ttcatatatg agtgacaaaa ttgaacactt agtgtgtgtc   106140
tcagactaat agataatttt ctctagtgca gggaaaatgg tgggactatt ttgttaaagt   106200
taaggaatta tagttgtctt ttttttttt  ttcatctctc agtgggttga cttgagttgt   106260
gtatgtgact atggatctcc taatgctgat agataagaat atgaactttg ggatcagaat   106320
gacctgaatt cagataatat tctgccagtt tcttgctcta tgactttgga agagttacct   106380
ctctgaaccc gtttcttctg taaaatgagg ttgaaaatag catctaacaa ttcttgtgag   106440
gattgcatta gccaacactt ataaagtaat tagaaaagta cctggtagag agtaagttta   106500
aagtgaatca tctcataata ttgttatgaa gattaaggca caaatttcct ggaagctgtc   106560
agtgcttgat tactgtagct gttttttatt tttaccttt  tttttttttt tttttttttt   106620
gagacggagt tttgctttgt cacccaggct ggagtgcagt agcccaatct cagctgactg   106680
caacctctgc ctcccaagtt caagcgattc tggtgcctca gcctcctgag taactgggc   106740 cacaggtgcg tgccaccaca cccggctaat ttttatattt tcagtagaga gggctttcac   106800
catgttggcc aggctggtct tgaactcctg acctcaagtg gtcctcccag tgcagtgtcc   106860
caaagtgctg agattacagg cctgagccac tgcgcctggc ctgtagctgt tttttagagt   106920
agaggtatat atgctatatt tgcattagag ctatgattca taaacaacag ttgtatgtat   106980
atgctgtact gatagaaagt aacatcttcc tatatacaat ttttttttt  taatttattt   107040 ttttattgat aattcttggg tgtttctcac agaggggat  ttggcagggt catgggacaa   107100
tagtggaggg aaggtcagca gataaacaag tgaacaaagg tctctggttt tcctaggcag   107160
aggaccctgc ggccttccgc ggtgtttgtg tccctgatta cttgagatta gggagtggtg   107220
atgactctta acgagcatgc tgccttcaag catctgttta acaaagcaca tcttgcactg   107280
```

```
cccttaatcc atttaaccct gagtggacac agcacatgtt tcagagagca cagggttggg  107340
ggtaaggtca cagatcaaca ggatcccaag gcagaggaat ttttcttagt gcagaacaaa  107400
atgaaaagtc tcccatgtct acttctttct acacagacac ggcaaccatc cgatttctca  107460
atcttttccc cacctttccc gcctttctat tccacaaagc cgccattgtc atcctggccc  107520
gttctcaatg agctgttggg cacacctccc agaaggggtg gtggccgggc agaggggctc  107580
ctcacttccc agtaggggcg gccggggcgg ctggccgggc gggggggctga cccccacct  107640 ccctcccgga cggggcggct ggccgggcag aggggctcct cacttcccag tagggcggc   107700 cgggcagagg cgcccctcac ctcccggacg ggcggctgg  ccgggcgggg ggctgacacc  107760
cccacctccc tcccggacgg ggcggctggc cgggcggggg gctgacaccc ccacctccct  107820
cccagacggg gcggctggcc gggcaggggg gctgaccccc ccacctccct cccggacggg  107880
gcggctggcc gggcgggggg ctgacacccc cacctcctc  ccggacgggg cggctggccg  107940
ggcagagggg ctcctcactt cccagtaggg gcggccgggc agaggcgccc ctcacctccc  108000
ggacggggcg gctggccggg cgggggggct gaccccccc  cacctccctc ccggacgggg  108060
acctatatac aattttttaa catttgggga gttgtggacc cttttgaaaa cctggtggac  108120
tattcctagt aaaatagggt taccagagta tctgattccc acagctgggt attaaactct  108180
tgctgtatta taaagtgacc gaatggaagg aaccttctgt ggagagtggg gagagggtac  108240
attttggaca gagaatgtag tatgtgtaca aaggctctgt ggggagaaat attgttctag  108300
ataccaaaaa ggcctgattg aagtacaaaa gtgaataagg gtggaggtgg gatgaggccc  108360
ttatcatttc caaacaaatc ttaagcaatg gaccaattaa gctcttttcc aaggattaga  108420
acattttgat taaaattaaa caagaaagac ttctccagta tgttcagaga ggctcattta  108480
actatataag aaggaaaggg aattcaggaa ggaaattttt attatttatt gatgtcaaat  108540
aaaataaccc tggatagttt cccaggtggg tttcgttttt ttttttttt  tgagatggag  108600 tcttgctctg tcacctaggt tggagtgcag tggcgtgatc ttggctcact gcaagctccg  108660
cctcccgggt tcacgccatt cttctgcctc agcctcccaa gtagctggga ctacaggcgc  108720
ccgccaccac gcccggctaa ttttttgtatt tttagtagag acggggtttc actatgttgg  108780
tcaggctggt ctcgatctcc tgacctcatg atcctcccgc ctcggcctcc caaagtgctg  108840
ggattacagg cgtgagccac cgcacccgac cccaggtggg tttctaagtc attataccta  108900
gtctgtaggt tgttgttgac atctatttgt agtaggttgg tatatttatt ctcctctgcc  108960
atcactcaag tatcagggct tgctcatttc tttctgcatc cttaacaact gaaaacaccc  109020
cctggttctg ataaacaccc acatctcctt gcccactccg attttttaaga ctttgtaact  109080 gttacccata tcactatgga cctgctgtaa tgtaatctat cctttgttgt caatgaaagc  109140
tgagcatctg tagtcaaaag agaatctctg aatttgggca acagttgccc tccatgggat  109200
taatgattct gggtgaatca caagatagaa acctgggaaa agcagtaagt cattggtttg  109260
attttaggga tggtagtgtg ctttctgtag cttgcttttc cccccatttt ttctctgaat  109320
tttattgttt gagaactctt tcaaagaaag cccctctagc agacaacatt gagcagcgaa  109380
aaagaaggaa ataatcattt atcatcctaa taatgttaag tgagggagat gggacataaa  109440
agacttttca agcacgattt tatattttaa ctttgggtta accagatgga agggaaggt   109500 agagaatcca acttgataaa tgtctttatt tcacagtaaa actttatcac tcttacaggt  109560
tgaacaaatt gaagcaggga caccaggccg actcagagta gtagctcagt ccaccaatag  109620
```

```
tgaggaaatc attgaaggag aatataatac ggtaaggaat gggcccaggt taatacttta    109680
tcagaaagca aataacatgc ttattgggta tcttatagga acttaaaatg gctcttagtg    109740
atttccaaat gtactggttc tatgccaatt cttagacatc tcaataactt atgatattaa    109800
aatttgtttt ggtggccagg tgtgttagct cacgcctgta atcccagcac tttgggaggc    109860
caaggcgggc agatcacgag gtcaagggat cgggaccatc ctggccaacg tggtgaaacc    109920
ccgactctac taaaaataca aaaattagcc gggcgtggtg gcgtgcgcct gtagtcccag    109980
ctattcggga cgttgaggca ggagaatcgc ttgaacccag gagacctagg ttgcagtgag    110040
ccgagattgt gccactgcac tccagcctgg gtgacagagc gagactccat ctcaaaaaaa    110100
aaaaaaaaaa gttgttttgg taaacggatg gcttcagatt ttttccactg taacttaaag    110160
tattattagt caaatggcta tacaaaggca acagaatttt taaatgagcc agaatttctg    110220
tcccgtgttc tttcctttca tctccccacg caaccactta aaaataatt tagttacaga    110280 ctatgatgtc attgtcttta aacttggata ggtttattaa ggcattatga attctctttt    110340
tcctaatcag aagtggaaaa taatttctac tatatcatat atgttcaaag gattttttc    110400 tgaagatttt aatttattta aactcttgca ttactttctt actgaaatat ttatttccaa    110460
gtttgaaaaa tgaaatcaga ttagcttaat aagcagagaa aaatatgatt aggtaataaa    110520
tgcaaagcct ttttgttatt agtcactaat atattaataa ttttttcaggt gatgctggca    110580 ataggaagag atgcttgcac aagaaaaatt ggcttagaaa ccgtaggggt gaagataaat    110640
gaaaagtaag aaaaaaatct ttattatgtc atatttgtgg gatttttttt tttttttttt    110700
ttttgagatg gagtttctct cttgtctccc aggctggagt acaatggcac gatctcggct    110760
cactgcaacc tccgtcccct gggatcaagc cattctcctg cctcagcctc ccatgtagct    110820
gggattacag gcatgcacca ccacacctgg ctaattttg tattttttagt agagatgggg    110880 tttcgccatg ttggtcaggc tggtgtcgaa ctcctgacct caggtgatcc acctgccttg    110940
gcctcccaaa gtgctgggat tacatgtgtg agccactgtg cctggcccat tatgtcatat    111000
ttaatactat ttcagttatt tacagcattg gtcaattata gaattttagt ttttttgttgg    111060 tatgtttgtt tttttgagac agagtctcgc tctgtcaccc aggctggagt gcagtagtgc    111120
aatctcatgt cactgccacc tctgcttcct gtgttcaagt gattcttgtg cctcagcctc    111180
cctggtagct ggattacagg cgcctgccat cacacctata atcatgctgg ccaggctggt    111240
ctccatcttt tggcctctag tgatctaccc acatcagcct cccaaagtgt tgggattaca    111300
ggtgtgagcc actgtgcctg ccgaatttt agattttta aacctaattt ttaccatagt    111360
tgagctcttc aactatgaag aaatgaaact tttcttccag tgccattcac attagtgttt    111420
cctgtttgtt ttcttttatc cattttgagg ggagttataa tttagaatcc tcactcttaa    111480
ccactgtgtt ggagttcttc cattctcaga tttcttagag ttttcttatt tctttgattt    111540
tcagaaccgt ggacagaatt gtcattatct gataagattt tgttccttt gagctgtttt    111600 gttttatttt taacacatta gaacattgcc ctcagctaga gtcacaattt tgggcttccc    111660
tgaaaaaacg gaagattttg ttctccttaa ttaataatgg taattaatga tgattttta    111720 ctgaataaaa ttgcaggact ggaaaaatac ctgtcacaga tgaagaacag accaatgtgc    111780
cttacatcta tgccattggc gatatattgg aggataaggt ggagctcacc ccagttgcaa    111840
tccaggcagg aagattgctg gctcagaggc tctatgcagg ttccactgtc aaggtgagtg    111900
ttgtgcttgt tgcccattag atactgttgt cagtaatact cccagttcct tatttagggg    111960
gcagttggga agtttcgcag atcttgaata atttagttat tttggtgatg gcatcctaga    112020
```

```
tgtcctttat tagttgtatt ccagacaaga tattattaag gctgctgtac attgtgactt  112080
tattatgaag atcgacactc cgccgggcac agtggctcat gcctgtaatc ccaatacttt  112140
gggaggctga ggcaggcaga tcaccaggtc aggagttcaa gaccagcctg gccaacatgg  112200
cgaaacccca tctctactaa aaatacaaaa attagctggg catggtggcg catgcctgta  112260
atcccagcta ctcaggaggc tgaggcagga gaattgcttg aacgggaac tgggaggcag   112320 aggttgcagt gagccaagat tgtgccactc tactcctgcc atggctacag agcgagactc  112380
catctaaaaa aaaaaattaa aaaaaaaaaa aagaaaattg acatcttgga ttcacattat  112440
gaataaaaag agcttgatta atcaagtttt cagcactgtt gttgaatagt gtactttata  112500
tccatatact ctaaacagtt gtattttatg tcaatttcat cattaccagt ataaataaaa  112560
tgttctgagt cttttatgg cacttatcta ggctataaaa ggacttgagg atttaggtaa   112620
tggtgtcagt gtacaaagta gcttaaacca ctattcaggc cttattaccc agtccttaga  112680
aaatatctgt cttagaggcc aggtgcgttg gctcatgcct gtaatcccag cactttggga  112740
ggctgatgca ggcagatcac gaggtcagga gattgagacc attctggcta acatggtgaa  112800
accctgtgtc tactaaaaat acaaaaaatt agccggccgt ggtggtggcg ggcgcctgta  112860
gtcccaccta ctctggaggc tgaggcagga gaatggcctg aacccgggag gcggagcttg  112920
ccgtgagccg agattgcacc actgcactcc agcctgggtg acagagtgag actctgcctc  112980 aaaaaaaaa aaaaaaaaa aggaaaatat ctgttttagg atgttgaata tgttaaatgt    113040
tatattgaat tttaaaatga ttttttaaaa gtcagtatag gatgttaaaa ctcttcagta  113100
tgtttcatgg gactagatgg ccagaaaaga ataaagacag ctgttttta aaaggtttc    113160 cagaaacatt agttgtaaag aattttggca ttacccattt tccttacatt ggtttcagtt  113220
ggttacagta atgggaatct caaaaagtga tgctagcaaa atttgtgacc tggggttatt  113280
tgggatgtag cataataaaa tctcatattt tgaattaatg gattgagggt taaaaaagat  113340
tttgaatgcc agattgactg attattgagg gaatagcagt tggttcgtat tactatttag  113400
aataaattta acaagactac ctctttgaat tacatcttgt atgcattgtt gcagttgttg  113460
agtatctggt acctcaatat agcttgagat tggatgcact taatttattc ttaaattcat  113520
gtctcagtgg tttccttaaa aaaaaaaggc taaaacattg aatggagttg tactttaaag  113580 taagggggtac agctgggcac agtggctcac acctgtaacc cagcacattg ggaggctgag  113640
gcaggaggat cacttgccca ggaattcgaa accagcctgg gcaacatggt gaaaccctat  113700
ctctacaaaa tatacaaaaa atgagatcgg tgaggtggtg cgtgcctcta gtcccagcta  113760
cacagagcgc tgaggtggaa gaatcacccg aacttgggag gtgaaggctg cagtgagctg  113820
tgatcacaca ctgcagtcca gcctgggcat cagagtaaga ccctgtctcc aaaaaaaaaa  113880
ataaataaat aaaataaatt catggatctt tttgtttctg ttggacatac tcttctctgt  113940
ctcagccgta atctaggaag acctctacag acctcaagaa ctctctttat gcgtgcaatt  114000
ccatcctttc tggttttctg ccttgcaact tgaaaccacc ttggcttcca ggaaagaccc  114060
tgggctctgt ttgagctctc cctctctgca ctgaggctta gaaactgtct ctgagcagta  114120
agctggagca gtcacaggac tcatctcatt tgtttccctt cccgcaggga tcacaggctt  114180
gcactgcctc ttggtcgatg tcttaaaatg tgttgcttca tccctgtctg gtttcctagt  114240
tgtttaaagc aggagggtaa atgtggtccc tgatacacca ctgtggtata agtggttgtc  114300
tgcctttact tttaaattag aattccaagg ttctatgtat ttttttttag agaaaatgga  114360
```

```
ttatatttat tgtttctaga ggggagcata ttttaaagat tttatctccc tgttttagag   114420
agtgagaatt gtacttctct tattttaaat gcagaatgtt actttggatc gcctctgtgt   114480
ataagtataa ctgctaggct tttaccagat ggcattataa acccttggca tttacataat   114540 atatttttc acaattcaca gcatattaaa agttctgaga atctgatag aggaactcat    114600 ttatttgctt aatccagttc tttacaagtt catttgacta tggaatcccc ttgtcatcta   114660
tacctgttaa catcatacag tatgctttga aaaatagtcc taagagttaa ccttttttc    114720 cccatggtct tctttaccat tttaatggct gcatagtgca gttttacatt aagggtgtga   114780
actatagaac catttcctaa ttgggatttt ttttactttt tttttgagac gaagactcac   114840
tcttgtcccc caggctggag tgcaatggcg tgatcttggc tcactgcaac ctctgcctcc   114900
cgggttcaag cgattctcct gcctcagcct cccgagtagc tgagattaca ggcgcctgcc   114960
accacgccca gctaattttt gtatttttta gtagagatgg ggtttcacca tgttagccag   115020
gctggtctcg aactcctgac ctcaggtgat ccactagcct cagcctccca aagtgctcgg   115080
attacaggtg tgagccactg cgcccggccc taattgggat ttttaagcca ttccaacatt   115140
gccactattg agtactacag caatgttcag ttaatacatg tagcctttc tgtatatcaa    115200 actattacta tgttagtatt gtatattata gtaaatata gtaatatc gtactatata      115260 tctatatgtt aaattataat atctataatc ttattataga tttctaaagg tgggattatt   115320
gggccaaaag gataaaatgt tttatggctg ttaatattac ctaattgatg ttttaaagaa   115380 atctttaat tttttatcac tgataatcca aaactatcag atttgggtac accagtatta    115440
tttttggctg ctttattaag gggaaaaaag tgtgtcattg ttgataacat cagttggttg   115500
atggatggag aagctgcatg aatctttttc tcatagtctt accagacttc acacttctat   115560
ccactaaact tttcaaataa gttaatggtt ctcaatgtag tagattaatt aattaatatc   115620
tcggattgag acttcacata ctttggtaga aatttattac tcttatatcc tttgtcaatt   115680 ttgactttt tgaataccTt tttttttaag ttataacttt gcctattata actccttacc    115740 tccatttta aacagtgtga ctatgaaaat gttccaacca ctgtatttac tcctttggaa    115800
tatggtgctt gtggccttc tgaggagaaa gctgtggaga agtttgggga agaaaatatt    115860
gaggtaagtt cttttcctct tttctcctat gttatatcac tactttttt tcttcagaat    115920 ttaaaatata tagaagactt aaaaaatagt acaaagcatt ttcatatacc cgttatccag   115980
attcatatat tactaacatt gtgccaattt attttataca cttttagtag tctctcattc   116040
tgtgtgtgtg tgtgtgtgtt tctgtgaatc atttgagagt aagttgaatt ctcctttacc   116100
cctaaatact ttattgtgta tttctatgaa cgagggcatt ttcttatata gccgtagtgt   116160
agttaccact ttcaggaaat ttggtattgg tgtaatattt ttatctgatt taattttcat   116220
tttctaattc tgtcagttga cccaatcgta tttccttta cttttaaaa tcacatttat     116280 tgatttctct gggttaatta taggaaaatg aaaagaaaaa ataaaatttt ttcactgctc   116340
ctaccattag tactacttgt ttctagcatt actctctaat ttgtactaac ttttctgctc   116400 acatttatc atggagtcaa agaaaatgca catgaaatac actgtttctg tatacacaaa    116460
taatgccacc caaaaggact gctgttttaa atcatttag ggaaaatttc caataaaacc    116520
ttttgaaaga ccaaatttgt gaataagtca attttttaaaa ataaaaagcc tattttaaat  116580
ctcttaataa tcttttcttt tattacatgc actggtagta gcatgtaata tgttggtcta   116640
ttagtaacac attattaacc tttttttctg attataagaa tagtatatct ggctggcatg   116700
gtggctcatg cctgtaatct cagcactttg ggaggccgag gtgggtggat cacctgaggc   116760
```

```
caggagtttg agaccagcct gaccaacgtg gagaaacccc atctctacta aaaatatgaa   116820
attagccagg agtggtggtg catgcctgta atcccagcta cttgggaagc tgaggcagga   116880
gaatcgcttg aacccgggag gcggaggttg cagtgagcca agattgcgcc attgcactcc   116940
agcctgggca acaagagaga aactccgtct caaaaaaaaa aaaaaaaaaa aaagaatagt   117000
atatctttat tataggaagt ttcaaaatta ggaaaatatc aaaaaggaaa ttttaattca   117060
tgaagagata actgctatta atattttgt gtatttcctt ccagtttctt tttctctaaa   117120
tattttgatg cgtttttata ttttatgtat atatatatgt gtgtgtgatt ttgtgtgagt   117180
atgtatgtct taatgttttt caaagtttga tgaagttaca gttttaggtc caagcttaat   117240
attaatgtta tgtcatgaac atttcctgtc tttaattctc taaaatctcc atttaaaaaa   117300
aatgtgtaat tcttcttta aggggtgcta tactgtaatt tgttaagcca ttctttgatt   117360
aggttgttta cagtttttca ttattataaa tagaattgac atcttcataa ttcattgttt   117420
ctcagtttat tttttgaaga tagatttcct gtgtgagtgt gtatatacat gacatacata   117480
tataattaaa atttgaaatt tttaatatat atttcatatt tcttgataga caatatttaa   117540
gttttttaaa atttgctttg ttattataga agtataacgt gtttgagttg aagaaacttt   117600
gaaaaatgta agggaaagag gaaacaatta cttatggagt tagagctgta acagcaattg   117660
ttagcaattt ggggtgattc ctttaatttt tttcctatat aattgtgata ctatgatact   117720
gtacattaaa ttttgtaacc catgtttatt tttaaaatta tattatttat cacaacatcg   117780
aagaacactt gttatgtctt cataatcagt ttgctcgtaa aaggtagcga atcatgtttt   117840
gaactgaggc tagcagctgg aggaaaaaaa aaatccattt agtcaaccag caattaaatt   117900
agtaaggatg ctgtcgttcc acccttcctt cctcctttcc ttccctatct ccttccttct   117960
ttccttccct atctccttcc ttcattgctt ttagtgaata atgccaaagg aggaaatgtc   118020
ttttggaagc atttagcaag agaactagat aattacctta attgatcctg gcaccttatt   118080
tgtttcttgc ccaagttgtc attcacagtg gataacaaga tagtattgag tttgggtgtg   118140
tgtgtgtttt caatgtatga cagcaggtaa ttaaatggct tatttctgtc attcccttgc   118200
tcttttttgt tattagttag ggtgtactat tttgaggtag agatatacat aattaaggga   118260
tgagcttata gcaaaagtgc ctgacagcaa ggagttgaaa gtcatttacc ttttgaccag   118320
attcctattt attccatgaa ttttattatt taatgaaagt ctacttatta aagagtctct   118380
actgtctttc accatatatg tttgacagac ttaatgttta aaataatggg tctaaatttt   118440
gcttttgtat cttcttaggt ttaccatagt tacttttggc cattggaatg gacgattccg   118500
tcaagagata acaacaaatg ttatgcaaaa ataatctgta atactaaaga caatgtaagt   118560
ttaattctca atcctttcca gtaatttat ttagttgttg tttttgttg ttgtttttt    118620 tttagatgga gtcttgctct gttgcccagg ctggagtgca gtggcgctat ctctgctcac   118680
tgcaacctcc gcctcccggg ttcaagtgat tctcctgcct cagcctccca actaactggg   118740
attacagact tgcgccacca cactggctaa ttttttgtaga cgggggtttc accatgttgg   118800
ccaggctggt cttgaacacc tgacctcgta atctgcctgt ctcggcctcc caaggtgctg   118860
gaatgtacag gcgtgagcca ccatacccgg ctttagtttt taatatatag cttagttggt   118920
cacatggtgc agatggcatt ccttcagtat ttcgcgtgcc agttgtctca gctgatagat   118980
atcagcagct ggcaaggacc ttggctgcac tgcctgctgc cccctcatct tcactggcac   119040
agggccctac acttagtcaa caggcagcca aaacttactg agtgaaggaa ccaaaggcac   119100
```

```
aacttgagaa ctgtctatgt ttgtgtttat agaagaggaa caataaagtc atcgactatc   119160
taaatataat gaataacaaa aaagaacagg agcaatgcac gtttgatcct cagcagctgg   119220
cactactaag aaagagctct taattgagtt ctaagatttc attgcctgat gctacatgta   119280
atgctagtct ggtgttatta cgtgtaaatc taatgtattt taagtgcttt ttagtagtcc   119340
tcccacagat atactttatt cataccataa accccccaact gtccaggtga ataagagtac   119400
aatatgcaat atattacagt ccttttttt ttttttttt tgagacggag tcttgctctg    119460
ttgcccaggc tggagtgcag tggcgtgatc ttggttcact gcaaccttcg cctcccaggt   119520
tcaagtgatt ttcctgcctc agcctcccaa gtagctggga ttacaggcac ccaccaccat   119580
gcccagctat tctgtatttt tagtagagac ggggtttcac catgttggcc aggctggtct   119640
cgaactcctg acctcaggtg atccgtctgc cttggtctcc caaagtgctg ggattacagg   119700
tgtgagccac cgcgcccggc ctattacagt acttttttag cagaaacctg tgaaagcctg   119760
tgagcaaact ctatacctca cagggttttt ttccatatat atgaaatgag ggattggata   119820
attcatattt tttaaagttt tttgactgtg ggacactggt atattcatat acacacactc   119880
tctttaatat tgactcttaa gaaaactgat cttttaact tagctaacac tttttaaaga    119940
aacgacctca gtaaaaatat aaatgatgtt aaagaatctg tatgttaaaa gcctagtaaa   120000
ctgataatgt tttaatcttg aaatttgaat ataattaagc catgtatcct atttggaaac   120060
tactgcttta ggcagtagga cagttacagg ttggttttt ggtaaaacca agggttttag    120120
aaaacatttt cttgaatcct ctgcaaaaaa gattcaaatg aatatactag gataacccat   120180
aatgagctac acagctaaca taaataacaa ttgtatatat agttgtcttt ttcttttag    120240 gcaaattttc tcaaaagttt atttatatga gtatacatta gatatcactt ttactgcaga   120300
caaaaggaga aaatgtcagc cattctcact ggcagtatat taactgcccc tgtctcactg   120360
agagagactt caattgctca tagcagtcag tgaaaccttg aaggtttcct tcctaccaag   120420
caaatccatt ttaaccatat gtattttgct cttttttcaa tgttacattt gttcaaatgg   120480
cattgctaga ataatgtgga aaataatttt cctaccaata aacctgtcag tagttgaggt   120540
cataagtagg gtgacagtgt tttcggttat tttcatagat aaagatagta atagagaaga   120600
tgaatatctg ttactgctct tttgtcatga gtaatctgag gtaaaagctt gtagaacttc   120660
actatccctg gggcgtgctt tattcatttt gaatcagtca cttgacttca gtgtctaaat   120720
gtccttgatt ctaaattgta cttacaatgt ttattatctg ctggcttttg ttctctgcta   120780
ttttattttt tttacataa aatatttata ataaagatga agaaggtact caccatccaa    120840
agtcaaggaa tgttaacatt tttgctgtat ttgtttcagg gcttttttct tataagagat   120900
aaaccatcat atatgcagtt tataacagct tatatttatt gagcacttac tgtgtaccag   120960
gcactataga gctctacagg tattaactta tttaatcctt acacagtcct gtgaggtata   121020
tatgctattg tttccccctt tttatagatg aggaaactga agcacatgga agttaagtaa   121080
ctgtgctcaa atcatttacc tagggaaggg cagatctgta catttattct cacacaatgt   121140
agataccatg ctattaacta ttatcttatg cctatgcagt cttctgtctt ccttcacttc   121200
aaaaggtaaa actttgaagt cgaagggtct catgcttacg ttcttatgtt tgccacctat   121260
ttatgaatgc atacacatta tacagtgttc gtggtttaat tgcaggtggc atcctcatta   121320
tgtagagctc tgcaactttt taataatctc ttgttttttg agacccttt cacattatta    121380 catgaaaatc tattttaagt gctttttagt agttcctcct atggatacgc tttattcata   121440
ccataaaccc ggaatcgtca gggcgaatat gtgtaagagt accatatgca atatattaca   121500
```

```
gtccttttgt caacagaaca acctcctgat tgtttccagg gagtgatgga accttagaca   121560
agctctgcac cccacagcct gagttgcctc atctgttatg acgagattgc actagatagt   121620
ctagtcagag tctgcgctga aaatctatca gctcaacagt agagtgcatc agatttctct   121680
gcttttggca gaggtagcca gagtttgaga tttcaaattt atccaaaata atttctacac   121740
aggtatttta gagtgccaga cattttttctt ttgctttcaa aaatgttttc agactttgct   121800
gggcacagtg gctcacgcct gtaatcccag cactttggga ggccgaggtg ggtgaactgc   121860
ttaagctcac aagttcggga ccagcctaga aacatggca aaaccccatg tctattaaaa   121920
acaaaacaaa acaaaaatgt tttcagactt taatggtctt gcactattta tcctcaaaac   121980
cttatttaaa attacttta aaatttatt tgtattttat tttttagaga cagggtctta   122040
ctttatcacc caggatagag tgcagtggtg tgatcatagc tcactgcagc ctcgacctcc   122100
tgggctcaag cattcctccc acctcagcct cccaagtagc tgggactaca gatgtgagcc   122160
actgtgccca gctaattttt ttttttttttt tttttcctg tagggacaga gtctccctat   122220
gttgccaggc tggtcttgaa tgcctggcct caggtgattc tcctgcctca gcctcccaaa   122280
gtgctgggat tacaggcttg agctatgatg cccagtcaaa attttaattt gaatgactac   122340
tcttaagggt cccagctatt acagatagcc tctgtggagc tgagatgatc aaatacagga   122400
cgtgaggaca ccctgccctt tgataatatt ttccagaaca ttttggtgat taaagacttg   122460
taggcatctt tgccttttgt atttttttctc ataaaattga gtaaacactt gtagctgtcc   122520
cttgtctctt tgttcctgtt tgaagtgaac atcatactct atgttttggt tcatgttggg   122580
gagtctttag cctaagtagc tgttagcagc agtcattaaa gtctctggcc attttttccag   122640
gtgcggtggc tcacacctgt aatcccagca ctttgggagg ccgaggtgcg tggatcacct   122700
gagatcaggc attcgagacc agcctggcca acatggcgaa accccgtctc tactaaaaat   122760
acaaaaaaat tagccgggca tggtagcgcc tgcctgtagt cccagctact cgggaggctg   122820
aggcaagaga atcgcttgaa tccaggaggc ggaggttgcg gtgagtggag atcgcgccat   122880
tgcactccag cctgggcaag aagagcaata ctccatctca aaaaaaaaa aaagtctctg   122940
gtcattttct ttttttgaga tggagtctcg ctctgtcgtc taggctggag tgcagtggca   123000
cgatctcggc tcactgcaag ctctgcctcc tgggttcacg ccattctcct gcctcagcct   123060
ctcaagtagc tggaactaca ggcacccgcc accacgcccg gctaattttt tgtattttta   123120
gtagagacgg ggtttcaccg tgttaaccag gatggtctcg acctcctgac ctcgtgatcc   123180
acctgcctcg gcctcccaaa gtgctgggat tacaggcgtg agccactgcg cccggccagt   123240
ctctggtcat ttttgagttg gattttttaag aaacagactg gagaaatgct ctaagctgtg   123300
taggaagagg aggggagaaa aatcagctta attgcattat tgtatttttt tttgccttag   123360
gaacgtgttg tgggctttca cgtactgggt ccaaatgctg gagaagttac acaaggcttt   123420
gcagctgcgc tcaaatgtgg actgaccaaa aagcagctgg acagcacaat ggaatccac    123480
cctgtctgtg cagaggtggg tcatctacac ttatacagtt taaaatgttt aaaatgtgcc   123540
acatagaagc acaccaccca gcttatacat ggcagatgta ggaccctgag tttgatgatg   123600
attcctcaaa agagggcttt gtctctaaaa attagttttt gtctttcaat actgattgct   123660
catggtatga actggaggct tccgtcatgt cgttaagtgg taaaaattat gagagtgatt   123720
tatagagctg tgccttaaat attttatta tcatatcttc taaattattt tcatggcaat   123780
cagttaataa tggaagagct tcaatcttag ttattccaca gctatcttga ggctaattga   123840
```

```
tactgtctgc ctcttcagct tatggtatca gtgaatgaga tttgaaaatg atgctttcaa    123900
aagatcaaat gacagtagaa ctagaaattg accaatctag gcctctgggt gtcagtgttt    123960
cttcgctacc agtgatcatc aagagttga atattgtaat acttaactgc ataggaatgg     124020
taagccaaaa atgtgtttat attggagaac ttgggaaggt gtgggaggag gcacgtcata    124080
ctataccagc ttatatatgg agttgaaaat tgcagtgatt atctgttgta gccagtggct    124140
tccaaggtgt acattgcact tgcaaacacg cacacacaca catatgcaca ttgttgccag    124200
atttcatcca gcagctccat gactggttgt tctgtctgtt catggttgct tttgtacaac    124260
tgaactcatt gctgagtatg tggaatgtca gctttaagac ctggaaaaac attttagctt    124320
tcttttgctt tgtcttctct gtgatcgaga atcctcctct attaataggc acctggctgg    124380
gatataagcc taaaatatta acatgttgag agattagggc atcatttatt tctttcattt    124440
atagaaagct gctgtttttg tgacggaaat agaattaagc ttcaaaaaaa tataaaaact    124500
gaagtcttga ttaatgcctt taatgtgcaa tagatctttt attcagtgta atgactcaaa    124560
ctgcctgtgt tgggaaggag ccaattaact ttgctttctt gagtacatta gtttcccagg    124620
gctattgtaa caaagtacca caaactgggg ggcttaaaaa tagcagatat ttcctccctc    124680
tcagttctgg aggcaaaaaa gtccaaactc aagatgtcag cagggccaag ctccctccaa    124740
aggcactagg gaagaatcct cccttgcctc ttcttctgtc ttctagtagc aatggcaatc    124800
cttggcgttc cttggcttgc agatgtatca ctttaatctc tgccccctc ttcacatggc      124860 ctcatccctt gtgtgtctgt gtccaaattt ccctcctctt tcttataaag aaactccagt    124920
cattggatta gggcccactc taatccaaca tgatctcatt ttcacttgat tacatctgca    124980 aatacccctat ttccaaattc acaaatactg ggggttacga cttgatcatg ccttttaggg    125040
ttatggggac acaattcaac ccacaatagt gagtatattt aaaaatgtag atgccatttc    125100
aagatactca caagcttcaa tagccatttt tgatagggac gaaggaaaag acgatttat     125160 tgtcttttgt atatgagtgt ctaattttt gtctgaattc agctctcagt gggcttgttg     125220
aaagactgct gtgtgctggc ctctgacccc ctcaggaggc tattgtgctg tgatccagca    125280
gcagcgtaca tggcagcatc tggcagggtg actgccagct gagcagaagg atgcagtgag    125340
gacacaggac gtctcctgaa gcccatggct gtggggaggt cagccaaagg cctgttctcc    125400
ttggtatgcc tggcacattt gaggctgtgc atctccatct gttggtcctc ttatgatgtt    125460
gaagctcaga ggctgaatgt tctggtgctt tgataggact ctgatacttt gttttcccca    125520
agctgttggc tgattaagaa gataaaaaaa attgggtgaa atcgcactct gtgaacacac    125580
ttctcaagct gtgtacacag tgccgtgctg gacactgggg acacagcagg gatttgagat    125640
aagcttagga ggagaggagg cagctaggtg atgtgccagt taacaattct gcctgacggg    125700
tcctaggatc agggtagata taaagtgctg gaggcactgg ggtgccacat ttgtggtctt    125760
tgcctcaggg attcttgtga tctgtttttt tactcacaga gcacttctga ccccagattt    125820
gtggggtttt tgctcacacg accaattctc cagctttcta gacaccagct gggtgtctag    125880
aaacaaccaa ttgtctagaa caaccaattc tccagctttc tagacaccag ctgggtgacc    125940
tctaatgtaa ctcaattctg ataccagctg cctggagtta gcatcagatc ctgcaagggc    126000
tcattcccat aagactgcct ccactgcaga ggccagtgtc aagcccaggc ctcctgtact    126060
tctgacctac cagctataaa gtcaaggggt tcccatgata aattgctagc atggctcaca    126120
gaactcagga ataaacttta cttatatta cttgtttatt ataaaggttg caactcagga      126180
acagccaaat ggaagagata cacagggcaa ggtggttgtg gggaggcggg ggacaacaga    126240
```

```
gcttccatgt cctctctagg tgtggcatct tcccagcacc ttgatattca ccaacctgga   126300
agttctccaa acccctatt tagggggtgtt tatagaggtc ccattatgta ggcatgattg   126360
attaatcatt ggccattggt aattacccaa tctcctgctc cctccccaga tgtaggggac   126420
cagaactggg gctaaaaatt ctacctctga tgacatggtt ggttcctctg caaccagct   126480 gccatcttga agctatctag ggccccacca agagtcacat cattagcata agctcaggtg   126540
tggttgaaag gggctcatta tgaatagcaa aagatgctca tctcactagt gtcactcggg   126600
aaattccaag ggttttagaa gctcccttgc caggaaccag ggacaggatg gaagaccaaa   126660
tacatatttc ttctcatttc acaatatcgt aggatgttgg ggcaggatga ttctggaggg   126720
agttcttacc taagactaga acaatgtgtg agtgttagct agtgagagaa cactgtacaa   126780
aaggcctggg tgggaaagcg gatggctcat tcaaggaact gaagaagacc ctcaatattg   126840
gcatagctta aagagcttag agagttaaaa atatatattt atttttttatt tttttgtata   126900 tatatgctgg agaaacaggt gggtaagtga tggtcttgta aactaaggaa gggtattttg   126960
actgcctttg gggcattgtg attcagccaa aaggtctaaa gcagggagta atatgatcag   127020
gtacattgtt cagaaacatt cctccagctg caccgtggaa gcgggactga gcgagcaagt   127080
gaagtggcag atccagttat gtggctggtg aggtgcatga gaggagatga tagtggccgg   127140
aggtgtggca gtggaaatgg agtgacacgg ttatatttga gggcagagtt gatagtactt   127200
ggcagctggc tgggaatggg aagagggaga gctgaagacc actcaggttt gtgtcctgca   127260
gcaggaagta atagcaagag cagactcgag gtgacagcga ggacgaaacc actgatgtgt   127320
gtgagggcct gctgtgtgct gggtactgtg tccctgcctg ttgactaact tagtcgttgt   127380
gagcacccca tgcggtggat gcggtagtat atctatttga cagacgagga aaccaaggac   127440
aaagaggttg agtaacttgc ccatggtaac ccagcctggt catggccgag ctgggattca   127500
aacccaggca gcccagaccc caaagcacca cattgtgcag ctgatacttc atctccacag   127560
actgtcctac catatttggc atagaattta aaaatggaaa tgattcttgg tagcaacacg   127620
aatgtagtgg agacacacag acctgggttg taatctcact cagccaattc ctcttagtga   127680
gacctggcca taccacccag gttttcagaa gcttagtttc cacattaaat aaagtaagag   127740
gccaggcgtg gtggctcact cctataatcc cagcactttg ggagcctgag gcgagtggat   127800
cacttgaagc ccggagtttg agaccagcct ggccacatag caaaacccaa tctctaccaa   127860
aaataacaaa aaaataactg tgcattgtgg cgtatgcctg taatcccagc tatgttggag   127920
accgaggcac aagaatcact tgaacccagg aggcagaggt tgtactgagc caagatcacg   127980
ccactgcact ccagcctggg cgacagtgag accctgtctc aaaaaaaaaa aataaaacaa   128040
aatggcctgg ctcagtggct cacgcctgta atcccagcac tttaggaggc caaggtgggc   128100
agatcatctg aggtcaggag ttcaagacca gcctggccaa catggcaaaa ccttgtctct   128160
actaaaaata cgaaaatggc ctgatgtggt ggtgcatacc tgtagtccca gctactcagg   128220
aggctgaggc atgagaattg cttgaatctg ggaggtggag gtttcagtga gccgagatca   128280
cgacactgca ctccagcctg gagcgagact ctatctcaaa taaaaaaaaa agtaaaataa   128340
aataagggaa tatctaactg tagggttgat taaaatgcaa cctgtaaagt gtgtaggaga   128400
gttcctggca tttaatagat gccgaatagc tgcacctgtt agctgttttt tccccaggat   128460
attatagatg tggctgtggc ttgggagggg agacgatgtg gctggactga aaggtcatca   128520
tgccagtatt tttaatgggg gttggagaga gatacatatt gtgaaaaagc tccagtgatt   128580
```

```
tttttttttt taaaccctg gttgtgaact acttgcgttg atactggatt tgaaaaacc    128640 aaaggcttta aactcctggt tatggacatt ttaaaaaatt attttaatt gacacaataa    128700 ttgtacatat ttatggggtg catagtgatg ttttgaaaca cagagtttat agtgatcaga   128760
ttagggtaat tagcctatca atcatctcaa acattgacca tttctttgtg ttgagaacat   128820
tccatatcct tctagctatt tgaaagtatg cattattgtt taactgtagt tatcctaagg   128880
tgctatagaa catattcctc ctatctagct gtagttttat atcctttaac aaatctctcc   128940
ctatctcctt ctcccaaccc ttaccagcct ctagtaatct ctgttctact ttttacttct   129000
gtgagtaagc tagcacagcc actgtggtca acagtatgga ggttcctcaa aaatctgcaa   129060
atagagctac catatgatcc agcaatccca ctacttaact gggcatttat cccaaggaag   129120
tcttttaggg gttcatagga ggaactcttt tctctgccaa atgctgggtt ctgacttgga   129180
tagtatttgg atttgctact ggacccactg tttttatcgt ccagacatat tctgtgggga   129240
atgtgatatt ctgtggggaa tgcggttcag aagtggtcca cagaatgttt gttattagtc   129300
cataatgata gaaggctaga aacgaagaag aaagtttaga aattttaaca ataatttgac   129360
agtgactgat ctagtaataa acaatggtgt tttaattta catgcctttt aaaatttcat    129420
ttccccagta cattgtcagt gaatttcaca agtgttagtc cagtggatga attagaaata   129480
ataataattt ttaaaccagt cctgagtact actttaaact gagtgctcaa aaatagctgc   129540
agctccagag ccagctgtgg taggctggca cagtgactca ctttggtaaa atcctgggc    129600 aattgagagc agtctttgac tctgaggagt aattacttac aaaagttgac aaattcctta   129660
gcaaagtaat ttccaaaggg aattactaga attctagaat tgctgtaaga ggagaggcta   129720
ctcttgtttg tcctgtgtga gagggattct cagcgcctgg ggcattagca atgcatttgc    129780
cgtattcagt gtgagatggg gttggtggtc atttattctg aacacctgag ccgcagtcat   129840
tgagtaggaa acggattaca catagttatg aagttcactt gtagaggaga aaaacaatag   129900
ttcaagagga aaacatttga aaatacttcc ttgtaatgtc ttaaatgaat tttagtgcca   129960
aatattaaaa gttttgtgt ttttgtttg ttttaattt aatagtcaat ataatcccac       130020
tctaaagtga gggagccttc tgcggctgga agtggtgggg acagataaga gtatgtgagg    130080
tggaaagcct ccagcagctc ctgacccttg tacgagtcct gtgtgttggg atggaagggc    130140
atggaggctg cccttctgc tcatttttta aaaatacatg ttttatataa aattctaaaa     130200
cagttgtgta cgaatgaaat ctgtcaattg acccaagcag ttttttcat ttatttgaga     130260 tagggttcct gtcacccagg ctggagtgca gtggtgtgat ctcagttcac tgcagccttg    130320 accttttcaag ctcaagcgat gttcctgcct cagtctcctg agtagctggg accacaggta   130380
catgccactg tttccagcta atatatatat atatatttga gacagggtcg cattatgttg    130440
cccaggctgg tctcaaactc ctgggctcaa gcaatcctcc cgccttggct tcccaaagtg    130500
ctgggattgc aggcgtgagc cacggtgcct ggccagtttt ttatttagac tgatcaacga   130560
tggcagtttg gcttcctcca tcttttttaac ataagaacaa catcaatatg agaaaaaaca   130620
gataagagct cattttggtg gatttagttt tgtatccaca tctcctacaa gttctatttc    130680
taaatcagtt tctgagaaat agaacccagg cttgcaaatt gataagcctg gaatttgttt   130740
aaatgtattc tttggctctt tatttttttc ctcattataa aaatggaaaa gaaagcatgt    130800
ttgaattgcc cttaatacccc ctttctaaca cagttatttt tattatcatg tattgtttcc   130860
ccgtcctcat ctgtactcct acattttttt taaacaaagg aatttattg ccttttccaaa    130920 aaagttgtac tagtttataa tgtcaccagc attgcatata agagtgctaa ttaaaatgtt   130980
```

```
gcaaaattca gtgtcaatgt tttttctata atgagtataa aaaggataac tattggccag   131040
gcacagtggc tcatgcctgt aatctaagca ctttgggagg ccgaggcagg tgggtcacct   131100
gaggtcagga gtttgagaca agcctggtca acgtggtgaa accctgtctc tactaaaaat   131160
ccaaaaatta tccgagcatg gtggcaggtg cctgtaatcc cacctactcg ggaggctgag   131220
gcaggagaat cgcttgaacc taggaggcag aggttgcagt gagccaagat tgtgccgctg   131280
cactccagcc tgggtgacag agtgagactg tctcaaaaat aaaataata ataaataac   131340 gatttcaagg attttagcat atctttgcta acaatgatga gcctctttct tcttataatg   131400 atttttttt ttggatatga attatccata ttttctaatg catttgtatt ttaaaacttt   131460
ttaagatact ggccattagt atttggtctg gattttttg agaagtaaag gctttgtcac   131520
cctctgaggc taaacagac taagactttt tctcagtatt gttcctccct tacacaaaac   131580
tgttttcccc cttattcaca agtattttg tttttacgta caggcaatct tgagcagtag   131640
caagtaaaga ttgtctaaaa ctgtcaagtc cacaaccatc aaatgtttgc aaggatgatga 131700 aacaaggaga acttgttagt cactgcaaat gagagtatag gttggttcag gtaccttgaa   131760
aatctagtca agccaaagtt tcacctgccc tctgactcag cagttgtact ccagctctgt   131820
gtgcaaggag atgtgctgga atgtcacagc atcgtattgc aaagagcata ttggcaacag   131880
cttggatggc cagcagaagg agcccaaatg tgtgattcat attcactagt cgaataattg   131940
aatactacaa tatacaccat atatactaca ctgtatgtgt tgttctatac tatagtgatt   132000
gactcgaact ccattcagtg aaaaaaatgg aagaattagc tatttgtatc catatgggat   132060
acaaaaaagc agggtaacaa aagaatctac atcatcttgc catttgcagg taaagcttct   132120
taaaaaaaca agagaaatgc aggaagaaat gcctaggaat gataagacca actcggtgga   132180
gggaaaggag gaaaaggcca atgggtggc acacacaggg ctaactgggc actttatacc   132240 cttcttata tccaaaatat tttatggtga atttctttta gagggttgac aagcacctgt   132300
gggtacctga tctgtttaa tcatcctcat gctaacaaaa ttcttcagta gatataaaccct   132360 aaatttttt tctctttcat cttggtttta aaatgtcttc cccctttat tctctggaga   132420 aatagaagat atccttgatc atactacttc tctgttttat tcatttggt agtcgcctaa   132480 gatggtttta atgcatatgg cattatctga actgttccct gttacctcat ttgctcaggc   132540
atctgaagat gttgtgcttt ctcttcccct gcaggtattc acaacattgt ctgtgaccaa   132600
gcgctctggg gcaagcatcc tccaggctgg ctgctgaggt taagcccag tgtggatgct   132660 gttgccaaga ctgcaaacca ctggctcgtt tccgtgccca aatccaaggc gaagttttct   132720
agagggttct tgggctcttg gcacctgcgt gtcctgtgct taccaccgcc caaggccccc   132780
ttggatctct tggataggag ttggtgaata aaggcaggc agcatcacac tggggtcact   132840
gacagacttg aagctgacat ttggcagggc atcgaaggga tgcatccatg aagtcaccag   132900
tctcaagccc atgtggtagg cggtgatgga acaactgtca aatcagtttt agcatgacct   132960
ttccttgtgg atttttctat tctcgttgtc aagttttcta gggttgaatt ttttcttt   133020 ttctccatgg tgttaatgat attagagatg aaaacgtta gcagttgatt tttgtccaaa   133080
agcaagtcat ggctagagta tccatgcaag gtgtcttgtt gcatggaagg gatagtttgg   133140
ctcccttgga ggctatgtag gcttgtcccg ggaaagagaa ctgtcctgca gctgaaatgg   133200
actgttcttt actgacctgc tcagcagttt cttctctcat atattcccaa aacaagtaca   133260
tctgcgatca actctagcca aatttgcccc tgtgtgctac atgatggatg attattattt   133320
```

| | | | |
|---|---|---|---|
| taaggtctgt | ttaggaaggg | aaatggctac ttggccagcc attgcctggc atttggtagt | 133380 |
| atagtatgat | tctcaccatt | atttgtcatg gaggcagaca tacaccagaa atggggggaga | 133440 |
| aacagtacat | atctttctgt | ctttagttta ttgtgtgctg gtctaagcaa gctgagatca | 133500 |
| tttgcaatgg | aaaacacgta | acttgtttaa aagttttttct ggtagcttta gctttatgct | 133560 |
| aaaaaaaata | atgacattgg | gtatctattt cttttctaaga ctacattagt aggaaaataa | 133620 |
| gtcttttcat | gcttatgatt | tagctgtttt gtggtaattg cttttttaaag gaagttatta | 133680 |
| atatcataag | ttattattaa | tattttgaac acaggtggat gtgaaggatt ttcatttaaa | 133740 |
| aaccaagtgg | ttttgacttt | ttctgttgaa tgaacaactg tgccttgtgg aattttttgca | 133800 |
| gaagtgttta | tgctttgtta | gcatttcaac ttgcattatt ataaagaggt attaatgcct | 133860 |
| cagttatgtg | tttgtcaatg | tactggctga ggattctatc tcagctgtct tttctaactg | 133920 |
| tgtaggttga | gttttgaaca | cgtgcttgtg gacatcaggc ctcctgccag cagttcttga | 133980 |
| agcttctttt | tcattcctgc | tactctacct gtatttctca gttgcagcac tgagtggtca | 134040 |
| aaatacattt | ctgggccacc | tcagggaacc catgcatctg cctggcattt aggcagcaga | 134100 |
| gcccctgacc | gtcccccaca | gggctctgcc tcacgtcctc atctcatttg gctgtgtaaa | 134160 |
| gaaatgggaa | aagggaaaag | gagagagcaa ttgaggcagt tgaccatatt cagttttatt | 134220 |
| tatttatttt | taatttgttt | ttttctccaa gtccaccagt ctctgaaatt agaacagtag | 134280 |
| gcggtatgag | ataatcaggc | ctaatcatgt tgtgattctc ttttcttagt ggagtggaat | 134340 |
| gttctatccc | cacaagaagg | attatatctt atagacttgt cttgttcaga ttctgtatt | 134400 |
| acccattta | ttgaaacata | tactaagttc catgtatttt tgttacaaat cttctgaaaa | 134460 |
| aaaacaaaac | aatgtgaaac | attaaaatta aaaggcatta ataatatcca cgtgtgcctt | 134520 |
| cttactgaa | | | 134529 |

<210> SEQ ID NO 8
<211> LENGTH: 11856
<212> TYPE: DNA
<213> ORGANISM: human

<400> SEQUENCE: 8

| | | | |
|---|---|---|---|
| gtgcttgtag | tcccagacac | tccggaggtg aggcgggaga atcgcttgag cccgggaggt | 60 |
| ggaggttgca | gtaagccaac | accgtgccac tgcactacag cctgggcgac agggtgagtg | 120 |
| agactccgtc | tcaaaaaaat | gtggaataga acaaacttta gttttaggaa ctagacttta | 180 |
| tattgtagat | ctagttgcaa | ttgacacgtc cttgttttat gggaggctac atactttaaa | 240 |
| ggtttccagg | ggagcaaata | attaattatg attttgtgta tgtgtgtttg tgggggggtag | 300 |
| tcatcaggaa | atgtctgagg | ccttttgcct taccgtgtgg gtctggctaa tgtgtaatgt | 360 |
| tttgactcaa | gattgtaaag | tcaaattatt catccgggga gaggatggtc gtgtaactga | 420 |
| atcagcctcc | caagatgaac | tttccctctg gcgtaagttt aggagtcctg atattttatt | 480 |
| ttcctttaca | acagaaagca | gcaaccctgt aattaaagag aacaatgaag gaagctatct | 540 |
| aagccatgag | ggttactgag | gatctgcgct gggggttaagg ctgcgaactt aagaaatatt | 600 |
| tggatagaca | gttctcatgg | cttggtgtgg ttagacgtgg tcctccgtgg gcagcagcta | 660 |
| agacgcttac | tccagtttgg | gcattgaggg cacagtgcgt agtggtcctg gaagtaaaga | 720 |
| gaatcctggt | tttccgcaga | gatctaggat taacctaagc gttcgggttc gggagcggcc | 780 |
| acaagggcgc | ctcactccaa | cctcagccat ccgcaacagg gtgggggtatt agtatttttc | 840 |
| cgcacccgcc | ccaacgaggg | aaagcgccga gtcattccgg cggggcgcgc cgggcggggc | 900 |

```
tcgggccaca tccccctcct ctctctcctc ctccggcacc cccgtccgtt ccgactctcg      960
cgagatccct actggctata aaggcagcgc cccggagagc tcttgcgcgt cttgttcttg     1020
cctggtgtcg gtggttagtt tctgcgactt gtgttgggac tggtgagtgt gggcagtgcg     1080
gccccctgcgg agtgaggcgc ggcgcgccct tcttgcctgt tgcctcttcc tcctcctgtc    1140
cggggcccgc ccgcgctcgg gtgggggtgc tgtgatgcgt gaggcagccg ggggaggccc     1200
ggagtccgag actgcttgag cgctgcgcac acccctctcg tgggcccccc acgtaggtgc     1260
gggaacctgg ttgaacccca aggcaagcgt ggactcgagt cgagtcttcc cccggcaact     1320
cgagcacgtg gcgcggcgtc tgggcgggct ggtggtgggg gtctccgaga ctagcctcct     1380
gccggacggg gtgggttcgg gaagcttctg gaatggacct gtatccagac tcgtggctgt     1440
agaagacagc ctctatgtat ttggctgttc cgggtcctga gccttgacta gctgcggagc     1500
ttcgggtacc ctttccccgt ctttattttc ctgtacgtgg aatggagtta gcgatgagcc     1560
caaatgtccc cgctgaagca ctctctctgc tggtgctttc tccagtgctg gggagggaca     1620
ggggcacct gaagtgggt ttagggatgt ggccctctac gctgggcaga tccctgaag      1680
gggcccggtg gcggcctgaa tcccagcagc ctttaccccg aattggttgg gttttgtact     1740
tgggggccac ttgggaaaga aggattggac gagaaggcca tttgggggca ccaagttgca     1800
gcatgcctta gttttggtt tttgttttt gtcgttaaag gtgttaagga cttttaaaa       1860
aacagttaaa agtttgctaa gatccatgct tacaaaattt cttttgcttg tggtattgtg     1920
aactaagaac tttgggactt ggaaaagctt tcagaccgcg gcttagtggg ttaaatctct     1980
gtttttgag ctagagtctc gctctgtcgg ccaggctgga gtgcagtggc gcggtctcgg      2040
cttactgcaa cccctgtctc ccgaattcaa gcaattcttc tgcctcagcc ttaggagtag     2100
ctgggattac aggcttgtgc caccaagccc cggctaattt ttgtattttt ttttttttt      2160
ttttttgag acgagtctc gctctgtcgc ccaggctgga gtgcagtggc tggatctcgg       2220
ctcactgcag cctccgcctc ccgggttcac gccattctcc tgcctcagcc tcccgagtag     2280
ctgggactgc aggcgcgtgc caccacccc ggctaatttt ttgtatttt gttagagacg       2340
gggtttcact atgatggcca ggctggtctc gaacttctga cctcaggtga tctgcctgcc     2400
tcggcctccc aaagtgctgg gattacaggc ttgagccaca gcgcttggcc aagatctcaa     2460
tactaatctt ggtgttgatc tgggtgaatc cagtgcaacc ttccttttca gcagtaaatt     2520
gattcttata cttgttttcg ccctgggata ttagccccaa agtcaggaac ccaccttcac     2580
aaatggtgaa gggaattcta gggcttacac aatacctaaa gatttgaaat taagcagatg     2640
ccaatcaata tcttggtctt gcctcttttt tttttttttt ttttggaga cagagtctca     2700
ctctgttgcc caggctggag tgcagtgcg cgatctcagc ttactgcaac ctctgcctcc      2760
cgggttcaag tgattctcct gcttcagcct cctgagtagt tgcgattaca ggcatgcacc     2820
accacgcccg actaattttt gtgtttctag tagagacggg gtttcaccat gttggccaga     2880
ctggtctcga actcctgacc cggtgatccg cccgcctgag cctctcaaag tgctgggatt     2940
acaggtgtga gacactgcgc ccagtggtct tgcctcttaa aagttggact gactggaagg     3000
gcgcggtggc tcacgcctgt aatcccagca ttttgggaga ctgagttggg caatcatctg     3060
aggtgaggag tttgagacta gcctgaccaa catggagaaa tcccgtctct aatagaagta     3120
caaaaaatt agccgggtgt ggtggcctgc gcctgtaatc ccagctacta tggaggctga     3180
ggcaggagaa tcccttgaac ctgagaggtg gaggttgcag tgagccgaga taatgccatt     3240
```

```
gcattccagc ctgggcccca agagcgaaac tccgtcaaaa aaacaaaaca aaacaaaaac   3300
aaataaaaca agttgaatta gttataggtt gtgtgctgtc ttggacaaag ctacctggag   3360
aaaagtcaaa tatgcttctg atgttatgaa ggcaggtgga ggcacagtga tgggaaaggt   3420
caacgtgact tttggggagc caaacaaaag tgtttgtggc attgtgcatt tggattctgg   3480
tttgagagtc ttcatctgcc tctctctctg cttctgtata atgaataaga tgccactgca   3540
ctaattatgg ttcagaaaga atgagaggtt atctcagtat ataaagaaat tgccttgctg   3600
tttttaaatg aaaacaaagg ctgagattca gagacttgtt tcgttccaaa agttggaaag   3660
ctcagactgt gaccctgac tgctggctgg agcttcttac taaaacaaca tttaatgtat   3720
tcagggacac tggacaatgc cttgattgtt tacagctaag tctctttaag taggtgaagg   3780
ctgctggtta tgtagaaaat taaggcttgt ttctaattca tttctgttat ttctagctga   3840
taggaagatg tcttcaggaa atgctaaaat tgggcaccct gcccccaact tcaaagccac   3900
agctgttatg ccagatggtc agtttaaaga tatcagcctg tctgactaca aaggtgagag   3960
aattaacact gggctcattg agatggagtt atttatatt ctaggggtgg cttgttagat   4020
ttgtgtcaat gttgtttgac tgtaaaatgt tttgtctcct aggaagaagt atttaggttg   4080
ttaccttcat gttgaagtgg tgattatcaa gtgattacag ggtatatatc ctaggaccaa   4140
accacttctg gagaaaccac atgcttcatt atgtctggac atactagctc aattatcttt   4200
tcagtattcc tcgtctattt tctttctta tttttatttt tgagacaggg tctcattctg   4260
tcacccaggc tggagtgcag tggcgcagtc atggctcact gcagcctcta cctctctggg   4320
ctcaggtggt cctcctacct cagcctccca agtagctggg actgtagggg catgctgcca   4380
tgcctggcta attttttgtac tttttttttt tttttttttt tttgagatgg agttttgctc   4440
ttgttgccca ggctagagtg caatggcgtg atctcggctc accacaacct ccactgccca   4500
ggttcaagca attctcctgc ctcagcctcc cgagtagctg ggattacagg catgcgccat   4560
catgcctggc taattttttt ttgtattttt agtagacg gggtttctcc atggtggtca   4620
ggctggtctc gaactcctga cctcagatga tccgcccacc tcggcgtccc aaaatgctgg   4680
gattacaggc atgagccacc acgcctggct taatttttgt acttttttgta gagctgggcg   4740 ccatgttgcc caggctggtc tccaactcct gggctcaagc cctctgcctg ccctagcctt   4800
tcaaagtgct gggataacag gtgtgagcca ctgcctctgg ccctcctcta ttttattatt   4860
ggagaaatac tcattatctc ttgttataag agacattcta catttaaagt ctcagagctc   4920
actcaaatct ctggagctgt gacactgctc gttcagtttg tttgggtcac gtatatatca   4980
cagctgttaa tattaggctg agggctaggc actttcccctt gcctgttttg accccggagg   5040
agagttgata ttacagatgg aacaactctc ctttctgttg tcatagtttt ttttttttt   5100 tttttttttg agacggagtc tcgctttgtc gcccaggcta gagtgcagtg gtgcgatctc   5160
agctcactgc aagctccgcc ttctgggttc atgccattct caggcctcag cctcttgagt   5220
agctgggact acaggcgccc gcaaccatgc ttggctaatt ttttgtatt tttagtagag   5280 acggggtttc accatgtttg ccaggatggt ctcgatctcc tgaccttgtg atccgcctgc   5340
cttggcctcc caaagttctg ggattacagg cgtgagccac tgcgcccggc ctctgttgtc   5400
atagtttcat gcagacactt ggcaagttct gttgaggctc ctccttcctt taccttgtag   5460
ttccagagca gctcgatctc ctgggacagt tgaggatata gattcctag aatgctaacc   5520 tgaaactcag gtgtcaagtg tccttttctc agtggtgtag cattagtccc tggagttagt   5580
ttttggtaga acatttgact aggtttcctg acataatcac actttgttct tggggcttct   5640
```

```
cccagcaaac aaggtaagtt gcaccatagg gaggtgacct gggcccaggg gtataagcag    5700
gaggtctagg aggagctgtt ctctgccctc cagagcttga cctgctgagg ccccaaagtg    5760
cttgttaggc aaagctggaa gggttgttta gatgagttag tttccagtga tactgcaaag    5820
tggtaaatgt caaaagggc tgcttgtttg gcttttttt tttttttttg aggtggaatt    5880
ttgatcttgt cgcacaggct gtagtgcagt ggcatgatct caggtcactg cgacctccat    5940
ctccccggtt caagtgattc tcctggctca gcctccccag tagctgagat tcaggcccc    6000 cgctgtcaca cccagctaat ttttgtattt ttagtagaga catgttttac catgttggtc    6060
agcctggtct tgaactcctg acctcaggtg atccacccgc ctcggcctcc caaactgcct    6120
cccaaactgc tgggattaca gacgtcagcc accatgccac cacacccagc ctgtttgact    6180
tttcaaacat tgctgctacc tggaaatgag tgaatatttg gaattgttct agtatttaag    6240
cctggtgggt gtggcgagaa ggctgcctgg ccagtttgaa gatctgttat ttcagtggtt    6300
aatcccagtg acttcattaa aattgcagct agaagttctg ttactcacta gtacttttgt    6360
cttttctgtc tctctctgtc tccctctttc tctctctctc tctgtgtata tgtatatata    6420
tatttctgtt gttttgagac agtcttgctg tgttgcccag gctggcctca aactcctggg    6480
gtcaagggat cctcccacct cagcctccca agtagctggg actacagaca cgcaccactg    6540
tgcctggctt aaaattttc ctgtcctgtc aggcacgtta ggaacacatg tgatcactta    6600
aaccatgctt gttccattac tatggttcat cacgggagaa gtgcaaaggc tgtgacttct    6660
tattggtgtc ttatctctac agcagaggag tactgcaatt cagctttctc tgggtattgt    6720
taagcattgg cattaggcca tgcttataag tgcatccttg cttttgctat ctttggagaa    6780
cttggtgttt atgttaattt tagccactca gaaaagatca aaattagact gaacagtgtt    6840
tactctgtat tggtagctat gacatggagg caggagaata aagtatggga ttggaagttt    6900
ttttcattca ggtattccta atgcaccagg ttctaaaagt agcttctagg agacatctgt    6960
attgagcatc ttggcagtta gtggttattg tgtcagccat caacttgctt cttttgtat    7020 aggaaaatat aaagcaagga agtctgtgtc aaatgctaac catgactccg attttccccc    7080
caggaaaata tgttgtgttc ttcttttacc ctcttgactt caccttgtg tgccccacgg    7140 agatcattgc tttcagtgat agggcagaag aatttaagaa actcaactgc caagtgattg    7200
gtgcttctgt ggattctcac ttctgtcatc tagcatggta aatctcttgg tctatttggc    7260
atgtgaactt tttttttttt tttttttttt ttgagatgga gtcttgcttt gtcgcccagg    7320
ctggagtgca gtggtgtgat ctccgctcac ttcaagctct gcctcccagt tcacgccat    7380 tctcctgcct cagcctcctg agtagctggg actacaggcg cctgccacca tacctggcta    7440 atttttgta tttcagtag agacggtgtt tcaccgtgtt agtcaggatg ttcttgatct    7500
cctgacctcg tgatctgccc acctcagcct cccaaagtgc tgggattaca ggtgtgagcc    7560
actgcacctg gctggcatgt gaactttaa aacagcaact gggaagcttt ggcaatagac    7620
tttcaagtat tgccttctca ttgaagggag tgcaaagtct gactttctct tattgctctc    7680
atgacctggc agcagagaag aagcagcttc aattgcagtt gagtgtaccc tagtgaccta    7740
ccttaactgt tctcagcatt cactttattg ctggaaaacg gaaaaaaaac agtctttttg    7800
gaaagttaga ttaggaatat gggaaagggg aaagaggaat gcgtacagtc aagtcaagag    7860
tttgaatgta actgtatgtt tgccttttgc catagggtca atacacctaa gaaacaagga    7920
ggactgggac ccatgaacat tcctttggta tcagacccga agcgcaccat tgctcaggat    7980
```

```
tatgggtct taaaggctga tgaaggcatc tcgttcaggt atgtcatcag acaagtatc   8040
cagttggctg aaagccttt  atttggagag atctagagcc ctgatctgta gagactcctt  8100
gtcatttcat tcctttatgc aggggcctcc tcactaaggc caggccagta ggagtgtgga  8160
gaccagtcca tttccttcag gcttcaagcc tctgtattct aacaaagcac atctctaaac  8220
ctgtattgct tttcctttca tctcttttcc caggggcctt tttatcattg atgataaggg  8280
tattcttcgg cagatcactg taaatgacct ccctgttggc cgctctgtgg atgagacttt  8340
gagactagtt caggccttcc agttcactga caaacatggg gaaggtaagc catctgtctg  8400
ataacaggac aacagagtgg tggtatgaag gggtgggttg cccctcaca cctgtgggtg   8460
tttctcgtta ggtggaatga gagacttgga aaaagacacg tagacaaagt atagagaaag  8520
aaataagggg gcccagggga ccagtgttca gcatacagag gatcccgccg gcctctgagt  8580
tcccttagta tttattgatc attcttgggt gtttctcgga gaggggatg tggcagggtc   8640
ataggataat agtggagaga aggtcagcag ataaacacgt gaacaaaggt ctctgcatca  8700
tgaacaaggt aaagaattaa gtgctgtgct ttagatgtgc atacacataa acatctcaat  8760
gccttaaaga gcagtattgc tgcccgcatg tcccacctcc accctgagg cggttttccc   8820
ctgtctcagt agatggaaca tacaattggg ttttacactg acattcca ttgcccaggg    8880
actggctgga gacagatgcc ttcctcttgt ctcaactgca agaggcgtt  ccttcctctt   8940
ttactaatcc tccttagcac aggggtgtcag gctgggggac cccggtcagg tcttcccctt  9000
cccacgaggc catatttcag actatcacat ggggagaaac cttggacaat acctgggttt   9060
cctaggcaga ggtccctgtg gccttccgca gtgtttgtgt ccccggatac ttgagattag  9120
ggagtggtga tgactcttaa aacgagcatg ctgccttcaa gcatttgttt taacaaagca  9180
tatcttgcac agcccttaat ccatttaacc ctgagttgac acagcacatg tttcaggag   9240
cacagggttg gggataaggt tacagattaa cagcatctca aggcagaaga attttttctta  9300
gtacagaaca aaatggagtc tcctctgtct acttctttct acacagagac agtaacaatc  9360
tgatctctct tttccccaca gtggtagaat gggaaagata gtaggaacag aagctaccaa  9420
ataagaaaat gggtatctct cttcataaat tgaagcccct ggattacagt gtgttgtgag  9480
ggtgagggta atggaaaagc ttgggaagga gaatataaag gctttttatt caaagtatac  9540
atactcctct cttctgtcct gctcatttag aatcagtcac tcccaaagat ctaacttact  9600
gaatgtagga tgatctcaca gatgtattag ggcaaaacaa aatggttggg aatcacctct  9660
agagataaag catgccattt tttaaataac tttattgaga gaagaggtta atccatatag  9720
ttcatatttt tatttattta tttattttt  gcaagatgga gtcttgctct gttgcccagg   9780
ctggagtgca gtggcgcagt cttggctcac tgcaacctcc gcctccctg  agccattgcg   9840
cccagcccag actagctttc taaggcctat ttcagctctg atcttgtaat ttaaaggaaa  9900
tgaagttatt agagtctgga ttagtggtgt atgtttggga agacccaaag gtgctagctt  9960
ggctagcacc aagtaatctt tttacaggga ttagagtctg attatatagg gatcagtgag 10020
cactgataac caagaggtac ccttttgcaga aggatgtgtg ggcagttagc ctggacagat 10080
gacacatggc tcagctgaca cctgctgaga ctgccccctt gtgggagatg aggttcagca  10140
ttaagaagga ggcagcagtg gcaaagtagg cccttaact  ggactttcct aggaacctac  10200
atataggtta gtctcctgaa cccaggcttt cataactcag aagcttgctt cttcagactc  10260
tgttggtctc tgctgcttcc catcccactg gaacatgtac agcctcttaa ataggtacca 10320
tttaagagcc aatgaatgcc aaacactttt  ttttttgag acagagtctt gttttgtcgc 10380
```

```
ccagactgga gtgcagtggt gtgatctcag ctcactgcag cctccacctc ctgggttcaa    10440
gtgattctct tgcctcagcc tcctgagtag ctaggactac aggggtccac caccacgccc    10500 cactatttt gtatagtccc agctactcgg gaggctgagg caggagaatg gcatgaaccc    10560
cggaggtgga gcttgcagtg agctgagatc gcgccactgc actccagcct gggcgacaat    10620
gtgagactgt ctcaaaaatt agccaggtgt ggtggtgggc gcctgtaatc ctagctattt    10680
gggaggctga tgcaggagaa tcgcttgaac ccgggagacc gaggttgcag tgagacggag    10740
gtggagattg cgccaccgta ctccagcctg gcaacagag ggagactcca tctcaaaaaa    10800
aaaaaaaaaa aaaaaaaaaa agaaaaataa gagattagtc cccttgcctc attttcttca    10860
ggctagcctg aggcacattc ttaggcattg tcaggaaaag gttgaaggct gtgctttctg    10920
tataaatcta tgaaaaattt caaactctgc cttttgctta ccaaggggta gatggcagtt    10980
acttaatgaa acaagcgggg gcttctgtta agttcttgat cctttataag gttcaggcta    11040
tccagtttgg tagagttaga agaatgctga aaggcagac tgagtttgct gtcttcagag    11100
ctctgaaggg ctgtcagaaa cagtttagtg ttaagggttt acatagtcct atgtgtgtcg    11160
tttatttagc ttttttttcc ccttaaggat tagagagtgt tggcaaatta tttaaacttt    11220 gcctttttt gtggaaaatt taaatttcaa gtgctacatg aataaattag gcatgatagt    11280
atcttaaggc tgtggtgatg attatatgtt tgtaaaatgg ttagctcata ctaaaagggt    11340
gaatgatcta agactgattg caggggtagg tttcctggta tctgagtgtt caggtgcaga    11400
actggttttg tccataggag aatggtggtg cataccattg agaaggttat taattagtgg    11460
tgcctttctc ttgcagtgtg cccagctggc tggaaacctg gcagtgatac catcaagcct    11520
gatgtccaaa agagcaaaga atatttctcc aagcagaagt gagcgctggg ctgttttagt    11580
gccaggctgc ggtgggcagc catgagaaca aaacctcttc tgtattttt ttttccatta    11640 gtaaaacaca agacttcaga ttcagccgaa ttgtggtgtc ttacaaggca ggcctttcct    11700 acaggggtg gagagaccag ccttcttcc tttggtagga atggcctgag ttggcgttgt    11760
gggcaggcta ctggtttgta tgatgtatta gtagagcaac ccattaatct tttgtagttt    11820
gtattaaact tgaactgaga ccttgatgag tcttta                              11856
```

<210> SEQ ID NO 9
<211> LENGTH: 13148
<212> TYPE: DNA
<213> ORGANISM: human

<400> SEQUENCE: 9

```
aaatgtgacc ggccgcggct ccggcagtca acgcctgcct cctctcgagc gtcctcagcg      60
cagccgccgc ccgcggagcc agcacgaacg agcccagcac cggccggatg gagcgtccgc     120
aacccgacag gcaagcgcgg ggcgcgggac gcgggacggg cgcctttctc tcccaaccct     180
gcttgcgtcc tagccccacc ccgggacact gccacacagc gacagagccc aggagccaga     240
aacttgggct ctggagtcag gaggtgcggg gttctgatcc tgcctgtgcc cgtagggtag     300
ttggagggag gaacggtaat ttacatgcct ggcaccctgg tatgcggttg gtgaccaaga     360
tgggagtgtc cctagagtat ccagtctttg aggtagccaa ttttttttt aatcctactt     420 tcgaggtgtg tttggagttg ctctctgctg aatctagatc tctgggctc tgccagcctg     480 ggggagcatg cttggttctc ttggtggcat ctgtccctca ctagctacgg aggacctgag     540
ccagacatca ccctggctgc ggtgttccat gtctcacaga tagcccagtt cagggaggcg     600
```

```
acatgcccaa gagtgctcag ttagctggtg tcagaactgg gccttgaacc ttggtctgcc      660
cacctccagg tctcactcat tcccttcttt caataatttg ttagtatttt ttttttttaac    720 tcctgggctt aagcatcctc ccacctcagc ctccagagta gctgggactt acagacatgt      780
gccatttctc ctgagacttt gaccagctgt gttgtagaac agggaagcag ggcaggagaa      840
aagggaaaaa tgacaattct gtggggaggc agggatacgg acccatgaca gaaatactcc      900
cagaaagact ttttctttga ctaaagcaga cttttctcagg cttttttaacc ctgacgcctt    960 catgatgagc ataacatgat aggggtcat gagatttgca tctggaactt taacaaaata     1020
actgaattaa atattgggtc taaaagccaa tcaaagcaat tacaaacttg agatgccgg     1080 ttcatggggc tgctgcttct tcctgggtta tgctgtacct cctcctcctc tccactgcga    1140
actacctgta ccaggatttc cccttggtt tggggactg tattatttag tgttttaatg     1200
actgaagagt gtttacaaag ctgcgagagc caccatgccc agcctgaatt tgttttttgt    1260
tttttgtttt tttgtttttt tgcttttttg cttttctttt tttgagatgg agtgttgctc     1320
tgttgcccag gctggagtgc agtggcgcga tctcggctca ctgcaacctc tgcctcctgg     1380
gttcaagcga ttctcctgcc tcagcctccc aagtagttgg gattacaggc gcccactacc    1440
atgcccggct atttttttt tttttttgt attttttagta gagatagggt ttcaccatgt    1500
tggccaggct gggctcaaac tcctggcctc aggtgatctg cccgcctcag cctcccaaag     1560
tgctaggatt acaggcgtga gccaccatgc ctggcccttt tttctttttt ttttcttttt     1620
ttgagatgga gtctctctgt caccaagtct ggagtgcagt ggtgtgatct cagctcactg     1680
caacctctgc ctccgggatt caagcaatta caggcataat tgctgggatt acaggcacct     1740
gccaccatgc ccggctaatt tttgtatttt tagtagagac ggggtttcac catgtttgcc     1800
aggctggtct cgaactcctg acctcaggtg atccacctgc cttggcctcc caaagcgctg     1860
ggattacagg cgtgagccac cgtgcccagc cacaaggctg catcttaaag cgattgagaa     1920
cgtggcctga atgaggatgg gagtctcttg aaggcctgcc cacaggtggg aggctcagca     1980
gttgggaagg accccacccc cagccagctt tgtgttcacc tttcccatttt cctcctcagc     2040 atgccccagg atttgtcaga ggccctgaag gaggccacca aggaggtgca cacccaggca     2100
gagaatgctg agttcatgag gaactttcag aagggccagg tgacccgaga cggcttcaag    2160
gtatgtggct tggtgggact agccctggtg gaggtgtgg caggtgtggg tggacccaag     2220
gctcagacca gtggtttaag tggggatgct gagggaccag atgggcatgt ccaatagaat     2280
catcttaaaa atgatgacac tgaggctcag agagggaagg tgagttaccc aaggtcacac     2340
agcaagttca gcctgctctg taatgttgtg gaggggctgg ggcagcagtg ccgttgactg     2400
agcaccggtt ccatgttggg cattttgtac acgtggtttc taatctgtgc ttcaaccctg     2460
acgagaaaga tgaggactgg aaggctcaga gaggttcagt gactaacaga aggtcacaca     2520
gccagtaagt ggaaaaggct gaaatcaacc aagaccgatt tcagccttgt actccttgta     2580
tttcagagct tgtactcctg atctaactcg aatttgcctc tgaagataag gaataatata    2640
ggttggagtc ttaacagaac ccttttctaa cagtgagact gagggtgcct catctaatct     2700
ccctaagcca cgttttcccc atctgtaaaa gagtatttca acagcagggt ttcttaagc     2760 acccactata tgccaggtac tgattttgct gtttcccagc actgttgtga aattcatgca     2820
aatagaagga aagcacttga tgaagaaccg ggaagatact gggtgttaaa acatcagcgt     2880
ggggaagagc ttgttcaggt tgaacagagg gtgtgggggt ggggagtagg gagctatatc     2940
ccaccacctt catcccagtc ccttttgcaa tctgcaccct ctgccacccc ctacttccaa     3000
```

| | | | | |
|---|---|---|---|---|
| catgagacat | gctttattta | ttttatttta | tctgagacag | agtctcactc tgttgtccgg | 3060 |
| gctggagtgc | aatggcaaga | tctcggtgcc | ctgaaacctc | cgcatcctaa gttcaagcga | 3120 |
| ttctcctgcc | tcagcctccc | aagtagctgg | gactacaggt | gcccaccacc acacctggcc | 3180 |
| aattttgta | ttttttagt | agagacaggg | ttttaccatg | ttggccaggc tggtctcgaa | 3240 |
| ctcctgacct | cagatgatcc | acccgtcttg | gtctcccaaa | gtgctgggat tagaggtgtg | 3300 |
| agccaccacc | cggccgagac | atgctttaat | gaggagagat | ttaatctgtg gttccaggct | 3360 |
| gggtggggtc | cttgggcctg | taatgggtct | tcctcatcct | cctcccctct cccttaaaaa | 3420 |
| gatgaggtac | acccagttgc | tgcagtgtga | ctggagacag | tgggtgcagg gaggtgaatg | 3480 |
| ctggaatatc | ccatccccag | ccagcttaga | ctttggattt | tgcctctaag tcacagggtt | 3540 |
| ctaaggaggc | gccaagatcc | atgagagaat | ccagtgctca | cttacattaa gctggtggac | 3600 |
| gtggcactta | tcacagccct | tctcatgtga | gcgctaagtg | ccaggctgcc ctctgtgctg | 3660 |
| gcccagatcc | tctcacttaa | tcctcacacc | agcccatct | agtatgtggc aggtgaggga | 3720 |
| actgactagc | acagttggct | agcacagtca | cacggacctc | agatcatctg ctctaggata | 3780 |
| ggataggaag | ctgggaccag | agaaagcaag | tggctcaccc | atggtcacac agttaaggac | 3840 |
| tggcagagtt | gggtaagaac | caggtccgtc | acactcaaaa | acccaggctc ttttgtacca | 3900 |
| gactgcctgg | ctttctgtcc | cctcaaggaa | tagagctgct | ttgaatgttt gtggctcaga | 3960 |
| aataactcag | aaactccaac | ctaaatgtct | taactttgtt | ctccttcaaa tttaaacggg | 4020 |
| cgtattaatg | tgtaacggga | gttagtgccc | caagccaagg | tacactcaag acctgttgcc | 4080 |
| tcagcccagc | atgcagaggt | ggtggggttc | agaataggcc | tccaggaagg agaattgtgc | 4140 |
| cctgtagttg | gttacgcaga | ggtcaaaagc | cagaagcaca | tggccaatct cctttaagca | 4200 |
| cttctcatttc | agctgttccc | ctctcctgag | ccatggtggg | tccctggcaa tgcccggtct | 4260 |
| tcaatctagt | ttcatttctt | actagctgtg | caacctccat | gtctcatacc ctctctgagc | 4320 |
| cttagttcc | ttttctgtaa | aatgggaata | gcaattcctt | tgttggattt tttttttt | 4380 |
| ttttctgag | acagggtctt | gctcactctg | ttccccaagc | tggagtacag tgatatgatc | 4440 |
| acagctcact | gcaaccttga | aatcctgggc | tcaagtgata | cccctgcctc cgcctctgga | 4500 |
| gtagctggga | ctataggcat | gcaccccac | agccatacct | ggctttttt tttttttt | 4560 |
| ttttctgag | tcaaagtctt | gctctgtcgc | ccaggctgga | gcgcaatggc gtgatctcgg | 4620 |
| ctcactgcaa | ccactgcctc | ctgggttcaa | gcaattctcc | tgactcagcc tcccgagtag | 4680 |
| ctgggattat | aggtgcctgc | caccatgcct | ggcaatttt | tgtgttttta gtagagatag | 4740 |
| ggtttcacca | tattgcccag | gctggtctct | tggccaggct | ggtctcgaac tcctgatctc | 4800 |
| gtgatccgcc | tgcctcagcc | tcccaaagtg | ctgggattac | aggcgtgagc caccgcgtcc | 4860 |
| agctggctag | tttatttat | tatttattta | ttttatttta | ttttttgag acagaatttc | 4920 |
| gctgtgttgc | ccaggctgga | gtgcagtggc | gagatctcag | ctcactgcaa gctccacctc | 4980 |
| ccgggttcac | gccattctcc | tgcctcagcc | tcctgagtag | ctggaactac aggcgcccgc | 5040 |
| caccacgccc | ggctaatttt | tttgtattt | taatagagac | ggggtttcac cttgttagcc | 5100 |
| aggatggtct | tgatgtcctg | accttgtgat | cctcccgcct | cggcctccca agtgctgggg | 5160 |
| attacaggcg | tgagccaccg | cacctggccc | cagccagcta | gttttttaaa ataattttt | 5220 |
| gtagaggtgg | gttttgggct | atgttgccca | ggctggtctc | agactcctgg ctttaagcaa | 5280 |
| tcctccagcc | ttagcctccc | aaagtgcagg | gattacaggg | gtttgagcca ccacactggg | 5340 |

```
ccagtttgtt agatctttat ataaggattc aattaggctg cttgttttgc ccagtggggt    5400
aaaaggtttt taggctgaga aagtgcatga tcgtcttttc ctcttgtaaa aaccectctg    5460
gctgctgtgt gaagaggatt gtagcgaggg gtggcagaag gagtcagagc ccagctgcga    5520
agtgaggagg gcctttccaa aggcagtagt ggacgggacg gacagaggtg ggggtcttct    5580
atgtggctgg cggcctgacc tgctcactct gctttcagct ggtgatggcc tccctgtacc    5640
acatctatgt ggccctggag gaggagattg agcgcaacaa ggagagccca gtcttcgccc    5700
ctgtctactt cccagaagag ctgcaccgca aggctgccct ggagcaggac ctggccttct    5760
ggtacgggcc ccgctggcag gaggtcatcc cctacacacc agccatgcag cgctatgtga    5820
agcggctcca cgaggtgggg cgcacagagc ccgagctgct ggtggcccac gcctacaccc    5880
gctacctggg tgacctgtct gggggccagg tgctcaaaaa gattgcccag aaagccctgg    5940
acctgcccag ctctggcgag ggcctggcct tcttcacctt ccccaacatt gccagtgcca    6000
ccaagttcaa gcagctctac cgctcccgca tgaactccct ggagatgact cccgcagtca    6060
ggcagagggt gatagaagag gccaagactg cgttcctgct caacatccag gtgagggtcg    6120
ggcagcctgg ggcagcctct gcctcccccc gttgttcctc caagggaccc ttctcattgt    6180
aggggagggt gctataggtc atggttaaca cagggaacca gagttccagc actgccactt    6240
actagctggg tgatcttggg caaatgcctt catctctctg tacctcagtt tccctatctg    6300
taaaatagg ataataatgg tacctatatc ttagacttat aaggcttgag tgaatttaca    6360
gcagtaaagt ccccacagca gtgtctggca cagaggaagc cctcaaacat tcactactgt    6420
cataatggga catgagaatc agttgtagct ctctgtgaca acagtctgtg gcaatgtata    6480
agttgtgtgt gcactagtgt atagccaggt tggcactccc agggttacag gtggcctctg    6540
ccttccaggc actctcagcc tagccagaga ggtttacctc tttctacaag tgtctcaaat    6600
ccaggggaa ggtggggttt gcgcaaagcc tggaaggatg aattcttggg cagaggtgga    6660
ggggtgaggg gctccttcta accagatgtc atagagcctt ctctctctgc cacccctgg    6720
aggtgccatg gggcctgggg ctcggggtca tgccctcctg gctccctact cccagccgtg    6780
gattgcagaa gattctggtc ctggcccctg ttacggaaca aggcctttcc cttccaccct    6840
cccccttcag aaaatccagt ccgtcttgga ggaagaaaat ctgtgtcttt cagagaagtg    6900
taggcaaaag aaaagggcca ggtgcagtgg ctcgcgcctg taatcccagc actttgggaa    6960
gccgaggtgg gcggattgct tgagctcagg agtttcagac cagcctgagc aacatggtga    7020
gaccctgtct ctatcaaaaa taaaaaataa aaaaaatttt aaaggaaaaa aatgttttta    7080
aaagaaaagg gatttggaat cagaactggc tctcaggctc gtgcctataa taccaacact    7140
ttgggaggcc aaagcaggaa aatggcttga gcccaggagt ttgagaccag ccctggcaac    7200
acagtgagac cccatctcta caaaaacatg aaaaaattag ccagacatag tagcgtgcac    7260
ctgtagtccc agctacttgg gaggctgagg tgggaggatt gcttgagccc aggaggtcaa    7320
ggctgcagta agccatgatt atgctactgc actccagcct gggcaacggc aacagagcaa    7380
gactctgtct caaaaaccaa aaaaacaaaa acaaaaacaa aaaaaacgg ctcttggctg    7440
gccgggcgtg gtgggtcacg cctgtaattc cagcactttg ggaggccgag gcgggtggat    7500
cacgaagtca ggagatcgag accatcctga ctaacacggt gaaacccat ctctactaaa    7560
aaaagaaaa tacaaaaaaa attagctggg catggtggtg gcacctgta gtcccagcta    7620
ctcaggaggc tgaggcagga gaatggcgtg aaccgggag gcggagcttg cagtgagcag    7680
agatcgcgcc actgcactcc agcctgggag acagagtgag actccgtatt aaaaacaaaa    7740
```

```
aacaaacaaa aaaaaacggc tcttagtgcc tgacctctgg atcagtcctt gggcaaagca   7800
cttaacctgt aggagctaca gtttcctcat ctgcaaggct aacaaatacc attcagcaca   7860
cctcaccaag gctgaatttc acaaatctaa actcaagaga agaaagcagc ggcagaagag   7920
tgcatgtact aggataccac ttaatattat ttcaaaacaa gcaacgcagc cttttgcatg   7980
gagacacagg ctaaggacat gggcggccac agtgaactct aaatccagga tcattgttat   8040
cggttgggag ggcaagagca ggcagggag ccaattgggc ttggaacatc ttatctctta    8100
aggtggatga aagggatatg aattttcttt cttttcttt ttcttctct cttctttct      8160 ttctttcttt cttttctt cttttctctc tctctctc tctctctcct ctctctctct       8220
ctcttctttc ttctttcttt ctttctttct ttcttcttc tttctttctt tcttctcctt   8280
ccttccttcc ttccttcctt ccttccttcc ttccttcctt ccttccttcc tttctttctt   8340 tctttcttc tttctttctt tctatctttc tttctttctt tcttttcttt ctttcttgca   8400
gagtctcgcc ctgtcacccg ggctggagtg caatggggcg atcttggctc actgcaacct   8460
cagcttccca ggttcaagca tttctcctgc ctcagcctcc cgagtagctg ggattacagg   8520
catgcaccac cacgcccggc taattttttg tatctttact agagatgggg tttcactatg   8580
ttggctaggc tggtctcaaa cttctgaccc gtgatgtgcc catcttggcc tcccaaagtg   8640
ctgggattac aggggcgcac caccgtgtcc ggccaatatt tttcttacca tcttgttatt   8700
tccaaagtat ttcctaacac aacttaaggt cctaccttca gctgggacct ggtagcatct   8760
ctcactgaga taggcatgtg tgtcttttgt cttttagctc tttgaggagt tgcaggagct   8820
gctgacccat gacaccaagg accagagccc ctcacgggca ccagggcttc gccagcgggc   8880
cagcaacaaa gtgcaaggtg agagcatcca ggaaggggca cttcctctgg gctacacatg   8940
gagggacttg gctgtctgac tgtagtatct ctattcctct gttttctgaa tgtttggtgg   9000
tggtgggtgt tgtttcctgc tgccccaccc cactgcccct gtaaggacag gttctcgcta   9060
tattgcccag gccagtcttg aacacctgac ttcaagcaat cctcttgcct ctgcctcccc   9120
acatgctgca gttacaggcg cgagccacca tgccagcctg aatgtttgtt gttgttgttg   9180
tttgagatgg agtctcaccc aggctggagt gcagtggcgc gatctcagct cactgcaacc   9240
tctgcctccc gggttcaagc aattatcctg cctcagcccc ccgagtagct gggattacag   9300
gcgcccacca ccatgcctgg ctaatttttt ttttgtatgt ttagtagaga tggggtttca   9360
ccatgttggc caggctggtc tcgaactcct gacctcaggt gatccgccca ccttggcctc   9420
ccaaagtgct gagattacag gcgtgagtca ctgtgcccgg ccacctgcgt gttttttgtat  9480 gagaagtgga gtgcaggcaa aaggacctgg ggtcaacctt cagcgtgtgg ctctgggcaa   9540
gccatgagac ttctccctac ctcagtttcc ccacccgtaa atccagtgaa ggttcagcta   9600
cttctagctt attggctcag aagtgcacaa gaacccctca gaaatcatgg gaaactcctg   9660
cctccttaat ttagactcct ttttaggcct ttggtcccct gatgtgggcc agggagttgg   9720
ggacctgtat ccagctatga acccaccaca ggaagatgtc ccttctgagt cttgttgtgt   9780
gtgagcccct ccctcatgtg cctaagaacg atcaaggctg gctgtactga aacatcttgg   9840
aaacttccaa aaagaccaaa gtgctccaca aaatgtaccc tcactaagcc taaaacactg   9900
agggagggag tgtggctttg ggatgggtag caataaagag gtaaggctta gctacctcct   9960
ggcaggttat attaggcctc ccctcctgtg ccacccctaac ctacctggct tgtggctttc   10020
tcacttgtgc cagaccacac ggacccctct gctagggggtt tgtaacccg gagggcttgg   10080
```

```
ctatttggtg gggtagggag acgtcaccct aatgaagcag ttctcaaagt gtggtaccct   10140
ggctgtggga ggtggtaatc ctagtatccc ctcaacgggg tctgtgagga caaagcattt   10200
ttataacact actactattt ttttggtttt ttttttttcg tttgagacag tcttgctgtc   10260
acccaggctg gagtgcagtg gcatgatctc ggctcactgc aagctccgcc tcccaggttc   10320
acgccattct cctgcctcag cctcccgagt agctgggact acaggtgccc gccaccatgc   10380
ctggctaatt ttttgtattt ttagtagaga cggggtttca ctgtgttagc caggatggtc   10440
tcgatctcct gaccttgtga tccgcccgcc tcggcctccc aaagtgctgt aattacaggt   10500
gtgagccacc gcgcccggcc ttttttttt ttttttttt tttttgagac agggtctcgc    10560
tctttcaccc agtctggagt gtagtggcac aatcacagct cactgcagct tcaacctccc   10620
aggttcaagg gattctccca cctcagcctc ctgagtaact gggactatag gcacgtgcca   10680
ccacacccag atttttttt ttttggctt ttttaaaaa agccaaaaat aaatgagaaa      10740
attagagttt cacttctca tgaatgtgtg ttggcatttt ccaaaggtta tgtgacatgt    10800
gatgctctct catggatttg atggctcatg gaatgtgtgc ctgtatgttc ttgtatgtta   10860
agaatttctc agttttggcc gggcacgatg gctcatgcct gtaatcccag cactttggga   10920
ggctgaggca cggggatcac ttgaggtaag gagtttgaga ccaacctggc caatgtggtg   10980
agacccatc tctactaaaa tataaaaatt agctgggtgt gatggtgcac acctgtaatc    11040
ccagctactc gggaggctga ggcaggagaa tctcctaagt ccgggaggca gaggttgcag   11100
tgagccgaga ttgcaccact gtactccatc ctgggcgaca gcgagactcc atctcaaaaa   11160
aaaaaaaaa agaagaaaa gaaaagaaaa agaatttctc agttttaata tctaattttg     11220
taaatagtga tagctatact cacacaaaca aaagctcttt tggatccttg gttgcatttg   11280
agtataaagg agttttggaa ccaaaacatt tgagaactgc acccctaatg catcagaagg   11340
agcaggagcc tttaatatga acaacacaca tgtaaatgtc acagtgtacc tgcttgcttg   11400
cttgcttgct tgtacttcct gtgaccgcag ccctgggcca ccagacctaa ggccctgttt   11460
tctctgggga agcccttctc atagcccagg gcggggctag gattgaaacc cagctggtct   11520
ggctccagag acctgccctg gactctgtcc tgcttctaaa gacctaggga gcacccactc   11580
tgtgcctgag gaggcaggtg gcacatctac ccaggttgca tggttggctc tggcctatca   11640
tgttttaaat ctttttttt ttttttttg aaatggagtc tcactctgtt gcccaggctg     11700
gagtacagtg gcgcaatctt ggctcactgc aacctctgcc tcctgggttc aagcaattct   11760
ctgcctcagc ctcccgagta gctgggatta ctggcactcg caaccatacc cggctaattt   11820
tttgtatttt tagtagagac ggggtttcac catattggcc aggctggtct tgaactcctg   11880
acctcgtgat ccacctgcct tggcctccca aagtgctggg attacaggcg tgagccactg   11940
cgcccggccc tatcacattt taataaccag ggatgggact gaacttgaat tttgacctca   12000
gagctcctgc tttctagctc ctgccccatc atcaccatgc ttagcaaacg tgtgagtttg   12060
agaggaagat ttacagctca gacctaattg ctggcaaagt ttaaggagag acagggagc    12120
aggcagaagt ctgaaaacca cgcctgggcc caagaatgtt ttcacaatgt ggcctggctg   12180
cacagggaag aacagacagc ttgaagaagt agtgagctgc cgtctttga aggtattcaa    12240
gcagtggcta gagggacacc tgtctgtggt cttgcagaat cctggcgttg ggcagtgact   12300
gtaccacaga ccctgaggcc gctctgcttt gctttcctat gacatcagac acctgatgc    12360
acgcccacct gttaatgacc ttgccccatt ttctctttca gattctgccc ccgtggagac   12420
tcccagaggg aagcccccac tcaacacccg ctcccaggct ccgcttctcc gatgggtcct   12480
```

| | | | | |
|---|---|---|---|---|
| tacactcagc | tttctggtgg | cgacagttgc | tgtagggctt | tatgccatgt gaatgcaggc | 12540 |
| atgctggctc | ccagggccat | gaactttgtc | cggtggaagg | ccttctttct agagagggaa | 12600 |
| ttctcttggc | tggcttcctt | accgtgggca | ctgaaggctt | tcagggcctc cagccctctc | 12660 |
| actgtgtccc | tctctctgga | aaggaggaag | gagcctatgg | catcttcccc aacgaaaagc | 12720 |
| acatccaggc | aatggcctaa | acttcagagg | gggcgaaggg | atcagccctg cccttcagca | 12780 |
| tcctcagttc | ctgcagcaga | gcctggaaga | caccctaatg | tggcagctgt ctcaaacctc | 12840 |
| caaaagccct | gagtttcaag | tatccttgtt | gacacggcca | tgaccacttt ccccgtgggc | 12900 |
| catggcaatt | tttacacaaa | cctgaaaaga | tgttgtgtct | tgtgttttg tcttattttt | 12960 |
| gttggagcca | ctctgttcct | ggctcagcct | caaatgcagt | attttgttg tgttctgttg | 13020 |
| tttttatagc | agggttgggg | tggttttga | gccatgcgtg | ggtggggagg gaggtgttta | 13080 |
| acggcactgt | ggccttggtc | taactttgt | gtgaaataat | aaacaacatt gtctgatagt | 13140 |
| agcttgaa | | | | | 13148 |

<210> SEQ ID NO 10
<211> LENGTH: 22423
<212> TYPE: DNA
<213> ORGANISM: human

<400> SEQUENCE: 10

| | | | | |
|---|---|---|---|---|
| attgtcttcc | aggaaacagc | tccctcagtt | tggaatcagc | tctcccgctg cggccgcagt | 60 |
| agccggagcc | ggagccgcag | ccaccggtgc | cttcctttcc | cgccgccgcc cagccgccgt | 120 |
| ccggcctccc | tcgggcccga | gcgcagacca | ggctccagcc | gcgcggcgcc ggcagcctcg | 180 |
| cgctccctct | cgggtctctc | tcgggcctcg | gcaccgcgt | cctgtgggc ggccgcctgc | 240 |
| ctgcccgccc | gcccgcagcc | ccttcgctgc | gcggcccctg | ggcggccgct gccatgggca | 300 |
| ccgacagccg | cgcggccaag | gcgctcctgg | cgcgggcccg | caccctgcac ctgcagacgg | 360 |
| ggaacctgct | gaactggggc | cgcctgcgga | agaagtgccc | gtccacgcac agcgaggagg | 420 |
| tgagcgtggc | gacactcgcc | gcggggctcc | cggggcaggc | ctcgggcggg gccgggcggt | 480 |
| tccggcaagg | gagaagcgcc | cgcgggcgag | ggagggtggc | agggcctcgc gcgcacctgg | 540 |
| gctccgcccg | cggtcagatg | ctgaggccag | tgtcgacgcg | accttgggtc caaacccgct | 600 |
| gccgagggca | acgcgtctaa | aaaacttagc | cggtgcagct | gcgcactgag tgacacctct | 660 |
| ctcggtgctt | aaggctggta | gcaaaactct | caaacatcct | gggtccctct tcctggcacg | 720 |
| gaggtcacag | agggccagga | cgtcgctccg | tctctctcca | catctctcgc ttccttcccc | 780 |
| caccctgtcc | aggtaaagga | atattttcgg | agattatcct | ttggtgcatt cagatgaagt | 840 |
| agtattcata | gtacacctaa | cttttagaat | gttgacatta | gactctctat tgcagtgagg | 900 |
| caaatgagta | agcactcaat | tttggctttg | gaatacccta | aatacctga ctttagtcat | 960 |
| tacacatttt | atgcacttat | ctgtgcgtct | atgtatgctt | tatcagtaca cattctatgc | 1020 |
| atgtaacaat | atcattgtac | attctatgca | tgtaacagaa | tatcacatgt gccccataaa | 1080 |
| tatgtacaaa | tataatctat | caattcaaaa | attaaagtttt | tgtaaaaact ggaaaataaa | 1140 |
| aagactagtc | actagttgga | ggtgacagag | attaatctgg | aattacaaac ttgttaccta | 1200 |
| tttgttggcc | atttctgagc | ggatagtcat | ccactgcaca | ttgtgcatat tggtggtatg | 1260 |
| ggacaatttt | agtatttaaa | aaataacaaa | atctttagat | ttaggagcta tatgactttg | 1320 |
| gaaaattact | ttaaagttgg | ataataacac | cttcctcatc | aggttgttgt gagaattaag | 1380 |

```
aggtaatata tgaaaacgct caccatgcag gcatctatct ccctgtcatc tggttccatc    1440
agaaagataa atcttaatta agagaaaaac cttcctaaac tatgtgtgtt tagaaaaacc    1500
ttcctaaatc agctgtgttc ctaagtggtt tctgctctct tctatgagat gttggtaaca    1560
gaccatgcag cagcacacgg catccctctg agttaagtgc tggacctgtg cccaggcctg    1620
ttgttggggt cagtgcccat caagagatga gaactcttgc ttgtaacttt agtaggaatc    1680
tgagtctgta ccatattctg tgttcacgtt ccagctcagt gtgtatgttt tgttttattt    1740
aaaccaccta ctttggctgt ttctcccaca gataaatatt tctgtattcg gtacatagac    1800
tcttaatttc ttccagtact gttggtggta gttcaataca gaattttgca cgtatattga    1860
tattattggg tgaaatttta cctatctcac aatagcatac tctaaagtag tgactcaaaa    1920
gagtttctga ctgcaaacac agtaagaagt acatttact ttgcaatcca gttaatagtt    1980
gtataatcag tatatctgaa acaggtttca caaaaagata ttagccctta taccgtatat    2040
tctgattttt tcttttattt taattttta aatgttgatt tcttgatgct cagagtcaca    2100
caccacagtt tgtaaaacat tgttcaaagg actaattctg gtttctagtg ttttatttag    2160
ggtgcttcat aacagtagga taaaactaaa gaaactagaa acatttcag gaaaacttga    2220 aggaatggca tcatactgta gggaaactat gactgcttgg taagagcaaa aggggaggca    2280
cattttgttt ctatgtaaaa gaactttgta acacccagag ctccaaattg ggatgtacta    2340
cttggaacag ttccgcttca ctgaagaaat taagtaaact gaacaaatca cttattttg    2400 agaaaatgta cgtgttgggt caagagttca gttaaatttc ttacaaggtc tcttctagtt    2460 ctaattttt aaaaaatgtt atgacctctg cccagatttt ttgtctcact ggaatttat    2520 gaaatcaaat agtttgtaag tggaccatta taggactgtt ttgcccagtt ctttgttgta    2580
agggtgtttg accggttgaa tcatggtatt taaaaaattc ttatacaact ccagatctaa    2640
tggtaggcta agttgtggtg atgcttatac tcagtgatat tgggtgtgta ttataagaat    2700
gaagagagcg gagaacaaac ataaacatta atgttaatga caaacattaa cccaagtaca    2760
aggttaatgt ttagtcaata tagcaaacat gtaatttaca agattaaaaa taattaggct    2820
tgtgataaag tcaatgaatt tcctacgtaa ttgtaacatt agactgtttt attatttgtc    2880 ctgcatttt gcagaatcca agattaatta agaaatggt ttcaagaaga gggtgaatac    2940
tataaaaata gacttacctt cctgaattga ggaattcatc aggaaagcct caagtgtgca    3000
aatgagccat ccttccagag ggaaatttct tagaattatc ccacgatttg agccaaagca    3060
cttccgatag aattttaac ctctagttgg ttctgctcct tccatttta ctaattttta    3120 agaaaatact atgacttata attgtatctg gaatgattat caactccttt tcatccactg    3180
acttaaattt gattataaat atgctttaca taaagatcta gaccttataa tttgaattca    3240
agtgaattgt tgtgactagc atgtaaatta ttattatgga ttgtaaatct taacataggt    3300
agttctgtgc ccttaaattg ataaaccagt tatctcttgt aatcatgtgt actaagatat    3360
acgtagtaaa gtgattgtat cagttttat cataagcagt catagttcag atagttcaga    3420
agtttagtgt ctgctgtttc tattaggaaa gtgcttttgc aattcagggg cttgcctcta    3480
gttactcatt tgtgttttca ttgattgccc acagaagaat gcaaacact gtgtccttgg    3540 ttatctaata aggcagtgat ttcagattgc caggtttggc ccattagtgg tcataaatca    3600 gtcagtgag tcatggacca gtatatttt tctaattaat atattggaag ccattagagt    3660
gcctggcatg ttgtgagcat aaataccgct ttatgactgt tttgttccat tatatgtata    3720
taggtctttg ctcactatgt gaatgtatgt cttactttgg actactatca aataagtctg    3780
```

```
aaatacactt taataaagta tgtttgaatt aatttacaac atactataat atttgtataa    3840 atttttttt gtttatctaa gaaaacatgg aagataggtt agaggtgcac ctaaatgtta    3900
cgaaatgact tctggagtgt catacaagtt gagttctgca agatatgtct atcctggtgg    3960
ttctcagact ttagagtacg tagataaagt actctcctta ggatgcttgt taaaatgaaa    4020
gtccaaactg ctcttggaga atgattcagt gggtctagga ttaggctcag gagtctgaaa    4080
ttttaataaa cagcacaggt gaatctgagg taggatttac cagccacact tattctctaa    4140
taatttaatt tgtttgtctt tgagaaatgt agcatagttg tgatatgaat tctagtcaga    4200
cagcctgggc ttgactccaa gttcctttgt ttataaacct tatttttgtt tctttatgaa    4260
tgcctttttt tttttttttt tttggaaata gagtcttgct ctgttgccca ggctggaatg    4320
aaatggcatc atctcagcac actataacct ccacctcctg ggttcaagca aaattgtcct    4380
gcctcagcca cccgagtagc tactacaggc ttgcactact aggcccacat gattttttgta    4440 ttttagtag agacagggtt tcaccatgtt ggccaggctg tcttgaact cctgacctca    4500 agtgatttgc cccctcagc ctcccaaagt gctgggatta caggcatgag ccactatacc    4560
tggcctatga atgcttttgt gtctcaacag ttagcttaaa ttttcactgg tacaaaaaaa    4620
gctttaaagt aattagacaa cttctttagt tcaagaacat ttgagaaaca agagtaggat    4680
gaaaacaggc ctgaatttat gtatgttgaa ggaaacaaaa accttgtagg attaaaattg    4740
gggtttgtat ggtatttcct gttgctatct ttttttttcct gcttatcaaa ttaatatatt    4800
cttattgtag aagtacagaa aagtatatag actttgatta acagtttcaa aatgcattcc    4860
ttttgcagct tcatgattgt atccaaaaaa ccttgaatga atggagttcc caaatcaacc    4920
cagatttggt cagggtaagt gaaatgtgaa tgcaaaaatc atgcaggtca aaaaggaagt    4980
aaagtaaaca ggaagttaat ttcttcagtt ttgtgaggga agtcaaatag gcaattagcc    5040
ataaactctc tgtggttgat ttgctgagac ggcactctga tccagtaggc ttatgcataa    5100
aacagaaaat ctagaccgta ggcaactctt taaccagaca agatactagg attctcatgc    5160
ttaattctca ccatggtttc ctcactatca gtgttttatt tcagtttata tttggtctag    5220
gagaggaatg attatcaatt gtgattggta gattgcttta gtagactcaa catcactaga    5280
agtaattttt caaatgtcag tttctgatga aacaataagg aactgtgttc cactaaatgt    5340
cagtatatgg ctactatcat aaatgttaat gttcaaaacc ctaaaacaca ttttgaaatc    5400
caactcagtc aaaggctcac agcacattac ttaggctact ttaaaagtat ggaaaaggac    5460
atgtgctgga aatactggtt cccctgggca tactgcaacc atgtaactct atagctacta    5520
tatagacatt gagttatggt ttttttttaaa tcaatctctg tttctctgaa atgactgttt    5580
attctactta tgcttgactt gtaaacactt actgaacccc tgatacgtgc tgtgaaagtg    5640
ctcaagaatc atgggaaagc ctttgccgtt tactttgtat gatattgtaa atgtaagtta    5700
atatgtatct gatttatatg tactaatatt ttctcattat ccttgtaaat tattcattaa    5760
aatacattca aatagccttt gctttttttct gctgcactca ggaaaaaaaa agttttggtt    5820
tacaatgctt gtgattacag gctgggcgca gtggctcacg cctataatcc cagcactttg    5880
ggaggctaaa gcaggtagat cacctgaggt caggagtttg agaccagtct ggccaacatg    5940
gcgaaacccc atgtctacta aaaatacaaa aaaaaaaaaa aagccaggcg tggtggtacc    6000
cgcctgtaat cccagctact cgggaggctg aggcaggaga atcacttgaa cctgggaggc    6060
agaggttgca gtgagctgag atcacaccac tgcactctag cctgagcaag agagtgagac    6120
```

```
tctgtctcaa aaaataata ataataaat taaataaata aataaataag aataaaatgc    6180
ttgtgattat aaaactaaat atactattgt cataaaatca gcaattatgc tccttagtat    6240
ctacccaaag aagctaagaa cttatttcca cacacagacc tatgcatgga tatttatagc    6300
agctccattc ataattgcta aaatttgaag caaccaagat gttcttcagt aggcgagtgt    6360
atatataaat tatgaatgca tatataaact atccagacaa tataatatta ttcagtgctt    6420
aaaagaaatg agctatcaag ccatgaaaag acatagagga aacttgaatg catatttcta    6480
agtaaaagaa gccaatctga aaaagctaca taatgtatga tatcaactat ttgatattct    6540
ggaaaaaaca aaactatgta gactatagtt ttgctagtct agtaaaaaaa actagtaaaa    6600
agatcagttg ttgccagggg ttagcaggga cggagggatg aataggcaga gcacaggatt    6660
tgtatgtcaa tgaaactact gcatatgata ttgtaatggt ggatacatgt tattatatgg    6720
ttttctaaat ccataaacta tgcagcacca agagtaaacc ctaagataaa ctggacttgg    6780
gtgattatga catgtcaatg taggttcatc aagtgtaaca aatgtatacc actgtggtgg    6840
gtatgttgat aatgggggag gctgtgtgga tgtgagtgta gggagtgaat gagaaatctg    6900
ttcaatctac cttctacttg atattcttgt gaacctaaaa ctgctctaaa aaaaagtat    6960
atttaaaaaa aaaaaaacag gctgggcgcg gtggctcatg cctgtaatcc cagcactttg    7020
ggaggccgag gtgggcggat cacaaggtca ggagatcgag accatcctgg ctaacacggt    7080
gaaaccctgt ctctactaaa aatacaaaaa attagtcagg cgtggcggcg tgcacctgta    7140
gtcccagcta ctcgggacac tgaggcagga ggaatggcgt gaacccggga ggcagagctt    7200
gcagtgagcc gagatcgtgc cactgcactc cagcctgggc gacagagcga gactctgtct    7260
caaaacaaaa caaaacaaaa caaacaaaca aaaaaaccca aaaactaaat ccccttacag    7320
gttaaagttc aaataacatt aaaatccaaa taaattaaaa agtaaaagaa aatgcttgta    7380
attaatgtag aacgtgttta ttatgtcatc tagagtggat attattttca ttggtttctt    7440
tttagagtaa aattatctgc tgtgctactg tttctaactc ctcacatatc cctccactgc    7500
ttgtttattt ttaattttt tgatcatgct tctttctaaa tacctggtca aaatgagata    7560
cattttccta gaaaatagat acacacacac aaacacacac acacacccca ctttacccttt    7620
atttcagagc tttacaaccc ttgtgaagcc cacccagacc tcaggtagag aactctgttg    7680
tcttataggt tctctgattc taaaaggcat tatggataat agaaaatttt ataattaatc    7740
agaagcatta aattttatat ttgttttaaa tattgtgttt attataggag tttccagatg    7800
tcttggaatg cactgtatct catgcagtag aaaagataaa tcctgatgaa agagaagaaa    7860
tgaaagtttc tggtaaagtc cagtcttttc tgtttatttt gttacatagc ggaagcgata    7920
gattttgtta ggcattagaa taagcctttc tttgctcaga cactaaatgt gggaaataca    7980
gaaattcttt tttagcataa ttttacttaa actccaagat ggagttataa gaggtcagtg    8040
ctggctatta tataagagtc agaatagaac ttcaacttgc tgttcttcat gatgatgtca    8100
tcatgtcatg taatttatgt gtcaaacttc agagcagtag aaagattaag atgaaggaga    8160
tggaaaggat aaagggaagg cttagaagca gcatccaccc aaagcaagca taagcaccc    8220
cttcctggta agatactggt aagcaatgtg tgaggtcacc tgggaatata aaagaaacc    8280
tgggcaagtt acatgaagag aaagaaaata ctgtaacacc cattcaggaa atgtagtaag    8340
tgacaaattc cagaaactgt actatactca aggaatacaa aaatgaaaag atgcgccatc    8400
tctgccctca ccttacaatt agcatagcat agtcattaaa agcttgagct ttgaagtttc    8460
ggggtgtgca gattacaggc tagtataatg ttgggctaac aaagacttta acctccctga    8520
```

```
gtctcagttt tctcttctat aaaatgggga tgtacctgtt tctccggctt ctttgtaaac    8580
tggatgaaat aacaaaagaa gcacttagca cagtgtttgc ctcaaagtaa gttctaggta    8640
gctattattt gctaccatgt tgttattatt gtggttgttg ctattttatt attattgaga    8700
tggataataa taataaatta catgtaagat gagatagggt attgtctctt tttaatctaa    8760
ttatagtaac taccatttat tgagtcttgc tttgtgccag gcactgtgct tggtacttta    8820
tggttatatt ttctcattta attctcaaga caatcctgca agttaagtct gttactgcat    8880
tgcattagtg atactaaata acttgaaggt tgtcatacaa ccagtaagtg gttgaaccag    8940
gaatccactc aggtatgcct aactccaaaa cccatttttt cctgttaatt tcacattgct    9000
gtttgtgttg gaaaggacgt aaagcaacat tctttctgag gttgactgta attcatgatt    9060
tagttccatc ttgggtctct tagaagtcct cagttcctag agggcttgag attttttat    9120 aggtatcaaa attctcccca tataaagagc tttcctcttt ctacctatcc aaaaaagcct    9180
catccttcag agagaagagg ccatttcaga tggcacaaat tcatggacag agaaatagta    9240 ttggggggggg ctttcataga gttatagggg ctaaagttag accaaaatag taaatactga    9300
ctctcatcta gtagagaagc taggatggct gttcaatagg gagtaatctc agggaagcag    9360 tgttttagg gagatcacct agcagtagga aggaagggac tcatataaga aacgtagaag    9420
aaaatgtgtt gcatatatcg aatgtcagca ctttatgtaa gggtatttca ttagccttat    9480
ttttctccat ttcctctttt gatttttttt gttgctcttc tgctactcta cctgtttgtc    9540
tattgaatac atttatttt ttgaacagtg agtttacata agtaaatat gtacatataa     9600 agttgaattt gaatgaaacc aaaacctcaa tattacaaat atagaaaatg actcaacttt    9660
cctagtaacc aaagaaatga caattaatgt ggtcttgggt aggtatgcat tgtacctact    9720
aagttttaaa aaaaattaa taatagcatc ctatgttgtt agaagagcaa ttgttaattg     9780
gtggtggtgt ggtaaactgg cacacatctt ttaaaatata ataagactca cacaaaacgt    9840
cacatgcttt gactcataat aacatttcta acaattcatc cctgggaaat tatatagtat    9900
aatgctgaat aaaaagttac taagatgttt gttttggcat tatatatgcg aaaacagaaa    9960
actggaacta gtactggaac atttactaac ctaaatgttc aataagtaga actcatttaa   10020
taaatgacac tcttcaaaat ttacaaaata atattcaacc attaaaaaat gagcatgtaa   10080
aattggctgg gcgcagtggc tcacgcctgt aatcccagca ctttgggagg cgagtcgggt   10140
ggatcacttg aggccaggag ttcgagacca gcctggacaa catggcaaaa ccccgtctct   10200
actaaaaata caaaaattag ccaggcatgg tggcgcaggc ctataatccc agctacttgg   10260
gtggctgagg catgagaatt gcttgaaccc aggaggaggt tgcaatgaac caagatggca   10320
ccactgggcg acagagtgag actctgtctc aaaaaaaaaa agtatgtaaa attatacact   10380
aaaaacatag aatacgttca aggccacccc taagtggaaa aaagccaca gaatacacag    10440 aaatctaaac agtaatttgg gtgatgagac tggcaattct ttttggtctt tctgcttta    10500 taggtcttcg ttatttctac agtaagcaca tgactattag gataaaaaaa atcttggcct   10560
ggtgtggtgc tgtaatccta gcaccttggg aagattgttt gagaccggga gttcaagagc   10620
ccctgggcaa catatcgaga ccctgtgtct acaaaaaaat gaaaattagc caggtgtatt   10680
ggtacatgcc tgtagtccta gctacttggg aggctgaggt gaaggaaca cttgagctca    10740 gaaggttgat gctgcagtga gccgtgatcg caccactgca ctccagcctg gatgaaagtg   10800
agaccctgtc tcaaaaaaaa aaattgtggt gattcacacc tgtaatcaca gcactttggg   10860
```

```
aagccgaagc gggagggtcc tttgaggcca agagttcaag gccagcctgg gcagtataat    10920
gagaccctgt ctctacaaaa aattttaaa agtaaagaaa ttttaagata actaaatact     10980
acatagacat atattttaaa tatttattac ataaaggtaa accaaataga agaggaaata    11040
atgttatgcc ctacttcata tgaccaaaaa ctggaagata gtgtctgaaa atgaaaatga    11100
ttgtattggg aaggtagaat tgtggccttt ttttttttt ttttttttt tttcagtttt      11160
cttctcatta cattttcaat ttagtctttg tatatagatt ttggtttatt ggagaatata    11220
taatgtgctc tattaatgtt taagtcataa aaatataaat ttcaagtaat ttaagctcca    11280
atagttatct aacctgcctt ctaataaatg ggaaataaat atttactttt tgttttgata    11340
aacatatatt tgttggcaac tagcacatga ttttaaaagt atagtggaac tatacattta    11400
tgtcttaaaa ttaaaactat aaagttatgt gactgggaaa ggaaaaataa ttcattcagg    11460
attatctgac atcttagtat tatagtagtg ttaatactag catatagtga aatgtgtatc    11520
caaatgtagt aatcagtttt gttttctttg ttacccagca aaactgttca ttgtagaatc    11580
aaactcttca tcatcaacta gaagtgcagt tgacatggg aagcaaaaac tgaattttt     11640
atcttaatag tggactttaa attagtatag gtgtattagt tataacttgt gcttaggtcc    11700
aggtaaaaag aaaatgagtt gattccaatt ttacctttta aagttctagc ttagtttctt    11760
aaggcttctg taaaatcata ctgacttatg tagggtcata ttttgatatg caagaggaat    11820
gtaaaaggtg taatgtactt aaatgttcac tatccgtttg gagatagaag ttcttattct    11880
tagccctttt agtactagag gtgaaatatc aaaaccaaac aacggcaaaa aaaaaaaat    11940
ccaaaaaaaa tccaagtata tctgttttta gcacttaggt tattgtgata ttaaagttat    12000
tcaatactta aataaaaaat tattccagta tttacatata ttgaaaactt aaataattgg    12060
ctctttaatg taactttaga atgaataatc atttaaaata agctcttaaa ttatttttat    12120
agaattaaga aattatctac ctctataaat atggattaag accaaacatt cagttttca    12180
gtgtctcaag cttattcttt gctgtgacta ctagttacag aatattaggt cataattctt    12240
gtgatcatcc atatgcgata gtagtgagca agtagaactg gagaagaaaa ttttatgaag    12300
ataagggagc tactaaaaac ttctgggacc taggaaacaa gaagaaattt tgttccctag    12360
aaagaggagc atgtagtagt agctgcaagc tgcctaggaa taaggcaggt cagagaaacc    12420
cacttgtctg ccacacagag caagtaggta aatgggcact tacacatttt tgaaagatag    12480
aaatgttcta aatgaaaagt aaactatgaa ataatctgtt attttgaaaa caagtgaaga    12540
atatggacag aattcagtgg gatactttga aaacattaga aatatttgtt tttatgatgt    12600
aagcatttat tttctttgtg tcttccttcc tatcagcctg ttcagtcctt ggagttgcac    12660
agctggattc tgtgatcatt gcttcacctc ctattgaaga tggagttaat ctttccttgg    12720
agcatttaca gccttactgg gaggaattag aaaacttagt tcagagcaaa aagattgttg    12780
ccataggtac ctctgatcta gacaaaacac agttggaaca gctgtatcag tgggcacagg    12840
tgagggatgg caggatcatg agcactccag gaagaacttg cccttttcag tctttgctgc    12900
acactgttga gcatcatgca catagtggcc acccctgcgg ggtgactttt ccacatgtgg    12960
gagtttttgtt ttgtttctgc aggagttttg aggcaggttt tatctaaatc atttgaggtt    13020
tttgttttgtt tttatttaaa tatatctctg attgaactga atgttaatcc tggttaaaat    13080
gagtgacaaa aatactagaa gatgtgtgtt aaaacattta taccaaatga attaaggcca    13140
tttccttcag ttctacttat gtgctgaaaa caataatacc taaagaaaaa ccttacggcc    13200
gggtgtggtg gctcacatct gtaatcccag cactttggga ggccgaggcg agcagatcat    13260
```

```
gaggtcagga gttcgagacc agcctgacca acatggtgaa accctgtctc tactaaaaat   13320
aaaaaaatta gccaggcatg gtggcgtgca cctgtaatcc cagctactca ggagggtgag   13380
gcaggagaat cacttgaacc tcagaggcgg aggttgcagt gagctgagat tgcgccactg   13440
tactccagcc tgggtgacag agcaagactc tgtctcaaaa aaaaaaaaaa aaagaaagaa   13500
aaaccttctt tttctttagg tactattaga ccatggctct aatttcctaa gtaagggaat   13560
attttatata taacagatat tttgctgtta ttcaaagatg tgtaagactg tcagttcata   13620
caacttgata tggagtgagt gtcataaatt aattattccc actctctggt ctaataacct   13680
acaaaattat taggaaagtc acttactagc gttttacctt tactctcagt atttctttat   13740
tccttttact tcttcttcag ccttctcctt ttcagagctt tcagagtttc ttatggacag   13800
gaagacctag agaaagtatt tcccttctc cttgatgata gccagaatga ggacaagaaa   13860
gtattggaga gacttagatg attcagaatg taaattaacc agtgtagcta ctggaagctg   13920
tcaattcttc tctttcaaaa tgtgtctgat tcatagccat attttatact ttaacattaa   13980
aggtatttac ttgtatttga tcctttacct ttaagaacta tttgctctgt agctgaaacc   14040
atcacactta acaaactaac aaaaatcatg tttgtgttct aggcagatgt attagattgt   14100
taaatggttc tagcaggaga cttttttaata gtgtagtacc aggctgggca tggtggctca   14160
tgcctgtaag cccagcactt tgggaggccg aggtgggtag atcacctgag gtcaggagtt   14220
caagaccagc ctgaccaaca tggtgaaacc gcgtctctac taaaaataca aaaattagc    14280
tgggcatggt ggcaggcacc tgtaatccca gctacttggg aggctgaggc aggagaattg   14340
cttgcacctg gtatgtggag gttgcagtga gccaagatca cgccactgta ctccagcctg   14400
ggcgacagag caagactcca tctcaaaaaa aaaaaaaaaa aaagtgtag tactgttggc    14460
ttttttcgttc ccctagtgtt acacttcctt tccctattac atagggaaaa ggtaataggg   14520
aattcctatt ccctattact actaacctgg gttagaaaag catatattaa taagatatt    14580
aatgtaaaag tattttgtaa actttaatca ctgtggattg tgattttca tatgttctaa    14640
aattaagtta ttttattgct tattgctttc tacttttggt attatattta atttagtagt   14700
gatatcatga ttttattttc acttctaggt aaaaccaaat agtaaccaag ttaatcttgc   14760
ctcctgctgt gtgatgccac cagatttgac tgcatttgct aaacaatttg acatacagct   14820
gttgactcac aatgatccaa aaggtaaaac tgatattttc attatagaga ttgatcataa   14880
gcttttgtct tacaaaaagg tatttgttga tacataattt taaatgtgga cagtgataaa   14940
aatacagtgt tatctgaact attcttaatg gttagttcaa aacctatatg ccctcatttt   15000
attttcagaa aactttatct ctgtaccaat ggggaaaaaa aagtgaaggg atcatttcct   15060
gaacatctgg tcttttgagg ttcacaaata ttaaactaca cagaaaagat cttttgagac   15120
attctaaata gtaatatata taatcctatc tagtatagca aagactggac caaaaggcca   15180
cttgattttt ttagttttga gatggagtct tgttctgtcg cccaggctgg agtgcagtag   15240
catgatctca acctgactgc agtctccacc tcccggactc aagctctcct cctgcctcag   15300
ccttccgagt agctgggact acaggcgcat accaccacac ttagctaatt tttctatttt   15360
ttgcagagac agggtttcac catgtcaccc aggctgggct tgaatttctg gactcaagca   15420
attcccccac ctcggcctcc caaggtgctg ggattttagg catgagccac tgtgcctgga   15480
caaaaggcta ctttattcaa ggagataaat atctggaaaa agtggcacat gtaatttaat   15540
tcaaaactta ataagcatct taggataggt aagtaggtat tttattaaga cgtttagtgt   15600
```

```
taatcagaaa tatttgatta atgagaatgg cttgtctgcc ttttatagaa taatttttta    15660
caacattttg taagataact agaaagactt ggaagataat attgaacata acttgcaaag    15720
ataaatgttt cagagagcct gtatattatt aagtaatgta tattactaca tattttggt     15780 ataaatgaga aatgtttggt tataagtgag aaatgtcttg tgaaagtttt aattctcgat    15840 gacatttta  tagaagttct gatttaataa atattagagg aaattatatt tcatagataa    15900
ttcccgccga aaaatattc  agcttttatt tccatacct  aaaagatgac acaatatcag    15960
tgggttgatt cagtttgctc attttaagaa tgctatggat aatctattaa gactttatac    16020
tatttattag cagtctactt cattctcatt tcttcactgt ttcatcagag gaggggagga    16080
tggaggagaa agagttttaa tagttatttt tccttgaatg ccaagcatca tgccaaatgc    16140
ctcagagaga ttatctataa tcctcacaac aacggaaact atacattttt tttgtcagga    16200
aatagagcct cagagtgaaa ggaactagcc aaggtcaccc agctggcttt gggcaaagtt    16260
tgaacttggc ctaagtcttg gattattttg gagccttttc cactatacaa tctctttgat    16320
ttgaaacatt agtattacag tattacagtc tgaaaacttc atccattttc atttaaatca    16380
taccagaata aaatacagtg acttttgcct tcccagtaga gctttcacaa tcaagtaaat    16440 tgattttta  agccattta  gtgaaaatct aacaaattgt tatgctgatt tattctgaac    16500
tataagtcat ttaaattta  actttccata tgttggcaga tgtcatgtgt ctgtttactt    16560
tttggaggct cttctaacag taattgttac caacagctga tgatccagcc tgtaccctct    16620
tctagcttca cttgaaaaaa actcaatcct tttactagta ggaaggaag  taggaaaaga    16680 ttaaggttcc tagtgtttta ttttcacata tctaaatgtt gacatttaga atgtgtgcta    16740
atacattatt gttatggcaa aatatattgc atatgtatat gaggagagag atttaatcct    16800 ttttatatt  ttttgtatta cataatttga tacttagttg tctttttta  ttctaagact    16860 tttggtgaaa atgtataggc ttatcctgca tttatcatta atgaaccttc agacacttta    16920
atctataatg aagcaactct cgatttaatt tgtcatgttt actgactaaa gagttcaacc    16980
ataattaaat tttaaaagca gttaaatgaa tagcatagtc tctgattttg tgtcatattt    17040 tttattttt  taagcaacca aactgaaaaa actgtaaaac atttaactct gtaaaattta    17100
actctgtaaa actgtaaaac atttaactct gcttgtcatc taaaatagaa ttttgtttat    17160
aaattccctg aaggtctacc cctgttctaa aaattaccct tactccccat aatgggttta    17220
ttttccatta cccttttgttc tagaagtgta ataacaattt aactagagag taaaattgta    17280
aagtagatga tcctgaattt agaactttcc attttttatt gttccccgcc ccccatttcg    17340
attaaatcca atctgtatta tgtctctttc cctcagggtc ttctctgtta gaaaatctga    17400
taaacaaatc catattaatg ttacttttcc aaggagacat ttgtgttcta tatatgaaaa    17460
ctaccattta ctagtggtgt gaccttggcc aacttaccga acctctctgc cttggtttcc    17520
ccccataaag agataataga atctatctca tagggttagc atgtggatta actgagttaa    17580
tacatgtaaa gtactcagaa aagtacctcg cacatgaaaa tagctaacat tgattgagcg    17640
tttactgtta atgctattca ggtatcacag cagtttggga gtaggtgggt cctttagcac    17700
tccgaaatca aactgtgaag atgctcactt aatccctatc tgtaggttgc ttctgacccc    17760
agtggaatct ttccatattg attgatgcat ttaatagacg tttgagcacc atttgccagc    17820
cattgttctg ggtactagag ataaaggatc aagtcagaca aaaccaacc  ctcatggaat    17880 ttatattcta atgggaggag acagacaata aaataaatgt tacatatgat aagtggtagt    17940
atatgctatg gagataactt ggctgaagga gaaagagtat ccaagttaat tgttgtttta    18000
```

-continued

```
tatggtacag tcagagaggc ctctctacta agggaatgtt aatcagagac ctgcaggaag   18060
ggagtgagcc atgtgaatat ctggaaaaag tgtgttcaag gaaaaggcag aagctaattc   18120
agaggctcca aggtgtgaat gtgcttgagg ttttcaggat acagcaagga ggtgaggcca   18180
gtgtggccag aggagtgagg cagtgaggag aggagtggtg ggatatggca tcagagcagt   18240
catagagagc ttggatataa acttggaatt tgctgggcat ggtggctcac acctgtaatc   18300
ccagcacttt gggaggccaa ggcagggdat cacttgagtc caggagtttg agaccagcct   18360
aagcaacata gtaagacctc atatctacaa aaataataat aataataatt aaattagctg   18420
gccttggtga cgcacacctc tagtcctagc tactcaggag aatgaggtgg aaggatgcat   18480
tgagcccaga agtttgaggc tgcagtgagc tgtgatcatg ccactgcact ccagcctggg   18540
caacagagta agacattgcc tcaaaaaaaa aaaaaatag aaaagaaaaa aagaattggc   18600
actgcggcac tctcaaatta tcaactgctg gtagaagtgt aaagtatagc ctttctgtaa   18660
agcagttggc aatatagcgt gtatctagct ttaagaatgt acttgtactt tggcccttca   18720
ttccacagcc aggcatgcat tttaaaatgt tcatcatctg catcattgtg acggtttgtt   18780
tcttccatat ttggagataa atttatgtgt agactttttt tttgtaagac atagttgata   18840
atgaaaattt atttaaatgg tcttgcaatg atttaagtat tcaaatgctt aaagaaagca   18900
ttgctggtac aaatatttct atttttagaa agggttttta tggatcaatg ccccaagtgt   18960
catcagagcc attggtgttt tcattttttaa aatgtcacct gtaaaatggg cattatttat   19020
gtgtatatgg cttttttttgg cattcctgat aaatgtatta tataaagtct atacattgga   19080
taataacact agtatattta aacttacaga cttatttgta atgcaaacca ccattttaat   19140
gtactgtaat taatatggtt ataatatata tatagtcctt ctgtcctacc atcacacaac   19200
tttttgtgtg tgtaataaac cgcttttggt ttgaaaatat ttttcgaggc cgggcacggt   19260
ggctcacacc tgtaatccta gcactttagg aggccaaggt gggtggatca cctgaggtca   19320
ggagttcgag accagcctga ccaacatggt gaaaccccat ctctactaaa atataaaatt   19380
agccaggcat ggtggtgcat gcctgtaatc ccagttactt gggaggctga ggcagaagaa   19440
ttgcttgaac ccgggaggtg gaggttgcag tgggccaaga tcacaccatt gcactccagc   19500
ctgggcaaca gagtgagatg ccatctcaaa aaaaaatata tatatatata tttttttaaaa   19560 aaagaatgtt tatcctggca ttattcttat tagcaaaata ttaggaaaaa cataaatgtt   19620
ttgaccaata ataaggaaat atatgaatta tgatatctat gtaatatagt aatggggaaa   19680
ttattaaaaa tgatctttc acagactatt acatgggaaa atattcacaa tataagtgga   19740
aaaagataag caaataaggc tttaactaca gtgtgatttc taattttgta agatatggat   19800
atacacacac acatacagat ataagatcta gagatatata gagattcaag atatggatga   19860
agatatatat atatatatga agatatatac tcatatacac caaaaaagtt gtaaggaaat   19920
gcatgacaat gttatatcat ctccaattga taggattatc agttacttt tttttctttta   19980 gactttcctg tatttttccct gactatacat tagaatcacc tggagatctt taaaaaactg   20040
cagatgtcta ggctccactc accaaaaagtt aagaattaaa taggctgggg tacaggtgta   20100 gatactttt aaataactgc ctgggaattt ctaatattct ggttcagatt catagcacac   20160
acatgaagaa taagcatatt atatattaaa tgttgaggtg tttcttttgt tatgttaaat   20220
gcttacctac atactaaagt gcttttttgt tttccaattt aacacgctgg agttttgttt   20280
gttgttgttt cttttagaac tgctttctga agcaagtttc caagaagctc ttcaggaaag   20340
```

| | | | | | |
|---|---|---|---|---|---|
| cattcctgac | attcaagcgc | acgagtgggt | gccgctgtgg | ctactgcggt | attcggtcat | 20400 |
| tgtgaaaagt | agaggaatta | tcaaatcaaa | aggctacatt | ttacaagcta | aaagaagggg | 20460 |
| ttcttaactg | acttaggagc | ataacttacc | tgtaatttcc | ttcaatatga | gagaaaattg | 20520 |
| agatgtgtaa | aaatctagtt | actgcctgta | aatggtgtca | ttgaggcaga | tattctttcg | 20580 |
| tcatatttga | cagtatgttg | tctgtcaagt | tttaaatact | tatcttgcct | ccatatcaat | 20640 |
| ccattctcat | gaacctctgt | attgcttttcc | ttaaactatt | gttttctaat | tgaaattgtc | 20700 |
| tataaagaaa | atacttgcaa | tatattttc | ctttattttt | atgactaata | taaatcaaga | 20760 |
| aaatttgttg | ttagatatat | tttggcctag | gtatcagggt | aatgtatata | catattttt | 20820 |
| atttccaaaa | aaaattcatt | aattgcttct | taactcttat | tataaccaag | caatttaatt | 20880 |
| acaattgtta | aaactgaaat | actggaagaa | gatatttttc | ctgtcattga | tgagatatat | 20940 |
| cagagtaact | ggagtagctg | ggatttacta | gtagtgtaaa | taaaattcac | tcttcaatac | 21000 |
| atgaatggaa | acttaaattt | tttttatgt | gtccttgctt | atagtttagc | tgtaataatt | 21060 |
| taaccttgta | ttcttgtgcc | atattctgtc | tttttattac | ttataaagac | aaaccaaagt | 21120 |
| aaatctgaaa | ggagactaga | agctttgaaa | ttattgtttg | ggggttttat | aaaagcaact | 21180 |
| actgtcacct | ccatccagat | tcttttaaat | tattgatcca | tccatagtat | atattgctac | 21240 |
| tcattcaaga | atcctcaata | agtattgagt | atttaccata | tgttgggata | ctgtgggctc | 21300 |
| tggagagagg | aggggggcaat | agagctagga | attaagaatc | agttgagtaa | aatgtgtaat | 21360 |
| atttattccc | cattaataac | tgactaggaa | ggactaaaag | ccagaagggg | gatgaaaaaa | 21420 |
| aaatccttaa | ttcagggccg | acattatcta | cttaaacaac | tttgagatat | ggtcttaatt | 21480 |
| attttaaagc | agaataatat | aattgaaagt | ttatagctaa | aagagactat | ataggtcatt | 21540 |
| tagtataatt | cttcattagt | ttacgaacca | caaaattgca | aataaataag | ctatgaactt | 21600 |
| tgatgtacac | tataaatctc | cttaattcta | taaatttgtg | tctgtaacct | gaatagtttg | 21660 |
| aaaacttctt | taaaaatctc | ttgtatttca | tccgggcgca | gtggctcaca | cctgtaatcc | 21720 |
| cagcactttg | ggaggccgag | gtgggcagat | cacgaggtca | ggagtttgag | accagcctga | 21780 |
| ccaacatggt | aaaaccccat | ctctactaaa | atacaaaaat | tggctgggcg | tggtggcact | 21840 |
| cgcctgtaat | ctcagctact | tgggaggctg | aggcaggaga | atcgcttgaa | cccgggaggc | 21900 |
| ggaggttaca | gtgagccgag | atcacatcac | tgcactccag | cctgggcgac | agagcgagac | 21960 |
| tccatctcaa | aaaaaaaaa | aaactcttgt | atctcaatat | ttttaaacca | caggcctaaa | 22020 |
| taaaactaat | tttgctcaag | ttttctcaac | ctagggaaaa | agaactatgg | ttccatattc | 22080 |
| aaaataaata | ttatagaccc | ttttcctaag | taggattttg | tggtttactg | attgggtaat | 22140 |
| ttgatcatta | aaattatgtg | aaatctgccc | gggcacacct | catgcctgta | atcccagcac | 22200 |
| tctgggaggc | caaggcagat | gatcacctga | ggtcaggagt | tctagaccag | cctggctaac | 22260 |
| atggtgaaac | cctgtatctg | ctaaaaatac | aaaaattagc | caggcgtggt | ggcgggctcc | 22320 |
| tgtaatccca | gctactttgg | aggcgaggca | cgagaatcgc | ttgaacctgg | gaggcggagt | 22380 |
| ttgcagtgag | ccgagatcac | gccattgcac | tccagcctgg | gcg | | 22423 |

<210> SEQ ID NO 11
<211> LENGTH: 34829
<212> TYPE: DNA
<213> ORGANISM: human

<400> SEQUENCE: 11
aaatcaggga ggcgcagctc ctacaccaac gcctttccgg ggctccgggt gtgtttgttc      60

```
caactgttta aactgtttca aagcgtccga actccagcga ccttcgcaaa caactcttta    120
tctcgcgggc gagagcgctg cccttatttg cggggggaggg caaactgaac gccggcaccg    180
gggagctaac ggagacctcc tctaggtccc ccgcctgctg gaccccagc  tggcagtccc    240 ttcccgcccc cggaccgcga gcttcttgcg tcagccccgg cgcgggtggg ggattttcgg    300
aagctcagcc cgcgcggccg gcggggaag  gaagggcccg gactcttgcc ccgcccttgt    360
ggggcgggag gcggagcggg gcaggggccc gccggcgtgt agccgattac cgagtgccgg    420
ggagcccgga ggagccgccg acgcagccgc caccgccgcc gccgccgcca ccagagccgc    480
cctgtccgcg ccgcgcctcg gcagccggaa cagggccgcc gtcggggagc ccaacacac     540 ggtccacagc tcatcatgat ggacttggag ctgccgccgc cgggactccc gtcccagcag    600
gtgctgcctc ggccctctgg gccctgcggt ggtgccggga cggggcgggg ggagctaggg    660
aaccgcggcc cggagggac  agccgcaacc ggcttccccc acgtctggcc agagccagga    720
ccgcggcgct gggtagagcc gccgcgcttg cgccggggca gggcggggag gggcagcggg    780
gacgcggccg ggtgatccga ccgaccacga gcccgagggc gaacgggtgg aagttgcgg     840 gaaggtctgg ggactgagcc cgctcgcgtg ggccttgggg gagaatccag ccgcgtcccc    900
gggcccgaga gctgggactc cggagcccct aagtttgagc ggcccggtgg gcggcggggc    960 aagaggggc  ggacgctggc cgtctgagcc ggcgcgccc  ggcccttccg gggctgcgcg   1020
gctcccccgc ctcggtgccg gcaaaaatgt gcctagtcac ggggccgctc tcggggggaac   1080 tgaggtcgcc ttcgggctgg gacccggagc cccttgccg  cgcccaaga  cctccttgag   1140 tgcgggctgc gacgcgctca ccccgctggg ccgtctgtgg gcgcggcttt gcgaagtcat   1200
ccatctctcg gatcactctc tggcagcctt gagctctctt gaaagcccag ccccgggacg   1260
agggaggagc gccttaagtg cccagcgggc tcagaagccc cgacgtgtgg cggctgagcc   1320
gggccccgcg cactttctcg gccggggagg ggttcgggct cgggcacccg gagttggccc   1380
ctcgtaacgc cgcgggaaag tgcgggcgag ggcagtggac tctgaggccg gagtcggcgg   1440
cacccggggc ttctagttcg gacgcggtgc cccctggtgg cgctcaccgc gcgcgtggcc   1500
ttggcttccg tgacagcgct cggttggccg tcacagcagc cctcggttgg cccttttcctg   1560 ctttatagcg tgcaaacctc gccgcgccag ggccaaggga caggttggag ctgttgatct   1620
gttgcgcaat tgctattttc cccagagcgg cttttgtcttt ggatttagcg tttcagaatt   1680
gcaattccaa aatgtgtaag acgggatatt ctcttctgtg ctgtcaaggg taagagttgc   1740
gagtgtagat tagaatttct gttgcttta  gtctgttagt aatttttttgc tttcagctat   1800 tatttctccc ctgagtactt tatatatgtt tccttttcag ttgagaattt gcctcaattt   1860
cttaacatgt tccccctctt ctgcaggggc agagagtgga acgcttgcgt ttcaaaacac   1920
ttgctaattt ctgtgaattg ttataaaagt gaaagaagt  ttctgctcat cctttgtaga   1980
aactttaaaa gtagatattt atatttctaa cttcttttgt aaatgaattt taggaaaaaa   2040
attggaattc aaggaaatgt gtacttgatg tacagtaaat acgtttatgc tgttaaatgt   2100
aaagttttcg gttaattcca aagatctatt gtaaagtttt aagttatgga caatgtatta   2160
attgtgcttt tttccccctt taaagttgtt tgtcttgaac ttttccccag tcttcattgg   2220
gattgtattc ttctggttcc aactagtgaa gaattaaatt gtaccttccg atttatttaa   2280
tagctgctgt tcaagagtta tctataggaa tgcttgtttg actgaaggat atatgataaa   2340
aatgaacttt agttttctg  atttccggaa ttgtctacag ccctctatta tttttgaatt   2400
```

```
tttctttctt tgctgtgtaa tataacattc cttatacaaa aatgcgtgaa acatatgtac    2460
cgcattaagt gtgtatttc caattacgtt tgataaaaat aactgctttt ctacctttgt    2520
aatcagacat cgatttgcat atttgaaaac agaaaagaa caagaaaatt tagaattgat    2580
tttgtttatg attcatatta gattgttgtc atccataaag atttgaacag agtcaaacat    2640
tttcttgacc ttttgtcaaa aaaaactctc caggtgtgaa gtggtagtag gatatagttt    2700
ttcaccttct gtgcagagga tgtgttgata acagggcag taaggagagc cttagattca    2760
gtatctccat taggtggaag gaaccatcca ttactctttt caagggtgtc ttggagagat    2820
aaagcacttt cctagatgag ggatgaagtt gatattgaaa tagaccgatg agattatttt    2880
taagtcaaac aaaagaaaaa taggacaggc ctctcatctc ctgaatgaat gttaagcaaa    2940
gaacaacttg acttttaga tatgtgaaaa atctcttgag aggttgtgga agcagcatgt    3000
aggaggataa atgcataact cacatcagtc ttttacgcat aaaaataac ttgggccatt    3060 ttgaaatctt tctttcttgc cctgggttct tataagcaat gttgggggga aaactgactc    3120
tgtctttagg attaccagga aaagttgaaa gccaaatgca tcattttcct taatatttgt    3180
ttttattgag gataaatcat gtttaacaaa gctgcatgaa aaaaggaac ccaacaagta    3240 catttttttt tctgggaatt tcctctgtcc tgactgaaga catttaaagg gggttttgtg    3300
tcaatatttc ctccttaact gttcctcaag cctgggttaa cttttcagta tgcaggaaga    3360
atttggcact aagataataa tagataagtt actgggcacg tccctgggtg ccagacataa    3420
ttgcttcaca tgcataattt tacagtaacc tcacgggaaa tattattatc cctggtttcc    3480
aggttgggaa aaccaggcat aatagttaga tcaggcatta ggttaggaaa ggttaggaga    3540
gaggcataga gaaaggccag gacctgctaa ggtgaccata ctattgagtg gccaaggtag    3600
cattcaaaca ggtttgactc ctgggggctt ctaatcacca cttccagact gtaccaaaac    3660
tccttaaact ctaaatagga agaaaagctc acactttaaa aagtgggtaa gttgagattt    3720
gcctattctg ggggaaggag aggccggaat ataaagatt aatgtctgca gcttttccat    3780
ttagcaagac atttaatcac tgtatgtgac gtggggaggt ggaccttgtt aaatacaggg    3840
agagtgaata caatccatca atggtaccca ctgtggtcct tttaaggaag acacagaggc    3900
ctcggtggat tcaatttaga aaggcaggac tgttttttgt ttttttgttt tttttttttt    3960
tgagatgaag tcttgttctg ttgcccaggc tggaatgcag tggcctgatc ttggctcact    4020
gcagcctcta cttcccgggt tcaagtgatt ctcctgcttc agcctcccga gtagctggga    4080
ttataggcac ccactgcccg gctaattttt gtattttag tagagatggg gttttaccat    4140
gttggccagg ctgggctggt ctcgaactcc tgacctcagg tgatccaccc gcctcggcct    4200
cccaaagtgt tgggattaca ggtgtgagcc actgcgccag tctgtttctt aatataataa    4260
tagttttaaa aatttctgat gtttggcaat gtccaagatt ctgcctcaca ttttcagaa     4320 actgcctttt ttcttaatta aatctcttag ctactggagt ctttgccttt gtttgccttg    4380
ctacttggta catttcttct gttccattgg ctcttttgt tttgaagtag tgctcaaaaa    4440
taagtttggt agtaagaata tggtgaagag tgtgacagac agggttaaac caggctgaag    4500
gaaagagagc agaatgggga aaatttgagt tgaaacagc tagcagaaag ctgatggcgc    4560
aaattcaacc ctaatctcat gttttggcac ttctgaacta tagcaagcat aagggctcaa    4620
ctcttatcta gttgaagctt acttgggtct ttgagaatag tacatctcaa aattaaacac    4680
tttcttagtc cttattgtta agttgttttt ggaattattg tcttattgt ctgaattaag     4740 tgtgctgcag gacttatagg atctgatgga tgatttgcct aaaagttggt ccaggtcaac    4800
```

```
ctcagggcat ttaaatgctt ggtccagcca ctttctgaaa gttgactgaa atatgttgca    4860
cagcagggta gaggaggaca agtttactag atgtcatttt taacctgctt gtcttcatct    4920
ctgactgtag aaatgtatat tcattataag tttgccacaa atagagaata gagtttattc    4980
tttgatcatc taatttctag gagctattga aatttcactg ctacctgctt ttaaataagc    5040
gccaacaaac atttattaaa agggctttaa ggtataggcc aagatttatt caattgctaa    5100
tggtatgttt tctgtaaatg aaagcaaaaa tatgttcaag tgtataatat taaatattaa    5160
cattcagaaa cttggagaaa tacagatggc ttttttttt gagacgcagt cttgctctgt    5220
cgcccaggct ggagtgcagt ggcatgatct ccgctcactg caagctccac ctcccgggtt    5280
cacgccattc tcctgcccca gcctcccgag tagctggtac tacaggcacc cgccaccacg    5340
cctggctaat ttttgtatt tttagtagag atggggtttc actgtgttag ccaggatgat    5400
ctcgatctcc tgacctcatg atccgcctgc ctcagcctcc caagtgctg ggattacaag    5460 cttaagccac cgcgcctggc ctagatggat ttcttgtacc agactatacc ctagacatga    5520
aaacaagact gttaaacaaa atcctgtgct acctaaagtt tgagccttct gtgtgtcagt    5580
ttctgccata ataaataact cttaactatg attattaagt atattaagaa ctttgagtag    5640
gggaggcacg tttaatcatt cgttttacg gcatatgtac tataataccct gtgtgttgca    5700 aatcctggta tttaaaagtc tttttgtgta tttgagcatg taagtttatt tggtccaaac    5760
tgctggtact agtaaagaca agtccagggc ataagtagga cttacagcac caagttcgtc    5820
tttttttttt gagacagagt ctcagtcggt cacccaggct ggagtgcatt ggtacagtct    5880
gggctcactg caccctccac ctcccgagtt caagcgattc tcctgcctca gcctcccaag    5940
tagctgggat tacaagtgtg tgccgccacg cccggttaat ttttgtattt ttagtagaga    6000
tggagtttca ctatgttggc caggctgatc ccgacctcag gtgatgtgcc caccttggtc    6060
tccgaaagtg ctgggattat aggcgtgagc cactgcgcct gacctccaag tccatctttc    6120
aaaggctctg ttgataattg actcttgaga gtcattacag tccatcaaca gcctgtattc    6180
tgaatatttg ttttttaattc taagacaatg ctaaatagcc attccaaata aggtgagaac    6240
tgagacttta gggcctgtat tatcagctgt acactgacaa gctctgaact ctattgcttt    6300
ttcaaatcag agaagaaaaa tgagtaagaa aagaaaaata tggatcactt aggctttgat    6360
gcctcctctg agtttatagt gtttaccttc tgtattactt aggtgatcct ctctaatggc    6420 atttaaatc tctgttgata cttgtcttac ttatgtatct gttttttttt cctctatagt    6480
agatagaatt tatagatata tatgtatttt aaagtaagat acaatttacg taccttacaa    6540
tttacccatt taatctaatt cagggttatg caaccctatg aatttagtag tttattcata    6600
gagttatgca accatcactg taatcaattt tcaacaccct caaagaaac cccatatcca    6660 ttagcagtca cttcccattt cccctcaact ctcctggccc ctggtaacta ctcagttatt    6720
ttctgtacct atggatttgc ctattctgga catatcatgt aaatggaata gcatgtaaat    6780
ggaatcatac agtatttatc cttctgttgc tggcttcttt cacagcaata tgttttcaag    6840
gtttaaaaat gttgcaacgt atatcaatag cgtcattcct ttttatggct gcatactatt    6900
ccattgtatg gctataccac attttattta tccagttgat gatcatttga gttgtttcca    6960
ctttttatgt ttctgtttgt ttcttacagc agtggttctc aaactgttgt atattagact    7020
caccatcagt atttaaaaaa ctaatgccca ggccatatcc ctcatgaaat caaaatctct    7080
gggggtgggg cccaggcatc actatttttt aaagattctg aggggattct aacgagcagt    7140
```

```
caggtttgag agccagtgcc ctagggcagc agtccacaac cttttttagca ccagggacta    7200 gttttgtgga agacagtttt tccatagaag gaggtagagg atggtttcag gatgaaactg     7260
ttccacctca gatcatcagg cattagattg tcctaaggag ctggcaacct acatcccttg    7320
catactcagt ttacaacagg gttccggctt ctctgataaa ctaatgctgc tgctaatctg    7380
acaggaggtg gagctcaggc gggaatgctc gcctactgct cacctcctgc tgtgcggcct    7440
ggttcctaat gggccactga cccctccgca gccagcaggt ggggacccct gcccagggg      7500 acccacctca gtgcttggta tccattgaag tatatagtga tttagaaaat ctggttagga    7560
tgtcttattt aaatcatgaa agcaagtgct tttgtctttg atcattgccc ttcacagcct    7620
tacagttaac acctacattc aggaactgtg tttcaaagtg cctggcgagt gtttgaaact    7680
cactaaatat atataacctg ggctcattaa acccctccag aagatttggg taactttgtt    7740
atgaaagggc ttccctgaag tgggtcagca ggattgctct gtgttttttc aggaatgtgg    7800
cctgtgataa cttgcaatct agattatttg gaaatagcac tgagagaagc cagtgaggac    7860
agaatgctca gaagcttggg ataggtgttg aacatcctgg aggccaggac ggaacactgt    7920
cttactctag gaagctgtgt tcctgggcct cattatcttc ctccgttaaa aacaaaagac    7980
ttaaatctcc acagcagctt tcagcaactt catttttttgg ttctctgtat ctgcctgata    8040
aagtcccact ttgtagtggc tcccacttat atttacctga atggcttttg ggttgacata    8100
tttgaaaact ggggctaact tccaaactgt tggcaacttg tgtgtgggtg tgcgtgccac    8160
agcacagcag tcccacttga gagacttgat ggtgtggtgg tggttggggg gcttctgaag    8220
ctggcttagc cccagcccta tacacccacc ccacagatgg tgggaacaag cccagaagag    8280
agtgggtaac tctgtccact gtggcctcca cagccaaggt tgccaggcag agctcgcaag    8340
gcccaattcc agtcttgtct ttgaccgttg ccccttttgtg ttgggggggt gtatttagtc     8400
acctttctgg aagcatgctt ttctaattct agtcatcagt agtttgttgc tttaagattt    8460
tgaaaatggt atcctgttat tttacttagg agtttcgtat tgaatggtgt acataatgtg    8520
attcaagtac ctcaaaacag aaggacttca gttaagattt aggctctatg caacatacac    8580
ttcttgcatt ttctcattca atgtcctttc cttttttttt tttttttttt ttgcaagaat    8640
gtagctgaca ttcagagtag attagtacct tcaatgtctg tgtgaaagaa atgaccttaa    8700
tatgaggaca atattgactg tgtatttagg gggcccactg ttaaggcata tagaattttg    8760
ctttatttca gacctgacaa tctcttgtct gctctgcttc cgcataaaat tataatactg    8820
cacatggatg taaaacccaa cctattccct gcctgaggga ctagaataga gggaagaatg    8880
actatagttc tttgttgcct tttgtgaagg taacaggcac agaggtatga tgcatgatgg    8940
aattatatac ctcttcttga ggtgtttgag ggctgactaa ggacctgtac ttttttttttg    9000 gtttgttttg cagtactggg gccagggagc cttgctgttg tgtctagaga gtgttgaaga    9060
accatgaata tttcgcaaaa agaaaataat tttttttaacc attaaaattc ctggtagtga    9120
cttcctctgg caagtaaaaa actctcattt tccttaaaaa atgagagttt tttacttgca    9180
ataggaaaac ttgccaattt ttcaagttat ttttattctt gatgattctc aatgagacat    9240
aattaaaata cacatagaaa aaacaaccgt aggccaggtg cagtggctca ccagtaat      9300 cccaacactt tgggaagtca aggtgggagg atcactagag accaggagtt tgagatgagc    9360
ctgggcaaca tattgagaca ctgtctcctc aaaaaattaa aaaaattagc tggatccagt    9420
ggtgcacacc tgcaattgta gctatttggg aggctaaggt ggaagaatag cttgagccca    9480
ggagtttgaa ggtgcagtga gccataatca tgccactgta ctccagccca ggcaacagag    9540
```

```
taagatcatg tctcaatgaa aaaaagaaaa atcaaccctA gtggactgga acagggctgg    9600
tttactttgt gtcagctgca gtgccccccac tcgccaaccc acatgttctt ctcctgctgg   9660
ttcccaagca gagaccagaa ccaagaatga gaatcatcct gtgggtgcag gttgtatctt    9720
atcctccaga gacagcactt caccctctgt tagaaacttc tttaccacac tgcctgtttg    9780
gtgaaatcct tagggcagtg acttccaaac tgtgatccag gggccaccct tggtgggagg    9840
atcaggaagg aggggaatg tatcttaaga aaagttgggg gaagctcata tctcttctcg    9900
ttgatcctga gaagtaaagt cttctcctcc tcagagagatg cgggtagaca tgactcgcct    9960
agatagaagc tcattcatct ccctccctc tgcctctgca ggactcttgg aagtctgggt   10020
ccccgggagt atgcggctct tgctctgtgc tacaggtttc caagttcac ttgataacag    10080
tacaattgtg ctgtaaattg tgcagtaatg gagactgagg aaacaattag tctttcatct    10140
tcattcatgt taccagctca cttcctatgg tgtgaaaaga gccagacttt ggagttagga    10200
gacatctgaa tacagacaga actggcaaga ttatggggaa gaaaagggaa aagtaatgaa    10260
tattttcaaa gaggttaagc catttggcca ggacaacact gcttgcaggt agcagaactg    10320
ggatttgac tgtccataat ccctattctc tgcttgtttt actccttccc tctcttcttt    10380
ctttttcat tgtctaatga cctacagaca ttctgtcagc tgctaaagaa tgagggactc    10440
ctttataaag attgatagga cagtgtcgct acttaaggag ttccttccat gtggaccagt    10500
ggggcgctg ttgacgcatg gggctggact tctctttgga gcagagtcct gttccacgga    10560
tcgctgtgac aagcagaaag tgccccaccc cacctccata caattcctaa tgctcctggg    10620
tgatacaacc gccccagtgg aagcacggtg gtgcatggac ttctagagac catttgaagc    10680
caggacattg ctgcttgttc ttaggaaatg gcagaatatt actttcttgt tttttgtagg    10740
gaagcctgcc atctcaccag gtggcagctt gtttatacct tttatcctaa cctgaagcag    10800
gtgatgggac agaggtcatc gaatataatg aaagtgccac aaaggtagag tctgggtata    10860
ttttatttat gcaggtagag tgacttgtcc agatcccttc acacagagca acatttaata    10920
tggtaattgt tactgctgaa gttggccatt tctcggacct acagctgcaa ggaattggta    10980
acaaaaggat aaactaaaca ttgttactat tttaattttc aaggagatga agttaaaatc    11040
atatatgtca tatctctctg gggcttagcc acctttctg ctgggcactt tttgaagaag    11100
tctgaatact gagataggag agtaaagggg ggaaagtaag tttgcccact tctcatcctt    11160
tttctgacca tcagcctgag ggaagtaact agaatccgct aagaaaattc acttaatcag    11220
cagttgattg attgttatat tgtccacatt gcaaaattct ttaaaggata tttgaagata    11280
ttatcacatt tgttctctta caatctattg tattgtttat ttgaaggggt gagtgttaat    11340
agttcttaag atatcgtact ttatttccgg tagcatatcc aagaaataat ttagaagtat    11400
tgttaatggg aatgatgtta ataattttt ctatgactag tagttgggac atatatgata    11460
taaaacatgg tatctttgtt acttaagtaa tttgaactct aacccatat atcttaggta    11520
gacaatgaaa atactgaatt gttagtctaa ataatataca cgtactcatt ccgcaaatat    11580
ttattaggta tctacacacc ctaggaatct ttcagggcat gaagctgttt taatcttcca    11640
agataatgca gcacgtatcc cccttgaggg acatttgttt ttcaaattgc tcctctgtgt    11700
ctcctctgct taggatatga gttcctctaa gactgtattt taatctttg tgtaattctg    11760
atgtctagcg ccatgcctgg tgcttacgta atagttgctc agtcagtttg agggtgagtc    11820
cattaactgc cctctaggag cttgatattt aatataaact agtctgtgat acatgacaat    11880
```

```
gctgtgacag tgcagatgag aaaatgtgac ttctaactgg ggtgctcaga gaggatatcc    11940
tggaggaact gccattttaa ctagactttt cttttaagca ggtagatttt gtttggttca    12000
ggcttcagct ggaagcccaa gcaatggtgc agatatgagc tggactatga cagactattg    12060
ggccagtggg gctgacaagg ttaacttggg ggttgccata gagggccttc agtgctcatg    12120
tgcactgttt caagtttgta cagggcatct ggaaaccatg gaagaagatt ctggaaaggg    12180
cagggcaggt aaactggatg tggataggaa gttactgtgg caggtgaatt ggaagatgga    12240
caggttggag gcagggagat ggtgagcggg ctcctgccaa ggtgtaggtc tgagcattgt    12300
tgtgacggct tagttggttt gacatcagca cacagattga ggatctgtca ttgtaactct    12360
aaattgtatc cttgttagac atgtaaaaat aactttttag agcctccgtt tttaaggagg    12420
gaagtggatt gtgctcaagc ttgcatgctc cgctgttcct gtgctttaaa aatactcatc    12480
caccagtgtg gtcactgatg aaaggggagg aaaaactagc cagaagttgc cattttgctt    12540
aaagaatgga ttcatttctt cctcaaggtg gcacagagag agtttctctc tttttgcccc    12600
tctcttagat tgatttacta tttttagtaa attctaacag tctgatcctt gcttccaatt    12660
acaatgatta gcaatatttg cccaagacaa gaaaaaacaa tttcctctct tttctctcct    12720
atgagctttt cctgtgagcc ccaagcagac agatgtggac atctagcaat gctgttaaca    12780
acagctgcag tccgttggac tctctgcaac actgggcacg gtacaaagtg ctctgacaaa    12840
ctcttctgcc ctttgcaatc cttactacgc cctgtgaggt gaggagtatt cttcctgttt    12900
tgtaggtgaa gaactgaggc aaagagaggt tatgtcatta gatttcacaa tagggtgtgt    12960
ttccgtttca tcatctttag attgatgtta ctgtgacatc atcttcctag aattaacaaa    13020
gtgaactggg cacaggaaat agcacatggc acaccttcag caaatggtgg ttgtgatcat    13080
tttcatcatt ccatttcttc ttgaaaaaaa tccctttttt ttttttttt tgagacagag    13140 tctcactctg tcgcccaggc tggactggtg tgatctcggc tcactgcaag ctccgcctcc    13200
cgggttcacg ccattcttct gcctcagcct cctgagtagc tgggactaca ggcacgggcc    13260
accacgcctg gctaattttt ttgtattttt agtagagacg gagtttcacc gtgttagcca    13320
ggatggtctc gaactcctga cctcgtgatc cgcccacctc ggcctcccaa agtgctggga    13380
ttacaggcat gagccaccac gcctggcaaa atccctcga gttccagtgt aaacactcac    13440
gccctttttt gctgtttgct ataaacctct cattctcctt ggtcttcttg tccttgtgtg    13500
aggtcctggt tgttgtggag actgaggtct tctgagacag aaaaccaacc ccatagcagg    13560
cctggtgtgt gccctagaat ggcagaggcc ccacacgttg ccccggctcc tctggaagac    13620
cctccagcct gtctgctgga ttccttgtac ttatgaggat tgttaaacca tctcatagga    13680
ttcctttcca gactcagccc ttcacttgtg gcagcatttc ttactctgag gttctgggcc    13740
tagaaaccca gtgtccatag gcaaggtcta gggacagaga gagtttgtag aaagtgggaa    13800
tgcatcagtg gaaggctaaa tccaaacagg aactgagctg gcctgggtgg ctttgtcctt    13860
ttgccatctt cgtaaccctt taaaggcttt aagcacttc ttttgtaata actaccccaa    13920
ctaaatttgg ccagagctgt gaagggaaag aaaatctaag acccttgagg gagatgacag    13980
ccgaacgttt tacatttta ccaccttgt tgttgccatg cacagctgat acataaacaa    14040
gtaatggcct catcttctat tcttttattt actggttaga cccagaaccc taaaaggtag    14100
atgcttctca tggtcatttg gcatttgcaa caggagctga atttattaat agtactaata    14160
cctcatcctt ggacatcctt gggttgtccg atattttaa ggggcattta catcctttgt    14220
ttttcatatg gaaaactttt ccgtaagggc tggtatcatc ttggccttcc attgcaggaa    14280
```

```
cagcacaggg aggttcggtg gctaggccac agttacccac gcagctaggt agcagcagag   14340
gccccacctg gcacccctg gcttcctaag cacatcgcac tgtgcagcct ccctgaggaa    14400
gcctcgagtg gataggaact ctggttcttt aagataaacc tgagttggat ctcactgtca   14460
ccatttatca gatggggcga tgtcttcagg caaaagtact taacctctct gttttgttt    14520 ccttactcca aaatggtaat gatcatacta ctacccacct gggtggattg tgtgcatat    14580 gaaggaggtc atgggacaa gtggttggaa gagtgttgag cacatagaaa gtacaagata    14640
aatggtggcc attatgttac tacttagact atatcatact tgtctttatc tgggcttaga   14700
atcttgacac tgagatcttt cattctcaga tcttaatatg aaagcttacc aggtaaacac   14760
taccccaaca taattattta gtgggttcat acatgtgaaa gcagttgaaa tacaatttct   14820
gaactccggg ttaatttata tccttagttg gaacaggtag taccctccca gcacctaagg   14880
cctctcactt ctatccattc ttcagatgac ctttgcaata atcatggtaa ttgaatagca   14940
tctgcaccat aacattgttg aataacatca aaatgatcca tttagccatc atgagccttc   15000
ctagtaattc agactcacac cagttctttc aggttattga gtagctttta caaataattg   15060
ctaacagtac aaatactgtc tcaggtattt tggaagggtg aatttttccca ttgatttcag   15120 tgtatcttta ggaggtaatt tgcaaaaccg aagagtttgg ttccgtcaaa gtcaccccta   15180
aggagtgtgg aggaccacat tgtaggttta tactgcactg tccctcatgc ttgaaatttg   15240
gctcatgcaa ccaaggaact gaatttttaa tttcgttaaa ttttgattta aattttaaaa   15300
cagaaatagt ataaaatatt tttctgttaa atataccttg tagtgttggc aagactacat   15360
ttcgtgttac catgctgggt aagatttctt gtagtgtgta ttgtgttttg tcacctcgtt   15420
aataattttc ttattttggt tgcatgttaa aataattttg gatatattgg gttaaataaa   15480
tatattgtta aaattaaatt cacttgttta tttttttgtt ggtgaggcta ggctactaaa   15540
aaatttaaaa ttacccatgt ggattgcatt atatttctat tagtgctgct ttagctgcaa   15600
gtagcctatt taaaaaaaat cattattttc agacttatgg acttcataga atcagaggta   15660
tttagaggaa aggatcttgg gggtcaccta atccagctcc aacatttgc aagtgataag    15720 accaaggcca gaggctacaa taaaatgact gacctcctcc cagatgggga ctggatccca   15780
gtggctttat agccttgcc ttggatcctg gttttacttg gaaacatagc agacatcaga    15840
gctgcagaga acttctacca gatccggagt gaagaaaatg ccttatttat ttatttattt   15900
atttatttat ttatggagac cgggtattgc tgtggcctag gctgtagtat agtggcagaa   15960
acatggttca ctgcagcctc aacctcctgg gctccaggat cctcatgcct caaccttctg   16020
agtagccggg gccacaggta cgcgccacca cgcctggcta ttttttttt tctcttttgt    16080 agagactgcg tcttccatgt tggccaggct gatatcaaaa ctcctgggct caagtggtcc   16140
tcctaccttg gtcccccaaa gtgctgggat aacaggtgtg agccatcatg cctgttttgg   16200
cagtttttag gggcccacgc taattttgag ccaggtttgc gcttgataat gtaatgctgg   16260
aggctgggca ggggacatga tctgcctgaa agggctgaga actgggaggc tcttattcct   16320
atagtattga gagcaaaggc acagtcttac agaaccacac aatattcaga gcttgtgggt   16380
tggagaagga aagtcctctg aaaaataaaa aaagagtac agaggccaga ggcggtggct    16440
catgcctgta atgccagcac tttgggaggc ccaggcaggc ggatcaccta aggtgaggag   16500
atcgagacca gcctgaccaa catggagaaa ccctgtctct actaaaaatg caaaattggc   16560
caggcatggt ggcgcatgcc tgtaatccaa gctacttggg aggctgaggc aagagaatcg   16620
```

```
cttgaacccg ggaggcggcg gttgcggtga gctgagatca cgccattgca ctccagcctg    16680
ggcaacaaga gtgaaactct gtctcaaaaa aaaagaaac agagtacagg tcagacattg     16740
ggcaattttc tcataacaat ttcataggcc attaatttgg ttacagactt gaatagcaca    16800
caacagttct ctaagggtca gtttccaaag taattcctaa tatttaatga atttttaagt    16860
gatagaaatt gcagtaggaa agtctagctt gaaatctaat ttgtgttagg ttgaccaggt    16920
gacaaccacc caccccctgga ttctgctcag ttaggtcaga cctggggcca gttgcccatt   16980
tagcatctca ggcctcagga tcctcattta taaacctggg gtttgaactg cggtctccac    17040
gatcactgtc agctctcctt agtcagttgg ttgttctaaa tgtagtttag tggccagtaa    17100
acacctgttc ctgagtgata catctttaag gagccggtag atgggtcaac ctggctggac    17160 ttgcttttc aagtctgcct tgtctattag aaaggctgag cttactgatt ttgcctgtca     17220
cgtttgagtg ttcctgagac tttgcccagc ctcggtctta tctgcgggta ccccagcctc    17280
tgcattcctt gccctacaa aatgtgctgc cagttccaaa ggcacaaatg aaaattagct     17340
tggctggagc atggctaggc acacaccagt ggttaaagaa atgctgtttg ctggctgaca    17400
cttctggagt ggaagtttat tcttttttct tttttttttt tttttttgcg gggtggggca    17460
gagttttgct cttgttgccc aggttggagt gcaatggcac gatctcggct tggagcgatc    17520
ttgggtcacc ataacctccg cctcctgggt tcaagcgatt ctcttgcctc agcctctgga    17580
gtagctgaga ttataggctc ccgctaccac gcccggctaa ttttttgtat tttagtagaa    17640
dacagggttt caccatgttg gccaggctgg tcttgaactc ctgaccttac gatccacctg    17700
cctcggcctc ccaaagtgct gggattacag gcttgagcca cggcgccgg ccttttattcc    17760 tttctttggc ctcaattttta ttgttaagag atagtgggaa gggcccaatt ttgaaatgat    17820
cctggaatta atgtaggagg ccttgtataa gcagttaatg tgtatttatt gagtgggtac    17880
cctgtgccaa tatgatacaa ggtgtgaagg acacatgagt tgggaaaggc atggggaaat    17940
gcacgctcac actgctggtg cgagtgtaaa aggtacagtc tctatgtagg gctatttggc    18000
agtatatact ctttgaccca gcaactccac ttttaagtat ttatcttagg gatacccctca   18060 cacatttatg aaatgattta tatacaagga tattcattat agcaatattt gtaatggcaa    18120
aaagaaacaa aagtcagatg ggggactgat taaataatta tgttattaag taatactgtt    18180
tcagtacatc tgtgtaatga aataatgtcc agtcattaaa aatagtgagg caaagtctgg    18240
gtgcagtggc tcacgcctgt aatcccagca ccttgggagg ctgaagccgg aggattgctt    18300
gagaccagcc tgggcaacat agtgagaccc tgtctgtaca aaaaaaaaa aaaaaagta     18360 aaatattagc caggcatagt ggcacatgcc tgtaatctca gctattcagg aggctgaggt    18420
gggaagattg cttgagccca ggaggttgag gctgcagtga gctgtgattc tgccactgca    18480
ctccagcctg ggcaacagaa caagaccccta tcttagaaaa aagaaaaaa aagaaaaagg    18540 gacaacttac aactctgtgc cctgatgtag aaccatctcc aaaatatatt aaatgagtgt    18600
gggatactat gcttatatgc gattgtgtgt atttaatggc ttcctaagaa aacaaaaaaa    18660
aacctgatac tagtgattgc cttggaggag ggtaactggg aaattacttt tgcaactttt    18720
aaatcttata ccatgtacac ctggtatcta tttttaaaaa gccatttttca tgccctaaat   18780 gagtttagtc agaccatagt aagaaaatcc tgtaagacat acaaagtatg gggtaattac    18840 tggcttatg ggaagactga tttcaatgca aaactctccc tatgcaaggg agttgtcctg     18900
atttcaatgc taagctctct ttaggcaagt tacgttggcc tgatttgcct gttaagtcgt    18960
atggggcagg caagtctgag tgtccagagg gcagacccttt aactcttagt ttcctgcctt   19020
```

```
gggagaaggc acagggctaa agtggtttcc agaacgtgtc tgttgtggtg tgaacaccaa    19080
ggagcagtgg acaagcttcc caggctcaag gtcagaaggt ctggactgga gtcctgcctc    19140
tgctacttgg tgaatatgtg atttggggca ggttgcttaa tccccgaagc ctcaacgtgt    19200
tcatctagaa atgaagatta caggctggac gcagtggctc atgcctgtaa tcccagcact    19260
ttgggaggct gaggcaggca gatcatctga ggtcaggagt tcgagaccag cttggccaac    19320
atggcaaaac cccatcccta ctaaaaatac aaaaattagc tgggcatggt ggcaggtgcc    19380
tgtaatccca actactcggg aggctgaggc aggagaatca cttcaaccca ggaggtggag    19440
gttgcagtga gctgagattg tgccactgca ctccagccta gcaacagag tgagactctg    19500 tctcaaaaaa aaaaaagact acaatacctg gcccaactcc ctcatgctac tgtagtgagg    19560
ctcaaatgag atagcaccca tgaacactcc tgtaaaccat gaagtatgca acaccaggt    19620 gtaatagaag ctgttaggta cctgtgaggc cagcagacaa gagcaagaga tgctaattta    19680
aaaagaatta aggtgaagca aagatctttt ccctctgcca aataacttgg caagagttgt    19740
aaaattagaa aagtagaccc ttagtagttt gataatcctt tgacctctga ccctgcacaa    19800
atgatctcac cctttagacc tgttcccta tttgcaaaac aagagggget gtctgggtga    19860 ttcctgtggt cccttccagt tgtagcgttc cgtgacagtg tggcattaac agtaattccc    19920
atcttggctg agatggatga gtcatactaa ctgaaaagtc aaaatacgag gaagaagtct    19980
ctttatgtat gagaattttc cttgagctag agactcagag cctcttgggg aggagatgag    20040
ggaaaacatt gccaccacca agaagggaga cgaaggatgt ataaagagaa tggagatgta    20100
tttacttttt tttttttttt ttttttttg agacagagtc tcactctgtc cttctggctg    20160
gagtgcagtg gcacgatctt gggttactgc aatctccacc tcccaggttc acgccattct    20220
cctgcctcag cctcccaagt agctgggaca caggcgccca ccaccgcc cagctaattt    20280 tttgtgtttt tagtagagat ggggtttcac cgttagccag gatggtctcc atctcctgac    20340
ctcgtgatcc gcccgcctcg gcctcccaaa gtgctgggat tacaggcgtg tgccaccgca    20400
cccagccgag attatttact tcttgtgtgt tcttgccatc tccatagcct cctttgcttt    20460
caaatgccca cttgggctgg gcctttggaa aatagattta acccttgttt attggaagga    20520
tattcacaca gtaggccagt tatacacttt gtggcagtcg ttacctcttc tgtgaggtct    20580
ttctgtgcag atttagtggc acctcctcca tgctgcctgg gcttctactt gcttctcatc    20640
actttgtctc ataactcaga tcagagactg tgtcttactc atctttgtat ccctggcatc    20700 tgaggggtg gtatctgatg ggtagatgga ttagtgatcc acttagggta tttacactaa    20760
tcttgttgat cttgactact acctttataa ccaccaccat tctacaagtt ttaactttt    20820 tttttttttg agacagagtt ttgctcttgt cacccaggct ggagtgcaat ggcgcgatct    20880
tggctcactg caacctctgc ctccccgggt tcaagcgatt ctcctgcctc agcctcccga    20940
gtagctggga ctacaggcac ccgccaccat gcctggctaa ttttttttgta ttttagtag    21000 agacggggtt tcaccgtgtt agccaggatg gtctcaatct cctgatcctg tgatccacct    21060
acctcagcct cctaaagtgc tgggattaca ggcgtgagcc accgcaccca gcaaggatct    21120
tttttttttt ttttaaagct aagtgttta tacatataat aatattgtta ataaaatgta    21180
tctaaaattc ataccaccag cacacaaggt ctccggctag cagcagtaaa tggcatttag    21240
tacttactta gccccaagc ctggatgact gactatactg acttattatt acttttagct    21300
atttgtaggt agttacatct gaaaattgac caggcacagt ggttcatgcc tgtaatctca    21360
```

-continued

```
gcactttggg agaccaaggc aggaggatca gttggggcca agaatttgag accagcatga    21420
gtaacatagc aagaaccatc tctacaaaaa ataaaaatta accaggcatg gtgatgcatg    21480
ctacttggga ggccaaggtg ggaggatcac ttgagcctgg gaattagaag ctgcagtgag    21540
ctaggaaggt gccactgcac tccagcctgg gcaacagagc aagactctta atctctttta    21600
aaaaaaaaat ctgaaaagga ccccaaggat tgaactttat ctttacattt atctttacaa    21660
atccaggatc aaaagagagg gtaaaggatc acttggggag tttagaagtg gcagaagtat    21720
ctgtagaagc cttacggtgt gaatgtgctg gattgtgtgt gcccaccctc atggggact     21780
tccttggagg atgagggtac accagcatgg gcagcaaagc tgtttgacct caaggtggag    21840
atctgagcca cctggtcagt ccatgcccag ttaatttcta tggaggtttg gtaaagtagg    21900
ttagggagtt ggatccaatg ttcctgaagt ttctgttggt aatatggcag ggtcgggtc     21960
gggtgtgggg agggttggat cattctaagg gcagtacaag acctaatccc aaaggtgaga    22020
agttcctctc tgtggaggac agcatttaga actcaataca tacatggctt gttcaaaaat    22080
ggggaagaga ttagaaaaat ttatcctaat gtttgcttgt caaccaagc cattctctca     22140
gcaaagtagt gaaacccta cataagtcct ttgaagccta gcagcagtat cctactcaaa    22200
cacaaaccac caaaaaaaaa acaaaaaaaa aacaaaacct ccttggggac tcagatgtga    22260
acctctcatg gaaaattcag taccatgtgc ttttgtagc aggtaggatc acctgctgtt     22320
ttggaaatta acttttttc tgacatcttt ttgaccgaac tctgcatgtg cctcttgaga    22380
aaataatcca aattcttgct ttcttcactt tccagttttg ctttatcttt gcatcatgct    22440
ctgcagttta cagacaagca taatgggtga gagttccagt aaattggctg gatcatattt    22500
cttagattga gtcatgactg aggaacttgt ttgggaacag gaagcagccc atgaaaatgg    22560
ctgcacatag taacctgcca gattgaagaa accggaccac tttctagtgg aaagataaaa    22620
gggcagaaaa atggttctat aactcaggga atggtaaatt tgtgaactag gttttaact     22680
tgttgaataa tacgtctttg tgtgtatttg ggcttttta tgctgttaaa agtctctagt    22740
tattcaagat aagggaaagg aaaacttgga ttcgtggtaa ctgttgctac ctcttaaatg    22800
tctctgctga tgtatacaac atgttgctag gccagttatt ttttttaagg cactgtagtt    22860
acatagaaat aaacctggca acatttacac ttggcctcga taggctgtaa ggccccttt     22920
gtctccagta ttctgtgttt ctgtattta atcacctact ttacacttac tgtagcaaca    22980
caatcaagat agcaaatcag tctaataaaa ccaaaagtac tggaatgtgg gaaatagaaa    23040
gaatgaccta gaattcttgc tgagaaaaca attggtattg ctatattctt gtaatgcagt    23100
gtgagagaag ccagagaagt aaataggcag atacatatct atgaaatgta attagtcatc    23160
agcaagatgc attttaaaaa cacatctgct tggtgtcatt ttgctttatc taataaggat    23220
tacgactgca aggcagagat ttgtaaatga aggagatctc tgttgttttt gttttgtttt    23280
tgcttttgtt ttgttttaag acagggctgg agggcagtac atgatcatgg ctcactgcaa    23340
ccttcatctc ctgggctcaa gtgatcctcc cacatcagtt tcccaagtag ctgggactac    23400
agcagtgtct caccatgtct ggctaatttt taaattttt tgtagagttg aggcctgtgt    23460
tgcccaggct ggtctcaaac tcctgggctc aagtgattct cacacctcag cctcccaaag    23520
agctgggatt acaggtgtga gccaccgtgc ctggctgtta ttttatcaat tcctcaaaat    23580
tcaagcatgc cctcaaatat ttttgcagcc tcatatagct cttaatttgg tttatattca    23640
tccagatggt aggatatgat tcatgttcca cctggttttc ttcagaaaata cttagacagt    23700
gtctatggaa aaaaacattg aaccagattt agcttttagg taaataatat aatcacctgg    23760
```

```
gaataatatg aagaatgaaa tgaaagaaag aaaaatataa tcaagtgtaa cttagactct   23820
gaatgctggt aactaagatt tggatgaagg aaggatctca ggggaataac attaaaataa   23880
gatttttttt aaatggaaat acatgatttt aagaaggaat aacttaagac attccaactt   23940
tatactacat gaaagtaaaa agatcaagga tcagttttct ctttggagca aggctcagtt   24000
tcgctttctg ttgagagtta gtagtgtgta taattaattt tttttaacag tttattgatg   24060
aaatttattt ttagaaggaa atctcccacc accttcctgt cattctcagg gcaagataga   24120
gggtaggaga gggaagggag actcggggga atgggaggtg caagccttaa ttagacattt   24180
gagtgtctaa aagattactt ttcatttcaa atactttgtc tcagtttact gaatagcttt   24240
aatttaggac agggattgta ttatctttgc tttatctttt ccaatatttt ggatcatcta   24300
agcatgatag atgctggttt attcaaggca ctaaaattga cttgcaaaag acatatttaa   24360
tatggattct gtgttcaagt cctttcttct ttgtttatcc tggtacaaag atgtttgttt   24420
taaagtggta tgagttaatt gtccaacttc agatttccct aaaatgtgta acagattacc   24480
cagttggcaa atgatgatat atatttttta aacatgaata tttctgttag gccagatggt   24540
gatttaacat gaattgtcca acatttgtgt ttcttatcaa attgtcttct tttgtctaag   24600
ccaagctagc aacataattt ggaacacact caggaatcac taaaggacaa gagcaaaaaa   24660
aattcagaca ccaagtggca gacggcattt gctccatatg ccatgcaaag gctcctggcc   24720
agtgctcgca tggcccttgg gaagctttct cacccgttgt aagaaagtat ctgtgcagtg   24780
ctgtgcaacc catctacctg ctttcctctc tctacccaaa ccctacttat ctaacacttt   24840
gtactgtggc cttcctccat gggggacttg cacttcctca aagccctgga tttctgtgca   24900
gaagagcagt tttagttctt ccttaggcac ttccctttcc tcctgtccag tgtcatgttc   24960
ttgtttgtta tgggctccac ccagacgatt atttcctctt agatgatgtg tgagccttgc   25020
agagagctgg gtcatttgtg gaataaatca tgtgcccagt cacacggctc cttacaggaa   25080
atggttggtg catattagct tagcacaaaa tacagtagtg agcttgtggt ccccaacagt   25140
gagtcttcag ttaacttctg ctgtttttttt tttttttttt ttaacataaa gctttgaatg   25200
tttcatacag tatcaaatct ctgcaggatt ttgcctgctg aaacagatgt gaaaatctga   25260
gtagcacaga gtatgacatt aaggccataa caataaacct attgttgctg cattctaaat   25320
ttgatcaaga tgtctgtttt tgggaatcca aaatagttgc ttcaaattta gctttttct    25380
tttatgaagc agttttgttt tgttttgttt tgagacctct catagcaaga aaaaacatta   25440
cataaacttt tttttgagac aaggtctcac tttgttaccc aggctggagt gcagtggcac   25500
gatcttggct cactgcagcc tcgacctcct gggctcaagc agtcctccca ccttagtccc   25560
ccacgtagct gggactacag gcacatgcca ccacgcccgg ctaattttg tatttttagt    25620
agagacaggg tttcaccatg ttgcccaggc tggtctcgaa ctcctgagca caagcgatct   25680
gcccgcctcg gcctcccaaa gtgctaagat tataggcgtg agccaccatg cctgccaca    25740
taaatataaa cttaaaaata cacaggaaaa cctttcagaa cactttgaaa cctatttgg    25800
tcctattacg attgcactga atgtccccca gcctaatgaa gagcaattag atgtcatttg   25860
gtggcattct tggtggagac agtaagctag ggccgcagga gctgcttagt ctcccagggt   25920
ccagcattgt ttcaggtaac gtgaacagga tgctcaagag ctagtctaaa taatgcttca   25980
tgtcttattt ttcctgtttg ttgataagga ttcataaaga tgtctttttc tggtcatgtc   26040
aagggaaatt caaataaaaa acattgaatt ggtttggagc tgtccattga agggtactca   26100
```

```
cagcaggaat tgagtggcaa ttgaatgtgt gtgtgtgtat gtttgtaaac atttatatta    26160
gagtgtatgc aaatgtatat gggcgtgccc actgccatca ccattacccc caccaacagt    26220
aacaaaacca ccatcaagag caatatccac taaaacttct aatttgctta ttaatttgct    26280
ttattatttg taaataattc agaatctctg agatcaaaat cctttttat tacaacatgt     26340 taatagtagt ctaattcaga cctgccctga ggaagaacca agcaatgaag ctgtccatga    26400
ttttagaagt taattggctc attctttctg accatctagg tagtcccaac attattttag    26460
gctcccccta gttaggtcca caacctcatt attatccatt ggcctggact ttggtctcgc    26520
ttatacagca agtagtagag cctatcactg tcaacatgta aacatttgca tattttacat    26580
ttatagagag atacttttca cgtgcctcat ttgatccact aacatctgta tgcttgggta    26640
ggatggaata attaaacaat gtatagctaa agccatccaa accctcaaa tattatcatc      26700 tgatgggaag gaaaggggg ggaaaggaaa ttaaatagtt atttcaattc ttggcatgat      26760
tgacactgac aattataaat tccattcaat attttcttcc agctcatgag ggttggttgt    26820
aaggatactt tgcaagtcag atttatgagc agaagatgtt tgcaacctaa attgcttcag    26880
ttgcatgaaa aagtcacaac cttttactga tttttatcct gggatctcct taacaagaaa    26940
aaacctcagg cccaggaagt ctagggtgag gcagggatgt gtcaaagtac acttttcccc    27000
acgtacaggg acaagtattt gagtttcttt gattgacttt gcaaagagct ttgcacactt    27060
tgcacatcac ttcttgagat gggtgggaac atggactgcc tattttacag agttcaatta    27120
agatcgcagg atcatgcatt cctttcattt ttggtgctag tacctagaag atgggaacat    27180
attgaacact taataccttg cttgggcaga tagctccagt ttgcagaaag tctagacagg    27240
ataccctgct atgtatctag atttactgag aagaagcggc ccaagctaat cagaatttta    27300
aagtaggttt ctcagctggg cgtggtggct cacacctgta atcccagcac tttgggaggc    27360
cgaggcaggc agatcacttg aggtcagggg ttcgagacca gcctggccaa catggcgaaa    27420
tcctgtctct actaaaaata gaaaaattag ccgggcatgg tggcacgcac ctgtaatccc    27480
agctattcag gaggctgagg tgagagaact gcttgaaccc tggaggcgga agttgcagtg    27540
agctgagatt gtgccactgc actccagcct gggcgacaga gcgagactcc gtctcaaaaa    27600
aaaataaaat aaagtaggtt tctctatacc tttgaatttt ctgtctccca tgataacctt    27660
tgggtaaaca tgtccatcag aatggaaaca aatcattttt taaaatagaa attattctca    27720
tacctatttt agtgggaatc cccctgagaa gatagccatg tatagtcgac tgaatgctct    27780
gtggttgcta ttttgttgct cttggccagg aaactgatct aggtgaccta cagacttaat    27840
ctgacctgca gactggccgc ttcatactac caagattcca aagccaagtg tatatacagt    27900
cggcccatgc agcctctggt tccatgatgc aaccaatggc agattggttc aaaaatattt    27960
ggaaaaaggc caagcacagt ggagtggttc atgcctgtaa tcctagcact ttgggaagct    28020
gaggcaggaa aatcaatgga gcccgggaat tcaagaccag cctgggcaaa atggcaagac    28080
gccatctcta caaaaagtaa ttagctgggc ttggtggcat gtgcctgtag tcccagctac    28140
ttgggaggct gaggtgggag gatcacttga gcccaggtga aggctgcagt gagccatgat    28200
tgcatcacca cactccagcc tgggtgacag agtgagaccc tatctcaaaa tgagtaaata    28260
aataataaaa tttcaaaagg aaaaagtgg aaaaaaaacc cgaaaaaata acaatacaca     28320
cataaaatac agtataacaa ctatttacac agcatttaca ctttactagg tattgtaagt    28380
aatccaggga tgagttaaag tatataaagg gatatgcata ggttatttgc agcaaatgcc    28440
atgccatttt ataatagtgt aggctcatgg ctaataaagc atgaacccga ctgaagctgc    28500
```

```
ctgggtatgt gtctttgttc agccactttc tggtagtatc ttttttctta acctcagtat    28560
tcttatactg tataacagga atgttttctc tgtataaggc tgttttgagg aatagtttct    28620
atatgtaaag tacttagaac agtgcatagc ataataggaag cccttaatag atactggctt    28680
aaagataatt aggtatgtcc tagtgaggta tacctaacta caagtgctac tttaactatg    28740
cctactttgt gtgctttaca atatatattg ttcaaggcta gaataatgag ccccatgagc    28800
agggtttcat agcatttaag attccaacgc caaccttcaa tcatgacac aggtggcctg    28860 tgccatctag ctagctgcgc tgcctccagg ctgggtggcc tgctcctctg ttggataaaa    28920
atagcctgac tcctcactga aacaaccacc atgttatttg cgtccttggg aagctgaaag    28980
taatagaact ctaagtctgg cgttgccagc tgtcagcaga atgaaatgca aagtgtgacg    29040
tgtctacact gtacccactg gccttcaagt cccaactccc gttcccccat cttgattttt    29100
ttccattctc aaattaatta tttcccctat aggtgatttg tggaatggaa acagatttag    29160
atttcctacc tatttagatt tttccaaaga ctaaaattac aaatcagaaa aactgctatt    29220
gacacatttt tggttaggaa aatctggatg tggttcctat gcctagccta gtcatataaa    29280
ttctctcccc atgtatcttt ttgtgtgtgt gaaacagggt cttgtcaccc aagctggagt    29340
gcagtggtac aatcacagct caccatggcc ttgacttcct gggctcaagc aatcctctca    29400
cttcagtctc cctaatagtt gggactacag gctcgtatca ccacgtgcaa ctaatttgtt    29460
ttgattttgg gtagaaacag gtgtcactat ggtgcccagg ctagtaactc ctgtgctcca    29520
gcaatcctcc tgccttggcc tcccaaactc ctgggattac aggcctgagt caccaagctc    29580
agcctctcct catcaaaacc attccctctt tgtaagattc ttcctatgtc ttaaaactta    29640
atacctttaa tccttccctg gagccatagt tttatttatt tatttattta tttatgagac    29700
agggtctcac tttgttgccc gggctggagt gcagtgacac gatcatagct cactgctgcc    29760
atgacctcct ggactgaagt gatcctccta cctcagcctc ctgagtagct gggaccacag    29820
gtgtgcgcca ccacaccagt tgttgttgtt gttgtttgtt tttgttttgg tagaaacagg    29880
gtctctccat gttgcccagg ctggtcgcga actcctgggc tcaagcaatc cacctgcctc    29940
agcctcccaa agtgctgggc ttgtaggcgt gagccaccgc acctgtccct gtctgctttt    30000 atttttatttt tttttgagat ggagtcttgc tctgttgccc aggctggagt gcagtggtgc    30060
gatctcagct gactgcaacc tctgcctccc aggttcaagc cgattctcct gcctcagcct    30120
cctgagtagc tgggattaca ggcacgtacc accacacccg gctgattttt gtattttag    30180 tagagacgtg gtttcaccat gttggccagg ctgatctcga actccagacc tcaggtgatc    30240
cacccacctt ggcctcccaa agtgctggga ttacaggcat ataggtaagc cacagagata    30300
agagtagcaa gcagtgatgg ggagaagata atctagtgta ggaaagatgg aaagaatggt    30360
gatatttcac aactgctaga ttgacacttt aacttgagag ttatccctct ataaactgga    30420
tatttgctga gcaaagttta aagaaaactc catgtattca gtaatgtttt ccagacccca    30480
cttctcttat ataagccagt ggcttagagt gcttgctcta atttctatat tccattaaac    30540
aagggtggga tttcttctca ttcaaaccat ttgtgacttt gcccttagt gacctctacc    30600 atcaccctat cattaatgat ccaagtgatt agaatggatg ctatgtgtt tgtaggttgt    30660 ttgttgtctt taatgaatag attcattgaa tggaattaac tgtgctcttc tagaacattg    30720
gatctgtgtt ctcatttaga ttgtatttgt aatctcccca cttcccacca tcaacagtgg    30780
cataatgtga attaatttat gtggtatctg tcatttaaaa aacatgagct ctctccttcc    30840
```

```
ttttttttgtc ttaaacatag gacatggatt tgattgacat actttggagg caagatatag   30900
atcttggagt aagtcgagaa gtatttgact tcagtcagcg acggaaagag tatgagctgg   30960
aaaaacagaa aaaacttgaa aaggaaagac aagaacaact ccaaaaggag caagagaaag   31020
ccttttttcgc tcagttacaa ctagatgaag agacaggtga atttctccca attcagccag   31080
cccagcacat ccagtcagaa accagtggat ctgccaacta ctcccaggta cagagtactc   31140
agttcttggg aaagttatgg caggtttaag gaaacactga gcaaggaatt aaaatatctg   31200
gatttgagtt ccagctttgc ctttcttttta cttaaccttg tcaaatctac tttccaacct   31260
cagcctcctg atgagttcag tacctaacct gagttcagta cccaacctat tgatcttaac   31320
agtgttattg tgaggattgg gaagacttaa gttacaccaa agagttttgt aaagtataga   31380
aacatcctgt aaggatcaag tagcagcaac agaagtagta gcaggagaac caagtagcag   31440
ggattactgg cgttactgtg tgtggcaagc actgttttaa gaacatatac tgactgattt   31500
aattaacaca actatattaa ttagttacca ttatccctgt tttatctacg atgagcaact   31560
gaagctcaca aaggttaaat aatttgccca gatcactcag aaaattggag gagctaagat   31620
ctgaacccat gtggtctagt tcaaattgtg catcaaagtg atctctgaaa taagataaat   31680
atttacttaa cttgattata aatatttat gaacatcaat tattgaatat ttagcttggc   31740
aatggaatat ttaaccattt ttgttttcct ttgtgtcatt ccctttttatc aggttgccca   31800
cattcccaaa tcagatgctt tgtacttga tgactgcatg cagcttttgg cgcagacatt   31860
cccgtttgta gatgacaatg aggtgaggta taaaataacc tggttaatag aaaaactcca   31920
tcataactat aaaataacaa tctattctat gtaagtcccg tcaatgaatc tccatttaaa   31980
agaataaaaa cattttttagg aggaaatttt ttaaccaagg aaatactctt gtcaaggaaa   32040
ccttagccta taaataactt tacaattaag aaaaaaaaaa acccttcaca caatacaaaa   32100
ccaaaaccat tgactattgc atagccagaa acatggacag cataaccatg gaaacaaata   32160
acccatttgc tgcaagtatc taagaggttt ggtgagtaaa gagccagctg ggcaataaac   32220
gaagacttgt tcagttaaca attttaataa atctgtttta tctagtacca ctgtgctaga   32280
tattatataa actaaatcct aaagattgta cttacgcatt ttaaagttta ctttcaaatg   32340
cttaagctga aacagaccag caaattataa atttgagtca gtggggtagg aaaaaaagat   32400
ttgttattta caaacggggt catgactggt tagtaagtag agagacacag aactgcagct   32460
gattccattt tgttttgtag tggtgcctta gagcttactc atcccctgtt ggtggaagac   32520
tcataaatca atgccttatc aattttaggt ttcttcggct acgtttcagt cacttgttcc   32580
tgatattccc ggtcacatcg agagcccagt cttcattgct actaatcagg ctcagtcacc   32640
tgaaacttct gttgctcagg tagccccctgt tgatttagac ggtatgcaac aggacattga   32700
gcaagtttgg gaggagctat tatccattcc tgagttacag gtaactaaaa tagaatgtaa   32760
tactggagat ttttttttata ttcagtgcct ttagtcattc tgattattta tataccacct   32820
atttatagga aggattggag ggtgctatta acttagtcat gagtactgcc catgctagtt   32880
aaattggttg gacatcttga ggatagaatg ttataaacct gacgtctgat ctgggaactc   32940
tgaaaataat acataacgct taggcgtaaa tatgtattgg aaatgagaat tatctctgaa   33000
ttatagataa taaattatag agataagcct gaagataatg tgggtaggga gtttatctaa   33060
atttatcacg tattatcatg gattaacttt gatttatata gtataaactt ccttctcatg   33120
cagtgtctta atattgaaaa tgacaagctg gttgagacta ccatggttcc aagtccagaa   33180
gccaaactga cagaagttga caattatcat ttttactcat ctataccctc aatggaaaaa   33240
```

```
gaagtaggta actgtagtcc acattttctt aatgcttttg aggattccct cagcagcatc    33300
ctctccacag aagaccccaa ccagttgaca gtgaactcat taaattcaga tgccacagtc    33360
aacacagatt ttggtgatga attttattct gctttcatag ctgagcccag tatcagcaac    33420
agcatgccct cacctgctac tttaagccat tcactctctg aacttctaaa tgggcccatt    33480
gatgtttctg atctatcact ttgcaaagct ttcaaccaaa accaccctga agcacagca     33540 gaattcaatg attctgactc cggcatttca ctaaacacaa gtcccagtgt ggcatcacca    33600
gaacactcag tggaatcttc cagctatgga gacacactac ttggcctcag tgattctgaa    33660
gtggaagagc tagatagtgc ccctggaagt gtcaaacaga atggtcctaa aacaccagta    33720
cattcttctg gggatatggt acaacccttg tcaccatctc aggggcagag cactcacgtg    33780
catgatgccc aatgtgagaa cacaccagag aaagaattgc ctgtaagtcc tggtcatcgg    33840 aaaacccat tcacaaaaga caaacattca agccgcttgg aggctcatct cacaagagat     33900
gaacttaggg caaaagctct ccatatccca ttccctgtag aaaaaatcat taacctccct    33960
gttgttgact tcaacgaaat gatgtccaaa gagcagttca atgaagctca acttgcatta    34020 attcggata tacgtaggag gggtaagaat aaagtggctg ctcagaattg cagaaaaaga     34080
aaactggaaa atatagtaga actagagcaa gatttagatc atttgaaaga tgaaaaagaa    34140
aaattgctca agaaaaagg agaaaatgac aaaagccttc acctactgaa aaaacaactc     34200
agcaccttat atctcgaagt tttcagcatg ctacgtgatg aagatggaaa accttattct    34260
cctagtgaat actccctgca gcaaacaaga gatggcaatg ttttccttgt tcccaaaagt    34320
aagaagccag atgttaagaa aaactagatt taggaggatt tgacctttc tgagctagtt     34380 tttttgtact attatactaa aagctcctac tgtgatgtga atgctcata ctttataagt     34440 aattctatgc aaaatcatag ccaaaactag tatagaaaat aatacgaaac tttaaaaagc    34500
attggagtgt cagtatgttg aatcagtagt ttcactttaa ctgtaaacaa tttcttagga    34560
caccatttgg gctagtttct gtgtaagtgt aaatactaca aaaacttatt tatactgttc    34620
ttatgtcatt tgttatattc atagatttat atgatgatat gacatctggc taaaagaaa    34680 ttattgcaaa actaaccact atgtacttt ttataaatac tgtatggaca aaaatggca     34740 tttttatat taaattgttt agctctggca aaaaaaaaa attttaagag ctggtactaa     34800
taaaggatta ttatgactgt taaattatt                                     34829
```

<210> SEQ ID NO 12
<211> LENGTH: 59865
<212> TYPE: DNA
<213> ORGANISM: human

<400> SEQUENCE: 12

```
ctcatctttg tcagtgcaca aaatggcgcc ctacagccta ctggtgactc ggctgcaggt      60
gagcgagctc agggacctct gggttcacgg gggcggggtg cctcctactg tgccggcggc     120
tgtgggcgag gcagggcgag gcgggcccaa cctggggcca acttctcgtg tacctgtccc     180
ggttgtgggc ccggcacccg tgcccgcttc tctggtgccc taggtcaagg cgtcccggc     240 acagtcagct ttcctggccc tgtccctgcc tcgcaagaag cgtgggccca agcagcggcg     300
gccgggtgaa gagcggaggc acctcttct tctttttgag acagcattg cctgctcccg     360 tggggtgtgt ttccattcct caaggtgagg acaaggtgac tagggggcgc ggtcgttgtt     420
gagtcttcta ggcccagttc ctgaggcctc acttcccatc tcttagcaac agaggcatga     480
```

-continued

```
cagcatctac ggttgccagg cctggagtct ggagaagaaa ctaggaccct gtaccacctt      540
ttgaggaccc tgcggaacgt ggaatgtcgg ggagggggggc ggtcttctgg gcccatacgt     600
agtaaataat ataataatag tctctcacct tgcacaaga tttgaggcct gttttaattc       660
ttcataatat tatttgattc ctgtaatcgt aggaatgagg tggttttttct catttgatag     720 atgataaagc tggtagaaag taggtgaaag ttctgattct caagagtgtc accgaagtgc     780
tgtggcagaa gcatgggccc taccaccact cagttcttgt ttatgtcagc ctgccctcac     840
agaactttat gaaccacggt gcaattattt ctgtttgtca gaatgcagta cgaatatttt    900
gagcctcaca ataagttgct tgtcaaatat gggaggataa ggagactcca gtttgacctt    960
gactcccctg ttaggagcta tctagaaagc tgactgactg ccagatgatt ttttcacttc    1020
taacttgaca gccctgggaa ggtgttatac tcagaggttc aatgtcaaat gtgtactttg    1080
ttaataaaaa tcaagcaagc atctgtagac attctctgtc aaccttcac atttaacttt    1140 gtgaattcct tttggatcaa gtggcgcaac tttgataata gaattttacg agttgttatg    1200
cgttgtactc tcaggaagct tgtggtactt gaacttattt tcatcacat tgcttaaatt    1260 taaacttgaa cttattttc atcacattgc ttaaattgaa accatatggt ttaaagtaaa    1320
atcatcattt atctgaaaga aaatatttct gatctcaatt ccgggctaag ggaaaggatt    1380
tgcacctaat tatctctta catctttttt ttttttttt ttttttttt tttttttga       1440 gacagtcttg ctctgtcacc caggctggag tgcaatggcg caatcttggc tgactgcaac    1500
tctgcctcct gggttcaagt gactctcctg ccctcagctt cccgagtagc tgggattaca    1560
ggtgtgcacc accatgcttg gctaattttt gtattttag tagagacggg gtttcaccct    1620
gttgaccagg ctggtcacaa actcctgacc tcaagtaatc ggcctgcctt ggcctcccaa    1680
agtcctggga ttacaggtgt gagccaccac acctggcctc ttcacgtctt ttgattctct    1740
aggttaatga tgtggaaata gttgtttctt cctgtctcat gatttaaggg agtcaggcaa    1800
gattatttga taagataaat gattatagag ttcttgaact tggaagagaa gaatagtatc    1860
acaccatttt gaaccgaaaa ggatcttgga aagtatgagt attagactgg tgtagaagga    1920
gatctgggct ctcttttcctg atcctgtgac cttgagtaag ttacttcctg aatccattgt    1980
ccattggaga tgatcttcat tgaacaaatg tatattcagc aagtggatgt tagaaagtga    2040
tgagcaagta gaatgagttt acaaccatca cgtagactaa cctcttatac aggtggaaaa    2100
atctaagacc ttgagagcct gggtgacttc cagtagcaga gtcaggatta aaatcctggt    2160
ctccttgttt gttccttcag ctaagatgaa tgaacaatat tatgcagttt gcacactgcc    2220
tcccaataac caggctgtct caaataacca actaacacgg tttctctgag aagcttgtat    2280
atttacccct tttgtgctta gatacatttg agaagtgatg gttactacct taatagtcat    2340
gtatgcaaaa ccctatgcct gtagtcaatt cattcctacc tcattcacca tatatttact    2400
gagcgcccaa tgcttgttct ggataccgtg gtaagcaaag acagtccctg ttctcgtgga    2460
gcttccactg tattctaatg tacctgactg cagagggcct tggagatctt tctcagccaa    2520
atatagtatt tttctttcct tggctggacc aaaggtgaag gtagataata gaatgatggg    2580
tgttactccc agcactaaga gtacctaaca tttatcttac tgtgtatgac taatttcaca    2640
tgactctgtg agatgaggca ggcctattag cctgatttat agatgaagaa acaggattag    2700
agagcaaaca tagtgttatg gttgagagca tggactctgg catcaggcag cctagatttg    2760
aataccgtaa tgactctaac actcatgtag ctgtgttttg ggtaagttac tcaacctctc    2820
tgcacctgtt tccttgcctt tagatacaat aataatagta tgtctgtttc aatcatgtaa    2880
```

-continued

```
tagttgtaaa gtatttagaa ccctgcctgg tacttaataa gggctatata attgctaaat    2940
aaatttgtgg cagggtgcag tgtctcacgc ctgtaatccc agcactttgg gaggccaagg    3000
caggtggatc acaaggtcag gagttcgaga ccagcctggc caatatggtg aaaccccatc    3060
tctactaaaa acacaaaaat tagctgggtg tggtggcagg cgcctgtagt cccagctact    3120
cgggaggctg aggcagaaga atcccttgaa cccaggaggc ggaagttgca gtaagccgag    3180
atcgcgccac tgcactacag cctgggtgac agagtgagac tccgtctcaa aaaaaaaaa    3240
aaaaaattgc ctgggcbttt atcagtagtt gttagtaggt atggtttgaa tctggacatg    3300
tctgattccg aagcctgagg gcttagcaac tggcactatg ctgcttccct ttggcatcga    3360
gctcagcctg tggatcaggg caccataacc tcagaacagt gccaagttga atgtgtactc    3420
tcgtttgaca gtacctgcta ccaggtagta agattagaaa taagaaaata gaacgtgggt    3480
tttgttttat tttgttttgt ttttttaaag aaatgggggt ctcgctatgt tgcccaggct    3540
agtctcaaat tcctgggctc aagcaatcct ggcttggctt cccaaagtgc tgagattaca    3600
agcgtgagcc actgcaacca gctaaggagg tgagattttt gaaaaaccac atttattctc    3660
tggtttttag catttatttt tgtgcatatg actgagtagt acacaagagg ggctgagcag    3720
ttgcaagtat gtttattagg tgtttggttt tgccttgaga taactggggt gctgaggttt    3780
catgtgacct tgggggaagt catgtaacct cttgcatata aatttgtgat ggcagttaac    3840
tacaaaaata tttggcagaa actctgtgcc atgttaaaat aaaatcttgg tttgaattgt    3900
gaaacgatg attctggttg tatggtcact gtgataacct tcgcagatat cagttgttat    3960
tagaattgag tgaatgaatt ggtaaataag cttccatctt agatgtggac agagggaaca    4020
gacacaccat cctgaggatt aagggagcac agcattacct ttcaaaccaa ctgcttcaca    4080
gtgttctttg aaagctttgg ctgggctcgg tggctcacgc ctgtaattcc agcacattgg    4140
gaggccaagg cagatgcatc acctgagatc agaaattcaa gaccagcctg ccaacatgg    4200
tgaaacccaa tagctaataa aaacacaaaa taagccgggt gtggtggcac atgcctgtaa    4260
tcccagccac tcgggaggct gaggcaggag aatcacttga acccaggagg tggaggttgc    4320
agtgaaccga gatcacgcca ttacactcca gcctgggcaa caagagtgaa actctgtctc    4380
aagaaaaga aagaaaaagc ttaatgtcta gcactgccta gcattgttct agacactggg    4440
ggtgcagtag tgaacaagaa tagtgggggct taaattgttg tcctgggaa attacgtaga    4500
aaaataagaa tattgtatta ctgagtgttg tggggaagat aaggtagaga aatagggggt    4560
gggaacatgg catttttaac tggggtgttt ggggaagacc tcgtagaaga ggtgacatct    4620
gaactgggac ttaaatgata cgaacgcagc tgtttaccat ttttggagga gacttcaaat    4680
agaaggagca tgtgcagagc acccacctag gtatgagctg agtgtgttga ggataagagc    4740
taaggccagt gttgctacag tgtcctgagg agcgaaaggt ctgaacaaga ggctggggct    4800
agggtcaggc aggcttcggt aaggaaatcc aagtgtagtg aaaactggga gattttaagc    4860
caggagtga tgtgatctga tcatctgggc tgctgcgtgc atgatggacc atagagggtc    4920
aaaaggagga ggcagggaga ccagtggggg actgttggag tcatcccagg aatggcagag    4980
gagtctggga ctagggatct gggggggtgga gataatgaga tgtattcaaa attgggatat    5040
atttggaggc agatggggttg gcgcatggga gggatagaga ataagggtga ctcctgggtt    5100
tggggtctta gtaactgagg gatggtgag cttgattgaa ttcagtggtc gtgtgtttgc    5160
agtcattttt tttttttttt ttttttttgag acagggtctc gctctgtcac ccaggctggg    5220
```

```
gtgcagtggc gcgatctcgg ctcactgcaa gctctgcttc ctgggttcat gccattctcc   5280
tgcctcagcc tcccgagttg ctgggactac aggcgcctgc caccacgtct ggctaatttt   5340
ttgtgtgttt ttagtagaga cgggtttcac gtgttagcca ggatggtctc aatctcctga   5400
cctcatgatc cgcccgcctc tgcctcccaa agtgctggga ttacaggcgt gagccactgc   5460
gcctagcctt tttttttttt tttttttttt ttgagacgga gtctcactct gtcacccagg   5520
ctggagtgca gtggcgcgat cttggctcac tgcaagctcc gcctcccagg ttcacgccat   5580
tctcctgcct cagcctcctg agtagctgga actacaggcg cccgctacca tgcctggcta   5640
attttttttt gtattttttag tagagacagg gtttcactat tagccgggat ggtctcgatc   5700
tcctgacctc atgatctgcc tgcctcggcc tcccaaagtg ctgggattac aggcgtgagc   5760
cactgcaccc ggcctgcaca gtacttataa aaattagcta agggcagaat ctcattgata   5820
aatttttgat tctttcatca gttctcaagt actttatttc acaggtgaga aagccagatg   5880
acgtcaagtg tcttacccag gggccctcac ttgagtcgag tatgagcata ttgtctcatg   5940
tggactctgt cctatctggt cttattgtga aacctggtgt gtgtccaaga gggccatctt   6000
gtaaatgctt acctttttta taaaaaaaaa aaaattgttt tttcctttt tttttttttt   6060 tttttgaga tagggcctca ttctgtcagc caggctggag tgcagtggtg taattatagc   6120
tcactgcagc cttgacctcc tgggctcaag cagtcctccc accccagcct ccctagtagc   6180
tgggactaga ggcatgtggc accatgccca actaattttt tatttttgt ggagatgggg   6240 atcttgccat gtcacccaag ctggtcttga actcctgagc tcccaaagtg ctgggattat   6300
aggcgcgagc cactgtgcct ggctagtggg aagagagtgt tgagtcttcc ttggctccag   6360
ctttctttga cttgcctcgt tttcccagca cctggtttgg aaggcagtgg tgggctctgg   6420
gcctctcagc atgaaggaag gaaggtattg tagagagact tcttgtagcc tttaaaaagc   6480
agcaaatggg ccggacgtgg tggctcacgc ctgtaatccc agcactttgg gaggctgagg   6540
tgggtggatc acaagctcag gagttcgaga ccagcctggc caatatggtg aaaccccatc   6600
tttactaaaa atacaaaaaa aaaattagcc agtcgtggtg gcgcatgcct gtgatcccag   6660
ctactcagga ggctgaggca ggagaatcag ctgaacccag gaggtggagg ttgcagtgag   6720
ccgagatcgc gccactgcac tccagcctgg gcaacagggt gaaactctgt ctcaaaaaaa   6780 aaaaaaaag cagcagatgg accctcagga gccttaggag acttctgcca ctggcttact   6840
gggtagcttc gggcaaagtc tcaactctct gtggtcctgc agttagttac acatctgcaa   6900
aacagtgtaa ttaataacta cccttcagtt aagaagggtt ctgaaggcct aatatttgaa   6960
aagttgtttt gactctgttt gatgtgttat aaagcattgt gagccgggtg tggtgcctca   7020
tgcctgtaat cccagcactt tgggagccca aggcaggtgg atcacctgag gtcaggagct   7080
caagaccagc ctgaccaaca tggtgaaacc ccgtctgtac ttaaaataca aaattagtca   7140
ggtgtggtgg cgcatgcctg taatctcagt tactttgtgg gctaagacag gagaatcgtt   7200
tgaacctggg aggcggaggt tgtactgagt taagattgtg ccattgcact ccagcctggg   7260
caacaagaat gaaactctgt cttaaaaaaa aaaaaaaaa aggccagacg cagtggctca   7320
cacctgtaat cccagcattt gggaggcca aggcaggcag atcacctgag gtcaggagtt   7380
tgagaccagc ctgaccaaca tggtgaaact ccatctctac taaaaataga aaaaattag   7440 ctgggtgtgt gggtggtcgc ctgtagaccc agctactcgg gaggctgagg tacgagaatc   7500
gcttgaacct gggaggcaga gcttgcaatg agccagagatt gcgccactgt actccagctt   7560
gggcaacaga gcgagactct gtctcaaaaa caaaacaaaa caaaaaaaca aaaaacaca   7620
```

```
cacactgcaa atagtttctg atattatttt aggaataggc catttctaag attgagagta   7680
gggacagatt ttccccttgt agaatatctt cattttggaa gtcttgaaag gtagggagaa   7740
tgggccaggc atggtagctc acggctgtaa tcccaggact tgggaggcc gaggtgggtg    7800
gatcacttgg ggtcaggagt tcaagaccag cctggccaac atggtgaaac tctgtctcta   7860
ctaaaataca aaaattaac tgggcatggt ggcgtgtacc tgtaatccca tttacttggg    7920
agactgaggc aggagaatca ggttcaagcg agtctcctgc ctcagcctcc caagtaaatt    7980
aaaggtaggg agaatggttt ccatattatt tatttattta tttatttatt tatttattta    8040
ttttttgag acgagtctg ctctgtctc ccaggctgga gtgcagtggc gcgatctcca       8100
ctcagttcaa gctccgcctc ccgggttcac gccattctcc tgcctcagcc tcctgcgtag    8160
ctgggactac aggcacccgc caccacgccc agctaatttt ttgtattttt tttttagta     8220
gagatggggt ttcacggtgt tagccaggat ggtctcaatc tcctgacctt gtgatccacc    8280
tgcctcggcc tcccaaagtg ctgggattac aggcgtgagc caccgcaccc gacctcttta   8340
gttttattct gcagcacctg ggccagagga agggcacca gctttggagc caggcctgga    8400
attccacctt gctgcgtgac cctgggcaaa acagttagca ttccagagct tcagtttcct    8460
catccattaa atgggcacaa tgccttctgc ctcacagggt agtcgtggga ttgtgtggat    8520
aaagtacttg gggcaaatcc agtgcagggt agaggcactt ggtgaatatt catttctgtc    8580
tccagcccct gcagatggcc cgcggcatcc atcacccag cctttatcct tagctcatac    8640
gtttaaaaaa gaccagttgt ggccgggcac agtggctcac gcctgtaatc ccagcacttt    8700
gggaggccga gatgggtgga tcacgaggtc aggagtttga aacagtgtg gccaatgtag     8760
tgaaaccccg tctctactaa aaatacagat atgagccggg catggtggtg tgcgcctgta   8820
gtcccagcta cttgggaggc tgaggcagaa gaatcgcttg aactcaggaa gcagaggatg    8880
cagtgagccg agatcacgct gctgcactcc agcctgggca acagagcgag actctgtctc    8940
aaaaaaaaaa ccaaaccagt tgtgaaaatt gcttgttcct cccatcatct ccccagatag    9000
caggtaagtg gtagttgttc aaggaaacct ttttttcaag atagagtctc gctctgttgc    9060
tcagtctgga tgcagtggca tgatctcact gcaacctcca cctcctgggt tcaagcagtt    9120
cttttgcccc agcctcccaa gtagctggga tcacaggcac gcaccaccat gcccagctaa    9180
ttttttgtatt ttttgtttta gtagagacag ggtctcaccc tgttggcaaa gctggtctcc    9240
aactcctgac ctcaagtggt ccagctgccc cagcttccca aaatattgag attacaggcg    9300
tgagccactg cgcctggcca agaaaacct ttcaatactg ttttaaaaga gttggggga     9360
gaggtagaaa tgaatctttt ggtttagttt tttaattctc taaggacaac attggggaag    9420
tgagctttag agttatattt gcagtattta tttttatcat gaatattca agtctaggcc     9480
cttggtgaat tgaggcctgg tgagtatttc tgctttcccc ctggagagat tgagatggtt    9540
tctgattggg agctttaatt ctgtgggcat tgtgggact taccaaagag gtatctagag     9600
ttcctttaaa accccgccc tgtccctgcc acatatcttc tttttttttt tttttttttt    9660
gagaaggagt ctcactctgt agcccaagct ggagtgcagt gagtgacacg atctctgctc    9720
actgcaacct ttgcctctgg ggctcaagca attctcctgc ctcagcctcc caagtagctg    9780
ggaccagagg catgcgccac cacacctggt taattttctt gtatgccaca cttctttagt    9840
tccttgtagc cgggctcctt gaccttctgc agggcatctg tggttgtggt atttataagc    9900
actcactgtg tcatgagtgt gttcacagag ctctaagaca agggccctgt ctgtggaaga    9960
```

-continued

```
gcttttaggg tggtgaggga gaagtcatct aaatagctat aatacacggt actgaagcaa   10020
ggagtaggtg ggggaatttg ctgggtggga ctaagtacag cctcagccac ccgtcctgga   10080
acatggatgt agtggtggtg tgtttggtcc gcccacagac aatgacagat gcccatccag   10140
gcctggagga gcggagaaac gcattaccca ccatctgttg agcaatcagg ccctctgtgc   10200
cagtcacaga actaggtctt gttttacaaa tattgcctca tttgtccttc acaacaaccc   10260
taagaagtac atatgagtag cctgtttcac agtgatgaaa ctgagtccca gagaggttaa   10320
atagctcctc tgaggtcaca gctagcacat ggatgcagat ttgactgcag acccaggct   10380
ttttaccagt cagccaaacc gtttccccag agggagtaga aactgatctc tgtggagtgg   10440
gctggatata ggggatacag ttcagtcggc tctgtgcctg tttgggttat gtctttgaga   10500
ctgtgattgt ctcctgccct aaacaccagt gaggctggtg ggggagaggc tagaggggtg   10560
ggttgcacag aggcagcttt attccttgac tgagcttcag ctcagcctca caggctgcct   10620
gttgagcttg cagagaatgc ccgtctcaag tgtgtaggtg cagagctgct gcctgtgggg   10680
ccagagcagg gcttgggatt tgtatgcagt tcatagtgta cgactgatgt aggcagcaaa   10740
agagaattag tcagatgagc gaatctgtca tcagcctatt ccttaaagga acccctgct   10800
gcctttggta cccatttaga ggctttgact tggagagaca tggctccttg ctccctttcc   10860
aagcctctga aaaggactgc atcacttttg ttcctgccag ttgcatagca accaagctag   10920
ctgactgcct gctggcagga gggaattgtt tagctttgat ttcttaggag aggagccagg   10980
catcgcctac caggaggggg agaaaattgt tagaagccct gcaatggagg tgtgggaaga   11040
tgcttctcct taggagggtg tggactgatg tgcattcctg tgttgcccac ttagacagag   11100
tccacctgag acttctctgc caggaagggc taggcagtta gttgctaaga gatgtgagcc   11160
cgaagtcatc cttctgtgaa atgggctgcc gtgtaatgta tgagttcccc actgctggag   11220
acagcttggc taggttgggt gagtgtgtta ggcattcaaa tacagaagga gtggatagat   11280
gaggcctttt cagttccatt tcaattccaa gatgtgctgt cctggtgctt gggacctgct   11340
ctggggctct ggtctttggt ggctggggag ggagaagtag gcggcatagt ggaaaaacat   11400
ctgcccgtaa tcctctcccc agtacacagg caggccacgt tttagtagca gcatctcatt   11460
ctcccaggcg aactgagtaa tagcagctta cgtttattga atgcctgcca gaagcccagc   11520
taccaagctc tatgccttc gtatatattt tttgtaatag aatgcagtat attcataaaa   11580
gctctcttct ccccgtccca gtccccaggg caattttgtg tttatcattc tagacttttc   11640
ctctgtattt acaagtcttt ctaatcctca caaaatctct gccattttg ttgttgttgt   11700
tgttcttccg agatggagtc ttgctctgtc acccaggctg cagtacagtg gctcgatctt   11760
ggctcacagc agcctcaaac tcctgggctc aagcaattct cccacctcag tctcctgagt   11820
agctcagact atagacacag gctaatttt gtatttttt gtagagatgg gggtctcgct   11880
ttgttgccta gctggtctt gaactctggg ctcaggagtg tggtgatcc acctgtctcg   11940
gcttcctaaa gtgctgggat tacaggcatg agccattacc ctcggccaaa atctctgctc   12000
ttttacccc atgttacaga agaggaaatt aaggctcaga gaggtaaaga atcttacctg   12060
aggtcccaca gctagggaag ctgagattcc aagccagatc cctccagccc tagagtggat   12120
gccatttctg tgactcggca cttgtcttgg agtgtttcca tgatggcact ctgacaagtg   12180
cttggtgact tctctgtcag ttgttaaagc aactgtctca agagacctgg cctctcccgg   12240
accctggcct gtttgggtgg ctcggcaccc tcagctctgt agcttgctct gtatgctggg   12300
gctcactggt acatggctcc ccaacaagca gtgctgtatg caccatgctg gacaaggtgg   12360
```

```
gcagaagcct gcccgagaat aggtcagtcc gtttcgattg tagtattctc tgaatacaac    12420
tggtcccaag ggaagacctc cgacctccgt cctttgggaa gagagggcag catgtctgac    12480
tttggccgag tggggttgtg gggagttctg agtgggtgta catgtgatgt gccgtggggt    12540 gggcccttttt cccatctgcc acagctctga acccgtgctg ttgctcatca cggcttctgc    12600
cagaggcact taacttgagt ttgaaagcac aatccagaag gccggtggtc gtgtcacggc    12660
tctgccttca tctgtttcat cagtaagtct ttcttgaact tcttctatgt gttggacatt    12720
gtcctaggtt ctgaatatat tgtgaccaga atagaccatt ttttgtcccc atggagctta    12780
tattttagtg gactttactt tcccatctgg tccaagtctc tgtcttctca tgtaaacaag    12840
ggacagaatg acctgtagta atcccacttg gcacaattgt tagggtaaga gagctgttgt    12900
catctcgcca gcagcatcct ttcttccctt gtcttgccta gccgtgtggt gcctggctcc    12960
ccggtggggg tctgctgtgg ggatgcccct tccctcagcg tttgcccact gttctgtgtt    13020
ggtagatgca ggatcagcag agcctccctt actccctgga agccctggag atttgtggct    13080
catccagcta gactcagcaa aggcacttag ggtcagcagt tgggaccaac aaccccctgg    13140
aggactcagc ccacctggcc gctgggcctg aagcagaggt tgggagacac tgtcggtagc    13200
acagggagaa agtctcggcc tctgcaagtt cccagctgtt tgaccttagg caggcccctt    13260
cctgtctctg agcctctgca gcttcaggca gttaggagg ctgagctatg cacagcaagg    13320
ttcacaagag tcacacagag atgtgtggga ggtgatagtt actccaaaac agatctgtgg    13380
gcatctggct actggtcacc ctgatgggag actcccactt aggtgtaaaa ttaggaagtt    13440
gttttgtggc tgaggaagtg ctataacgat gcttaggatg gagaagacat aattgtggtt    13500
ttcagtgatt tgaagggctg gttgtggaag actgactagc ctcatttgat ctggttccaa    13560
aggataggac taggaagtta ggcctgtcat gtgccaggca ctggtctagg ttctctcctt    13620
tcatcctcac tgcagcctgt gaagcattat ccccatttac agatgggaaa aattgatgtt    13680
tagagggatt aaataaaacc acagaaggtt atacagcttg taaggggcag agctgggatt    13740
tgagcccaga tctccaaagc tggaatgatg taatgggggc acattttcat ttgatttaag    13800
aagcattagt ttaaaatctt agaactgacc agtagtagaa taggcttttg ggaagagagt    13860
gagcttccag acctagtcat gttgaaccag ggggcttatg ggagttgatg aggggagatt    13920
ttctgcctcg aggccacctc agtcctgccc tcagccccett tgttcccag aaagtgggg    13980 aaagtggagg gcgagggcgc agtgaaagta tttcttctag atgagggcct gggatttacc    14040
agtgaggatt ttacaaggcc tgagacgtag gctccaagta tgggaaaaaa ttttcccgtt    14100
tcccagtttt gggaaaactg tgttggatgg ccttatgggt gacctcagga atgtctctgt    14160
ggcctgaggt tgaactgagc attgagtgtg ttttactttt ggaatcagga aataaaaaca    14220
gaactctgta aagttatttt taaaaaatat ggctgggtgc agtggcttat gcctgtaatc    14280
ccagcacttt gggaggccaa ggcgggcgga tcacttgagg tcaggagttc gagaccagcc    14340
tagccaacat ggcaaaaccc tgtctttact aaaaatacaa aaattagctg gcgtggtgg    14400 tgcatgcctg taatcccagc tactcagcag gctgaggcag gagaatcgct tgaacccagg    14460
aggcagaggt tgtagtgagc caaggttgcg ccaccgtatt ccagcatggg cgacagagtg    14520
agactccgtc ttaaaaaaaa aaaaaagaa aattaaaaat atgcccaagg catcatcatc    14580
atccttcctt aaataatact gggctgggca tggtggctta cacctttaat cccagcactt    14640
taggaggctg cagtgggagg atggcagata cttgaggatg tgttctctca aaacgacagt    14700
```

```
aatctaagaa aaatccattg aatccaggaa acaagaatcc aactcaagag gaggacagga    14760
tattctaagg atactaatgg atgtgagttc cagagaggta ttagacctta tggggaagga    14820
gacagaggct ccaggagatg acgaggctgg tggatctcct gacgcattca taatatcgag    14880
tgtcgtagcc gatggagagt ttgagaatga atttgtgata agtacaccaa gtgttgaagt    14940
ttgttgtctt tggggcaggg aaatgggggg ttgggacttg agtcctggtt tcctttataa    15000
tgatagtttt taaattttaa taatgcgtaa agatgttact ctgatcaaaa tagaaaatta    15060
cattaaaaac aaaagtatca aatactacta ataaagatta gtattatcag ggttgtattt    15120
gctcagaaac ttcagccctg acacctgttc agtgtgggta caatggattc catggtacca    15180
gggattgtgg ggagggagag atgcagcatg gactagtgct tggtgccttg cttggagtca    15240
ttgagtatta gagacccaca agatatcctg taccaggcca gggagctggt ggatgggtaa    15300
tgatgataga tgtccctgga tgggcttcag ggagtctgta aaattgtgtg ttttatgatt    15360
tttctatatt ttctccatga aatatatctt gctttttata acggaggaaa aattctggta    15420 atttttttt taaatagaga ctaggtctca ctatgttgcc caggctggtc ttgaactcct    15480
gagctcaagt gatcctcctg cctcagcctc tcaaagtgct ggaattactt ttagtatttt    15540
acatattaca taattacata cttgctattc tttgggaacc cattcatatt atttcatgcc    15600
tcacagtaac tcagaataac attcatatca tttcattcct cacataatac tgcagatatt    15660 attcttttt tccaagtgag gaaattgggg tgaaatgtgc ttgtcatgta ggtagtaagt    15720
gacagagctg ggctttggag tcagctcttt tttttttttt tttttttgag atggagtttc    15780
actcttgttg cccaggctgg agtgcaatgg tgcagtctca gctcactgca acctccactt    15840
cccgggttca agtgattctc ctgcctcagc ctcctgagta gctgggatta ggcgtgtg    15900 cgaccacact ctgctaattt ttttgtattt ttattagaga cgaggtttct ccatgttggt    15960
caggctagtc tcaaactgcc aacctcaggt aatccaccca cctcagcctc ccaaagtgct    16020
gggatccgtg agccactgct cctggtcagg ttaagttatc ttcactgtgc cacattgccc    16080
cttgtaaaca gcaggttata gttcaggttt ttaggacagc gagccacacc ctccctgcc    16140 tggctgggtt tccaccctga tcttccacta tttcctgctt tgtctttttt ttcgagatgg    16200
agtttcactc ttgttgccca ggctggagtg caatggcaca atcttagctc accacaacct    16260 ctgcctccg agtagctggg attacagcat gcgctaccat gcccggctaa ttttttttt    16320 ttttttttt ttttgagacg gagtctcgct ctgtcgccca gtctggagtg cagtggcacg    16380
atctcggctc actgcaggct ccacctctca ggttcacgcc attctcctgc ctcagcctct    16440
cgagtagctg ggactacagg cgcccaccac cacgcccggc aaatttttt ttgtattttt    16500 agtagagatg gggtttcact gtgttagcca ggatggtctc gatctcctga ccttgtgatc    16560
cacccgcctt ggcctcccaa agtgctggga ttacaggtgt gagccacggc gctcggcccg    16620
cccggctaat ttttgtatta ttagtacaga ccgggtttct ccatgttggt caggctggtc    16680
tcaaactccc gacctcaggt gatccgcctt tcttggcctc ccaaagtgct gggattacag    16740
gctcgagcca ccgtgcctgg cctcctgctt tgtcttttac accccagcat tttgagtgat    16800
tggcagcttc tgcatgcttc acttggtgag tctctgtgtg catgctgtgt gttctcttca    16860
cctgccctgc aaatgcctgg ttgccctctg cgaccctgct caggcgctgc tctctctgtg    16920
aagccttgtg gaaacatccc aggcagagct tctcattctc tgtgctccac tcctgccct    16980 tgtgtgtgtg tgtgtccttc tttcaaaggt tacagtgagg ttttgcattt acttcctgat    17040
cttggctaga ctgaggcata ttagtctagt gactgtctca ctcttcttgg tatctgagtc    17100
```

```
ctattgcttg gcacataata gagtgcaaat gtgctgctag gaaagagggt acacgataag    17160
ctactgtcaa cctcttcttt ttttttgag acggagtctc gctctgtcac ccaggctgga    17220
gtgcagtggt gtaatcttgg ctcactgcaa cctctgcctc ccaggttcaa gcgattctcc    17280
tgcctcagcc tcccaagtag ctgggactac aggtgtgtgc caccacgccc ggctaacttt    17340
ttgtattttt tttttttttt ttttgagacg gagtcttact ctgtcgccca ggctggagtg    17400
cagtggcgcg atctctgctc actgcaagct ccacctccca ggttcatgcc attctcctac    17460
ctcagcctcc caagtagctg ggagtacagg cacccgccac cgtgcccggc cattttttg     17520 tattttagt agagacgggg tttcaccatg ttagccagga tggtctcgat ctcctgacgt     17580
tgtgatccgc tcgcctcggc ctcccaaagt gctgggatta caggcgtgag ccattgctcc    17640
cggcccattg tgtagcattt ctacaccttc aaggtccctc gtgatacctg gttccttttt    17700
gtctcctcag tcttattttc tgccatttct tcttcacttt gccacaacca agctgctttt    17760
cttttgtttt ctttttttg agacagtctg tctctgtcgc ccaggctgga gtgcagtggc    17820
gccatctcgg ctcactgtag cttccgcctc ccaggttcca gtgattctcc tgcctcagcc    17880
tcccgagtag ctgggattac aggcgcccac cactacgtcc ggctaatttt tgtattttg     17940 atagagacag ggtttcacca tgttgaccag gctggtctcg aactcctgtc ctcaggtgat    18000
tcacccacct cagcctccca gagtgctgag atgacaggca tgagccaccg tgcttggctg    18060
cttttctttt ctttcagttg caagtgcttt cttgcacatg ctgttctctc tgtgccaaat    18120
tccctggact ccttcccta aagcccattt gtttagcctc agatcaaaca tcactttctt    18180
ggagaagccc ttcccccatt ctggattaag ctgtccagct ttatgctgtt acagcagctt    18240
aactttttat cacagcactt ctctcacata gtcacttaca cagtcccttg agtgatgact    18300
tgacatgttt tctcacctaa aattcaggca ccacaacaca tagtctggga ctggagaaac    18360
atttaatgaa tcaggaagac gttagtttaa attggggagg tagtatggga gggaaagcat    18420
tgacttgata attggagggc ttgaattctg cccctaactt ctgttaacta ggtatgtgac    18480
cttggcattc atatcctcat ctgtcaaaca aagaaaaaat tcttggtgat ctggggtcat    18540
cttgagttgt gataatctat acttctagat gaatcatcaa attaacacag ctctagaggg    18600
ctgcttatct aggatgagaa tccacctgcc tgcttggcct ctccacttgg gtatcagata    18660
gtccaatgtc cagaaccaaa ctcctgatct caccgtgcat gcctgctctt cccgttgcct    18720
tccccatttc gtttatagca acccatttc ccagttactt aggtccaaaa cctaagttat     18780
attcttgatt ccttctctca cacccccttgg ccaacttttc agcaaatcct actattatta   18840
ccttcaaaat atatgcatct ctagccagtt tttttgaact tgaactcaaa catgatctgg    18900
tttgagcctg ataaaatctt gcctactttt gcgcttgatt gctcatattt ctgtggcctc    18960
actgaatctt gcacctaatg tgcacaatag caactataat actacagcac tttctgtttt    19020
ggtgtcttcc ttattctacc agatggtaat cctgacggta ggggcccat ggtggtgttc      19080 ccagtgtcca atgtggtaca actaggcatc cctcaggtgc gctatagcag atgggacgtg    19140
ggcatgtcaa gatagtgagc cctggcttta ccctacccta gcagggtgac atgctgagcc    19200
tgccggttgc ctcctggcag cagtttagtc tgcttactgc tctgtggtgt ccaaatgtat    19260
tattttgtta atgtgcctta acttggaaaa gcttggaagc ctcatggtaa cagcatttgg    19320
cacctaggaa ggtattcatt gttaaatgaa ttctttgtta agtgaggtag actacaggga    19380
tcattctccc tgttttatag aagaaagagt aagctgtgtg accagccagt ggcctgatca    19440
```

```
taatcgagtg ctgttctgag tctcatgtgc gttctggggc aacacactgg gttgcatttc   19500
acatgtgcac acatgtagct cgttgcttcc ttacctgcat gtacatgaag gtgaaggctg   19560
tggctaagcc agaagggcct gggttctggg ggtttcttcc ttgatacaga taaatccatt   19620
ctgacattgc tgtgctttcc tccaggcctt tggggattaa gggggtttac tggagagcct   19680
gcttgctggg gaggaatatt tatagactgt gagctggaag gaactttgga gaacatcagg   19740
ttcagtggtt accagatgtg gctatctcag agtaacctgg taatctttta ctgatgctta   19800
ggccctactg caggtgatct ggttcagagc tctgggagtg atagggctta aagctgagt    19860 ttttacaaaa ccttccaggt gattttgata cagctggaat aatccagttc ctcctcctcc   19920 ccttttttt  ttgagataag atcttgctct gtggtccagg ctggagtgca gtggcacaca   19980
tgatcacagc ccactgcagc cttgaccttc tggactaaag ctgtccttcc atctcagcat   20040
ctcagggagc tgggactaca ggcgtgtgcc accttgctcg gctaattttg tttatccttt   20100
gtggagacag ggtctcactg tgttgtccag gctggtctca aactcctggg ctcaaaccat   20160
ccttctgcct tggcctccca agtgctggg  attacaggtg ttgtgagccc tgcactggcc   20220
aaataataat actcttaata gtaatacccg accacattc  ttaatttctt ccaaaatgtc   20280
tttgatagct atctgtttcc aaatcgagat ctaataaaaa acatacattg catttgtttt   20340
tccatttctg cctgtcttaa tctacagcag cacccccgct ccctgcccca gcactttctt   20400
ccccatgaca ttgactcttt gaagagacca ggccagtttt cctgtagaat gtccaccttc   20460
tgggtttcat tgttcttttt tcctcctgca tttcccttac tctggaggta aggttccaaa   20520
gcttgcttag atgcaggtta aacattctgg gcaagactttc tttataggtg aggccgtgtc  20580
accaggaggc accggtgtcg ggtggtcctg ctgtcggtgg tgccgtgttt gatctctggg   20640
ttaaaatggt ggtaatcaga tcctgctatt gtaaaggtac attttttttt tccttttcct   20700
tcatagtgat aacttcctgt aagtaaactt gctgaaacaa agggtttgca catttcaaaa   20760
aaccaaaacg cttttgatta ttgtcaaatt gccgctaaac aattctgcta ttctatattt   20820
taaggagtat gcttttcttc actatttgcc tggtttattt tttcttttc  tgattacaaa   20880 agaaatgtat atatcatgca acatttaaaa gttacaggcc gggcacgtgt cttacacct   20940 gtaatcctag cactttggga ggcccaggcg gatggatcac ctgaggtcag gagttcaaga   21000
ccagcctggc aaacatggtg aaaccctgtc tttactaaaa atacaaaaat tagctgggcg   21060
tggtagcacg tgcctgtagt cccagctact cagtgggggg ctaaggcagg agaatcgctt   21120
aaacccggga ggcggaggtt gcagccagcc gagactgcgc cactgcactc cagcctgggc   21180
gacagagcaa gactctgtgt caaaaaaaaa aattgtggtc aaatctaaca gaaaatttga   21240
cattttaacc actttcagtg ttcaattcat tagtactaat tatgttcata atgttgtgca   21300
accatcacca ttatcttctt tgtaaacagc tgtagagtgg cattccatgg tgcatgagcc   21360
agaatttatt caatcagtgc cctgtgtatg gacaattggg ttgttctctt aaaaacagcg   21420
ccgcggacag tacctttgcc tgtctctctg ctctttttata tattttaatt agatagtttc   21480
ctggaagagg gaaagctagt caaagagtgc aaacacttta catttttaata tgtattacct   21540 aattgtcttt caaatgttg  aacctctttt cagtctaact aaaagcatct aagactgata   21600
aagtattgat ttgccttgat aactgttggc tctcacaaga ctaactcaac ctgctctgta   21660
ttttaatcct gcttagtaag gaagagctgg ttgggaaagt agaagcaaca tcccttttt    21720 taactaattg gtatttatgt aacacctcct gtgtatcggg cttgctttc  aggcgggggg   21780 attttagtta tgaataaaca gagacaatct ctccctagtg gagcttacag actaaaatat   21840
```

```
ttggagacag acatcatctc atgaatgaag tcaaggagag gtaaagggca tatataatag   21900
gaggctctca tagggctggg gattcggaga aggattccct gagaaagtga aatgtatttg   21960
gagtttgatg gatcaactgg atgttcccta ggcaaagggc agactgggaa tggaggtgga   22020
cagcaaacat tccaagcaga agaaaaactg catctgtaaa gacctgtggc aggtcccttt   22080
agaatgtgtt ctggccaagg aggttcatca tgttcagtgc ccttgaggaa ggcgggttct   22140
gaatttccca gataccagat agatgagatc ccactgccag gggcccatga gcagaagggg   22200
tttgagaggg atgggagact ttccaaggca aattctaaca aattacaaat aatctggaga   22260
ggagaaagag aggcacctaa ataaatcagt ttagagtttt agaatgactt gtccaaagtt   22320 ggaaggggt caggtaacca aggaggaaca gtgcagagca gctggaatac atcagaaggg    22380
ggtcaggaat gccaaaggac ctgatgagct aaggcttctg gaaatgcta atcagccaca     22440 agggccttta aaactgtctg cagtaagaaa aataagaaga ggcatgctgt ttctggcaac   22500
atccagagaa cgaacacaat gtcaccactt ctagttttac gttcatctcc tttatggagg   22560
aaacaatata gtataacaca tgtggagtgc tttttattatg aataggccat atgccaagca   22620
ctttatgtag atgatttcat ttttatcaat gctgtgaagt ttatcttcat tttatttatg   22680
gcaaaactaa gatgtgggga gcttaaataa cttccccagg gtcacagcag ttaagtggtg   22740
gagctgggtt gggcaatctg actatagttc ttcaatccga actaccacac tgttctggga   22800
aaggaggggc catatgaggt gagagggact ggccgagatt ctagaggtag caggatctag   22860
aagaagtgat ccatcacaga aggagagacc tgagcttgca tcctggagtc aactgcatac   22920
cagctatcga attctgactt acctccctga tctccagttt ccacatctgt gagatgggaa   22980
taagttactt gcactgttat attgggaatt caaaataggc acagaaagtg cttggcatgg   23040
aacagatgct taattagtaa tttttaattt ttattctaaa agcagggtaa atacccaaag   23100
ctagtctttt atttatttat ttaacatatg agagatatgt ggtccatgaa tgaatgatat   23160
gtggtgtctt agtccatttt gtgttgctat aacagaatat cacatactgg gtaatttata   23220
aaggaattta ggccgggcgt agtggctcat gcctgtaatc cctgcacttt gggaggccga   23280
ggcaggcgga tcacctgagg tcaggagttt gagaccagcc tggccaacat gatgaaaccc   23340
cgtctctact aaaaatacaa aaaattaggc caggcgcagt ggcttatgca tataatccga   23400
atactttgag aggcagaggc aggcagatca cctgagtttg ggagttaaag accagcctga   23460
ccaacatggt gaaaccccgt ctttactaaa aatacaaaat tagctgggtg tgctggtgca   23520
tgcctgtaat cccagttact cgggaggctg aggcaggaga ctcgcttgaa cctgggaggc   23580
agaggttacc gtgagccgag atcacgccat tgcactccag cctgggcaac aagagctaaa   23640
ctccatctca aaaaaataa aaaagaaaa ttagccaggc gtcatggcag gcgcctgtaa     23700
tcccagctac tcaggaggct gaggcggaag aatatcttga acctgggagg cggaggttgc   23760
agtgagacga gatagcgcca ctgtactcca acctgggcaa caatgtgaa actccgtctc     23820 aaaaaaagaa aagaaaagaa aaggaattta tttcttacag ttctggagga tgggaagtcc   23880
gagattgagg ggctgcatct ggtgagggcc atcatgctgt gtcatcactt agcagaaggc   23940
gtaagggcaa gagagagggg aggaagggg ccggatttat ccctttatca ggaaccgact    24000
cgcatgacaa ctaacccact tctgtaataa cagcattaat ccggtcatga gggtagcgcc   24060
cttctgacct aatcgcctct taaaggcccc acctctcaac actgacattg gcattgagt    24120 tgccaacaca taaactttgg gggacacatt caaaccacaa cacatggtgg ccttgcccctt  24180
```

```
gaagttagtc tacagggtaa gcatatttct tgcccatgtg tagagaatga aattaaaaaa    24240
aaaaaataca gggtaagcat gttgatatgg ccccctcttt taacagtttc catgtgacat    24300
ttcatgcact acagcctctc actgctctga agccaggagt caagctgaga tttcccctga    24360
ggactggaga agataggtga actggcaaag actgaaagtc tagctgtctt ttactttttt    24420
gttgcaatga gcagatagac tagtgagaat gagtgtttca tccttactaa tttataaacc    24480
taagctgttc aatctggcaa tttaaaattc agtgacataa gaaattccat tccttggctg    24540
ggtgcggtgg ctcatccctg taatcctagc actttgggag gccgagatgt gaggatctct    24600
tgagtccagg agttcgagac catcctgggc aacatgttgt aaaaaataaa aaggccaggc    24660
gcggtggctc acacctgtaa tcccagcact ttgggaggct gaggcaggca gatcatctga    24720
ggtcaggagt tcgagaccag tctgaccaat atggcaaaac ctcctctcta ctaaaagtac    24780
aaaaattagc caggtgtggt ggcacatgcc tgtaatccca gctacttggg aggtggagac    24840
aggagaattg cttgaaccct ggagacagag gttgcagtga gctgagatca caccagacag    24900
cacagatcta gaacatgttc atcaggacag gaagtcctct tggacagcac tggatgttgg    24960
gaacagacac tttcacatag ttggaaagca gaacggcaca gtgattaagg gtgaaatgtg    25020
tagctgattt catttgtgtt taacactgtg aagtgtatct ccattaagca cggaggttta    25080
aggagttaaa tgacttgtct ggggcaacag caggcacgtg ggtcactcag gctggatttg    25140
gatcccgcct gagataatca taggagccgc ttcactgggt ggctgtgaag attaggccat    25200
gtaatatatt ccaggtgcgt cacactgtgc ttgtctcata ttagagacat catagtcttt    25260
ctttacccat aagttgtatt ctgtatcttt tttttttttt ttttgagtca gagtttcgct    25320
cttgttgcct aggctggagt gcaatggcgt gatgtcggct cactgcaacc tccacttccc    25380
gggttcaagc gattctcctg cctcagcctc ctgagtagct gggattacag tcgtacgcca    25440
ccatgtccgg ctaatattgt atatttagtg gagatggggt ttcaccacgt tggtcaggct    25500
ggtcttgaac tcctgacctc aagtgatccg cctacctcgg cctcccaaag tactgggatt    25560
acaggcgtga gccactgcgc caggctgtat tctgtatcaa catatgattt tgtccttttt    25620
gttttttgag acagagtctc actctgtcac ccaggctgga gtgcaatggc gggatctcgg    25680
ctcactgcaa cctctgcctc ctgggttcaa gcaattctcc tgcctcagcc tcccgagtag    25740
ctgggattac aggcgtctgc caccacaccc tgctaatttt tgtattttta atagagatgg    25800
ggttttacca tgttggccag gctggtctcg aactcctgac ctcaggtgat ccactcgcct    25860
cagcctctca aagtgctgga attataggcg tgagtctcca cgcccagcct gttttgtttt    25920
gaggcaaggt cttgctctgt tgcccaggct ggagtgcagt ggtgagttca tagctcactg    25980
cagtctggaa ctcatgggct caagtgaccc tcctgcctca gcctcttgag cagctgggac    26040
tataggtgta tgccaccatg ctcagctaat ttatgtttta ttttatttg tagaaacaag    26100
gccttgctgt cttgcccagg ctggtcttga actcctgggc tcaattgatc ctcctgcctc    26160
agcctcccaa agtgttggga ttacaggtgt gagccactgt gcctggcctg ttttgtcctt    26220
gacaggtctt gctatgttgg ccgggttggt cttgaattcc cggtctcaag caatcttcct    26280
gtgtccgaaa gtgctaggat tacaggcatg agccaccgct cctggcccag cattatttct    26340
taagcccatc tacgtattga taagtagtct gtagtttgct taaccgtgcc ctggctgttg    26400
ggaattgggg ctttgccttt tcccggtact atagataaga ttacaatgta ttgtcttgcc    26460
tactgaccag gcaataggta ttgttacagt tattttatt tcttttttt ttttgagact    26520
gagtcttgct ctgtcgtcca ggctggagtg cagtgatgtg atctcggctc actgcaagct    26580
```

```
ccacctcctg ggttcatgcc gttctcctgc ctcagcctcc cgagtagctg gggctacagg    26640
cgcccgccac cacgccgtag tagagacggg gtttcaccgt gttagccagg actgtctcca    26700
tctcctgacc tcgtgatcca cccacctcgg cctcccaaag tgctgggatt acaggcgtga    26760
gccaccgcgc tcagccacag ttgttttttat ttctaaggaa actgaaactt agggcaatta   26820
atttgtaaaa ataaagaaac aggttggtaa tttcacattg gaaagctgtc tgagatttgt    26880
tagtaagtga aaaagatgag ttgcaggcca ggtgtggtgg ctcacacctg taatcccagc    26940
actctgggag gccaaggtgg gtggatcact tgaggtcagg agtttgagac cagcctgggc    27000
aacgtggtga aaccccatct ccaccaagaa agtacaaaaa ttaaccaggt gtggtagtgc    27060
acgcctgtag tgcccagcta cttggggggac tgaggcagga gaattgcttg aacctgggag   27120
gcagaagttg ccgtgagctg agatcgtgcc actacactcc agcctgggcg atgagagcaa    27180
gaccctgtct caaaaaaaaa gtaaaagaag aagagttgca gaacaacttg tatggtttct    27240
catttgtgtg tagaacatgg tgggggtagc tgtgtgtaca cttaggaacg cacagggtaa    27300
taatcatgga aacgtactca gtactttata taatccctcc agatcctcac aatagctctg    27360
tgaagaaatg attgcttgga gaggttaaat tgtccaggat cagtaagttg tggggccatc    27420
cttaaaccca gggctctgct actccatcta ccccatgcac tgggctcctc cacccgtcac    27480
agggatagcg tttatcactg cagcagaaat acactacctt cttcctatgc acacgcactg    27540
tggaaggtcc tttgatgtca tgtcattggt gggttctttg cacctaccca gtgaggcagg    27600
cagtgaggag ccatcagtca ggtttgagct tgagggcaaa tggatgtgaa gtctggactg    27660
gggatgttgc ccctgccata ggttagaatg ggtgatggtc aggggtgctg tttcagaatg    27720
tggcctgttc ttactgctgg gtgactcgaa cagggaatgg ctgctctggg tacatactgg    27780
gttcaggtgc tgagattgac agcgtttgga ttatatatcc aggtgacata cagaagggag    27840
cctggggcag tggcttcagc tttgcctctt cccttaccca aggtatgacg aggaacacca    27900
accacctaga agggaagcag ctcttccctt cttgctgtca tttctttttt cttttttttt    27960
tcgagacgga gtttcgctct gtcacccagg ctggagtgaa gtggggtgat cttggctcac    28020
tgcaacctct gcccctgggt tcaagcaat tctcctgcct cagcctcctg agtagctggg     28080
attataggtg cccgccacca tgcccagcta atttttgtgt ttttagtaga cagggttt      28140 caccacgttg gccaggctgg tttcaaattg ctgacctcag gcgatccacc tgcctcagcc    28200
tcccaaagtg ctgggattac aggtgtgaac cactgcaccc ggcctcttgc tgtcatttct    28260
ttggattcat ttattcttct ctggtaacaa ggtacccttg aaggttgtta ttcatagttt    28320
aagattaact aatacaggcc cggtacagcg gctcatgcct gtaatctctg ctttgggagg    28380
ctgaggcggg aggattgctt gaggccagga gtttgaaatc agcctgggca atgtagtgag    28440
accctatcac tacaaaaaat aaacctaaaa gaattagggt gggcgcagtg gctcacgcct    28500
gtaatcctag cactttggga ggccgaggca ggtggatcac ctgaggtcag gagttcaaga    28560
ctagcctgac caatatgtag aaactgcatc tctactaaaa atacaaaaat tagcaaagtg    28620
tggcggcgtg tgcctgtagt cccagctact tgggaggctg agacaggaga gttacttgaa    28680
cccgtgaggt ggaggttgca gtgagccaag atcatgccac tgcacttcaa cctgggcaac    28740
agagcaagac tccctttaaa aaaaaataaa aaaatattg ggaggccgag gcaggcggat     28800
cacgagttca agagatcgag aacatcctgg ccaacatggt gaaaccctgt ctctattaaa    28860
aatacaaaaa ttagctgggc atggtggtgg gtgcctgtag tcccagctac gcgggaggct    28920
```

```
gaggcaggag aagtgcttga acccgggagg cggaggttgc agtgagctga gatcgctcca   28980
ctgcattcta gcctggcgac agagcaagaa tccatctcaa aaataagtaa ataaacaaat   29040
aattgggtgt agtagtgtgc gcctgtagtc ccagctaccg aggaggctaa gatgggagga   29100
tcatttgaag tcaggagttt cagactgcag ggaagtatga tcttgcccct gcactccagc   29160
ctggacaaca gaacaagaca ctatctctta aaaaaaaaaa attaactaat acagatccca   29220
ccataacaat catttattta ttgctgtgta acaaattgcc cccaaactta aaggcttaaa   29280
acaacaacaa gcatttatct catattttg tgggccagga atttgggagt ggcttggctg    29340
ggtggttctg gcttggggcc tctccagaag ttgcagtgaa gatgtcagcc ggggctagcc   29400
atctgacggg ttgaaccggg gctggagcat tcgcttgcaa gatggctcac tcacacctgg   29460
caaggtggtg ctggttattg gcaagaggcc cctgttcctg tctaggtggg cctctcccag   29520
gattgcttaa caatatgggg actgtcttcc cccagagcaa tccaagagag agagcaagcc   29580
aggcagaagc tgttcttctt atgacctagt ctcaaagtcc aatagcatcc cttgtcacat   29640
tctataaagt agaagtaagt ccgccacaca ttcaaaggga gggtaatggc tgggcacggt   29700
ggctcatgcc tgtaatccca gcactttggg aggccgaggc agatggatca cttgaggtca   29760
ggagtttgag accagcctgg ccaacgtggt gaaaccccgt ctctactaaa aatacaaaaa   29820
ttagacaggc atggtggtgc gtgcctgtaa tcccagctac tgggaagctg aggcaggaga   29880
aattgaagct tgaacccagg aggcggcggt atcagtgagc cgagatccca ccactgcact   29940
cccacctggg cggcaagact ccgtctcaaa aaaaaaaaaa aaaggaaggg aattaggcac   30000
caccttttga agggatgagg aaacatccaa agctcacgca cagggttttc ctcattcatt   30060
cttccctctg acccatggat atttgttgaa tctccagtat gtgccaggta gtccagacat   30120
agagatgagt aagataaata aggcttgatc tcaaccctca agaagcttat agtgcaggta   30180
gactaatagc tatggtttgg atagtgtttt acagcttaat gagcactttc acttatggtc   30240
ttatttaacc ttcccagtac cccgtgtgat caccagagct ggttatatcc ctatttcta    30300
tctcctctgg gttttagtca atgagggctt ttcttacatt gatacacctt acatgataga   30360
acttgacttt gatcccagcg attttttgtct ataaatccct tgcactttt tcctacccca   30420
ggctgtgttc cttgtggctg cttttgtcatc cctgtcctgc agatgaggaa gctgaggctg   30480
cagttactga acagctcttg acactttaat tcctggattt ttttcaccat actgagctgc   30540
cctcggggat ggactctcct aagtgctcca ttgacagtgg ctgtcatgtt tcttcttgca   30600
gaaagctctg ggtgtgcggc agtaccatgt ggcctcagtc ctgtgccaac gggcaaggt    30660
ggcgatgagc cactttgagc ccaacgagta catccattat gacctgctag agaagaacat   30720
taacattgtt cgcaaacggt aaggctgcag atgggaggct gtgactgtca agggcattgc   30780
gtctgctgcc tgcccgtcag gcagagaagg aggtgttttg tgaaggatgc ttggtgatag   30840
tggcagggtc aaggtattca aggtacaaag gtttctgctg aggaaaggca ttccagatca   30900
gtggtgtaac ttctgtcctc tctgccaagg gagaatctgt gttatcaaga agcctctaga   30960
tgtgaaccac agccaggtct ctgagacact ttggcactat aacctgaacc tcccaacctt   31020
ttcagggcag gctgctgacc ctcggcctgc cctctggaag ccaccaggcc cagtgcctgg   31080
agaatcatct tctatttcct cttcagtgca caggcacaga ggagagctca ggtctgagac   31140
ccagaagata aactaagatg ggaccttttt aatttaattt tattttattt tattttattt   31200
tatttatata tatttgaggc agagtatata tatatttata tatataaaat aaaaatatat   31260
ataaatatat atatatttga ggcatagtct cgccctgttg cccagactgg attgcagtgg   31320
```

```
tgcaatcttg gctcactgca acctctgtct ccccagttgg aacgattctt gtgcctcagc   31380
ttcctgagta gctgcaatta caggcacctg ccaccacacc cggctgattt ttgtagtttt   31440
agtagagatg gggttttgcc atgttgccca ggctggtctc gaattcctga gctcaagcaa   31500
tcagcttgcc tcggcttccc aaagtcctgg gattatagac gtaagccact gcgcctggcc   31560
tattttattt tatgatttta tgttatgtta ttttattttt tgagacagtc tcactctggt   31620
ccaggctgga gtacagtggt gcagtctcgg ctcactgcaa cctccgcccc caggttcca    31680 gcaattctca tgcctcagcc tcccgagtag ctgggactac agggacgcac cacgatgcct   31740
ggctaatttt ttgtattttt gtggagatgg ggtttcatca tgttggccag gctggcctca   31800
aactcctgac ctcaggtgat ccacctgcct cagcttccca aagtgctggg attacaagtg   31860
tgagccactg tgcccagctg ggactatttt tttttttgag acagggtctc actctcttgc   31920
ccacactgga gtgtagtggc acgatcacag ctcactgcaa cctcaatctc tgggtttga    31980 gtgatcctcc cacctcagcc tcctgagtac ctgggaccac aggcgtgagc caccatgctc   32040
acctactttt tttattttt gtagagatgg ggtatcgcca cattgccact gatctcgaac    32100
tcctgggctc aaaactgttc tcccaccgtg gtctcccaaa gtgctgggat tacaggcgcg   32160
agccatggtg cctggcctaa ggtgggatct tgagcatgtc tttttttctgg acctcatttt   32220 cctcacttgg taaatggca gtcagctctg ccctgctgtc ctgtgtgcca ggtcctgggt    32280
tagatgctgc caccaaaagg atgaataagg taccacagag gatgaggagt cggggctggc   32340
aatgcacacc agcctgcact gccacacttc caccttgctc ttcatcaggc atgaaggaga   32400
gctgtcatag aagtttgctt tgattgattg gaacctgaac aactgcagat ggggctgtgc   32460
ccttgcctgc ctggtggctt ctttgatact gacagtggtg atcctgggag agaacaaatc   32520
tgagtctacc cgctgggtag ctgaggctca gctggagaag gaacctgccc acaaccatgc   32580
agtgcatgag tggtggtgtc tcgtctttgt accctctagt actctaacca ctaccccata   32640
ctccctttct catgccactt tgctttctat ctactggtat ccccacttcg ttttaaggg    32700 tagggacttc cttaatctgg atctccagcc tccagcacag catcatctaa ttatagtaaa   32760
ggacctattg tttgtcaagg acggctgtga caggagtacc caccttgttg tccagtctgg   32820
cctgggtact tgacacacat tatttctgtt ctcaacaacc cctgtaggtt gttgctttcc   32880
atctctgccc cccaccattc tgcaggtaac aaaattgaaa gtcaggttgg ggaaataccc   32940
taaggccata catgtattga gtgactgacc ccacactcaa gcctgggtct ctgtgactcc   33000
agggcttgtt cttgtgggtt tcttctgggc tccatgttag aatcacctgg gaagcttaa    33060 aaatgacgga cacctgggcc ccactcccag caattctgat tcaagtgatc taggcattgc   33120
tattcaaaat gtggtccatg gccagcagc attggcatca cctaggagct tgttagaatt    33180
ccagcatctt agaccccact ccagacccac tgagtcagaa ccggccattt aacaggatcc   33240
ccaagggact tacgtgcctg tcaaaatgtg agaagcactg gcccgttccc cagcaggtcc   33300
catagtgcag tcaggacgaa gaaccactgt ccctgtcaat ataggacgtt gtatttattc   33360
ttggagctct cacaccgctg ctcagtggaa aagtgataga ttttctctta ctctgtaaaa   33420
cacttccacc ttgctttcat caggtatgaa ggagagctgt catagagatt tgttttgttg   33480
ttgtttgtgt ttgtttctgt tttagactga gcctcactct gtcacccagg ctggagtgca   33540
gttgtgcaat ctcggctcac tgcaacctcc acctcccagg ctcaagcgat tgtcctgcct   33600
cagcctcctg agtagctggg attacaggcg tgcatcacca tgcccaggta attttttgtat  33660
```

```
ttttagtaaa gatgggggtt tcaccatgtt ggccaggctg gtctcgaact cctgacctca    33720
agtgatccac ctgtctcagc ctcccaaagt gctgggatta caggtgtgag ccactgcgcc    33780
tggcctttt ttttttaatt aataaaaaaa ttttaaagat gggctgccca agctggtctt    33840
gaactcctag gctcaagtga tccccctgcc tttggcctcc caaagtgttg ggattacagg    33900
cctgagccac tgtgcccagc aagaggttcg ctttgagata acttgacaac agagtattat    33960
tcactattta gttttgcat taaacaatta ataacaacaa caaatacccc tttaaggcac    34020
tgggagtttt ttagttttaa ttttatcatt aaaattgaca actacaacaa tattttttcct   34080
tgcttacttt tattccaacc ttgctttgca accagaaaag tccaataaat ttttttcttt    34140
tttttttaa agtccaataa ctttgaacat tttccagatt agtacagacg aggggattgt    34200
tctctgtttt ctttttttt gaaacggagt ctcgctctgt cgcccaggct ggctggagta    34260
cagtggaacg atctcggctc actgcaacct ctgcctccca agttcaagtg attctcctgc    34320
ctcagcctcc cgagtagctg ggattacagg cgcctgccac cacgcccagc taattttttgt   34380
atttttagta gagaagggt tcaccatgt tagccgggat ggtctcaatc tcctgacctt     34440
gtgatccacc cgcctcagtc tcccaaagtg ctgaggtgac aggtgtgagc caccacacct    34500
ggtctgttct ctgttttcat tgttgccaca gagcaggtct caacaaggtg gggggtggtc    34560
agttttgtcc ctagggccca tttggtgatg tctagagata ttttttggttg tcataacttg   34620
gctggggttg gggcttactg ttacccaatg ggtaaccagg aatactacca agcatcctac    34680
agcgcacagg gcagccccac aacaaagaa ttctgcggcc caaataggtt catagtgccc     34740
tggctgagaa accctgacac ggagaaagag ggcagaggtg aggttatgct aaaaagaatt    34800
atattctagc cgggtatggt agcccacgcc tgtaatcccg gcactttggg aggccgaggc    34860
aggcggatca cttaaggcca ggagtttgag accagcctgg ccaacatggt gaaacactgt    34920
gtctactaaa aatacaaaaa aattagtcag gcatggtggc gagcgcctgt aatcccggcc    34980
actcgggagg ctgaggcagg agagccgctt gaacccagga ggtggatgtt gcagtgagct    35040
gagaccacac cacagcactc cagccagagt ggtgtctctg gtgacagagg aagagactct    35100
ggctcaaaaa ataaaaataa agcgttctat tctaagaatt ttttagaagg ccaggggact    35160
tgctgggcga cttctcttcc accttgtgtc tccaacagaa ggggtctaag tctgttcttg    35220
agaactggat ctgtgtcatc tggagagcag agggacagat ggatatgaag acccatttg     35280
tcatcctcag ttaatcctca gggacattca atgatgaacc catcctaaag cttcagcatt    35340
gctgagcttt tttatatagc ttcaatcatt tgcttccaag gtcttgggtt tttaagccca    35400
tgtgctatt tttgtctccc tcggggccca gaaggagggg ctgtgagtca ttgcccgtac     35460
accagccttg gcggtgctgc cgcaatcggc gcaggctgta cctcaggcta gtgctgttt    35520
tattcataga gatgctcaga gttgccagtt ggtctgctgt tgccagcaga tccagcacct    35580
tagggacttt tttttttttt ttttttttt ttttttgag gtagggtctt gctctgttac     35640
ccaggctgga gtgcagtggt tcgatcatgg cttactgcag ccttgacctt ctgggggtcaa   35700
tccatcctcc cacctcagcc ttcccagtat ctgggactat aggcacatgc caccatgcct    35760
ggcttctttt tatgttttt gtacaggtgg agttgcccag gctagtctca aaacgcctgg     35820
actcaagtga tctgtctgcc tcggcctcct aaagtgctag gatgacaatc gtgagccacc    35880
acacccagct gggaactctt actttgaaga ggttgggtaa acttggggt gagggactgg    35940
aacccagctt gcagaaggaa gtttctctgc catctcacta tgcatattga tgataacagt    36000
aatgataact gagaaaggat gaggtggctc acacctgtaa tcccagctct cgggaagat    36060
```

```
catgtgagcc taggagttca agaccagcct ggtcaataca gtgaaaaccc atttctacaa  36120
aaataaaata aataaataaa taaaattagc caatgtggtg gtgcgtgcct ataatcccag  36180
ttactcagag gctgaggtgg gaggatcgct tgagcctgaa aggttgaggc tgcagtgagc  36240
tacaattgtg ccactacact ccagcctggg tgacagagca agaccctgtc tcaaaataat  36300
aacaataata ataataataa taataataat gaaaatggaa cattcaccat gtgctggccc  36360
tattccagat tccaggtgtg gagagaccgg gtagattagc gtcaggagca cagccgtagg  36420
gccacactgc tgcctcttcg tggtccagct gtacccctca ctggcttcgt ggtctggagc  36480
aaagctactc tgtccctctg tgctgcagct tcctcatctg tgctgtgagg ataaaatgag  36540 tttttatacat gaaaatactt aagataatgc tgagctgaaa gtaaatgcta cgataacgct  36600
ggtctctagt gacagaaagc caatcagtag tggcaaaggg gcgggaggga gttaaccaag  36660
gggtggggaa acttgaagga gagatggtca gtatcttgat tgtggtgctg gtttcacagg  36720
tgtatacagt gtcaaaactt agcaaattgt gtaccttaaa tatgcagttt attgtatgcc  36780
aattatacct ctgtttaaag ctgtttaaaa atgaaaggct atagaagtgg aagctgttat  36840
ctcatcccag tgcaagccct ggtatttaga gatgggctgg ctgagctgag gagagcagtt  36900
gcttatcttg ttaaatagtg gtttcagtaa taggtcaggt ttgggctttt ttgttttttt  36960
tttgtttgtt tgttttatt agagacagca tgtcactctg ttgctcaagc tggagtgcag  37020
tgatgtgatc agggctcact gcagccttga tctcctgggc ttaagtgatc ctcccgcctc  37080
agcctcctgc gtagttggga ctacaggcac gcatcaccct gtctggctca ttcttttttt  37140 tttttttgaga tagagtcttg ctctattgcc caggctggag tgcagtggcg ctatctcagc  37200
tcactgcaag ctccgcctcc cgggttcacg ccattctcct gcctcagcct cccgagtagc  37260
tgggactaca ggcgcccgcc accacgcctg gctaattttt ttgtattttt agtagagaca  37320
gtgtttcacc atgttagcca ggatggtctc catctcctga cctcatgatc cgcctgtctc  37380
ggcctcccaa agtgctgaga ttacaggcat gagccaccgc acccggcctc attctgtttt  37440
ttatagagac aaggtctcac tctgttgtcc aggctgatct tgaactgcc tcaagcgatc  37500 ctcctgcttt ggtctcccaa aatgctagga ttacaggcgt gagccaccac accaggcccc  37560
caggtcaggg ttaaactcag agcttctgac tcccagtctg aaacttttt cttggcctca  37620 aacaatagga cagagcctgt caggtgtggg ttgaactctg ctcctcctta ggaaggaagt  37680
ctcaagcttg gcctaagctt tgagaattct gggggcaga gcgtgaggtc tgaaaggggc  37740
tgttgtggca ggcagggcgg ccacaacagc cccttgctc tgttgtgtgg gtgcagccgg  37800
gagtcagccg gaacgttgag cctggcaggg agagtggacc cgcgcagagc tcagtctaga  37860
tggctgggag gcttgtgggg agaagacggt tgagtcctga cagggccgga ccccagggca  37920
ggtttggact gccattttgg ctctgatgag gaagggaggg gtgggcctc cggggaaatg  37980 gggtctagga ggaggaggag ctgtgagagg ccagtggcag tgaccccggtc tctgttcttg  38040 aaaactgaca gatactcctg tctatgtctg gagctaatgg gcaaagtctt agtgtcatag  38100
ttgggtagcc aggcatccca ggcctgaggt gtggagggtt gtagatggcg gacagggtgg  38160
acaggtgaag gggatgctgg tcctgattcc ctgtgcctta gtgggctga gggcacagag  38220 ggaagtagcg aaatctagct gtgaacttgg tcactctcct gagcctgttt cttggttgtt  38280
gttaaatggc tttcttggtt gttgttgttg ttaaatggca ggaatgatga gatatgcatg  38340
ttgcggggac ttagtaggaa ttacgatgct gggaaagcca ggatcctttg aaaagaacca  38400
```

```
gcgctgccct cttgtgatgt tgtcattcac ttactcatca agtaattgtg gagcacctaa   38460
caagtgccag gtgctgcagg aggtgaggag gtggtgcagt gaacaggacc cagcagtccc   38520
cacccaagtg gaacgttgag gtcctgagtt cagactccct gtccctggcc actgttgagg   38580
ttgccacatg gactgagagg gagaggcagg gcgggaggag gccgtgcagc tagcaccagg   38640
ccacccttct gctcttctcc ccacagactg aaccggccgc tgacactctc ggagaagatt   38700
gtgtatggac acctggatga ccccgccagc caggaaattg agcgaggcaa gtcgtacctg   38760
cggctgcggc cggaccgtgt ggccatgcag gatgcgacgg cccagatggc catgctccag   38820
ttcatcagca gcgggctgtc caaggtggct gtgccatcca ccatccactg tgaccatctg   38880
attgaagccc aggttggggg cgagaaagac ctgcgccggg ccaaggtgag cagaaggtgg   38940
ctttgggggt gggcaagtgg gcaagactgg gcgagaggcc tcaccctcac actggagcaa   39000
accagggcat tgcctccaaa ttctcacacc tctttggatt ggtctgcttt taaaacttga   39060
ttttacttgt ttctctttct aaaaatagca cttgctcatt atgttaaaaa atacagagga   39120
agcctaaaga aagaaaaaat catccttgac cttaccacac tgcaggtcct tttctgtcc   39180 tgttggagga tgatgtggat cctgccaggt gctctggaag gggccatgca ggcctccctg   39240
tctgcctgag cagtgagggg tgcatcttag catagtttgc cagcatccca tttgcaccca   39300
ctcccgctct cctctgaccc tccaaggacc ctctccggga ggtaggcgtg ctagggtcac   39360
tatttgtaaa tttgaggcgg cagtggcatc atacttgagt tctgtaacta catgagggca   39420
cgattagggc tcaatgctga tcctggctcc cactctggtg ctctgtcact gaggagcctc   39480
ctttgggggc cattcttctg tgagttttgc ttaactacat ggggtggct gtatgccatg   39540 ctgaaggctt tccccccacc cttctatgaa atcgagttcc tgctccttct cccaggctcg   39600
gcttgtggga cctttgtgtc agcctgctct tggcaacagc gggcctctct ctcccagctc   39660
tgggcctccc cactctccag cccctgcagt gggagtgggt cccctcacg ggaggggcg   39720 ttggcaggag ctgaatgctg gcagggctgc ggcctgtggg catgtgattg aaagtgctcc   39780
agctcccagg gtcagcatgg ctcaaagcct cccagcccca tgggaaacac tcggggcggc   39840
gctctcactc agaccctctc ttccacccctg gccccctggt ggtatcctgg ctccacagtg   39900
gctctttccc ctcagctgaa aggacagtcc tgcctgccgg ccggcggttt ccacattagc   39960
aacaacactg gtggggtaa taatgttaca ggagctccca cagtgccggg aactgcacat   40020
ggccgggaac gtgggtcctc tgcagccctg gggacagctg cccacaacag gctgctacc   40080 ttctgggggct ggcttctgc ttgctttatg ggctcagagt gaatcttctg gagatgagat   40140
gcacactcat agcattcaga gctcattccc tcatgcgttc aacaaattga acattcttta   40200
tgtgccaggc actgggctag gtactgaggt tcagtgtgaa caagtcaggc aggggccctg   40260
ccttcaggga tctgcttgtg ggtgtggaca ctaaacaatg gccgaggtag gtaactgcag   40320
atctgggtat gtgttaggaa gggaaagtgc gggacttggt cagtataaaa aagaggtcta   40380
atttagatgc tgggggaaag agagagcttc tttgaggatg tgacagataa cctgaggact   40440
gaacatatga gttgcattga ctggaggaag aacatgctag aaagaacagc atttgcaaag   40500
accctgagcc aggaagaaac ttgatgcttt tgtggaagtg agaggggcc tgtactgctg   40560 gagttctctg tgtttggaag agcgggtggt atgaggtggg caggggcagc caggaacgcg   40620
agggctgtgg gaacgctatg gtcaccatcc tcagagtcct agaacagttt aagcggagaa   40680
agaatatggt cttttttttt ttttttttt tgagacagag tcttgctcta tcccccaggc   40740
tggagtgcag tgacacacaa tctcggctca ctgcaatctc ggctcactgc aacctccgcc   40800
```

```
tcctgggttc aagcgattct catgcctcag cctcccgagt agctgggatt acaggcaccc    40860
accaccatac ctggctaatt tttgtatttt tactagagac agggtttcac cacgttggcc    40920
aggctggttt caaactcctg acctcaggtg atccacccac ctcggcctcc caaagtgctg    40980
ggattatagg tgtgagccac cacgcccggc ctagaatgtg gtcattatta cgtgtatttg    41040
taaagtgtcc ctctggctag ggctcagagg cagtgacctg tctagggtca cagaaccaga    41100
gatggatcca ggctgagtcc aggccgagac tctggcacca gtctgggtc ctcccacacc     41160
ccttcctcac acttaacaca gacgtgtagt cacatgcgcc cagacacgac cacagcctcc    41220
tgtcctggat accaatttca taagtgaccg atttgtaaat gaaaaagctg atgtattaat    41280
tattaattgg aaagagactg ctctggaaac ccacgttctt tgccattctc ttacctgggg    41340
gaacccagtg ggccttcaga gggcacacac tggtctggag tttcagtgaa ggggtgtgtg    41400
gtttgagtgt atctcatcaa gggtccgagg gcactggctg aggtccctc tctgaagcat     41460
cgctctccca tgccggaggc tggcaggtcc catttcctag ttcctccttt gagactcagt    41520
agagtccact agaatcccac cgttttgtta ctggggtcag tctcactgac cccacacagg    41580
gacctcccat gtcttccaga taaacccctgg cctcacatct gctgtgcagt gggcccttcc   41640
ctgtccctca aggaagcttc cttcagatta taggcaggat ggctacagcc cgtgtcatca    41700
tttcgtttgg ctgaaacctc cttttcagaa cagtggtccc ttcgacagcc ttccatttgg    41760
gcccatcaaa cacattacca agaattcagc acttccgaca gtcagacacc agtccagggg    41820
gctctctcag gtgtcgtcta agcctgggat ctccagcaag ttatttcaaa aaaagcctct    41880
ggggtttttg ttttgttttg aggcagggtc ttgccctgtc actcaggctg gagtgtagtg    41940
gtgcgatctc ggctcattgc agccttgaac tcctgggctc aagtgatctt cctgcctcgg    42000
cctgcaagta gctgggaccg caggtgcaca gctaattttt atttatttta ttcttatttt    42060
tatttttga dacagtctcg ctctgtcttg taggctggag tgcagtggca cgatctcggc     42120
tcattgcatc cttgtctccc aggttcaacc aattcttgtg cctcagcctc ccgagtaact    42180
ggaattacag gtgtgcacta ccatgcctgg ctaattttg tatttttagt agagacaggg     42240
tttcgccatg ttggccaggc tggtcttgaa ctcctgacct caagtgatct gcctgcctca    42300
gcctcccaaa gtgttgggat tacaggcgtg agccactgca cccagccact gcgcctaggc    42360
cagggcctgc ctctgcactg ctggcctcat ctggggactt gagtgccaca ggcactcttg    42420
gcaattattt agaccagtcc cttctccaga taaggaaact gagacccaga ccagggcagg    42480
gacttgttcc agacccacca ccctggccag gtgtcacaga actggggctc catctctgct    42540
cccctgtcct tctctctgac actgctagtg gagactgggc caacatccaa gctctttgga    42600
attattttta gaaggtctct aagagagggc ctgtctccag tgccagtatt tcagagtcag    42660
aagggaggct gatggggtgg ggagggcttg gtgagggtca cctggacaca aaccatgttg    42720
ctaacgccca attattgatt tgtctcaata ggacatcaac caggaagttt ataatttcct    42780
ggcaactgca ggtgccaaat atggcgtggg cttctggaag cctggatctg gaatcattca    42840
ccaggtaaag ctgggctcag tctgccgtcc caagggccca agccagagaa gtatgttcca    42900
ggcctatggg gggagggggt ttgaggccca gggggctga ggggaactgg atgacatatc     42960
catcagctct tatgctcttc ctcctttgtt ttgaaactga ttttcattat gtcattatac    43020
gtgctcattt tctgggtgag aagttaaaat aatacctcct aaccacccag gtaaccagca    43080
ttttaagtgc gacatgtttc tttccacatt gtcttctggg tgtgtactca agcatctcta    43140
```

```
ttcccataaa ctctcataca gaacatggta ttattttgtt ttttttcaca agtgtcaccc   43200
cttgtggcat gcatcactga catttgatga gcccatactg tgtctcaggt actaggctga   43260
gcacttgaaa gatatttgcc atgccctgtg aggtaggtgc ttttactatc cacaccctac   43320
agaggaggca gctgaggcac agagatgtta accttcttgc ccagggacac ctagctggct   43380
tactgtggag ccaggcctgt gggcaggagg gctggtctgg agcgagtgcc ccatgccacc   43440
gtgctgctct gccgcctccc tcgccccag agctctttct gcttctgcac gtggcgctcc    43500
tcggatttct ttttggctcc ttcatggtgt tctgtagggt gaaggtacca taggtcatgt   43560
ggccatgtca gccgggggct cctctgaggt gtcccaagga tggatcttct tttggtggac   43620
agttggacag ttttgtctct ggaagtgcaa gtgtgaacgt gtatatcctg gggaggtggg   43680
tgcttccctt tcttccaagg gcactgttag ggaccactga cctagtttgt gtccatttac   43740
atccaccctg tatgtatgaa acctgcctct tcgcaccttt gcaaggtggc ccttccccc    43800
acctccatcc cagacctcac tgtcctggcc tcctcaggat gtgctgagtc aggctgtaat   43860
ctgacgccgc atgggctccc agcaccgccc cgctctgaaa ccagagccag caggggatca   43920
ctcctctgcc ctgcccaacc atcactcttg ccaggaaggg gctgcgtgga atggccgttt   43980
gcagcggcct gtggggacta gaaagcccct ctctgcagca gggttaggga gtcaggtgga   44040
cccagtcttg gccttctgtt acaaagggca ctgcaatgca ggtgtctccc tttctacctc   44100
agtacaaatg cccaggcctt tatggcagct cctgggccaa agtttggagc cgtgagtgat   44160
ggcagctcac atctgccacc ggctagctgc taagcataca gcagctcgtg tgtttgtttc   44220
tttaaaaga aaatgcccag gggccatggg agtactttgc agctttactt tcttcccgcc   44280
ttgatgtcac gtcttcagca gcctcagtcc attaggtcca acccaaacct gaacccctt    44340
ccctctggga agtgccctgg ccccacttgg cccgcagacc ttcctccaca tcacagcttt   44400
ctggttcctc tgtggagcct ccccggccct ccccgtgcct ggcacagtgg cttccagtgg   44460
atcctctgtg ggatctcttc acattatgtt ccagcatctg ccaagtgctt tctgcactgg   44520
atcatgtgct ctgtggggac agggactgtg gcttatttat tcctctctag ctctgggttt   44580
gggaccaggt cagtacagag caggtcctta atgtatgtgt gtgttgtgtg gatgtgtggc   44640 ? 
tgaatttcca ggtgtagttc taggcattag tccttcttcc cagccctcac ccccatctgt   44700
ccagccacac ccacagaccg gggagctcac tgtcacggcc agcgtcatcg tgacatcttc   44760
tgcagtcctc atgtctgcct gacctctccc cctggatgtg gaccacaagt gtctacaccg   44820
tgtggaccaa aagtgtctac accgtgtaga ccaccccgaa ttctgtgtgc ccagccttcg   44880
tggatccaac ttttacaagc ttgaggctct ttagggatgc actagtctta aatccttgta   44940
cgtggcagca ttggccagtt cttcgcagcc aggtcttccc tctgcatccc caagagatga   45000
gacctttgga ccttagagtc tgctaggcag atgcttgtcc tgaggcagag gccctggggt   45060
ttctgtaaga tttctgggag cactggtggg tcctgagagt tcacagagcc tgtcacacct   45120
ctcatgtgtt cttccccaca tccccgggtg gggcactaac tccatctgac tgatgagcgg   45180
cagaacctca ggtgaaggct cttgctgcaa acaataaat aaaaatgttg cttcccgcag    45240
gcactattct gtgcctcatg gacaggatct catccagtca tcagtgaacc aatgatgtga   45300
gcacgattgt tagctatttc ttgatagtga aactgagctc cgagagaagt gacttgtcca   45360
tggtcccaca acaactagta gatggtgggg ccagacctca gacccccga tacaggacgc    45420
ctggctcagg gcttgccaag cagtgtcctg cagcttcagg gggccagtgc ctcagaggtg   45480
cctggtgcct gggccacact tgggtgttga gcctatacag cacccaaggt gttgagcact   45540
```

```
tgggtgttga ggtgttgctg cctttcttac caaatgtttt gggggaagtg ctccccacgg    45600
ctgggaggag cgcctcagtg aagggagtac tgtgaaatgg acaggtgat gaggcagggt    45660 ggcatcgcgc cttgagcaag tcacatgggt tctcagagcc acctccagat gctgaagtgg    45720
acgaggcatc acctattctt tgcagttgag gaaaagttca tagctttgtg tacccactgg    45780
ggcctcccag gacttcttcc tcaggggcct tgtgggctg gagccagctc ctggaagaac     45840
caccaacccc gatgagaagc caggtgggga tgctccacac ccaggatgag gccgggcctg    45900
ggcccatcac aggacagttt ctctggttct tgtcacatcc tggggtcatg gtggtatggg    45960
tgtttggtta ctgtgctaca aatgaggaaa ctgaggcatg gggcagcatt caaaggccca    46020
agacatatag caggaaatat cagagctatt caagagccca ggccacctgt ctcccaaggc    46080
tctggctctt cttggccacc ctggagacgg cctggattaa atggggctgc tcctaccagt    46140
tccatcctgg gagagtggct ggacgtggtt gggaggcccc gggtcagtgg ggccattttt    46200
tggtattctc ggctgagggc ttctaaatat aacatcttgg attattttc agattattct      46260 ggaaaactat gcgtaccctg gtgttcttct gattggcact gactcccaca cccccaatgg    46320
tggcggcctt gggggcatct gcattggagt tggggtgcc gatgctgtgg atgtcatggc     46380
tgggatcccc tgggagctga agtgccccaa ggtgagggtg gggagggact cattctgggc    46440
tggctgtggg gtggtggttg gtggggatga acgggagacg gtgggaccca ggagggaaaa    46500
gggaacaagt tagactcgaa tcttctggga gggaggtaga gaccaataag cagcaatgtg    46560
aatggcagca gggccatcct gacttcgtgg ctggcacagg cacacacggc ctctcacagc    46620
cgcctcgccc cctcctgtcc aggtgattgg cgtgaagctg acgggctctc tctccggttg    46680
gtcctcaccc aaagatgtga tcctgaaggt ggcaggcatc ctcacggtga aaggtggcac    46740
aggtgcaatc gtggaatacc acgggcctgg tgtagactcc atctcctgca ctggtgagga    46800
aggcggccag cgcacgtggc ccctaccctg tgctgggcct gatgggtctc cagttgggag    46860
tagaagcggt gaatggcctt cacttgagaa tctgtctgtt ccatttgggg acttgggata    46920
gacagaggta gaaggaaaat tggagacagc attagagatt gtctagtcca catcctcatt    46980
aaacagatga agagattgag atacctgtcg aggctgccgg tgacttccta actgtgtggc    47040
cacacacggt taggagccaa gtcagcttct gctgctgggc ccaggccata gcactaggcc    47100
accttgggtg atctagacga atccagagag gacagaggca gtggtgggaa tgggcagagc    47160
cagggcttca ttcatgaagc agctgcaggc ccacatcctc ccttcgctga agttcgagcc    47220
tcactcactt cccttggatt agagatcggt gcctgtccgc ctccaagacc aggtaggagc    47280
cagctgctcc ctgcctgtca ctcctggtga cctggcctgg atgcctggtc ctcagaaatc    47340
cagggagatt tgtaacagtc tagacttccc aggtgcctgc ctgggctccc tggcagccct    47400
gcagaactct ggttcccctg cagtgatggg ggctcactcc tgccacggga ctgctcagtc    47460
aggacgttgg taacaggccc atacctccgt cctagtggct cctgaggcag gtggcctggt    47520
agcagctgca gtacctgtga gccccaccag ttctgtgacg ctttgtggtc cagacagtgt    47580
gtatcatttc agttttgtt tttgttcttg ttttttgaga cagagtctaa ctctgtcgcc     47640
caggctggaa tgcagtggtg caatctcggc tcactacaac ctccgcctcc tgggttcaag    47700
caattctccg gtctcagcct cctgagtagc tgggattaca ggtgtgcacc atgatgcctg    47760 gctaatttt tttgtatttt tttttagtag agatgggttt tcaccatgtt ggccaggctg     47820
gtctcaaact cctgacctca ggtgatccac ccacctcggc ctccatcact ggaaaacttg    47880
```

```
agacacagaa aagtgtctcc accatggtat ggctgaagga gggcaggcca ccaggcagac   47940
agaccaagat ccgaatgtca gcatctacct ttatgtgctt tatggcatga ccttgaatct   48000
ctctgagcca gttcctcccc tgccaaaaag aatagcaact gggcagtgtc tggtcaggtc   48060
agcctacagt acgtggtgcc tgttcaatct cttgggcgac agtcaggccc caagctcgca   48120
gctcagtgtg tgggggctga atcttcacct gagtcctctt cattctaccc agcagccacc   48180
ctgagctggg gccctgagct ctgatcccca tggcctcccc tcaccggccc aggtttttac   48240
ccagggcctc aagggatgag tcggcccgct gtcaccacat ctctctgagt gggaggagaa   48300
gcaatgcagc tccctggtgt gaagatgcag gtggccgcgt agcaggtgtg tgggaccctg   48360
gcccggccac cagccaatgc ccggggctct gttgctccac aggcatggcg acaatctgca   48420
acatgggtgc agaaattggg gccaccactt ccgtgttccc ttacaaccac aggatgaaga   48480
agtacctgag caagaccggc cgggaaggtg agctggcagg ggcaggcccg tgtgggtgga   48540
acagtcacat gcccgctcct ccccaagaca gagctatgcc tttccctgta gggcaggggt   48600
tcttaaccca ttgtctccag acaggcgtcc gaggctctga aaagccctg aagaggtgca   48660 atatgtttct gagtagattg tctggagctc tctccagctt ctcaaagggc ctggcatctg   48720
agttcaagat agccccacct caggatgggc atttcatttt ccctggaagg tggctgaatg   48780 cccgccttc tcggcctggt ccctgctgcc ccctacagga aactccgaa atgacatgga   48840 tcgcttctgt tgataattcc tgacctagca ggggaacatt tggaaggaga accactttcc   48900
cagcctcccc tgacaacttc cctgaggctc tagcctggct tctttggagc tcagagggca   48960
ttggcacctg tgaagggtgg tgcgttgtgg gagtgaacga ggagccagag accaggggcc   49020
atggggagag ccgtaagcac gtggaatcct tggaaggctc ctcccttttcc ttattgagtg   49080 actgcttctt caaaacccag ctcttcactt ccaggacacc ctccccggct ctgaacctta   49140
gctggcgctc ctcctctgtg tctccgtgtc cctgacagct cctgcactag ggtgtgagct   49200
ctgtaagggc agagacagca gccttggttt cttcattggc ctagtcagtg cccagggtgg   49260
gcctggtgtt tggcaggtgc tcaggtgggt ggtgagtgaa ctctcaagaa cagtttatgt   49320
ttcacgtgct ccatccccgt cccttgttga tttcagacat tgccaatcta gctgatgaat   49380
tcaaggatca cttggtgcct gaccctggct gccattatga ccaactaatt gaaattaacc   49440
tcagtgaggt gaggagacaa ttaactgggt tcaagaagtt tctgagagta gtggggagca   49500
gggcgggtcc tgcctaaata ctcactgagg gccgggtggt ggctcacagc tgtaatccca   49560
gcactttggg aggccaaggc aggtgggtca gttgaggtca gcagttcaag accagcctgt   49620
ccaacatagt gaaaccccgt ctctactaaa aaaaaaaaaa aaaatacaaa aattagctcg   49680
gcatagtgcc atgtgcctat aatcccagct attcaggagg ctgaggcaag ataatcgctt   49740
gaacccggga cgcagaggtt gcagtcagcc gagatcgcac cactgcactc cagcctgggc   49800
gacagagcga cactgtctca aaaacaaaac aagaaaaacc tcagggtgac tcgtgggccc   49860
ctgggtcccc agtgttcctg caaactgctt cctgaagcag cctggagcag tgggtgggga   49920 gggggggagac acagccacgg ggagagcaga ggtagctctg gctgctgaac cagaagtgga   49980
tgtcagtttg ccaccagctc agctttagga gaagccaagg tttcaccctg aagggttttt   50040
gttatctgag ttcagagggc aaatcccagc agggttaggc accctgagac gcacagatca   50100
gagcaggtgt ttgcagagcc agaggaaggg caggctagag gatcccgtct gcaggagttc   50160
acacctcggc tctgccactt aagttgtgtg gccttggtca cgcacttagc ctctgtaggc   50220
cccttgctcc atcacgtgtg gaacctacag cagtcgtgag gattgaatga attcatgtaa   50280
```

```
ctaacactga cggaggttta ctgcatgctg cgcacatagc tgagtgcctc gcatttactg    50340
atgattatga tatgtaaagc gtctggcctt aagtccattt ttgtcatgat tccaaaagcg    50400
gccgggcatg gtggctgaca cctgtaatcc cagcactttg ggaggccgag gcgggcagat    50460
catgaggtca ggagattgag accatcctgg ctaatgtgat gaaacccgt ctctactaaa     50520 aaaatacaaa aaaattagcc agacgtggtg gcgggcgcct gtagtcccag ctactcggga    50580
ggctgaggca gaagaatggt gtgaacccga gaggcggagg ctgccgtgag ccaagatcgt    50640
gccactgcac tccagcctgg gcagcagagc gagactccat ctcaaaaaa aaaaaaagat     50700 tccaaaagca acatcgaatg ggagataatg aacttaggaa gctgacagcc ttgatccatt    50760
ccatgcctct gctgtctcct agctatgtga cttcaagcac agcatgtcac ttctgagctt    50820
cagttccttc atctgcagag ctgagcccag ccttgcaggg ctggagggag cccgggagcg    50880
ggtgtgtgca gagccaactg ctcagttctt ccctgtgatg aggtttcagt caagagaaag    50940
tcgttggcct ctctgtgggg acgtggtgag gcagtgaaag aggctgtccc cgcttcaagg    51000
tttcttccct cctctctttc ttctccttgc atgtttgttt cttcagctga agccacacat    51060
caatgggccc ttcaccctg acctggctca ccctgtggca gaagtgggca aggtggcaga    51120
gaaggaagga tggcctctgg acatccgagt gggtgagcac cttccacccc atctgtttag    51180
caggtctcag ggccagtggc tctgcccagg gctgtagaca atcacctatg cctactgtgt    51240
ggcactttct aaggtgggca gtttctgaaa tgggtttatt attgaaaat tactttttcg      51300 gccagaagtg gtggctcatg cttgaaatcc cagcatttca ggaggccaat gcaggtggat    51360
tacttgagtc tagggttca agaccagcct gggcaacatg gaaaaacccc gtctcttaaa     51420
agaaaatgca aaaattggcc aggggcagtg gctcacacct gtaatcccag cactttggga    51480
ggccgagatg ggtggatcat gaggtcagga gatcgagacc atcctggcta acacggtgaa    51540 acccatctc tactaaaaat acaaaaaatt agccaggggt ggtggcaggc acctgtagcc      51600
ccagctactt gggaggctga ggcaggagaa tcgcttgaac ccaggaggcg gaggttgcaa    51660
tgaaccgaga ttgtgtcact gcactccagc ctgggtgaca gagcgaggct ccgtctcaga    51720 aaaaaaaaa aaaattggcc aggtgtggag gcgcatgcct atagtcctag ctactcagga     51780
ggctaaggtg ggaggatcac ttgagtcctg gaggtcaagg ctacagtgag ccgagatggt    51840
accactgcat tccagcctgg gcaacaaagg cagactcaaa actgcagact caagcaacag    51900
agcctgcctc caaaaaaaaa aaaaaaaaa aaaagaaaag aaaagaaaaa ttacttttc       51960 ttggcagaaa agaaaaatat gtttattgta gagaatattc acaatcaaga gaattttta     52020 aaactcctaa tctcaacccc cagccaggag caagctctta gagctcttgg agaggtgtgc    52080
tgtgtttctg tgtattgtgt gcatagattt tcccgtttta catttatat cacccatgct      52140 gctttatgtg acttttcatg ctttacacat gcagacgccc tggcatgcca gtcactggca    52200
tctgctgctg ctgggtacag tgtggctgtg aagagcatgg agcctggagc cagatggcct    52260
gggcttgaat cctggctctg ccacctaaca gccactaaca gctgagtgac cctgagcaaa    52320
ctacttcact gtctatgtgt gggttcccca tctgtaaaac aggagtcatg atcgtactga    52380 caccttgaa ggtggtgttg ggcctactgc tgctatcacc aatgagaaaa ataaataaaa      52440
aataaagttg tctggagaag tgacaatatg tgaaagaga tttctatacc gtctggccga     52500
aaataagggc aatataatgt gttcgcccctt attcattgaa gtaattttaa gaaaaaaaat   52560
atttggtggt ttaataatta gaaagtaaat tactaaatta ataaaagaaa ctatcttggc    52620
```

```
tggttatatg ggcttttgcc agtaatccca acccttttt tttttttga gacagagtct    52680
tgctctgtca cccaggctgg agtgcagtgg cacaatctcg gctcactgca gcctccgcct    52740
cccaggttca agcagttctg cctcagcctc ccgagtagct gggactacag gcgcccgcca    52800
ccatgcctgg ctaattttg tatttttagt agagatgggg gtttcactgt gttagccagg    52860
ctagtctgga actcctgacc tcaagtgatc tgcctgcctc ggcctctcaa agttgtggga    52920
ttacaggtgt gagccaccgc gcctggccag tcccaacact ttgagaggct gaggcaggag    52980
gatcatttga tcccaggagt tcaagagcag cctgggcaac atggtgagac tttgtctcta    53040
caaaaacaat ttattgaatt agccaggtgt ggtggtactc acctgtgggt cccagctact    53100
caggaagttg aggcaggagg agttgcttga gccccaggag ttagagactg cagtgagcaa    53160
gcctcgactg tgcccttgca ctccagcctg ggcgacagag caagacccca tctcaacaac    53220
aacaaaaaga gactgtctag acagaaagtg cgatgttatt caggttttat agactttta    53280
aaaagaactc ttattgccct gattataaaa caatctttaa acccagaaa atactagaaa    53340
gtataaaaga agaaaattag catctcctgt cagccccagc ccatcaagga tggctgttcg    53400
tatgagccct ctgacgtgcc tacacgtgta catgatattg ctgtaaaagg ggtcatagtc    53460
ctaatgtgtt cagcatcatg gccaatggct acagcatctt tcttcaaatg acgccacgtc    53520
atgagttagc ctgtccttta ttgttggata tttcggttgc ttgcaactgg tctctgttaa    53580
aaaagtctct ggcccagccc agatggtgaa ctcttttggc caagtctgga taattttgaag    53640
tcaggtggag acctctgctc actgtctcct cctgacccct aaccccacca cccacaatgc    53700
accaggtcta attggtagct gcaccaattc aagctatgaa gatatggggc gctcagcagc    53760
tgtggccaag caggcactgg cccatggcct caagtgcaag tcccagttca ccatcactcc    53820
aggttccgag cagatccgcg ccaccattga gcgggacggc tatgtgagtg cccatatccc    53880
cctgcccatc tccccacccc catgctgagt aatgcctcca ggcggcacaa gcccagaggc    53940
ctgttgggcc ggggctgggg caggtcccag tggctgccct gggggtccag tacagcactt    54000
cgtcctgcag ccaccacatc acccccttccc atcagactct cacccacccct tgacattctg    54060
tcttcctctc tccctggcag gcacagatct tgagggatct gggtggcatt gtcctggcca    54120
atgcttgtgg cccctgcatt ggccagtggg acaggtaaga ggcgtatctt ttgacaagac    54180
agcccccttgt gcacagggta cagagcccca gaagttggag ggggaattat tggggtggag    54240
agaagagact ccagccaagg tctctagctc cagggactct tgcccattag aagcctctgg    54300
cagacatgcc tgggaagagg ggctgggtga ggaagggccc tgcagaggca ctgggggcca    54360
acttggctga agcctgggct ggcaggagga agccagcgcg gcctcaccct gacggacaca    54420
gcaggagccg tttgggagga ggcagtgccc caggtcagga aactcaggcc ttgaccaagg    54480
ccttgcctct ggcttacgtg tggttgcagg ctgggcccag tgatcctgag gttcccttct    54540
gctctgcgcg tggccccagg aggaggcaac cctggcaggg cctcttcatt ttccctcggt    54600
aggagctagg ctgggctgcg ccacaggaac ccagcttatc tgtcctcggg acaggccagg    54660
tgacaaggcc agatatccct aaccctgatc cctctgacct ggcaggaagg acatcaagaa    54720
gggggagaag aacacaatcg tcacctccta caacaggaac ttcacgggcc gcaacgacgc    54780
aaaccccgag acccatgcct ttgtcacgtc cccagaggtg agactgccca gctgcgcaca    54840
agcctgggat ggcctctggg ggtccctggc gggtcagagg aggaggcaga aggagatggg    54900
gactggggtc atccaagtgg tagccaggag ctacaggcct tcccagcctc aggcgcatgc    54960
ttggtgcttc ctgcctgggg ctccctgggt catgggatta tgagatattt atacagtggt    55020
```

```
ttgtgcttat gagcatggaa tttggaatct cactcactgc ctaggacaca tcccagccct   55080
gcctctaact cgctgtatga gtgtggccaa gtcacttacc ttctctgtgt ccccgtaatc   55140
ctcgggatta cctgggaaag tgcgtgggac acatgcagtt tccaacccca ggtaggagtt   55200
ccacaaaagc gaggcctttg ccattgttcc cgtggccaga gtgagccttg cccttggcgg   55260
tattcagccc tggccgtgac tggcacatgg ccaggctctc ttgacttggt tgtttatctg   55320
cgtgttctac aaatatgtct tgctaaatgg gtgaaggaat ggctccttcc atgttttag    55380
tgtcctgcgc actgagcagg tttgcatcat accagcattt ctgcgccagg gcccccactc   55440
cctccaggat agctgtgagg agagagaaca gcactgccgg cccggccctg cagggatggg   55500
agaggccgca ctgcccttgg cttcctgagt cctctgcagg cccaaggccc cgtggtccca   55560
aagatcgtcc tgcagctctg gcctctgagg aacacagggg tctgggaaga acatggaaat   55620
ttcctgggtt cctttctcag ttttggccta ggcttttggt aggtgcagga gacaggagtg   55680
gcaattggtg ctgaccaaca aactggccac ctccatttca gattgtcaca gccctggcca   55740
tgcgggaac ccctcaagttc aacccagaga ccgactacct gacgggcacg gatggcaaga   55800
agttcaggct ggaggctccg gatgcagatg agcttcccaa aggggtgagc gcccacgccc   55860
cctgcttgct ggttgctgtg tggccacgtc acttccttct caacctcaca gcacctcctg   55920
tgcaggcagg gagggcgctg ctagtgagaa ggaagcagct ctgttccctg ggaggggagg   55980
tggggcccga ggaaacttgc cttctgagag tctgtccttg tgggaactga ggactcagca   56040
ccccacgcat cccccattccc tgctgcagga gtttgaccca gggcaggaca cctaccagca   56100
cccacccaag gacagcagcg ggcagcatgt ggacgtgagc cccaccagcc agcgcctgca   56160
gctcctggag ccttttgaca gtgggatgg caaggacctg gaggacctgc agatcctcat    56220
caaggtcagc agcatgggga cggcaggaca gccccaccct gccagggccc ccgtcccct    56280
gagcatcggg aagggccatg aacctggagg aagtgagcac agtcaagacg caggtgggag   56340
atggaaggga ggtttggctg cagagcagag agggtatcgc aacgcagtcc agcgtccccc   56400
ttctctgtgg ccccgaactg ggcagagcta gatctggcca gcctccgtct ggggccctca   56460
gccatccagc agcagctgat cagagccacc tccagtgggt gtgggcaggt gagtacagct   56520
caggctgggc tgggacagtg tgtgtgattg cacagcaggc tccacacctg gcacgtccac   56580
acaggctctg gaagccatgg acaactcctg ccccacagt tgggcacccg tggatatggg    56640
atggcttgtg tttggcaccg accaaaaaca agccttttttg gtgtggccag aggcctccaa   56700
tctgtgtcag atatttattt atgctgctta ttaaggggtc tccaggcacc cctgtgacag   56760
aagagactaa tcagtcatca gccaggaccc aggcatgtcc tgggctcctg tgtccagcat   56820
gaggtctgtg gctgatcttg cagctgaggc ctgaagggtg agcgaacatt gacctgtccc   56880
aactttgggc ggcctctgcc ccataaggga gactgagcag ccagaggcct ttgaggggat   56940
gaaggcctgg cctgagccca tgtggcctta gggtggaagc accaggacca cagaacacgt   57000
gtctgaagac ttgcctgcct ctcaccctc tgtcacccct cctgggcccc ggggcctgct    57060
gcctgcctct ggagggcttg tcatccaccc ctccagggcc atgccctgac ctctgtcctc   57120
tctacttacc acccaaggtc aaagggaagt gtaccactga ccacatctca gctgctggcc   57180
cctggctcaa gttccgtggg cacttggata acatctccaa caacctgctc attggtgcca   57240
tcaacattga aaacggcaag gccaactccg tgcgcaatgc cgtcactcag gagtttggcc   57300
ccgtccctga cactgcccgc tactacaagg tgggtcagag ttgataggg caatgccagt    57360
```

```
ggtcactcct gaaggggcct gcaaggcagg tgcagggagg acattagggg agtggaaact   57420
gggaaggagg ccgaccaagc ccaaagggga ctgctgtgga agggaggaga ggcctgcagc   57480
ccctccctgt ggctgagaag gcatgaggcc caggtccggt ggtacagccg ggtccctgca   57540
ccaggaggag ttagtgagag atatcttagg atatctggcc ctagacaaag acaaggaagg   57600
gggccgactc aggaagtcag aggccaaaag ctcagagagg gggctacacg gggcctcaca   57660
gtgagcaggc agagagggtc tgaggtgatt ggacttttc tgctttgaga aacaaacaga    57720
accagggctg aacccaagtc ctggcccagc cgggtgaaag gactctggca ccccctggtg   57780
gctgggtggg gcagagggtg ctcccaggaa ggggcgcct tgagcttcac agatgcatct     57840 tgtgtgggc ccggaggccg tccctgtctc acccaacctc cctccacaca cacctgcctc    57900
tgccaagcac caatgggtgg cttctgtctt ctttgccact gcaaacaacc acgtgcctct   57960
gtcccctcgg ggcctcgttt gggtctcatt cacgcaggct tcacttgccc ttaggcagca   58020
ggcgaggaag ggcccctcca gccccttac cgggagcctc aggatgccca ggcgccaggt    58080
gggtgaggcc aggcaggtag ggccagacag gtgaggacgg tgccctcctc tgccttataa   58140
ccttaccccc gcttgcctga cagaaacatg gcatcaggtg ggtggtgatc ggagacgaga   58200
actacggcga gggctcgagc cgggagcatg cagctctgga gcctcgccac cttggggcc    58260 gggccatcat caccaagagc tttgccagga tccacggtga gctggagtct gtacccaggc   58320
catcctcatc ccatccctag tgatcaaggt cactctccct gcccgtggct gagttgggcc   58380
tggttctagg ctgtgtccac tgcagcccac aggcccgtca gcctcttgcc ccttcttagg   58440
ctcacacagt gcacatccga cgctcagctt cccggcttcc cgcaggccct gcttccaggc   58500
ttgtagatct gagccgctga gatctaggac atgtgccagg gggttctttc tgatcatgaa   58560
tgtgcagcag gaaggcctcg cagacctcag caccagcgca cacttgctag ggcaccccct   58620
agtgaaaggg agcagaccag ggccccatag tcactgcccg ggcattgtcc caggcagcag   58680
gattaggggc atctcccaga gccccagatg ggttcagaaa atgaagctct ccaggctagt   58740 caggccccg atgaccgaat gccgcctgct ttccagagac caacctgaag aaacagggcc    58800
tgctgcctct gaccttcgct gacccggctg actacaacaa gattcaccct gtggacaagc   58860
tgaccattca gggcctgaag gacttcaccc ctggcaaggt taggggcccg ggtcccctg    58920 aggtggtggg gtgaggggca gccaccttgt ttcccctcct gcactggccc cagggtagct   58980
tctcccagga ggcttcattc cagctggaaa ggccccagt tctccaggtg gccccacaga    59040
gaaagcaaag tggcttctca gagttggggg ttggagtcaa cccggggccc tcacacctcc   59100
ccaacctccc tttactcacc aggacctggc actcagggga cagcccaccc actgcaggac   59160
cctctgggcc ccaggaatcc cctgtaggtg ccacctgggt ctgacctggg ccatcaggca   59220
cagactggcc taggatttgg tttgcctgct gacctcttag gtcccaggc agtgccctgt    59280 ctccctgacc cccctgcggg gccaagggca cacagtaccc accacttcca cccacaccca   59340
ccttctcctt gcagccctg aagtgcatca tcaagcaccc caacgggacc caggagacca    59400
tcctcctgaa ccacaccttc aacgagacgc agattgagtg gttccgcgct ggcagtgccc   59460
tcaacagaat gaaggaactg caacagtgag ggcagtgcct ccccgccccg ccgctggcgt   59520
caagttcagc tccacgtgtg ccatcagtgg atccgatccg tccagccatg gcttcctatt   59580
ccaagatggt gtgaccagac atgcttcctg ctccccgctt agcccacgga gtgactgtgg   59640
ttgtggtggg ggggttctta aaataacttt ttagcccccg tcttcctatt ttgagtttgg   59700
ttcagatctt aagcagctcc atgcaactgt atttattttt gatgacaaga ctcccatcta   59760
```

```
aagttttctct cctgcctgat catttcattg gtggctgaag gattctagag aacctttgt    59820 tcttgcaagg aaaacaagaa tccaaaacca gtgactgttc tgtga                    59865

<210> SEQ ID NO 13
<211> LENGTH: 32
<212> TYPE: RNA
<213> ORGANISM: human

<400> SEQUENCE: 13
cgtcatactc ctgcttgctg atccacatct gc                                  32

<210> SEQ ID NO 14
<211> LENGTH: 32
<212> TYPE: RNA
<213> ORGANISM: human

<400> SEQUENCE: 14
atctggcacc acaccttcta caatgagctg cg                                  32

<210> SEQ ID NO 15
<211> LENGTH: 19
<212> TYPE: RNA
<213> ORGANISM: human

<400> SEQUENCE: 15
aaagaaggcu guaccguua                                                 19

<210> SEQ ID NO 16
<211> LENGTH: 19
<212> TYPE: RNA
<213> ORGANISM: human

<400> SEQUENCE: 16
gauugugccu gacuuuaua                                                 19

<210> SEQ ID NO 17
<211> LENGTH: 21
<212> TYPE: RNA
<213> ORGANISM: human

<400> SEQUENCE: 17
ggacaaacct cagccctaac g                                              21

<210> SEQ ID NO 18
<211> LENGTH: 21
<212> TYPE: RNA
<213> ORGANISM: human

<400> SEQUENCE: 18
tttgatggct tccagcaact c                                              21

<210> SEQ ID NO 19
<211> LENGTH: 21
<212> TYPE: RNA
<213> ORGANISM: human

<400> SEQUENCE: 19
ttgggcaaag gtggaaatga a                                              21

<210> SEQ ID NO 20
<211> LENGTH: 20
<212> TYPE: RNA
```

```
<213> ORGANISM: human

<400> SEQUENCE: 20
caccacaagc caaacgactt                                          20

<210> SEQ ID NO 21
<211> LENGTH: 20
<212> TYPE: RNA
<213> ORGANISM: human

<400> SEQUENCE: 21
gtctgtgtga gaacattgcc                                          20

<210> SEQ ID NO 22
<211> LENGTH: 19
<212> TYPE: RNA
<213> ORGANISM: human

<400> SEQUENCE: 22
atgtggctcc cgtagtcag                                           19

<210> SEQ ID NO 23
<211> LENGTH: 21
<212> TYPE: RNA
<213> ORGANISM: human

<400> SEQUENCE: 23
aaaggacatt tccaccgcaa a                                        21

<210> SEQ ID NO 24
<211> LENGTH: 20
<212> TYPE: RNA
<213> ORGANISM: human

<400> SEQUENCE: 24
ggtcgggtca acgctaggct                                          20

<210> SEQ ID NO 25
<211> LENGTH: 21
<212> TYPE: RNA
<213> ORGANISM: human

<400> SEQUENCE: 25
cattctgaaa ggctggtttg a                                        21

<210> SEQ ID NO 26
<211> LENGTH: 20
<212> TYPE: RNA
<213> ORGANISM: human

<400> SEQUENCE: 26
ttgcagagag tacatggagc                                          20

<210> SEQ ID NO 27
<211> LENGTH: 19
<212> TYPE: RNA
<213> ORGANISM: human

<400> SEQUENCE: 27
gcaggagggc tcactcaaa                                           19

<210> SEQ ID NO 28
<211> LENGTH: 20
```

```
<212> TYPE: RNA
<213> ORGANISM: human

<400> SEQUENCE: 28
aggtgacgca ggatggtatt                                                    20

<210> SEQ ID NO 29
<211> LENGTH: 20
<212> TYPE: RNA
<213> ORGANISM: human

<400> SEQUENCE: 29
tgctgtcttg cagggaatgt                                                    20

<210> SEQ ID NO 30
<211> LENGTH: 19
<212> TYPE: RNA
<213> ORGANISM: human

<400> SEQUENCE: 30
cacaaccatc caccactgc                                                     19

<210> SEQ ID NO 31
<211> LENGTH: 20
<212> TYPE: RNA
<213> ORGANISM: human

<400> SEQUENCE: 31
atcccaactg tggtcttcag                                                    20

<210> SEQ ID NO 32
<211> LENGTH: 21
<212> TYPE: RNA
<213> ORGANISM: human

<400> SEQUENCE: 32
cacgttgaat aggtcttcac a                                                  21

<210> SEQ ID NO 33
<211> LENGTH: 24
<212> TYPE: RNA
<213> ORGANISM: human

<400> SEQUENCE: 33
ttcctctgct gccattagtc agtc                                               24

<210> SEQ ID NO 34
<211> LENGTH: 23
<212> TYPE: RNA
<213> ORGANISM: human

<400> SEQUENCE: 34
gtccttccat ttccgagtca ctg                                                23

<210> SEQ ID NO 35
<211> LENGTH: 22
<212> TYPE: RNA
<213> ORGANISM: human

<400> SEQUENCE: 35
cacccagctt atcttgcaag tg                                                 22

<210> SEQ ID NO 36
```

```
<211> LENGTH: 22
<212> TYPE: RNA
<213> ORGANISM: human

<400> SEQUENCE: 36
aaagcgcccg taacatacat cg                                              22

<210> SEQ ID NO 37
<211> LENGTH: 22
<212> TYPE: RNA
<213> ORGANISM: human

<400> SEQUENCE: 37
aaacatctac cttccagctg cg                                              22

<210> SEQ ID NO 38
<211> LENGTH: 22
<212> TYPE: RNA
<213> ORGANISM: human

<400> SEQUENCE: 38
tggatctact tctactcctc gg                                              22

<210> SEQ ID NO 39
<211> LENGTH: 22
<212> TYPE: RNA
<213> ORGANISM: human

<400> SEQUENCE: 39
gtcaaatgga ccctcatgga ag                                              22

<210> SEQ ID NO 40
<211> LENGTH: 22
<212> TYPE: RNA
<213> ORGANISM: human

<400> SEQUENCE: 40
cccaagcaac ctctactgct tt                                              22

<210> SEQ ID NO 41
<211> LENGTH: 22
<212> TYPE: RNA
<213> ORGANISM: human

<400> SEQUENCE: 41
tggaaatgat tgcccaagct cg                                              22

<210> SEQ ID NO 42
<211> LENGTH: 22
<212> TYPE: RNA
<213> ORGANISM: human

<400> SEQUENCE: 42
caatgctttc agagctgttc cc                                              22

<210> SEQ ID NO 43
<211> LENGTH: 20
<212> TYPE: RNA
<213> ORGANISM: human

<400> SEQUENCE: 43
ggattgtgcc tgacattgtg                                                 20
```

```
<210> SEQ ID NO 44
<211> LENGTH: 22
<212> TYPE: RNA
<213> ORGANISM: human

<400> SEQUENCE: 44
cactcagagt caccttaact gg                                              22

<210> SEQ ID NO 45
<211> LENGTH: 22
<212> TYPE: RNA
<213> ORGANISM: human

<400> SEQUENCE: 45
ctgtgaggtc tgccagtctt ta                                              22

<210> SEQ ID NO 46
<211> LENGTH: 22
<212> TYPE: RNA
<213> ORGANISM: human

<400> SEQUENCE: 46
gcttgtcact ttcagatcca cg                                              22
```

METHOD AND KIT FOR PROGNOSIS OF OPA1 GENE INDUCED DISEASES, E.G. KJERS OPTIC ATROPHY

FIELD OF THE INVENTION

The invention relates to a method, process and kit for prognosis of OPA1 gene or OPA1 gene product-deficit induced diseases.

BACKGROUND OF THE INVENTION

Mitochondria are double membrane organelles, containing their own genome, acting as cellular powerhouse via oxidative phosphorylation (Osellame et al., 2012).

Mitochondrial diseases can be caused by mutations in the genes of mitochondrial or nuclear DNA (Koopman et al., 2013). Defects may affect subunits of respiratory chain complexes, mitochondrial assembly proteins, mtDNA maintenance and expression, phospholipid composition of the inner mitochondrial membrane or mitochondrial dynamics; the later controlling the organelle's morphology, with fusion leading to the formation of elongated tubules and fission to isolated punctua. Although many of mitochondrial diseases are multisystemic, some appear to be tissue specific such as optic neuropathies.

Dominant optic atrophy (DOA; OMIM: #165500) is associated with mutations in nuclear genes encoding mitochondrial proteins, primarily the OPA1 gene (opticatrophy gene1 (OPA1; OMIM: *605290)).

Dominant optic atrophy (DOA), Kjer type; or Kjer's autosomal dominant optic atrophy, is an autosomally inherited disease that occurs with an estimated disease prevalence of between 1:12,000 and 1:50,000. (Kivlin, J. D., Lovrien, E. W., Bishop, D. T. & Maumenee, I. H. Linkage analysis in dominant optic atrophy. Am. J. Hum. Genet. 35, 1190-1195 (1983), Kjer, B., Eiberg, H., Kjer, P. & Rosenberg, T. Dominant optic atrophy mapped to chromosome 3q region. II. Clinical and epidemiological aspects. Acta Ophthalmol. Scand. 1996 74, 3-7 (1996) and Lyle, W. M. Genetic risks. Waterloo, Ontario, University of Waterloo Press (1990), Amati-Bonneau et al., 2009, Yu-Wai-Man et al., 2011, Lenaers et al., 2012).

Patients with DOA experience progressive and diffuse atrophy of the retinal ganglion cell layer, loss of myelin and fibrillary gliosis along the anterior visual pathways extending to the lateral geniculate body. This disease is affecting the retina, optic nerves, causing a progressive bilateral reduction in visual acuity beginning in childhood and ultimately could result in blindness.

This pathology remains without effective whether curative or preventive treatment to date, partly due to the complex aetiology of the disease and to unpredictable phases of worsening.

A link between DOA and the OPA1 gene was described in international application WO0227022.

Based on identification of OPA1 mutations as one cause of DOA, a method of diagnosis and treatment of DOA was provided in international application WO00227022. In this application, methods of screening for and detection of carriers of a defective OPA1 gene, diagnosis of a defective OPA1 gene, prenatal OPA1 gene defect screening and detection, gene therapy utilising recombinant technologies and drug therapy using the information derived from the OPA1 gene or OPA1 protein, are disclosed.

A molecular diagnosis is therefore provided by the identification of mutation(s) in the OPA1 gene.

Thus, the majority of patients (about 75%) with DOA harbors at least a mutation in the OPA1 gene (Delettre et al., 2000).

280 different OPA1 mutations have been reported to date (http://mitodyn.org), the majority of which results in premature termination codons and lead to haploinsufficiency by the reduction in OPA1 protein levels (Amati-Bonneau et al 2009).

Other genes were found to be linked to the disease (review in Lenaers et al., 2012), including OPA3 (P Reynier et al., 2004) and more recently NR2F1. (Bosch et al., 2014).

There is a considerable inter- and intra-familial variation in visual acuity, and the penetrance may be as low as about 40% (Cohn et al., 2007).

There is also a marked inter- and intra-familial variability in the rate of disease progression, and a significant proportion of patients (50-75%) will experience further worsening of their visual function in later life (Yu-Wai-Man et al., 2010) (Yu-Wai-Man et al., 2010).

Recent studies evidenced a severe multi-systemic disorder associated with particular OPA1 mutations, named "DOA plus" syndrome (OMIM#125250) (Amati-Bonneau 2008, Zeviani 2008 (Yu-Wai-Man et al., 2010). Nevertheless, although syndromal DOA variants show significant phenotypic variability even within the same family, a consistent finding is a worse visual prognosis among this patient subgroup.

These "DOA plus" patients present additional neurological complications, such as ataxia, sensorineural deafness, chronic progressive external ophtalmoplegia (CPEO) and sensory-motor neuropathy and myopathy in adult life.

Considering these multiple variables, it is difficult to predict when and to which extend a patient with a risk of developing DOA will experience a first symptom, whether said patient may experience complications associated with OPA1 mutations and the seriousness of said complications.

The only method available to evaluate the severity of DOA is the ophthalmological examination.

Using funduscopic examination, the main sign of DOA consists in optic nerve pallor, usually bilateral and symmetric on the temporal side, which is observed in about 50% of patients and is global in the other 50%, especially in old or severely affected patients. However, in moderate cases, the optic nerve atrophy may not be visible.

These ophthalmological examinations are not very sensitive and do not allow to evaluate precisely the disease progression and the extent of damages in retina and optic nerves.

These tests do not allow a sensitive and accurate evaluation or prediction of the severity of the disease or to predict a worsening of the pathological condition(s) and/or whether patient may experience additional complications.

Obviously, invasive tests such as retina biopsies can not be used to evaluate the prognosis of DOA and complications can not be predicted using this method.

Moreover, there are no tests available allowing diagnosing/prognosing OPA1-deficit-induced "DOA plus" syndrome.

There is thus a critical and unmet need for providing effective, sensitive and reliable prognostic of DOA or "DOA plus" syndrome and of its complications, in particular of OPA1-deficit-induced dominant optic atrophy or "DOA plus" syndrome and of its complications.

According to one aspect, the present invention provides means of determining whether or not DOA has a risk of developing, a risk to be affected by a complication a means of assessing its seriousness, and ultimately of identifying the most suitable treatment and of preventing the disease in asymptomatic patients. The process according to the invention will ultimately allow preventive treatment to be administered before irremediable damages of optic neurons and extra-ocular tissues or cells.

In particular, they have demonstrated that the level of expression and/or activity of specific factors are predictive of DOA progression and/or severity.

More particularly, they could identify within DOA patients a subgroup of patients that corresponded to patients experiencing a worsening of the pathological condition.

The method according to this invention particularly makes it possible to anticipate and/or determine DOA seriousness, identify the most suitable treatment. This is an essential means in the follow up of patients.

This invention makes up for the drawbacks of the earlier art by offering a new method, process and kit for prognosis of DOA and opens up the possibility of new preventive treatments.

Additionally, the method according to the invention is simple and reproducible, while being less expensive.

The method according to the invention is more specific and much more sensitive than those previously described. The process according to the invention is non invasive and not painful.

The present invention provides Nuclear Factor (erythroid-derived 2)-like 2 (NRF2)-activated genes products for their use in the prognosis of an OPA1 gene- or OPA1 gene product-deficit-induced disease, or related complications, in a biological sample selected from fibroblasts, epithelial cells, blood samples or a mixture thereof, of a patient affected or suspected to be affected by said disease.

The present invention provides the use of Nuclear Factor (erythroid-derived 2)-like 2 (NRF2)-activated genes products for the in vitro prognosis of an OPA1 gene- or OPA1 gene product-deficit-induced disease, and/or related complications, in a biological sample selected from fibroblasts, epithelial cells, blood samples or a mixture thereof, of a patient affected or suspected to be affected by said disease.

An in vitro prognosis according to the invention is a prognosis performed on a sample collected on a patient by a non-invasive method.

The present invention provides the use of Nuclear Factor (erythroid-derived 2)-like 2 (NRF2)-activated genes products for the in vitro prognosis of an OPA1 gene- or OPA1 gene product-deficit-induced disease, and/or related complications, in a biological sample selected from fibroblasts, epithelial cells, blood samples or a mixture thereof, of a patient affected or suspected to be affected by said disease, in particular wherein said NRF2-activated genes products are selected from the group consisting in NRF2, SOD1, SOD2, catalase, GSTP1, NQO1, Glutathione Reductase, Peroxiredoxin 1, Heme oxigenase 1, Thioredoxin reductase 1, Glutamate Cystein Ligase.

Surprisingly, the inventors have shown that subjects suffering DOA displayed an abnormal level and/or activity of factors involved in the oxidative response in fibroblasts or epithelial cells; further, this change in the level and/or activity of factors involved in the oxidative response in fibroblasts is a hallmark signing an increase in sensitivity and early warning sign of a worsening phase of the disease, or of a complication.

According to an embodiment, the invention relates to Nuclear Factor (erythroid-derived 2)-like 2 (NRF2)-activated genes products for their use in the prognosis of an OPA1 gene- or OPA1 gene product-deficit-induced disease, said prognosis being done from birth of said patient.

According to another embodiment, the invention relates to nuclear factor (erythroid-derived 2)-like 2 (NRF2)-activated genes products for their use in the prognosis of OPA1 deficiency induced diseases and/or complications comprising detecting said NRF2-activated genes products and another marker of said prognosis such as aconitase.

According to an embodiment, the invention relates to the use of Nuclear Factor (erythroid-derived 2)-like 2 (NRF2)-activated genes products for the in vitro prognosis of OPA-1 deficiency induced diseases and/or complications wherein said use comprises detecting said NRF2-activated genes products and another marker of said prognosis such as aconitase.

According to a preferred embodiment, the invention provides Nuclear factor (erythroid-derived 2)-like 2 (NRF2)-activated genes products for their use in the prognosis of OPA-1 deficiency induced diseases and/or complications wherein said use comprises detecting said NRF2-activated genes products and another marker of said prognosis such as aconitase.

According to another embodiment, the invention relates to Nuclear Factor (erythroid-derived 2)-like 2 (NRF2)-activated genes products for their use in the prognosis of an OPA1 gene- or OPA1 gene product-deficit-induced disease, or related complications, in a biological sample selected from fibroblasts, epithelial cells, blood samples or a mixture thereof of a patient having an OPA1 gene- or OPA1 gene product-deficit.

According to another embodiment, the invention relates to Nuclear Factor (erythroid-derived 2)-like 2 (NRF2)-activated genes products for their use in the diagnosis and prognosis of an OPA1 gene- or OPA1 gene product-deficit-induced disease, or related complications, in a biological sample selected from fibroblasts, epithelial cells, blood samples or a mixture thereof of a patient suspected to have an OPA1 gene- or OPA1 gene product-deficit.

According to another embodiment, the invention relates to Nuclear Factor (erythroid-derived 2)-like 2 (NRF2)-activated genes products for their use in the prognosis of an OPA1 gene- or OPA1 gene product-deficit-induced disease, or related complications, in a biological sample selected from fibroblasts, epithelial cells, blood samples or a mixture thereof, comprising a first step of diagnosis of said OPA1 gene- or OPA1 gene product-deficit-induced disease, or related complications by detecting an OPA1 gene- or OPA1 gene product-deficit.

According to another embodiment, the invention relates to the use of Nuclear Factor (erythroid-derived 2)-like 2 (NRF2)-activated genes products for the in vitro prognosis of an OPA1 gene- or OPA1 gene product-deficit-induced disease, or related complications, in a biological sample selected from fibroblasts, epithelial cells, blood samples or a mixture thereof, comprising a first step of diagnosis of said OPA1 gene- or OPA1 gene product-deficit-induced disease, or related complications by detecting an OPA1 gene- or OPA1 gene product-deficit.

According to another embodiment, the invention relates to the use of Nuclear Factor (erythroid-derived 2)-like 2 (NRF2)-activated genes products for the in vitro prognosis of an OPA1 gene- or OPA1 gene product-deficit-induced disease, or related complications, in a biological sample selected from fibroblasts, epithelial cells, blood samples or a mixture thereof, wherein said prognosis is performed on patients having an OPA1 gene- or OPA1 gene product-deficit-induced disease and for which the mutation of OPA1 gene has been identified.

In fact, the prognosis according to the invention is performed on subjects for whom a first step of diagnosis of said OPA1 gene- or OPA1 gene product-deficit has been realized by detecting an OPA1 gene- or OPA1 gene product-deficit.

According to another embodiment, the invention relates to Nuclear Factor (erythroid-derived 2)-like 2 (NRF2)-activated genes products for their use in the prognosis of an OPA1 gene- or OPA1 gene product-deficit-induced disease, or related complications, in a biological sample selected from fibroblasts, blood samples or a mixture thereof, comprising a first step of diagnosis of said OPA1 gene- or OPA1 gene product-deficit-induced disease, or related complications by detecting an OPA1 gene- or OPA1 gene product-deficit.

According to another embodiment, the invention relates to Nuclear Factor (erythroid-derived 2)-like 2 (NRF2)-activated genes products for their use in the prognosis of an OPA1 gene- or OPA1 gene product-deficit-induced disease, or related complications, in a biological sample selected from fibroblasts, epithelial cells, blood samples or a mixture thereof, said use comprising a first step of diagnosis of said OPA1 gene- or OPA1 gene product-deficit-induced disease, or related complications by detecting an OPA1 gene- or OPA1 gene product-deficit.

According to another embodiment, the invention relates to Nuclear Factor (erythroid-derived 2)-like 2 (NRF2)-activated genes products for their use as above defined wherein OPA1-deficit induced disease is an OPA1-deficit induced optic neuropathy, OPA1-deficit induced autosomal dominant optic atrophy (DOA, OMIM#165500), and/or complications associated with OPA1-deficit induced DOA, in particular—severe multi-systemic syndromes, "DOA plus" disorders as external ophthalmoplegia, ataxia, and deafness or glaucoma, in particular Primary Open Angle Glaucoma, myopathy, peripheral neuropathy, neurodegenerative diseases related to the age (Alzheimer, Parkinson).

According to another embodiment, the invention relates to the use of Nuclear Factor (erythroid-derived 2)-like 2 (NRF2)-activated genes products for the in vitro prognosis, wherein OPA1-deficit induced disease is an OPA1-deficit induced optic neuropathy, OPA1-deficit induced autosomal dominant optic atrophy (DOA, OMIM#165500), and/or complications associated with OPA1-deficit induced DOA, in particular—severe multi-systemic syndromes, "DOA plus" disorders, external ophthalmoplegia, ataxia, myopathy and deafness or glaucoma, in particular Primary Open Angle Glaucoma, peripheral neuropathy, neurodegenerative diseases related to the age (Alzheimer, Parkinson).

According to another embodiment, the invention relates to the use of Nuclear Factor (erythroid-derived 2)-like 2 (NRF2)-activated genes products for the in vitro prognosis, wherein OPA1-deficit induced disease is autosomal dominant optic atrophy (DOA, OMIM#165500), and/or complications associated with OPA1-deficit induced DOA, in particular—severe multi-systemic syndromes, "DOA plus" disorders, external ophthalmoplegia, ataxia and deafness or glaucoma, in particular Primary Open Angle Glaucoma.

According to another embodiment, the invention relates to NRF2-activated genes products for their use as defined above, the expression and/or activity of which, determined in a biological sample selected from fibroblasts, epithelial cells, blood samples or a mixture thereof is modulated with respect to that of healthy subjects of the same age having no OPA1 gene- or OPA1 gene product deficit or to that of healthy subjects of the same age having no OPA1 gene- or OPA1 gene product deficit and to the same patient for whom at least one prognosis test has been previously done.

According to another embodiment, the invention relates to NRF2-activated genes products for their use as defined above, the expression and/or activity of which, determined in a biological sample selected from fibroblasts, epithelial cells, blood samples or a mixture thereof, is modulated with respect to that of healthy subjects of the same age having no OPA1 gene- or OPA1 gene product deficit or to that of healthy subjects of the same age having no OPA1 gene- or OPA1 gene product deficit and to the same patient for whom at least one prognosis test has been previously done.

According to another embodiment, the invention relates to the use of NRF2-activated genes products for the in vitro prognosis, the expression and/or activity of which, determined in a biological sample selected from fibroblasts, epithelial cells, blood samples or a mixture thereof is modulated with respect to that of healthy subjects of the same age having no OPA1 gene- or OPA1 gene product deficit or to that of healthy subjects of the same age having no OPA1 gene- or OPA1 gene product deficit and to the same patient for whom at least one prognosis test has been previously done.

According to another embodiment, the invention relates to NRF2-activated genes products for their use as above defined, the expression of which is increased or decreased with respect to that of healthy subjects of the same age having no OPA1 gene- or OPA1 gene product deficit or to that of healthy subjects of the same age having no OPA1 gene- or OPA1 gene product deficit and to the same patient for whom at least one prognosis test has been previously done.

According to another embodiment, the invention relates to the use of NRF2-activated genes products for the in vitro prognosis, the expression of which is increased or decreased with respect to that of healthy subjects of the same age having no OPA1 gene- or OPA1 gene product deficit.

According to another embodiment, the invention relates to NRF2-activated genes products for their use as above defined, the expression of which is increased with respect to that of healthy subjects of the same age having no OPA1 gene- or OPA1 gene product deficit or to that of healthy subjects of the same age having no OPA1 gene- or OPA1 gene product deficit and to the same patient for whom at least one prognosis test has been previously done.

According to another embodiment, the invention relates to NRF2-activated genes products for their use as above defined, the expression of which is decreased with respect to that of healthy subjects of the same age having no OPA1 gene- or OPA1 gene product deficit or to that of healthy subjects of the same age having no OPA1 gene- or OPA1 gene product deficit and to the same patient for whom at least one prognosis test has been previously done.

According to another embodiment, the invention relates to NRF2-activated genes products for their use as above defined, the activity of which is increased with respect to that of healthy subjects of the same age having no OPA1 gene- or OPA1 gene product deficit or to that of healthy subjects of the same age having no OPA1 gene- or OPA1 gene product deficit and to the same patient for whom at least one prognosis test has been previously done.

In a particularly advantageous embodiment, the expression of said marker is not modified as compared to a control, and the activity of the NRF2-activated genes products for their use according the invention, is increased or decreased with respect to that of healthy subjects of the same age having no OPA1 gene- or OPA1 gene product deficit or to that of healthy subjects of the same age having no OPA1 gene- or OPA1 gene product deficit and to the same patient for whom at least one prognosis test has been previously done.

According to another embodiment, the invention relates to the use of NRF2-activated genes products for the in vitro prognosis, the activity of which is increased or decreased with respect to that of healthy subjects of the same age having no OPA1 gene- or OPA1 gene product deficit.

Controls according to the invention may be and is not limited to, healthy subjects of the same age having no OPA1 gene- or OPA1 gene product deficit.

A control according to the invention may be the same patient at another time (just before a worsening phase, after a worsening phase, during a worsening phase or latence phase).

According to another embodiment, the invention relates to NRF2-activated genes products for their use as above defined, the activity of which is decreased with respect to that of healthy subjects of the same age having no OPA1 gene- or OPA1 gene product deficit or to that of healthy subjects of the same age having no OPA1 gene- or OPA1 gene product deficit and to the same patient for whom at least one prognosis test has been previously done.

According to another embodiment, the invention relates to NRF2-activated genes products for their use as above defined, the expression and activity of which are decreased with respect to that of healthy subjects of the same age having no OPA1 gene- or OPA1 gene product deficit.

According to another embodiment, the invention relates to NRF2-activated genes products for their use as above defined, the expression and activity of which are increased with respect to that of healthy subjects of the same age having no OPA1 gene- or OPA1 gene product deficit.

According to the present invention an increase means a statistically significant increase as compared to a control ranging from 0.2 to 100 fold increase as compared to a control, preferably 0.5 to 50 fold increase, more preferably a 2 to 100, 5 to 100, 10 to 100, 20 to 100, 50 to 100, and even more particularly a 2, 3, 4, 5, 6, 7, 8, 9, 10, 15, 20, 25, 30, 35, 40, 45, 50 fold increase as compared to a control.

According to the present invention a decrease means a statistically significant decrease as compared to a control ranging from 0.2 to 100 fold decreased as compared to a control, preferably 0.5 to 50 fold decrease, more preferably a 2 to 100, 5 to 100, 10 to 100, 20 to 100, 50 to 100, and even more particularly a 2, 3, 4, 5, 6, 7, 8, 9, 10, 15, 20, 25, 30, 35, 40, 45, 50 fold decrease as compared to a control.

A control as used herein, means a negative control. Usually a negative control correspond to the situation or condition without treatment, or with a mock treatment, it corresponds to a condition wherein one expects no modulation.

According to another embodiment, the invention relates to NRF2-activated genes products for their use as above defined, wherein said NRF2-activated gene product is a detoxifying enzyme or an antioxidant protein.

According to another embodiment, the invention relates to NRF2-activated genes products for their use as above defined, wherein said NRF2-activated genes products are selected from the group consisting in NRF2, SOD1, SOD2, catalase, GSTP1, NQO1, Glutathione Reductase, Peroxiredoxin 1, Heme oxigenase 1, Thioredoxin reductase 1, Glutamate Cystein Ligase.

According to another embodiment, the invention relates to the use of NRF2-activated genes products for the in vitro prognosis wherein said NRF2-activated genes products are selected from the group consisting in NRF2, SOD1, SOD2, catalase, GSTP1, NQO1, Glutathione Reductase, Peroxiredoxin 1, Heme oxigenase 1, Thioredoxin reductase 1, Glutamate Cystein Ligase.

According to another embodiment, the invention relates to the use of Nuclear Factor (erythroid-derived 2)-like 2 (NRF2)-activated genes products for the in vitro prognosis of an OPA1 gene- or OPA1 gene product-deficit-induced disease, and/or related complications, in a biological sample selected from fibroblasts, epithelial cells, blood samples or a mixture thereof, of a patient affected or suspected to be affected by said disease, wherein said NRF2-activated genes products are selected from the group consisting in NRF2, SOD1, SOD2, catalase, GSTP1, NQO1, Glutathione Reductase, Peroxiredoxin 1, Heme oxigenase 1, Thioredoxin reductase 1, Glutamate Cystein Ligase.

In another more advantageous embodiment, the NRF2-activated genes products according to the invention are Superoxide dismutase 1 (SOD1) (SEQ ID No 1), superoxide dismutase 2 (SOD2) (SEQ ID No 2), catalase (CAT) (SEQ ID No 3), glutathione S-transferase pi 1 (GSTP1) (SEQ ID No 4), NAD(P)H dehydrogenase quinone 1 (NQO1) (SEQ ID No 5), glutathione reductase (GSR) (SEQ ID No 6), thioredoxin reductase 1 (TXNRD1) (SEQ ID No 7), Peroxiredoxin (SEQ ID No 8), heme oxygenase (decycling) 1 (HMOX1) (SEQ ID No 9), glutamate-cysteine ligase modifier subunit (GCLM) (SEQ ID No 10), NRF2 (SEQ ID No 11).

In the invention, said expression and/or activity of said NRF2-activated genes products is detected in a biological sample selected from fibroblasts, epithelial cells, blood samples or a mixture thereof by immunoblotting or by RT-PCR (Reverse transcription polymerase chain reaction).

In a preferred embodiment, a NRF2-activated gene product expression and/or activity is detected by RT-PCR, using primers SEQ ID No 17 and SEQ ID No 18, SEQ ID No 19 and SEQ ID No 20, SEQ ID No 21 and SEQ ID No 22, SEQ ID No 25 and SEQ ID No 26, SEQ ID No 27 and SEQ ID No 28, SEQ ID No 29 and SEQ ID No 30, SEQ ID No 31 and SEQ ID No 32, or SEQ ID No 33 and SEQ ID No 34.

The invention also relates to a human aconitase for its use in the prognosis of an OPA1 gene- or OPA1 gene product-deficit-induced disease or related complications in a biological sample selected from fibroblasts, blood samples or a mixture thereof in a patient affected or suspected to be affected by said disease.

In the invention, said expression and/or activity of said aconitase is detected in a biological sample selected from fibroblasts, epithelial cells, blood samples or a mixture thereof by immunoblotting or by RT-PCR and by colorimetric assay.

In a preferred embodiment, the invention relates to a method as defined above, wherein the expression of said NRF2-activated genes products expression and/or activity is detected by RT-PCR, in particular by quantitative RT-PCR and more particularly by quantitative RT-PCR using primers of SEQ ID No 17 and SEQ ID No 18, SEQ ID No 19 and SEQ ID No 20, SEQ ID No 21 and SEQ ID No 22, SEQ ID No 25 and SEQ ID No 26, SEQ ID No 27 and SEQ ID No 28, SEQ ID No 29 and SEQ ID No 30, SEQ ID No 31 and SEQ ID No 32, SEQ ID No 33 and SEQ ID No 34.

According to another embodiment, the invention relates to the use of Nuclear Factor (erythroid-derived 2)-like 2 (NRF2)-activated genes products for the in vitro prognosis, wherein the prognosis is a prognosis of worsening of the disease and/or related complications.

For patients presenting a "strict DOA" disease, meaning a "light" phenotype of DOA disease without neurological complications, the worsening of the disease and/or related complications means that the "strict DOA" disease evolves to a DOA "plus" syndrome and/or to related complications.

For patients presenting a DOA "plus" syndrome which correspond to patients presenting additional neurological complications, the worsening of the disease and/or related complications means that the syndrome and/or related complications are worsened.

According to another embodiment, the invention relates to the use of Nuclear Factor (erythroid-derived 2)-like 2 (NRF2)-activated genes products for the in vitro prognosis, wherein, in a group of patients having an OPA1 gene- or OPA1 gene product deficit, a subgroup of patients having:
- an expression level of Nuclear Factor (erythroid-derived 2)-like 2 (NRF2)-activated genes products lower than that of healthy subjects at the same age having no OPA1 gene- or OPA1 gene product deficit,
- and an expression level of Nuclear Factor (erythroid-derived 2)-like 2 (NRF2)-activated genes products lower than that of patients at the same age having an OPA1 gene- or OPA1 gene product deficit, is identified as having a prognosis of worsening of the disease and/or related complications.

According to another embodiment, the invention relates to the use of Nuclear Factor (erythroid-derived 2)-like 2 (NRF2)-activated genes products for the in vitro prognosis, wherein said NRF2-activated genes products is SOD1 and wherein, in a group of patients having an OPA1 gene- or OPA1 gene product deficit, a subgroup of patients having:
- an expression level of SOD1 lower than that of healthy subjects at the same age having no OPA1 gene- or OPA1 gene product deficit,
- and an expression level of SOD1 lower than that of patients at the same age having an OPA1 gene- or OPA1 gene product deficit, is identified as having a prognosis of worsening of worsening of the disease and/or related complications.

According to another embodiment, the invention relates to the use of Nuclear Factor (erythroid-derived 2)-like 2 (NRF2)-activated genes products for the in vitro prognosis, wherein said NRF2-activated genes products is SOD2 and wherein, in a group of patients having an OPA1 gene- or OPA1 gene product deficit, a subgroup of patients having:
- an expression level of SOD2 lower than that of healthy subjects at the same age having no OPA1 gene- or OPA1 gene product deficit,
- and an expression level of SOD2 lower than that of patients at the same age having an OPA1 gene- or OPA1 gene product deficit, is identified as having a prognosis of worsening of the disease and/or related complications.

According to another embodiment, the invention relates to the use of Nuclear Factor (erythroid-derived 2)-like 2 (NRF2)-activated genes products for the in vitro prognosis, wherein said NRF2-activated genes products are SOD1 and SOD2 and wherein, in a group of patients having an OPA1 gene- or OPA1 gene product deficit, a subgroup of patients having
- expression levels of SOD1 and SOD2 lower than those of healthy subjects at the same age having no OPA1 gene- or OPA1 gene product deficit,
- and expression levels of SOD1 and SOD2 lower than those of patients at the same age having an OPA1 gene- or OPA1 gene product deficit, is identified as having a prognosis of worsening of the disease and/or related complications.

According to another embodiment, the invention relates to the use of Nuclear Factor (erythroid-derived 2)-like 2 (NRF2)-activated genes products for the in vitro prognosis, wherein said NRF2-activated genes products are SOD1 and SOD2 and wherein, in a group of patients having an OPA1 gene- or OPA1 gene product deficit and suffering from DOA pathology, a subgroup of patients having
- expression levels of SOD1 and SOD2 lower than those of healthy subjects at the same age having no OPA1 gene- or OPA1 gene product deficit,
- and expression levels of SOD1 and SOD2 lower than those of patients at the same age having an OPA1 gene- or OPA1 gene product deficit, is identified as having a prognosis of worsening of the DOA pathology.

According to another embodiment, the invention relates to the use of NRF2-activated genes products for the in vitro prognosis wherein said NRF2-activated genes products is NRF2.

According to another embodiment, the invention relates to the use of NRF2-activated genes products for the in vitro prognosis wherein said NRF2-activated genes products is NRF2, and wherein the total cell expression of which is increased with respect to that of healthy subjects of the same age having no OPA1 gene- or OPA1 gene product deficit.

According to another embodiment, the invention relates to the use of NRF2-activated genes products for the in vitro prognosis wherein said NRF2-activated genes products is NRF2, and wherein the nuclear translocation of which is increased with respect to that of healthy subjects of the same age having no OPA1 gene- or OPA1 gene product deficit.

In an advantageous embodiment, the present invention provides an aconitase or a NRF2-activated gene product for its use in the prognosis of an OPA1-deficit-induced disease and/or complication, the expression and/or activity of said aconitase or of said NRF2-activated gene product is increased or decreased as a function of disease progression, and/or complications.

In this embodiment, the expression and/or activity of said aconitase is increased or decreased as compared to the expression and/or activity of said aconitase measured in the same patient during a worsening phase or a latent phase.

In a particular embodiment, the present invention provides an aconitase, or for its use in the prognosis of an OPA1-deficit-induced disease and/or complication the expression and/or activity of said aconitase was increased or decreased as compared to that of healthy volunteers, as a function of disease progression, and/or complications.

In a preferred embodiment, the present invention provides an human aconitase 2 (SEQ ID No 12), or for its use in the prognosis of an OPA1-deficit-induced disease and/or complication the expression and/or activity of said aconitase was increased or decreased as compared to that of healthy volunteers, as a function of disease progression, and/or complications.

The present invention relates to an in vitro method for the prognosis of an OPA1 gene or OPA1 gene product deficit-induced disease comprising detecting in a biological sample selected from fibroblasts, epithelial cells, blood samples or a mixture thereof, of a patient affected or suspected to be affected by said disease, a modulation in the expression and/or the activity of NRF2-activated genes products with respect to those of healthy subjects of the same age having no deficit in the OPA1 gene or OPA1 gene product or to that of healthy subjects of the same age having no OPA1 gene- or OPA1 gene product deficit and to the same patient for whom at least one prognosis test has been previously done.

The in vitro method for the prognosis of an OPA1 gene or OPA1 gene product deficit-induced disease above defined comprises:
(a) detecting in a biological sample selected from fibroblasts, epithelial cells, blood samples or a mixture thereof, of a patient affected or suspected to be affected by said disease, the expression and/or the activity of NRF2-activated genes products.
(b) comparing said expression to those of healthy subjects of the same age having no deficit in the OPA1 gene or OPA1 gene product, or to that of healthy subjects of the same age having no OPA1 gene- or OPA1 gene product deficit and to the same patient for whom at least one prognosis test has been previously done.
(c) deducing from said comparison whether said individual may expect suffering and/or the severity of said OPA1 gene or OPA1 gene product deficit-induced disease or related complication.

The in vitro method for the prognosis of an OPA1 gene or OPA1 gene product deficit-induced disease above defined comprises:
(a) detecting in a biological sample selected from fibroblasts, epithelial cells, blood samples or a mixture thereof, of a patient affected or suspected to be affected by said disease, the expression and/or the activity of NRF2-activated genes products, and without the use of an invasive sample,
(b) comparing said expression to those of healthy subjects of the same age having no deficit in the OPA1 gene or OPA1 gene product, or to that of healthy subjects of the same age having no OPA1 gene- or OPA1 gene product deficit and to the same patient for whom at least one prognosis test has been previously done,
(c) deducing from said comparison whether said individual may expect suffering and/or the severity of said OPA1 gene or OPA1 gene product deficit-induced disease or related complication.

The in vitro method for the prognosis of an OPA1 gene or OPA1 gene product deficit-induced disease above defined comprises:
(a) detecting in a biological sample selected from fibroblasts, epithelial cells, blood samples or a mixture thereof, of a patient affected or suspected to be affected by said disease, the expression and/or the activity of NRF2-activated genes products and without the use of an invasive sample, and in particular without the use of retina sample or optic nerve sample,
(b) comparing said expression to those of healthy subjects of the same age having no deficit in the OPA1 gene or OPA1 gene product, or to that of healthy subjects of the same age having no OPA1 gene- or OPA1 gene product deficit and to the same patient for whom at least one prognosis test has been previously done,
(c) deducing from said comparison whether said individual may expect suffering and/or the severity of said OPA1 gene or OPA1 gene product deficit-induced disease or related complication.

According to an embodiment, the invention relates to a method for the prognosis of an OPA1 gene or OPA1 gene product deficit-induced disease comprising detecting in a biological sample selected from fibroblasts, epithelial cells, blood samples or a mixture thereof, of a patient suspected to be affected by said disease, a modulation in the expression and/or the activity of NRF2-activated genes products with respect to those of a healthy subject having no deficit in the OPA1 gene or OPA1 gene product, from birth of said patient or to that of healthy subjects of the same age having no OPA1 gene- or OPA1 gene product deficit and to the same patient for whom at least one prognosis test has been previously done.

According to an embodiment, the invention relates to a method for the prognosis of an OPA1 gene or OPA1 gene product deficit-induced disease comprising detecting in a biological sample selected from fibroblasts, epithelial cells, blood samples or a mixture thereof, of a patient suspected to be affected by said disease, a modulation in the expression and/or the activity of NRF2-activated genes products and of another marker of prognosis such as aconitase with respect to those of a healthy subject having no deficit in the OPA1 gene or OPA1 gene product, from birth of said patient or to that of healthy subjects of the same age having no OPA1 gene- or OPA1 gene product deficit and to the same patient for whom at least one prognosis test has been previously done.

According to another embodiment, the invention relates to a method as defined above for the prognosis of an OPA1 gene- or OPA1 gene product-deficit-induced disease, or related complications using a biological sample selected from fibroblasts, epithelial cells, blood samples or a mixture thereof, in a patient having an OPA1 gene- or OPA1 gene product-deficit.

According to another embodiment, the invention relates to a method as defined above for the diagnosis and prognosis of an OPA1 gene- or OPA1 gene product-deficit-induced disease, or related complications using a biological sample selected from fibroblasts, epithelial cells, blood samples or a mixture thereof, from a patient suspected to have an OPA1 gene- or OPA1 gene product-deficit, According to another embodiment, the invention relates to a method as defined above for the prognosis of an OPA1 gene or OPA1 gene product deficit-induced disease comprising detecting in a biological sample selected from fibroblasts, epithelial cells, blood samples or a mixture thereof, of a patient affected or suspected to be affected by said disease, a modulation in the expression and/or the activity of NRF2-activated genes products with respect to those of healthy subjects of the same age having no deficit in the OPA1 gene or OPA1 gene product or to that of healthy subjects of the same age having no OPA1 gene- or OPA1 gene product deficit and to the same patient for whom at least one prognosis test has been previously done, comprising a first step of diagnosis of said OPA1 gene- or OPA1 gene product-deficit-induced disease by detecting an OPA1 gene- or OPA1 gene product-deficit.

According to another embodiment, the invention relates to a method as defined above, wherein said OPA1-deficit induced disease is an OPA1-deficit induced optic neuropathy, particularly OPA1-deficit induced autosomal dominant optic atrophy (DOA, OMIM#165500), and/or complications associated with OPA1-deficit induced DOA, severe multisystemic syndromes, "DOA plus" disorders, external ophthalmoplegia, ataxia and deafness and/or glaucoma, in particular Primary Open Angle Glaucoma, myopathy, peripheral neuropathy, neurodegenerative diseases related to the age (Alzheimer, Parkinson).

According to another embodiment, the invention relates to a method as defined above, wherein the expression and/or activity of NRF2-activated genes products, determined in a biological sample selected from fibroblasts, epithelial cells, blood samples or a mixture thereof, is modulated with respect to that of healthy subjects of the same age having no OPA1 gene- or OPA1 gene product deficit or to that of healthy subjects of the same age having no OPA1 gene- or OPA1 gene product deficit and to the same patient for whom at least one prognosis test has been previously done.

According to another embodiment, the invention relates to a method as defined above, wherein the expression and/or activity of NRF2-activated genes products, determined in a biological sample selected from fibroblasts, epithelial cells, epithelial cells, blood samples or a mixture thereof, is modulated with respect to that of healthy subjects of the same age having no OPA1 gene- or OPA1 gene product deficit or to that of healthy subjects of the same age having no OPA1 gene- or OPA1 gene product deficit and to the same patient for whom at least one prognosis test has been previously done.

According to another embodiment, the invention relates to a method as defined above, wherein said expression is increased with respect to that of healthy subjects of the same age having no OPA1 gene- or OPA1 gene product deficit or to that of healthy subjects of the same age having no OPA1 gene- or OPA1 gene product deficit and to the same patient for whom at least one prognosis test has been previously done.

According to another embodiment, the invention relates to a method as defined above wherein said expression is decreased with respect to that of healthy subjects of the same age having no OPA1 gene- or OPA1 gene product deficit or to that of healthy subjects of the same age having no OPA1 gene- or OPA1 gene product deficit and to the same patient for whom at least one prognosis test has been previously done.

According to another embodiment, the invention relates to a method as defined above, wherein said activity is increased with respect to that of healthy subjects of the same age having no OPA1 gene- or OPA1 gene product deficit or to that of healthy subjects of the same age having no OPA1 gene- or OPA1 gene product deficit and to the same patient for whom at least one prognosis test has been previously done.

According to another embodiment, the invention relates to a method as defined above, wherein said activity is decreased with respect to that of healthy subjects of the same age having no OPA1 gene- or OPA1 gene product deficit or to that of healthy subjects of the same age having no OPA1 gene- or OPA1 gene product deficit and to the same patient for whom at least one prognosis test has been previously done.

According to another embodiment, the invention relates to a method as defined above, wherein said expression and activity are decreased with respect to that of healthy subjects of the same age having no OPA1 gene- or OPA1 gene product deficit or to that of healthy subjects of the same age having no OPA1 gene- or OPA1 gene product deficit and to the same patient for whom at least one prognosis test has been previously done.

According to another embodiment, the invention relates to a method as defined above, wherein said expression and activity are increased with respect to that of healthy subjects of the same age having no OPA1 gene- or OPA1 gene product deficit or to that of healthy subjects of the same age having no OPA1 gene- or OPA1 gene product deficit and to the same patient for whom at least one prognosis test has been previously done.

According to another embodiment, the invention relates to a method as defined above, wherein said NRF2-activated gene product is a detoxifying enzyme or an antioxidant protein.

According to another embodiment, the invention relates to a method as defined above, wherein said NRF2-activated genes products are selected from the group consisting in NRF2, SOD1, SOD2, catalase, GSTP1, NQO1, Glutathione Reductase, Peroxiredoxin 1, Heme oxigenase 1, Thioredoxin reductase 1, Glutamate Cystein Ligase.

According to another embodiment, the invention relates to an in vitro method for the prognosis of an OPA1 gene or OPA1 gene product deficit-induced disease comprising detecting in a biological sample selected from fibroblasts, epithelial cells, blood samples or a mixture thereof, of a patient affected or suspected to be affected by said disease, a modulation in the expression and/or the activity of aconitase with respect to those of a healthy subject of the same age having no deficit in the OPA1 gene or OPA1 gene product.

According to another embodiment, the invention relates to a method as defined above, wherein the expression and/or activity of said NRF2-activated genes products or of aconitase is detected in a biological sample by RT-PCR or by immunoblotting.

According to another embodiment, the invention relates to a method as defined above, wherein the expression of said NRF2-activated genes products expression and/or activity is detected by RT-PCR, in particular by quantitative RT-PCR and more particularly by quantitative RT-PCR using primers designed with the following sequence ID: NRF2, SOD1, SOD2, catalase, GSTP1, NQO1, Glutathione Reductase, Peroxiredoxin 1, Heme oxigenase 1, Thioredoxin reductase 1, Glutamate Cystein Ligase.

In a preferred embodiment, the invention relates to a method as defined above, wherein the expression of said NRF2-activated genes products expression and/or activity is detected by RT-PCR, in particular by quantitative RT-PCR and more particularly by quantitative RT-PCR using primers of SEQ ID No 17 and SEQ ID No 18, SEQ ID No 19 and SEQ ID No 20, SEQ ID No 21 and SEQ ID No 22, SEQ ID No 25 and SEQ ID No 26, SEQ ID No 27 and SEQ ID No 28, SEQ ID No 29 and SEQ ID No 30, SEQ ID No 31 and SEQ ID No 32, SEQ ID No 33 and SEQ ID No 34.

According to another embodiment, the invention relates to a method as defined above, wherein said method is a non invasive method.

The invention also relates to an in vitro method for the prognosis of an OPA1 gene or OPA1 gene product deficit-induced disease comprising detecting in a biological sample selected from fibroblasts, epithelial cells, blood samples or a mixture thereof, of a patient affected or suspected to be affected by said disease, a modulation in the expression and/or the activity of aconitase with respect to those of healthy subjects of the same age having no deficit in the OPA1 gene or OPA1 gene product or to that of healthy subjects of the same age having no OPA1 gene- or OPA1 gene product deficit and to the same patient for whom at least one prognosis test has been previously done.

According to another embodiment, the invention relates to a method as defined above, wherein said modulation in the expression or activity of NRF2-activated genes products or of aconitase is a decrease or an increase.

According to another embodiment, the invention relates to a method for preventing or treating OPA1 deficiency induced diseases and/or complications further comprising administering a treatment comprising administering at least one compound selected from:

Glutathione, Vitamin A, Vitamin C, Vitamin E, Vitamin cofactors (Coenzyme Q10 and Coenzyme Q10 analogs), Minerals (Manganese and Iodide) Carotenoid terpenoids, Natural phenols (Flavonoïdes (such as resveratrol)), Phenolic acids and their esters, Other nonflavonoid phenolics (such as curcuminoids), organic antioxidants (Capsaicin, Bilirubin, oxalic acid, phytic acid, N-Acetylcysteine, R-α-Lipoic acid, fat and water soluble Uric acid), ARE inducers (Sulforafane, Nordihydroguaiaretic acid, Diallyl Sulfid, Diallyl disulfid, Diallyl trisulfid, Pterostilbene, D3T (1,2-dithiole-3-thione), CPDT (5,6-dihydro-cyclopento-(c)-1,2-dithiole-(4H)-thione), Oltipraz, Salicylcurcuminoids, BG12, Bardoxolonemethyl), a combination thereof.

The present invention encompasses these compounds for their use in the prevention and or treatments of worsening phases of DOA, wherein said compounds could be administered daily from birth.

The invention also relates to a kit for the prognosis of OPA1 deficiency induced diseases and/or complications comprising at least one means of detection of NRF2-activated genes products and/or aconitase optionally, comprising at least one means of diagnostic of detection of OPA1 mutated or deficient gene or gene product.

According to an embodiment of the invention, the in vitro method for the prognosis of patient having an OPA1 gene or OPA1 gene product deficit-induced disease comprises:
- detecting in a biological sample selected from fibroblasts, epithelial cells, blood samples or a mixture thereof, of a patient affected or suspected to be affected by said disease, the expressions of NRF2-activated genes products, and without the use of retina sample or optic nerve sample,
- comparing said expressions to those of healthy subjects having no OPA1 gene- or no OPA1 gene-product deficit.

Said healthy subjects who are used as controls are preferably healthy subjects of the same age as said patients.

According to an embodiment of the invention, the in vitro method for the prognosis of patient having an OPA1 gene or OPA1 gene product deficit-induced disease comprises:
- detecting in a biological sample selected from fibroblasts, epithelial cells, blood samples or a mixture thereof, of a patient affected or suspected to be affected by said disease, the expressions of NRF2-activated genes products, and without the use of retina sample or optic nerve sample,
- comparing said expressions to those of healthy subjects at the same age having no OPA1 gene- or no OPA1 gene product deficit.

According to an embodiment of the invention, the in vitro method for the prognosis of patient having an OPA1 gene or OPA1 gene product deficit-induced disease comprises:
- detecting in a biological sample selected from fibroblasts, epithelial cells, blood samples or a mixture thereof, of a patient affected or suspected to be affected by said disease, the expression of NRF2-activated genes products, and without the use of retina sample or optic nerve sample,
- comparing said expressions to those of same patient having OPA1 gene- or OPA1 gene product deficit at an early stage and to those of healthy subjects at the same age having no OPA1 gene- or no OPA1 gene product deficit.

According to an embodiment of the invention, the in vitro method for the prognosis of patient having an OPA1 gene or OPA1 gene product deficit-induced disease, comprises the comparison of the expressions of NRF2-activated genes products of patient having an OPA1 gene or OPA1 gene product deficit-induced disease, to NRF2-activated genes products expressions of healthy subjects having no OPA1 gene- or no OPA1 gene-product deficit, and when NRF2-activated genes products expressions of patient having an OPA1 gene or OPA1 gene product deficit-induced disease are lower than those of said healthy subjects, the prognosis is the worsening of the disease and/or related complications.

According to an embodiment of the invention, the in vitro method for the prognosis of patient having an OPA1 gene or OPA1 gene product deficit-induced disease comprises the comparison of the expressions of NRF2-activated genes products of patient having an OPA1 gene or OPA1 gene product deficit-induced disease, to NRF2-activated genes products expressions of healthy subjects having no OPA1 gene- or no OPA1 gene-product deficit, and when NRF2-activated genes products expressions of patient having an OPA1 gene or OPA1 gene product deficit-induced disease are similar to those of said healthy subjects, the prognosis is that the disease and/or related complications are not worsened with respect to the antioxidant mechanism related to the NRF2 activation.

According to an embodiment of the invention, the in vitro method for the prognosis of patient having an OPA1 gene or OPA1 gene product deficit-induced disease comprises the comparison of the expressions of NRF2-activated genes products of patient having an OPA1 gene or OPA1 gene product deficit-induced disease, to NRF2-activated genes products expressions of healthy subjects having no OPA1 gene- or no OPA1 gene-product deficit, and when NRF2-activated genes products expressions of patient having an OPA1 gene or OPA1 gene product deficit-induced disease are upper than those of said healthy subjects, the prognosis is that the disease and/or related complications are not worsened with respect to the antioxidant mechanism related to the NRF2 activation.

According to an embodiment of the invention, the in vitro method for the prognosis of patient having an OPA1 gene or OPA1 gene product deficit-induced disease comprises the comparison of the expressions of NRF2-activated genes products of patient having an OPA1 gene or OPA1 gene product deficit-induced disease, to NRF2-activated genes products expressions of healthy subjects at the same age having no OPA1 gene- or no OPA1 gene-product deficit,
and when NRF2-activated genes products expressions of patient having an OPA1 gene or OPA1 gene product deficit-induced disease are lower than those of said healthy subjects, the prognosis is the worsening of the disease and/or related complications.

According to an embodiment of the invention, the in vitro method for the prognosis of patient having an OPA1 gene or OPA1 gene product deficit-induced disease comprises the comparison of the expressions of NRF2-activated genes products of patient having an OPA1 gene or OPA1 gene product deficit-induced disease, to NRF2-activated genes products expressions of healthy subjects at the same age having no OPA1 gene- or no OPA1 gene-product deficit,
and when NRF2-activated genes products expressions of patient having an OPA1 gene or OPA1 gene product deficit-induced disease are similar to those of said healthy subjects, the prognosis is that the disease and/or related complications are not worsened with respect to the antioxidant mechanism related to the NRF2 activation.

According to an embodiment of the invention, the in vitro method for the prognosis of patient having an OPA1 gene or OPA1 gene product deficit-induced disease comprises the comparison of the expressions of NRF2-activated genes products of patient having an OPA1 gene or OPA1 gene product deficit-induced disease, to NRF2-activated genes products expressions of healthy subjects at the same age having no OPA1 gene- or no OPA1 gene-product deficit,
and when NRF2-activated genes products expressions of patient having an OPA1 gene or OPA1 gene product deficit-induced disease are upper than those of said healthy subjects, the prognosis is that the disease and/or related complications are not worsened with respect to the antioxidant mechanism related to the NRF2 activation.

According to an embodiment of the invention, the in vitro method for the prognosis of patient having an OPA1 gene or OPA1 gene product deficit-induced disease comprises the comparison of the expressions of NRF2-activated genes products of patient having an OPA1 gene or OPA1 gene product deficit-induced disease, to NRF2-activated genes products expressions of the same patient at an early stage, and to those of healthy subjects at the same age having no OPA1 gene- or no OPA1 gene product deficit, and when NRF2-activated genes products expressions of patient having an OPA1 gene or OPA1 gene product deficit-induced disease are lower than those of the same patients at early stage, the prognosis is associated to a worsening of the disease and/or related complications.

According to an embodiment of the invention, the in vitro method for the prognosis of patient having an OPA1 gene or OPA1 gene product deficit-induced disease comprises the comparison of the expressions of NRF2-activated genes products of patient having an OPA1 gene or OPA1 gene product deficit-induced disease, to NRF2-activated genes products expressions of the same patient at an early stage, and to those of healthy subjects at the same age having no OPA1 gene- or no OPA1 gene product deficit, and when NRF2-activated genes products expressions of patient having an OPA1 gene or OPA1 gene product deficit-induced disease are similar to those of the same patients at early stage, the prognosis is that the disease and/or related complications are not worsened with respect to the antioxidant mechanism related to the NRF2 activation.

According to an embodiment of the invention, the in vitro method for the prognosis of patient having an OPA1 gene or OPA1 gene product deficit-induced disease comprises the comparison of the expressions of NRF2-activated genes products of patient having an OPA1 gene or OPA1 gene product deficit-induced disease, to NRF2-activated genes products expressions of the same patient at an early stage, and to those of healthy subjects at the same age having no OPA1 gene- or no OPA1 gene product deficit and when NRF2-activated genes products expressions of patient having an OPA1 gene or OPA1 gene product deficit-induced disease are upper than those of the same patients at early stage, the prognosis is that the disease and/or related complications are not worsened with respect to the antioxidant mechanism related to the NRF2 activation.

According to an embodiment of the invention, the in vitro method for the patient prognosis of an OPA1 gene or OPA1 gene product deficit-induced disease comprises:
  detecting in a biological sample selected from fibroblasts, epithelial cells, blood samples or a mixture thereof, of a patient affected or suspected to be affected by said disease, the expression of NRF2-activated genes products, and without the use of retina sample or optic nerve sample,
  comparing said expression to those of healthy subjects at the same age having no OPA1 gene- or OPA1 gene product deficit,
  comparing said expression to those of patients at the same age having an OPA1 gene- or OPA1 gene product deficit and having the same expression than that of healthy subjects at the same age having no OPA1 gene- or OPA1 gene product deficit,
  deducing from comparison of expression of NRF2-activated genes products of said patient
    to the expression of NRF2-activated genes products of patients at the same age having an OPA1 gene- or OPA1 gene product deficit and having the same expression as that of healthy subjects at the same age having no OPA1 gene- or OPA1 gene product deficit
    and to the expression of NRF2-activated genes products of healthy subjects at the same age having no OPA1 gene- or OPA1 gene product deficit,
  that whether said patient has
    expression levels of NRF2-activated genes products lower than those of healthy subjects at the same age having no OPA1 gene- or OPA1 gene product deficit,
    and expression levels of NRF2-activated genes products lower than those of patients at the same age having an OPA1 gene- or OPA1 gene product deficit,
  said patient may expect suffering and/or the severity of said OPA1 gene or OPA1 gene product deficit-induced disease or related complication.

According to an embodiment of the invention, the in vitro method for the prognosis of patient having an OPA1 gene or OPA1 gene product deficit-induced disease comprises:
  detecting in a biological sample selected from fibroblasts, epithelial cells, blood samples or a mixture thereof, of a patient affected or suspected to be affected by said disease, the expressions of SOD 1 and SOD2, and without the use of retina sample or optic nerve sample,
  comparing said expressions to those of healthy subjects having no OPA1 gene- or no OPA1 gene-product deficit.

Said healthy subjects who are used as controls are preferably healthy subjects of the same age as said patients.

According to an embodiment of the invention, the in vitro method for the prognosis of patient having an OPA1 gene or OPA1 gene product deficit-induced disease comprises:
  detecting in a biological sample selected from fibroblasts, epithelial cells, blood samples or a mixture thereof, of a patient affected or suspected to be affected by said disease, the expressions of SOD 1 and SOD2, and without the use of retina sample or optic nerve sample,
  comparing said expressions to those of healthy subjects at the same age having no OPA1 gene- or no OPA1 gene product deficit.

According to an embodiment of the invention, the in vitro method for the prognosis of patient having an OPA1 gene or OPA1 gene product deficit-induced disease comprises:
  detecting in a biological sample selected from fibroblasts, epithelial cells, blood samples or a mixture thereof, of a patient affected or suspected to be affected by said disease, the expression of SOD 1 and SOD2, and without the use of retina sample or optic nerve sample,
  comparing said expressions to those of same patient having OPA1 gene- or OPA1 gene product deficit at an early stage and to those of healthy subjects at the same age having no OPA1 gene- or no OPA1 gene product deficit.

According to an embodiment of the invention, the in vitro method for the prognosis of patient having an OPA1 gene or OPA1 gene product deficit-induced disease comprises the comparison of the expressions of SOD 1 and SOD2 of patient having an OPA1 gene or OPA1 gene product deficit-induced disease, to SOD1 and SOD2 expressions of healthy subjects having no OPA1 gene- or no OPA1 gene-product deficit, and when SOD1 and SOD2 expressions of patient having an OPA1 gene or OPA1 gene product deficit-induced disease are lower than those of said healthy subjects, the prognosis is the worsening of the disease and/or related complications.

According to an embodiment of the invention, the in vitro method for the prognosis of patient having an OPA1 gene or OPA1 gene product deficit-induced disease comprises the comparison of the expressions of SOD 1 and SOD2 of patient having an OPA1 gene or OPA1 gene product deficit-induced disease, to SOD1 and SOD2 expressions of healthy subjects having no OPA1 gene- or no OPA1 gene-product deficit, and when SOD1 and SOD2 expressions of patient having an OPA1 gene or OPA1 gene product deficit-induced disease are similar to those of said healthy subjects, the prognosis is that the disease and/or related complications are not worsened with respect to SOD1 and SOD2 expressions.

According to an embodiment of the invention, the in vitro method for the prognosis of patient having an OPA1 gene or OPA1 gene product deficit-induced disease comprises the comparison of the expressions of SOD 1 and SOD2 of patient having an OPA1 gene or OPA1 gene product deficit-induced disease, to SOD1 and SOD2 expressions of healthy subjects having no OPA1 gene- or no OPA1 gene-product deficit, and when SOD1 and SOD2 expressions of patient having an OPA1 gene or OPA1 gene product deficit-induced disease are upper than those of said healthy subjects, the prognosis is that the disease and/or related complications are not worsened with respect to SOD1 and SOD2 expressions.

According to an embodiment of the invention, the in vitro method for the prognosis of patient having an OPA1 gene or OPA1 gene product deficit-induced disease comprises the comparison of the expressions of SOD 1 and SOD2 of patient having an OPA1 gene or OPA1 gene product deficit-induced disease, to SOD1 and SOD2 expressions of healthy subjects at the same age having no OPA1 gene- or no OPA1 gene-product deficit, and when SOD1 and SOD2 expressions of patient having an OPA1 gene or OPA1 gene product deficit-induced disease are lower than those of said healthy subjects, the prognosis is the worsening of the disease and/or related complications.

According to an embodiment of the invention, the in vitro method for the prognosis of patient having an OPA1 gene or OPA1 gene product deficit-induced disease comprises the comparison of the expressions of SOD 1 and SOD2 of patient having an OPA1 gene or OPA1 gene product deficit-induced disease, to SOD1 and SOD2 expressions of healthy subjects at the same age having no OPA1 gene- or no OPA1 gene-product deficit, and when SOD1 and SOD2 expressions of patient having an OPA1 gene or OPA1 gene product deficit-induced disease are similar to those of said healthy subjects, the prognosis is that the disease and/or related complications are not worsened with respect to SOD1 and SOD2 expressions.

According to an embodiment of the invention, the in vitro method for the prognosis of patient having an OPA1 gene or OPA1 gene product deficit-induced disease comprises the comparison of the expressions of SOD 1 and SOD2 of patient having an OPA1 gene or OPA1 gene product deficit-induced disease, to SOD1 and SOD2 expressions of healthy subjects at the same age having no OPA1 gene- or no OPA1 gene-product deficit, and when SOD1 and SOD2 expressions of patient having an OPA1 gene or OPA1 gene product deficit-induced disease are upper than those of said healthy subjects, the prognosis is that the disease and/or related complications are not worsened with respect to SOD1 and SOD2 expressions.

According to an embodiment of the invention, the in vitro method for the prognosis of patient having an OPA1 gene or OPA1 gene product deficit-induced disease comprises the comparison of the expressions of SOD 1 and SOD2 of patient having an OPA1 gene or OPA1 gene product deficit-induced disease, to SOD1 and SOD2 expressions of the same patient at an early stage, and to those of healthy subjects at the same age having no OPA1 gene- or no OPA1 gene product deficit, and when SOD1 and SOD2 expressions of patient having an OPA1 gene or OPA1 gene product deficit-induced disease are lower than those of the same patients at early stage, the prognosis is associated to a worsening of the disease and/or related complications.

According to an embodiment of the invention, the in vitro method for the prognosis of patient having an OPA1 gene or OPA1 gene product deficit-induced disease comprises the comparison of the expressions of SOD 1 and SOD2 of patient having an OPA1 gene or OPA1 gene product deficit-induced disease, to SOD1 and SOD2 expressions of the same patient at an early stage, and to those of healthy subjects at the same age having no OPA1 gene- or no OPA1 gene product deficit, and when SOD1 and SOD2 expressions of patient having an OPA1 gene or OPA1 gene product deficit-induced disease are similar to those of the same patients at early stage, the prognosis is that the disease and/or related complications are not worsened with respect to SOD1 and SOD2 expressions.

According to an embodiment of the invention, the in vitro method for the prognosis of patient having an OPA1 gene or OPA1 gene product deficit-induced disease comprises the comparison of the expressions of SOD 1 and SOD2 of patient having an OPA1 gene or OPA1 gene product deficit-induced disease, to SOD1 and SOD2 expressions of the same patient at an early stage, and to those of healthy subjects at the same age having no OPA1 gene- or no OPA1 gene product deficit, and when SOD1 and SOD2 expressions of patient having an OPA1 gene or OPA1 gene product deficit-induced disease are upper than those of the same patients at early stage, the prognosis is that the disease and/or related complications are not worsened with respect to SOD1 and SOD2 expressions.

According to an embodiment of the invention, the in vitro method for the prognosis of patient having an OPA1 gene or OPA1 gene product deficit-induced disease comprises:
  detecting in a biological sample selected from fibroblasts, epithelial cells, blood samples or a mixture thereof, of a patient affected or suspected to be affected by said disease, the expression of SOD 1 and SOD2, and without the use of retina sample or optic nerve sample,
  comparing said expression to those of healthy subjects at the same age having no OPA1 gene- or OPA1 gene product deficit,
  comparing said expression to those of patients at the same age having an OPA1 gene- or OPA1 gene product deficit and having the same expression than that of healthy subjects at the same age having no OPA1 gene- or OPA1 gene product deficit,
  deducing from comparison of expression of SOD1 and SOD2 of said patient
    to the expression of SOD1 and SOD2 of patients at the same age having an OPA1 gene- or OPA1 gene product deficit and having the same expression as that of healthy subjects at the same age having no OPA1 gene- or OPA1 gene product deficit
    and to the expression of SOD1 and SOD2 of healthy subjects at the same age having no OPA1 gene- or OPA1 gene product deficit, that whether said patient has
expression levels of SOD1 and SOD2 lower than those of healthy subjects at the same age having no OPA1 gene- or OPA1 gene product deficit,
and expression levels of SOD1 and SOD2 lower than those of patients at the same age having an OPA1 gene- or OPA1 gene product deficit,
said patient may expect suffering and/or the severity of said OPA1 gene or OPA1 gene product deficit-induced disease or related complication.

According to an embodiment of the invention, the in vitro method for the prognosis of patient having an OPA1 gene or OPA1 gene product deficit-induced disease comprises:
detecting in a biological sample selected from fibroblasts, epithelial cells, blood samples or a mixture thereof, of a patient affected or suspected to be affected by said disease, the expression of catalase, and without the use of retina sample or optic nerve sample,
comparing said expressions to that of healthy subjects having no OPA1 gene- or no OPA1 gene-product deficit.

Said healthy subjects who are used as controls are preferably healthy subjects of the same age as said patients.

According to an embodiment of the invention, the in vitro method for the prognosis of patient having an OPA1 gene or OPA1 gene product deficit-induced disease comprises:
detecting in a biological sample selected from fibroblasts, epithelial cells, blood samples or a mixture thereof, of a patient affected or suspected to be affected by said disease, the expression of catalase, and without the use of retina sample or optic nerve sample,
comparing said expressions to that of healthy subjects at the same age having no OPA1 gene- or no OPA1 gene product deficit.

According to an embodiment of the invention, the in vitro method for the prognosis of patient having an OPA1 gene or OPA1 gene product deficit-induced disease comprises:
detecting in a biological sample selected from fibroblasts, epithelial cells, blood samples or a mixture thereof, of a patient affected or suspected to be affected by said disease, the expression of catalase, and without the use of retina sample or optic nerve sample,
comparing said expressions to that of same patient having OPA1 gene- or OPA1 gene product deficit at an early stage, and to those of healthy subjects at the same age having no OPA1 gene- or no OPA1 gene product deficit.

According to an embodiment of the invention, the in vitro method for the prognosis of patient having an OPA1 gene or OPA1 gene product deficit-induced disease comprises the comparison of the expression of catalase of patient having an OPA1 gene or OPA1 gene product deficit-induced disease, to catalase expression of healthy subjects having no OPA1 gene- or no OPA1 gene-product deficit,
and when catalase expression of patient having an OPA1 gene or OPA1 gene product deficit-induced disease is lower than that of said healthy subjects, the prognosis is the worsening of the disease and/or related complications.

Said healthy subjects who are used as controls are preferably healthy subjects of the same age as said patients.

According to an embodiment of the invention, the in vitro method for the prognosis of patient having an OPA1 gene or OPA1 gene product deficit-induced disease comprises the comparison of the expression of catalase of patient having an OPA1 gene or OPA1 gene product deficit-induced disease, to catalase expression of healthy subjects having no OPA1 gene- or no OPA1 gene-product deficit, and when catalase expression of patient having an OPA1 gene or OPA1 gene product deficit-induced disease is similar to that of said healthy subjects, the prognosis is that the disease and/or related complications are not worsened with respect to catalase expression.

According to an embodiment of the invention, the in vitro method for the prognosis of patient having an OPA1 gene or OPA1 gene product deficit-induced disease comprises the comparison of the expressions of catalase of patient having an OPA1 gene or OPA1 gene product deficit-induced disease, to catalase expression of healthy subjects having no OPA1 gene- or no OPA1 gene-product deficit,
and when catalase expression of patient having an OPA1 gene or OPA1 gene product deficit-induced disease is upper than that of said healthy subjects, the prognosis is that the disease and/or related complications are not worsened with respect to catalase expression.

According to an embodiment of the invention, the in vitro method for the prognosis of patient having an OPA1 gene or OPA1 gene product deficit-induced disease comprises the comparison of the expression of catalase of patient having an OPA1 gene or OPA1 gene product deficit-induced disease, to catalase expression of healthy subjects at the same age having no OPA1 gene- or no OPA1 gene-product deficit,
and when catalase expression of patient having an OPA1 gene or OPA1 gene product deficit-induced disease is lower than that of said healthy subjects, the prognosis is the worsening of the disease and/or related complications.

According to an embodiment of the invention, the in vitro method for the prognosis of patient having an OPA1 gene or OPA1 gene product deficit-induced disease comprises the comparison of the expression of catalase of patient having an OPA1 gene or OPA1 gene product deficit-induced disease, to catalase expression of healthy subjects at the same age having no OPA1 gene- or no OPA1 gene-product deficit,
and when catalase expression of patient having an OPA1 gene or OPA1 gene product deficit-induced disease is similar to that of said healthy subjects, the prognosis is that the disease and/or related complications are not worsened with respect to catalase expression.

According to an embodiment of the invention, the in vitro method for the prognosis of patient having an OPA1 gene or OPA1 gene product deficit-induced disease comprises the comparison of the expression of catalase of patient having an OPA1 gene or OPA1 gene product deficit-induced disease, to catalase expression of healthy subjects at the same age having no OPA1 gene- or no OPA1 gene-product deficit,
and when catalase expression of patient having an OPA1 gene or OPA1 gene product deficit-induced disease is upper than that of said healthy subjects, the prognosis is that the disease and/or related complications are not worsened with respect to catalase expression.

According to an embodiment of the invention, the in vitro method for the prognosis of patient having an OPA1 gene or OPA1 gene product deficit-induced disease comprises the comparison of the expression of catalase of patient having an OPA1 gene or OPA1 gene product deficit-induced disease, to catalase expression of the same patient at an early stage, and to those of healthy subjects at the same age having no OPA1 gene- or no OPA1 gene product deficit,
and when catalase expression of patient having an OPA1 gene or OPA1 gene product deficit-induced disease is lower than that of the same patients at early stage, the prognosis is associated to a worsening of the disease and/or related complications.

According to an embodiment of the invention, the in vitro method for the prognosis of patient having an OPA1 gene or OPA1 gene product deficit-induced disease comprises the comparison of the expression of catalase of patient having an OPA1 gene or OPA1 gene product deficit-induced disease, to catalase expression of the same patient at an early stage, and to those of healthy subjects at the same age having no OPA1 gene- or no OPA1 gene product deficit, and when catalase expression of patient having an OPA1 gene or OPA1 gene product deficit-induced disease is similar to that of the same patients at early stage, the prognosis is that the disease and/or related complications are not worsened with respect to catalase expression.

According to an embodiment of the invention, the in vitro method for the prognosis of patient having an OPA1 gene or OPA1 gene product deficit-induced disease comprising the comparison of the expression of catalase of patient having an OPA1 gene or OPA1 gene product deficit-induced disease, to catalase expression of the same patient at an early stage, and to those of healthy subjects at the same age having no OPA1 gene- or no OPA1 gene product deficit, and when catalase expression of patient having an OPA1 gene or OPA1 gene product deficit-induced disease is upper than that of the same patients at early stage, the prognosis is that the disease and/or related complications are not worsened with respect to catalase expression.

According to an embodiment of the invention, the in vitro method for the prognosis of patient having an OPA1 gene or OPA1 gene product deficit-induced disease comprises:
- detecting in a biological sample selected from fibroblasts, epithelial cells, blood samples or a mixture thereof, of a patient affected or suspected to be affected by said disease, the activity of aconitase, and without the use of retina sample or optic nerve sample,
- comparing said expressions to that of healthy subjects having no OPA1 gene- or no OPA1 gene-product deficit.

Said healthy subjects who are used as controls are preferably healthy subjects of the same age as said patients.

According to an embodiment of the invention, the in vitro method for the prognosis of patient having an OPA1 gene or OPA1 gene product deficit-induced disease comprises:
- detecting in a biological sample selected from fibroblasts, epithelial cells, blood samples or a mixture thereof, of a patient affected or suspected to be affected by said disease, the activity of aconitase, and without the use of retina sample or optic nerve sample,
- comparing said expressions to that of healthy subjects at the same age having no OPA1 gene- or no OPA1 gene product deficit.

According to an embodiment of the invention, the in vitro method for the prognosis of patient having an OPA1 gene or OPA1 gene product deficit-induced disease comprises:
- detecting in a biological sample selected from fibroblasts, epithelial cells, blood samples or a mixture thereof, of a patient affected or suspected to be affected by said disease, the activity of aconitase, and without the use of retina sample or optic nerve sample,
- comparing said expressions to that of same patient having OPA1 gene- or OPA1 gene product deficit at an early stage, and to those of healthy subjects at the same age having no OPA1 gene- or no OPA1 gene product deficit.

According to an embodiment of the invention, the in vitro method for the prognosis of patient having an OPA1 gene or OPA1 gene product deficit-induced disease comprises the comparison of the expression of aconitase of patient having an OPA1 gene or OPA1 gene product deficit-induced disease, to aconitase expression of healthy subjects having no OPA1 gene- or no OPA1 gene-product deficit, and when aconitase expression of patient having an OPA1 gene or OPA1 gene product deficit-induced disease is lower than that of said healthy subjects, the prognosis is associated to a worsening of the disease and/or related complications.

According to an embodiment of the invention, the in vitro method for the prognosis of patient having an OPA1 gene or OPA1 gene product deficit-induced disease comprises the comparison of the activity of aconitase of patient having an OPA1 gene or OPA1 gene product deficit-induced disease, to aconitase activity of healthy subjects having no OPA1 gene- or no OPA1 gene-product deficit, and when aconitase activity of patient having an OPA1 gene or OPA1 gene product deficit-induced disease is similar to that of said healthy subjects, the prognosis is that the disease and/or related complications are not worsened with respect to the antioxidant mechanism related to the NRF2 activation.

According to an embodiment of the invention, the in vitro method for the prognosis of patient having an OPA1 gene or OPA1 gene product deficit-induced disease comprises the comparison of the activity of aconitase of patient having an OPA1 gene or OPA1 gene product deficit-induced disease, to aconitase activity of healthy subjects having no OPA1 gene- or no OPA1 gene-product deficit, and when aconitase activity of patient having an OPA1 gene or OPA1 gene product deficit-induced disease is upper than that of said healthy subjects, the prognosis is that the disease and/or related complications are not worsened with respect to the antioxidant mechanism related to the NRF2 activation.

According to an embodiment of the invention, the in vitro method for the prognosis of patient having an OPA1 gene or OPA1 gene product deficit-induced disease comprises the comparison of the expression of aconitase of patient having an OPA1 gene or OPA1 gene product deficit-induced disease, to aconitase expression of healthy subjects at the same age having no OPA1 gene- or no OPA1 gene-product deficit, and when aconitase expression of patient having an OPA1 gene or OPA1 gene product deficit-induced disease is lower than that of said healthy subjects, the prognosis is associated to a worsening of the disease and/or related complications According to an embodiment of the invention, the in vitro method for the prognosis of patient having an OPA1 gene or OPA1 gene product deficit-induced disease comprises the comparison of the expression of aconitase of patient having an OPA1 gene or OPA1 gene product deficit-induced disease, to aconitase activity of healthy subjects at the same age having no OPA1 gene- or no OPA1 gene-product deficit, and when aconitase activity of patient having an OPA1 gene or OPA1 gene product deficit-induced disease is similar to that of said healthy subjects, the prognosis is that the disease and/or related complications are not worsened with respect to the antioxidant mechanism related to the NRF2 activation.

According to an embodiment of the invention, the in vitro method for the prognosis of patient having an OPA1 gene or OPA1 gene product deficit-induced disease comprises the comparison of the activity of aconitase of patient having an OPA1 gene or OPA1 gene product deficit-induced disease, to aconitase expression of healthy subjects at the same age having no OPA1 gene- or no OPA1 gene-product deficit, and when aconitase activity of patient having an OPA1 gene or OPA1 gene product deficit-induced disease is upper than that of said healthy subjects, the prognosis is that the disease and/or related complications are not worsened with respect to the antioxidant mechanism related to the NRF2 activation.

According to an embodiment of the invention, the in vitro method for the prognosis of patient having an OPA1 gene or OPA1 gene product deficit-induced disease comprises the comparison of the expression of aconitase of patient having an OPA1 gene or OPA1 gene product deficit-induced disease, to aconitase activity of the same patient at an early stage, and to those of healthy subjects at the same age having no OPA1 gene- or no OPA1 gene product deficit, and when aconitase expression of patient having an OPA1 gene or OPA1 gene product deficit-induced disease is lower than that of the same patients at early stage, the prognosis is associated to a worsening of the disease and/or related complications.

According to an embodiment of the invention, the in vitro method for the prognosis of patient having an OPA1 gene or OPA1 gene product deficit-induced disease comprises the comparison of the expression of aconitase of patient having an OPA1 gene or OPA1 gene product deficit-induced disease, to aconitase expression of the same patient at an early stage, and to those of healthy subjects at the same age having no OPA1 gene- or no OPA1 gene product deficit, and when aconitase expression of patient having an OPA1 gene or OPA1 gene product deficit-induced disease is similar to that of the same patients at early stage, the prognosis is that the disease and/or related complications are not worsened with respect to the antioxidant mechanism related to the NRF2 activation.

According to an embodiment of the invention, the in vitro method for the prognosis of patient having an OPA1 gene or OPA1 gene product deficit-induced disease comprises the comparison of the expression of aconitase of patient having an OPA1 gene or OPA1 gene product deficit-induced disease, to aconitase expression of the same patient at an early stage, and to those of healthy subjects at the same age having no OPA1 gene- or no OPA1 gene product deficit, and when aconitase expression of patient having an OPA1 gene or OPA1 gene product deficit-induced disease is upper than that of the same patients at early stage, the prognosis is that the disease and/or related complications are not worsened with respect to the antioxidant mechanism related to the NRF2 activation.

DETAILED DESCRIPTION OF THE INVENTION

The present invention provides a prognostic biomarker of an OPA1 gene- or OPA1 gene product-deficit-induced disease, or related complications.

A prognostic biomarker is a biomarker that provides information on the likely course of the disease in an untreated individual.

The present invention also provides a predictive biomarker of an OPA1 gene- or OPA1 gene product-deficit-induced disease, or related complications.

A predictive biomarker is defined as a marker, which can be used to identify subpopulations of patients who are most likely to respond to a given therapy.

The present invention provides a factor involved the cellular response to oxidative stress for its use in prognosis of an OPA1 gene- or OPA1 gene product-deficit-induced disease, or related complications using a sample containing fibroblasts, epithelial cells or a blood sample in a patient suspected to be affected by said disease.

The present invention relates to SOD1, SOD2, catalase and aconitase as effective predictive markers for prognosing an optic neuropathy, in particular an OPA1 mutation-induced optic neuropathy, a phase of worsening of the pathological condition, the extend to which the pathological condition may worsen.

Biology tests on the search for mutations of an OPA1 gene present in the samples of individuals with retinopathy or suspected to be at risk for DOA may be performed at the same time as prognosis.

The OPA1 gene codes a 960 amino acids protein, and is described in WO0227022, which is incorporated herein by reference. "OPA1 gene", as used herein encompasses, except where otherwise specified, an OPA1 gene of a human being, including a normal OPA1 gene, the various forms of OPA1 gene, its functional equivalents and any mutant or deleted form of the OPA1 gene.

"Normal OPA1 gene", as used herein encompasses an OPA1 gene which, upon transcription and translation, gives rise to a normal OPA1 polypeptide, expressed at a normal level for example a form or level of expression of the gene found in a subject who does not have clinically and molecularly diagnosed autosomal dominant optic atrophy.

"OPA1 peptide", "OPA1 protein" and "OPA1 gene product" are used herein interchangeably and encompass, except where otherwise specified, a peptide encoded by the coding sequence of any OPA1 gene, including a normal OPA1 gene and any mutant or deleted form of the gene, any forms of the OPA1 gene and including any fragment of less than full length and including any immature peptide.

"Defective OPA1 gene" is taken herein to mean an OPA1 gene comprising one or more mutations, which may be in the coding sequence or in a control sequence, which cause the gene product of the gene not to carry out its normal function and/or cause the gene product to be produced at so low a level that it does not carry out its function effectively.

NRF2 (Nuclear Factor-Erythroid-derived 2-like 2) is a transcription factor that in humans is encoded by the NFE2L2 gene (SEQ ID No: 11). NRF2 regulates the transcriptional activation of antioxidant and protective genes, including its own transcription.

In the present invention, a complication means extraocular attempts and includes but is not limited to neuromuscular complications, deafness, chronic progressive external ophthalmoplegia, myopathy and neuropathy.

Examples of NRF2 activated antioxidant proteins include heme oxygenase 1, superoxide dismutase, in particular superoxide dismutase 1 or 2 (SOD1 or SOD2) glutathione S-transferase (GST), and NAD(P)H dehydrogenase quinone 1 (NQO1).

Examples of NRF2-activated factors are selected from NFR2, superoxide dismutase 1 (SOD1) (SEQ ID No 1), superoxide dismutase 2 (SOD2) (SEQ ID No 2), catalase (CAT) (SEQ ID No 3), glutathione S-transferase pi 1 (GSTP1) (SEQ ID No 4), NAD(P)H dehydrogenase quinone 1 (NQO1) (SEQ ID No 5), glutathione reductase (GSR) (SEQ ID No 6), thioredoxin reductase 1 (TXNRD1) (SEQ ID No 7), Peroxiredoxin (SEQ ID No 8), heme oxygenase (decycling) 1 (HMOX1) (SEQ ID No 9), glutamate-cysteine ligase modifier subunit (GCLM) (SEQ ID No 10).

"Gene", as used herein, includes the coding sequence, non-coding introns, and upstream and downstream control elements of a gene.

"Diagnosis" means the determination of the affection of a person suffering from a given disorder or suspected to develop a given disorder.

"Prognosis" means the degree of seriousness indicative of the subsequent development/evolution of a disorder and/or of complications.

"Therapeutic" refers to the preventive, curative or palliative treatment offered to an individual.

DOA and ADOA are used herein interchangeably. In the very early stages, eye affection is difficult to detect and it is not easy to determine the speed and extent of progression of the disease.

A "biological sample" is a sample obtained from an individual for the purpose of detecting, screening/diagnosis/follow-up of OPA1-deficiency induced disease, preferably DOA, evaluating DOA development, complications or glaucoma.

In a preferred embodiment said sample is a biological sample selected from a sample containing fibroblasts, preferably skin fibroblasts or epithelial cells or a blood sample, or a mixture thereof.

A "patient" is an individual with a least one alteration of the OPA1 gene or OPA1 gene product. A patient may be an asymptomatic patient, namely a patient with no symptoms or signs of DOA or of DOA complications.

A patient suspected to be affected is a patient suffering at least one symptom or sign of DOA or of DOA complications who may or may not be diagnosed with DOA or "DOA plus syndrome", said patient is a patient for whom none of the known mutation of OPA1 and responsible for DOA, has been detected yet and having at least one mutation of said gene(s).

A patient according to the invention may be an individual suspected to develop a disease related to OPA1 deficiency or deficit, in particular DOA, "DOA plus syndrome", a complication related to DOA.

As used here a patient may also be an individual diagnosed with glaucoma or suspected to have glaucoma, in particular glaucoma related to an OPA1-gene deficit, a more particularly a patient with primary open angle glaucoma.

A "nucleotide sequence" is a sequence of nucleotide patterns, i.e. a sequence of nucleic acids or polynucleotides or fragments thereof.

The structures and modifications of these sequences are either natural or the result of genetic recombination or chemical synthesis.

According to this invention, an "amplification primer" is a nucleic sequence including 10 to 200 nucleotide patterns, preferably 15 to 25 base pairs of at least one target sequence of genetic material.

"Hybridisation" is a process by which two nucleic sequences, such as for instance a primer and a target sequence, are linked.

A "hybridisation probe" is a nucleic sequence of 15 to 200 nucleotide patterns, preferably 100 to 190 base pairs of at least one target sequence of genetic material. The probe has hybridisation specificity so that it hybridises with the target nucleic sequence, not with other sequences.

The present inventors have focused their search on assays of specific proteins or nucleic acids of a specific NRF2-activated gene or genes products in a biological sample selected from a sample containing fibroblasts, epithelial cells, a blood sample, a mixture thereof, in order to create a biomarker for the detection of DOA, in particular DOA prognosis.

For example, the presence of aconitase mRNA or protein directly in a biological sample, or the presence of NRF2-activated genes products mRNA or protein in the sample of a patient.

As an illustration, they have been able to show that the aconitase protein could be detected directly in fibroblasts of an individual with DOA.

The expression of NRF2 in individuals with DOA or ADOA associated with complications and in healthy individuals. The data shows that the expression of the SOD gene product in individuals with DOA, is significantly lower than in healthy individuals or individuals DOA without complications.

Further, the method according to the invention also relates to the use of nucleotide sequences of a target sequence, particularly those of the SOD1, SOD2, catalase, aconitase gene, or a mixture thereof which may be used as amplification primers or hybridisation probes for the purposes of detection and/or prognosis and/or follow up of individuals suffering from DOA.

Advantageously, the invention also relates to a kit for the diagnosis/prognosis/follow-up of DOA comprising at least one means for detection of OPA1 deficiency and at least one means for the detection of NRF2-activated gene product.

More advantageously, the invention relates to a kit for the diagnosis/prognosis/follow-up of DOA comprising at least one means for the detection of the activity of NRF2-activated gene product, at least one means for the detection of the activity of human aconitase.

This invention offers a method, process, test and kit for DOA for the purpose of prognosis, diagnosis based on the detection of at least one specific biomarker in material taken from a biological sample which is a sample containing fibroblast, epithelial cells, of blood cells.

General Procedures

Mice of the ENU: B6;C3-Opa$^{1329-355del}$Strain and wt control mice were described elsewhere (Alavi et al., 2007). Briefly, Mice were kept in a 12 h light (10 lux)/12 h dark cycle with food and water available ad libitum in full-barrier facilities free of specific pathogens.

Cell

Skin or blood samples, epithelial cells of DOA patients and of healthy controls may be obtained during routine diagnostic procedures with their informed consent. Sampling sites may include the trunk, hand, knee, arm, and mouth. Samples are snap-frozen in liquid nitrogen and processed for RNA isolation as outlined below.

Fibroblasts, obtained from DOA patients or from healthy volunteers after obtaining their informed consent, were cultured in Dulbecco's Modified Eagle's Medium 4.5 g/l glucose (DMEM, Invitrogen), supplemented with 10% FCS, penicillin (100 U/ml) and streptomycin (100 mg/ml) and maintained for up to 20 passages.

Epithelial cells obtained from DOA patients or from healthy volunteers after obtaining their informed consent, were cultured in Dulbecco's Modified Eagle's Medium 4.5 g/l glucose (DMEM, Invitrogen), supplemented with 10% FCS, penicillin (100 U/ml) and streptomycin (100 mg/ml) and maintained for up to 10 passages.

HeLa cells, (transformed human epithelial cells) from the American Type Culture Collection (Manassas, Va.) were cultured in Dulbecco's Modified Eagle's Medium 4.5 g/l glucose (DMEM, Invitrogen), supplemented with 10% FCS, penicillin (100 units/ml) and streptomycin (100 mg/ml), in an incubator at 37° C. and 5% $CO_2$. HeLa cells were electroporated using Cell line kit R (Amaxa, Lonza) with 1.5 µg of control siRNA (D-001210-02, Dharmacon Research) or human OPA1 siRNA (D-005273-03, target sequence AAAGAAGGCUGUACCGUUA, (SEQ ID No 25) Dharmacon Research) per $1.10^6$ cells.

Cortical neurons were obtained at embryonic Day 17 from pregnant Wistar rats (Janvier) under intraperitoneal pentobarbitol (Sigma) anaesthesia. All animals (n=45, 350 embryos) in this study were ethically maintained and used. Cortices were dissected, enzymatically dissociated with papain (10 U/ml, Sigma), and exposed for 5 min in a solution that inactivated papain: DNAse I (Invitrogen) and B27 (Gibco), diluted in PBS 1× with D-Glucose (33 mM, Sigma). Cells were dissociated by trituration and filtered through a membrane (70 μm, BD Falcon). Cells were then purified through a BSA solution (8%, Sigma) diluted in Neurobasal A-25 (Invitrogen). Dishes, with or without glass cover-slips, were coated with poly-D-lysine (0.1 mg/ml, Sigma) 24 h prior to culturing. For each experiment, cortices from 8 to 12 embryos per rat are mixed. Experiments were reproduced three to eight times. Cultures were grown in Neurobasal® (Eurobio) supplemented with B27 (Invitrogen), 2 mM glutamine, 0.1% penicillin and streptomycin (Gibco), 250 U/ml amphotericin (Invitrogen) and 1 mM lactic acid (Sigma) at a density of $6.10^5$ cells per $cm^2$.

Neurons ($5.10^6$) were electroporated after dissociation using the Rat Neuron Nucleofector Kit (Amaxa, Lonza) using an optimized protocol for primary rat cortical neurons (http://bio.lonza.com/fileadmin/groups/marketing/Downloads/Protocols/Generate d/Optimized_Protocol_101.pdf). Three micrograms of control luciferase-targeting (D-001210-02, Dharmacon Research) or OPA1-targeting (target sequence GAUUGUGCCUGACUUUAUA, Dharmacon Research (SEQ ID No 26) small interfering RNA (Dharmacon).

Measurement of Oxygen Consumption

Oxygen consumption rates (OCR) were performed using the XF24 Extracellular Flux Analyser (Seahorse Bioscience, North Billerica, Mass.). HeLa cells ($15.10^3$) or neurons ($3.10^5$) transfected with control siRNA or siRNA targeting OPA1 were plated on XF24 microplates, respectively 3 days or 6 days before OCR measurements. Dual-analyte sensor cartridges were soaked in XF Calibrant Solution (Seahorse Biosciences) in 24 well cell culture microplates overnight at 37° C. to hydrate. Approximately one hour prior to experimentation, three of four injection ports (A, B and C) on the sensor cartridge were filled with oligomycin (A: 0.6 μM for neurons, 1 μM for HeLa cells), Carbonyl cyanide 4-(trifluoromethoxy)phenylhydrazone (FCCP) (B: 6 μM for neurons, 1 μM for HeLa cells) or rotenone (C: 50 nM for neurons, 1 μM for HeLa cells) with antimycin A (C: 0.182 μM for neurons and 1 μM for HeLa cells). The plate was the loaded into the XF24 instrument for calibration. For oxygen consumption measurement, growth media of neurons or HeLa cells were replaced one hour before experimentation with incubation media, which consisted of DMEM supplemented with NaCl (143 mM), PhénolRed (3 mg/ml), glucose (10 mM), glutamine (2 mM) and pyruvate (2 mM) at pH 7.4, and kept at 37° C. in a non-CO2 incubator until the completion of sensor cartridge calibration. The XF24 microplate was then loaded into the Seahorse XF24 analyser following the manufacturer's instructions. All experiments were carried out at 37° C.

Immunoblot Analysis

Cells were lysed for 30 min in a buffer containing 50 mM Tris-HCL pH 7.5, 250 mM NaCl, 5 mM EDTA, 5 mM EGTA, 1 mM Dithiothreitol, 0.1% Triton X-100, 0.1% SDS, 1% Deoxycholate, 1% NP40 plus protease inhibitors («Complete» protease inhibitor mixture, Roche Applied Science). Cell lysates were centrifuged at 14,000 rpm at 4° C. for 10 min. The supernatant corresponding to total proteins was obtained and protein concentration was determined using the Bradford Protein-assay (Bio-Rad). 100 μg proteins were separated by SDS-PAGE (8-15%) and transferred to nitrocellulose membranes (Whatman, Protran). Free binding sites were blocked with 5% non fat dry milk, 0.2% Tween 20 in Tris Buffer Saline 1× pH 7.6 (blocking buffer). The membranes were probed with a primary antibody (anti-OPA1 (1/300, BD-Biosciences), anti-actin (1/25000, Chemicon), anti-HSP60 (1/8000, Sigma), anti-citrate synthase (1/3000, Abcam), anti-OXPHOS (1/200, Mitosciences), anti-NDUFB4 (1/500, Mitosciences), anti-NDUFA9 (1/100, Mitosciences), anti-SDHA (1/1000, Abcam), anti-Core 1 (1/500, Invotrogen), anti-COXIV (1/250, Cell Signaling Technology), anti-ATP5C1 (1/500, Abgent), anti-ATP5H (1/2000, Abcam), anti-aconitase (1/500, Abcam), anti-SOD1 and anti-SOD2 (1/2000, Epitomics), anti-catalase (1/3000, Abcam)) and incubated overnight at 4° C. in blocking buffer. After chemiluminescent detection of horseradish peroxidase-conjugated secondary antibody (1/10000, Abcam), scanned photographic films were analysed using ImageJ software.

Immunocytochemistry

Cells were fixed with PBS 1× containing 3.7% formaldehyde for 20 min.

Cells were permeabilized for 5 min in PBS 1×, 0.25% to 0.3% Triton™ X-100 optionally 1% bovine serum albumin, and incubated for 10 min at −20° C. with methanol prior to nuclear NRF2 detection. Nonspecific binding sites were blocked with 3% BSA in PBS 1× optionally comprising containing 5% normal goat serum, and/or 0.5% Tween 20 for 15-30 min to 1 hour at room temperature. Optionally Methanol fixation (10 min, −20° C.) was performed prior to nuclear NRF2 detection.

Cells were immunostained with rabbit polyclonal anti-NRF2 antibody (1/50, Santa Cruz Biotechnology) for 1 h at 37° C. or with Polyclonal antibodies against NRF2 (1/50, Santa Cruz Biotechnology) incubated overnight at 4° C. in blocking solution.

Cells were then incubated with Alexa fluor 488-conjugated secondary antibodies (1/300, Molecular Probes), labelled with 0.25 μg/ml Hoechst in PBS 1× over 5 min and mounted in Mowiol. Immunolabelling was visualized under a fluorescence microscope (Nikon Eclipse 80i or Zeiss 710 Big) and images were acquired using NIS-Element (Nikon Digital Sight DUS2 camera) or ZEN 2011 software. Cells with accumulation of NRF2 staining in nucleus were counted by stack with Hoechst labelling nucleus using ImageJ software. Nucleus raw integrated densities (sum of pixel values) of NRF2 by $μm^2$ in neurons were measured using ImageJ software and confocal images.

RT-PCR

RNA Extraction

The detection of the presence of RNA from a biological sample requires the extraction of total RNA from the said sample.

Such extraction is carried out by any protocol for the extraction of nucleic acid from biological samples of a type known in itself. This step of purification consists in separating the nucleic acid from the other constituents and concentrating it.

For example, the biological sample may be blood (5 ml), which is then centrifuged at 1200 g for 10 minutes at 4° C. In that way, the serum is separated before the total RNA is extracted.

The extraction of total RNA may be carried out, for instance, using the RNeasy kit from Qiagen in accordance with the manufacturer's recommendations.

The RNA samples are then stored at −80° C. until use.

Of course, those skilled in the art know how to adapt the extraction, purification and preservation of nucleic acids depending on the biological samples from which they are derived.

Nucleic acids circulating in the free state, that is extracellular nucleic acids, it is not necessary to lyse the circulating cells. That results in a simpler process that is less time consuming and is less expensive.

Reverse Transcription

Total RNA (1 µg) was reverse-transcribed with a RevertAid First-Strand cDNA Synthesis kit (Fermentas, St. Leon-Rot, Germany) using oligo(dT) primers.

Primers against the housekeeping gene product β-actin were 5'-CGTCATACTCCTGCTTGCTGATCCA-CATCTGC-3' (sense) and 5'-ATCTGGCACCACACCTTC-TACAATGAGCTGCG-3' (antisense). (SEQ ID No 13 and SEQ ID No 14).

Negative controls with RNA instead of the complementary DNA (cDNA) templates were consistently negative.

The relative intensity of the bands may be assessed using ImageQuant 5.0 software (Molecular Dynamics, Sunnyvale, Calif.) followed by normalization for β-actin.

PCR (Polymerase Chain Reaction) Amplification of the cDNA.

The process of amplification by enzymatic polymerisation (targeted in vitro replication technique called "PCR" or Polymerase Chain Reaction) makes it possible to obtain, from a sample containing cDNA, important quantities of a specific DNA fragment, such as a prognostic marker, with a definite length by using a pair of nucleotide primers.

This step is carried out with the help of amplification primers in order to generate amplicons of at least one target sequence of the nucleic material and a control target.

The said primer and/or said probe include at least 10 nucleotide from a sequence selected from:
a sequence from any one of SEQ ID No 1 to 12; or their complementary sequences;
a homologous sequence of SEQ ID nos. 1 to 12 complementary or sufficiently complementary; or sufficiently homologous to hybridise with SEQ ID nos. 1 to 12 or their complementary sequences;

The primer sequences and/or probes of a nucleotide sequence of the studied genes are designed from:
SEQ ID No 1: *Homo sapiens* superoxide dismutase 1, soluble (SOD1),
SEQ ID No 2: *Homo sapiens* superoxide dismutase 2, mitochondrial (SOD2),
SEQ ID No 3: gi|262331523:5001-38136 *Homo sapiens* catalase (CAT), RefSeqGene on chromosome 11
SEQ ID No 4: *Homo sapiens* glutathione S-transferase pi 1 (GSTP1), RefSeqGene on chromosome 11
SEQ ID No 5: *Homo sapiens* NAD(P)H dehydrogenase, quinone 1 (NQO1), RefSeqGene on chromosome 16
SEQ ID No 6: *Homo sapiens* glutathione reductase (GSR), RefSeqGene on chromosome 8
SEQ ID No 7: *Homo sapiens* thioredoxin reductase 1 (TXNRD1), RefSeqGene on chromosome 12
SEQ ID No 8: *Homo sapiens* Peroxiredoxin
SEQ ID No 9: *Homo sapiens* heme oxygenase (decycling) 1 (HMOX1), RefSeqGene on chromosome 22
SEQ ID No 10: *Homo sapiens* glutamate-cysteine ligase, modifier subunit (GCLM), RefSeqGene on chromosome 1
SEQ ID No 11: *Homo sapiens* NRF2 (NFE2L2)
SEQ ID No 12: *Homo sapiens* aconitase 2, mitochondrial (ACO2)

These primers are designed so as to overlap the splice junction in order to eliminate the signals generated by genome contamination.

As an illustration, conventional PCR may be carried out with the Eppendorf MasterMix kit according to the manufacturer's recommendations or using any method known in itself.

Adapted PCR cycle may be used to carry out the gene amplification of any specific sequence using a thermal cycler (for example Perkin Elmer). The primer hybridisation temperature must be calculated depending on the Tm of each primer.

Alternatively, when the mRNA from a biological sample is to be analysed, reverse transcription and PCR (RT-PCR) may be carried out simultaneously in one step. One-step RT-PCR may be carried out using, for example, the kits Super Script™ One-Step RT-PCR and Platinum tag from Invitrogen in accordance with the manufacturer's recommendations. The RT-PCR reaction will also be carried out with a thermal cycler (for example Perkin Elmer).

For each PCR test, or RT-PCR test negative controls (with no nucleic acid) and positive controls (for example from a plasmid encoding the beta actin gene) are carried out in parallel.

The PCR may be quantitative. In this way, the SYBR green technique may be used, based on the standard curve obtained from plasmids encoding the studied gene.

Quantitative RT-PCR is carried out with the help of the QuantiTect SYBR Green PCR Master Mix kit from Qiagen in accordance with the manufacturer's recommendations.

Detection

During the target nucleic acid detection step, use may be made of a specific detection probe.

The hybridisation probe is a detection probe and is labelled for further detection.

Functional primers may be analysed with a fluorochrome or another fluorescent or quencher that links specifically with the amplification product (double-strand DNA).

To avoid primer dimers, a specific TaqMan probe may be linked to the sense and antisense primers.

To correct any possible variability of the enzymatic efficiency, the expression of a target gene may be standardised by determining a ratio between the target gene and a housekeeping gene (NADPH or β-actin for example), the expression of which is required and common in all individuals. The primers of housekeeping genes and particularly NADPH are for instance:

```
sense primer
                                       (SEQ ID No 23)
5' AAA GGA CAT TTC CAC CGC AAA 3' antisense primer
                                       (SEQ ID No 24)
5' GGT CGG GTC AAC GCT AGG CT 3'
```

Step of Detection and Quantification

For example, the products of PCR or amplicons may be separated by electrophoresis on 1.0% agarose gel, and then seen by illumination under UV after staining the DNA with ethidium bromide.

The expected fragment is identified by the co-migration of a molecular size marker.

Of course, the method according to the invention may be combined with or include other molecular markers in order to further increase its sensitivity and specificity depending on the condition to be searched.

This invention further makes it possible to improve the screening strategy and the treatment of early forms of DOA or DOA related complications.

ROS Measurement

Reactive oxygen species levels were measured using the fluorescent dye 2',7'-dichlorodihydrofluorescein diacetate (CM-H$_2$DCFDA, Molecular Probes) at 4 µM for 30 min at 37° C. or the fluorescent dye MitoSox (Molecular Probes) according to the manufacturer's recommendations.

Glutathione Levels

Cells were mixed with 200 µl of 5% metaphosphoric acid were then centrifuged 1,500 g at 4° C. during 10 min. Final supernatant was used for glutathione assay (reduced GSH and oxidized GSSG measurements) which is performed by reverse-phase high-performance liquid chromatography (HPLC) as previously described in Anne Galinier et al., 2006 which is incorporated herein by reference.

Enzymatic Activities

Superoxide dismutase (SOD) activities (Mn SOD2, Cu/Zn SOD1 or SOD3) were assayed by using the inhibition of pyrogallol auto-oxidation. One enzymatic unit of SOD activity was defined as the amount of enzyme that inhibited pyrogallol auto-oxidation by 50% Galinier). Briefly, the assay principle is based on the self-oxidation of pyrogallol property in the presence of EDTA, the reaction inhibited by SOD. The assay is based on competition between the reaction of oxidation of pyrogallol by the ROS and by dismutation of SOD. An enzyme unit is defined as the amount of enzyme able to inhibit 50% of the oxidation of pyrogallol in assay conditions.

Determination of Pyrogallol Volume Required for the Assay

Optic density (OD) of the pyrogallol at 420 nm should be 0.022 maximum in Tris-DTPA. This represents the maximum absorbance at 0% inhibition. Thus, OD in 1.9 ml of buffer is read using 30 to 50 µl of pyrogallol (10 mM). The reading is taken exactly 45 seconds after agitation of the tank by flipping and for 2 minutes. The required volume of pyrogallol (volume x) is fixed and will be the same throughout the assay.

Catalase activity was determined by measuring decomposition of H$_2$O$_2$ at 240 nm as previously described in described in (Galinier) incorporated herein by reference. Briefly, cells were lysed in 100 µl of Assay Buffer solution (assay the activity of aconitase, Bioxitech kit) using the "Tissue Lyse" (Qiagen) (2 minutes at 25 beats per minute). OD measurement is read from 1 ml of an H2O2 solution (19 mM final) diluted in 1×PBS and 20 µl of lysed sample added 60 s after reading 240 nm. The OD is measured at 25° C. for 4 minutes every 20 seconds. Part of the sample was used for protein dosage by assay microplate.

Data are analyzed as a function of the time of reading, slope of the curve is calculated using the 4 to 6 last points of the curve using the following formula: ΔOD×1000/(43.6× 0.9×20 µl×0.001× protein amount in µg). Activity is expressed in µmoles of decomposed H$_2$O$_2$ per minute and per mg of protein.

Aconitase activity measurements was performed using a protocol already described in the article of Anne-Laure Colombani et al., 2009, which is incorporated herein by reference.

Aconitase activity was determined using a kit (Bioxitech 21041) and measured by spectrophotometry using a lysate of HeLa or neuronal cells, in OPA1 or mock-depleted cells according to the instruction of the manufacturer.

Colorimetric Assay

Briefly, samples were lysed in 250 ml of Assay Buffer solution using a "Tissue Lyser" (Qiagen) (2 minutes at 25 beats per minute). Aconitase activity was measured in a vessel containing 200 µl of lysed sample, 200 µl of substrate, 200 µl of enzyme and 200 µl of NADP Enzyme Reagent. Part of the sample was used for protein content determination by microplate assay. The Optic density (OD) was read at 340 nm for samples zero (base line) (Buffer alone) and the positive control, mouse liver (200 µl of lysed liver as a sample) for 40 minutes at 37° C.

Data Analysis

After drafting the Graph OD versus time reading, the slope of the curve is determined (OD16 min OD15 min— . . . ) on a number of points and the average value is calculated. The activity of aconitase is calculated using the following formula: (Average OD/(2.4435×6.22×0.001× amount of protein in g)×4. The activity is expressed in milli unit enzymes micrograms of protein.

Statistical Analysis

Data were analyzed using paired student's t-test by systematic comparison between control small interfering RNA and small interfering RNA against OPA1. Oxygen consumption rates between siControl and siOPA1 treated cells were investigated using an unpaired student's t-test. Nucleus NRF2 raw integrated densities in control or OPA1 depleted-cells were carried out with a non-parametric test (Mann-Whitney test). *p<0.05, p<0.01, *p<0.001.

The results explained below are illustrative of comparison experiments carried out and are not limitative in any case.

Figure 9:
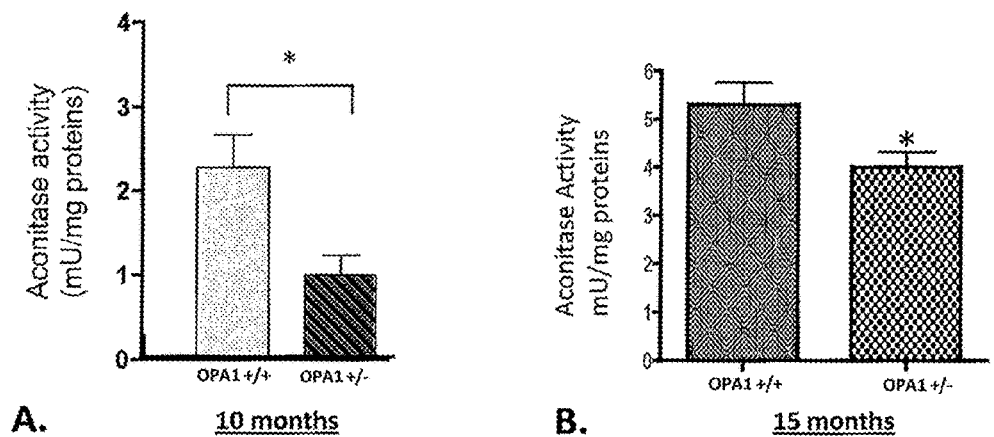

In FIGS. 9A and 9B, the aconitase activity expressed in mU/mg proteins is represented respectively at 10 months and 15 months. Aconitase activity was measured in 10 (n=6) (A) and 15 months old (n=9) (B) OPA1+/− and OPA1+/+ littermate mice cortices. Statistical significance was determined by Student's unpaired t-test and a nonparametric test (Mann-Whitney) p<0.05*, p<0.01**.

Figure 10:
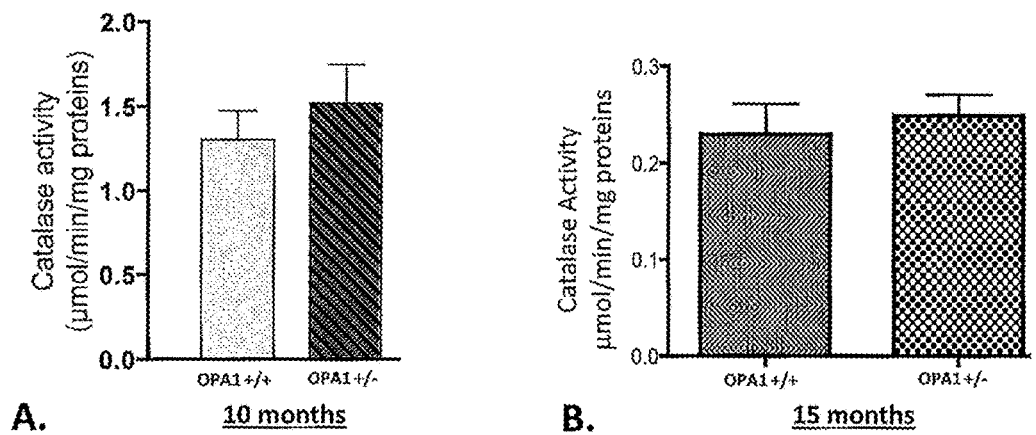

In FIGS. 10A and 10B, the catalase activity expressed in µmol/min/mg proteins is represented respectively at 10 months and 15 months. Catalase activity was measured in 10 (n=6) (A) and 15 months old (n=9) (B) OPA1+/− and OPA1+/+ littermate mice cortices. Statistical significance was determined by Student's unpaired t-test and a nonparametric test (Mann-Whitney) p<0.05*, p<0.01**.

Figure 11:
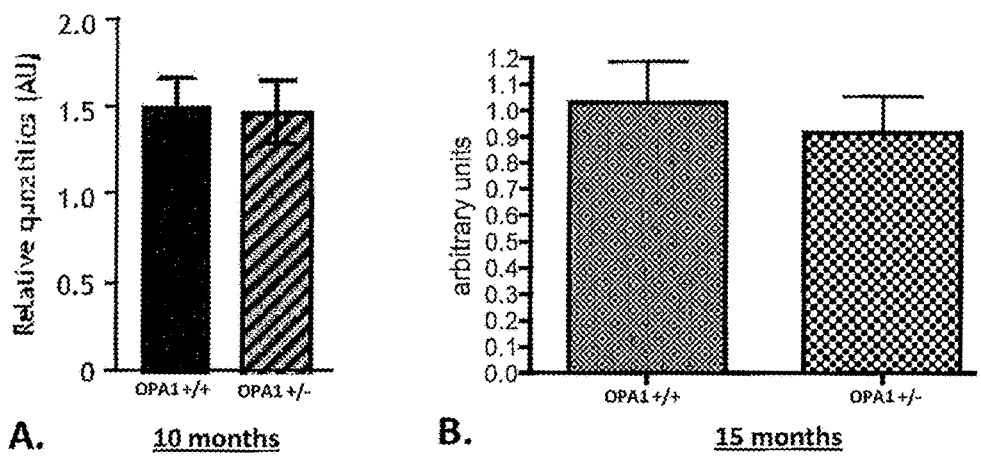

In FIGS. 11A and 11B, the SOD1 expression expressed in relative quantities (AU, Arbitrary Unit) is represented respectively at 10 months and 15 months. Immunoblot anti SOD1 in 10 (n=6) (A) and 15 months old (n=9) (B) OPA1+/− and OPA1+/+ littermate mice cortices. Unpaired t test with Welch's correction.

Figure 12:
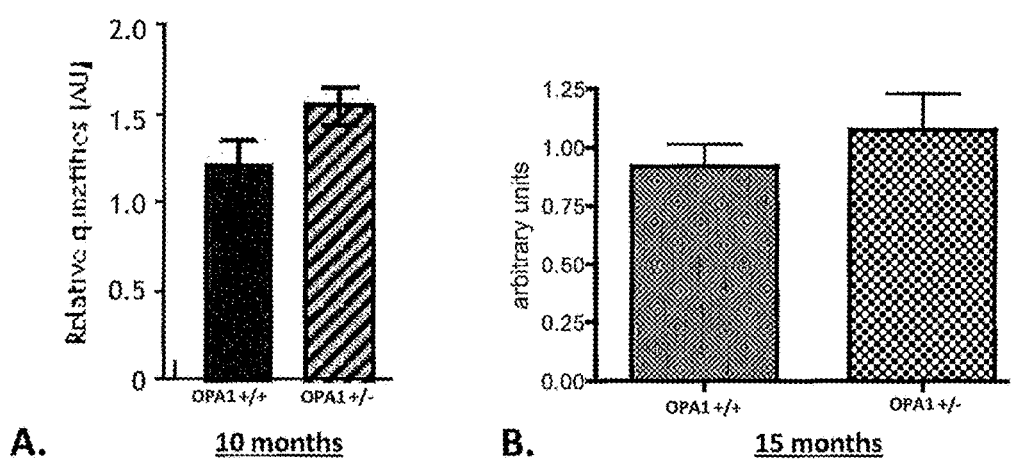

In FIGS. 12A and 12B, the SOD2 expression expressed in relative quantities (AU) is represented respectively at 10 months and 15 months. Immunoblot anti SOD2 in 10 (n=6) (A) and 15 months old (n=9) (B) OPA1+/− and OPA1+/+ littermate mice cortices. Unpaired t test with Welch's correction.

Figure 13:
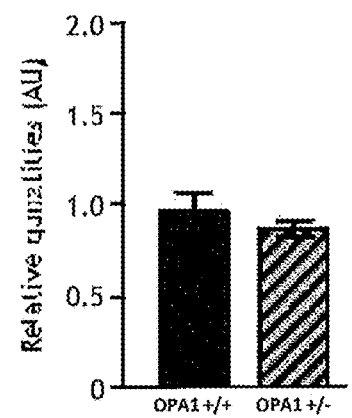
Figure 13:
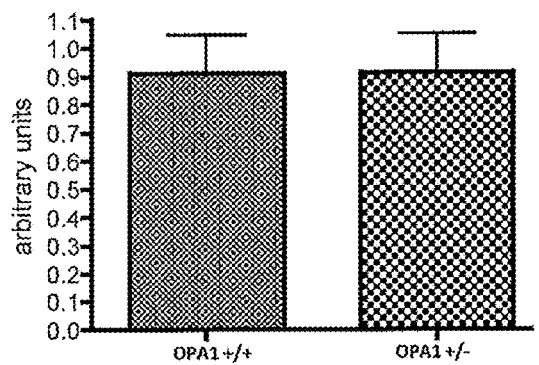

In FIGS. 13A and 13B, the catalase expression expressed in relative quantities (AU) is represented respectively at 10 months and 15 months. Immunoblot anti catalase in 10 (n=6) (A) and 15 months old (n=9) (B) OPA1+/− and OPA1+/+ littermate mice cortices. Unpaired t test with Welch's correction.

Figure 14:
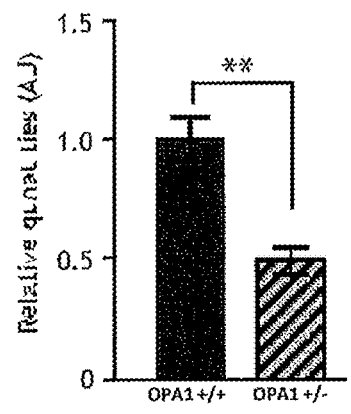
Figure 14:
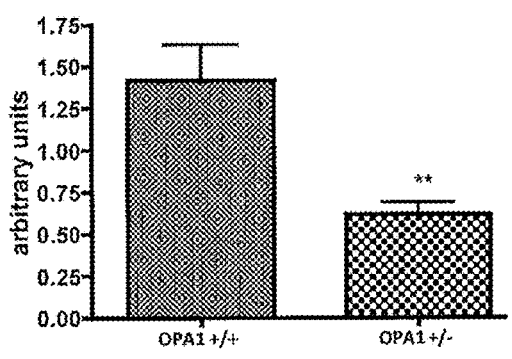

In FIGS. 14A and 14B, the OPA1 expression expressed in relative quantities (AU) is represented respectively at 10 months and 15 months. Immunoblot anti OPA1 in 10 (n=6) (A) and 15 months old (n=9) (B) OPA1+/− and OPA1+/+ littermate mice cortices. Unpaired t test with Welch's correction p>0.05*, p>0.01 for results at 10 months, p<0.05 for results at 15 months.

EXAMPLES

Example 1

Figure 1B:
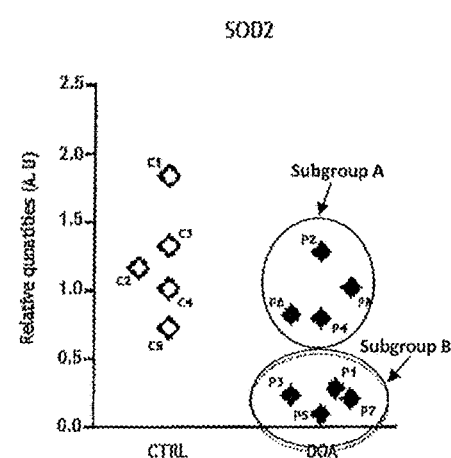
Figure 1B:
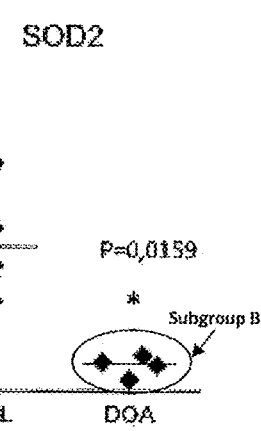

Cellular Antioxidant Defences are Impaired in Fibroblasts of DOA Patients FIG. 1A and FIG. 1B To address the question of antioxidant defences in DOA patients' fibroblasts, the expression and activity of several genes or gene products according to the invention were measured in fibroblasts from healthy volunteers and DOA patients (table 1).

TABLE 1

Characteristics of healthy volunteers with no OPA 1 gene- or no OPA1 gene product deficit (age, gender) and characteristics patients P1 to P8 used for measure of expression level of SOD1 and SOD2 in FIGS. 1A and 1B (age, gender, DNA change, protein mutation, exon, symptoms).

| Healthy volunteers | Age (year) | Gender | — | — | — | — |
|---|---|---|---|---|---|---|
| C1 | 43 | M | — | — | — | — |
| C2 | 28 | M | — | — | — | — |
| C3 | 25 | F | — | — | — | — |
| C4 | new born | M | — | — | — | — |
| C5 | — | — | — | — | — | — |

| DOA patients | Age (year) | Gender | DNA change/ variant 1 | Protein mutation | Exon | Disease (symptoms) |
|---|---|---|---|---|---|---|
| P1 | 20 | M | c.1770 G > C | splicing defect p? | Exon 18 | DOA |
| P2 | 11 | F | c.1334_G > A | p.R445H | Exon 14 | DOA 'plus' syndrome with deafness |
| P3 | 16 | F | c.1146_A > G | p.I382M | Exon 12 | DOA and deafness |
| P4 | 51 | F | c.2708_2711del | p.(Val903Glyfs*3) | Exon 27 | DOA |
| P5 | 30 | F | c.1334_G > A | p.R445H | Exon 14 | DOA 'plus' syndrome with deafness |
| P6 | 44 | M | c.1937_C > T | p.S646L | Exon 20 | DOA and multiple sclerosis |
| P7 | 10 | M | c.1146_A > G | p.I382M | Exon 12 | DOA and ataxia |
| P8 | 35 | M | c.1635_C > G | p.S545R | Exon 17 | DOA 'plus' syndrome and ataxia |

The level of mRNA expression, level of protein expression and activity (when accurate) of the following biomarker: NRF2, Superoxide dismutase 1 (SOD1) (SEQ ID No 1), superoxide dismutase 2 (SOD2) (SEQ ID No 2), catalase (CAT) (SEQ ID No 3), glutathione S-transferase pi 1 (GSTP1) (SEQ ID No 4), NAD(P)H dehydrogenase quinone 1 (NQO1) (SEQ ID No 5), glutathione reductase (GSR) (SEQ ID No 6), thioredoxin reductase 1 (TXNRD1) (SEQ ID No 7), Peroxiredoxin (SEQ ID No 8), heme oxygenase (decycling) 1 (HMOX1) (SEQ ID No 9), glutamate-cysteine ligase modifier subunit (GCLM) (SEQ ID No 10), aconitase 2 (SEQ ID No 12) were analyzed in biological samples or DOA patients and compared to the level of mRNA expression, level of protein expression and activity of the same marker in healthy volunteers.

The results show that some DOA patients showed altered expression of antioxidant proteins.

The data show heterogeneity in the level of expression of antioxidant proteins among DOA patients and allow differentiating a subgroup of patients with a reduced level of SODs (FIG. 1A and FIG. 1B).

As an example, patients P1, P3, P5, and P7 express particularly low levels of SOD1 and SOD2 proteins (FIG. 1A and FIG. 1B).

More precisely, the data show heterogeneity in the level of expression of antioxidant proteins among DOA patients.

The data allow differentiating two subgroups of patients with respect to the level of SOD1 and SOD2 proteins (FIG. 1A and FIG. 1B):

a subgroup named A consisting in patients P2, P4, P6 and P8, with an expression level of SOD1 and SOD2 similar to that of healthy volunteers with no OPA1 gene- or no OPA1 gene product deficit, a subgroup named B consisting in patients P1, P3, P5 and P7, with a low expression level of SOD1 and SOD2 with respect to the expression level of SOD1 and SOD2 of healthy volunteers and of patients from subgroup A.

Statistical difference was analyzed with a Mann and Whitney statistical test p=0.0159 for SOD1 and SOD2 corresponding to subgroup B.

The rates of expression of antioxidant proteins described above were not correlated with the age or sex of patients but may be correlated with progression of the disease (Table 1).

Patients from subgroup A present (table 1):

either a "strict DOA" disease that means a "light" DOA phenotype without neurological complications, such as patient P4, this sort of patients only present optic nerve atrophy;

or a DOA "plus" syndrome (multi-syndromic DOA) which corresponds to patients, such as P2, P6 and P8, presenting related complications, in particular additional neurological complications, such as ataxia, sensorineural deafness, multiple sclerosis, chronic progressive external ophtalmoplegia (CPEO) and sensory-motor neuropathy and myopathy in adult life.

For patients presenting a DOA plus syndrome, such as patients P2, P6 and P8, the DOA plus syndrome is not associated to the modulation of expression and the activity of NRF2-activated genes products.

For these patients of subgroup A, the disease and/or related complications are not worsened with respect to the antioxidant mechanism related to the NRF2 activation, because the expression and the activity of NRF2-activated genes products are not modulated by OPA1 gene or OPA1 gene product deficit. Thus, these patients can overcome oxidant stress caused by the inactivation of OPA gene.

For these patients, the phenotype of the disease and/or related complications could be worsened by other genes able to modify the phenotype.

Patients from subgroup A can present a "strict DOA" disease that means a "light" DOA phenotype without neurological complications, such as patient P4, this sort of patients only present optic nerve atrophy. On fundus examination, the optic disk typically presents a bilateral and symmetrical pallor of its temporal side, witnessing the loss of RGC (retinal ganglionic cells) fibers entering the optic nerve.

For patients presenting a DOA plus syndrome, such as patients P2, P6 and P8, the DOA plus syndrome is not associated to the decrease of SOD1 and SOD2 expressions.

For these patients of subgroup A, the disease and/or related complications are not worsened with respect to the antioxidant mechanism related to the NRF2 activation, because the expressions of SOD1 and SOD 2 are not modulated by OPA1 gene or OPA1 gene product deficit. Thus, these patients can overcome oxidant stress caused by the inactivation of OPA gene.

For these patients, the phenotype of the disease and/or related complications could be worsened by other genes able to modify the phenotype.

Patients from Subgroup B Present (Table 1):
  either a "strict DOA" disease that means a "light" phenotype of DOA disease without neurological complications, such as patient P1, this sort of patients only present optic nerve problems;
  or a DOA "plus" syndrome (multi-syndromic DOA) which corresponds to patients, such as P3, P5 and P7, presenting related complications, in particular additional neurological complications, such as ataxia, sensorineural deafness, multiple sclerosis, chronic progressive external ophtalmoplegia (CPEO) and sensory-motor neuropathy and myopathy in adult life.

For these patients of subgroup B, the disease and/or related complications are worsened with respect to the antioxidant mechanism related to the NRF2 activation, because the expression and the activity of NRF2-activated genes products are modulated by OPA1 gene or OPA1 gene product deficit. Thus, these patients cannot overcome oxidant stress caused by the inactivation of OPA gene.

For these patients of subgroup B, the disease and/or related complications are worsened with respect to the antioxidant mechanism related to the NRF2 activation, because the expression and the activity of NRF2-activated genes products are decreased by OPA1 gene or OPA1 gene product deficit. Thus, these patients cannot overcome oxidant stress caused by the inactivation of OPA gene.

For these patients of subgroup B, the disease and/or related complications are worsened with respect to the antioxidant mechanism related to the NRF2 activation, because the expressions of SOD1 and SOD2 are decreased by OPA1 gene or OPA1 gene product deficit. Thus, these patients cannot overcome oxidant stress caused by the inactivation of OPA gene.

Thus, for this subgroup of patients, a prognosis of a worsening of the disease and/or related complications can be established.

For patients presenting a "strict DOA" disease that means a "light" phenotype of DOA disease without neurological complications such as patient P1, the worsening of the disease and/or related complications means that the "strict DOA" disease evolves to a DOA "plus" syndrome and/or to related complications.

For patients presenting a DOA "plus" syndrome which correspond to patients presenting additional neurological complications, the worsening of the disease and/or related complications means that the syndrome and/or the related complications are worsened.

For example, the worsening of the disease and/or related complications means that:
  for a patient suffering from DOA "plus" syndrome with a loss of visual acuity, the worsening of this complication can lead to the blindness;
  for a patient suffering from DOA "plus" syndrome with a decline in hearing, the worsening of this complication can lead to deafness.

The worsening of the complications also means that a patient presenting a sort of complications, can present in addition another sort of complications.

For example, a patient suffering from DOA "plus" syndrome with ataxia, can present DOA "plus" syndrome with ataxia and deafness.

The antioxidant machinery was analysed in DOA patients and healthy volunteers fibroblasts. The results in FIG. 1A and FIG. 1B indicate that DOA patients showed altered expression of antioxidant genes.

The present invention provides SOD1 as a predictive biomarker for DOA, and SOD2 as another predictive biomarker for DOA. Within the group of DOA patient, a group of DOA patients showing an increased altered expression of antioxidant genes can be identified. This group corresponds to patients that experienced worsening of the disease.

The present invention provides SOD1 as a predictive biomarker for DOA, and SOD2 as another predictive biomarker for DOA. Within the group of DOA patient, a group of DOA patients showing a decreased altered expression of antioxidant genes can be identified. This group corresponds to patients that experienced worsening of the disease and/or related complications.

Thus, OPA1 mutations and/or decreased quantity in OPA1 induce an imbalance in the cellular redox state, weakening cells to exogenous pro-oxidative stresses. This phenomenon is one of the keys of the molecular mechanisms involved in DOA pathogenesis. The present invention provides a simple means of prognosis for OPA1-deficiency induced disease in human. The present invention provides a marker of prognosis selected from SOD1, Catalase, Aconitase, preferably SOD1, more preferably catalase, and even more preferably aconitase and SOD1, easily detectable in fibroblasts, blood cells or epithelial cells.

Example 2

To support these data and complete these results, the impact of OPA1 lowering on mitochondrial respiration oxidative metabolism in rat cortical neurons in primary culture and human epithelial HeLa cells was investigated.

Figure 8:
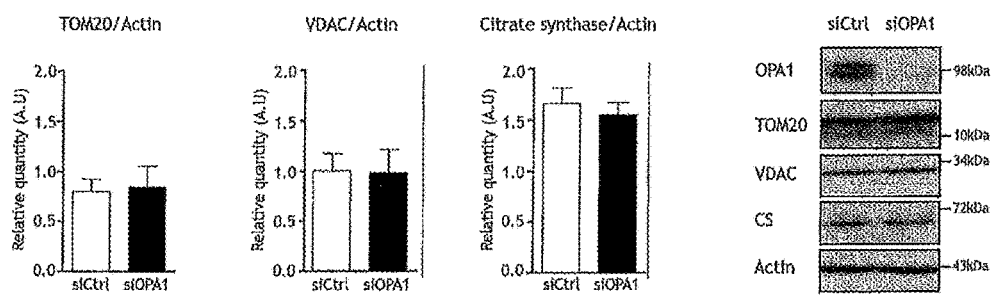
Figure 8:
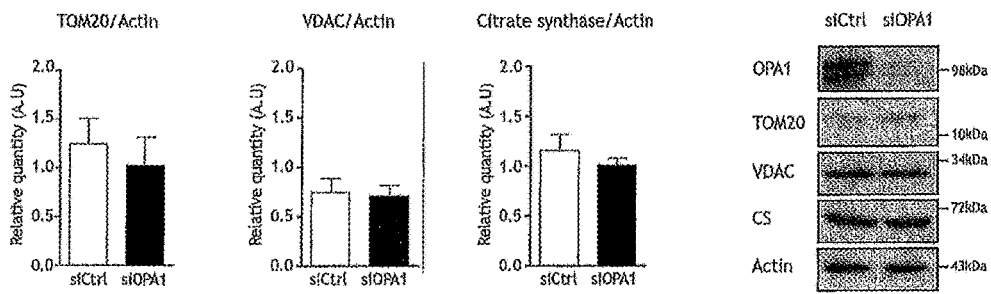

In both cellular models, cellular respiration is diminished when OPA1 is decreased (FIG. 2A, FIG. 2B). This is accompanied by a transient decrease in mitochondrial ROS production (FIG. 3A), which is buffered by the activation of NRF2 pathway (FIG. 3A, FIG. 3B, FIG. 4A, FIG. 4B) and variation in the levels and activities of several antioxidant proteins (FIG. 5A, to FIG. 5C and FIG. 6A and FIG. 6B). A change in superoxide dismutases and in catalase expression and/or activity in HeLa cells and in cortical neurons in primary culture is measured as observed in human fibroblasts, with no change in the amount of mitochondria (FIG. 8A, FIG. 8B).

Modulation of OPA1 Expression

Figure 2:
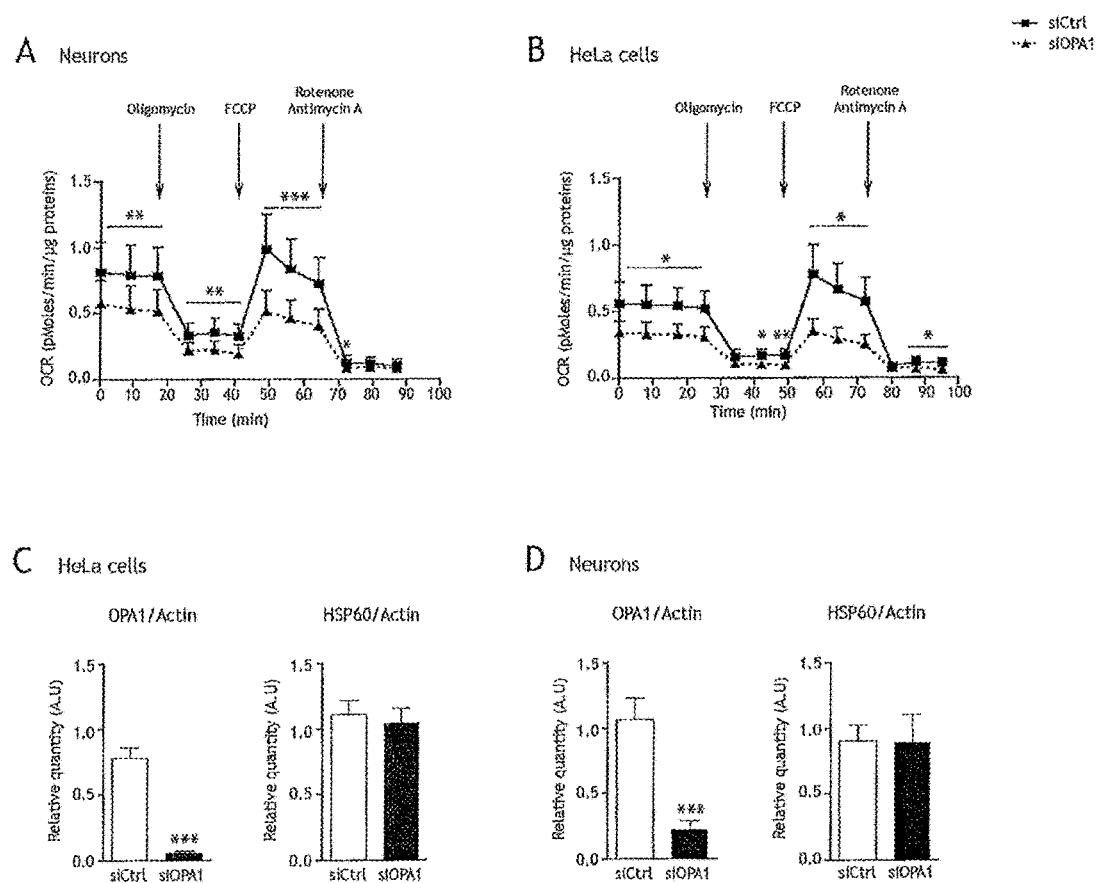

Both neurons and HeLa cells were transfected with siRNA directed against OPA1 (siOPA1) or against control RNA (siCtrl). OPA1 protein level relative to actin level was analysed by immunoblot. In neurons in primary culture treated with siOPA1, a decrease of 60% in OPA1 quantity was observed at 6 days after transfection (FIG. 2).

In HeLa cells, OPA1 quantity is decreased of about 90% 72 hours after transfection (FIG. 2C). As expected, neither Heat shock protein 60 (HSP60) nor citrate synthase, one of the translocase of the mitochondrial outer membrane (TOM), TOM20, nor Voltage-dependent anion channels (VDAC) (a class of porin ion channel located on the outer mitochondrial membrane) levels were changed both in neurons and in HeLa cells (FIG. 2C, FIG. 2D, FIG. 8A FIG. 8B). These data indicate that a decrease in OPA1 in these cells do not affect the amount of mitochondria.

Respiration is Impaired in OPA1 Down-Regulated Cells

The effect of OPA1 reduction levels on mitochondrial respiration was investigated using Seahorse XF24 analyzer (Seahorse Bioscience). In all conditions, rotenone and antimycin treatment drastically inhibited OCR showing that more than 95% of oxygen consumption was due to mitochondrial respiration (FIG. 2A and FIG. 2B). In siCtrl transfected cells, oligomycin inhibited respiration coupled with ATP synthesis resulting in spontaneous respiration, while addition of FCCP, a protonophore, that uncouples oxidation and phosphorylation in mitochondria resulted in maximal oxygen consumption rate (OCR).

In both siOPA1 transfected neurons (FIG. 2A) and HeLa cells (FIG. 2B), spontaneous respiration was reduced by 32.6 and 39.4% respectively, when compared to siCtrl treated cells. Furthermore, the spontaneous respiration was reduced by 66% and 61.1% and the maximal oxygen consumption rate by 45.8 and 58.2%. However, contrarily to siCtrl transfected cells, the maximal OCR in siOPA1 treated cells is not significantly different that spontaneous OCR.

Thus, depletion of OPA1 both in neurons and HeLa cells induced a drastic decrease in spontaneous and maximal mitochondrial respiration without affecting the mitochondrial biomass (FIG. 2A, 2B).

Total ATP cellular concentration did not vary in these conditions (data not shown). Furthermore, no difference in the total intracellular levels of NADH, $H^+/NAD^+$ was evidenced between siOPA1 and siCtrl treated HeLa cells (data not shown). The experiment suggests there is no major disruption of TCA cycle and furniture in NADH, $H^+$ to MRC in OPA1 siRNA treated HeLa cells (data not shown).

OPA1 Down Regulation Induces an Imbalance of the Redox State.

Figure 3:
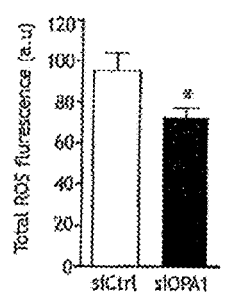
Figure 3:
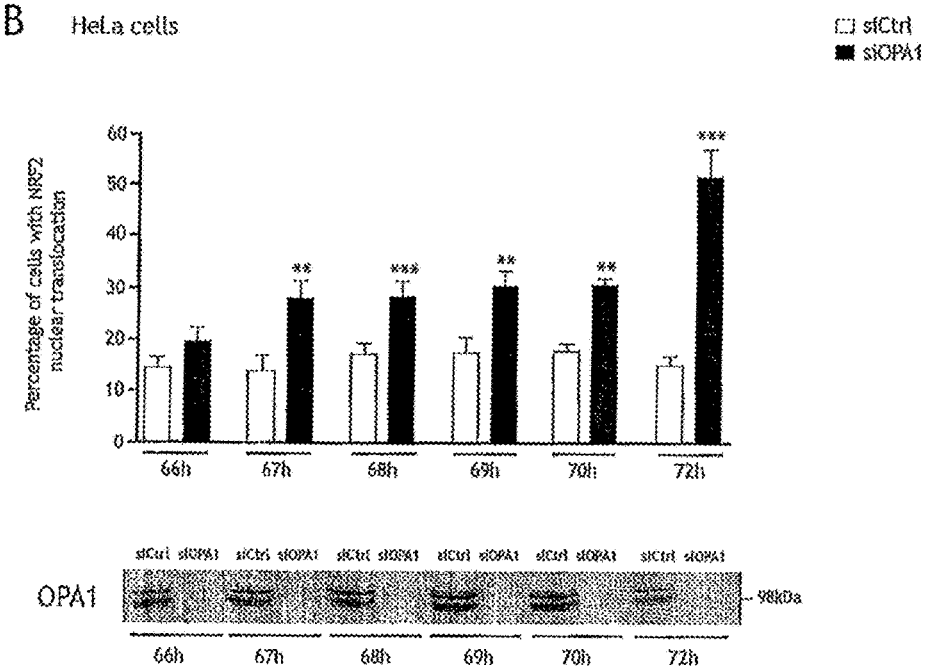

Total ROS content was measured with the $H_2DCFDA$ probe. As in siOPA1 treated neurons, a 24% decrease in ROS levels was observed in OPA1 down-regulated HeLa cells 72 hours after transfection (FIG. 3A).

Figure 5:
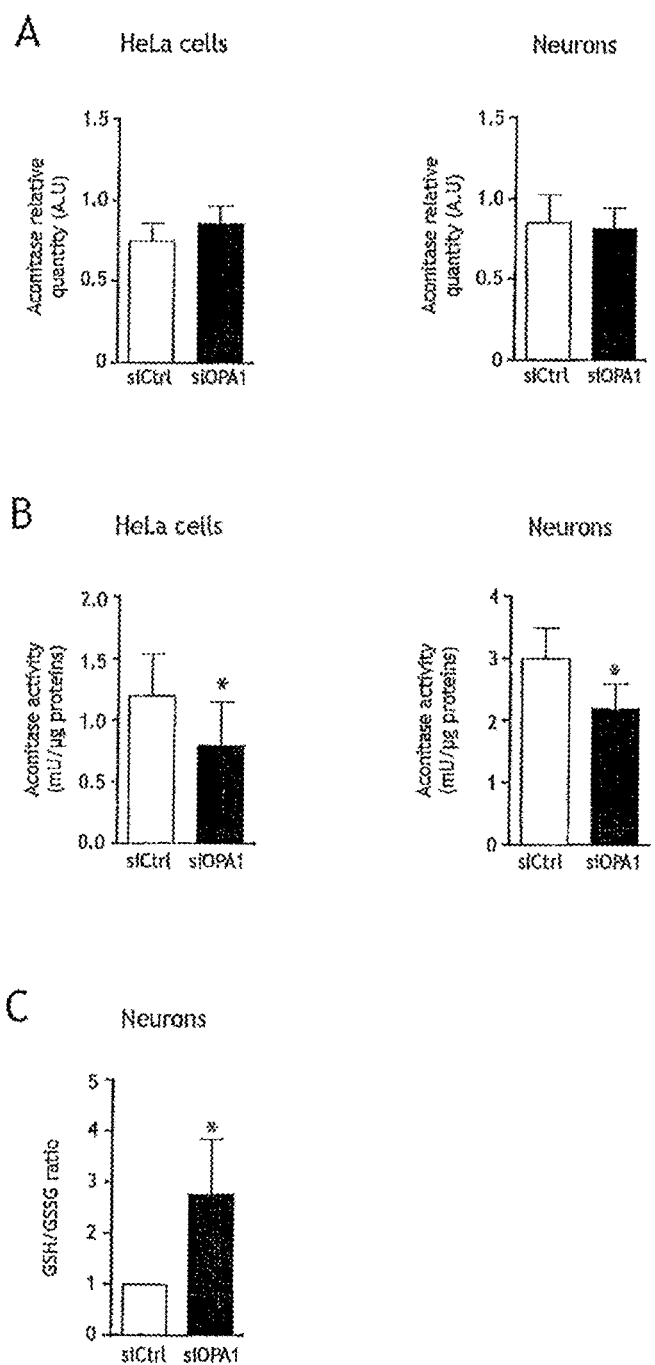

Aconitase activity was reduced both in siOPA1 treated HeLa cells and siOPA1 treated neurons of 33.8% and 26.8% respectively (FIG. 5B).

This drop could not be attributed to change in proteins quantities since aconitase protein levels are unchanged in HeLa cells and neurons (FIG. 5A).

Aconitase activity was previously shown to be highly sensitive to oxidation due to damaged FeS core and an inhibition of its activity is usually used as a signature of an increased production of mitochondrial ROS. The observed total ROS decrease with an increased production of mitochondrial ROS suggested an implementation of antioxidant response. To verify this hypothesis, expression of a redox state marker, glutathione, was measured. In siOPA1 treated neurons the ratio between reduced (GSH) to oxidized (GSSG) glutathione increased by 220.2% (FIG. 5C). Altogether, these results show that upon OPA1 down regulation, cells activated antioxidant responses to buffer an increased ROS production.

NRF2 Pathway is Activated upon Down Regulation of OPA1

Since NRF2 pathway accounts for a great part of oxidative stress response, it was asked whether this transcription factor could be involved in the response to oxidative metabolism imbalance due to a drop of OPAL Intra-cellular localisation of NRF2 was detected.

Figure 4:
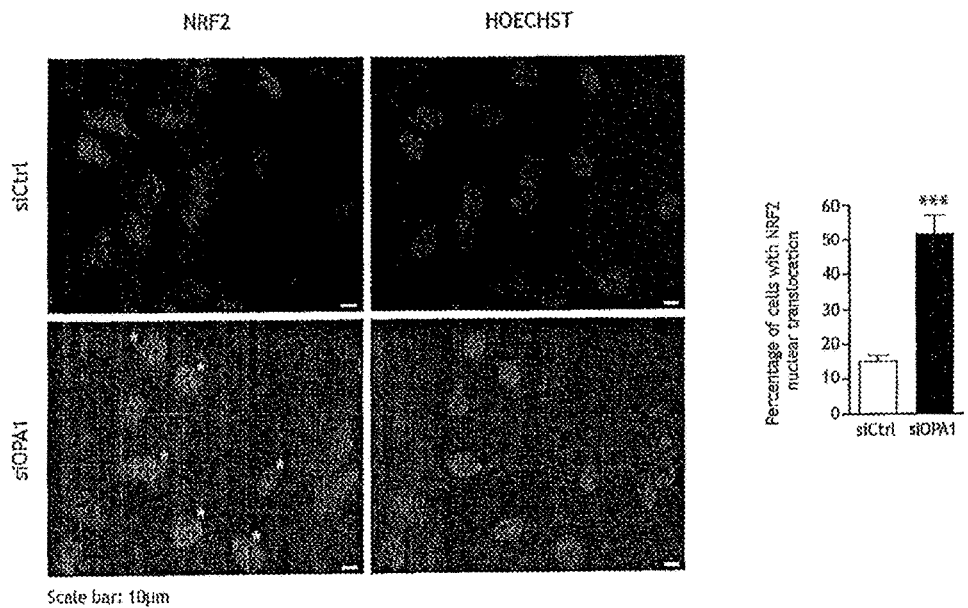
Figure 4:
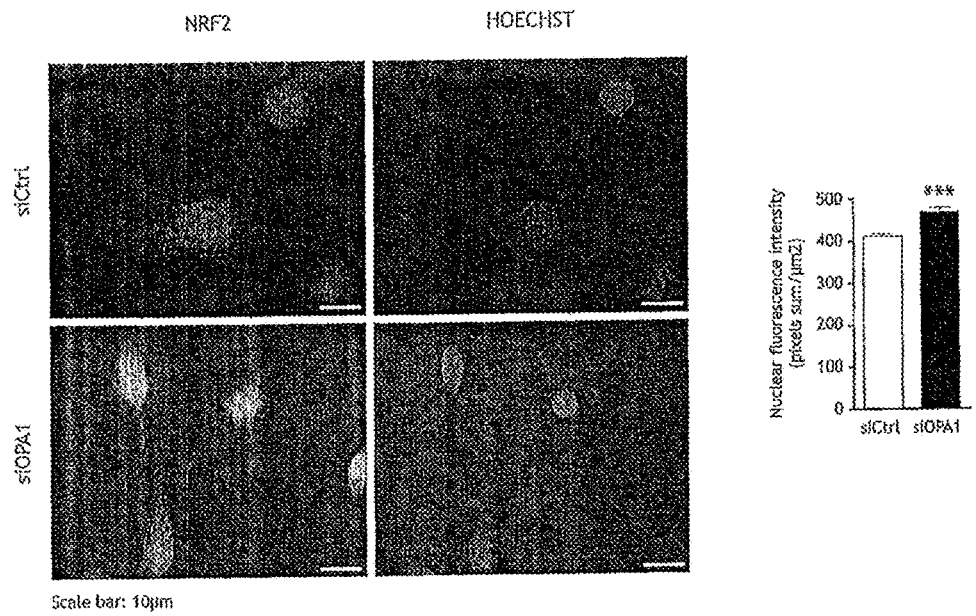

72 hours after transfection, 68% of siOPA1 treated HeLa cells presented a NRF2 nuclear localisation whereas only 15% of siCtrl-treated HeLa cells relocalised their NRF2 in the nucleus (FIG. 4A). Kinetics of NRF2 relocalisation from 66 hours to 72 hours post-transfection showed a significant NRF2 nuclear relocalisation 67 hours after transfection (FIG. 3B). Thus, since nuclear translocation of NRF-2 is part of its activation. Thus, down-regulation of OPA1 induced NRF2 activation.

The increase of nuclear translocation of NRF2 leads to an increase of the expression of NRF2.

Moreover as NRF2 is one of the NRF2-activated gene products, the nuclear translocation of NRF2 leads to an increase of cell expression of NRF2.

The nuclear factor NRF2 is, at the inactive state, blocked into the cell cytoplasm thanks to a cytoplasmic anchorage (KEAP1 protein). When a signal, such as an increase of the ROS, there is a dissociation between KEAP1 and NRF2. NRF2 is then translocated to the nucleus, where it is going to transactivate the expression of the target genes.

The present invention provides NRF2 as a predictive biomarker for DOA.

Figure 6:
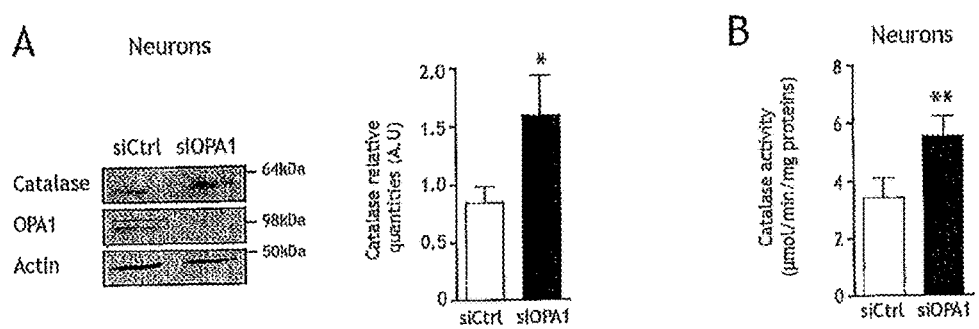

An increase of both catalase quantity (88%) and activity (66%) were revealed in neurons (FIGS. 6A and B). Altogether these results show that in HeLa cells and neurons a NRF2 detoxifying way of superoxide anion is activated when OPA1 is down regulated.

Similar results were obtained for GSTP1.

Example 3

Figure 7:
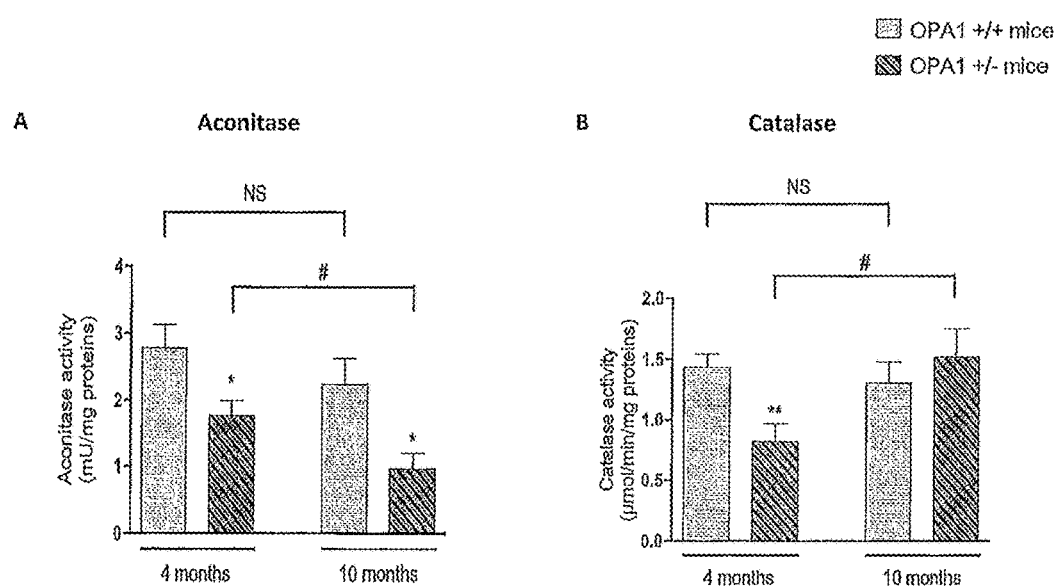

OPA1 Transgenic Mice Present an Imbalanced Oxidative Metabolism as Compared to Wild Type Mice of the Same Age Cortices from 4 and 10 months old transgenic mice were analyzed for their oxidative metabolism and contents in antioxidant defenses. Aconitase activity, which is a sensor of mitochondrial ROS production, was detected. A 63% inhibition of aconitase activity was measured in 4 months old OPA1 transgenic mice and a 43% inhibition in 10 months old OPA1 transgenic mice compared to litter mate mice (FIG. 7A). These results show that these mice present an oxidative stress. Next, the rate of expression of SOD1, SOD2 and catalase was evaluated in the same mice. Catalase activity was also measured and found to be decreased of about 60% at 4 months old and stable in 10 months old transgenic mice while catalase activity was stable in littermate mice (FIG. 7B). During the 6 first months of their life, mice activated their antioxidant defences but not sufficiently to buffer the mitochondrial ROS production leading to an oxidative stress well established in transgenic mice.

Data obtained in OPA1-deficit induced disease in mice confirmed that aconitase, catalase, or SOD1 (not shown) are biomarkers of disease progression (FIG. 7A, FIG. 7B).

Example 4

RT-PCR

Total RNA was isolated from samples, epithelial cells, fibroblasts or red blood cells, using ABI Prism Nucleic Acid PrepStation (PE Applied Biosystems, Foster City, Calif., USA) according to manufacturer recommendations.

Briefly, cells were washed twice in calcium/magnesium-free phosphate-buffered saline (PBS) and then lysed with 2× nucleic acid purification lysis solution at the final concentration of 1× with calcium/magnesium-free PBS. Lysed samples were transferred to a 96-well purification tray and placed on the instrument consisting of a specific membrane that physically captures the RNA passing through with wash solutions under precisely controlled vacuum conditions. A 'Method of isolation of total RNA from Cultured cells' was run. The isolated RNA was eluted in 100 µl Nucleic Acid Purification Elution Solution.

Total RNA may also be isolated from cells using an RNeasy Mini kit (Qiagen, Hilden, Germany); RNA from human samples, skin fibroblast epithelial cell or red blood cells may be derived using TRIzol (Invitrogen, Karlsruhe, Germany). DNA digestion is performed on RNeasy columns using the RNeasy-Free DNase set (Qiagen).

Total RNA (1 µg) was reverse-transcribed with a RevertAid First-Strand cDNA Synthesis kit (Fermentas, St. Leon-Rot, Germany) using oligo(dT) primers.

Primers against the housekeeping gene product β-actin were 5'-CGTCATACTCCTGCTTGCTGATCCA-CATCTGC-3' (sense) and 5'-ATCTGGCACCACACCTTC-TACAATGAGCTGCG-3' (antisense), (SEQ ID No 13 and 14).

Negative controls with RNA instead of the complementary DNA (cDNA) templates were consistently negative.

The relative intensity of the bands may be assessed using ImageQuant 5.0 software (Molecular Dynamics, Sunnyvale, Calif.) followed by normalization for β-actin.

Real-time PCR is carried out by real-time fluorescence detection using ABsolute SYBR Green ROX Mix (Thermo Fisher Scientific, Epsom, UK) in a total volume of 20 µl with the PCR MasterMix (Applied Biosystems, Foster City, Calif.) and with a 200 nM concentration of each primer.

For an initial step of diagnosis of OPA1 deficit or mutation the following sequences may be used:

```
                                  (SEQ ID No 35)
K1 S      5'-CACCCAGCTTATCTTGCAAGTG-3', (SEQ ID No 36)
K1 AS     5'-AAAGCGCCCGTAACATACATCG-3', (SEQ ID No 37)
K2 S      5'-AAACATCTACCTTCCAGCTGCG-3', (SEQ ID No 38)
K2 AS     5'-TGGATCTACTTCTACTCCTCGG-3', (SEQ ID No 39)
K3 S      5'-GTCAAATGGACCCTCATGGAAG-3'

(SEQ ID No 40)
K3 AS     5'-CCCAAGCAACCTCTACTGCTTT-3', (SEQ ID No 41)
K4 S      5'-TGGAAATGATTGCCCAAGCTCG-3'

(SEQ ID No 42)
K4 AS     5'-CAATGCTTTCAGAGCTGTTCCC-3'

(SEQ ID No 43)
K5 S      5'-GGATTGTGCCTGACATTGTG-3'

(SEQ ID No 44)
K5 AS     5'-CACTCAGAGTCACCTTAACTGG-3'

(SEQ ID No 45)
K8 S      5'-CTGTGAGGTCTGCCAGTCTTTA-3'

(SEQ ID No 46)
K8 AS     5'-GCTTGTCACTTTCAGATCCACG-3'.
```

Experimental conditions were as previously described in Delettre C, Griffoin J M, Kaplan J, Dollfus H, Lorenz B, Faivre L, Lenaers G, Belenguer P, Hamel C P. Mutation spectrum and splicing variants in the OPA1 gene. Hum Genet. 2001 December; 109(6):584-91. Epub 2001 Oct. 30. Incorporated herein by reference.

Primers for human SOD1 RT-PCR were synthesized as follows:

```
forward
                                  (SEQ ID No 19)
5'TTGGGCAAAGGTGGAAATGAA-3'
and reverse
                                  (SEQ ID No 20)
5'-CACCACAAGCCAAACGACTT-3',
```

Primers for human CATALASE RT-PCR were as follows:

```
forward
                                  SEQ ID No 21
5'-GTCTGTGTGAGAACATTGCC-3'
and reverse
                                  SEQ ID No 22
5'-ATGTGGCTCCCGTAGTCAG-3'
```

Primers against human heme oxygenase-1 [HO-1] were previously disclosed (Colombrita C, Lombardo G, Scapagnini G, Abraham N G. Heme oxygenase-1 expression levels are cell cycle dependent. *Biochem Biophys Res Commun* 2003; 308: 1001-1008) incorporated herein by reference or were designed with Primer Express software (Applied Biosystems) taking into account mono or multi spliced mRNA.

Primer sequences were as follows for human SOD2:

```
                                          (SEQ ID No 17)
    5'-GGACAAACCTCAGCCCTAACG-3' (forward)
    and (SEQ ID No 18)
    5'-TTTGATGGCTTCCAGCAACTC-3' (reverse).
```

The following primers may be used for human NQO1:

```
                                          SEQ ID No 25
    5'-CATTCTGAAAGGCTGGTTTGA-3' (forward)

SEQ ID No 26
    5'-TTGCAGAGAGTACATGGAGC-3' (reverse)
```

The following primers may be used for human GSTP1

```
                                          SEQ ID No 27
    5'-GCAGGAGGGCTCACTCAAA-3' (forward)
```

```
                                           SEQ ID No 28
    5'-AGGTGACGCAGGATGGTATT-3' (reverse)
```

The degenerate oligonucleotide primers used for aconitase and RT-PCR conditions were previously described in Duroy A. Navarre, David Wendehenne[2], Jörg Durner[3], Robert Noad and Daniel Klessig. Plant Physiology February 2000 vol. 122 no. 2 573-582. Experimental conditions were as previously described in this reference which is incorporated herein by reference.

The following primers may be used for human GCLC:

```
                                           SEQ ID No 29
    5'-TGCTGTCTTGCAGGGAATGT-3' (forward)

SEQ ID No 30
    5'-CACAACCATCCACCACTGC-3' (reverse)
```

The following primers may be used for human Glutathione Reductase:

```
                                           SEQ ID No 31
    5'-ATCCCAACTGTGGTCTTCAG-3' (forward)

SEQ ID No 32
    5'-CACGTTGAATAGGTC TTCACA-3' (reverse)
```

The following primers may be used for human NRF2:

```
                                           SEQ ID No 33
    5'-TTCCTCTGCTGCCATTAGTCAGTC-3' (forward)

SEQ ID No 34
    5'-GTCCTTCCATTTCCG-AGTCACTG-3' (reverse).
```

Reactions were performed in duplicate in an ABI Prism 7300 sequence detector (Applied Biosystems).

Experimental conditions for these experiments were as previously described in Paupe V, Dassa E P, Goncalves S, Auchère F, Lönn M, Holmgren A, Rustin P. Impaired nuclear Nrf2 translocation undermines the oxidative stress response in Friedreich ataxia. PLoS One. 2009; 4(1):e4253. doi: 10.1371/journal.pone.0004253. Epub 2009 Jan. 22;

Cheng Z G, Zhang G D, Shi P Q, Du B S. Expression and antioxidation of

Nrf2/ARE pathway in traumatic brain injury; Asian Pac J Trop Med. 2013 Apr. 13; 6(4):305-10. doi: 10.1016/S1995-7645(13)60061-9; and Kurzawski M, Dziedziejko V, Urasińska E, Post M, Wójcicki M, Miętkiewski J, Droździk M. Nuclear factor erythroid 2-like 2 (Nrf2) expression in end-stage liver disease. Environ Toxicol Pharmacol. 2012 July; 34(1):87-95. doi: 10.1016/j.etap.2012.03.001. Epub 2012 Mar. 11; and incorporated herein by reference.

For SOD1 or SOD2, under the following conditions: initial activation for 2 minutes at 50° C., denaturation for 15 minutes at 95° C., followed by 40 cycles of 15 seconds at 95° C. and 60 seconds at 60° C., and a final cycle of 15 seconds at 95° C., 15 seconds at 60° C., and 15 seconds at 95° C. Gene expression levels of each sample were quantified according to the comparative threshold cycle ($C_t$) method 2-$\Delta_t$ (Livak K J, Schmittgen T D. Analysis of relative gene expression data using real-time quantitative PCR and the 2-$\Delta_T$ Method. *Methods* 2001; 25: 402-8), using GAPDH as an internal standard. For each condition, the ground condition was set as 1.

Expression of each gene was assessed by 3 independent PCR analyses. Significance of the data was determined by Student's t-test.

The RNA was reverse-transcribed and PCR-amplified by using the ImProm-II Reverse Transcription System and Pfu DNA polymerase (Promega, Madison, Wis.).

The products of PCR were separated by electrophoresis on 1.0% agarose gel, and then detected by blue light illumination after staining the DNA with SYBR Safe DNA stain (invitrogen).

The data show a significant modulation in the expression of NRF-2 activated genes in fibroblasts when patient were going to experience a worsening phase of DOA.

Example 5

OPA1 Transgenic Mice Present an Imbalanced Oxidative Metabolism as Compared to Wild Type Mice of the Same Age Cortices from 10 and 15 months old transgenic mice were analyzed for their oxidative metabolism and contents in antioxidant defenses. Aconitase activity, which is a sensor of mitochondrial ROS production, was detected. A significant inhibition of aconitase activity was measured in 10 months old OPA1 transgenic mice and a significant inhibition in 15 months old OPA1 transgenic mice compared to litter mate mice (FIGS. 9A and 9B). These results show that these mice having OPA1+/− (FIGS. 14A and 14B) present an oxidative stress.

Next, the rate of expression of SOD1 (FIGS. 11A and 11B), SOD2 (FIGS. 12A and 12B) and catalase (FIGS. 13A and 13B) was evaluated in the same mice. Catalase activity (FIGS. 10A and 10B) was also measured and found stable at 10 months old and stable in 15 months old transgenic mice (FIGS. 10A and 10B). At 10 and 15 months, of mice did not activate more than control mice their antioxidant defences which is not sufficient to buffer the mitochondrial ROS production leading to an oxidative stress well established in transgenic mice.

Example 6

Results are also obtained on the prognosis of the progression of OPA1 gene or OPA1 gene product deficit-induced disease of transgenic OPA1+/− mice. and wild type mice by analysis of the amounts of SOD1, SOD 2 and catalase in their retina.

Results are also obtained on new born transgenic OPA1+/− mice and wild type new born mice by analysis of the amounts of SOD1, SOD2 and catalase in their cortices and retina.

Results are also obtained on patients in term of phenotype and analysis of kinetics of patients for whom the phenotype has already been determined.

REFERENCES

Alavi, M V, Stefanie Bette, Simone Schimpf, Frank Schuettauf, Ulrich Schraermeyer, Hans F. Wehrl, Lukas Ruttiger, Susanne C. Beck, Felix Tonagel, Bernd J. Pichler, Marlies Knipper, Thomas Peters, Juergen Laufs and Bernd Wissinger. A splice site mutation in themurine Opa1 gene features pathology of autosomal dominant optic atrophy Brain (2007), 130, 1029^1042.

Amati-Bonneau P, Milea D, Bonneau D, Chevrollier A, Ferre M, Guillet V, et al. OPA1-associated disorders: phenotypes and pathophysiology. The international journal of biochemistry & cell biology. 2009; 41(10): 1855-65.

Bosch et al., 2014. The American Journal of Human Genetics, Volume 94, Issue 2, 303-309, 23 Jan. 2014.

Cohn A C, Toomes C, Potter C, Towns K V, Hewitt A W, Inglehearn C F, et al. Autosomal dominant optic atrophy: penetrance and expressivity in patients with OPA1 mutations. American journal of ophthalmology. 2007; 143(4): 656-62.

Colombani, Anne-Laure.2009. Dysfonctionnement du glucose sensing cérébral. Altération de la signalisation redox dans l'hypersensibilité hypothalamique au glucose chez le rat Zücker obèse. 196 p Delettre C[1], Lenaers G, Griffoin J M, Gigarel N, Lorenzo C, Belenguer P, Pelloquin L, Grosgeorge J, Turc-Carel C, Perret E, Astarie-Dequeker C, Lasquellec L, Arnaud B, Ducommun B, Kaplan J, Hamel C P. Nuclear gene OPA1, encoding a mitochondrial dynamin-related protein, is mutated in dominant optic atrophy. Nat Genet. 2000 October; 26(2):207-10.

Koopman W J, Distelmaier F, Smeitink J A, Willems P H. OXPHOS mutations and neurodegeneration. The EMBO journal. 2013; 32(1):9-29.

Lenaers G, Hamel C, Delettre C, Amati-Bonneau P, Procaccio V, Bonneau D, et al. Dominant optic atrophy. Orphanet journal of rare diseases. 2012; 7:46.

Osellame L D, Blacker T S, Duchen M R. Cellular and molecular mechanisms of mitochondrial function. Best practice & research Clinical endocrinology & metabolism. 2012; 26(6):711-23.

P Reynier[1],*, P Amati-Bonneau[1],*, C Verny[2], A Olichon[3], G Simard[1], A Guichet[7], C Bonnemains[7], F Malecaze[4], M C Malinge[7], B Pelletier[7], P Calvas[6], H Dollfus[5], [3], Y Malthièry[1], G Lenaers[3], D Bonneau[7] 2004. *Med Genet;* 41:cl10 doi:10.1136/jmg.2003.016576

Yu-Wai-Man P, Griffiths P G, Burke A, Sellar P W, Clarke M P, Gnanaraj L, et al. The prevalence and natural history of dominant optic atrophy due to OPA1 mutations. Ophthalmology. 2010; 117(8):1538-46, 46 el.

Yu-Wai-Man P, Griffiths P G, Gorman G S, Lourenco C M, Wright A F, Auer-Grumbach M, et al. Multi-system neurological disease is common in patients with OPA1 mutations. Brain: a journal of neurology. 2010; 133 (Pt 3):771-86.

Yu-Wai-Man P, Trenell M I, Hollingsworth K G, Griffiths P G, Chinnery P F. OPA1 mutations impair mitochondrial function in both pure and complicated dominant optic atrophy. Brain: a journal of neurology. 2011; 134 (Pt 4):e164.

Zeviani M. OPA1 mutations and mitochondrial DNA damage: keeping the magic circle in shape. Brain: a journal of neurology. 2008; 131 (Pt 2):314-7.

---

The invention claimed is:

1. A method for the in vitro diagnosis and treatment of OPA1-deficit induced autosomal dominant optic atrophy (DOA, OMIM# 165500) and/or a complication associated with OPA1-deficit induced DOA selected from "DOA plus" syndrome disorders in a subject, comprising measuring in a biological sample selected from the group consisting of fibroblasts, epithelial cells, blood samples and mixtures thereof, of said subject, expression and/or activity of a Nuclear Factor (erythroid-derived 2)-like 2 (NRF2)-activated gene product selected from the group consisting of NRF2, SOD1, SOD2, catalase, GSTP1, NQO1, Glutathione Reductase, Peroxiredoxin 1, Hemeoxigenase 1, Thioredoxin reductase 1, and Glutamate Cystein Ligase, comparing said expression and/or activity measured in said biological sample of said subject to that of a measured expression and/or activity of a same NRF2-activated gene product in a biological sample selected from the group consisting of fibroblasts, epithelial cells, blood samples and a mixture thereof taken from a control subject, determining that said expression and/or activity measured in said biological sample from said subject is lower than said measured expression and/or activity in said biological sample from said control subject, and concluding said subject as suffering from said OPA1-deficit induced DOA and/or said complication associated with OPA1-deficit induced DOA, administering to said subject suffering from said OPA1-deficit induced DOA and/or said complication associated with OPA1-deficit induced DOA a treatment comprising administering at least one compound selected from the group consisting of Glutathione, Vitamin A, Vitamin C, Vitamin E, Coenzyme Q10 and Coenzyme Q10 analogs, Manganese, Iodide, Carotenoid terpenoids, Natural phenols, Phenolic acids and their esters, nonflavonoid phenolics, organic antioxidants selected from the group consisting of Capsaicin, Bilirubin, oxalic acid, phytic acid, N-Acetylcysteine, R-α-Lipoic acid, and fat and water soluble Uric acid, ARE inducers selected from the Sulforafane, Nordihydroguaiaretic acid, Diallyl Sulfid, Diallyl disulfid, Diallyl trisulfid, Pterostilbene, 1,2-dithiole-3-thione (D3T), 5,6-dihydro-cyclopento-(c)-1,2-dithiole-(4H)-thione (CPDT), Oltipraz, Salicylcurcuminoids, BG12, and Bardoxolonemethyl, and combinations thereof.

2. The method according to claim 1, wherein said "DOA plus" syndrome disorders are selected from the group consisting of external ophthalmoplegia, ataxia, deafness, glaucoma, Primary Open Angle Glaucoma, myopathy, peripheral neuropathy, and neurodegenerative diseases related to the age.

3. The method according to claim 1, wherein said control subject is one of:
  (i) a healthy subject not suffering from said OPA1-deficit induced DOA and/or said complication associated with OPA1-deficit induced DOA and having the same age as said subject, or
  (ii) said subject for whom said expression and/or activity has been previously measured.

4. The method according to claim 3 wherein said control subject is said subject for whom said expression and/or activity has been previously measured the said previous measure being performed at birth of said subject.

5. The in vitro method according to claim 1 wherein the biological sample of said subject is not an invasive sample obtained from a retina or an optic nerve.

* * * * *